(12) United States Patent
Lee et al.

(10) Patent No.: US 12,338,239 B2
(45) Date of Patent: Jun. 24, 2025

(54) HETEROCYCLIC COMPOUND AND ORGANIC LIGHT EMITTING DIODE COMPRISING SAME

(71) Applicant: LT MATERIALS CO., LTD., Yongin-Si (KR)

(72) Inventors: Gi-Back Lee, Yongin (KR); Hyun-Ju La, Yongin (KR); Won-Jang Jeong, Yongin (KR)

(73) Assignee: LT MATERIALS CO., LTD., Yongin (KR)

( * ) Notice: Subject to any disclaimer, the term of this patent is extended or adjusted under 35 U.S.C. 154(b) by 855 days.

(21) Appl. No.: 17/439,955

(22) PCT Filed: Jun. 19, 2020

(86) PCT No.: PCT/KR2020/007980
§ 371 (c)(1),
(2) Date: Sep. 16, 2021

(87) PCT Pub. No.: WO2020/262888
PCT Pub. Date: Dec. 30, 2020

(65) Prior Publication Data
US 2022/0267319 A1    Aug. 25, 2022

(30) Foreign Application Priority Data
Jun. 24, 2019 (KR) .................. 10-2019-0075030

(51) Int. Cl.
C07D 471/04 (2006.01)
C07D 519/00 (2006.01)
H01L 51/00 (2006.01)
H10K 85/60 (2023.01)
(Continued)

(52) U.S. Cl.
CPC ......... *C07D 471/04* (2013.01); *C07D 519/00* (2013.01); *H10K 85/622* (2023.02); *H10K 85/624* (2023.02); *H10K 85/654* (2023.02); *H10K 85/6572* (2023.02);
(Continued)

(58) Field of Classification Search
None
See application file for complete search history.

(56) References Cited

U.S. PATENT DOCUMENTS 11,081,653 B2    8/2021    Kim et al.
2013/0256637 A1  10/2013   Seo et al.
(Continued)

FOREIGN PATENT DOCUMENTS

| KR | 10-2014-0093163 A | 7/2014 |
| KR | 10-2019-0013139 A | 2/2019 |
| KR | 10-2019-0037925 A | 4/2019 |

(Continued)

OTHER PUBLICATIONS

International Search Report (PCT/ISA/210) issued in PCT/KR2020/007980 mailed on Sep. 18, 2020.
(Continued)

*Primary Examiner* — Jay Yang
(74) *Attorney, Agent, or Firm* — Birch, Stewart, Kolasch & Birch, LLP

(57) ABSTRACT

The present specification relates to a heterocyclic compound represented by Chemical Formula 1, and an organic light emitting device comprising the same.

13 Claims, 3 Drawing Sheets

(51) Int. Cl.
  *H10K 50/16* (2023.01)
  *H10K 50/17* (2023.01)
(52) U.S. Cl.
  CPC ..... *H10K 85/6574* (2023.02); *H10K 85/6576* (2023.02); *H10K 50/16* (2023.02); *H10K 50/171* (2023.02)

(56) References Cited

U.S. PATENT DOCUMENTS

2018/0323379 A1* 11/2018 Kim .................... C07D 471/04
2020/0308150 A1   10/2020 Lee et al.

FOREIGN PATENT DOCUMENTS

WO   WO 2015/034140 A1    3/2015
WO   WO 2017/086643 A1    5/2017
WO   WO-2019/066607 A1 *  4/2019

OTHER PUBLICATIONS

Kuwabara et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenylamino)triphenylamine (m-MTDATA), as Hole-Transport Materials", Advanced Materials, 1994, vol. 6, No. 9, pp. 677-679.

* cited by examiner

[FIG. 1]
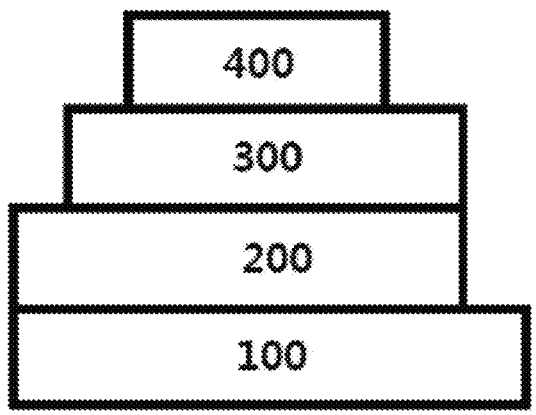
[FIG. 2]
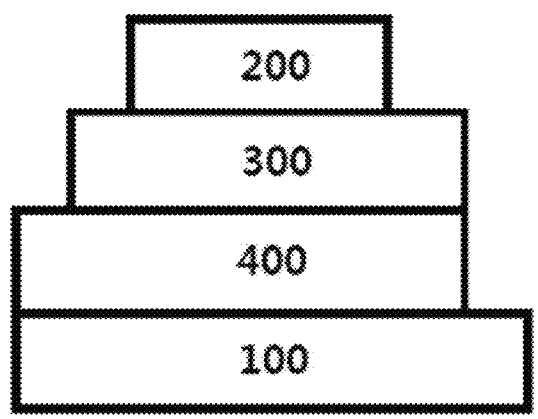

[FIG. 3]
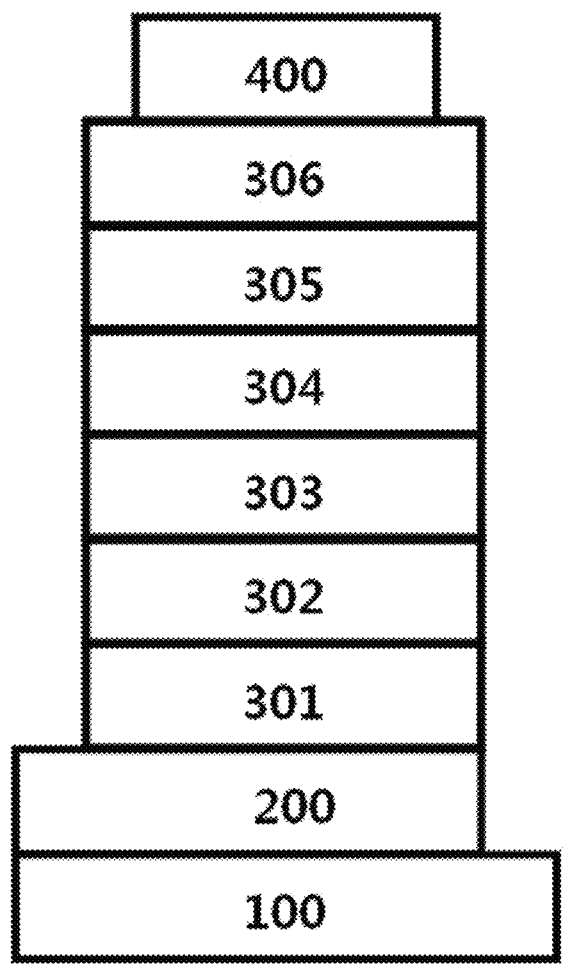

[FIG. 4]
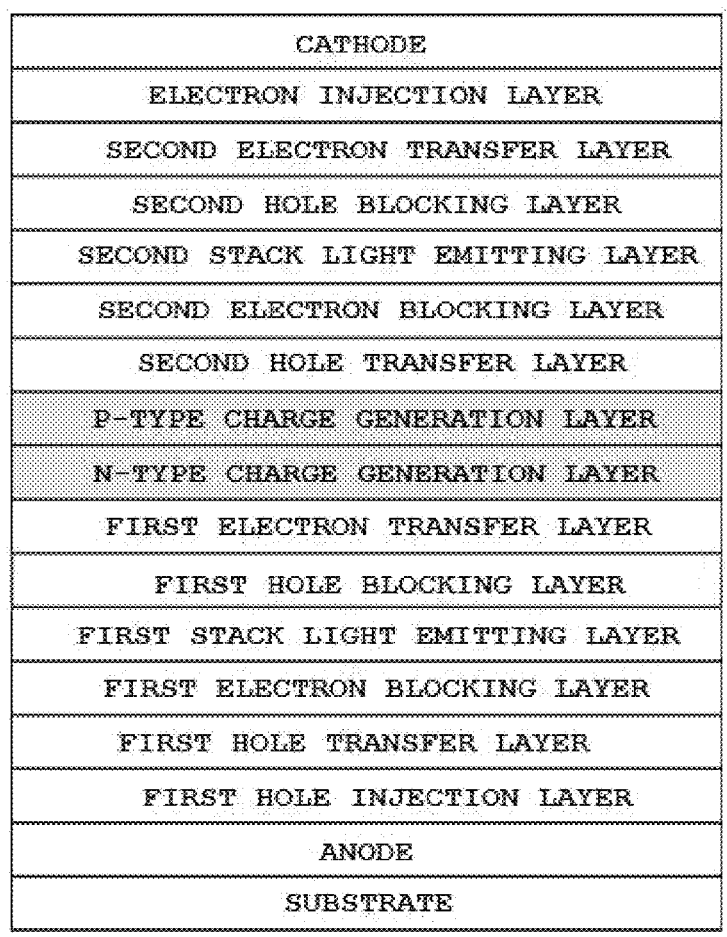

HETEROCYCLIC COMPOUND AND ORGANIC LIGHT EMITTING DIODE COMPRISING SAME

TECHNICAL FIELD

This application claims priority to and the benefits of Korean Patent Application No. 10-2019-0075030, filed with the Korean Intellectual Property Office on Jun. 24, 2019, the entire contents of which are incorporated herein by reference.

The present specification relates to a heterocyclic compound, and an organic light emitting device comprising the same.

BACKGROUND ART

An electroluminescent device is one type of self-emissive display devices, and has an advantage of having a wide viewing angle, and a high response speed as well as having an excellent contrast.

An organic light emitting device has a structure disposing an organic thin film between two electrodes. When a voltage is applied to an organic light emitting device having such a structure, electrons and holes injected from the two electrodes bind and pair in the organic thin film, and light emits as these annihilate. The organic thin film may be formed in a single layer or a multilayer as necessary.

A material of the organic thin film may have a light emitting function as necessary. For example, as a material of the organic thin film, compounds capable of foiling a light emitting layer themselves alone may be used, or compounds capable of performing a role of a host or a dopant of a host-dopant-based light emitting layer may also be used. In addition thereto, compounds capable of performing roles of hole injection, hole transfer, electron blocking, hole blocking, electron transfer, electron injection and the like may also be used as a material of the organic thin film.

Development of an organic thin film material has been continuously required for enhancing performance, lifetime or efficiency of an organic light emitting device.

PRIOR ART DOCUMENTS

Patent Documents

U.S. Pat. No. 4,356,429

DISCLOSURE

Technical Problem

The present disclosure is directed to providing a heterocyclic compound, and an organic light emitting device comprising the same.

Technical Solution

One embodiment of the present application provides a heterocyclic compound represented by the following Chemical Formula 1.

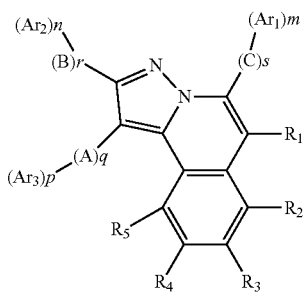

[Chemical Formula 1]

In Chemical Formula 1, $R_1$ to $R_5$ are the same as or different from each other, and each independently selected from the group consisting of hydrogen; deuterium; a substituted or unsubstituted C1 to C60 alkyl group; a substituted or unsubstituted C6 to C60 aryl group; a substituted or unsubstituted C2 to C60 heteroaryl group; —SiRR'R"; —P(=O)RR'; and an amine group unsubstituted or substituted with a substituted or unsubstituted C1 to C60 alkyl group, a substituted or unsubstituted C6 to C60 aryl group or a substituted or unsubstituted C2 to C60 heteroaryl group, or two or more groups adjacent to each other bond to each other to form a substituted or unsubstituted C6 to C60 aromatic hydrocarbon ring or a substituted or unsubstituted C2 to C60 heteroring, A, B and C are a direct bond; a substituted or unsubstituted C6 to C60 arylene group; or a substituted or unsubstituted C2 to C60 heteroarylene group, $Ar_1$ to $Ar_3$ are the same as or different from each other, and each independently selected from the group consisting of hydrogen; deuterium; a substituted or unsubstituted C1 to C60 alkyl group; a substituted or unsubstituted C6 to C60 aryl group; a substituted or unsubstituted C2 to C60 heteroaryl group; —SiRR'R"; —P(=O)RR'; and an amine group unsubstituted or substituted with a substituted or unsubstituted C1 to C60 alkyl group, a substituted or unsubstituted C6 to C60 aryl group or a substituted or unsubstituted C2 to C60 heteroaryl group, or two or more groups adjacent to each other bond to each other to form a substituted or unsubstituted C6 to C60 aromatic hydrocarbon ring or a substituted or unsubstituted C2 to C60 heteroring, q, r and s are an integer of 0 to 4, m, n and p are an integer of 1 to 6, R, R' and R" are the same as or different from each other, and each independently hydrogen; a substituted or unsubstituted C1 to C40 alkyl group; or a substituted or unsubstituted C6 to C40 aryl group, and at least one of $Ar_1$ to $Ar_3$ is represented by the following Chemical Formula 1-1,

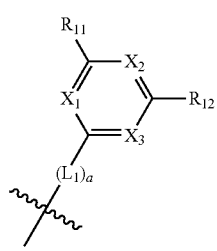

[Chemical Formula 1-1]

in Chemical Formula 1-1, $X_1$ to $X_3$ are N; or $CR_{13}$, and at least one thereof is N, $L_1$ is a direct bond; a substituted or unsubstituted C6 to C60 arylene group; or a substituted or unsubstituted C2 to C60 heteroarylene group, $R_{11}$ and $R_{12}$ are a substituted or unsubstituted C6 to C60 aryl group; or a substituted or unsubstituted C2 to C60 heteroaryl group, at least one of $R_{11}$ and $R_{12}$ is a substituted or unsubstituted C10 to C60 aryl group; or a substituted or unsubstituted C2 to C60 heteroaryl group, $R_{13}$ is hydrogen; a substituted or unsubstituted C1 to C60 alkyl group; a substituted or unsubstituted C6 to C60 aryl group; or a substituted or unsubstituted C2 to C60 heteroaryl group, and a is an integer of 0 to 3.

Another embodiment of the present application provides an organic light emitting device comprising a first electrode; a second electrode provided opposite to the first electrode; and one or more organic material layers provided between the first electrode and the second electrode, wherein one or more layers of the organic material layers comprise the heterocyclic compound represented by Chemical Formula 1.

Advantageous Effects

A compound described in the present specification can be used as a material of an organic material layer of an organic light emitting device. In the organic light emitting device, the compound is capable of performing a role of a hole injection material, a hole transfer material, a light emitting material, an electron transfer material, an electron injection material, a charge generation material or the like. Particularly, the compound can be used as an electron transfer layer material or a hole blocking layer material of the organic light emitting device.

When using the compound represented by Chemical Formula 1 in an organic material layer, a driving voltage of the device can be lowered, light efficiency can be enhanced, and lifetime properties of the device can be enhanced by thermal stability of the compound.

In the compound represented by Chemical Formula 1, at least one of $Ar_1$ to $Ar_3$ is represented by Chemical Formula 1-1, and Chemical Formula 1-1 stabilizes the compound in an excited state by having a substituent with strengthened hole properties and thereby receiving electrons under a specific condition. Particularly, when an excited state is formed in the hetero-skeleton site of the compound, the energy excited to the substituent with strengthened hole properties is shifted to a stable state before the excited hetero-skeleton site goes through other reactions, and excellent efficiency can be obtained as a material of an organic material layer of an organic light emitting device since the relatively stabilized compound is capable of efficiently transferring electrons without being decomposed or destroyed.

DESCRIPTION OF DRAWINGS

FIG. 1 to FIG. 4 each schematically illustrate a lamination structure of an organic light emitting device according to one embodiment of the present application.

REFERENCE NUMERAL

100: Substrate
200: Anode
300: Organic Material Layer
301: Hole Injection Layer
302: Hole Transfer Layer
303: Light Emitting Layer
304: Hole Blocking Layer
305: Electron Transfer Layer
306: Electron Injection Layer
400: Cathode

MODE FOR DISCLOSURE

Hereinafter, the present application will be described in detail.

In the present specification, the term "substitution" means a hydrogen atom bonding to a carbon atom of a compound being changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, "substituted or unsubstituted" means being substituted with one or more substituents selected from the group consisting of C1 to C60 linear or branched alkyl; C2 to C60 linear or branched alkenyl; C2 to C60 linear or branched alkynyl; C3 to C60 monocyclic or polycyclic cycloalkyl; C2 to C60 monocyclic or polycyclic heterocycloalkyl; C6 to C60 monocyclic or polycyclic aryl; C2 to C60 monocyclic or polycyclic heteroaryl; —SiRR'R''; —P(=O)RR'; C1 to C20 alkylamine; C6 to C60 monocyclic or polycyclic arylamine; and C2 to C60 monocyclic or polycyclic heteroarylamine, or being unsubstituted, or being substituted with a substituent linking two or more substituents selected from among the substituents illustrated above, or being unsubstituted.

In the present specification, the halogen may be fluorine, chlorine, bromine or iodine.

In the present specification, the alkyl group comprises linear or branched having 1 to 60 carbon atoms, and may be further substituted with other substituents. The number of carbon atoms of the alkyl group may be from 1 to 60, specifically from 1 to 40 and more specifically from 1 to 20. Specific examples thereof may comprise a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethylbutyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group and the like, but are not limited thereto.

In the present specification, the alkenyl group comprises linear or branched having 2 to 60 carbon atoms, and may be further substituted with other substituents. The number of carbon atoms of the alkenyl group may be from 2 to 60, specifically from 2 to 40 and more specifically from 2 to 20. Specific examples thereof may comprise a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenyl-vinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the alkynyl group comprises linear or branched having 2 to 60 carbon atoms, and may be further substituted with other substituents. The number of carbon atoms of the alkynyl group may be from 2 to 60, specifically from 2 to 40 and more specifically from 2 to 20.

In the present specification, the alkoxy group may be linear, branched or cyclic. The number of carbon atoms of the alkoxy group is not particularly limited, but is preferably from 1 to 20. Specific examples thereof may comprise methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the cycloalkyl group comprises monocyclic or polycyclic having 3 to 60 carbon atoms, and may be further substituted with other substituents. Herein, the polycyclic means a group in which the cycloalkyl group is directly linked to or fused with other cyclic groups. Herein, the other cyclic groups may be a cycloalkyl group, but may also be different types of cyclic groups such as a heterocycloalkyl group, an aryl group and a heteroaryl group. The number of carbon groups of the cycloalkyl group may be from 3 to 60, specifically from 3 to 40 and more specifically from 5 to 20. Specific examples thereof may comprise a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4 methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the heterocycloalkyl group comprises O, S, Se, N or Si as a heteroatom, comprises monocyclic or polycyclic having 2 to 60 carbon atoms, and may be further substituted with other substituents. Herein, the polycyclic means a group in which the heterocycloalkyl group is directly linked to or fused with other cyclic groups. Herein, the other cyclic groups may be a heterocycloalkyl group, but may also be different types of cyclic groups such as a cycloalkyl group, an aryl group and a heteroaryl group. The number of carbon atoms of the heterocycloalkyl group may be from 2 to 60, specifically from 2 to 40 and more specifically from 3 to 20.

In the present specification, the aryl group comprises monocyclic or polycyclic having 6 to 60 carbon atoms, and may be further substituted with other substituents. Herein, the polycyclic means a group in which the aryl group is directly linked to or fused with other cyclic groups. Herein, the other cyclic groups may be an aryl group, but may also be different types of cyclic groups such as a cycloalkyl group, a heterocycloalkyl group and a heteroaryl group. The aryl group comprises a spiro group. The number of carbon atoms of the aryl group may be from 6 to 60, specifically from 6 to 40 and more specifically from 6 to 25. Specific examples of the aryl group may comprise a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused ring thereof, and the like, but are not limited thereto.

In the present specification, the phosphine oxide group is represented by —P(=O)R101R102, and R101 and R102 are the same as or different from each other and may be each independently a substituent formed with at least one of hydrogen; deuterium; a halogen group; an alkyl group; an alkenyl group; an alkoxy group; a cycloalkyl group; an aryl group; and a hetero-cyclic group. Specific examples of the phosphine oxide may comprise a diphenylphosphine oxide group, a dinaphthylphosphine oxide group and the like, but are not limited thereto.

In the present specification, the silyl group is a substituent comprising Si, having the Si atom directly linked as a radical, and is represented by —SiR$_{104}$R$_{105}$R$_{106}$. R$_{104}$ to R$_{106}$ are the same as or different from each other, and may be each independently a substituent formed with at least one of hydrogen; deuterium; a halogen group; an alkyl group; an alkenyl group; an alkoxy group; a cycloalkyl group; an aryl group; and a hetero-cyclic group. Specific examples of the silyl group may comprise a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the fluorenyl group may be substituted, and adjacent substituents may bond to each other to form a ring.

When the fluorenyl group is substituted,

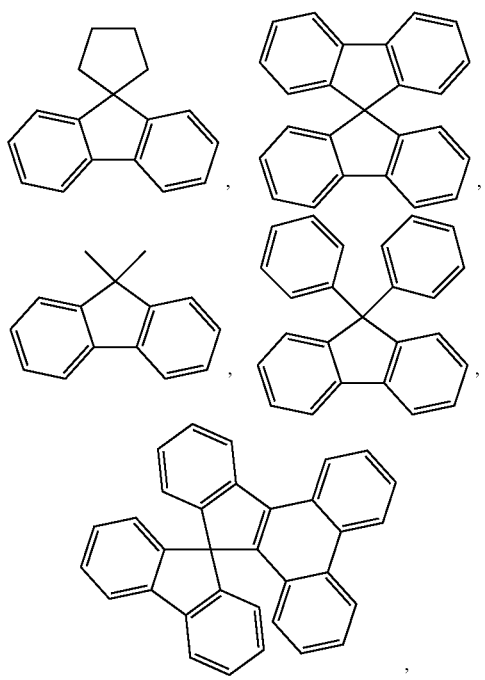

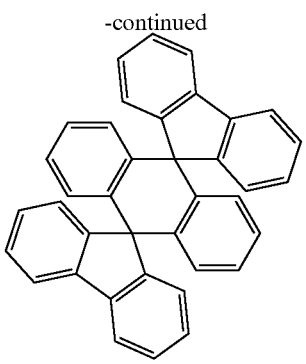

and the like may be included, however, the structure is not limited thereto.

In the present specification, the heteroaryl group comprises O, S, Se, N or Si as a heteroatom, comprises monocyclic or polycyclic having 2 to 60 carbon atoms, and may be further substituted with other substituents. Herein, the polycyclic means a group in which the heteroaryl group is directly linked to or fused with other cyclic groups. Herein, the other cyclic groups may be a heteroaryl group, but may also be different types of cyclic groups such as a cycloalkyl group, a heterocycloalkyl group and an aryl group. The number of carbon atoms of the heteroaryl group may be from 2 to 60, specifically from 2 to 40 and more specifically from 3 to 25. Specific examples of the heteroaryl group may comprise a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a thiazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a thiazinyl group, a dioxynyl group, a triazinyl group, a tetrazinyl group, a quinolyl group, an isoquinolyl group, a quinazolinyl group, an isoquinazolinyl group, a qninozolinyl group, a naphthyridyl group, an acridinyl group, a phenanthridinyl group, an imidazopyridinyl group, a diazanaphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi(dibenzosilole), a dihydrophenazinyl group, a phenoxazinyl group, a phenanthridyl group, an imidazopyridinyl group, a thienyl group, an indolo[2,3-a]carbazolyl group, an indolo[2,3-b]carbazolyl group, an indolinyl group, a 10,11-dihydrodibenzo[b,f]azepine group, a 9,10-dihydroacridinyl group, a phenanthrazinyl group, a phenothiathiazinyl group, a phthalazinyl group, a naphthylidinyl group, a phenanthrolinyl group, a benzo[c][1,2,5]thiadiazolyl group, a 5,10-dihydrobenzo[b,e][1,4]azasilinyl group, a pyrazolo[1,5-c]quinazolinyl group, a pyrido[1,2-b]indazolyl group, a pyrido[1,2-a]imidazo[1,2-e]indolinyl group, a 5,11-dihydroindeno[1,2-b]carbazolyl group and the like, but are not limited thereto.

In the present specification, the amine group may be selected from the group consisting of a monoalkylamine group; a monoarylamine group; a monoheteroarylamine group; —NH₂; a dialkylamine group; a diarylamine group; a diheteroarylamine group; an alkylarylamine group; an alkylheteroarylamine group; and an arylheteroarylamine group, and although not particularly limited thereto, the number of carbon atoms is preferably from 1 to 30. Specific examples of the amine group may comprise a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group and the like, but are not limited thereto.

In the present specification, the arylene group means the aryl group having two bonding sites, that is, a divalent group. The descriptions on the aryl group provided above may be applied thereto except for those that are each a divalent group. In addition, the heteroarylene group means the heteroaryl group having two bonding sites, that is, a divalent group. The descriptions on the heteroaryl group provided above may be applied thereto except for those that are each a divalent group.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

One embodiment of the present application provides a compound represented by Chemical Formula 1.

In Chemical Formula 1,

means a position linked to A, B and C of Chemical Formula 1.

In one embodiment of the present application, Chemical Formula 1 may be represented by the following Chemical Formula 2.

[Chemical Formula 2]

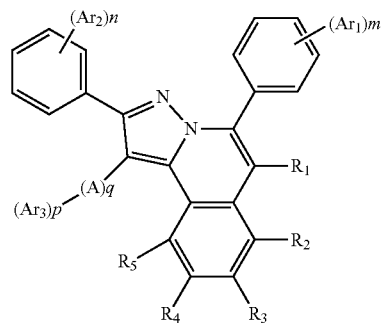

In Chemical Formula 2,

R$_1$ to R$_5$, Ar$_1$ to Ar$_3$, A, m, n, p and q have the same definitions as in Chemical Formula 1.

In one embodiment of the present application, Chemical Formula 1 may be represented by any one of the following Chemical Formula 3 to Chemical Formula 5.

[Chemical Formula 3]

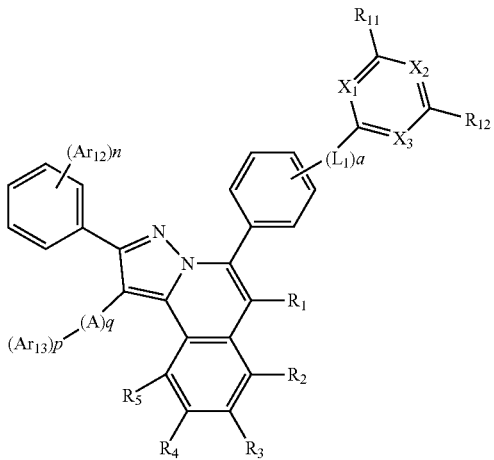

[Chemical Formula 4]

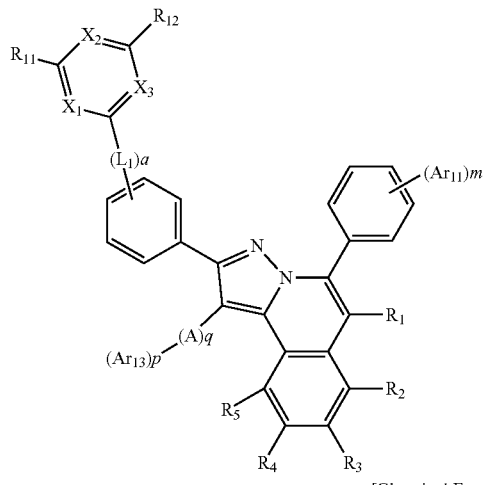

[Chemical Formula 5]

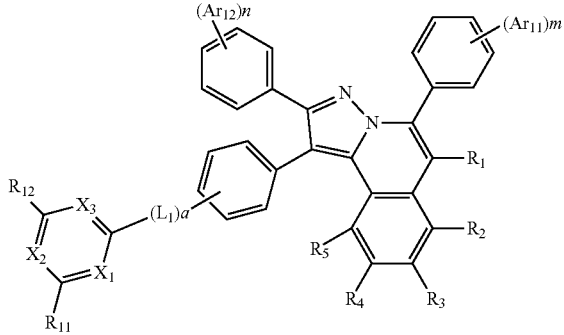

In Chemical Formulae 3 to 5,

R$_1$ to R$_5$, X$_1$ to X$_3$, R$_{11}$, R$_{12}$, L$_1$, A, a, m, n, p and q have the same definitions as in Chemical Formula 1, Ar$_{11}$ to Ar$_{13}$ are the same as or different from each other, and each independently hydrogen; a substituted or unsubstituted C1 to C60 alkyl group; or a substituted or unsubstituted C6 to C60 aryl group.

In one embodiment of the present application, R$_1$ to R$_5$ are the same as or different from each other, and each independently selected from the group consisting of hydrogen; deuterium; a substituted or unsubstituted C1 to C60 alkyl group; a substituted or unsubstituted C6 to C60 aryl group; a substituted or unsubstituted C2 to C60 heteroaryl group; —SiRR'R"; —P(=O)RR'; and an amine group unsubstituted or substituted with a substituted or unsubstituted C1 to C60 alkyl group, a substituted or unsubstituted C6 to C60 aryl group or a substituted or unsubstituted C2 to C60 heteroaryl group, or two or more groups adjacent to each other bond to each other to form a substituted or unsubstituted C6 to C60 aromatic hydrocarbon ring or a substituted or unsubstituted C2 to C60 heteroring.

In another embodiment, R$_1$ to R$_5$ are the same as or different from each other, and each independently selected from the group consisting of hydrogen; a substituted or unsubstituted C1 to C60 alkyl group; a substituted or unsubstituted C6 to C60 aryl group; and a substituted or unsubstituted C2 to C60 heteroaryl group, or two or more groups adjacent to each other bond to each other to form a substituted or unsubstituted C6 to C60 aromatic hydrocarbon ring or a substituted or unsubstituted C2 to C60 heteroring.

In another embodiment, R$_1$ to R$_5$ are the same as or different from each other, and each independently selected from the group consisting of hydrogen; a substituted or unsubstituted C1 to C40 alkyl group; a substituted or unsubstituted C6 to C40 aryl group; and a substituted or unsubstituted C2 to C40 heteroaryl group, or two or more groups adjacent to each other bond to each other to form a substituted or unsubstituted C6 to C40 aromatic hydrocarbon ring or a substituted or unsubstituted C2 to C40 heteroring.

In another embodiment, R$_1$ to R$_5$ are the same as or different from each other, and may be each independently selected from the group consisting of hydrogen; a substituted or unsubstituted C1 to C40 alkyl group; a substituted or unsubstituted C6 to C40 aryl group; and a substituted or unsubstituted C2 to C40 heteroaryl group.

In another embodiment, R$_1$ to R$_5$ may be hydrogen.

In one embodiment of the present application, A, B and C may be a direct bond; a substituted or unsubstituted C6 to C60 arylene group; or a substituted or unsubstituted C2 to C60 heteroarylene group.

In another embodiment, A, B and C may be a direct bond; a substituted or unsubstituted C6 to C40 arylene group; or a substituted or unsubstituted C2 to C40 heteroarylene group.

In another embodiment, A, B and C may be a direct bond; a C6 to C40 arylene group; or a C2 to C40 heteroarylene group.

In another embodiment, A, B and C may be a direct bond; or a phenylene group.

In one embodiment of the present application, Ar$_1$ to Ar$_3$ are the same as or different from each other, and each independently selected from the group consisting of hydrogen; deuterium; a substituted or unsubstituted C1 to C60 alkyl group; a substituted or unsubstituted C6 to C60 aryl group; a substituted or unsubstituted C2 to C60 heteroaryl group; —SiRR'R"; —P(=O)RR'; and an amine group unsubstituted or substituted with a substituted or unsubstituted C1 to C60 alkyl group, a substituted or unsubstituted C6 to C60 aryl group or a substituted or unsubstituted C2 to C60 heteroaryl group, or two or more groups adjacent to each other may bond to each other to form a substituted or unsubstituted C6 to C60 aromatic hydrocarbon ring or a substituted or unsubstituted C2 to C60 heteroring.

In one embodiment of the present application, at least one of $Ar_1$ to $Ar_3$ may be represented by Chemical Formula 1-1.

In one embodiment of the present application, one of $Ar_1$ to $Ar_3$ may be represented by Chemical Formula 1-1, and the rest may be hydrogen; or a substituted or unsubstituted C1 to C60 alkyl group.

In another embodiment, one of $Ar_1$ to $Ar_3$ may be represented by Chemical Formula 1-1, and the rest may be hydrogen; or a substituted or unsubstituted C1 to C40 alkyl group.

In another embodiment, one of $Ar_1$ to $Ar_3$ may be represented by Chemical Formula 1-1, and the rest may be hydrogen; or a C1 to C40 alkyl group.

In another embodiment, one of $Ar_1$ to $Ar_3$ may be represented by Chemical Formula 1-1, and the rest may be hydrogen; a methyl group; or an ethyl group.

In one embodiment of the present application, two of $Ar_1$ to $Ar_3$ may be represented by Chemical Formula 1-1, and the remaining one may be hydrogen; or a substituted or unsubstituted C1 to C60 alkyl group.

In another embodiment, two of $Ar_1$ to $Ar_3$ may be represented by Chemical Formula 1-1, and the remaining one may be hydrogen; or a substituted or unsubstituted C1 to C40 alkyl group.

In another embodiment, two of $Ar_1$ to $Ar_3$ may be represented by Chemical Formula 1-1, and the remaining one may be hydrogen; or a C1 to C40 alkyl group.

In another embodiment, two of $Ar_1$ to $Ar_3$ may be represented by Chemical Formula 1-1, and the remaining one may be hydrogen; a methyl group; or an ethyl group.

In one embodiment of the present application, Chemical Formula 1-1 is as follows.

[Chemical Formula 1-1]

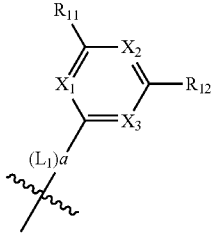

In Chemical Formula 1-1,
$X_1$ to $X_3$ are N; or $CR_{13}$, and at least one thereof is N,
$L_1$ is a direct bond; a substituted or unsubstituted C6 to C60 arylene group; or a substituted or unsubstituted C2 to C60 heteroarylene group,
$R_{11}$ and $R_{12}$ are a substituted or unsubstituted C6 to C60 aryl group; or a substituted or unsubstituted C2 to C60 heteroaryl group,
at least one of $R_{11}$ and $R_{12}$ is a substituted or unsubstituted C10 to C60 aryl group; or a substituted or unsubstituted C2 to C60 heteroaryl group,
$R_{13}$ is hydrogen; a substituted or unsubstituted C1 to C60 alkyl group; a substituted or unsubstituted C6 to C60 aryl group; or a substituted or unsubstituted C2 to C60 heteroaryl group, and
a is an integer of 0 to 3.

In one embodiment of the present application, $X_1$ to $X_3$ of Chemical Formula 1-1 may be N.

In one embodiment of the present application, two of $X_1$ to $X_3$ of Chemical Formula 1-1 are N, and the remaining one may be $CR_{13}$.

In one embodiment of the present application, one of $X_1$ to $X_3$ of Chemical Formula 1-1 is N, and the rest may be $CR_{13}$.

In one embodiment of the present application, Rn may be hydrogen; a substituted or unsubstituted C1 to C60 alkyl group; a substituted or unsubstituted C6 to C60 aryl group; or a substituted or unsubstituted C2 to C60 heteroaryl group.

In another embodiment, Rn may be hydrogen; a substituted or unsubstituted C1 to C40 alkyl group; a substituted or unsubstituted C6 to C40 aryl group; or a substituted or unsubstituted C2 to C40 heteroaryl group.

In another embodiment, Rn may be hydrogen; a C1 to C40 alkyl group; a C6 to C40 aryl group; or a C2 to C40 heteroaryl group.

In another embodiment, Rn may be hydrogen.

In one embodiment of the present application, $L_1$ may be a direct bond; a substituted or unsubstituted C6 to C60 arylene group; or a substituted or unsubstituted C2 to C60 heteroarylene group.

In another embodiment, $L_1$ may be a direct bond; a substituted or unsubstituted C6 to C40 arylene group; or a substituted or unsubstituted C2 to C40 heteroarylene group.

In another embodiment, $L_1$ may be a direct bond; a C6 to C40 arylene group; or a C2 to C40 heteroarylene group.

In another embodiment, $L_1$ may be a direct bond; a phenylene group; or a biphenylene group.

In one embodiment of the present application, $R_{11}$ and $R_{12}$ are a substituted or unsubstituted C6 to C60 aryl group; or a substituted or unsubstituted C2 to C60 heteroaryl group, and
at least one of $R_{11}$ and $R_{12}$ may be a substituted or unsubstituted C10 to C60 aryl group; or a substituted or unsubstituted C2 to C60 heteroaryl group.

In another embodiment, $R_{11}$ and $R_{12}$ are a substituted or unsubstituted C6 to C40 aryl group; or a substituted or unsubstituted C2 to C40 heteroaryl group, and
at least one of $R_{11}$ and $R_{12}$ may be a substituted or unsubstituted C10 to C40 aryl group; or a substituted or unsubstituted C2 to C40 heteroaryl group.

In another embodiment, $R_{11}$ and $R_{12}$ is a substituted or unsubstituted C6 to C40 aryl group; or a substituted or unsubstituted C2 to C40 heteroaryl group, and
at least one of $R_{11}$ and $R_{12}$ is a C6 to C40 aryl group, and the remaining one may be a substituted or unsubstituted C10 to C40 aryl group; or a substituted or unsubstituted C2 to C40 heteroaryl group.

In one embodiment of the present application, Chemical Formula 1-1 may be represented by the following Chemical Formula 1-2.

[Chemical Formula 1-2]

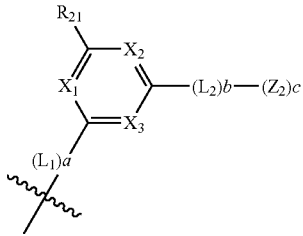

In Chemical Formula 1-2,
$L_1$, a, and $X_1$ to $X_3$ have the same definitions as in Chemical Formula 1-1, $R_{21}$ is a substituted or unsubstituted C6 to C60 aryl group, $L_2$ is a direct bond; a substituted or unsubstituted C6 to C60 arylene group; or a substituted or unsubstituted C2 to C60 heteroarylene group, $Z_2$ is a substituted or unsubstituted C10 to C60 aryl group; or a substituted or unsubstituted C2 to C60 heteroaryl group, b is an integer of 0 to 3, and c is an integer of 1 to 6.

In one embodiment of the present application, $R_{21}$ may be a substituted or unsubstituted C6 to C60 aryl group.

In another embodiment, $R_{21}$ may be a substituted or unsubstituted C6 to C40 aryl group.

In another embodiment, $R_{21}$ may be a C6 to C40 aryl group.

In another embodiment, $R_{21}$ may be a phenyl group.

In one embodiment of the present application, $L_2$ may be a direct bond; a substituted or unsubstituted C6 to C60 arylene group; or a substituted or unsubstituted C2 to C60 heteroarylene group.

In another embodiment, $L_2$ may be a direct bond; a substituted or unsubstituted C6 to C40 arylene group; or a substituted or unsubstituted C2 to C40 heteroarylene group.

In another embodiment, $L_2$ may be a direct bond; a C6 to C40 arylene group; or a C2 to C40 heteroarylene group.

In another embodiment, $L_2$ may be a direct bond; a phenylene group; or a biphenylene group.

In one embodiment of the present application, $Z_2$ may be a substituted or unsubstituted C10 to C60 aryl group; or a substituted or unsubstituted C2 to C60 heteroaryl group.

In another embodiment, $Z_2$ may be a substituted or unsubstituted C10 to C40 aryl group; or a substituted or unsubstituted C2 to C40 heteroaryl group.

In another embodiment, $Z_2$ may be a C10 to C40 aryl group unsubstituted or substituted with one or more substituents selected from the group consisting of a C1 to C40 alkyl group and a C6 to C60 aryl group; or a C2 to C40 heteroaryl group unsubstituted or substituted with a C6 to C40 aryl group.

In another embodiment, $Z_2$ may be a C10 to C40 aryl group unsubstituted or substituted with one or more substituents selected from the group consisting of a C1 to C40 alkyl group and a C6 to C60 aryl group; or represented by the following Chemical Formula 2-1; or the following Chemical Formula 2-2.

[Chemical Formula 2-1]

[Chemical Formula 2-2]

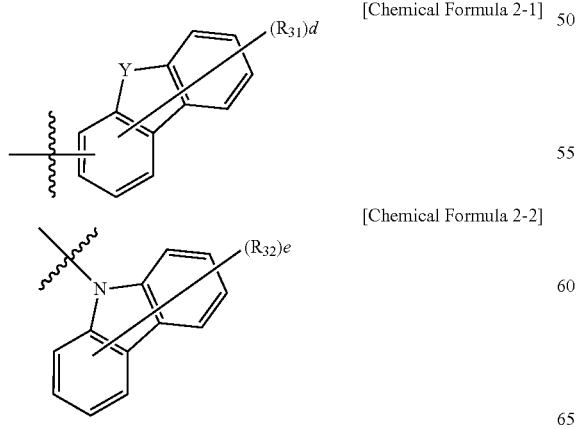

In Chemical Formulae 2-1 and 2-2,

Y is O; or S, $R_{31}$ and $R_{32}$ are the same as or different from each other, and each independently hydrogen; a substituted or unsubstituted C6 to C60 aryl group; or a substituted or unsubstituted C2 to C60 heteroaryl group, d is an integer of 0 to 7, and e is an integer of 0 to 8.

In Chemical Formulae 2-1 and 2-2,

means a position linked to $L_2$.

In another embodiment, $Z_2$ may be a triphenylenyl group; a dimethylfluorenyl group; a spirobifluorenyl group; a diphenylfluorenyl group; a dibenzofuran group; a dibenzothiophene group; a carbazole group unsubstituted or substituted with a phenyl group; or an indolo[3,2,1-jk]carbazole group.

In the compound represented by Chemical Formula 1, at least one of $Ar_1$ to $Ar_3$ is represented by Chemical Formula 1-2, and Chemical Formula 1-2 may stabilize the compound in an excited state by having a substituent with strengthened hole properties such as $Z_2$ and thereby receiving electrons under a specific condition. Particularly, when an excited state is formed in the hetero-skeleton site of the compound, the energy excited to the substituent with strengthened hole properties is shifted to a stable state before the excited hetero-skeleton site goes through other reactions, and excellent efficiency can be obtained as a material of an organic material layer of an organic light emitting device since the relatively stabilized compound is capable of efficiently transferring electrons without being decomposed or destroyed.

In the heterocyclic compound provided in one embodiment of the present application, Chemical Formula 1 is represented by any one of the following compounds.

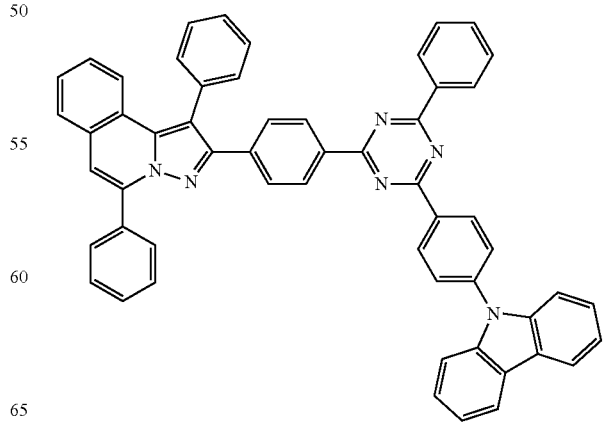

1

2
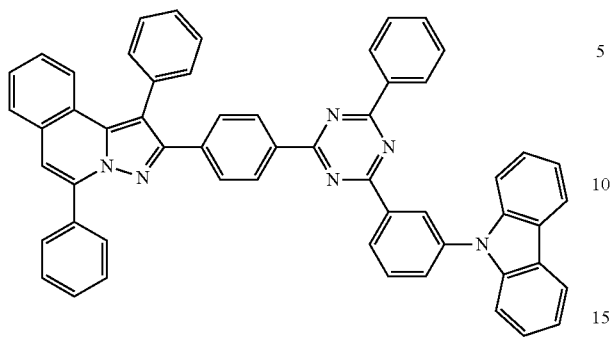
3
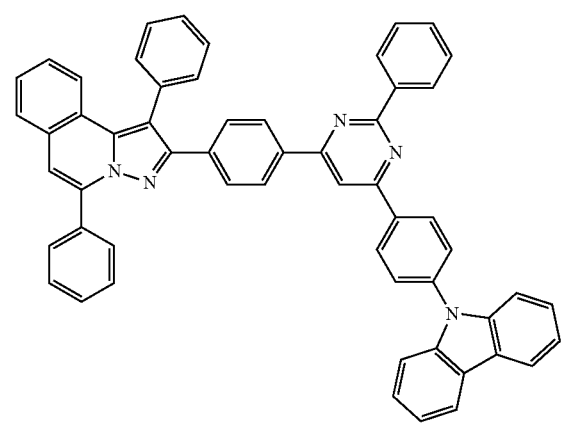
4
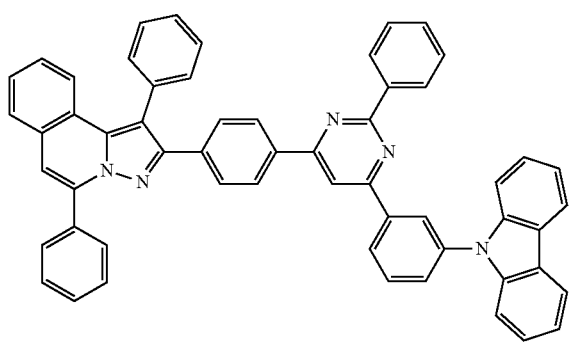
5
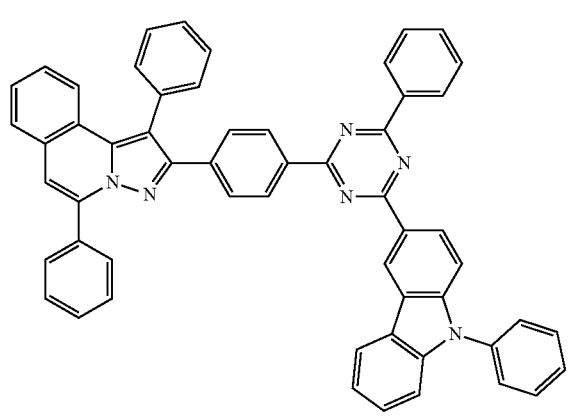
6
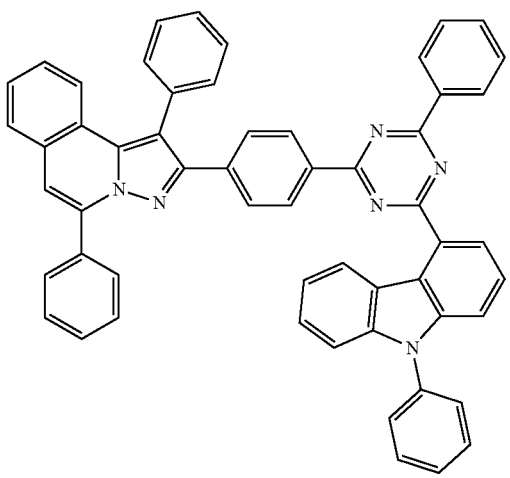
7
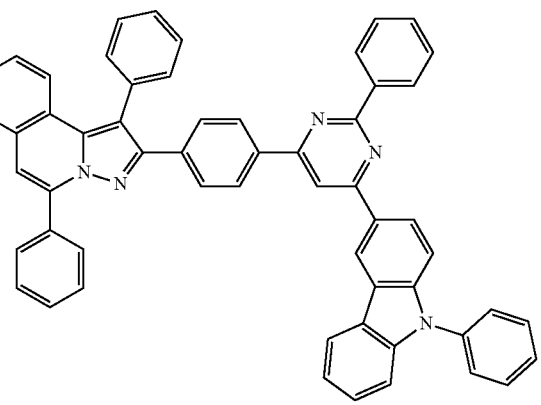
8
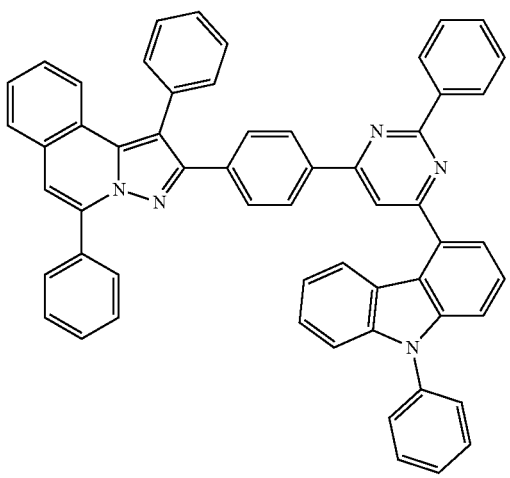

9
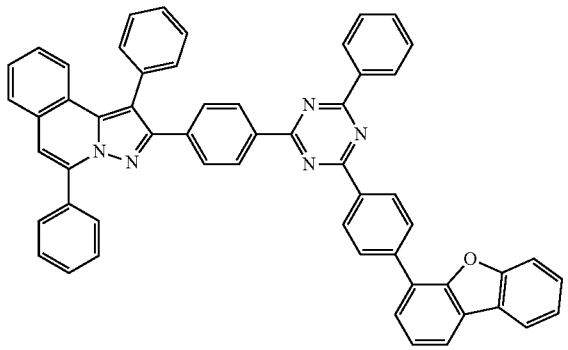
10
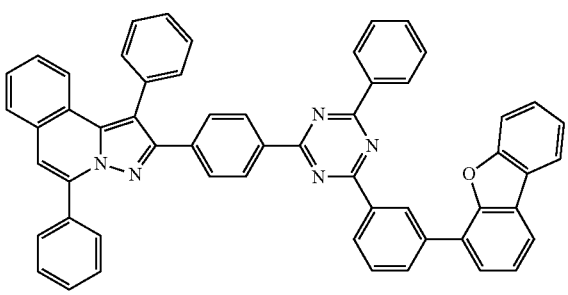
11
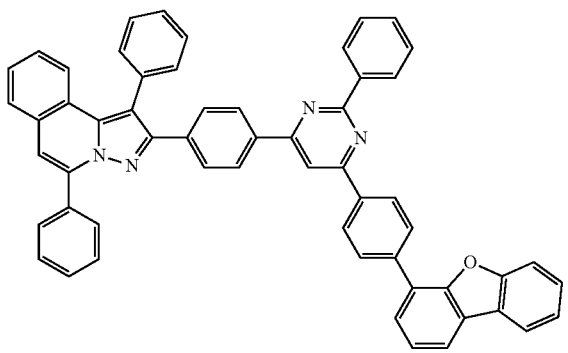
12
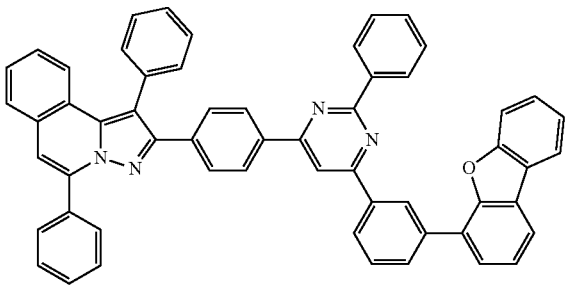
13
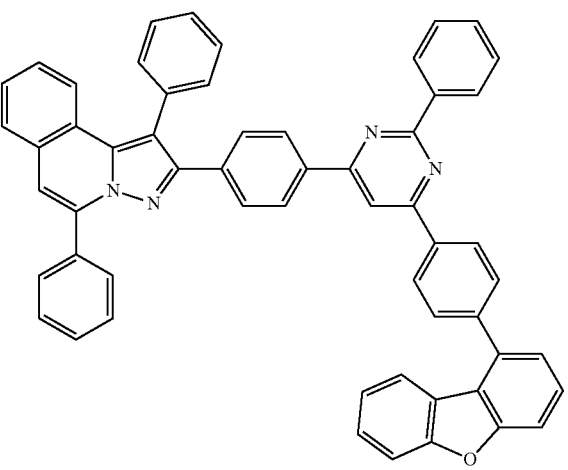
14
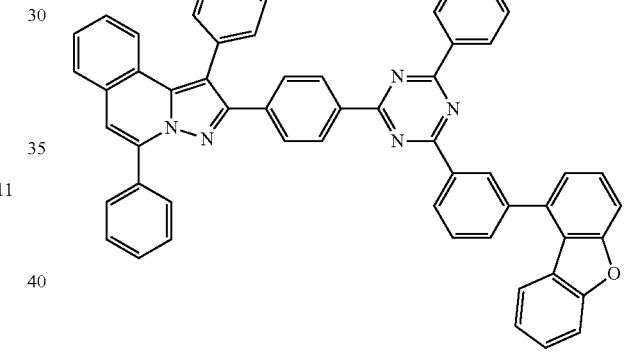
15
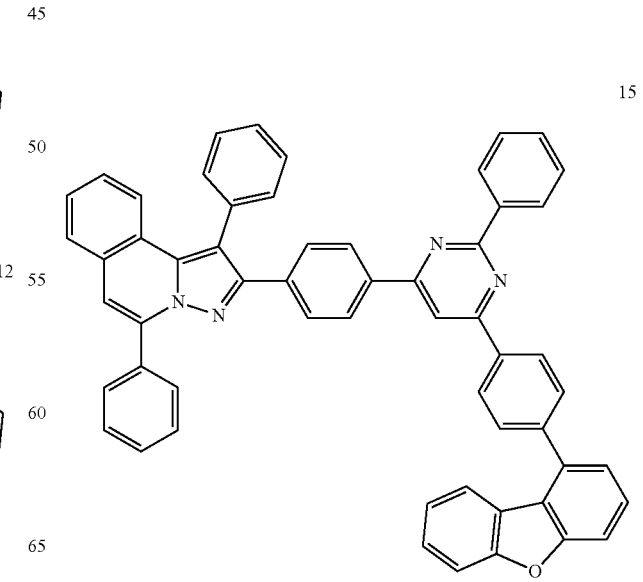

16
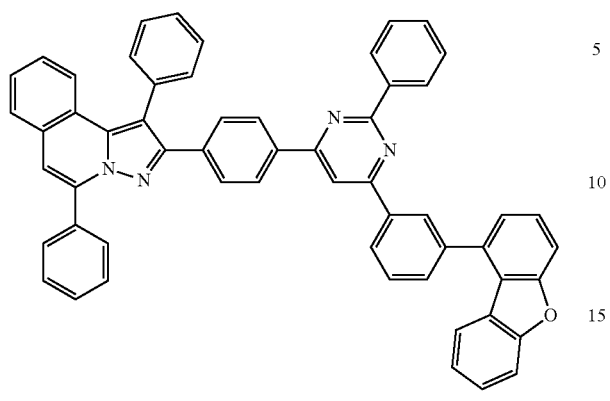
17
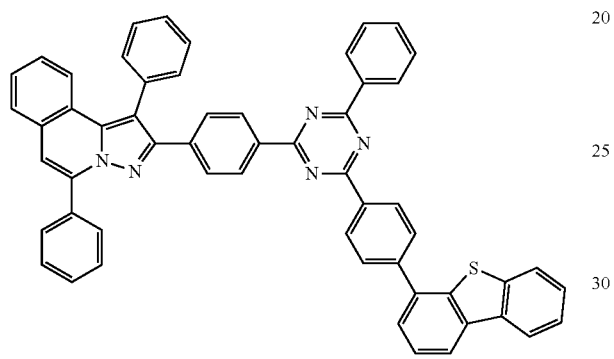
18
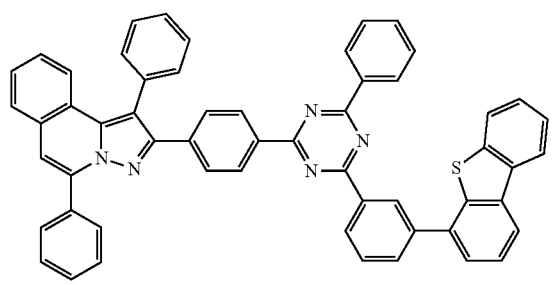
19
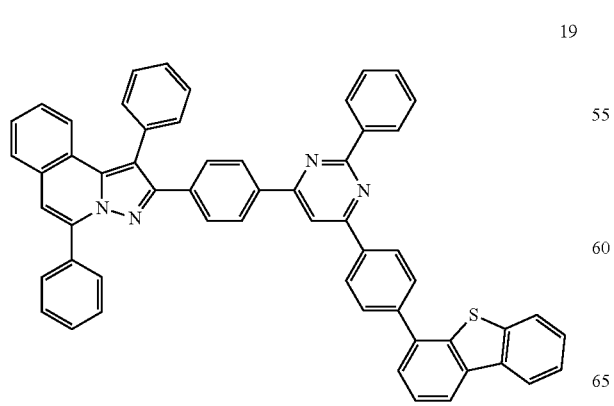
20
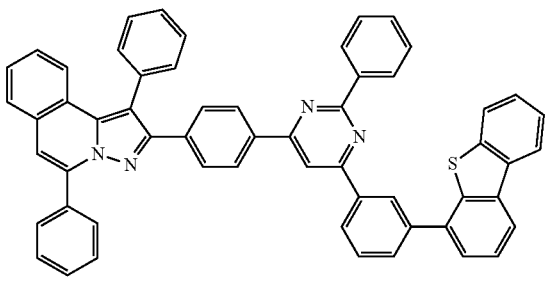
21
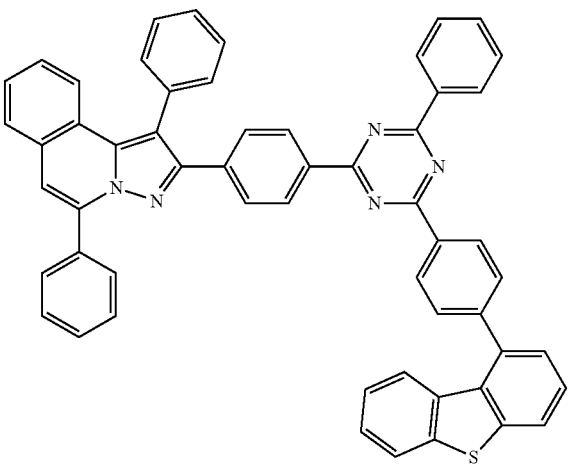
22
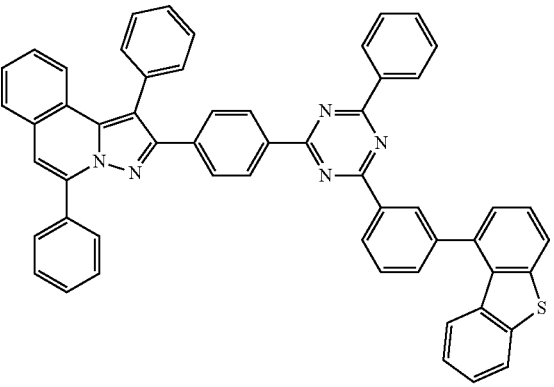

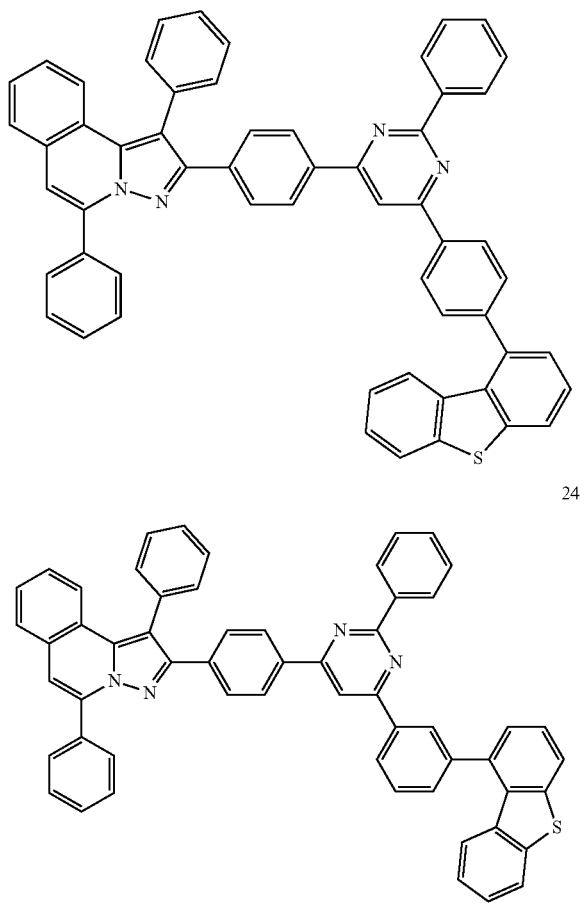
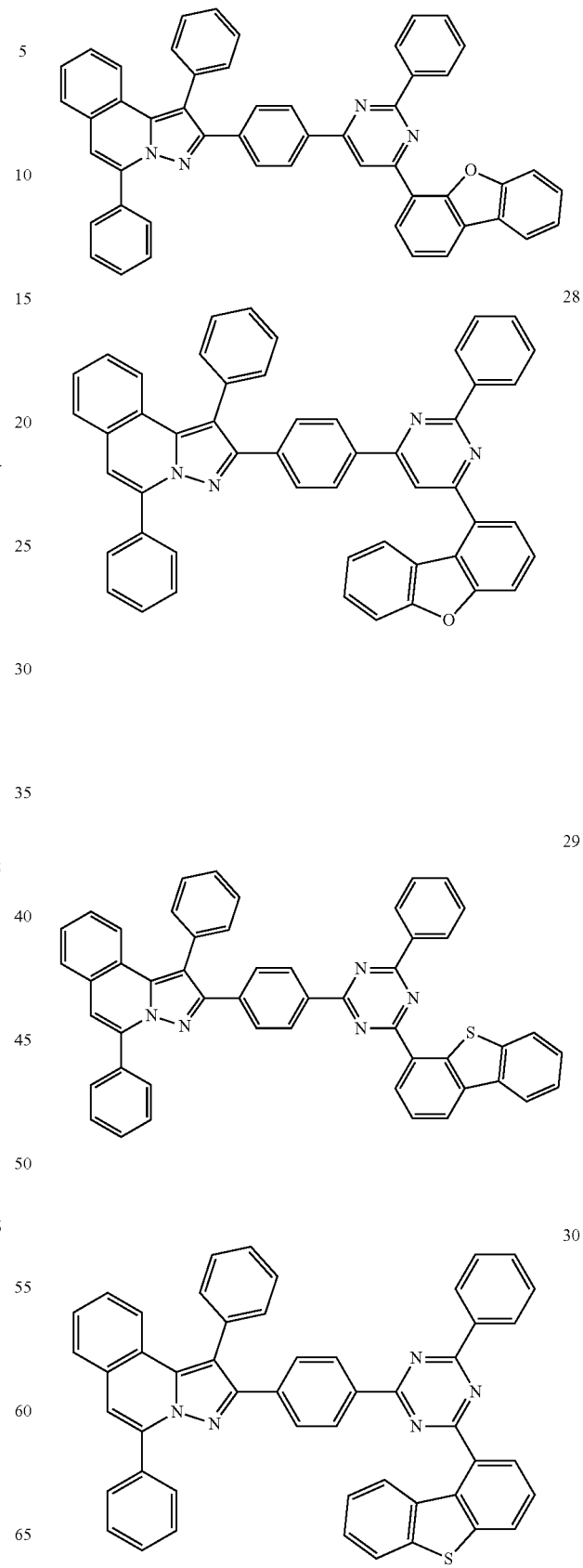

31
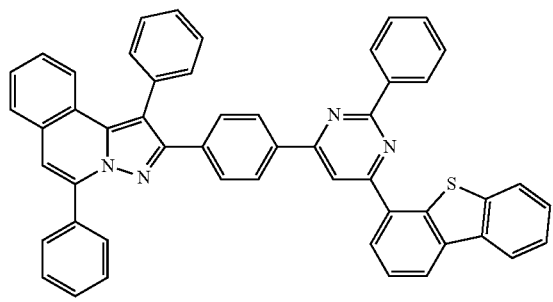
32
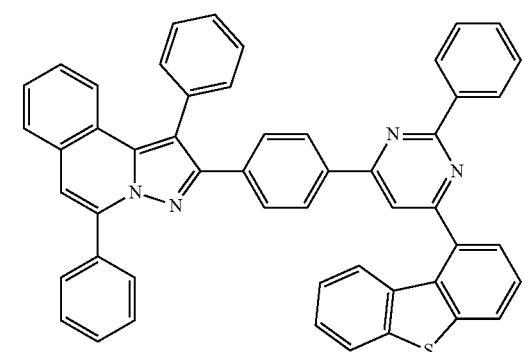
33
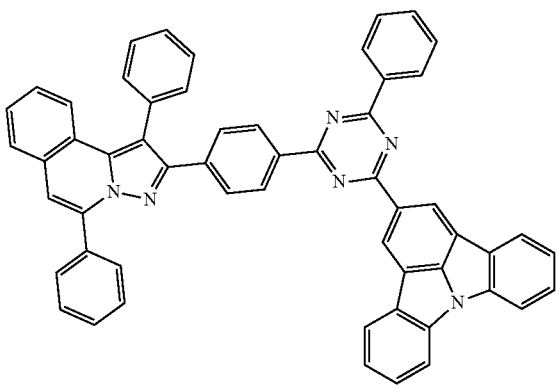
34
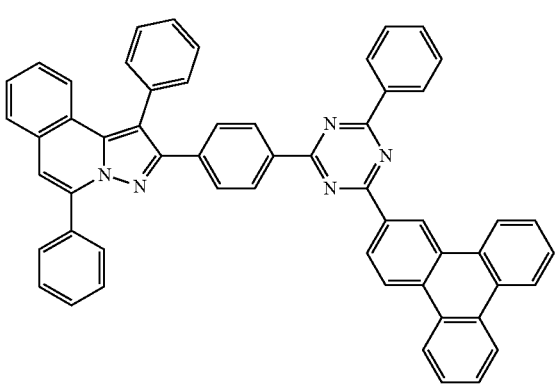
35
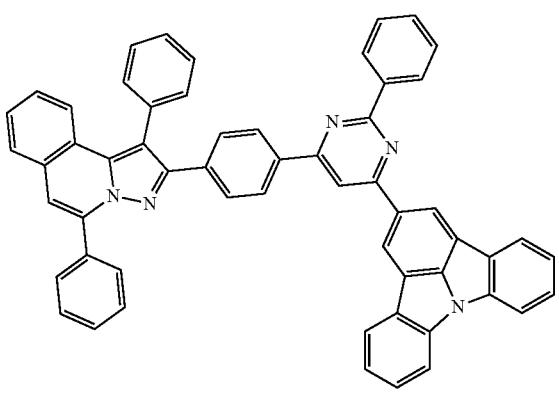
36
37
38
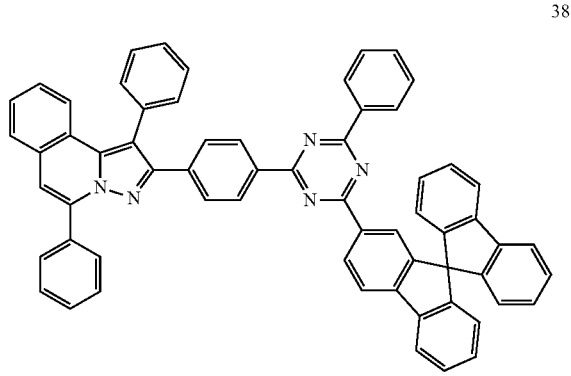

-continued
39
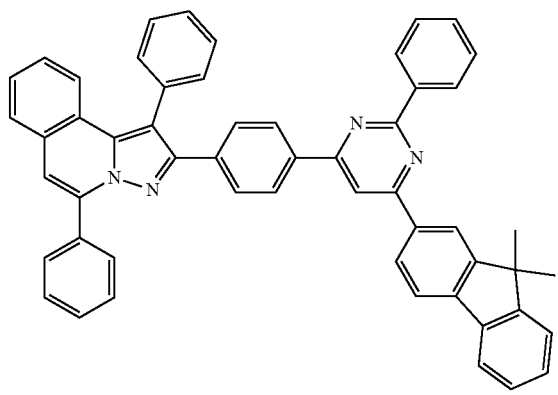
40
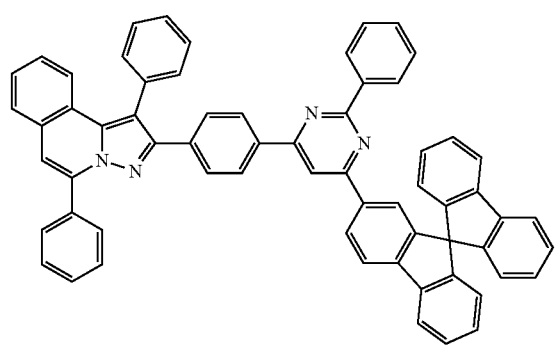
41
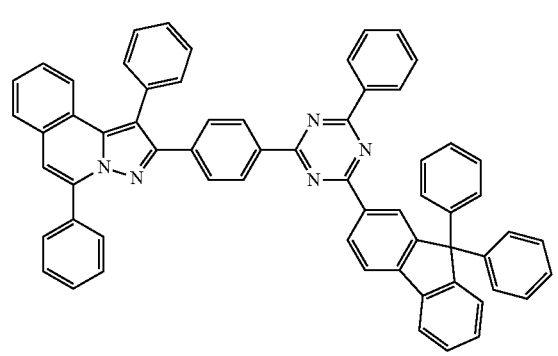
42
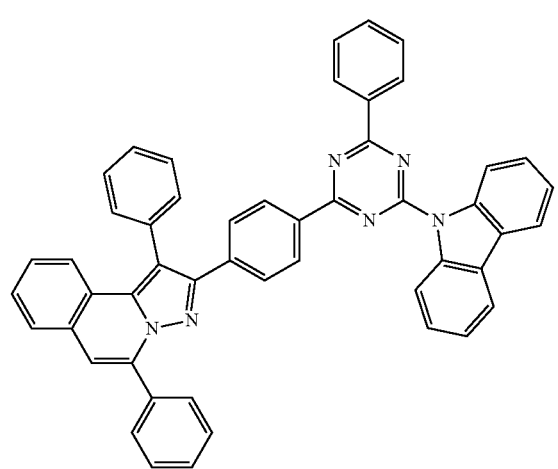
-continued
43
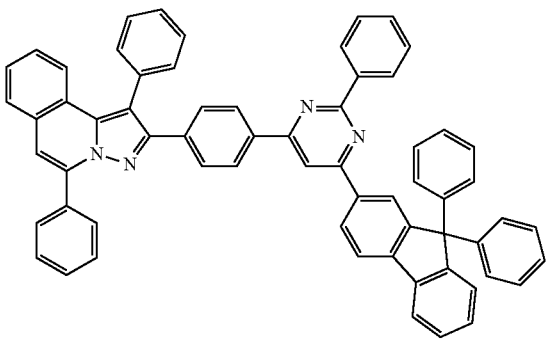
44
45

46
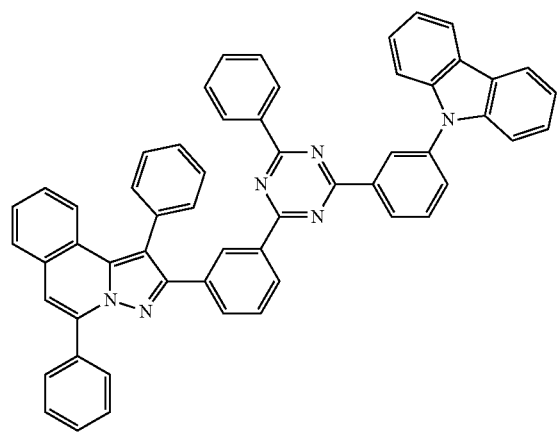
47
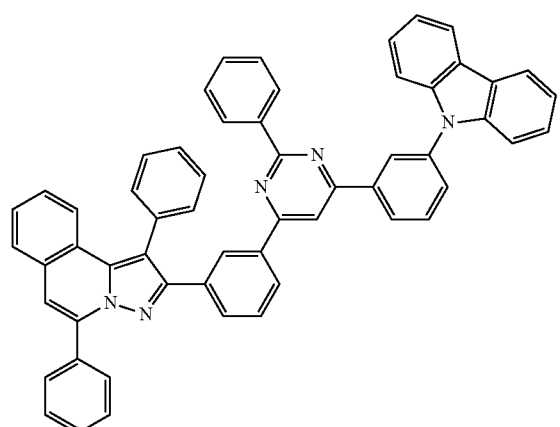
48
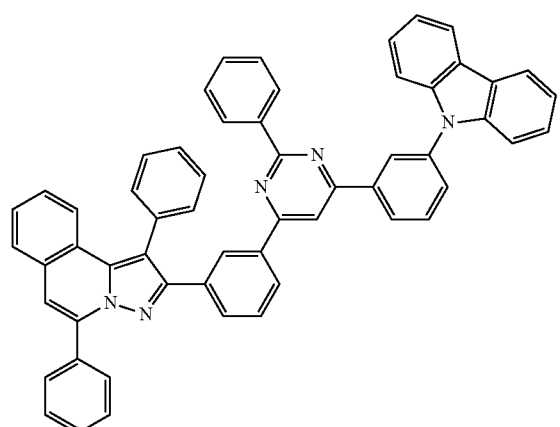
49
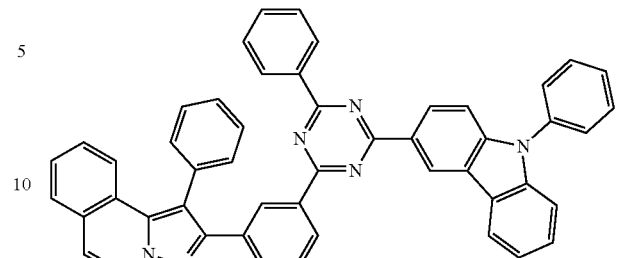
50
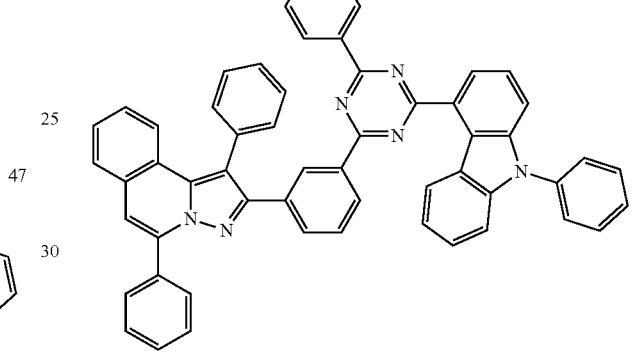
51
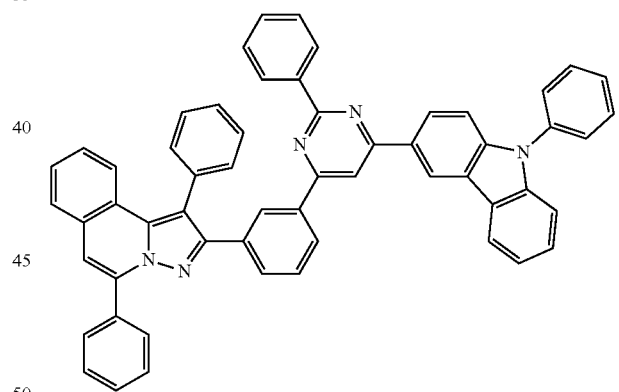
52
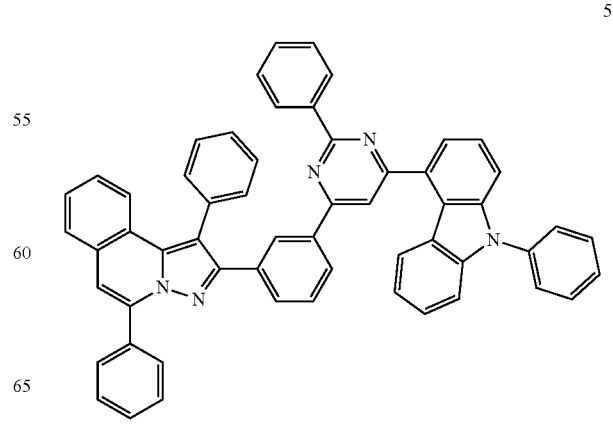

53
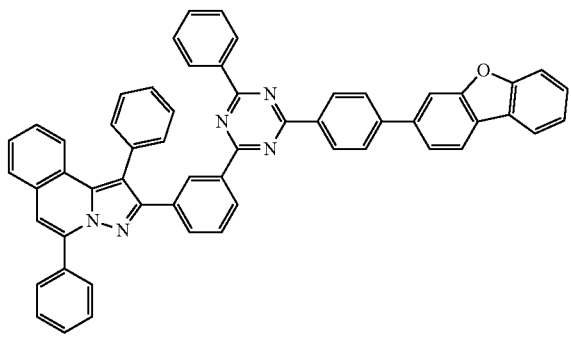
54
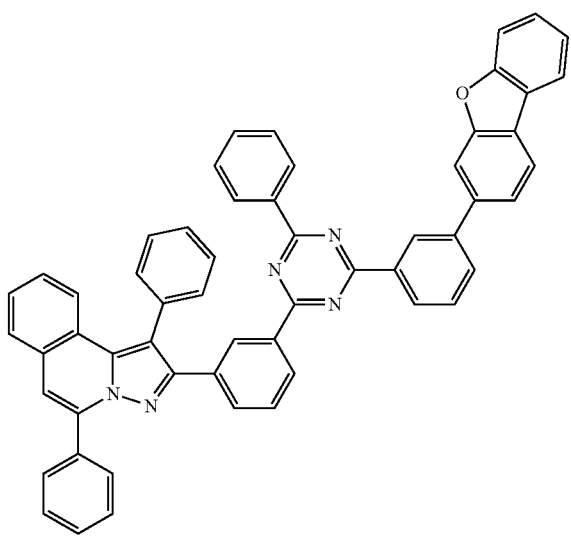
56
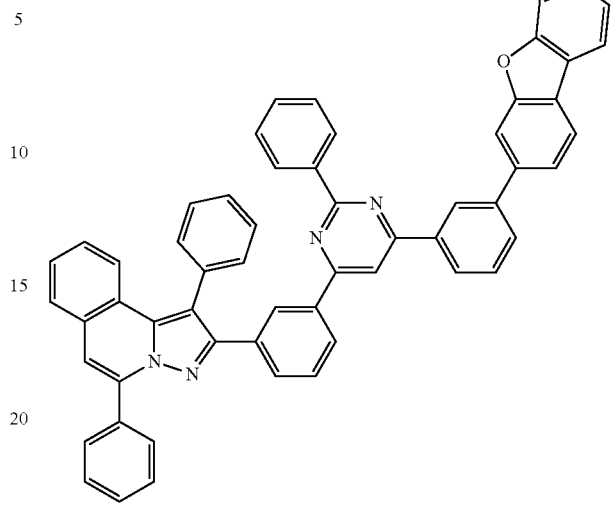
57
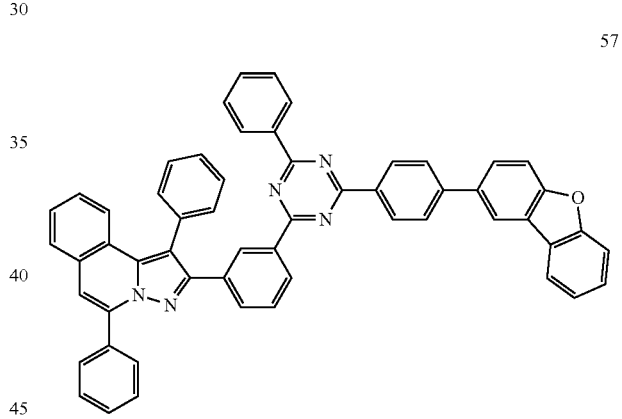
58
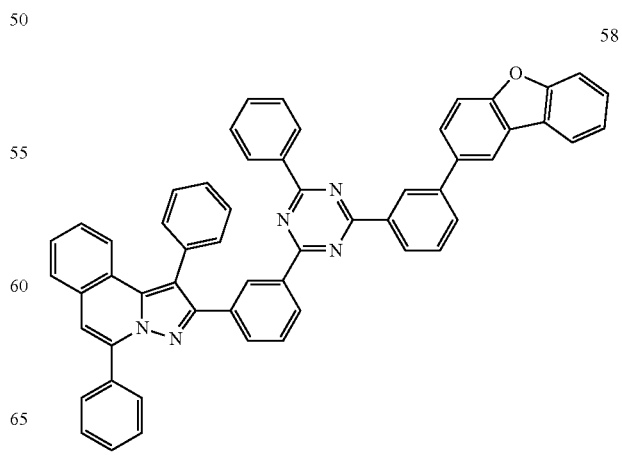

59
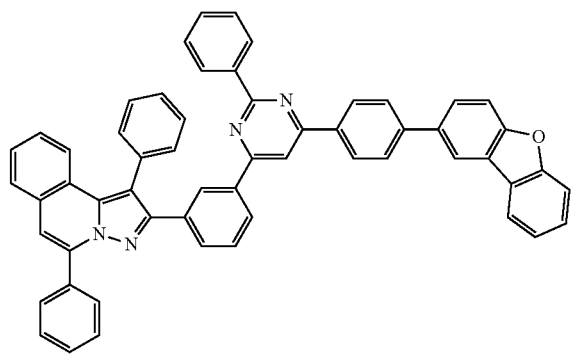
60
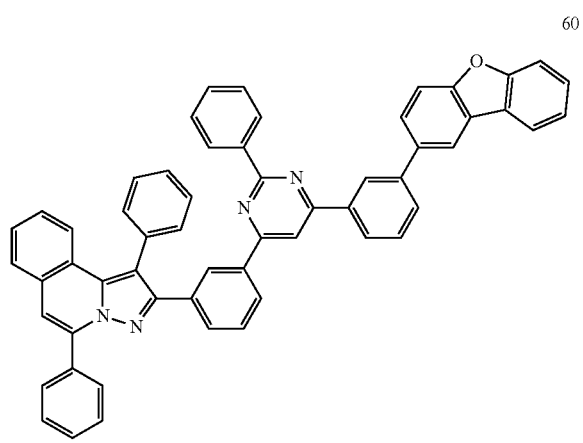
61
62
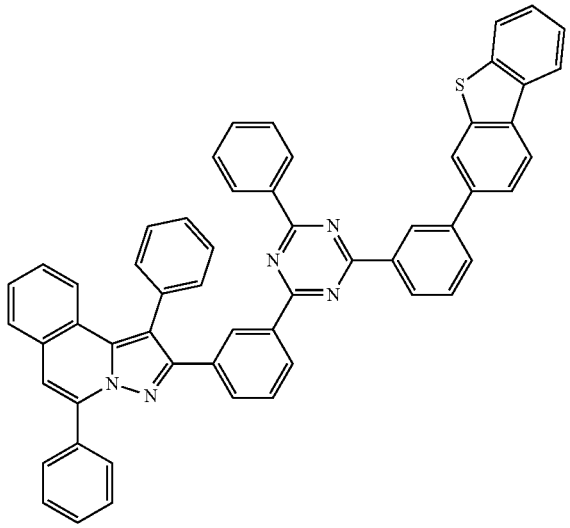
63
64
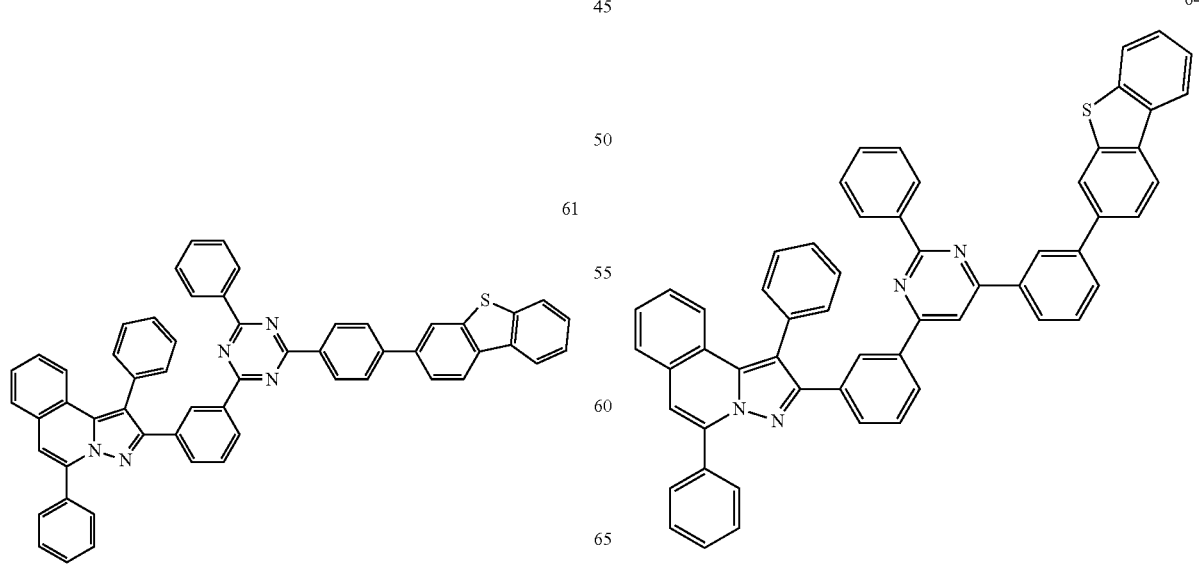

-continued
65
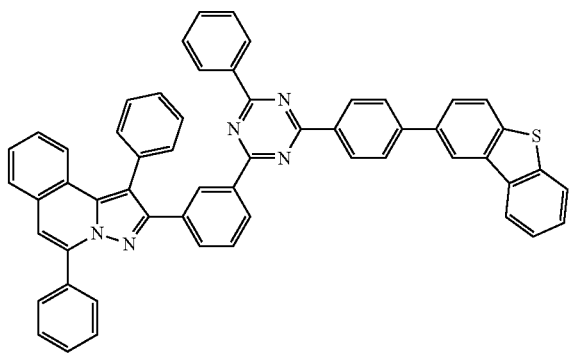
66
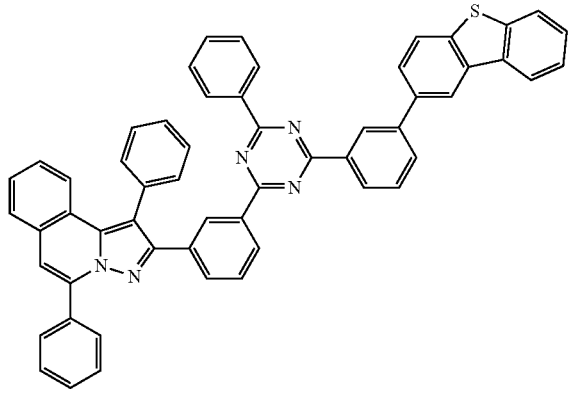
67
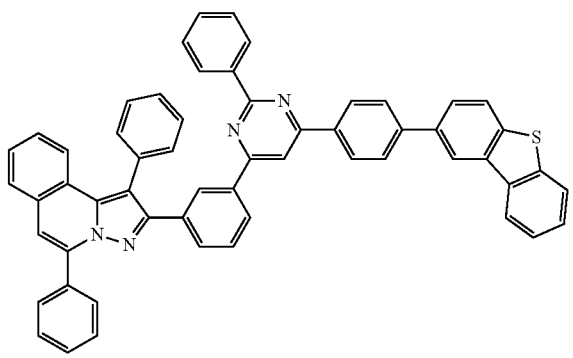
68
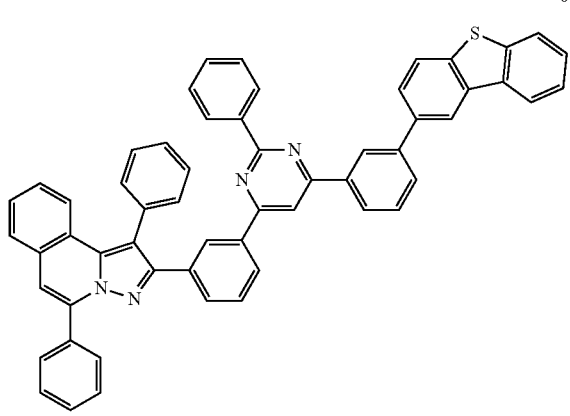
-continued
69
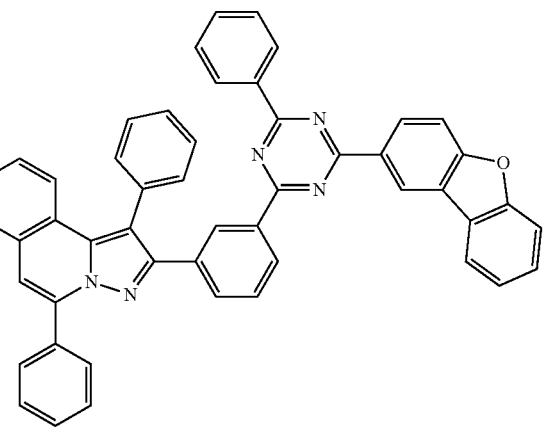
70
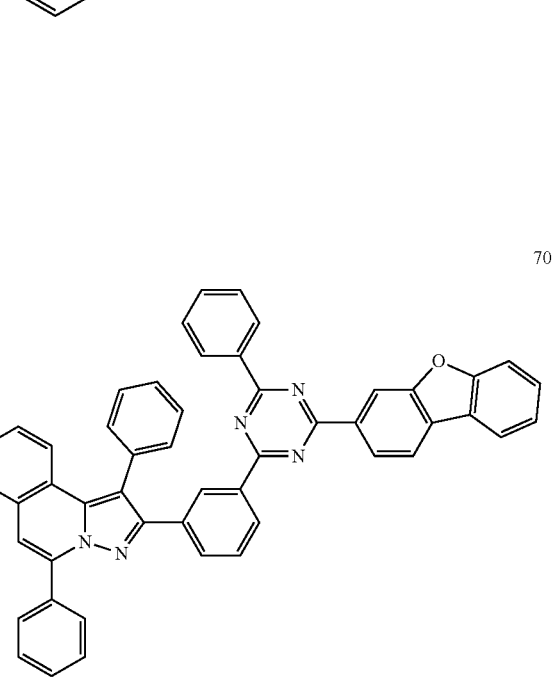
71
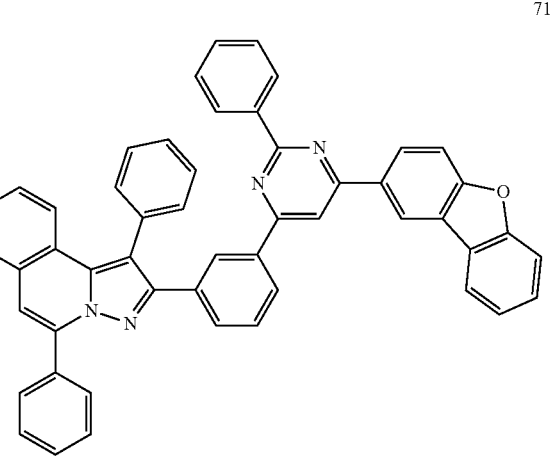

72
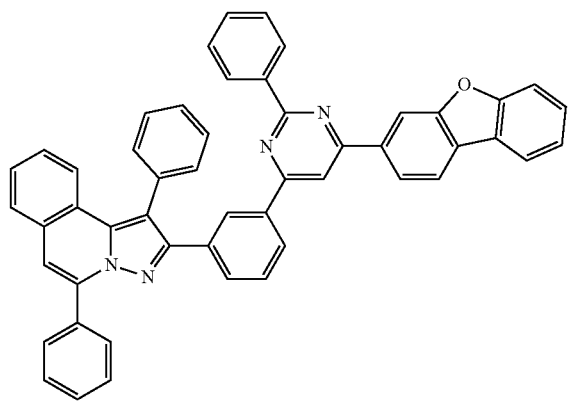
73
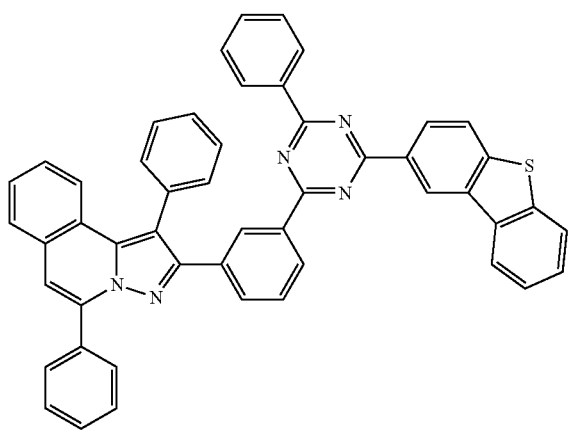
75
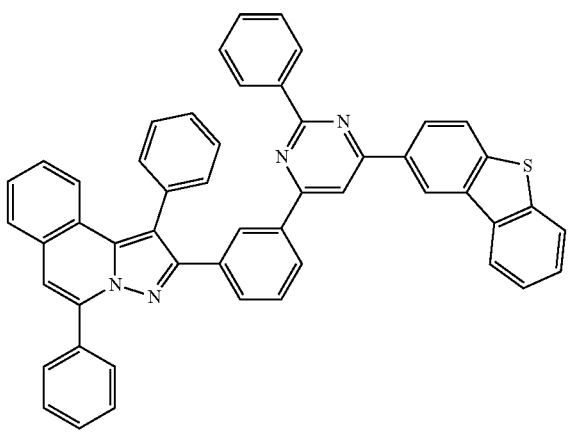
76
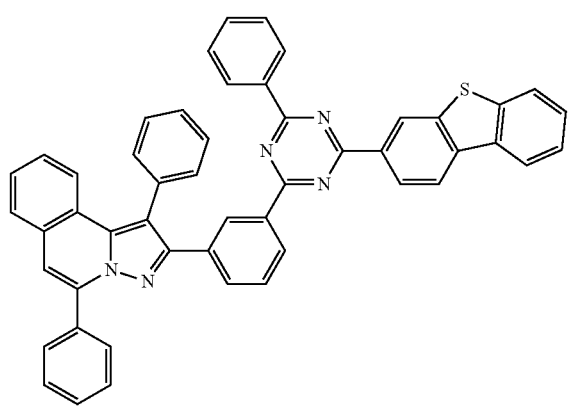
74
77
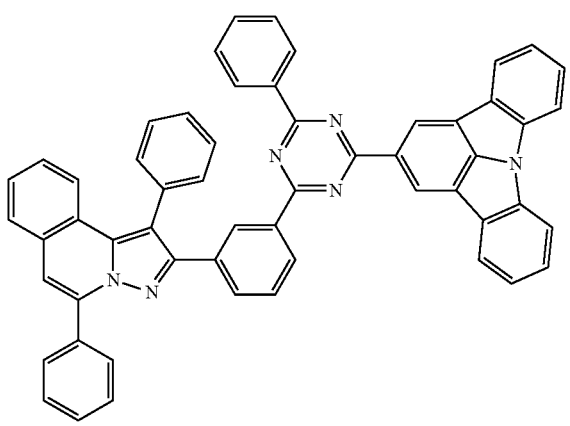

78
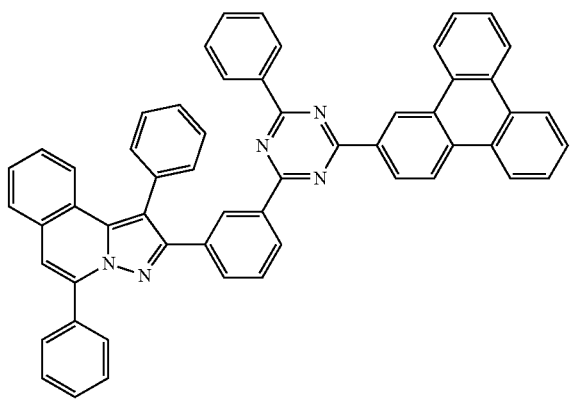
79
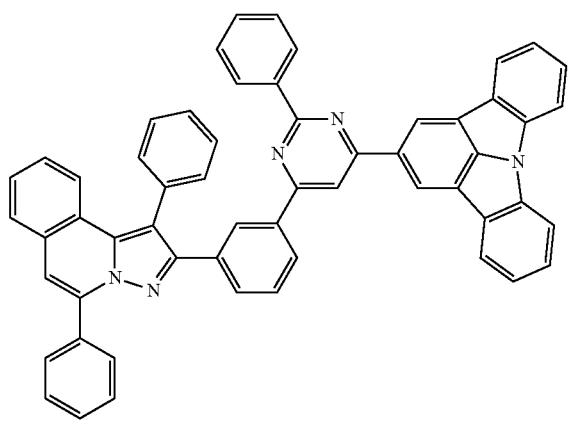
80
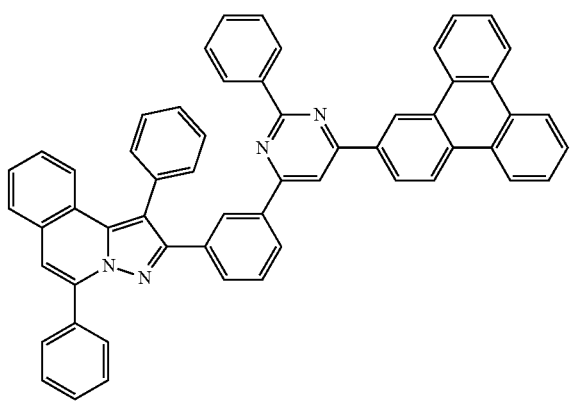
81
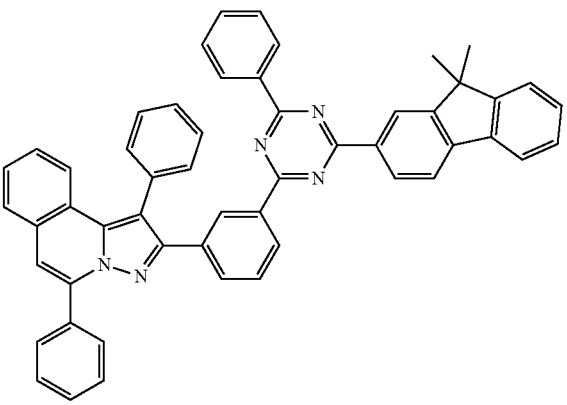
82
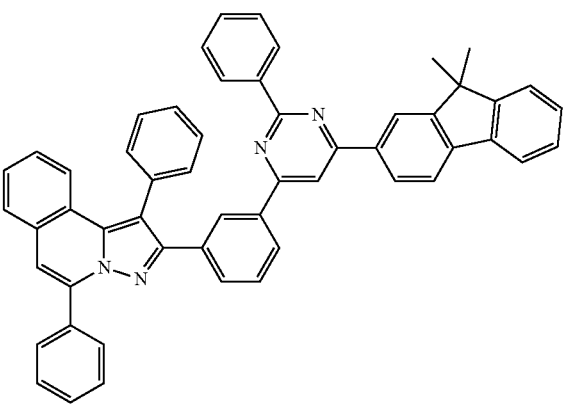
83

84
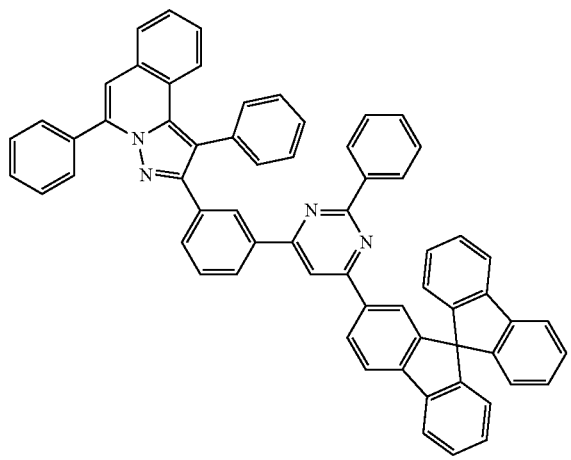
85
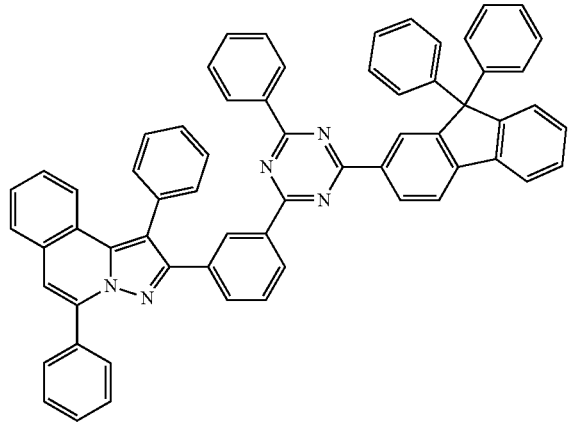
86
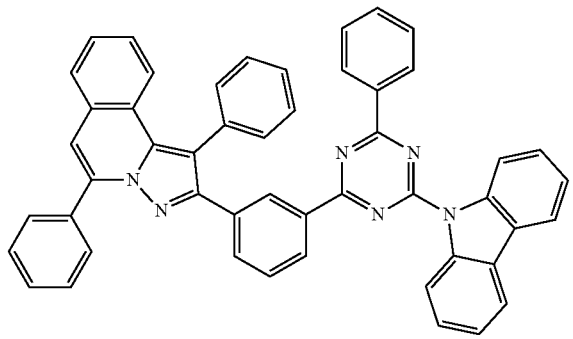
87
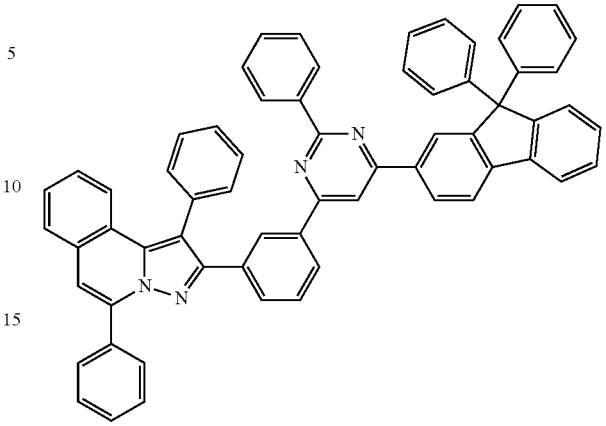
88
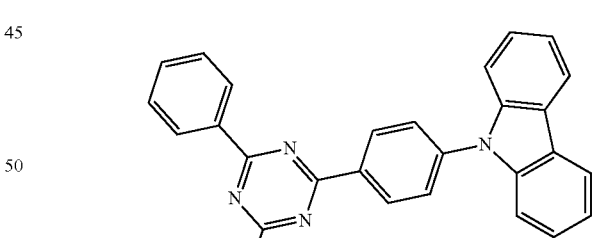
89
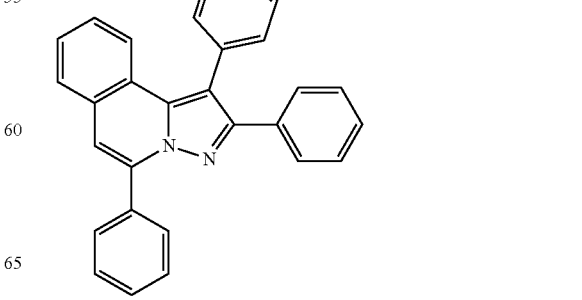

-continued
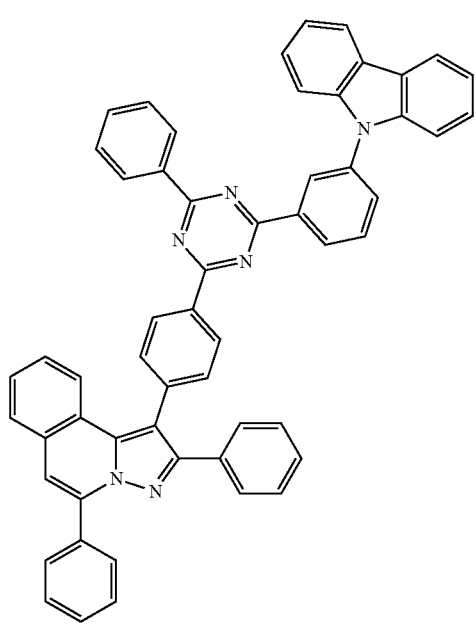
90
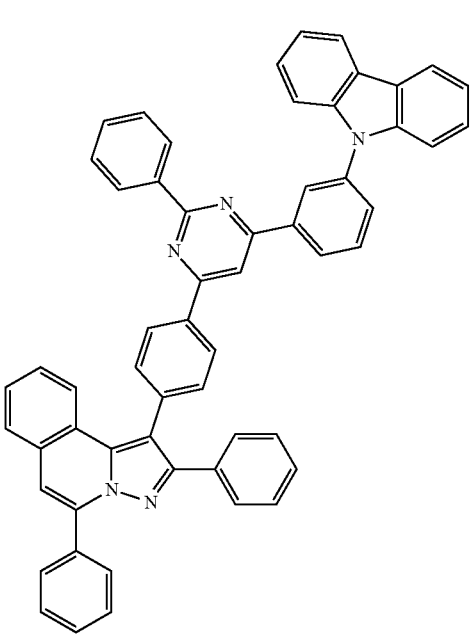
92
91
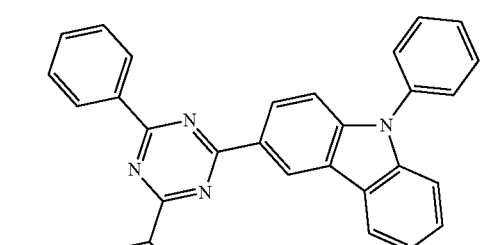
93

94
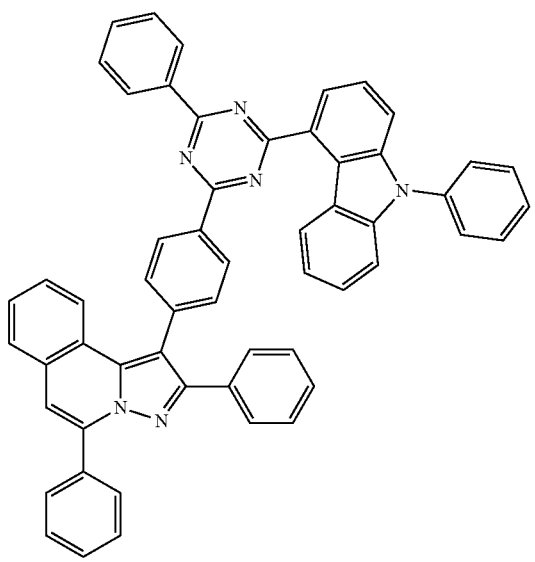
96
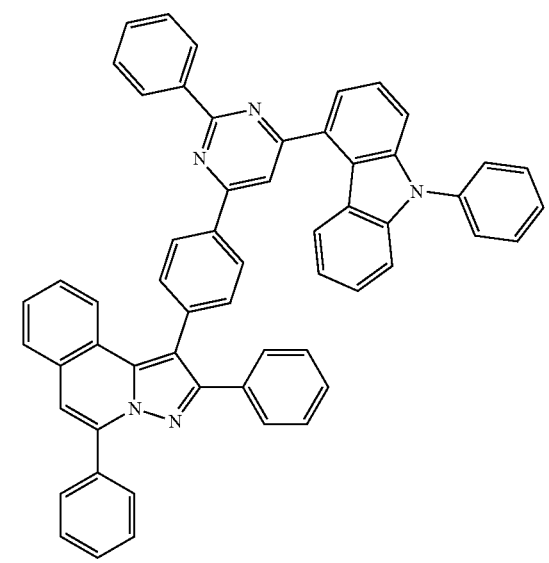
95
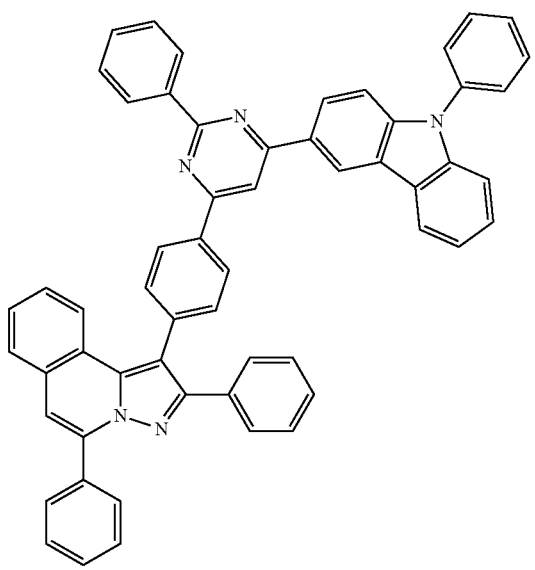
97
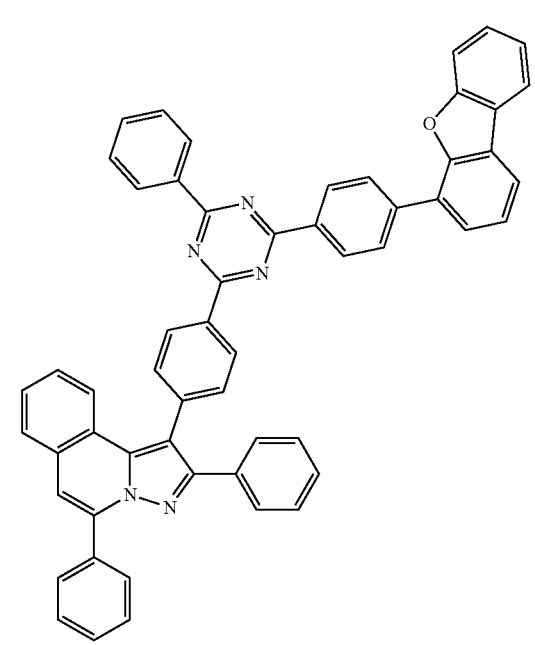

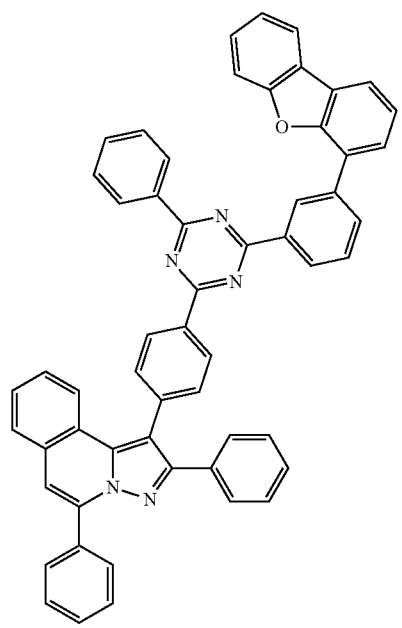
98
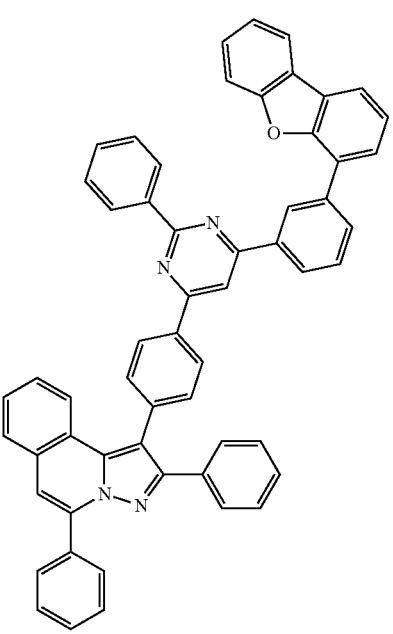
100
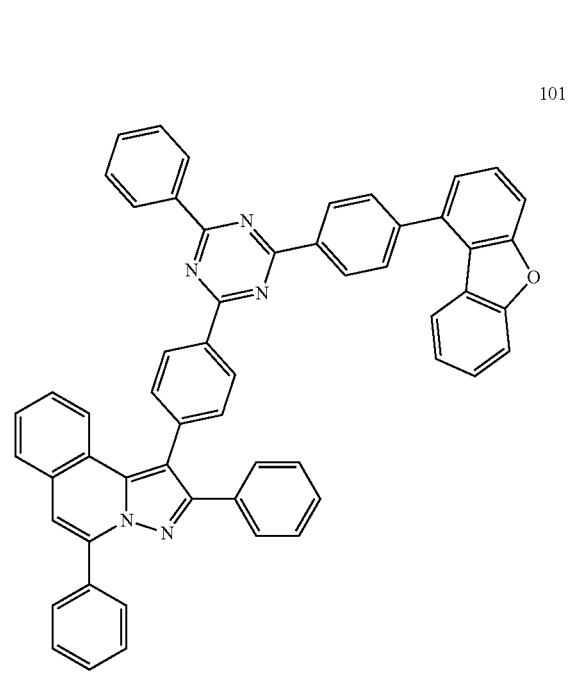
101
99

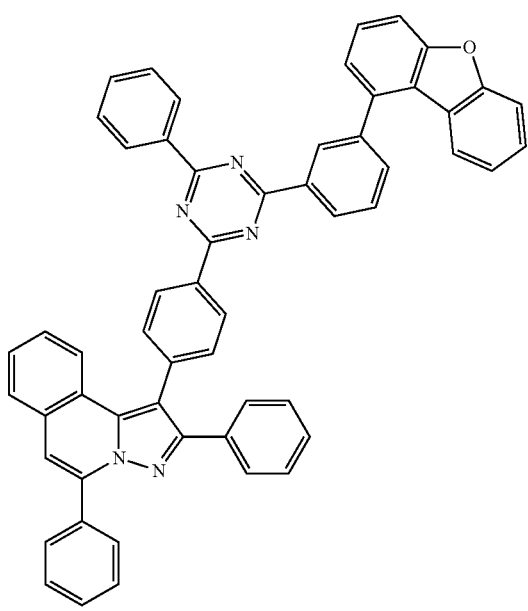
102
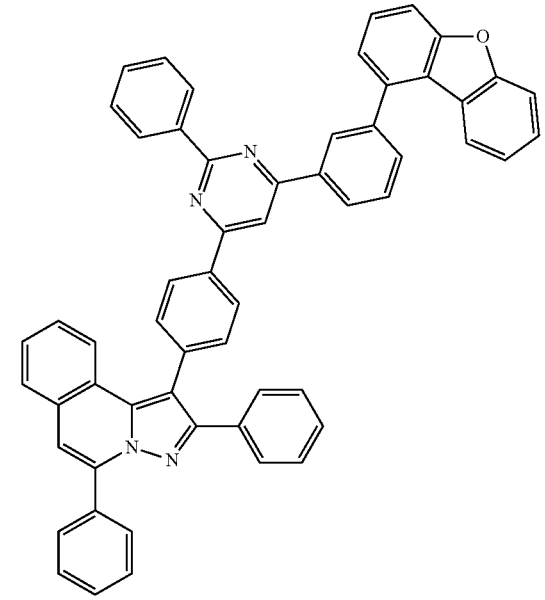
104
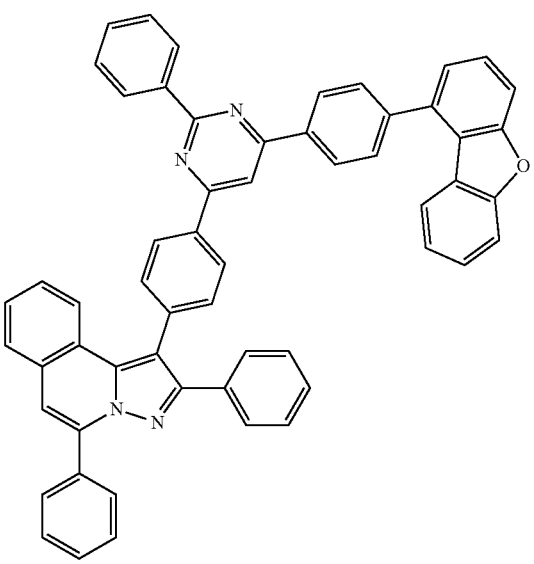
103
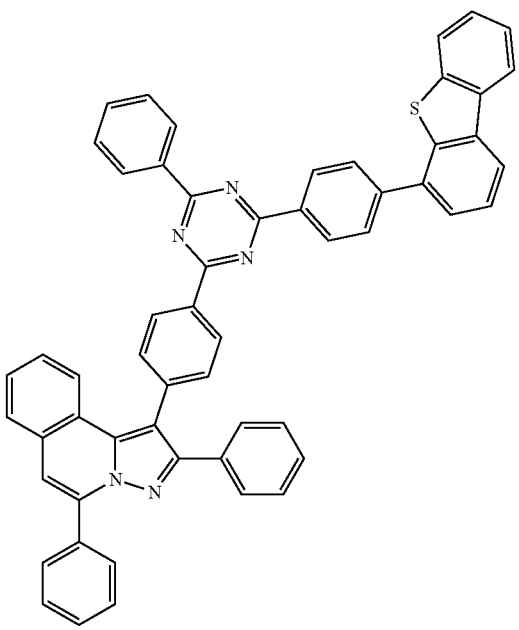
105

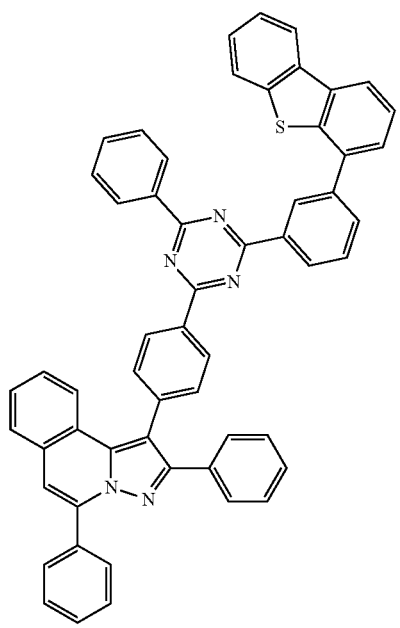
106
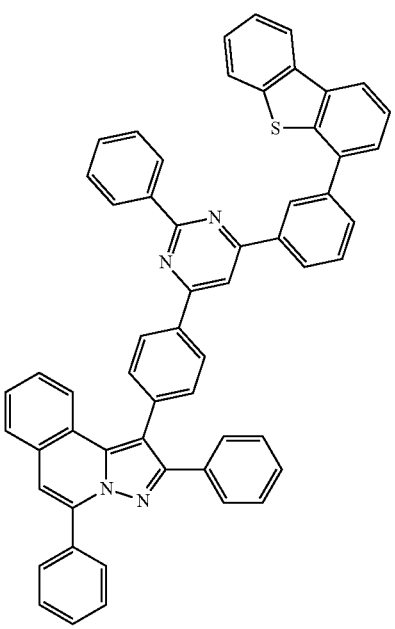
108
107
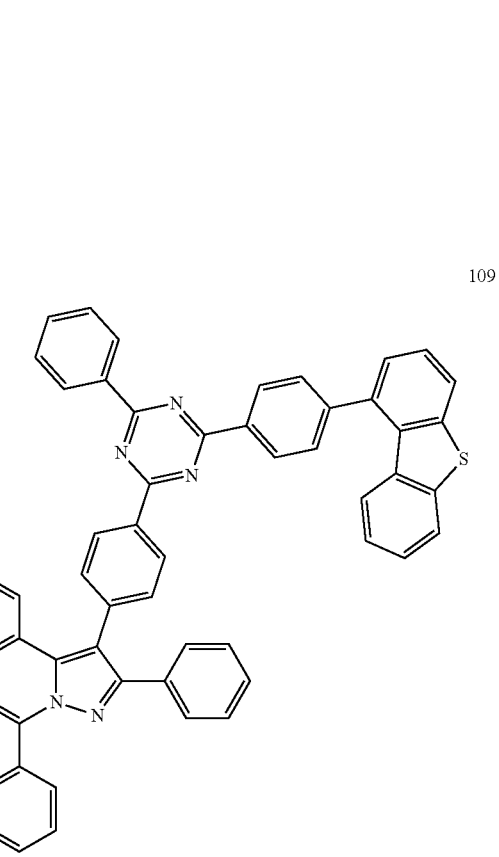
109

110
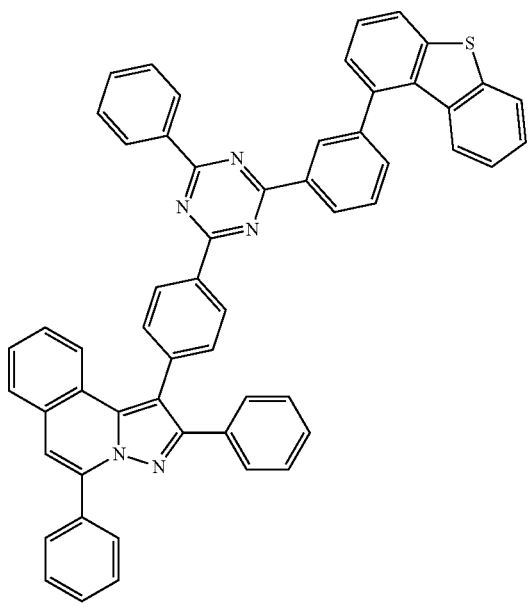
111
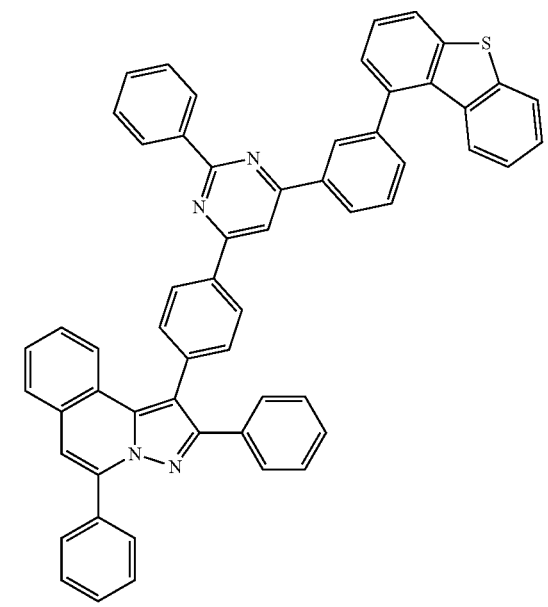
112
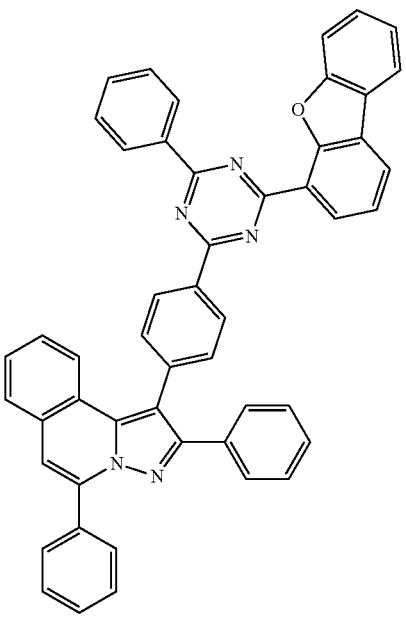
113

114
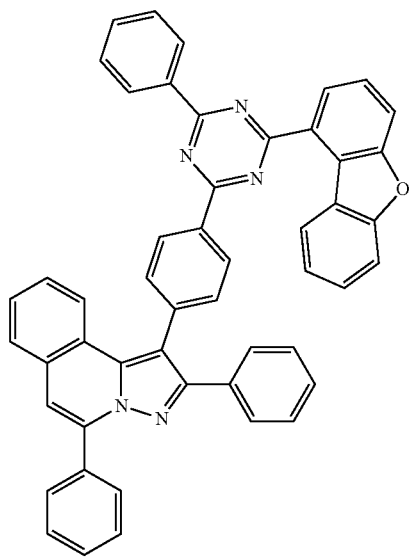
115
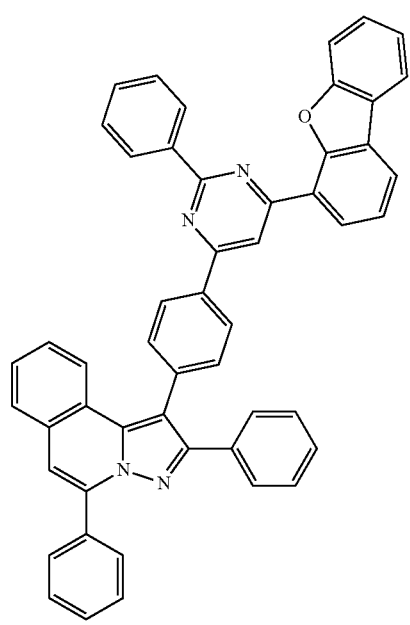
116
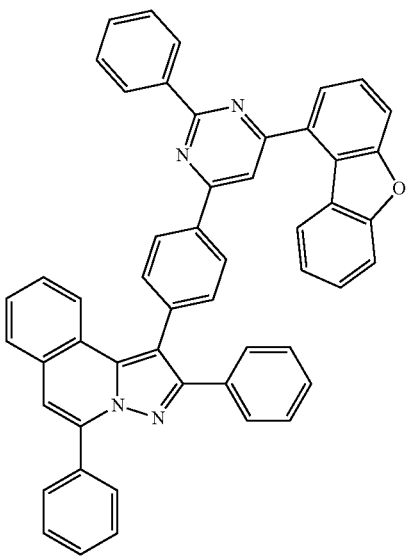
117
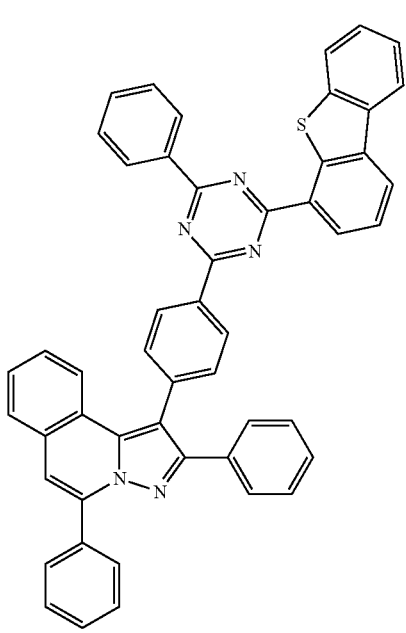

118
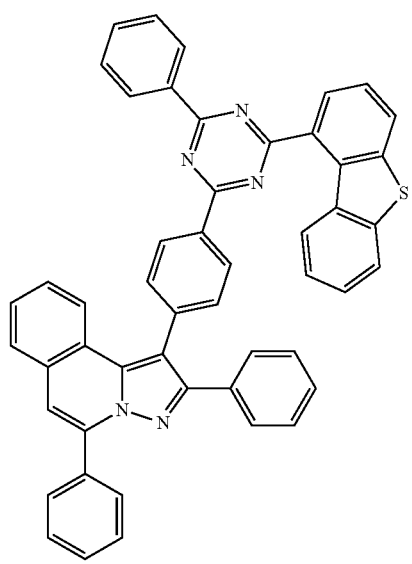
119
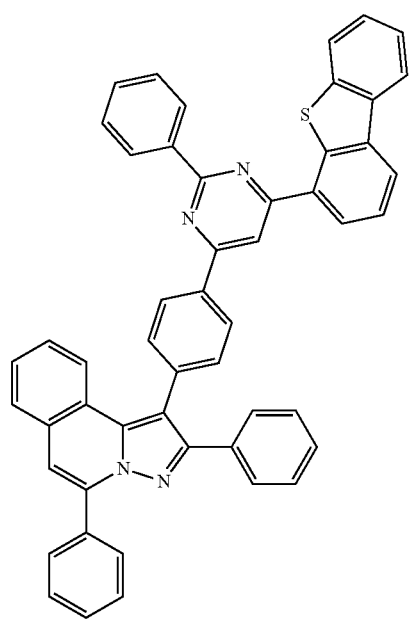
120
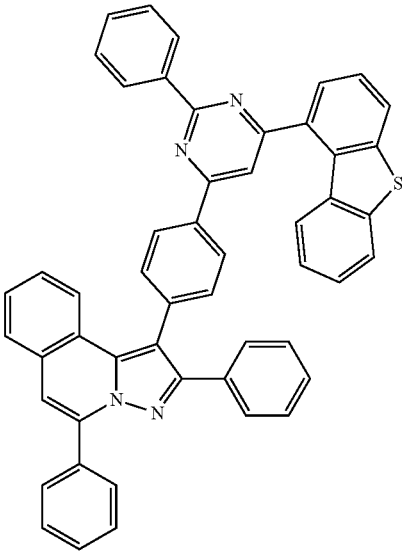
121
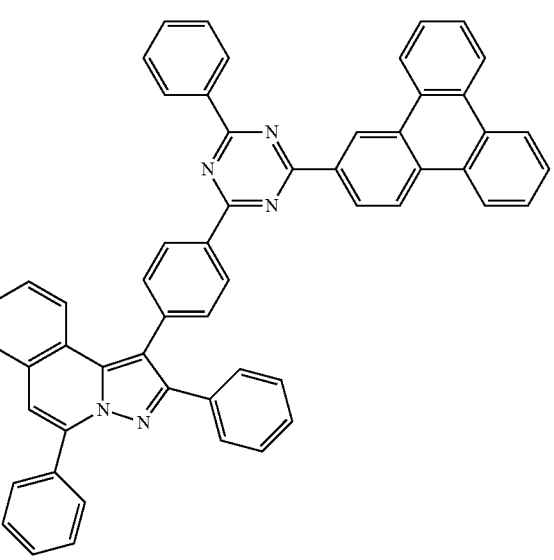
122

123
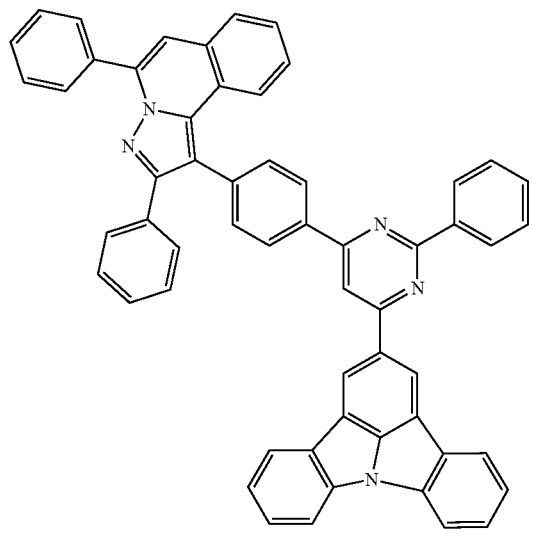
124
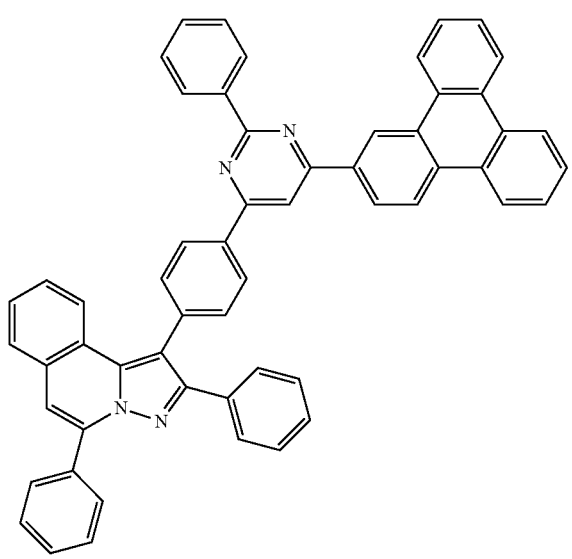
125
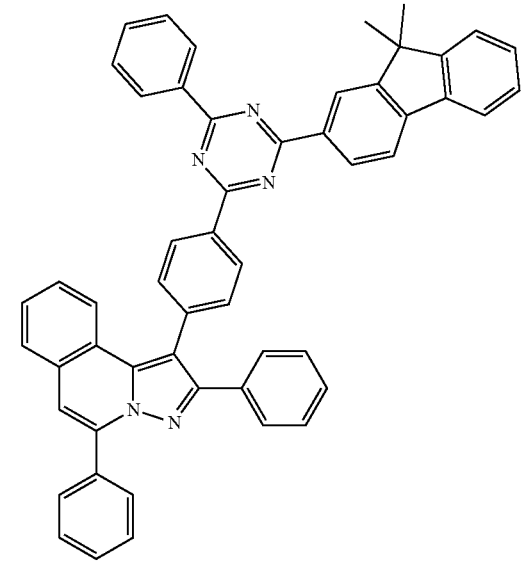
126
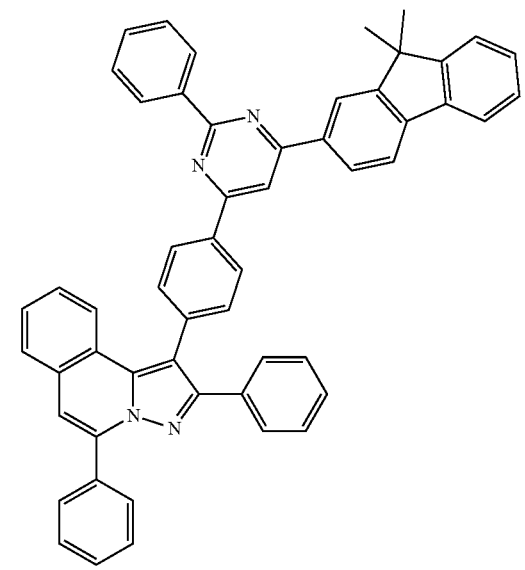
127

128
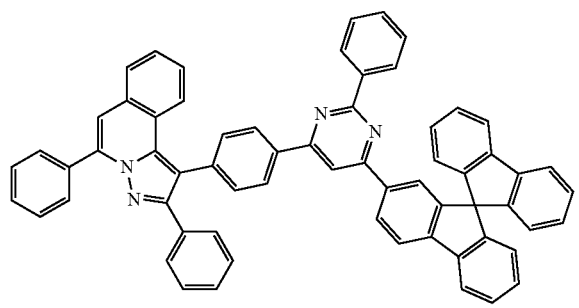
129
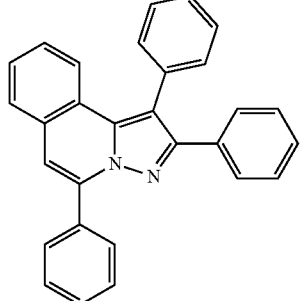
130
131
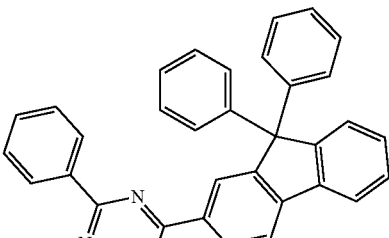
132
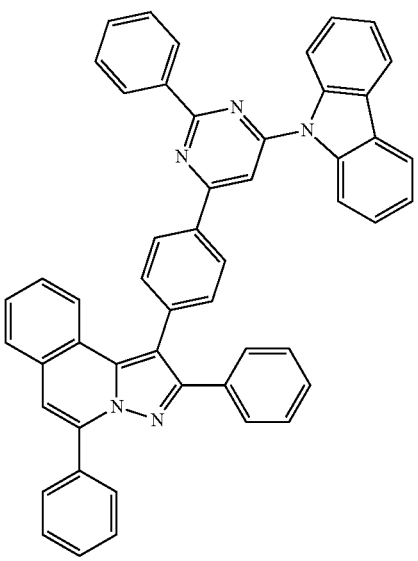

133
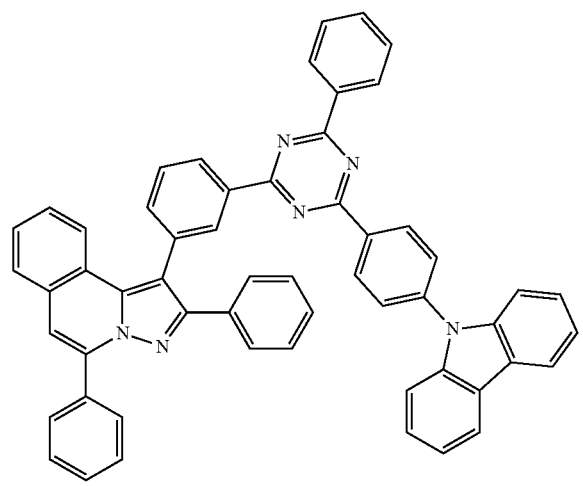
134
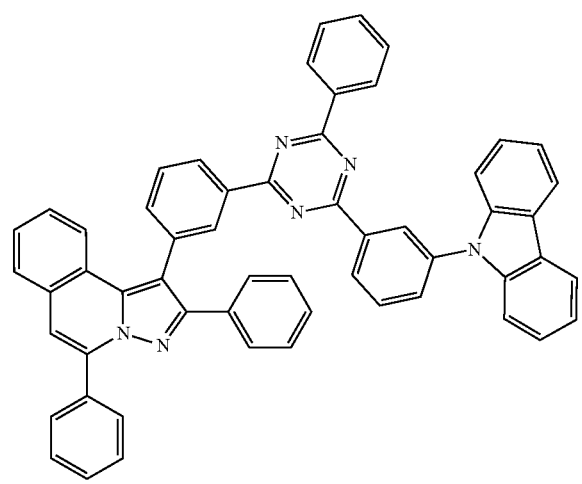
135
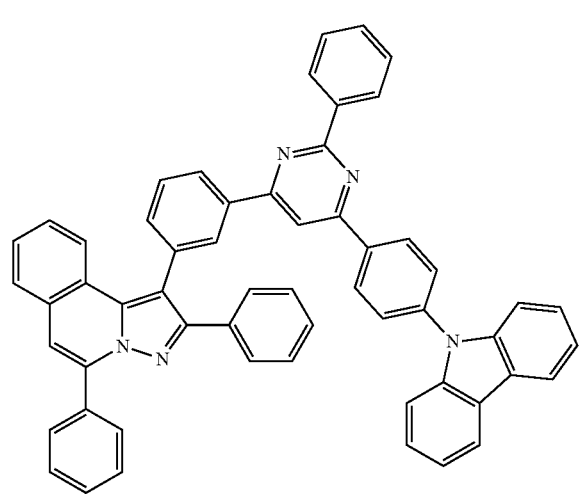
136
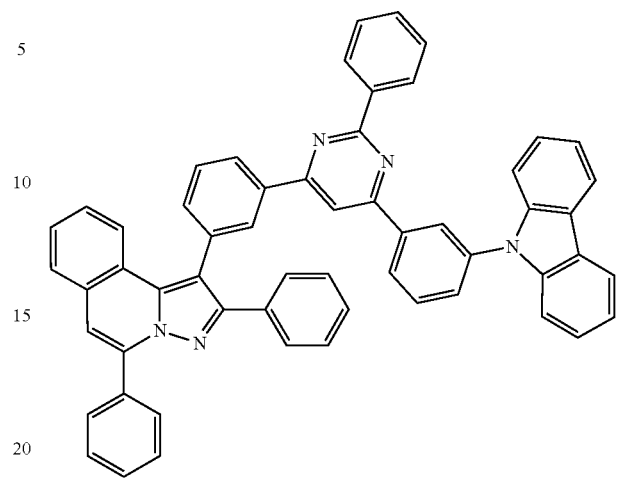
137
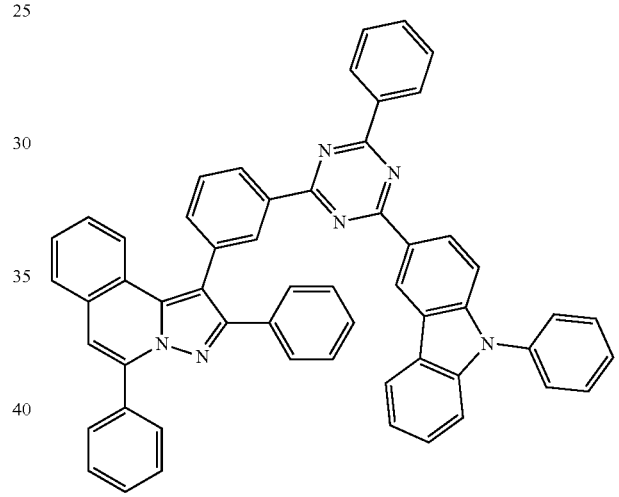
138
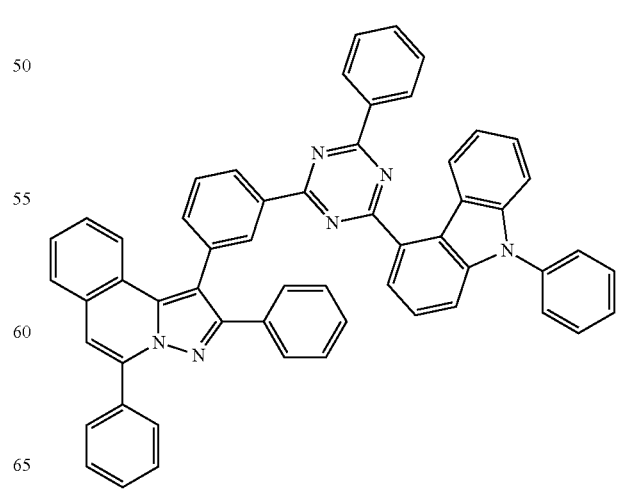

139
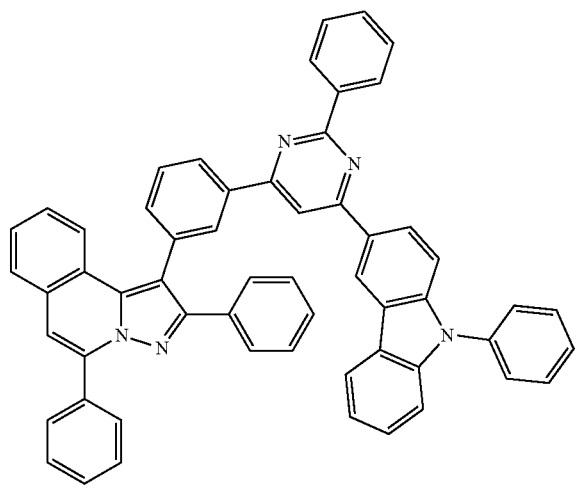
140
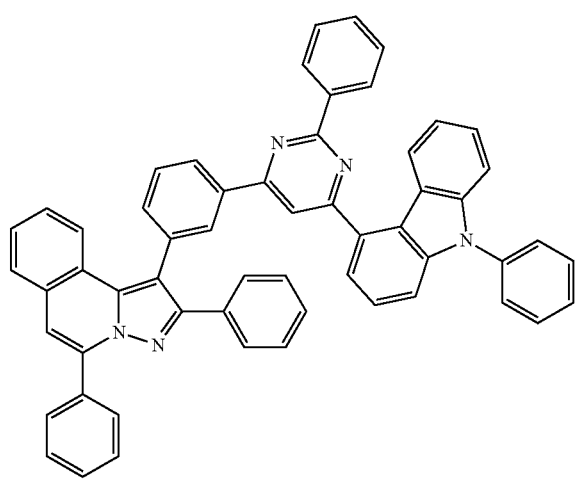
141
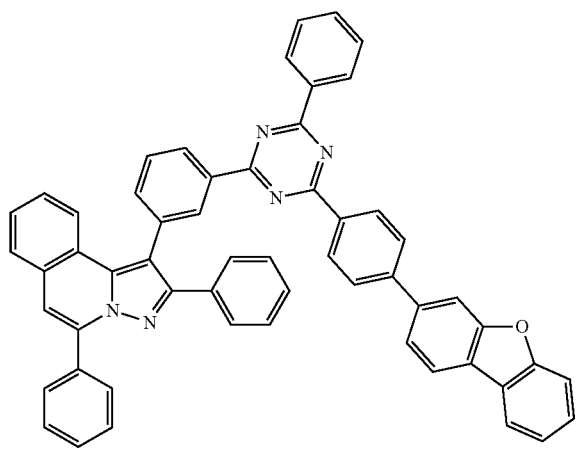
142
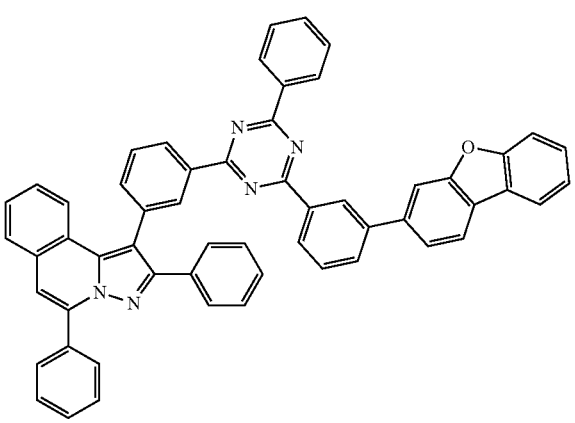
143
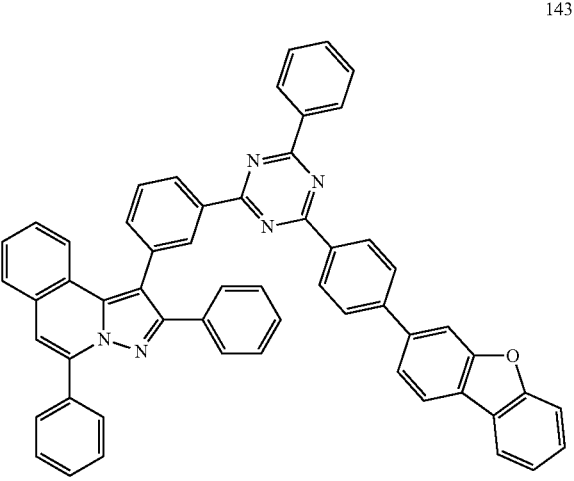
144
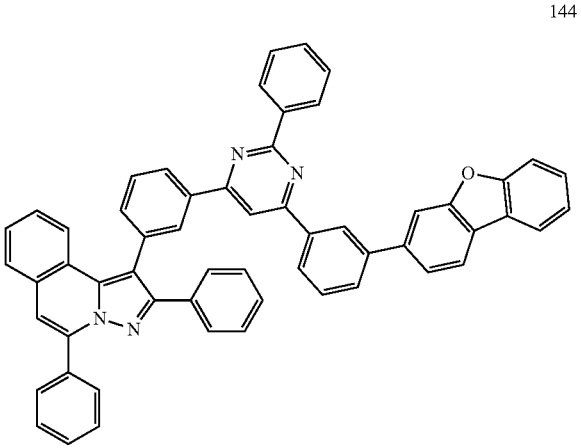

145
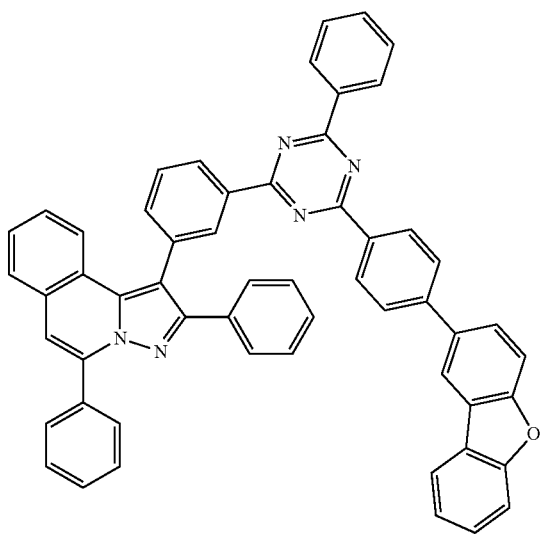
146
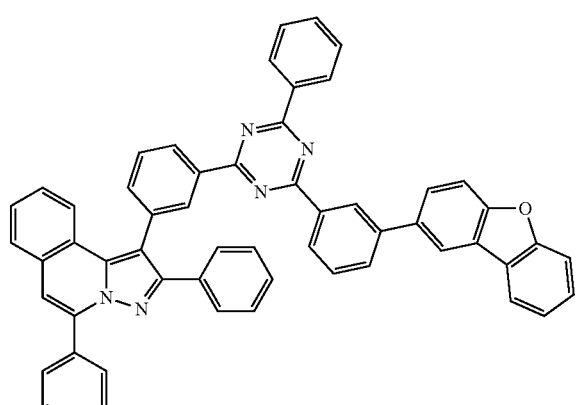
147
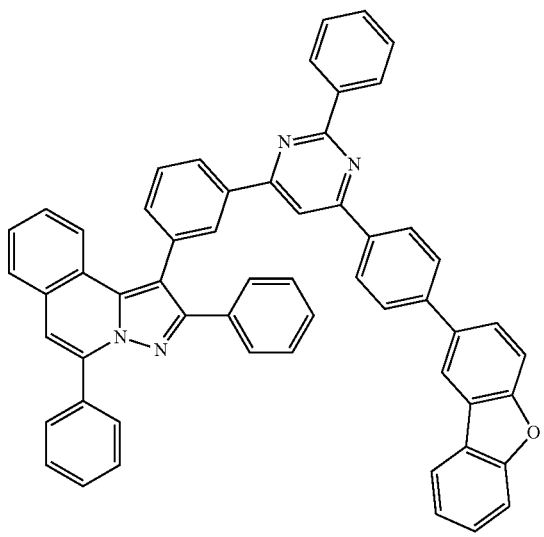
148
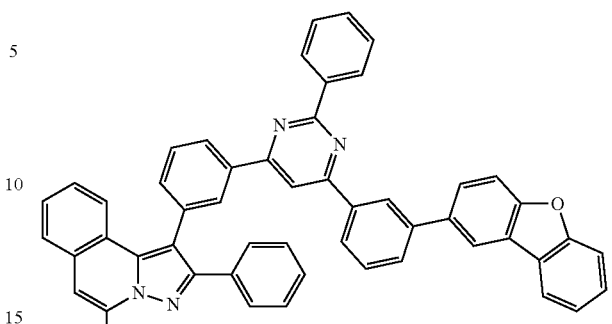
149
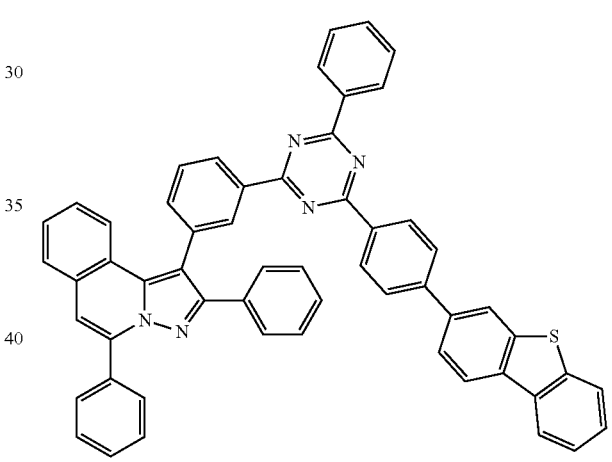
150

151
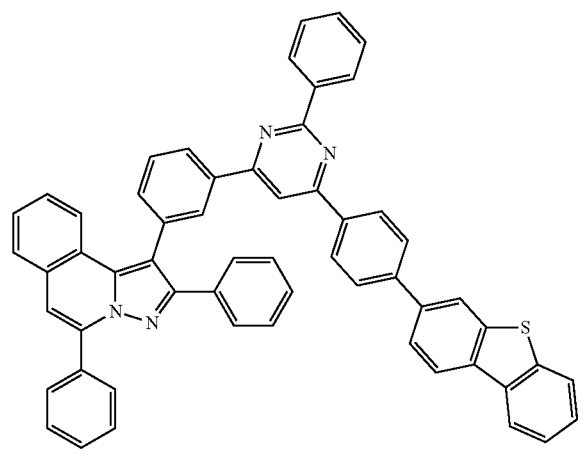
152
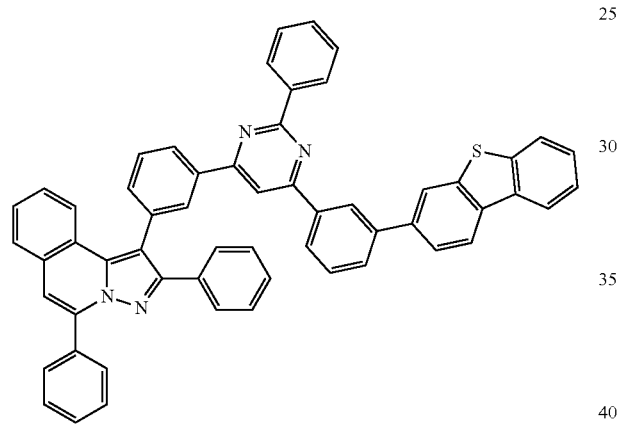
153
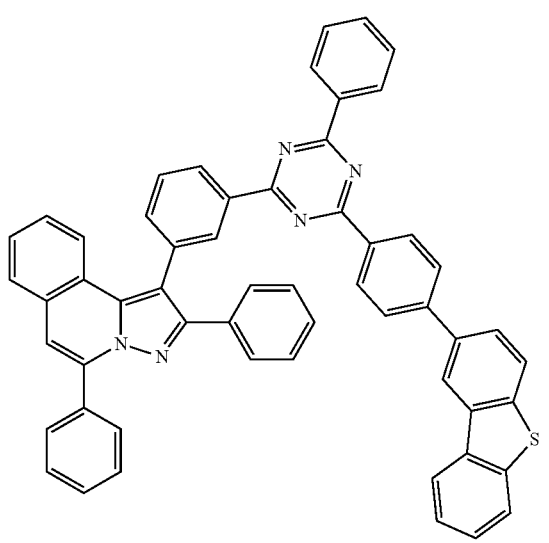
154
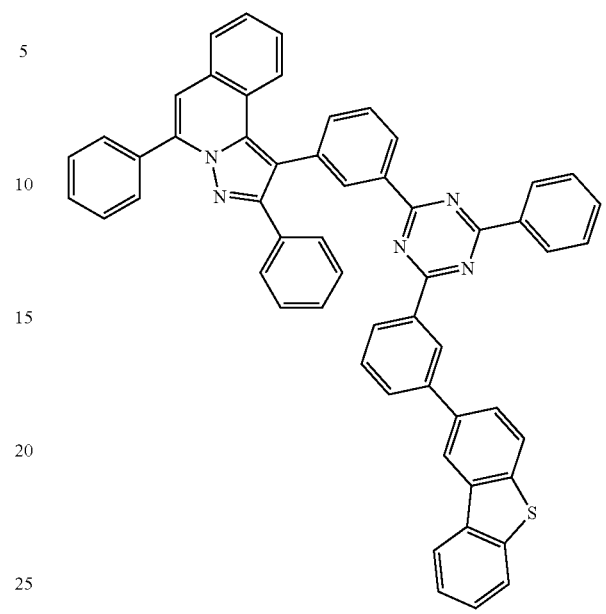
155
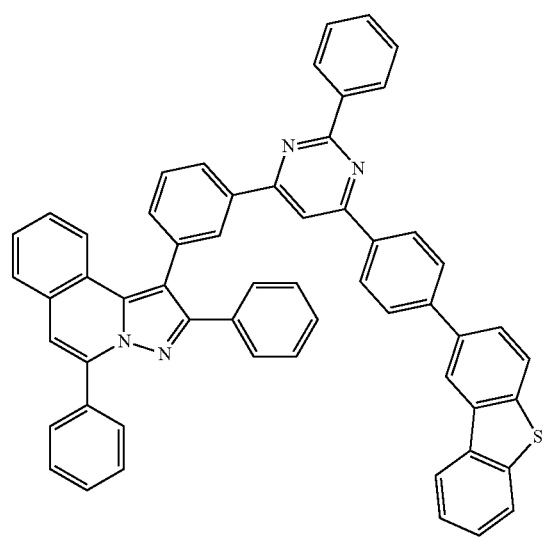

156
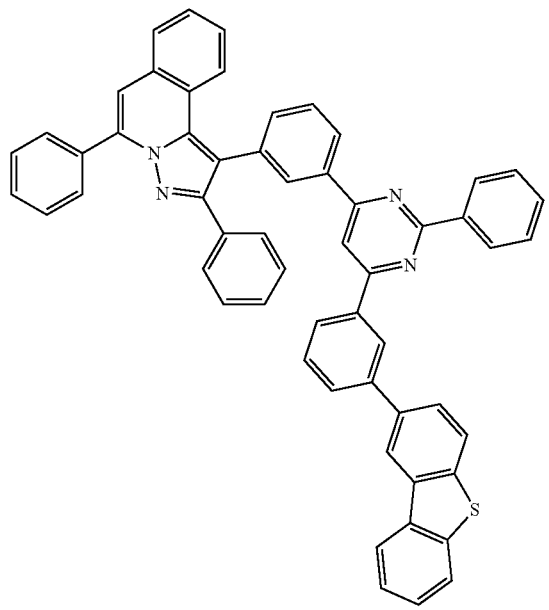
157
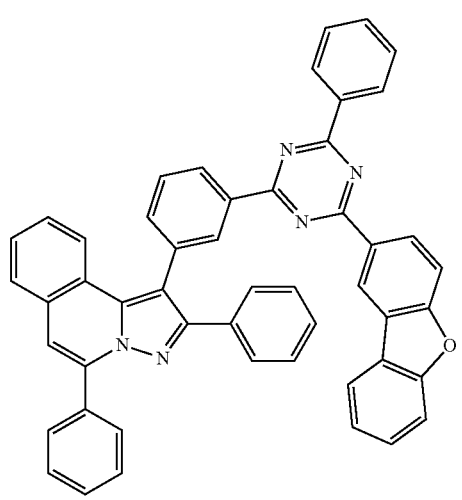
158
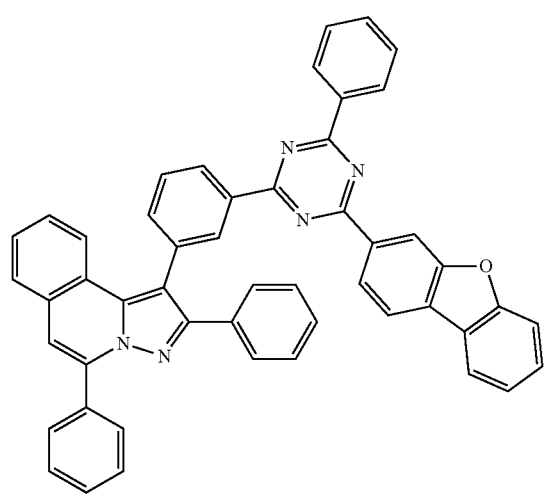
159
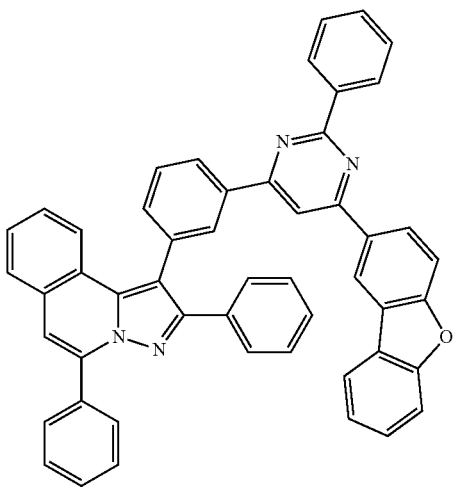
160
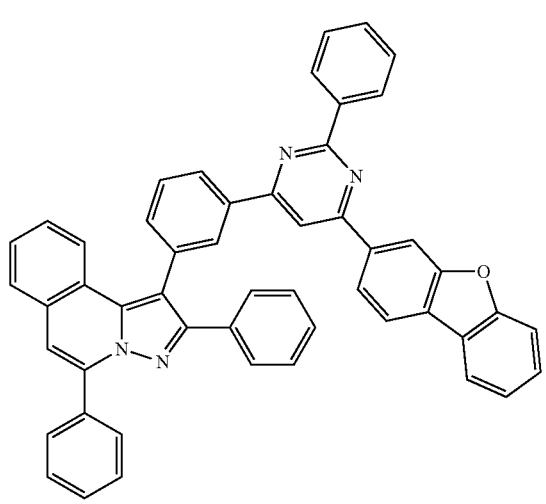
161
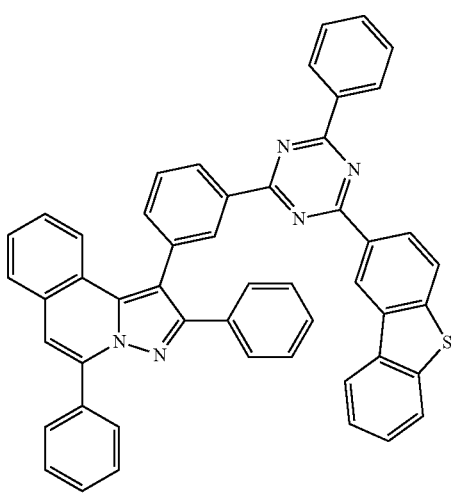

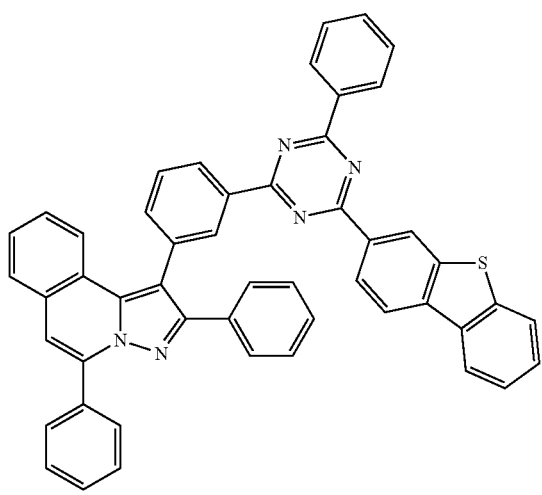
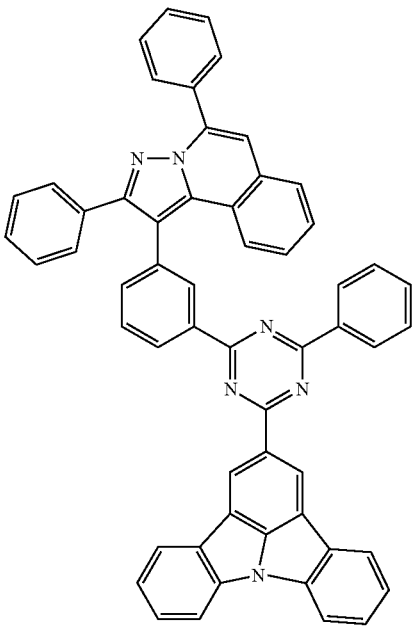
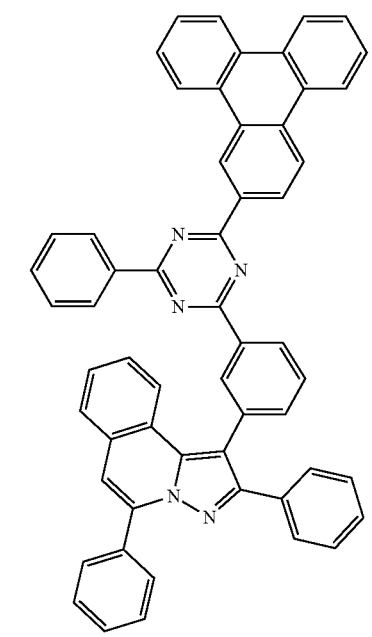

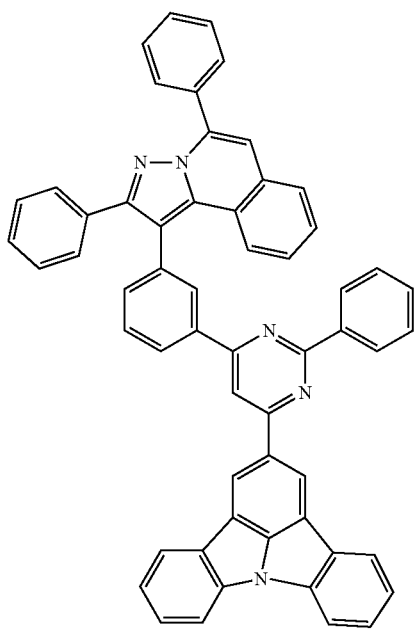
167
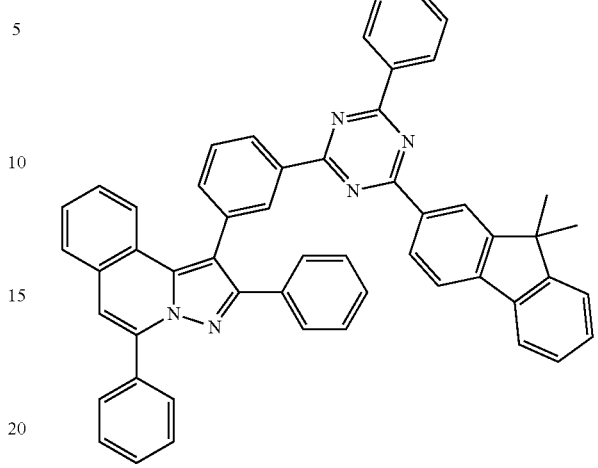
169
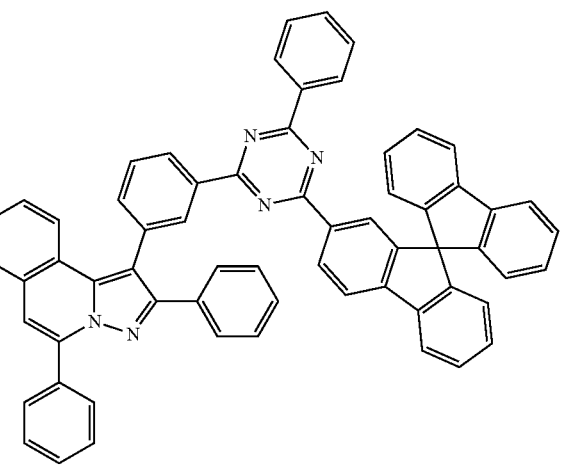
170
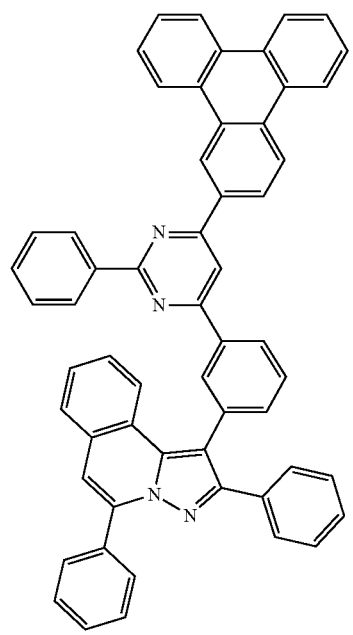
168
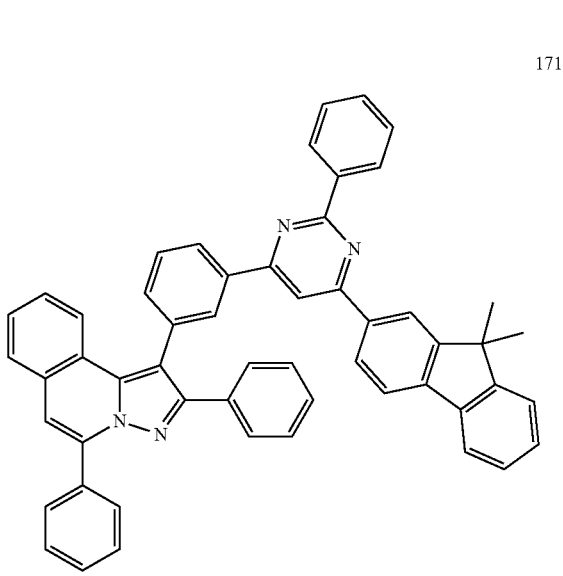 [SMILES: c1ccc(-c2cc(-c3ccc4c(c3)oc3ccccc34)nc(-c3cccc(-c4c(-c5ccccc5)nn5c(-c6ccccc6)cc6ccccc6c45)c3)n2)cc1]
171

172
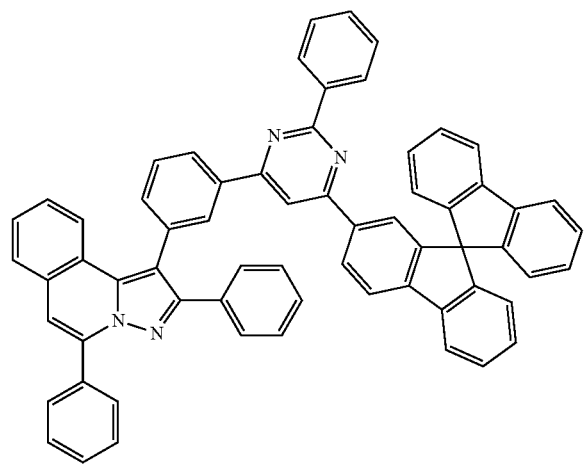
175
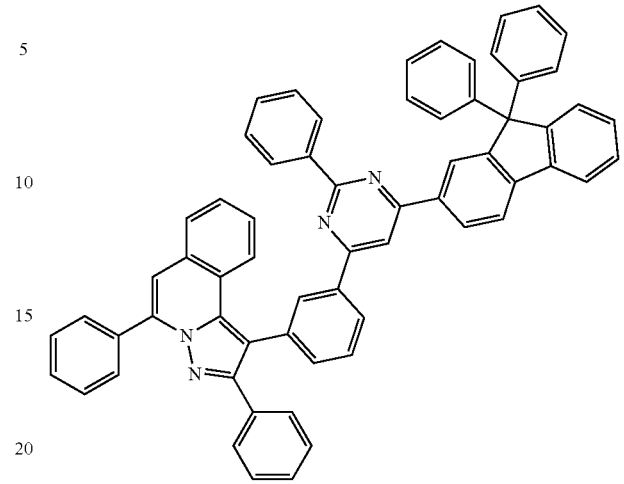
173
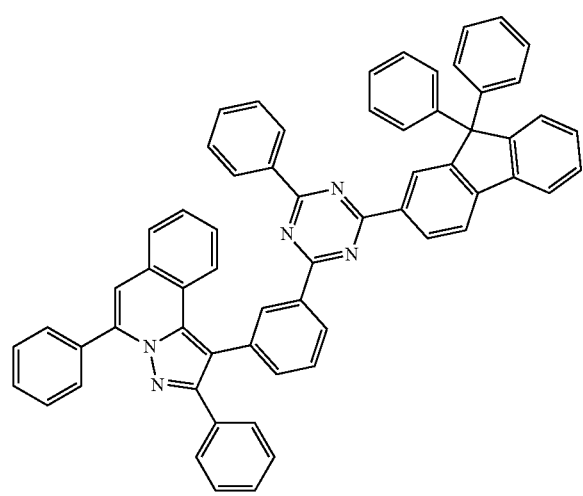
176
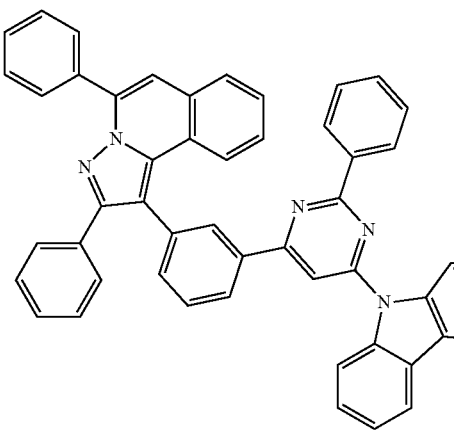
174
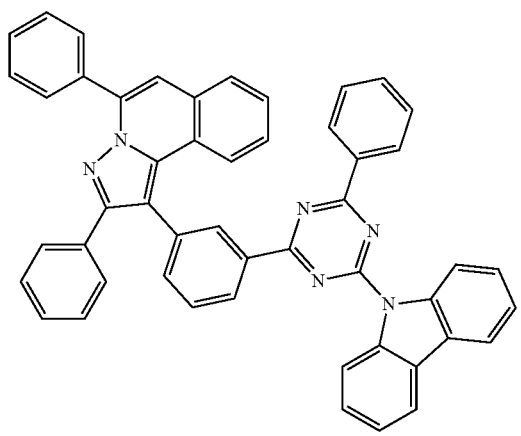
177
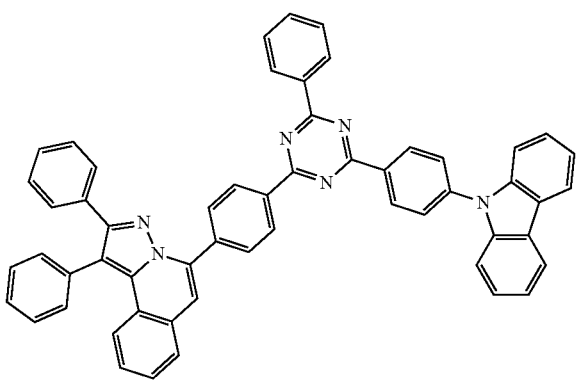

178
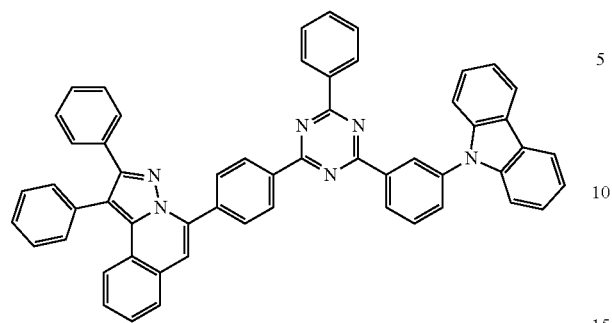
179
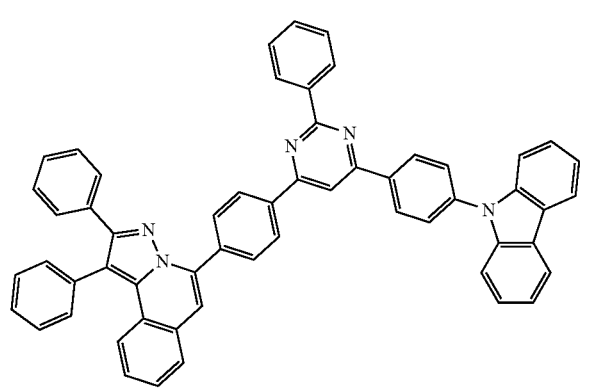
180
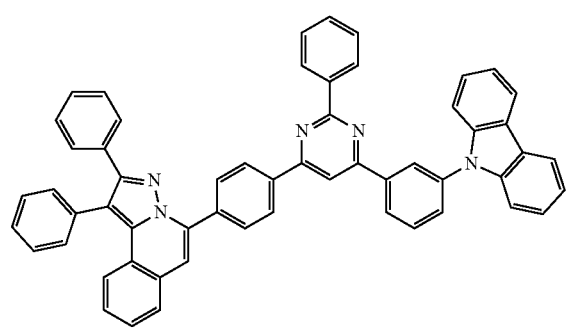
181
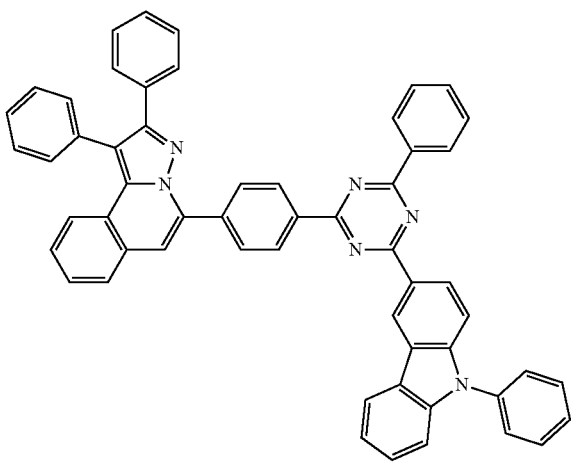
182
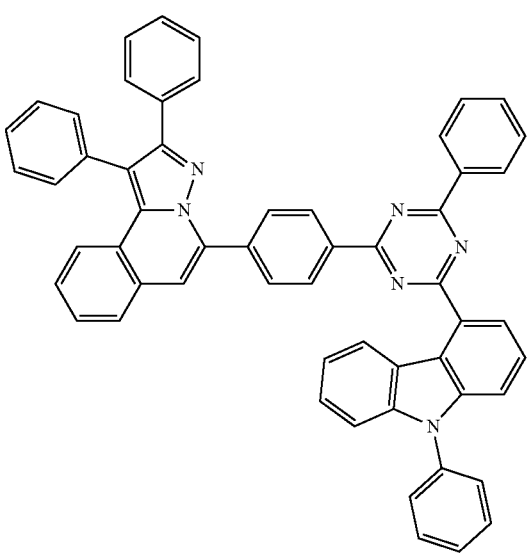
183
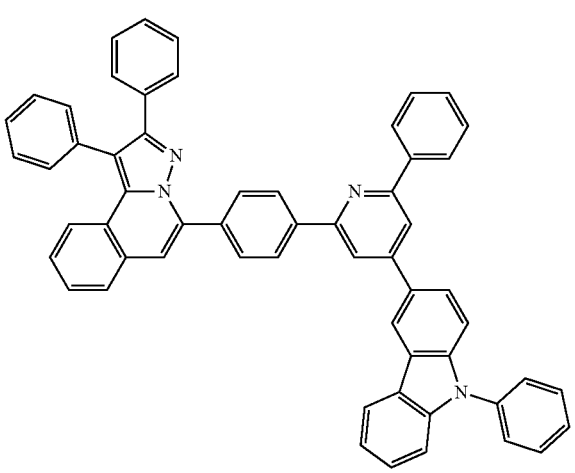
184
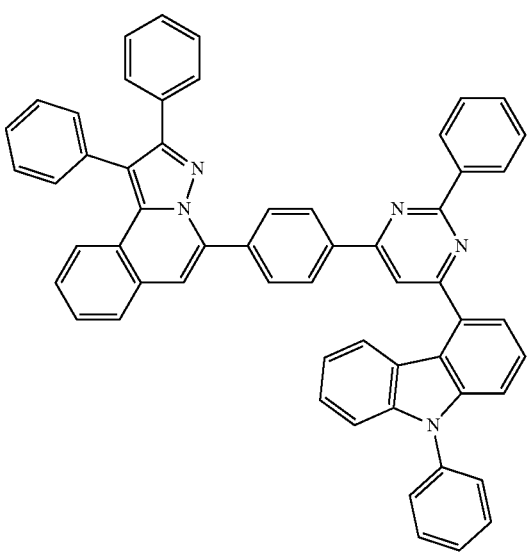

185
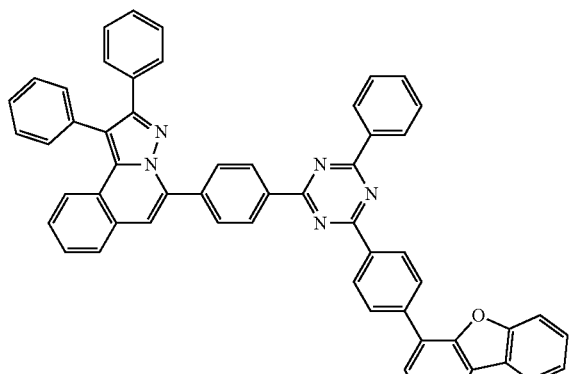
186
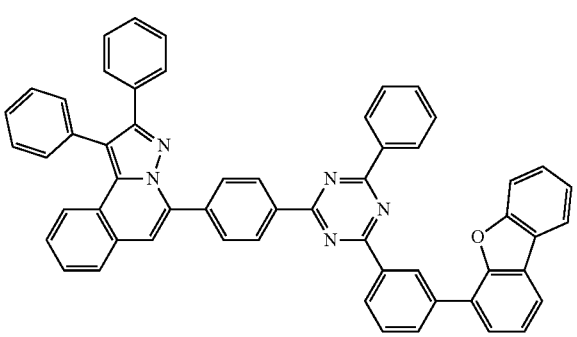
187
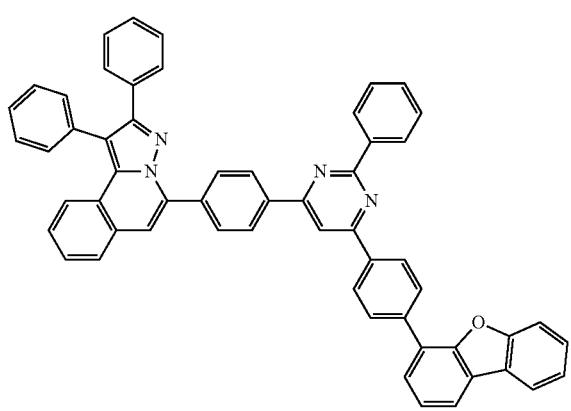
188
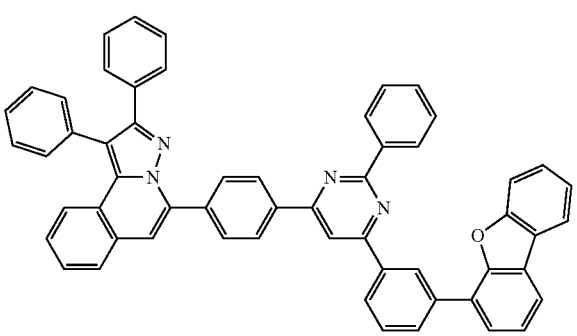
189
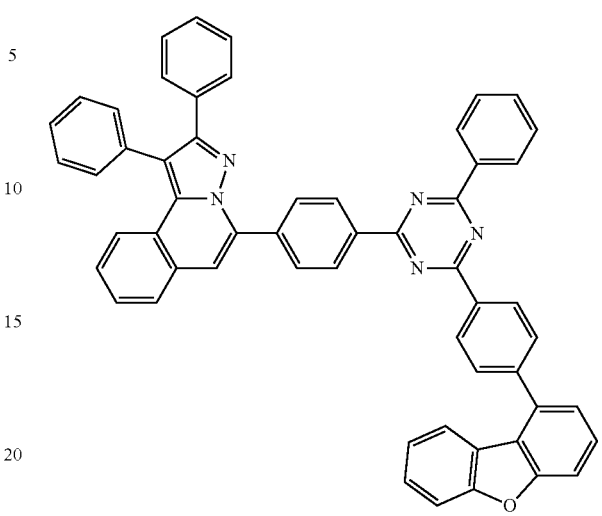
190
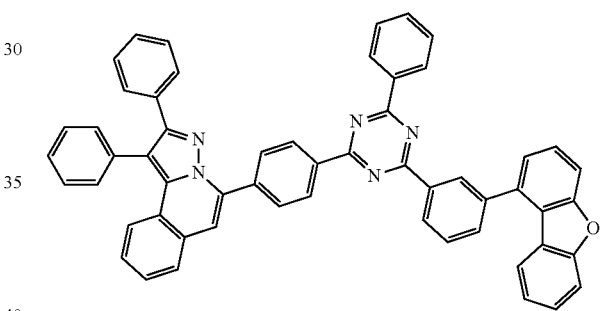
191
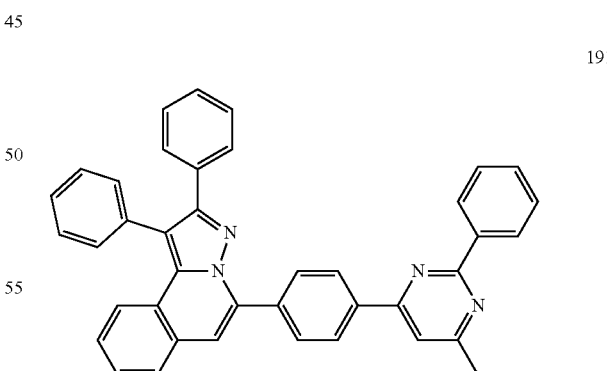
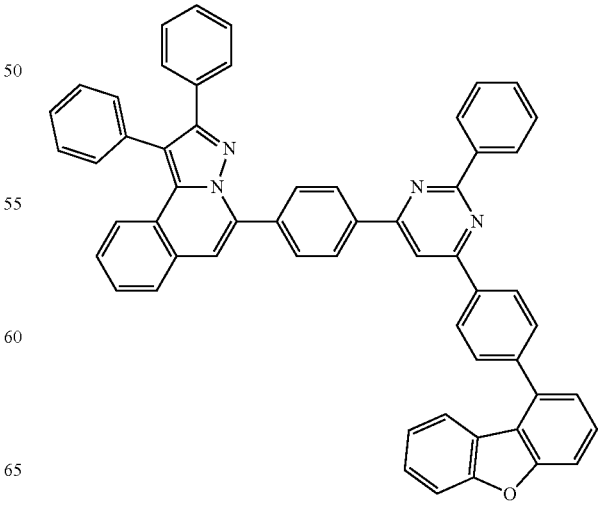

192
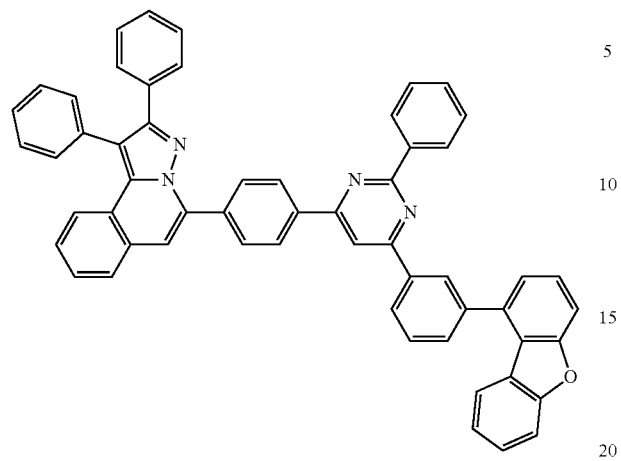
193
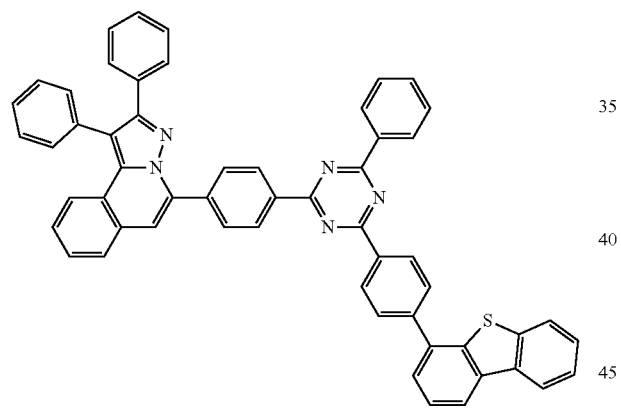
194
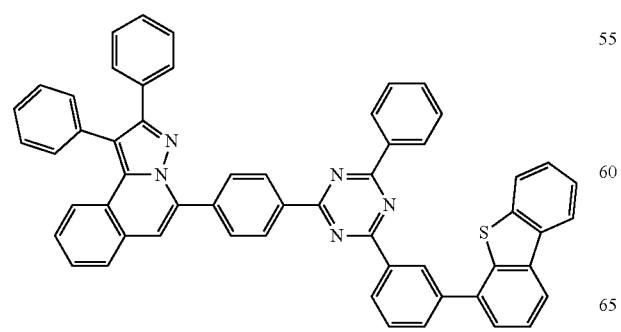
195
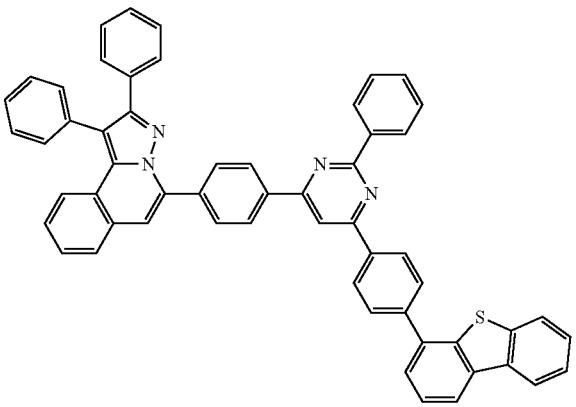
196
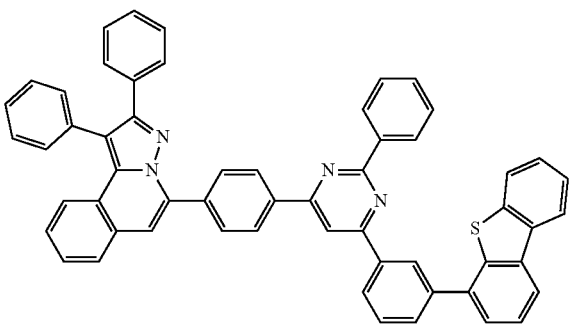
197
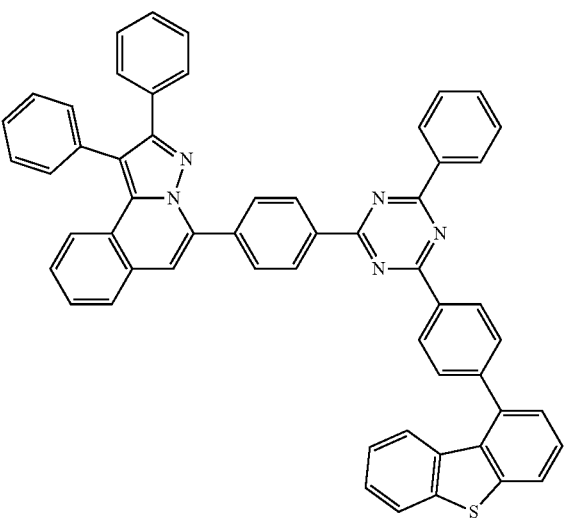

198
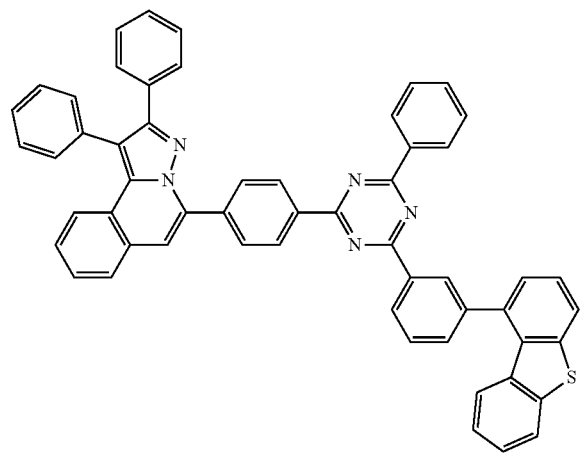
199
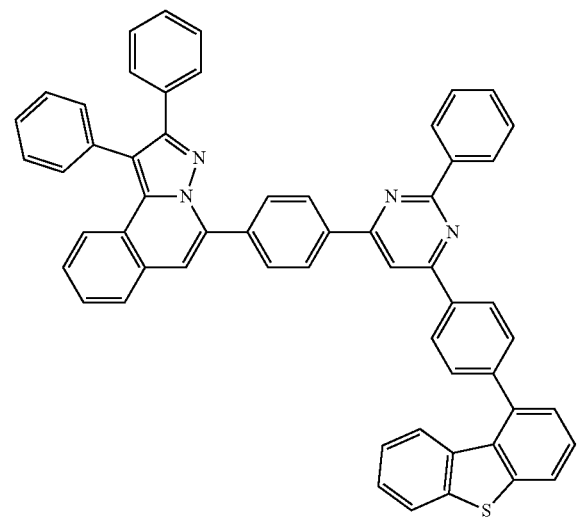
200
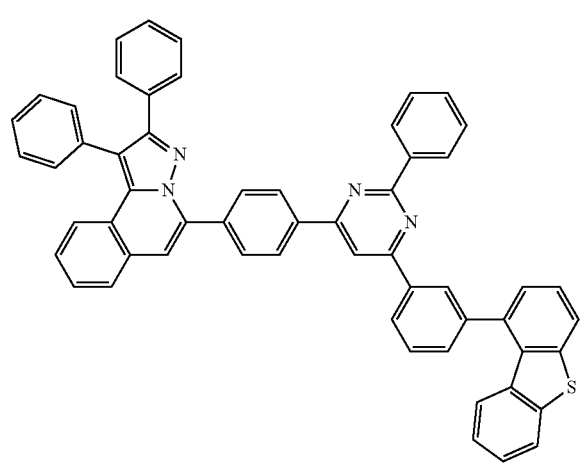
201
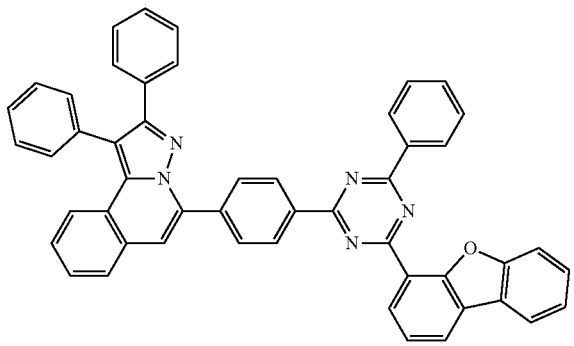
202
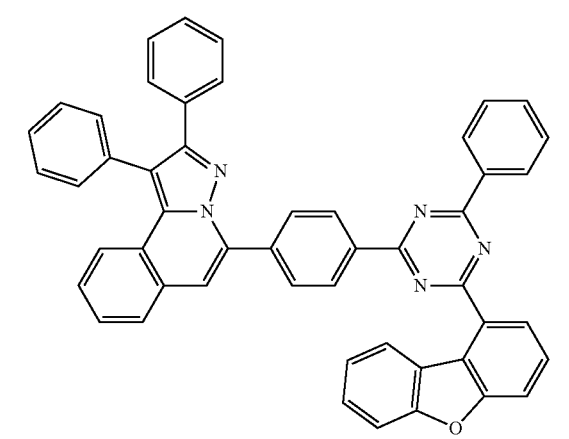
203
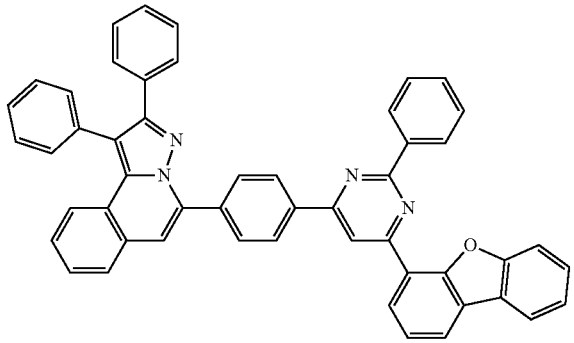
204
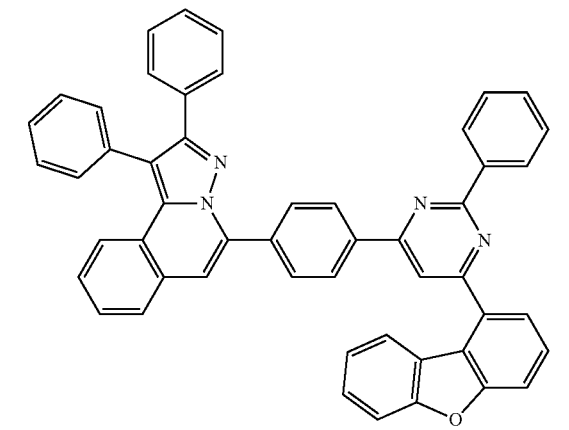

205
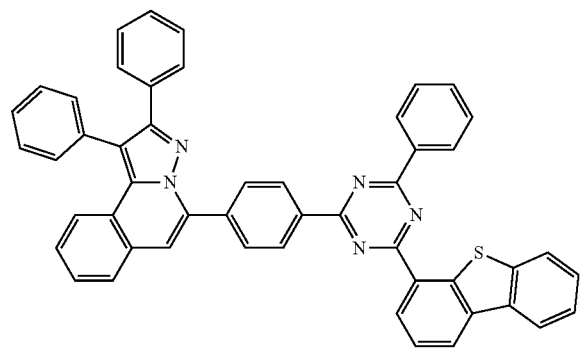
206
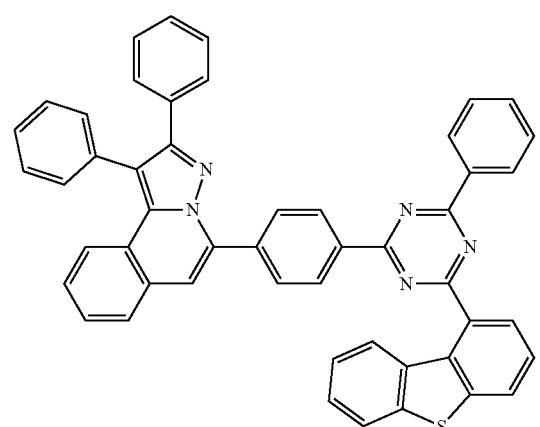
207
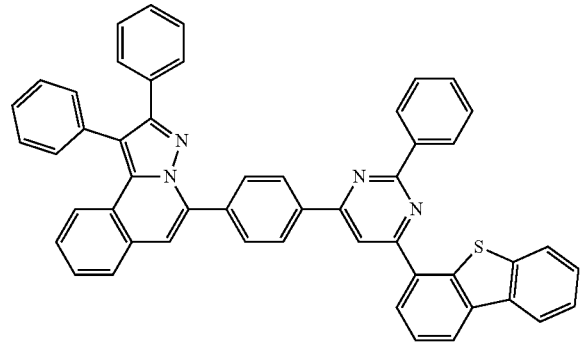
208
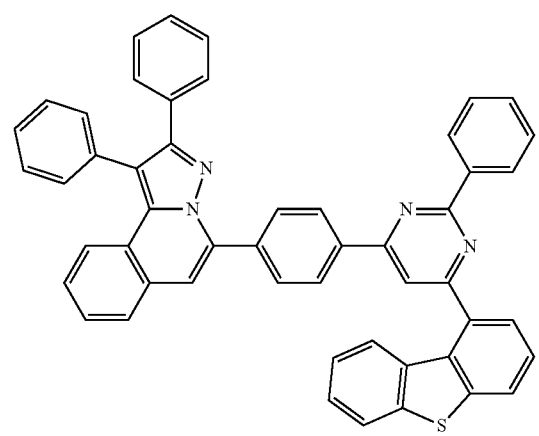
209
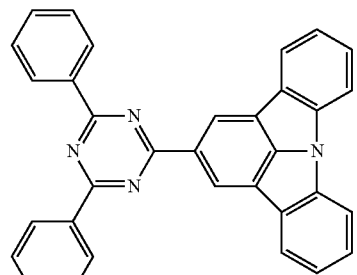
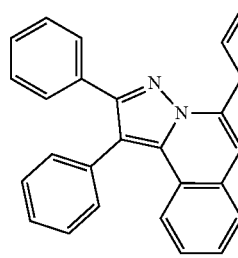
210
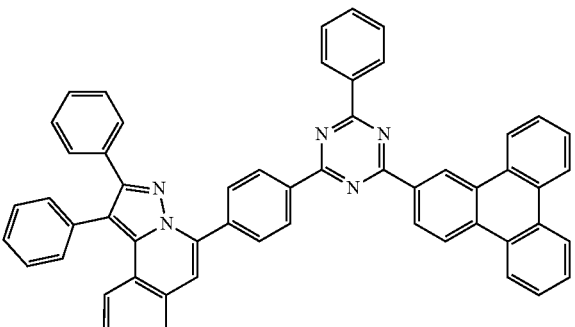
211
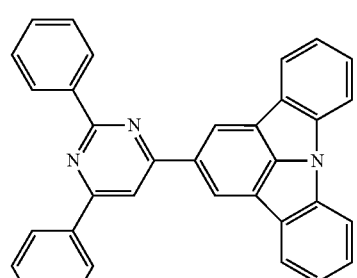

-continued
212
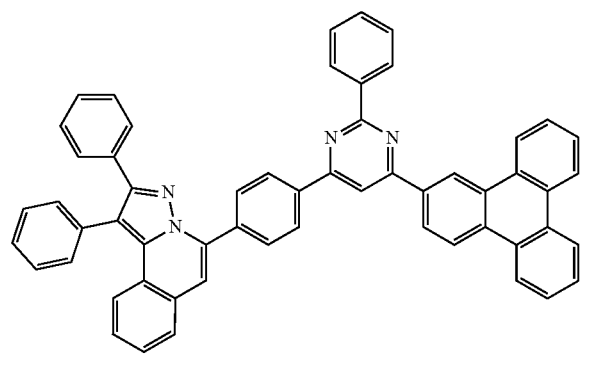
213
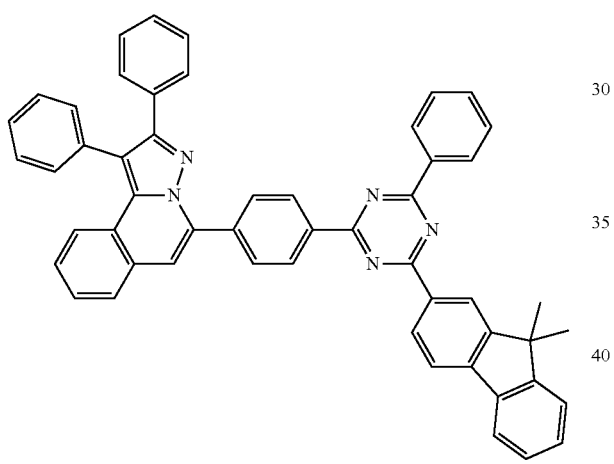
214
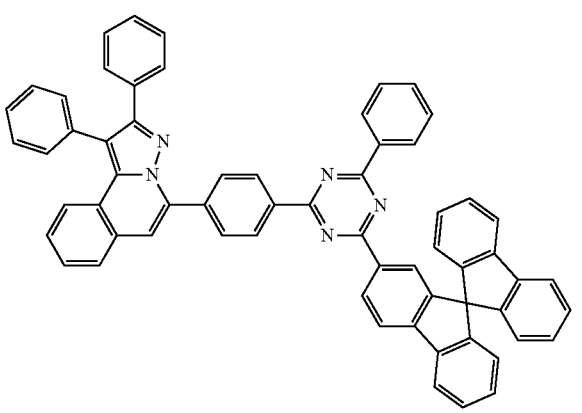
215
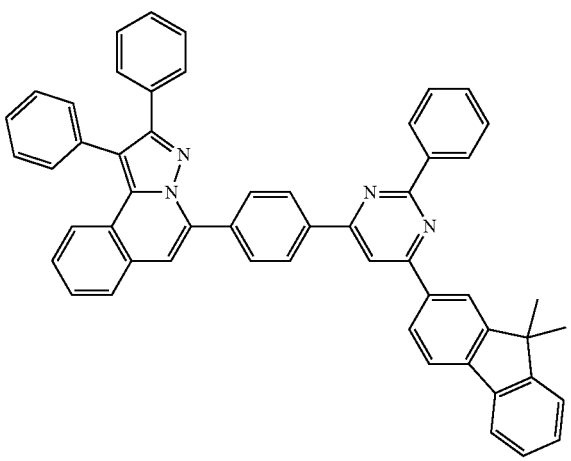
216
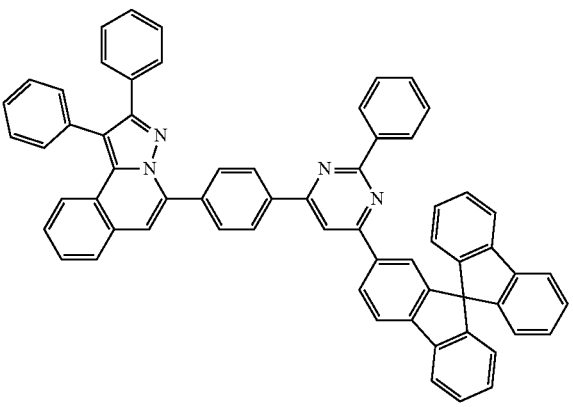
217
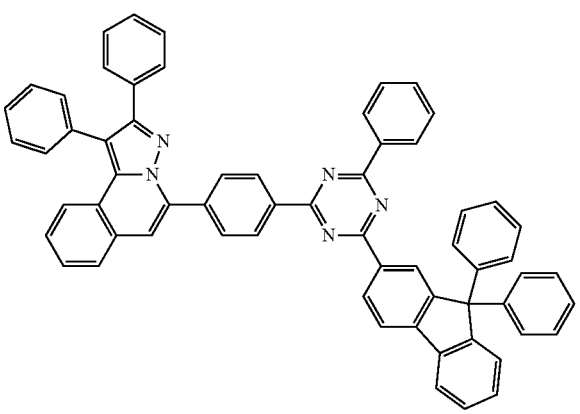

218
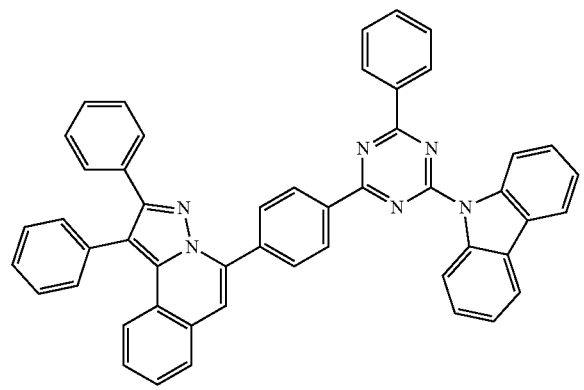
219
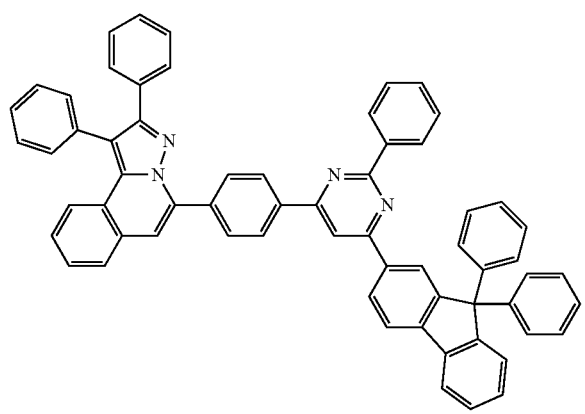
220
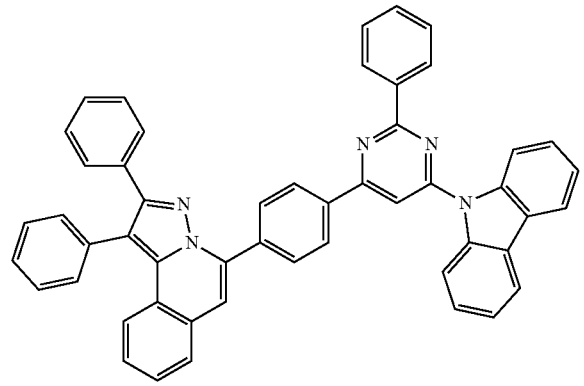
221
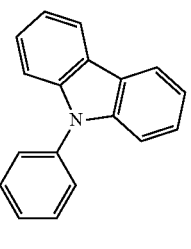
222
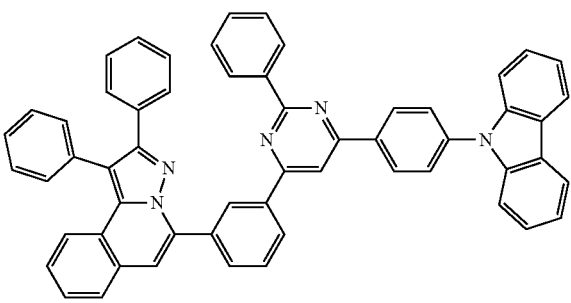
223
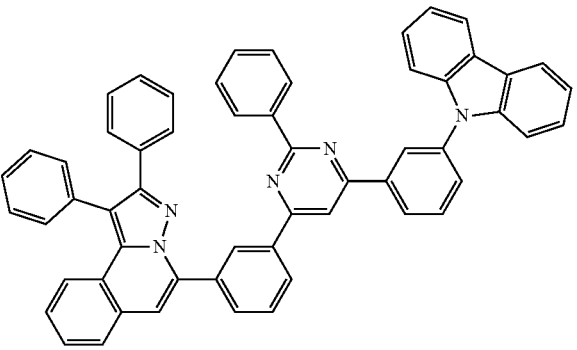
224
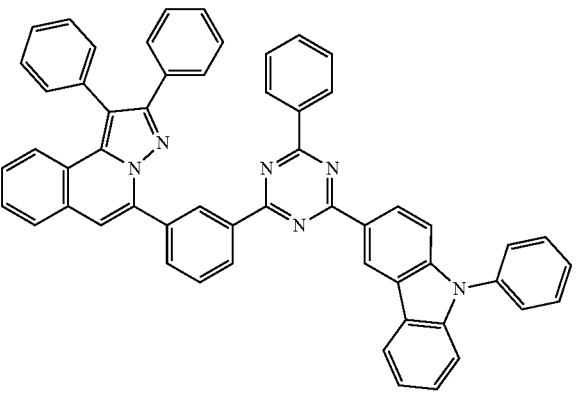
225

226
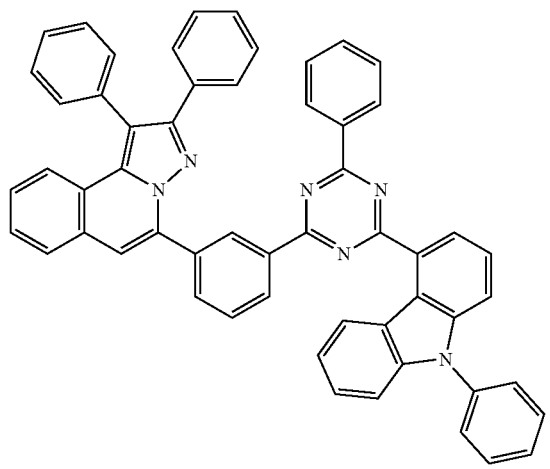
227
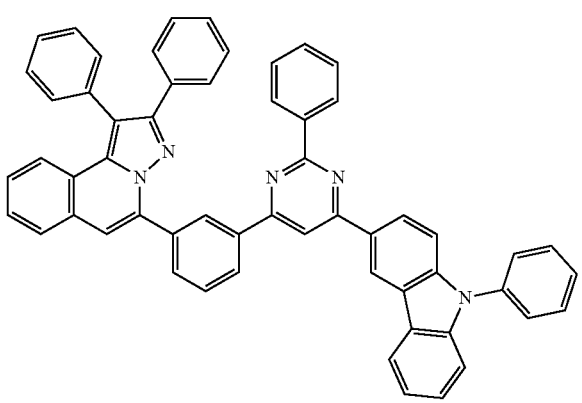
228
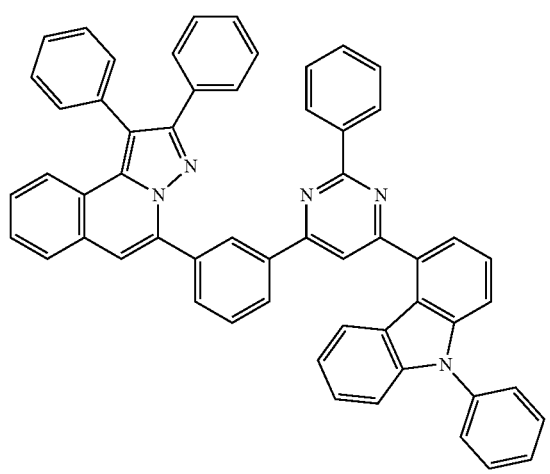
229
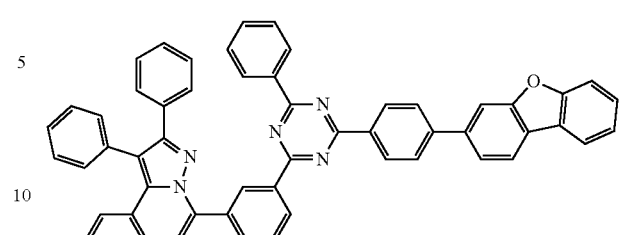
230
231
232

233
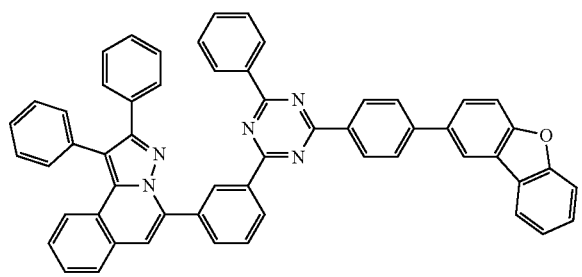
234
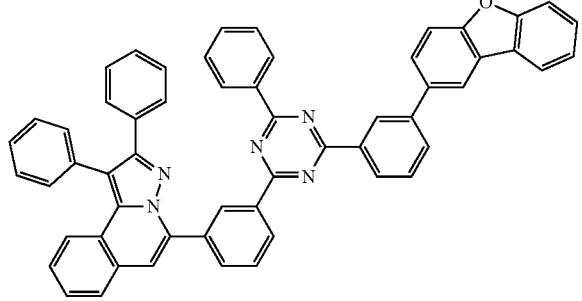
235
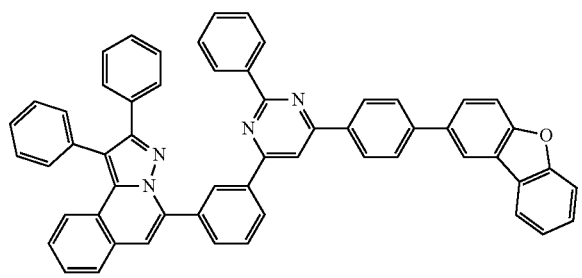
236
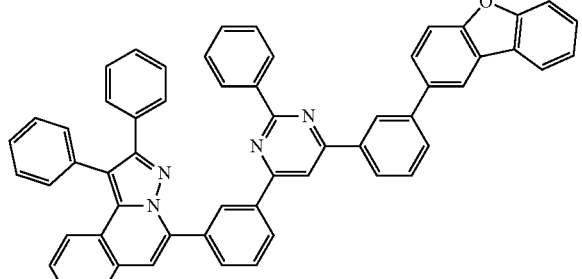
237
238
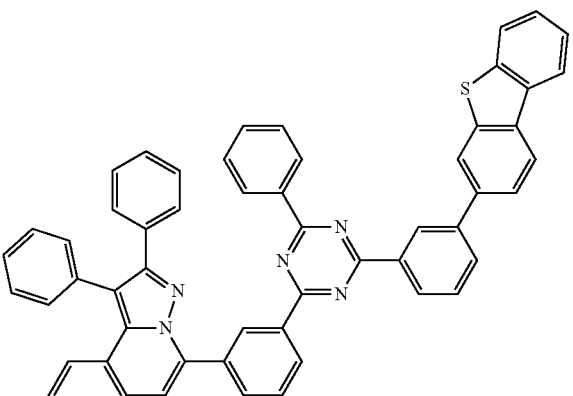
239
240
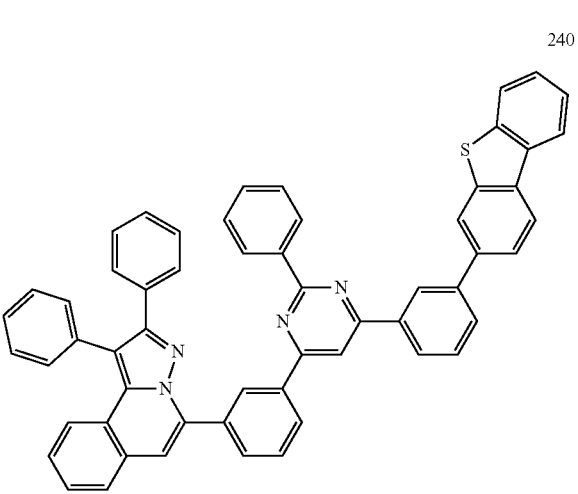

241
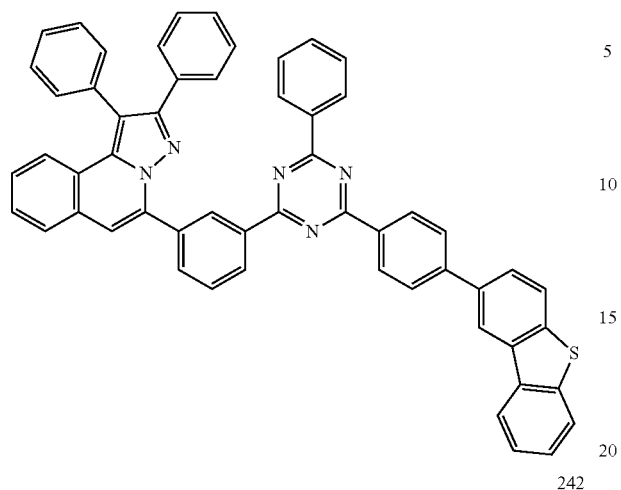
242
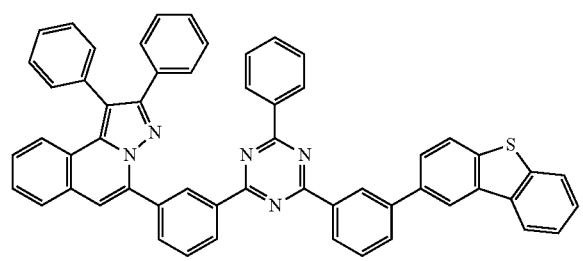
243
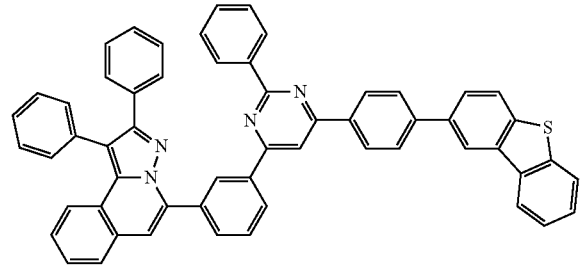
244
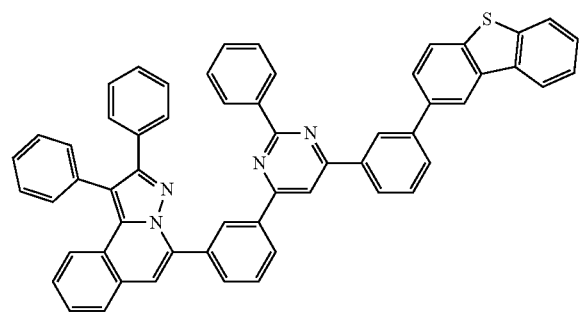
245
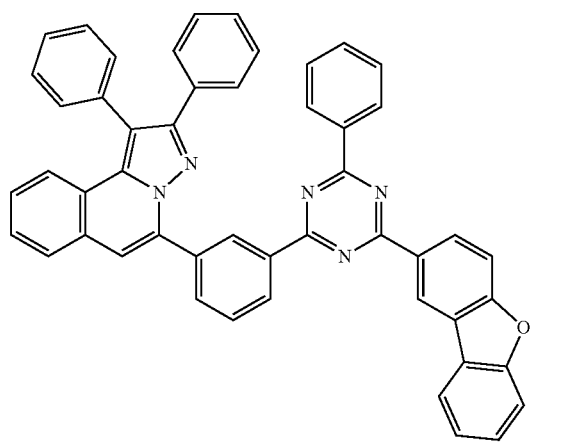
246
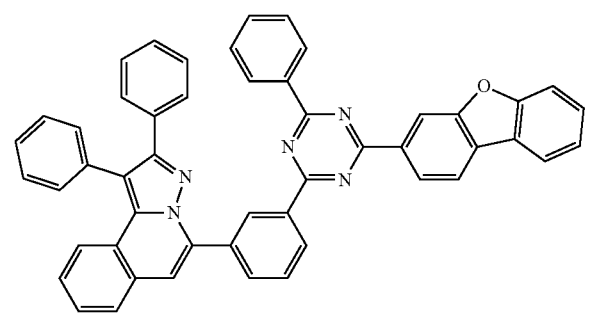
247
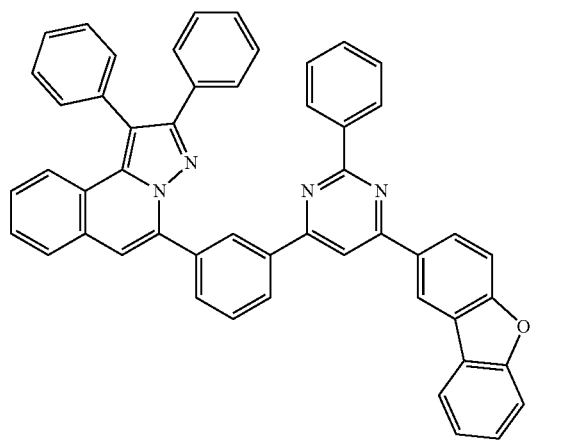
248
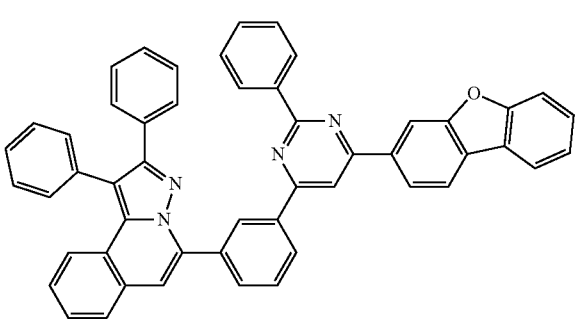

249
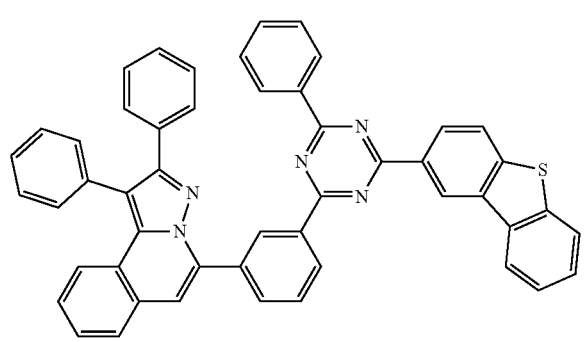
253
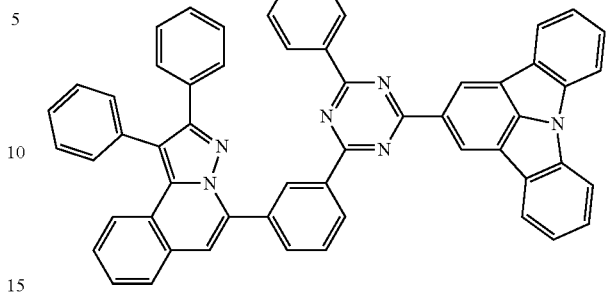
250
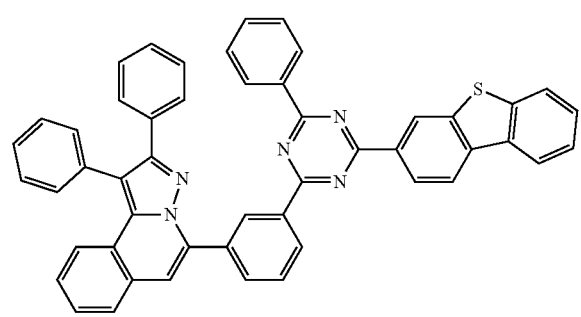
251
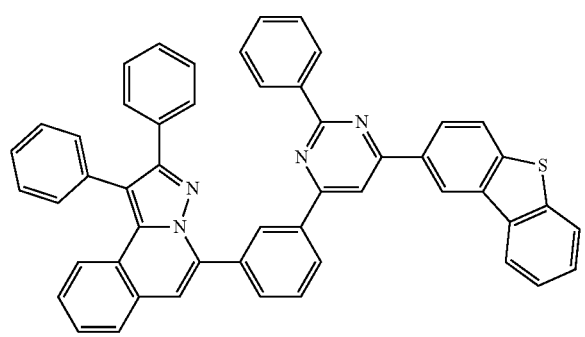
254
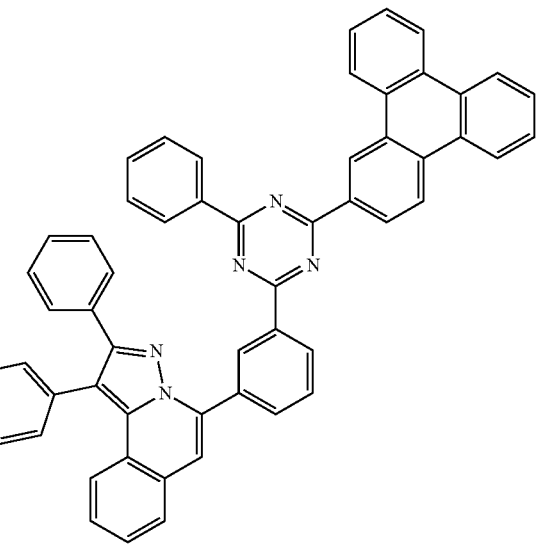
252
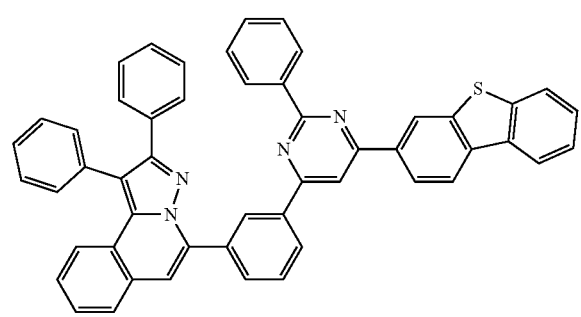
255
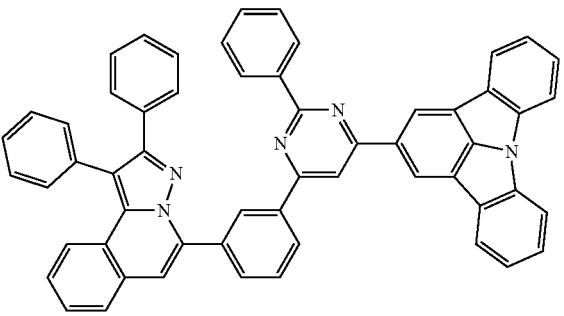

256
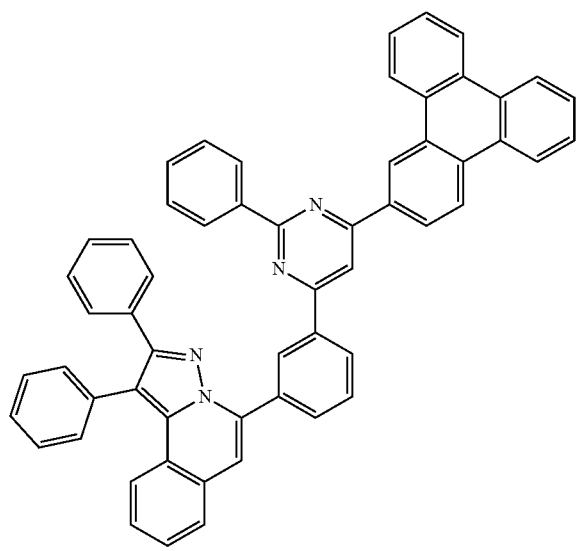
257
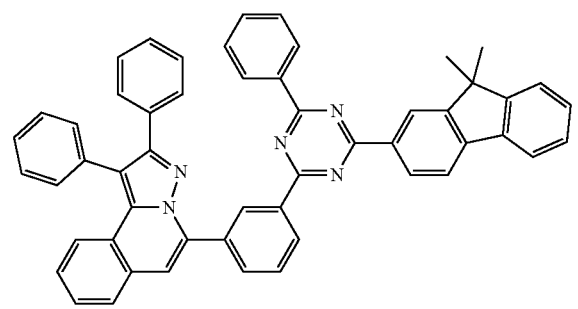
258
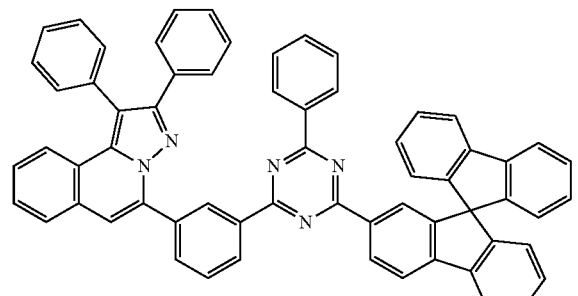
259
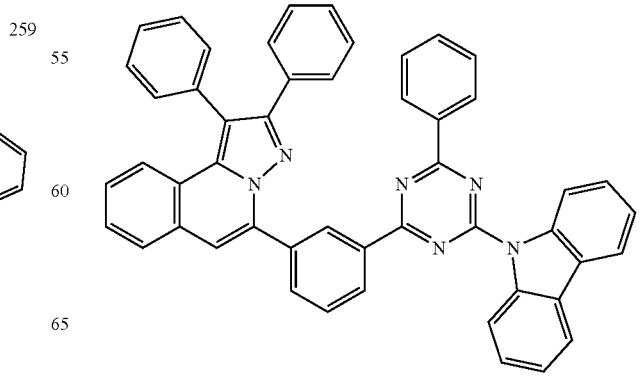
260
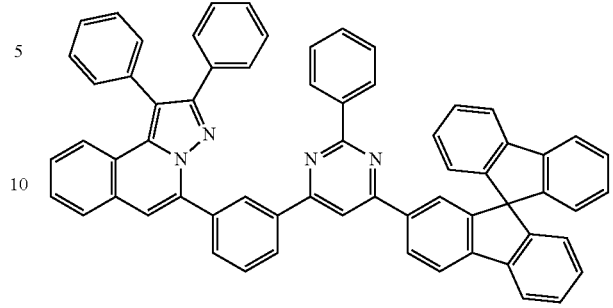
261
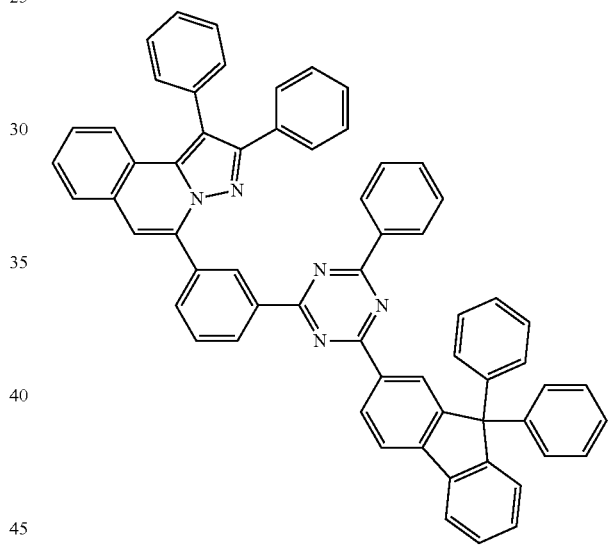
262

263
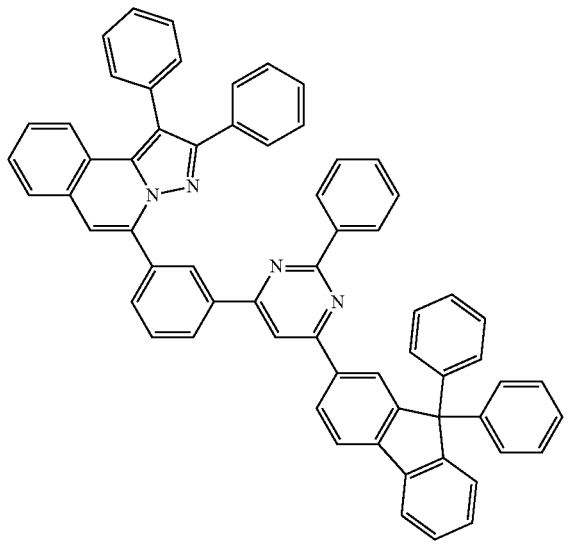
264
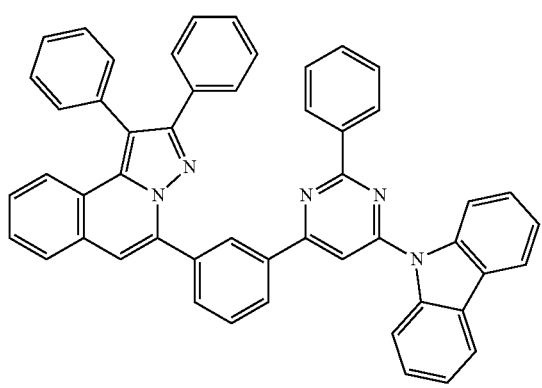
265
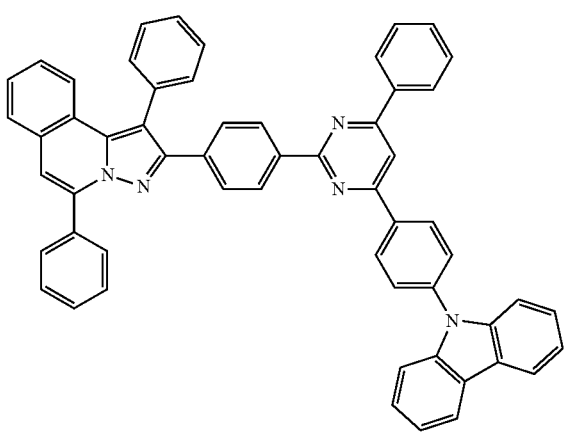
266
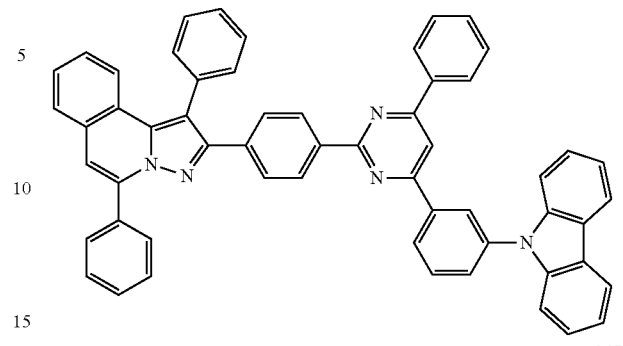
267
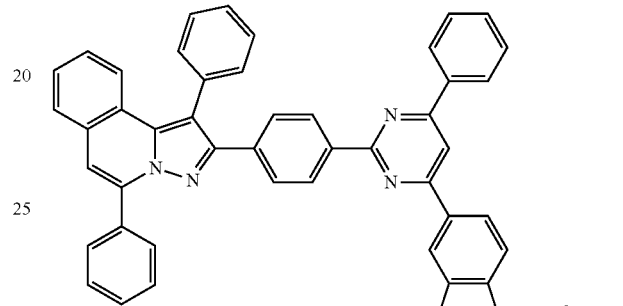
268
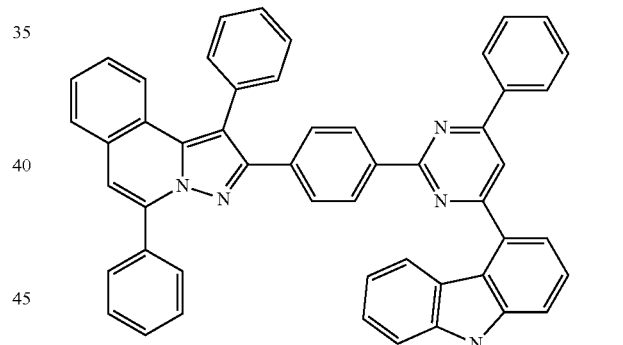
269
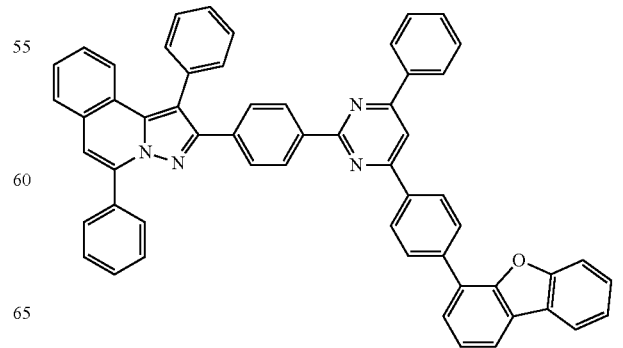

270
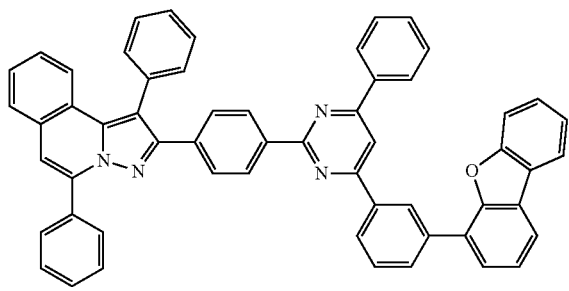
271
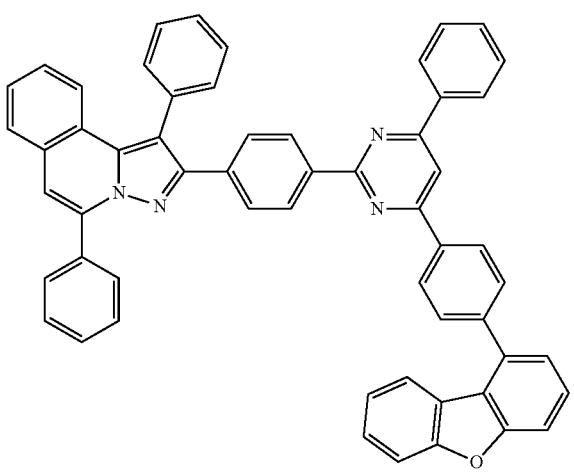
272
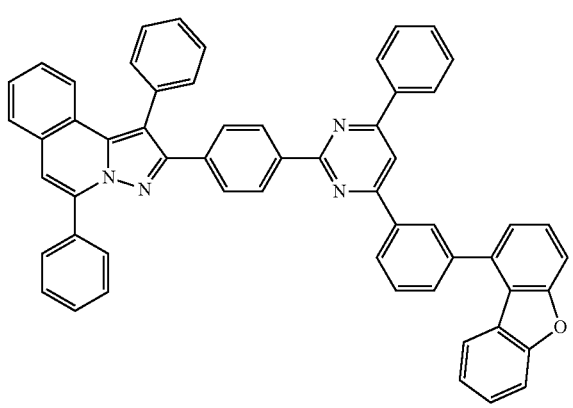
273
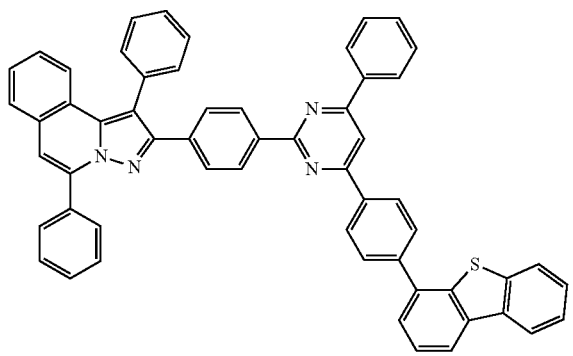
274
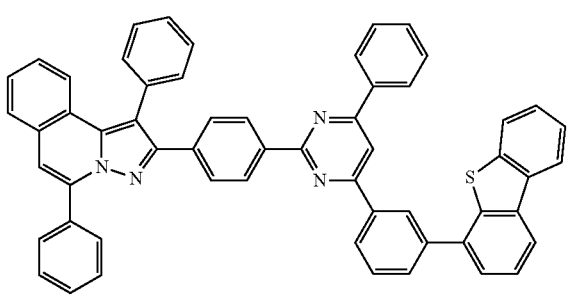
275
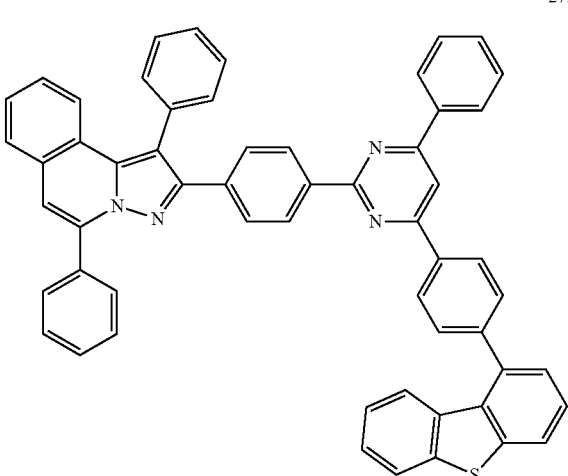
276
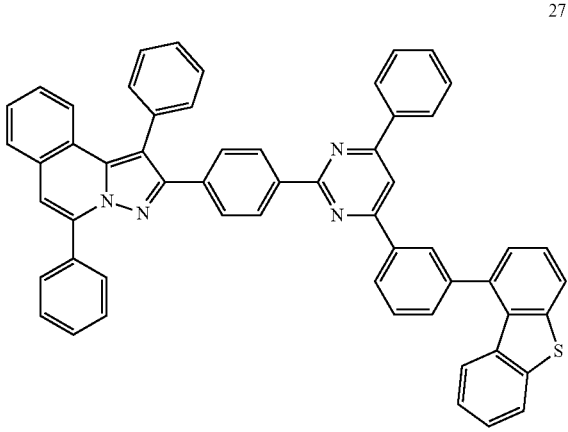
277
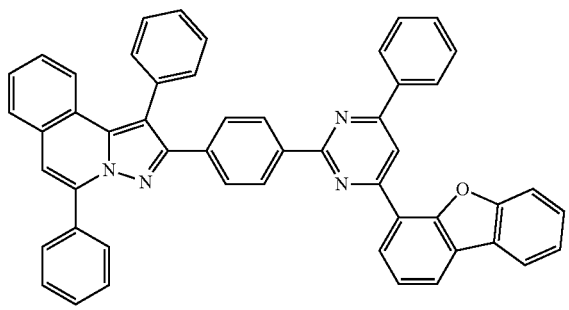

278
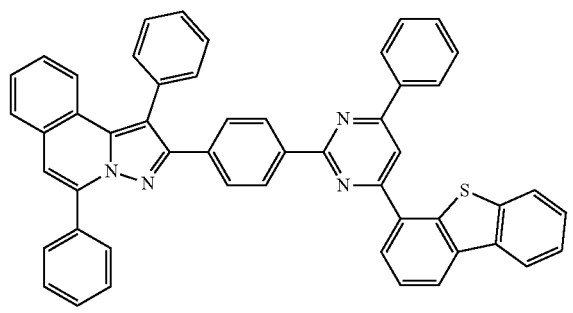
279
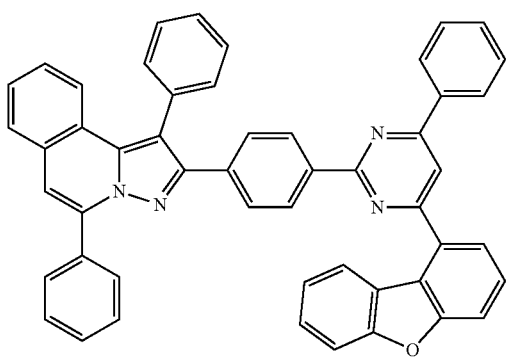
280
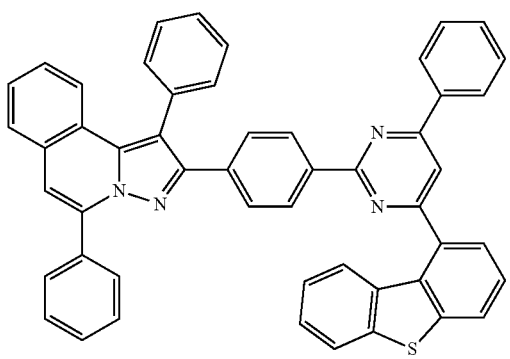
281
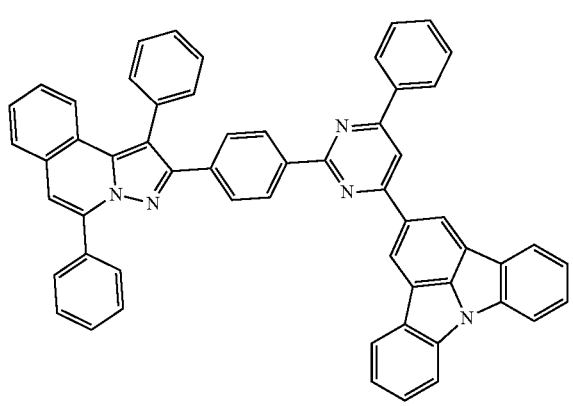
282
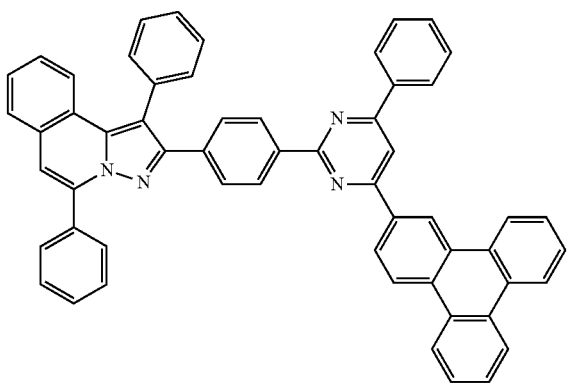
283
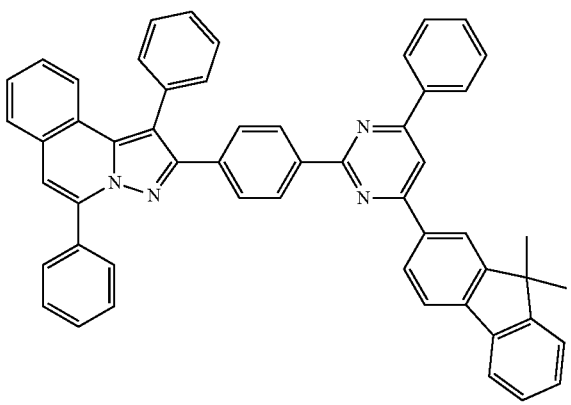
284
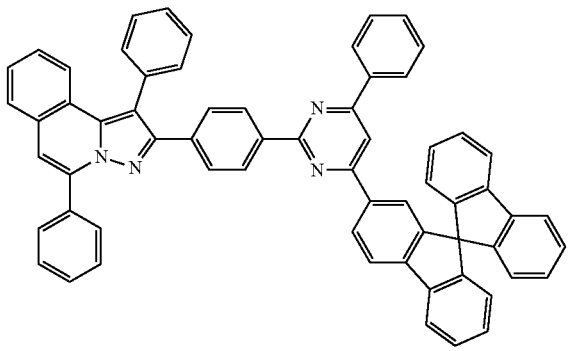
285
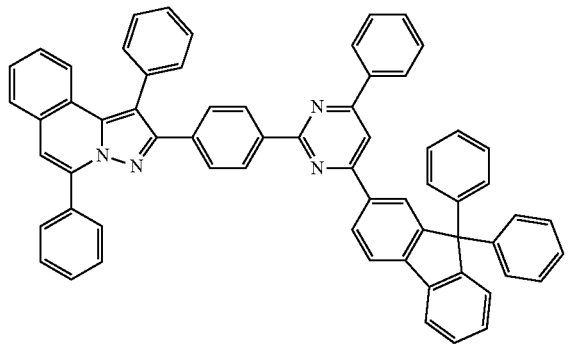

286
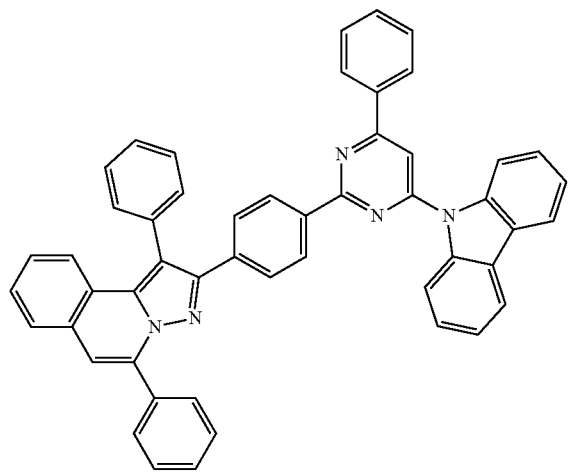
287
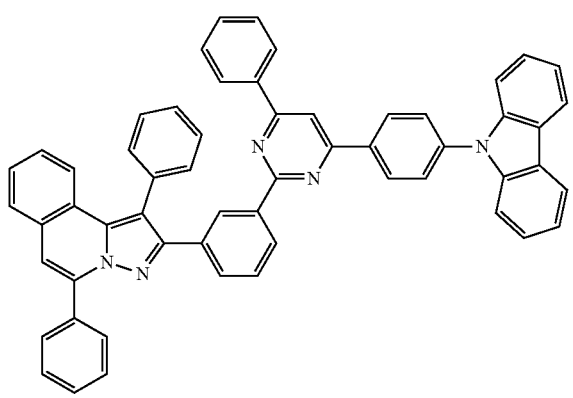
288
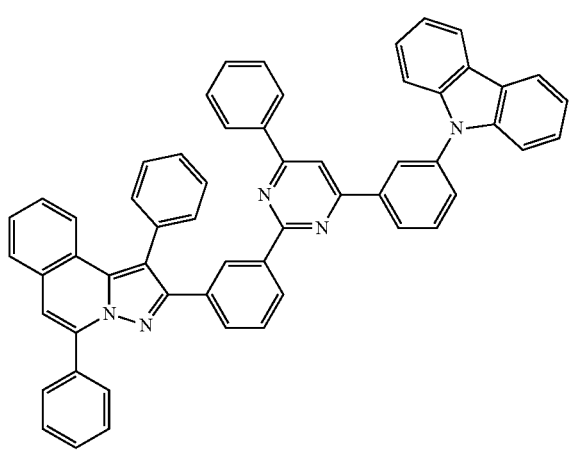
289
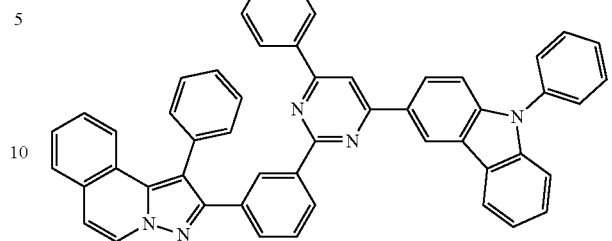
290
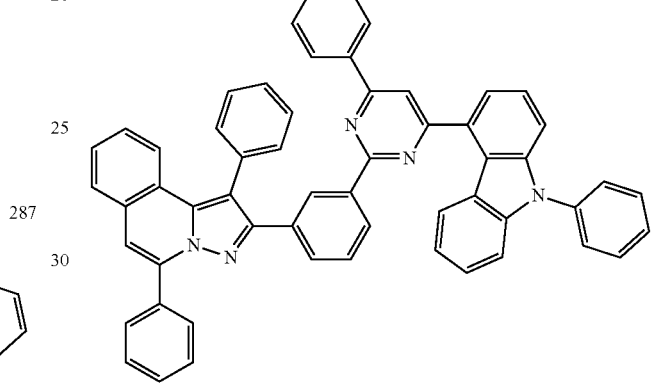
291
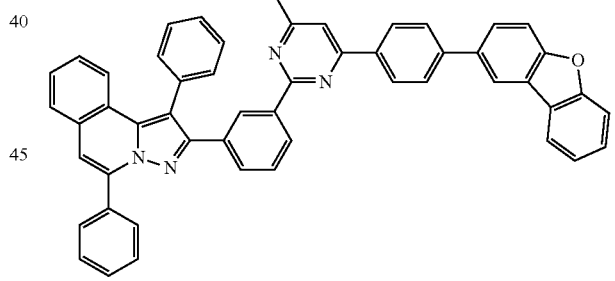
292
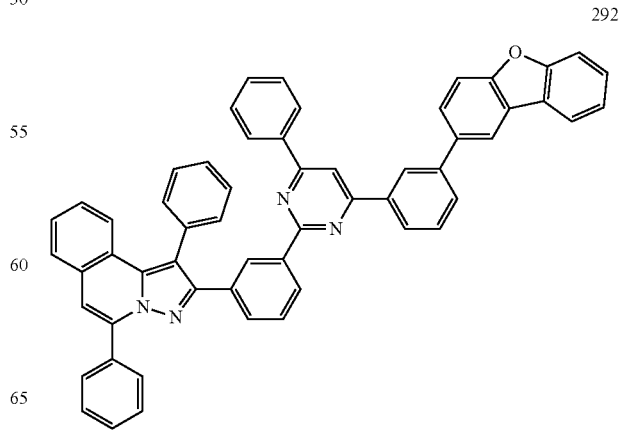

293
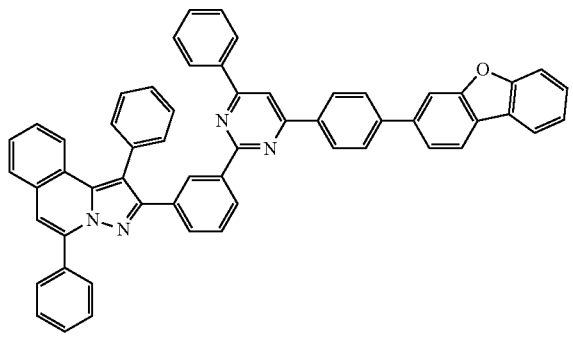
294
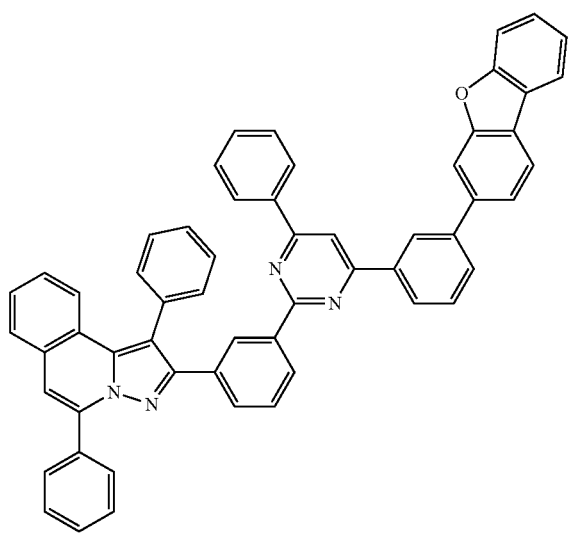
295
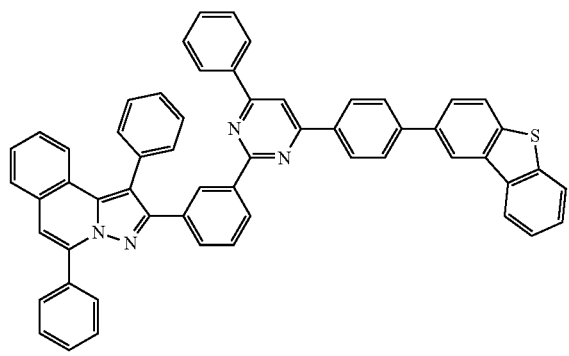
296
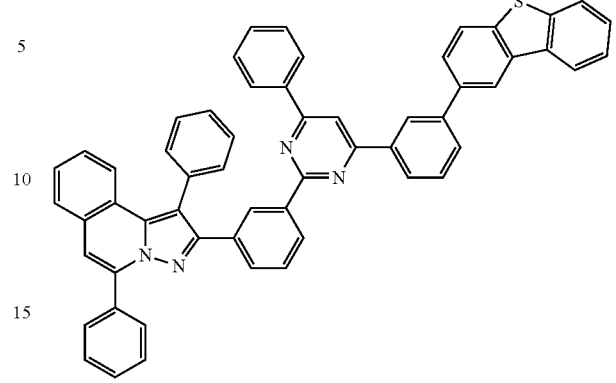
297
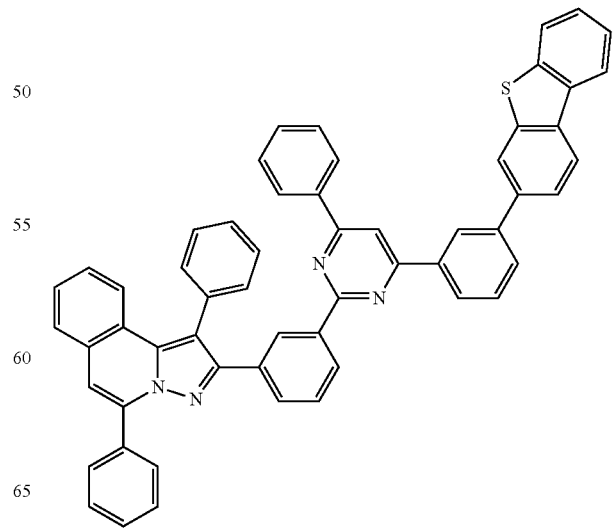
298

299
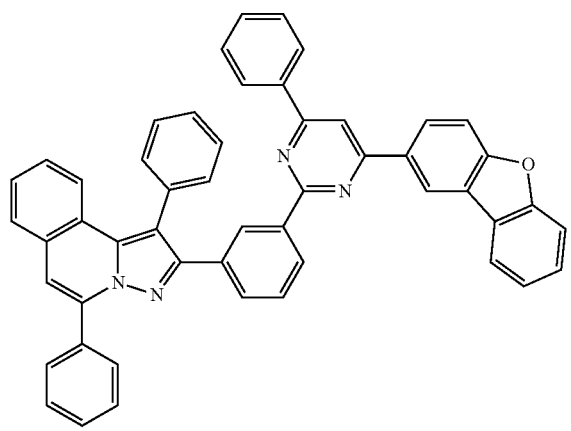
300
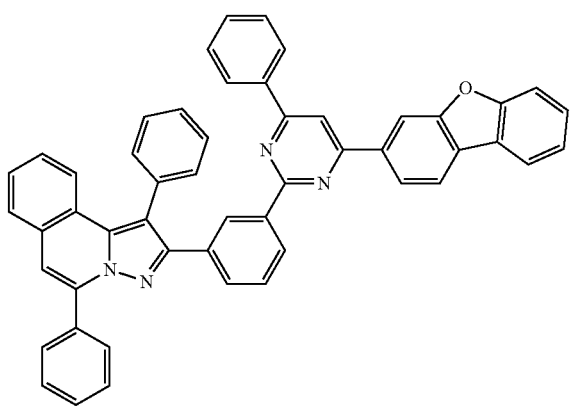
301
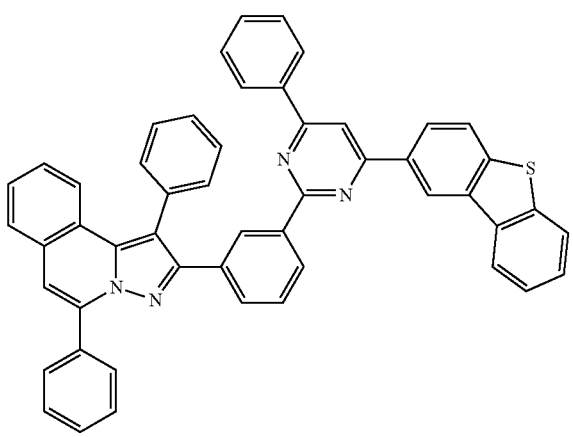
302
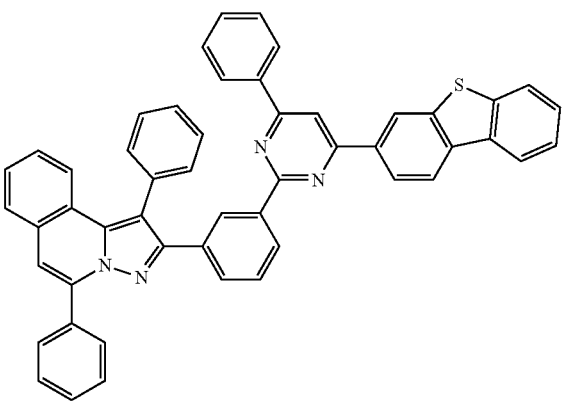
303
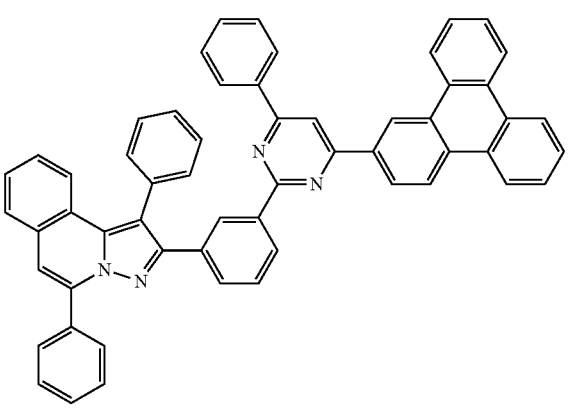
304

305
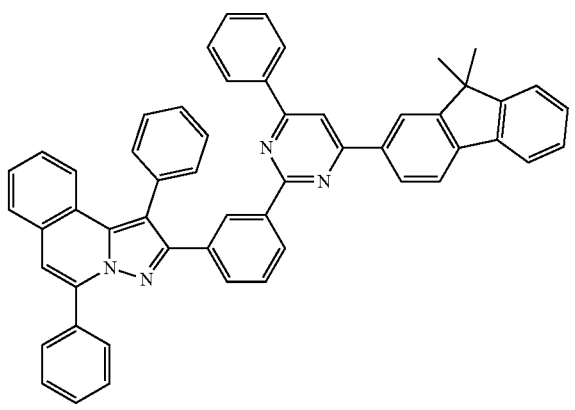
306
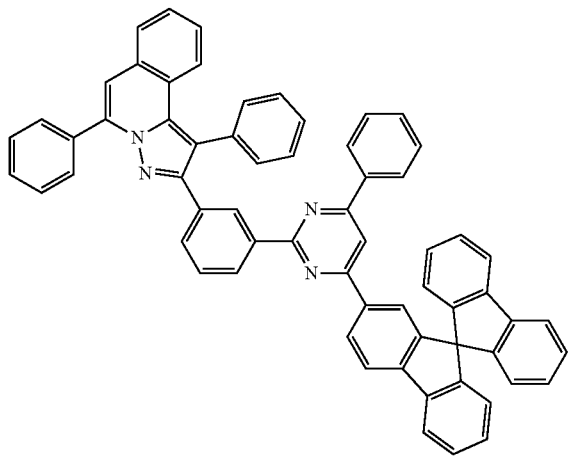
307
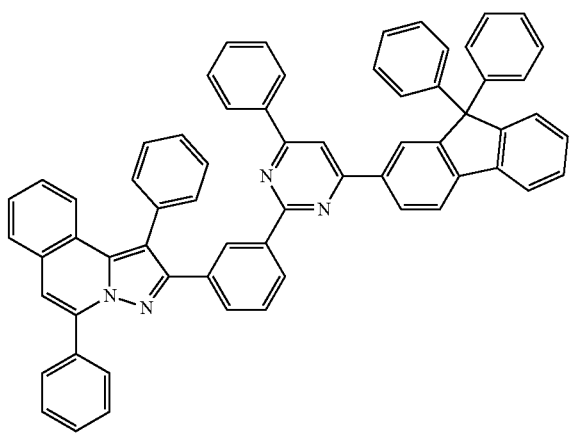
308
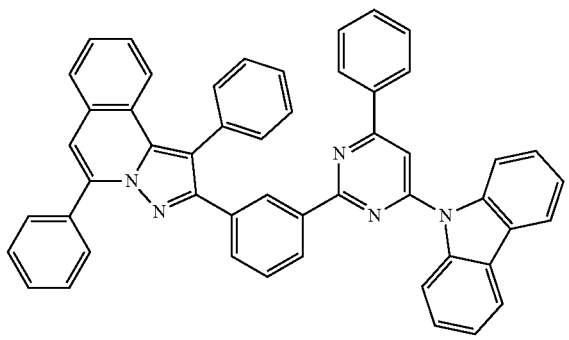
309
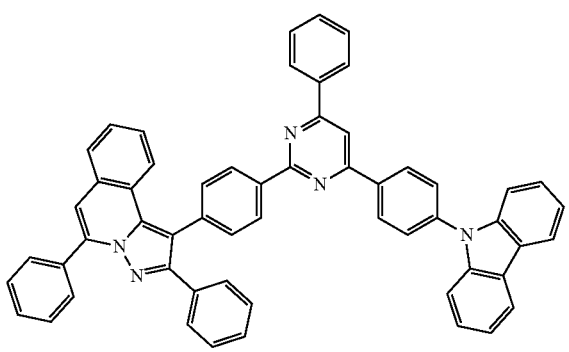
310
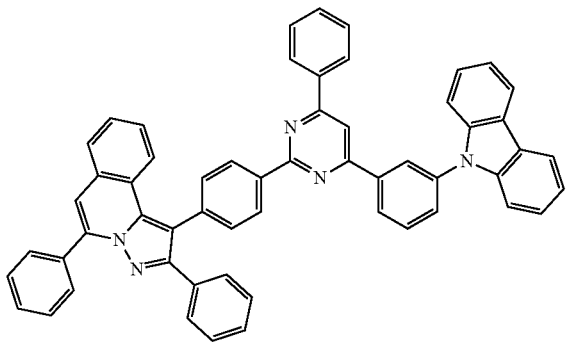
311
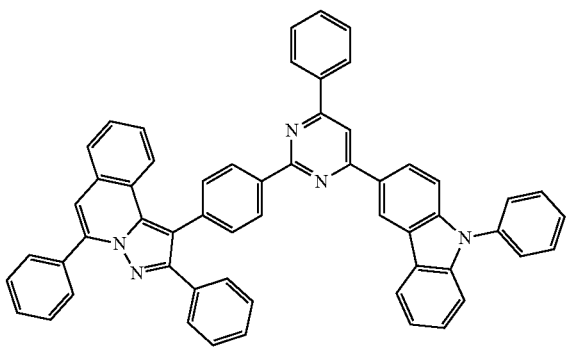

312
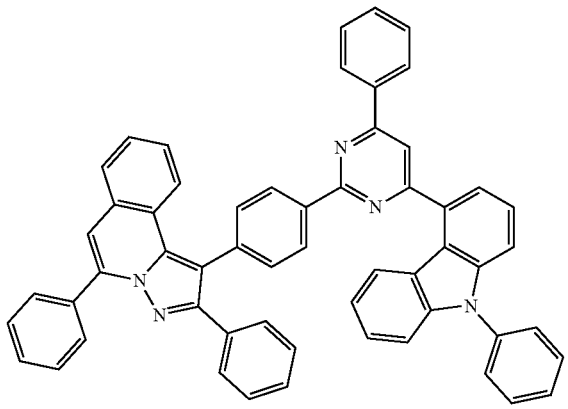
313
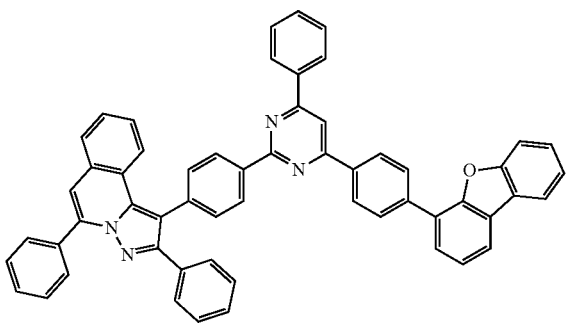
314
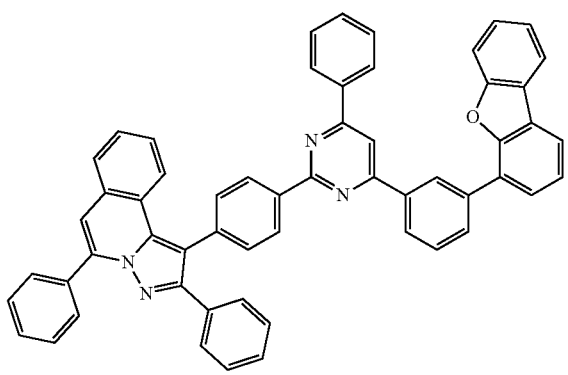
315
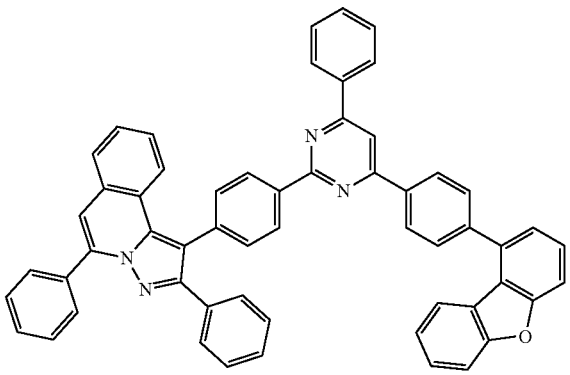
316
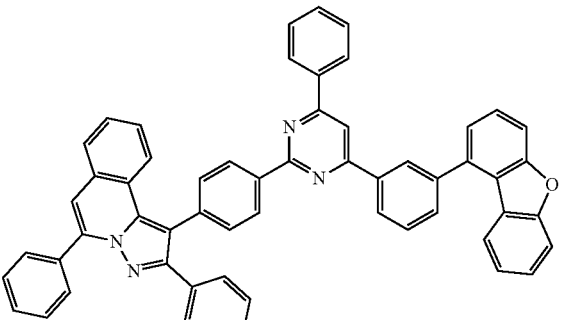
317
318
319
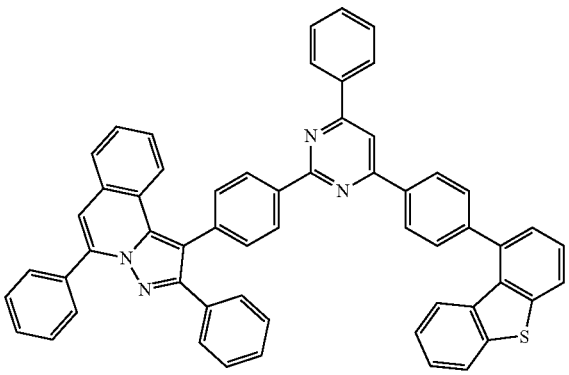

-continued
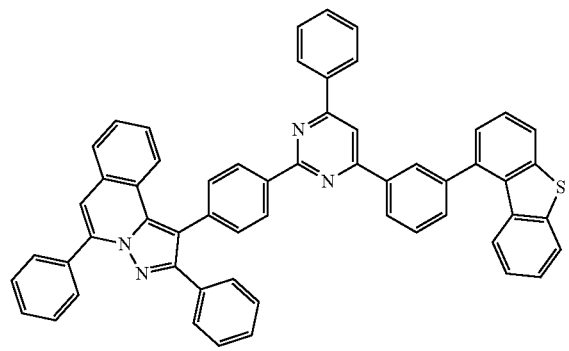
320
312
322
323
-continued
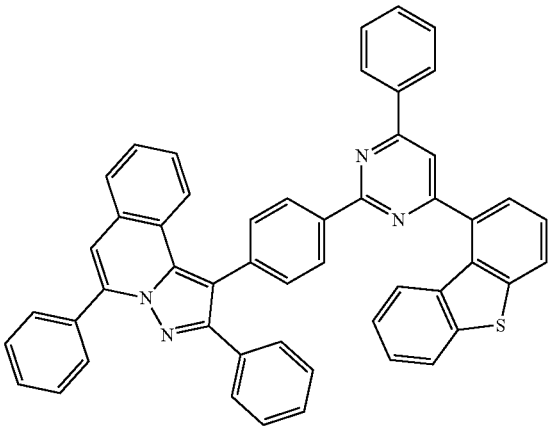
324
325
326
327

-continued
328
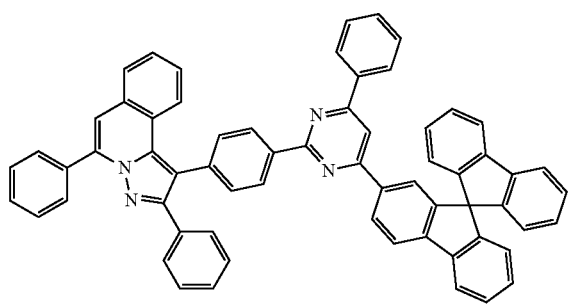
329
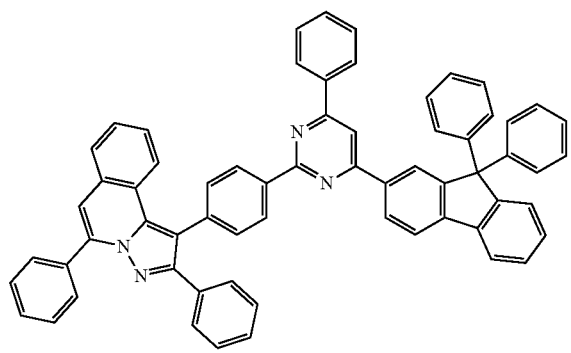
330
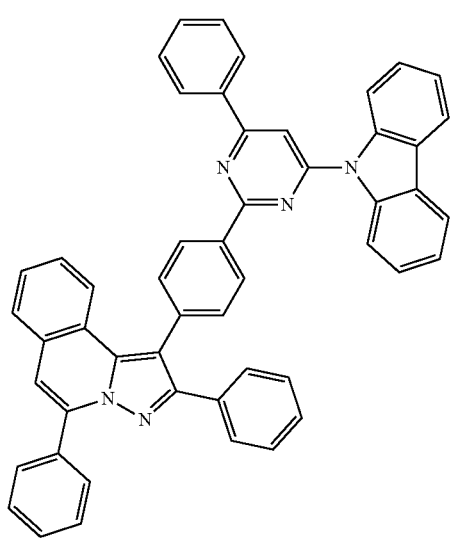
-continued
331
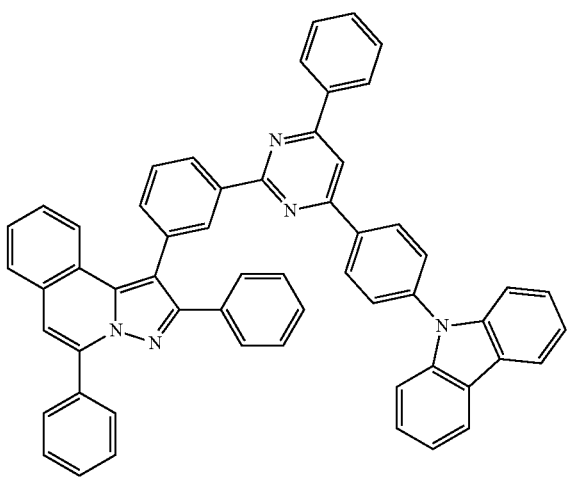
332
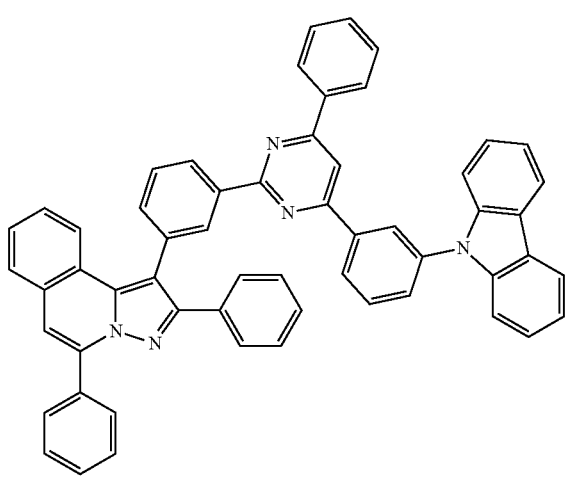
333

334
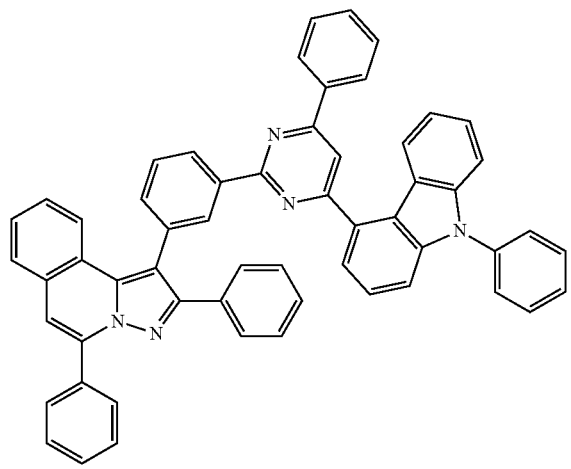
337
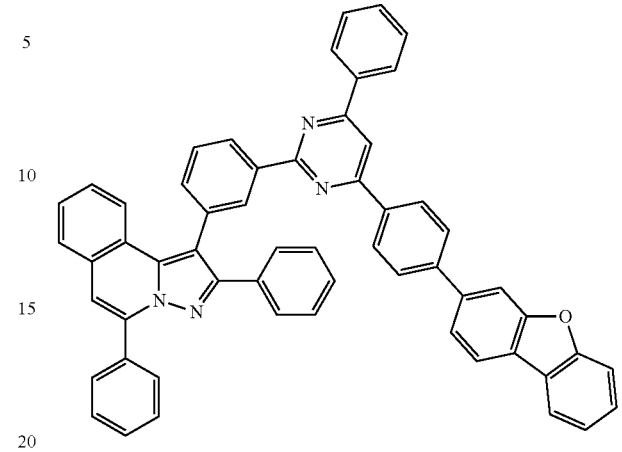
335
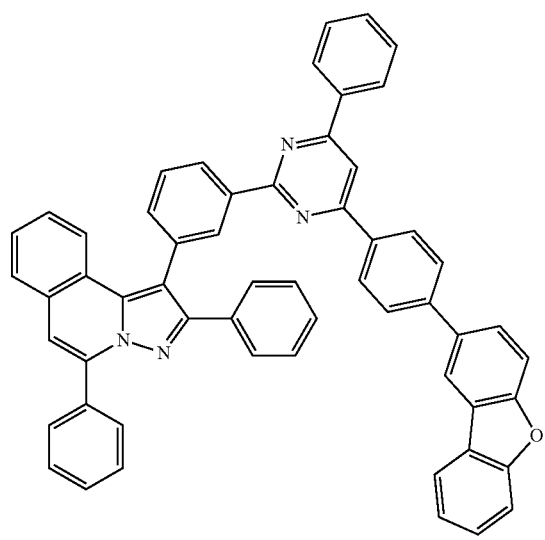
338
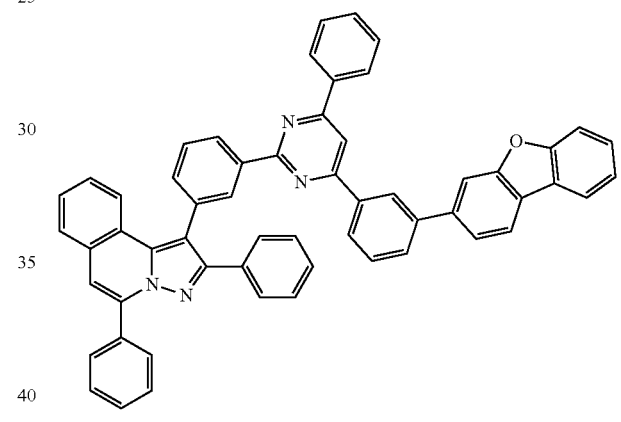
336
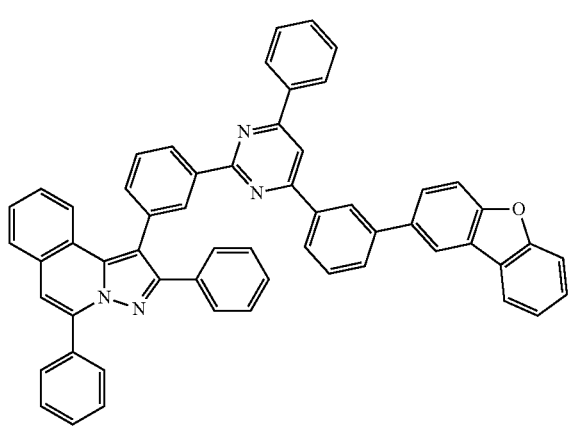
339
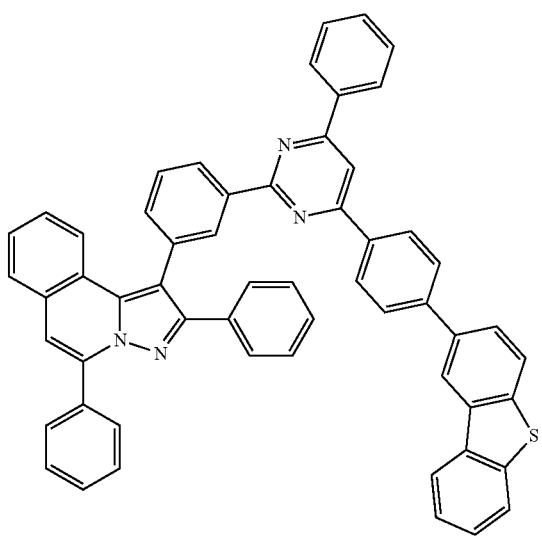

340
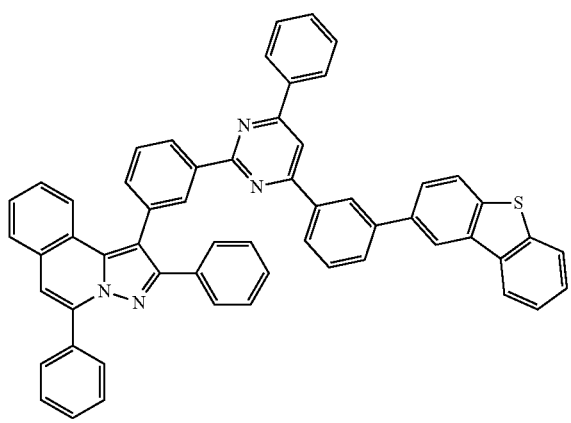
341
343
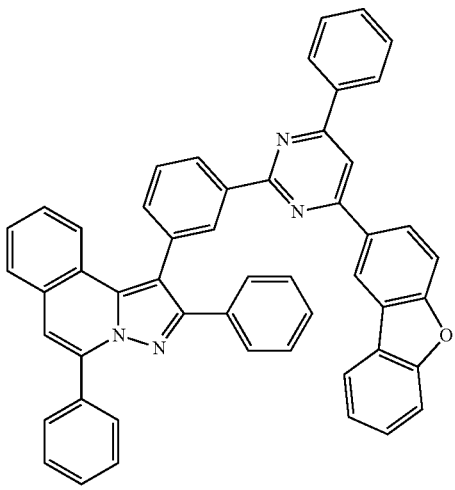
344
342
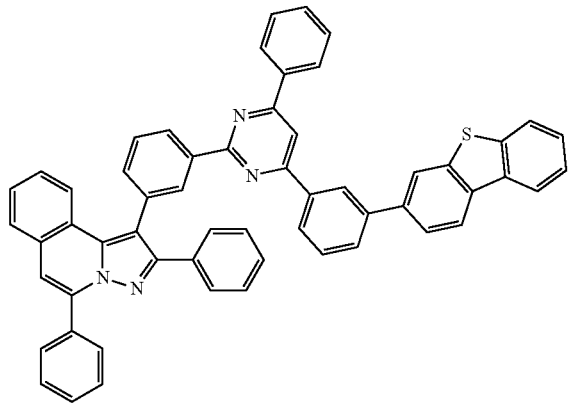
345
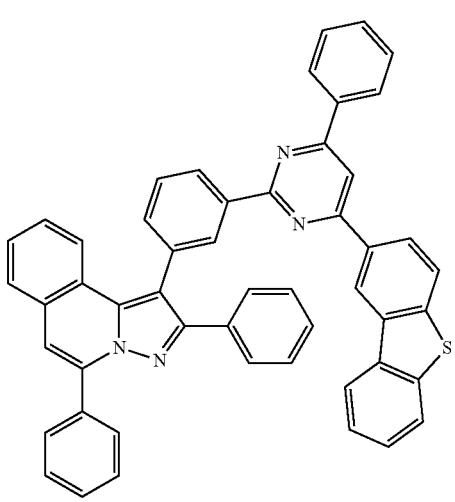

-continued
346
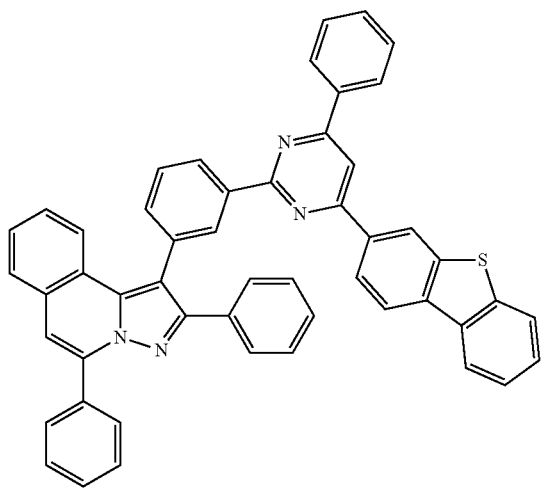
347
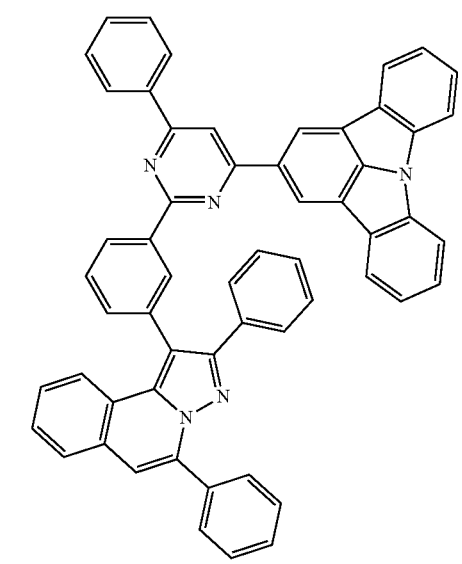
348
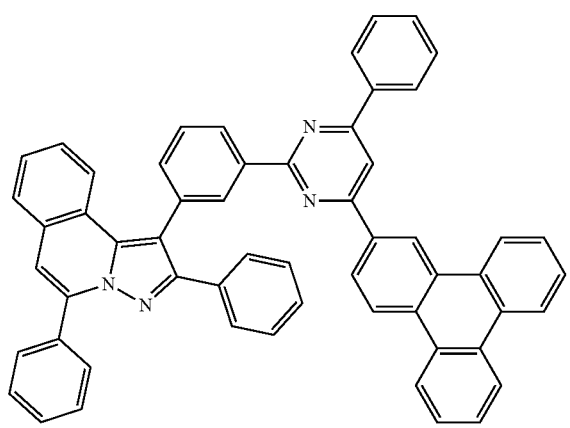
-continued
349
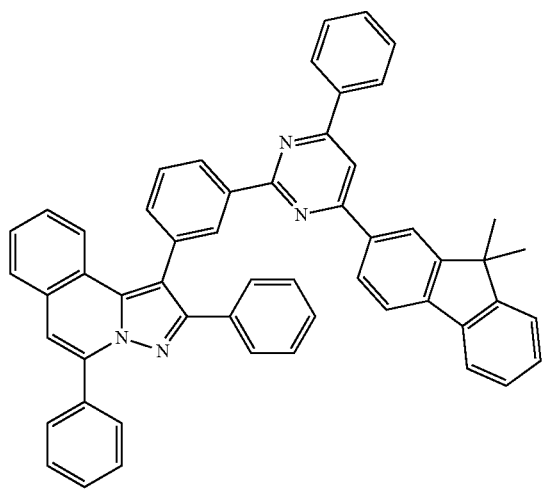
350
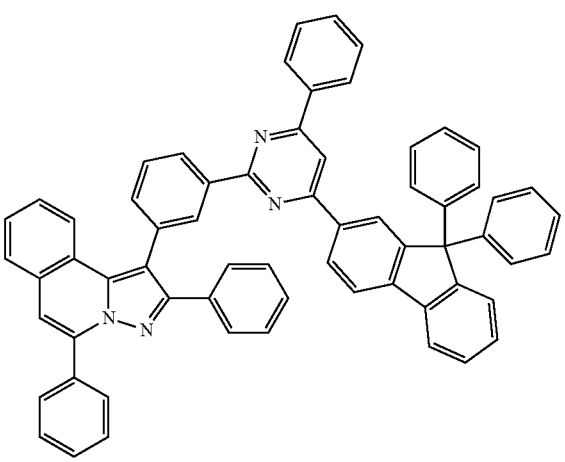
351

352
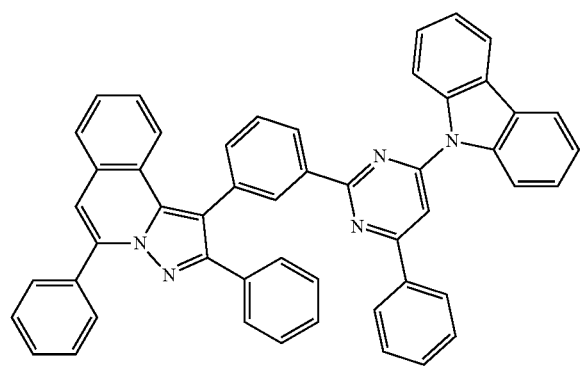
353
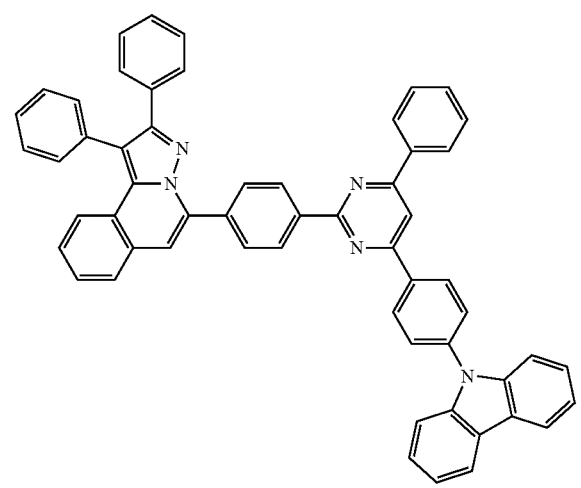
354
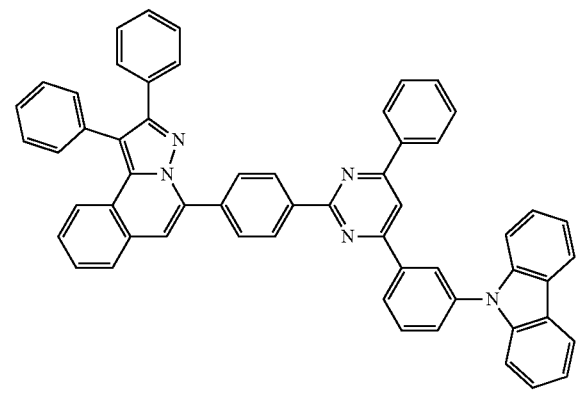
355
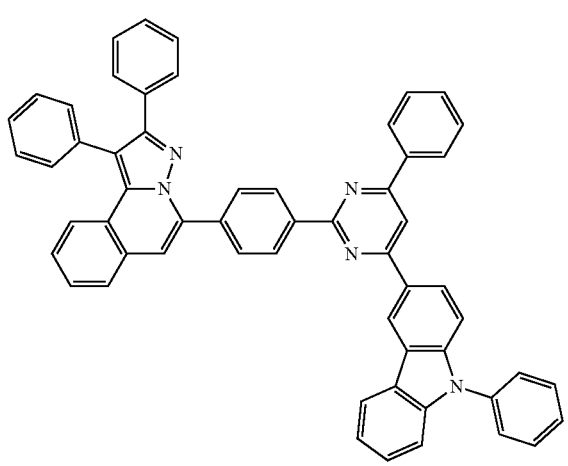
356
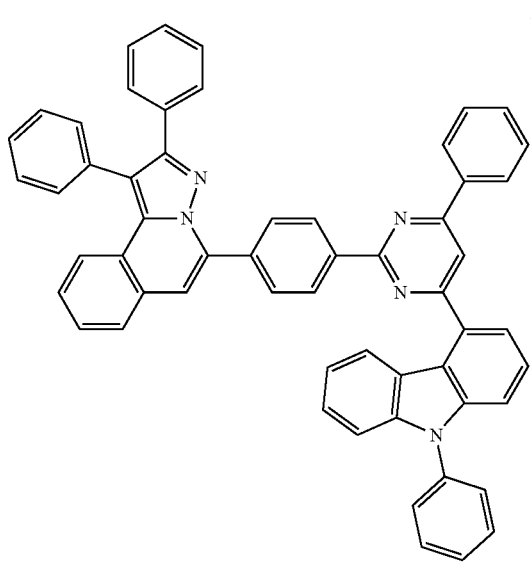
357
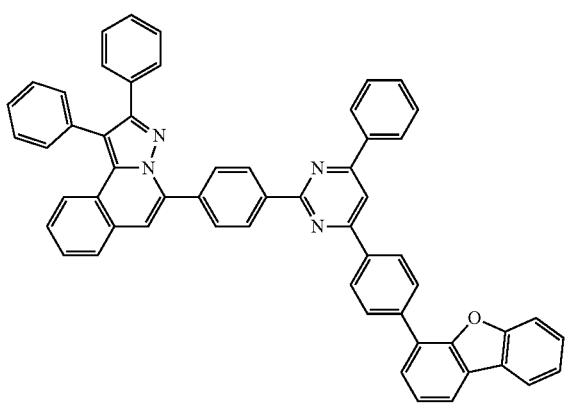

358
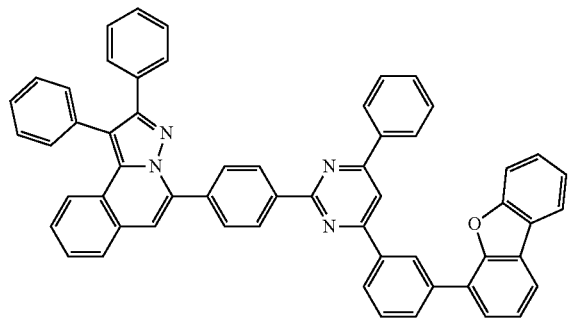
359
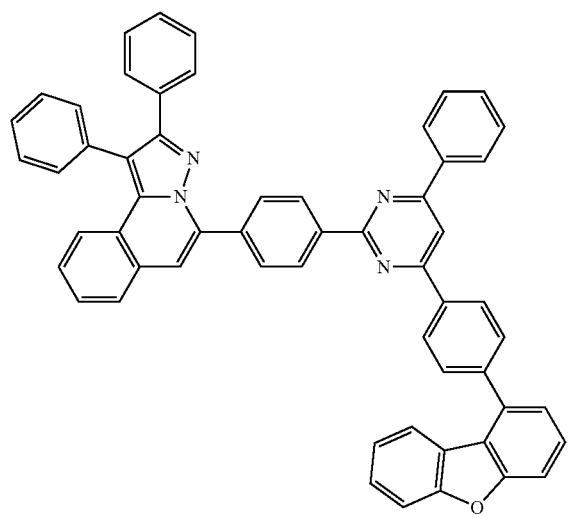
360
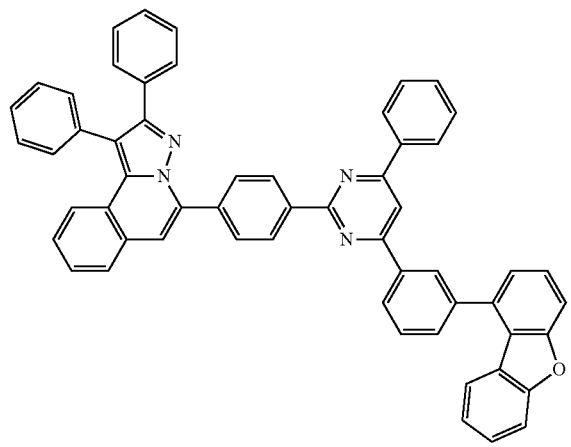
361
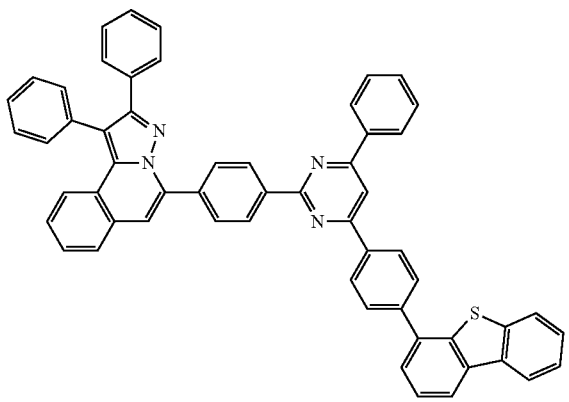
362
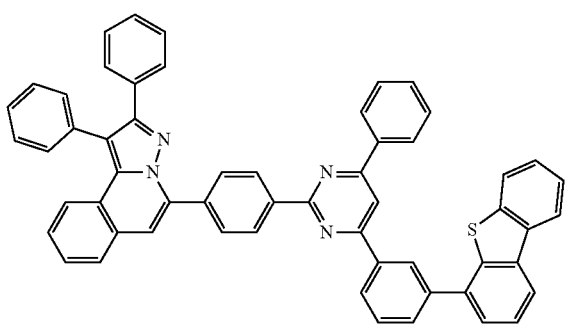
363
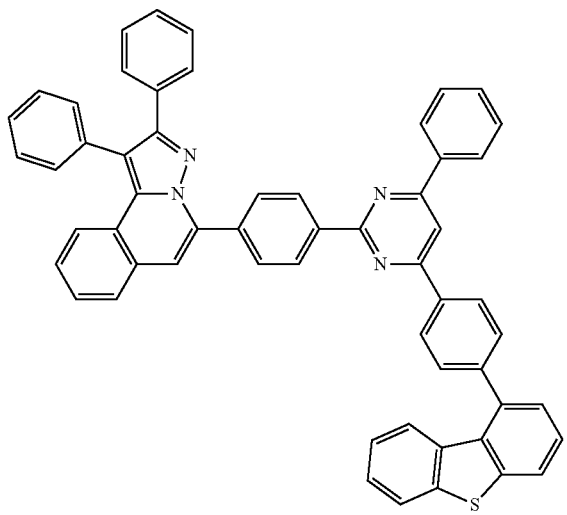

364
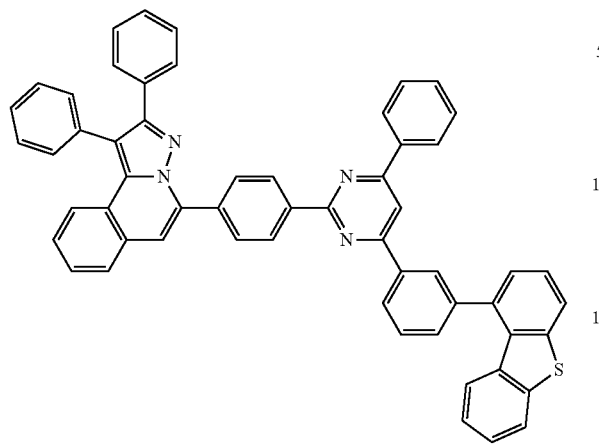
365
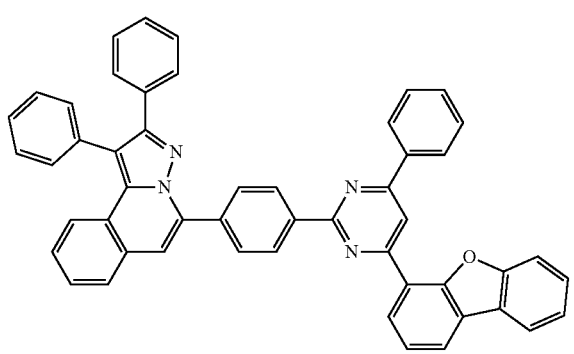
366
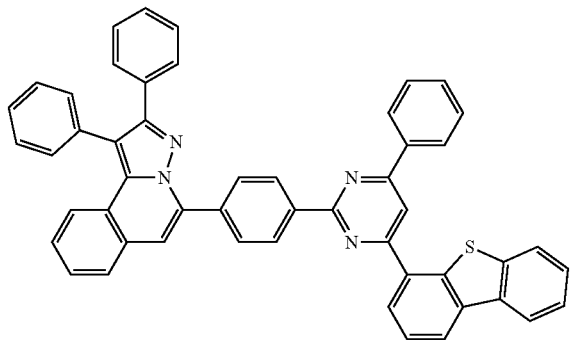
367
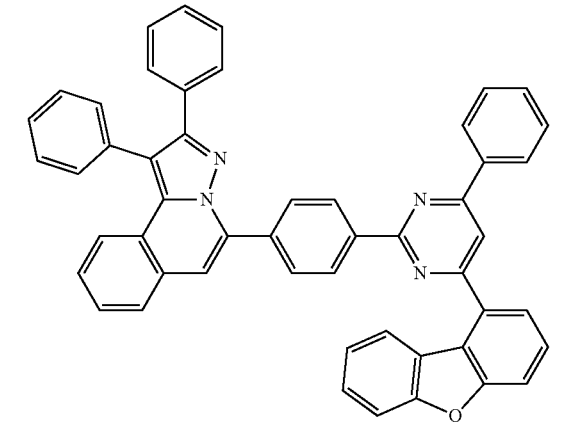
368
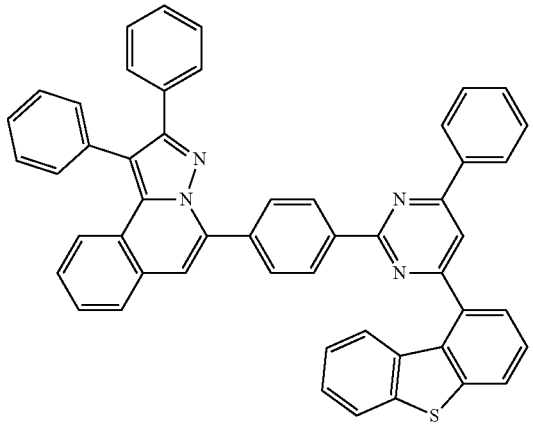
369
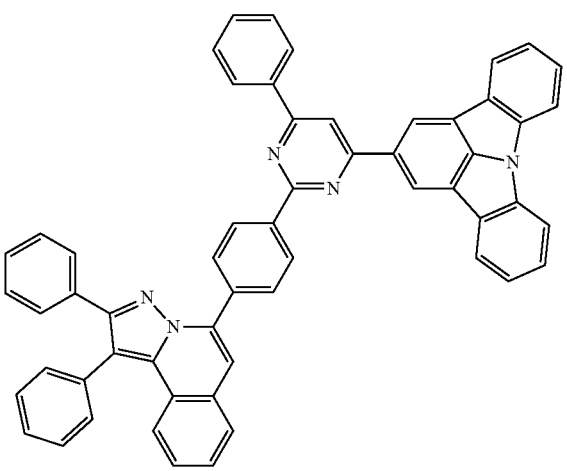
370
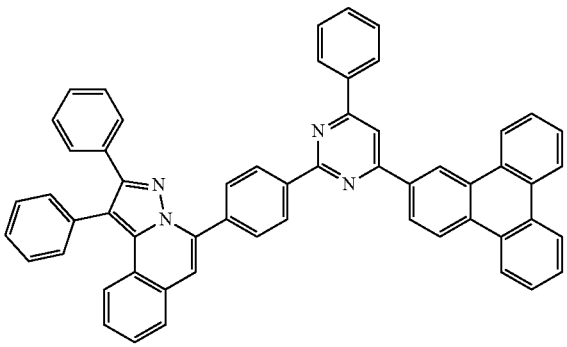
371
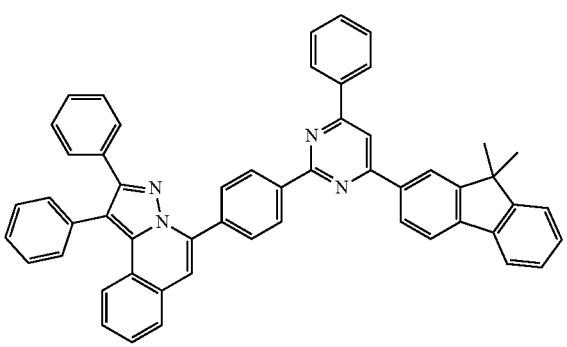

372
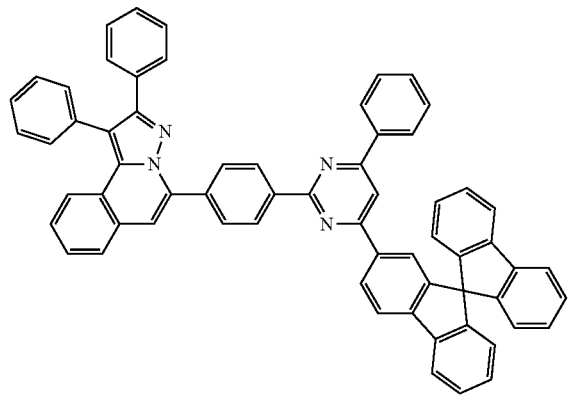
373
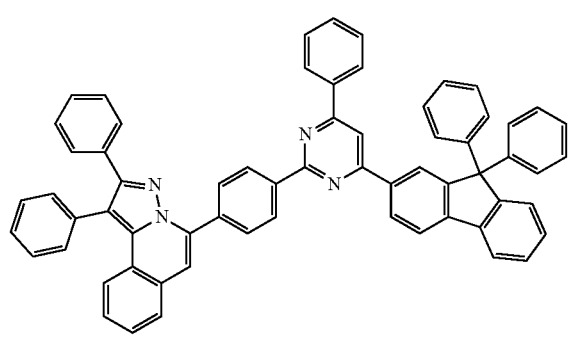
374
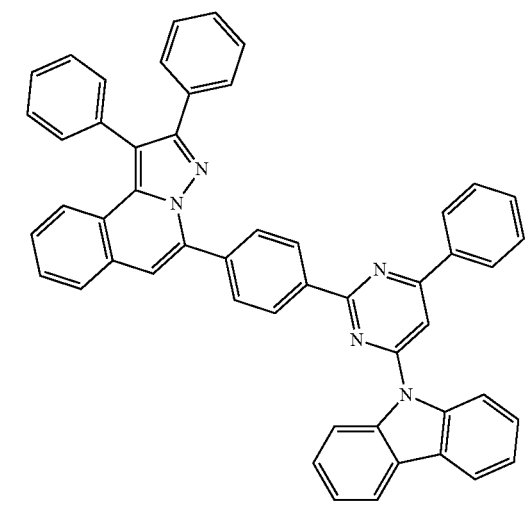
375
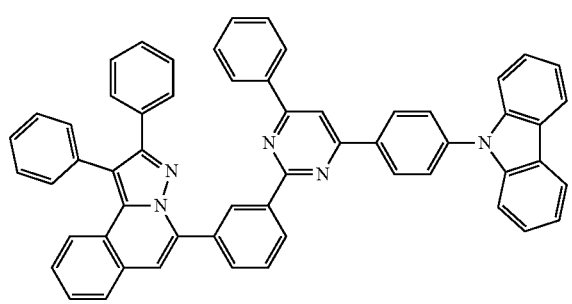
376
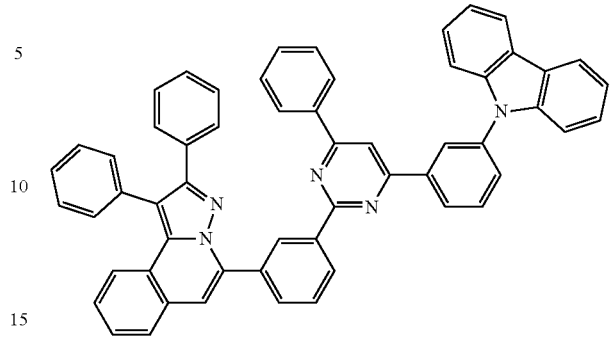
377
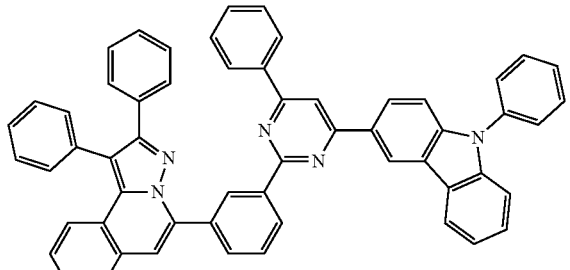
378
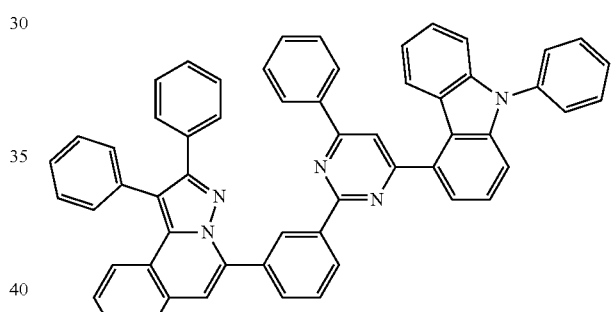
379
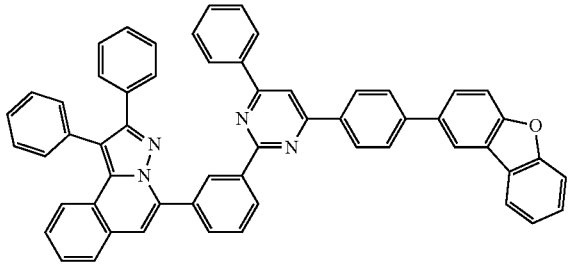
380
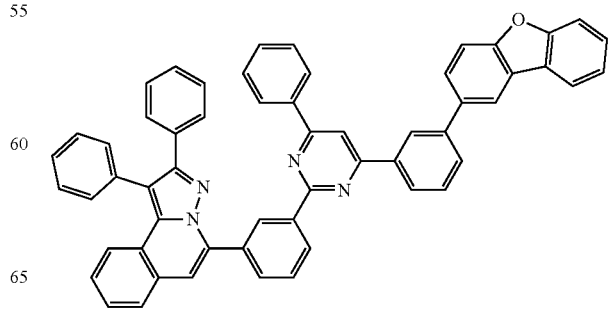

-continued
381
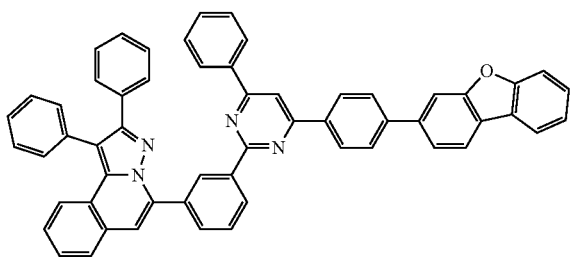
382
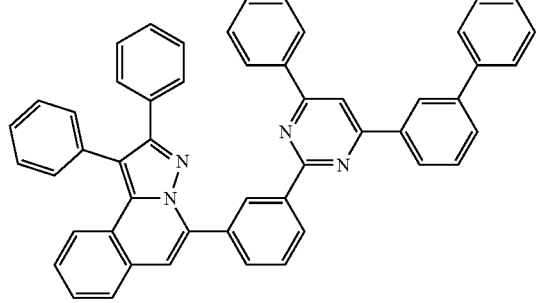
383
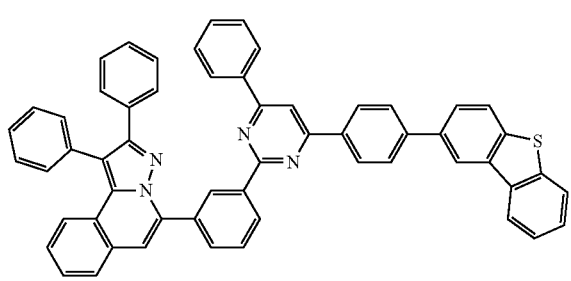
384
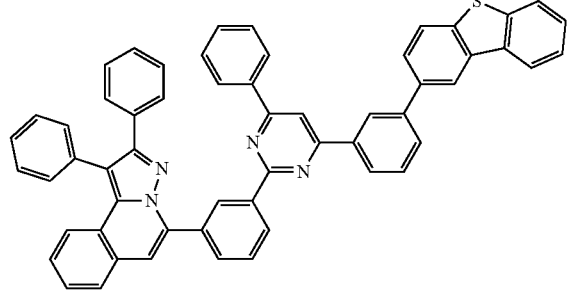
385
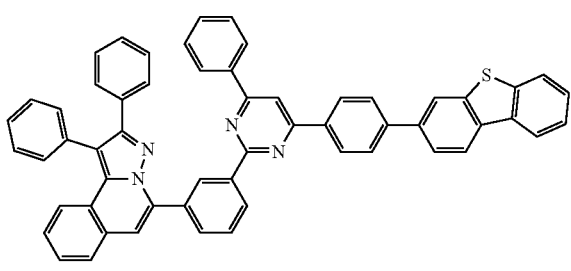
-continued
386
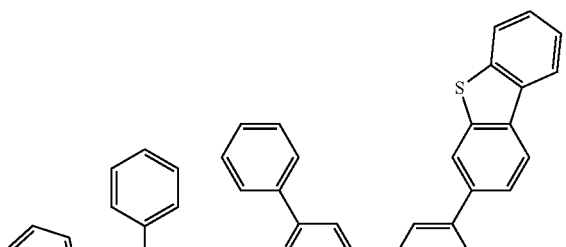
387
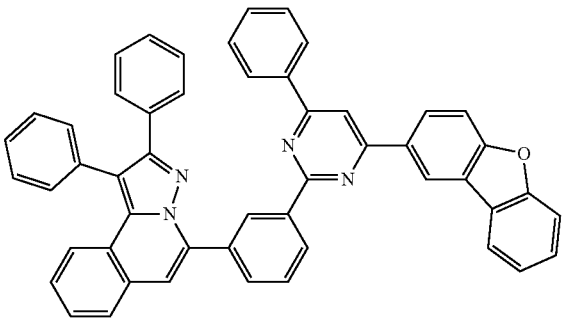
388
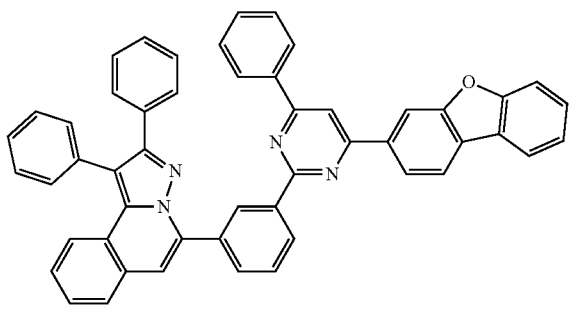
389
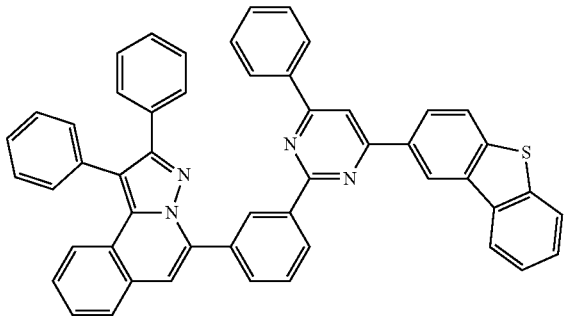

390
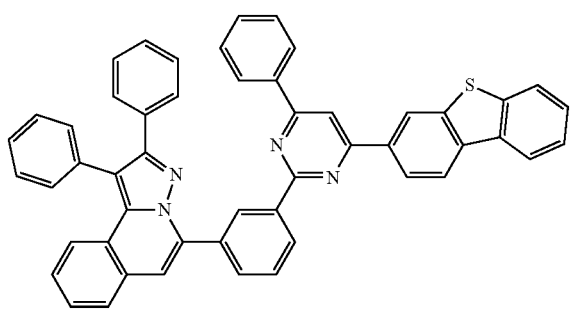
391
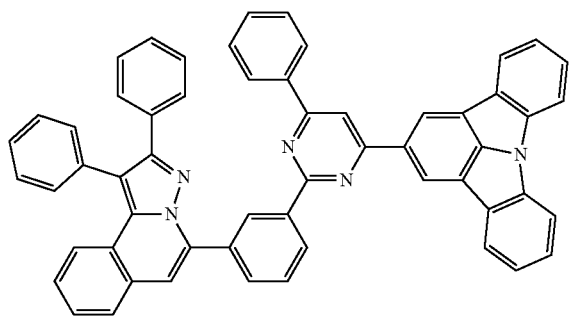
392
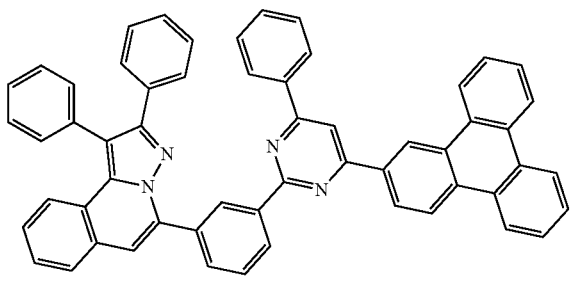
393
394
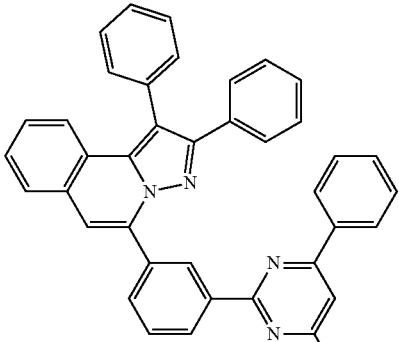
395
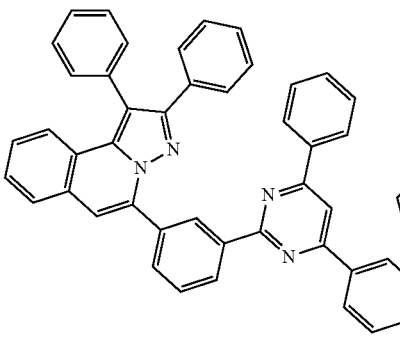
396
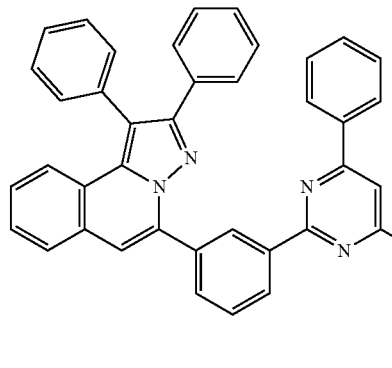

139
-continued
397
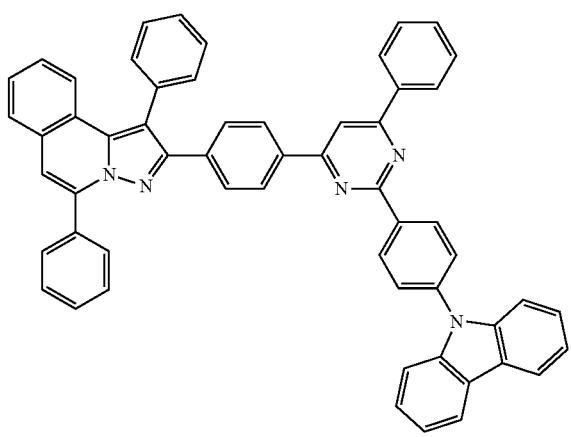
398
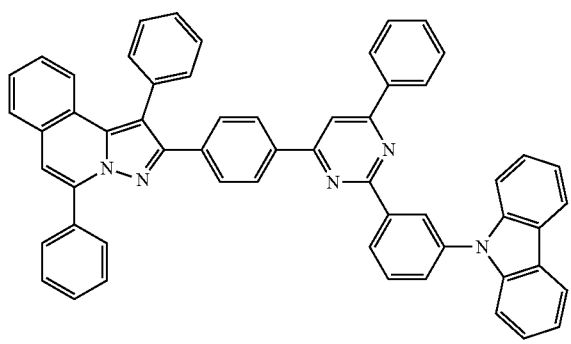
399
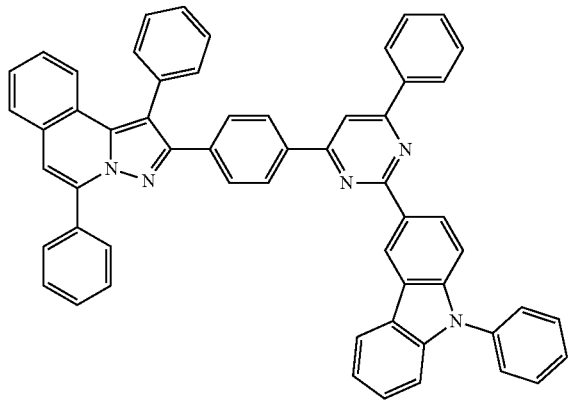
140
-continued
400
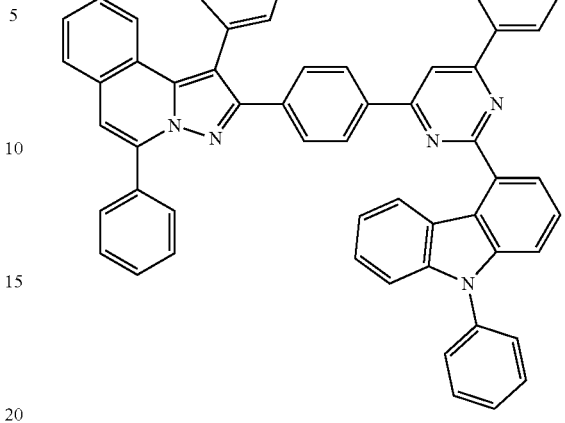
401
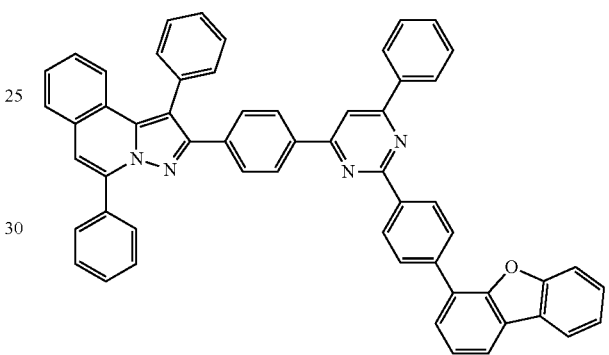
402
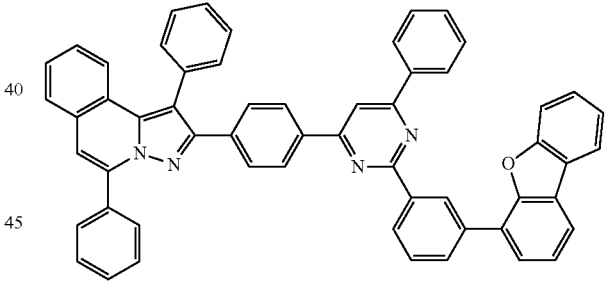
403
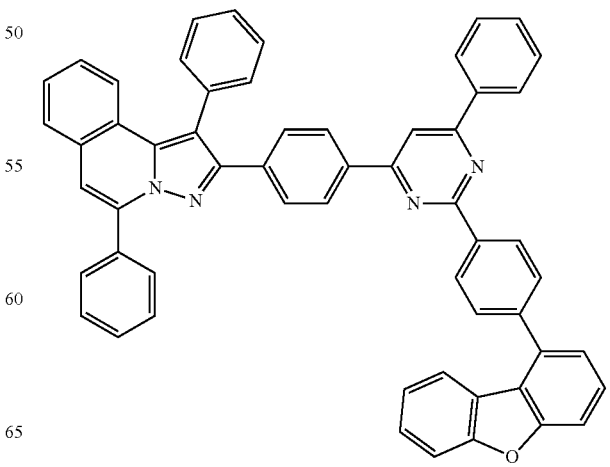

404
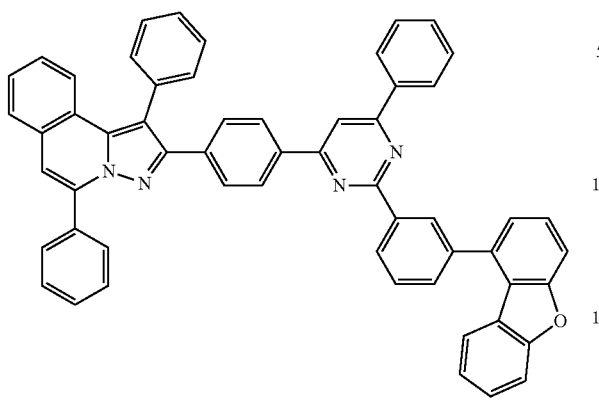
405
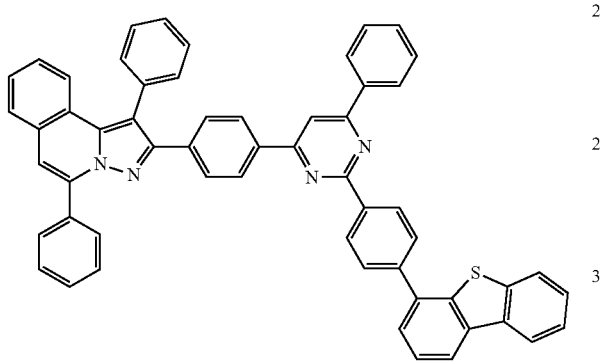
406
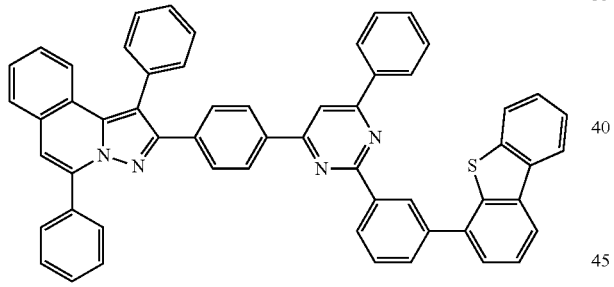
407
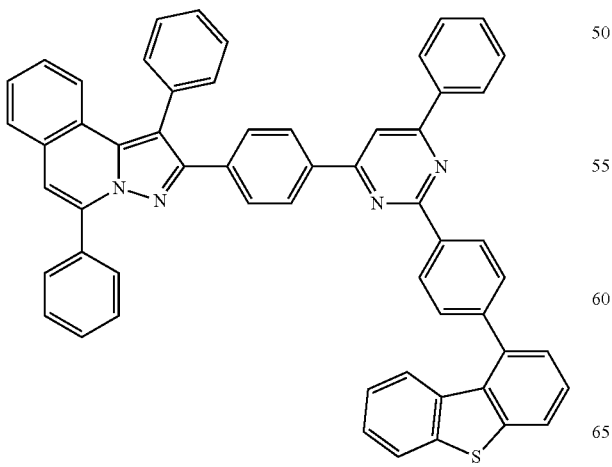
408
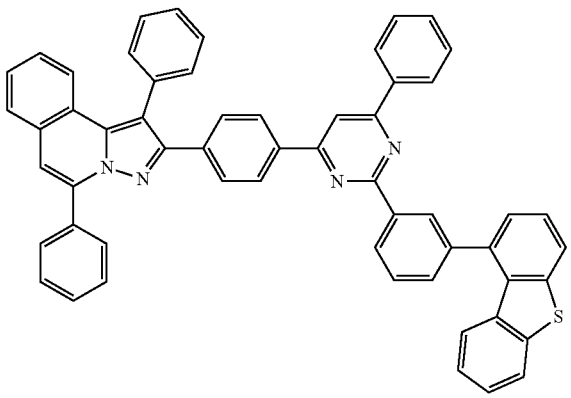
409
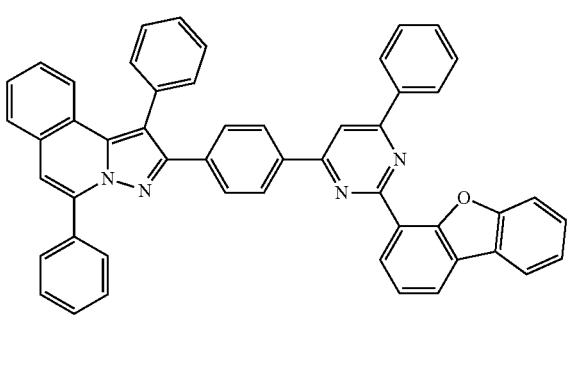
410
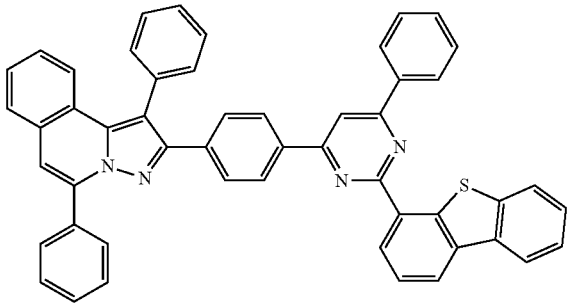
411

412
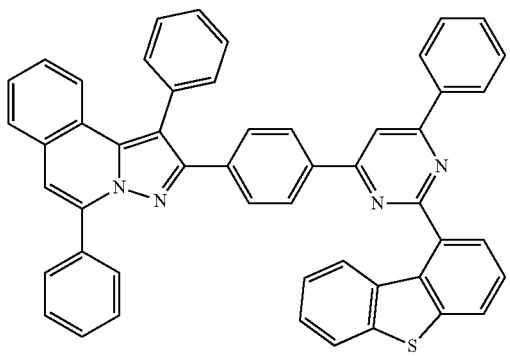
413
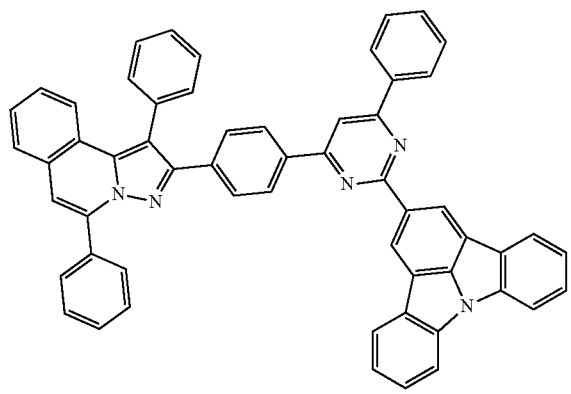
414
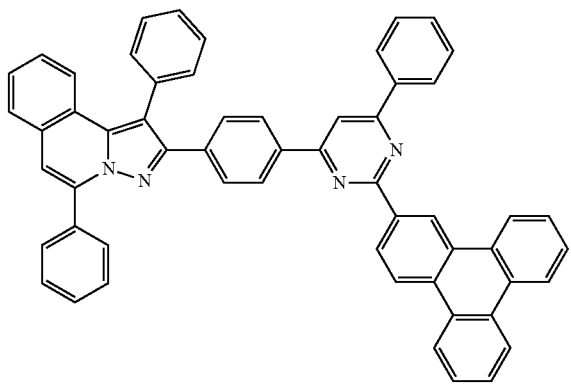
415
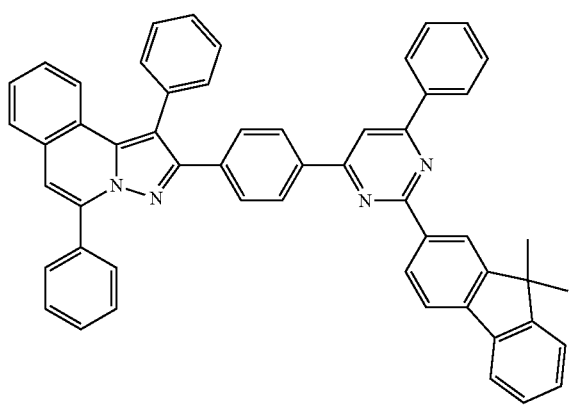
416
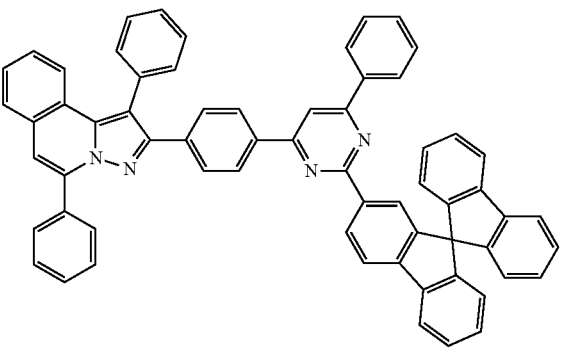
417
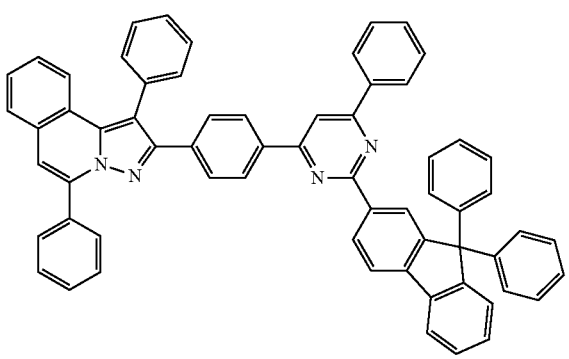
418
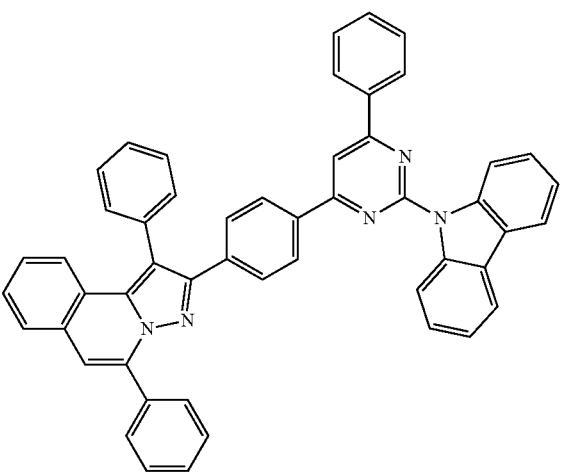
419
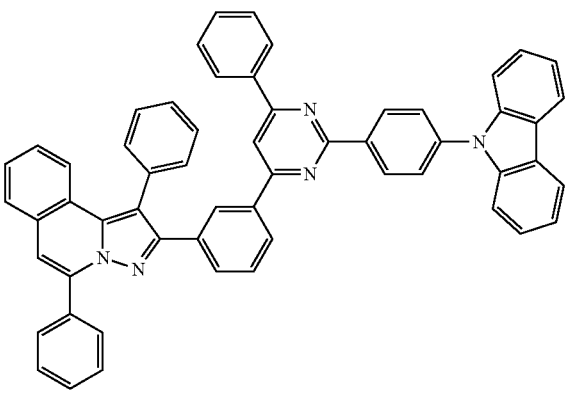

420
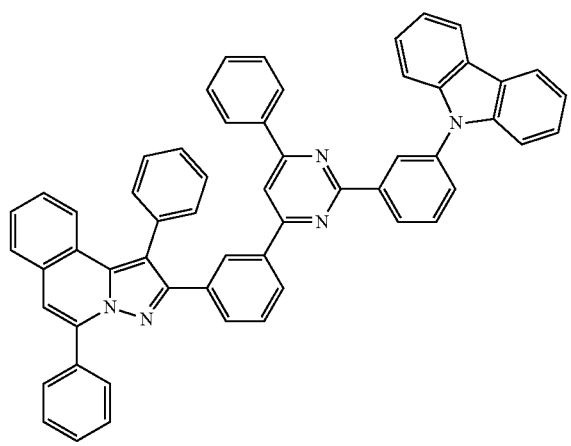
421
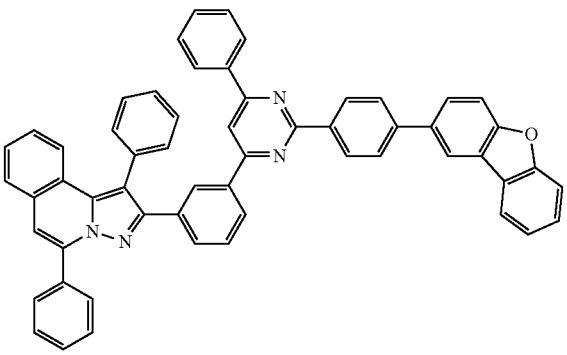
422
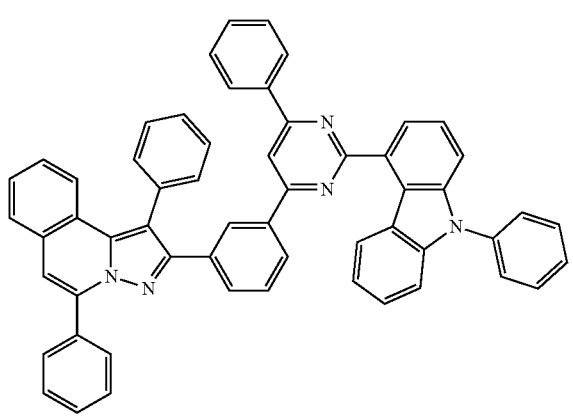
423
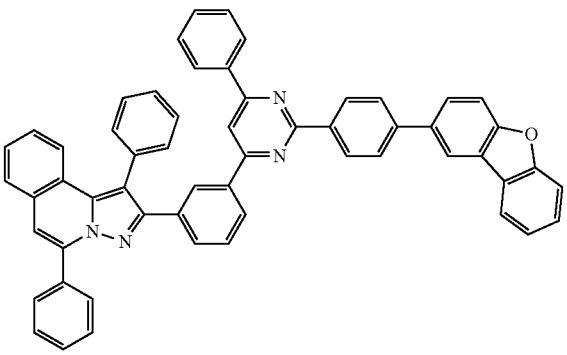
424
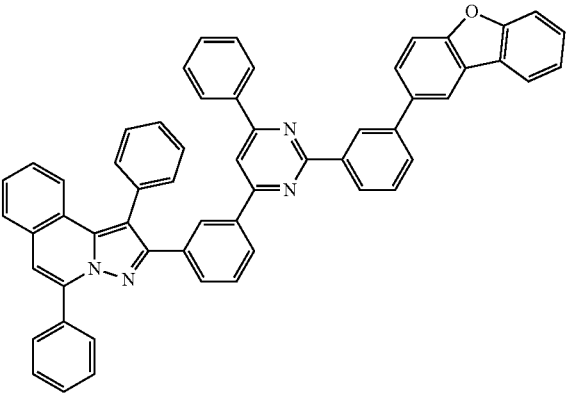
425
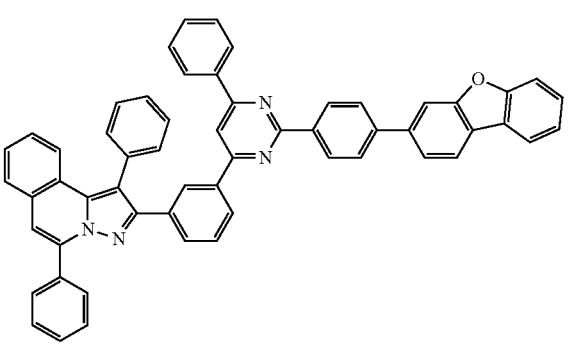

147
-continued
426
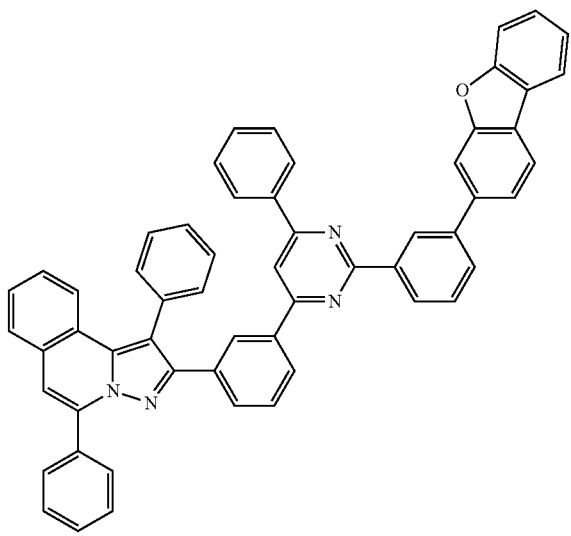
427
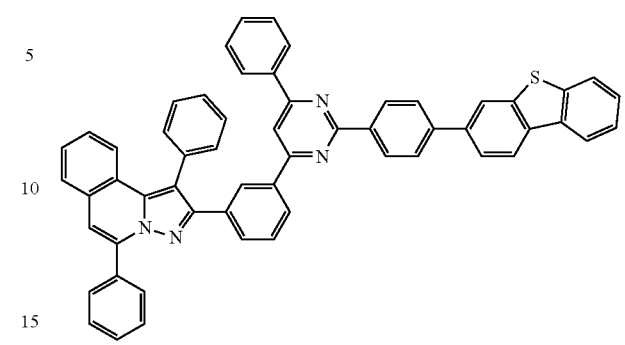
428
148
-continued
429
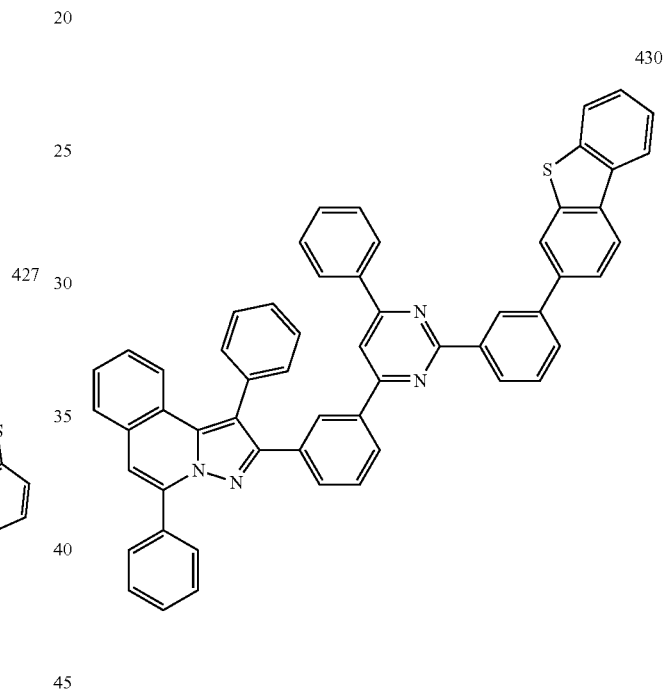
430
431
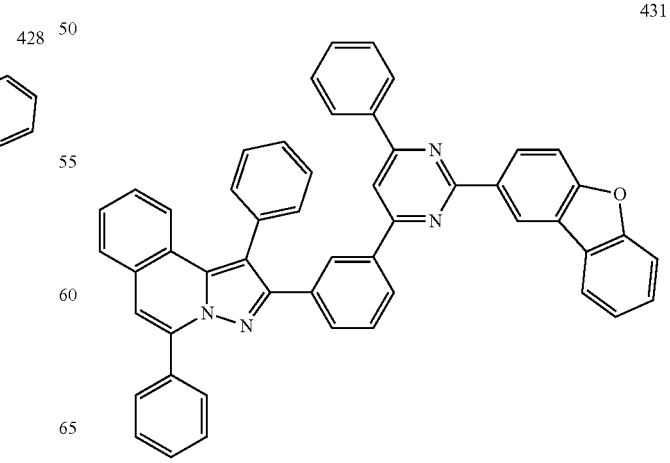

432
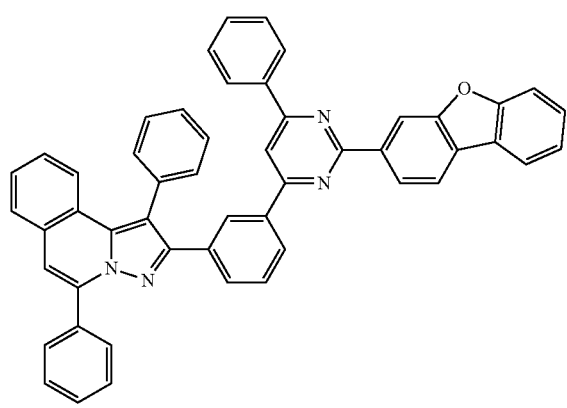
435
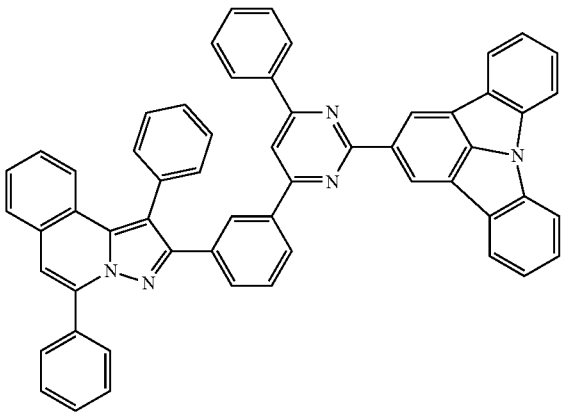
433
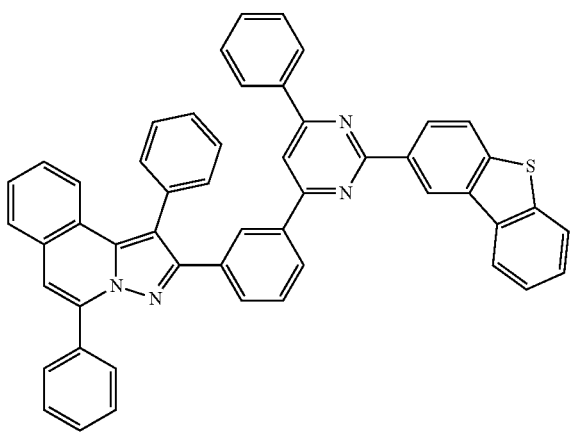
436
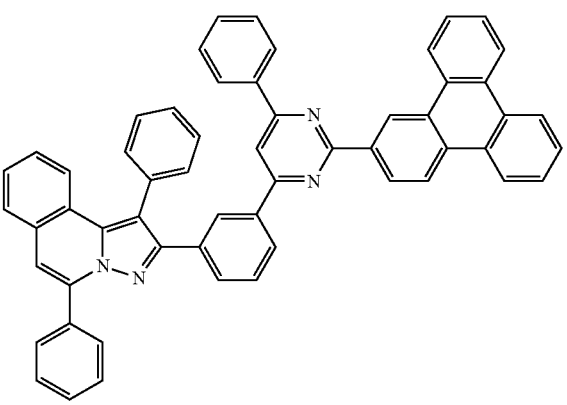
434
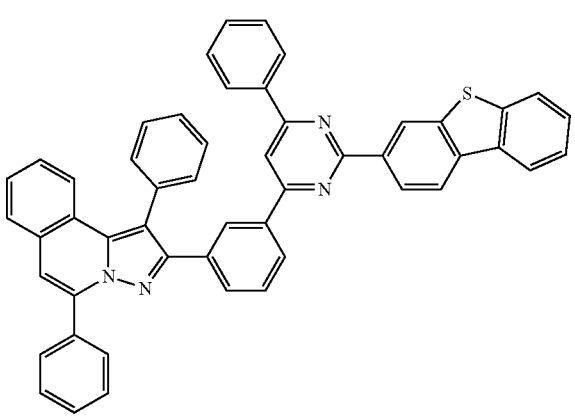
437
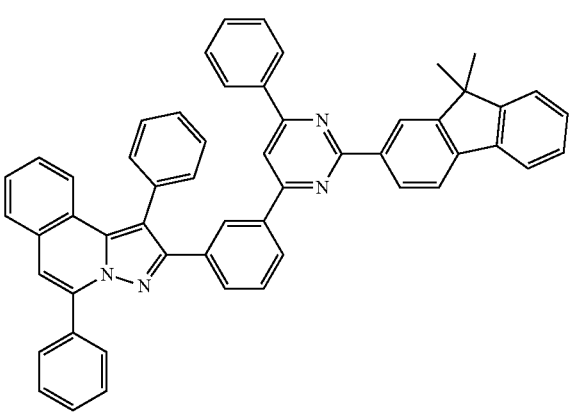

-continued
438
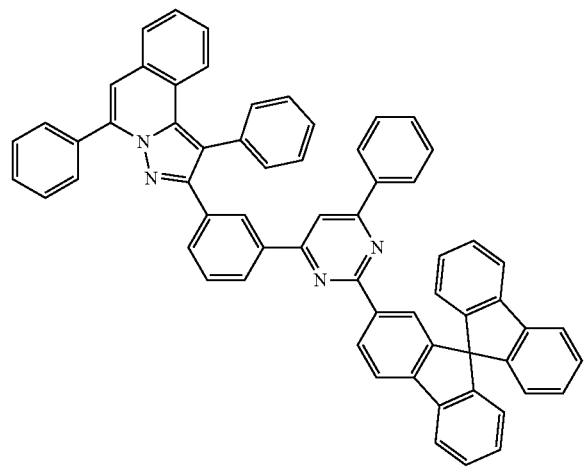
439
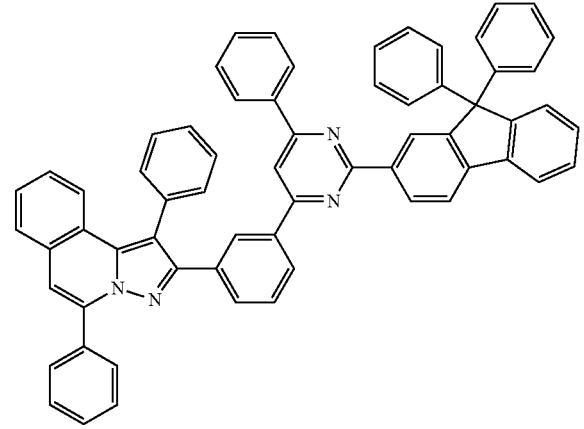
440
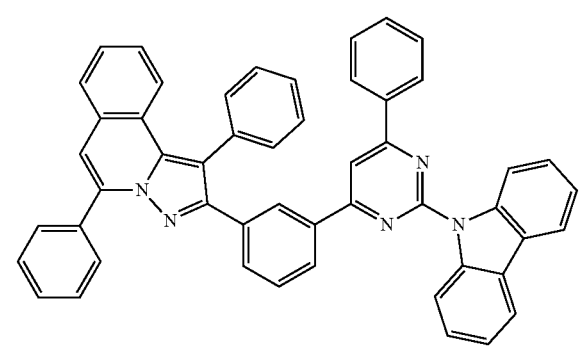
-continued
441
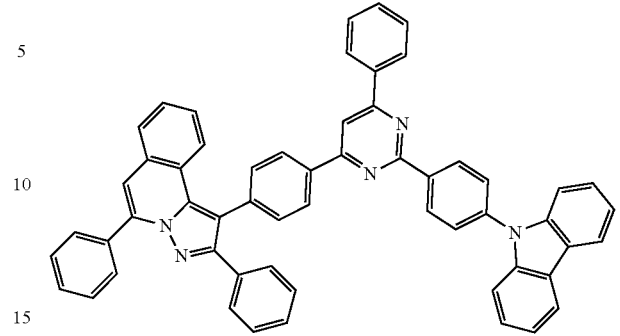
442
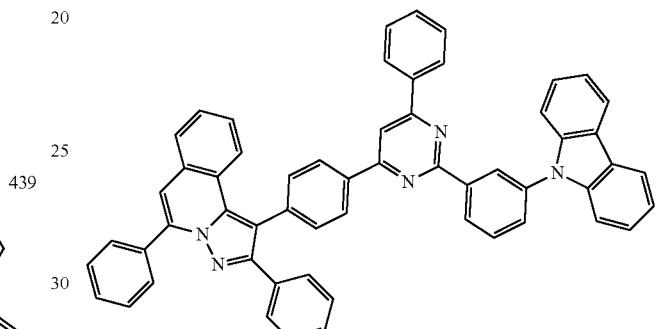
443
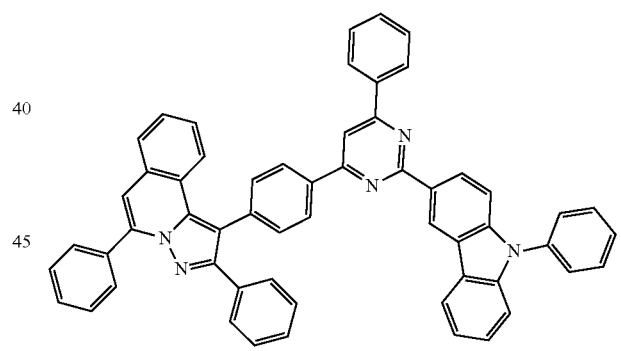
444
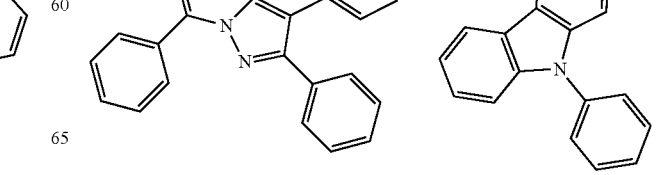

445
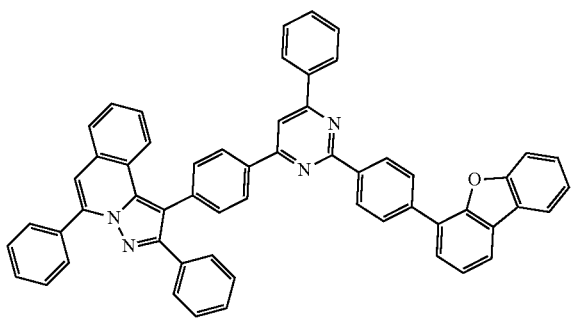
446
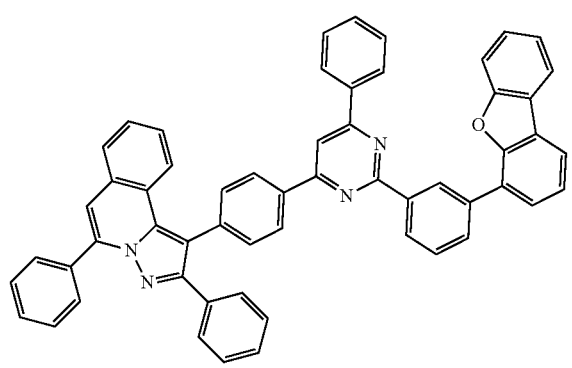
447
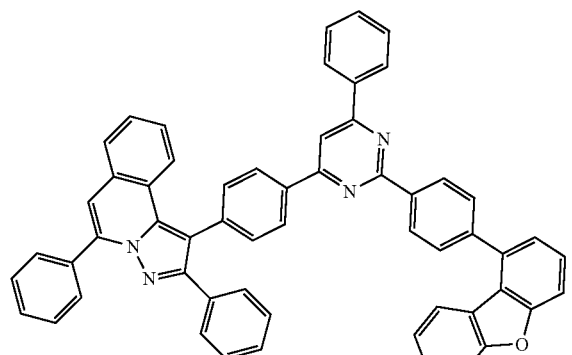
448
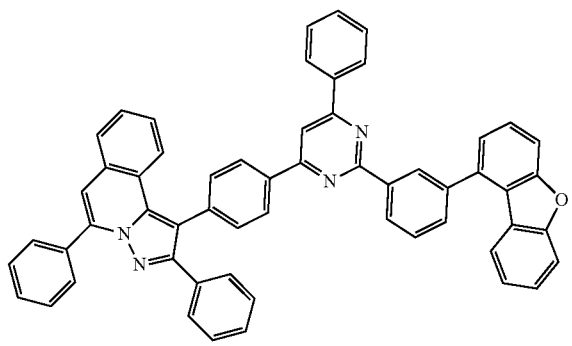
449
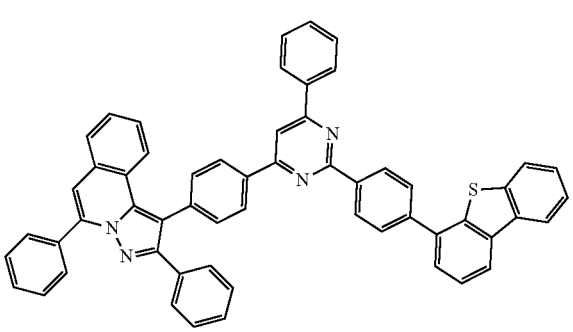
450
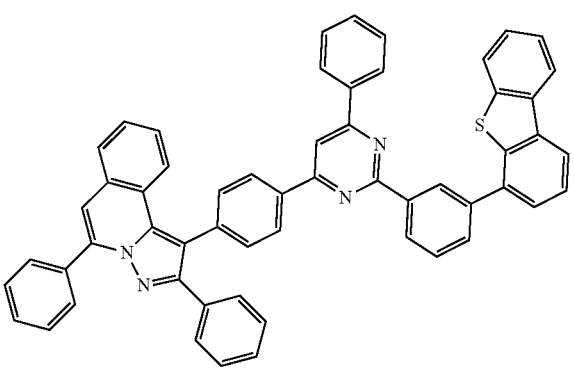
451
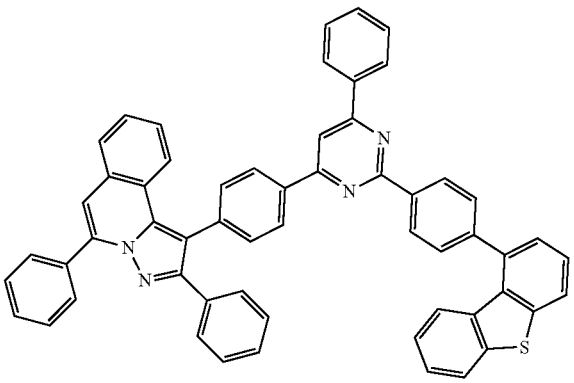
452
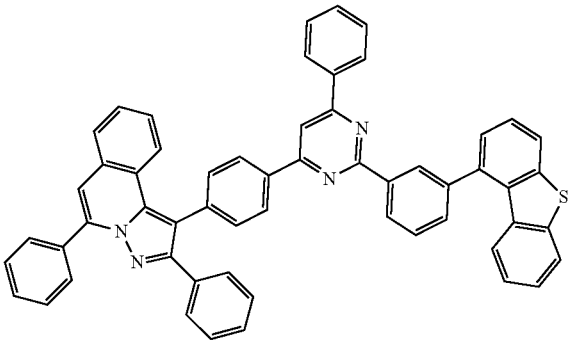

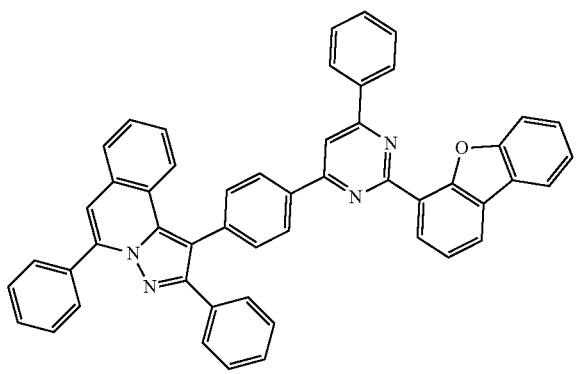
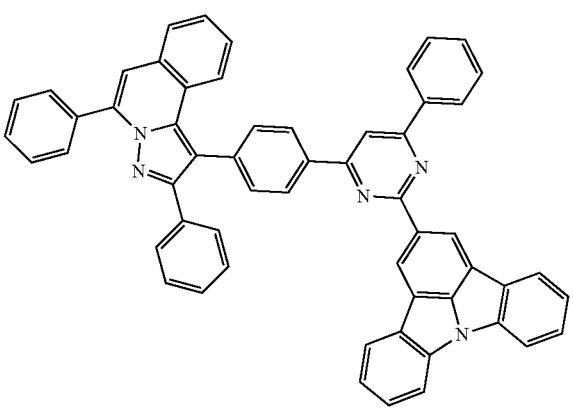

461
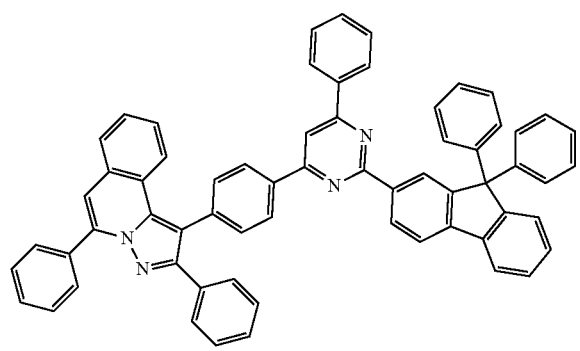
462
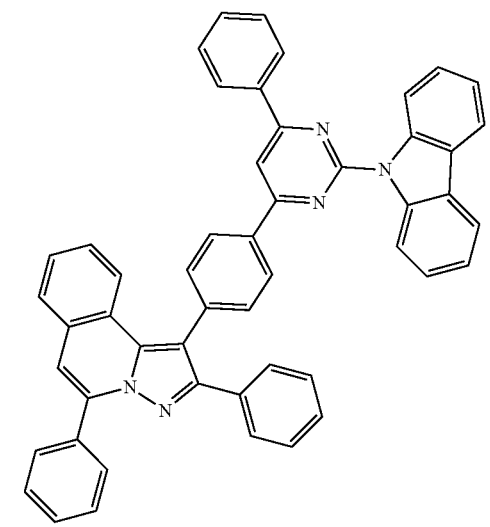
463
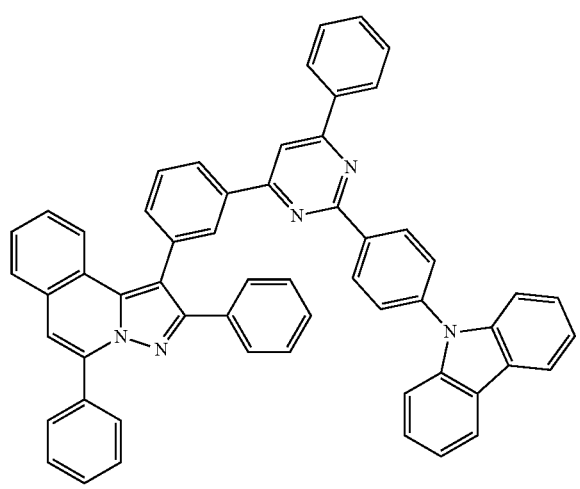
464
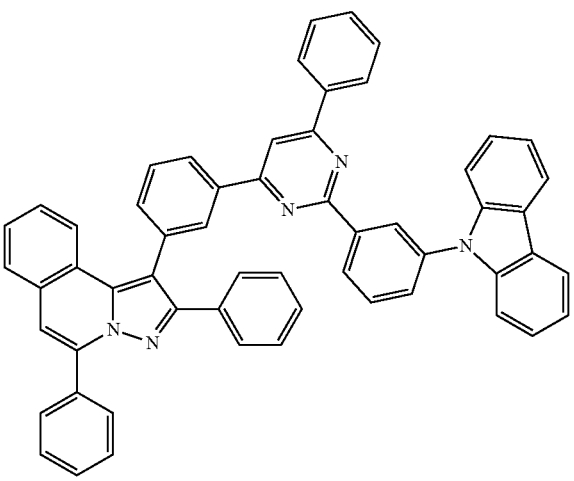
465
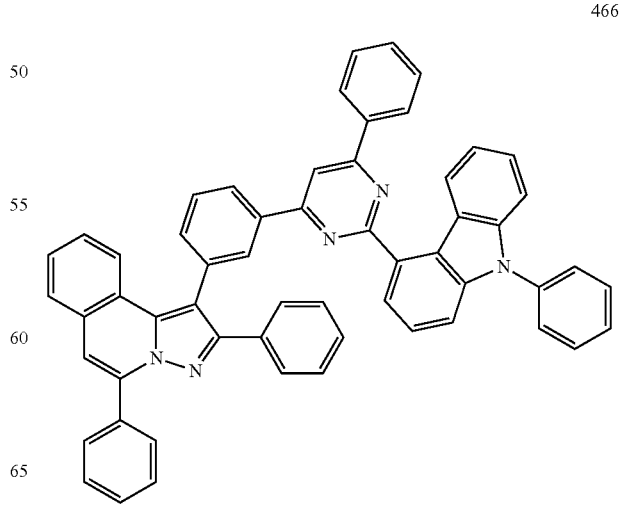
466

467
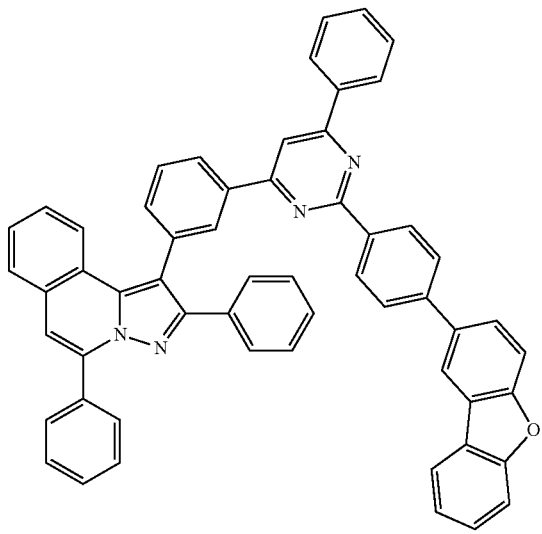
468
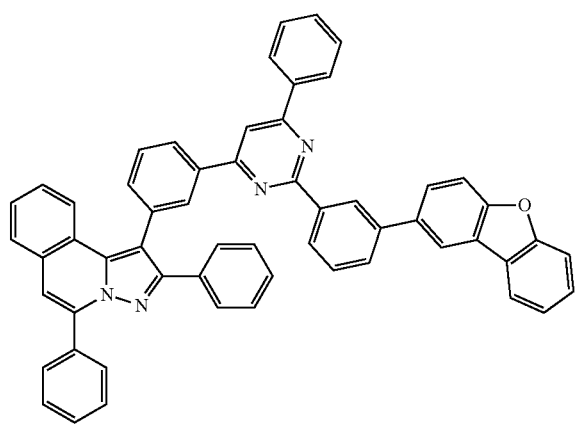
469
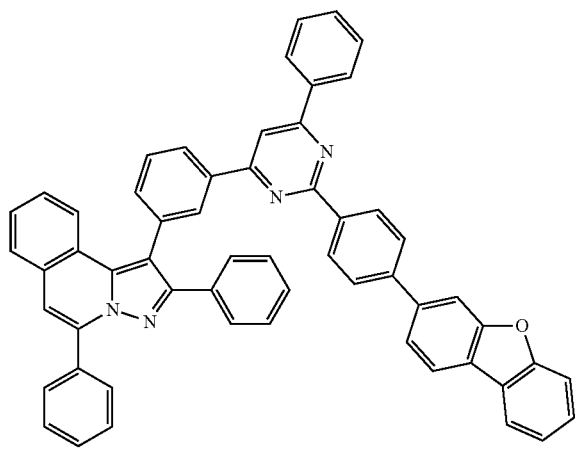
470
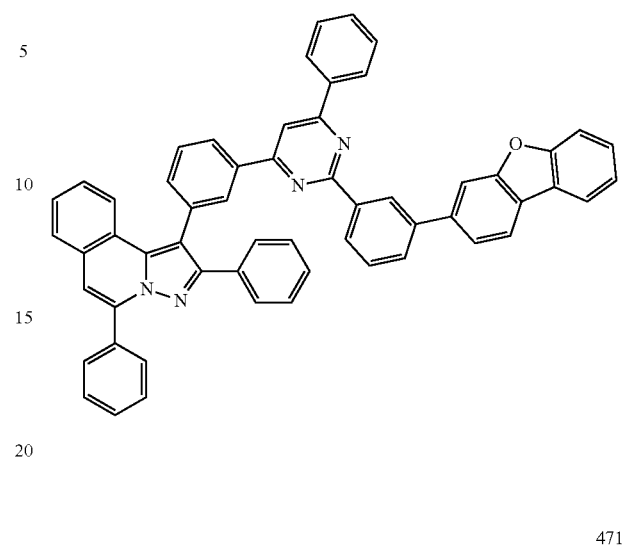
471
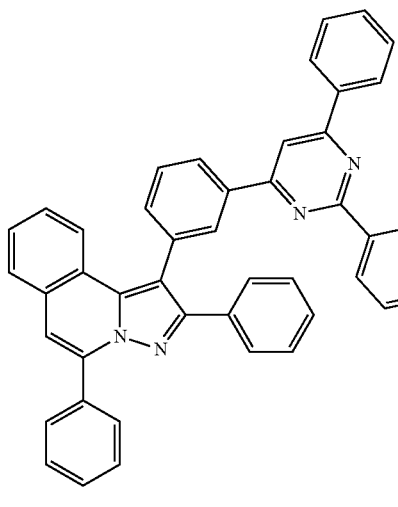
472
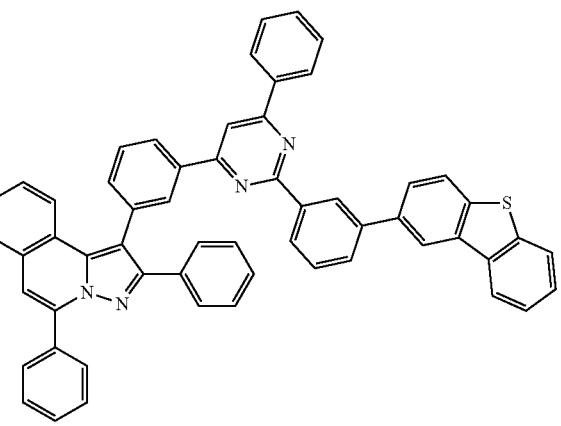

473
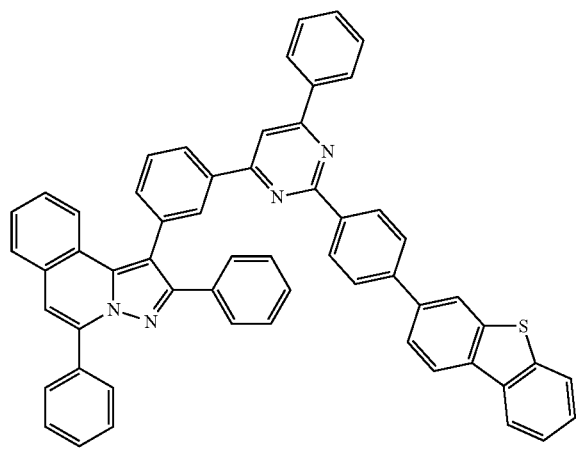
476
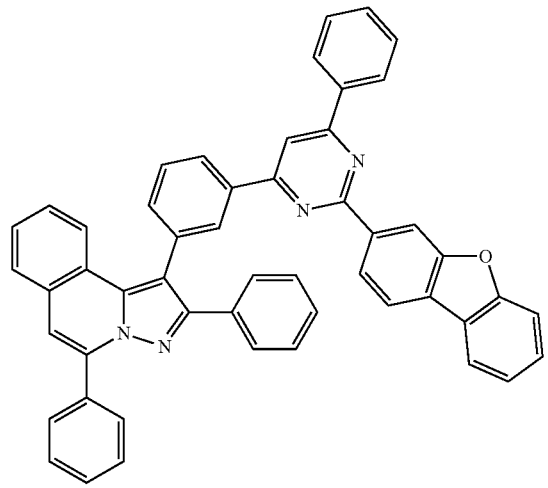
474
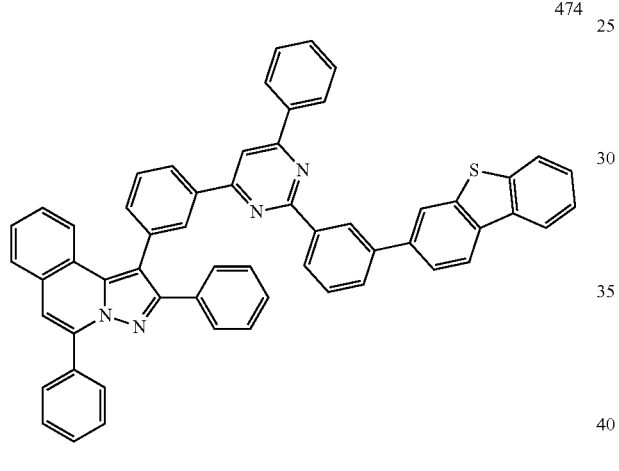
477
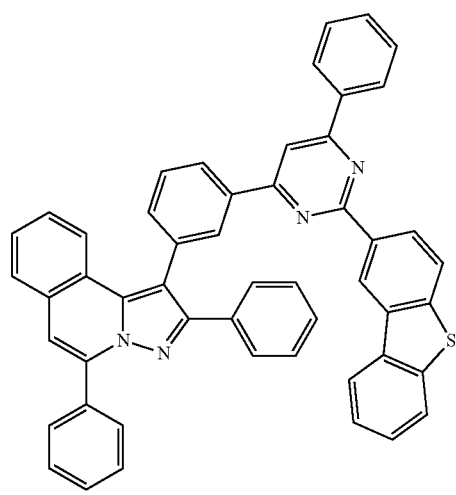
475
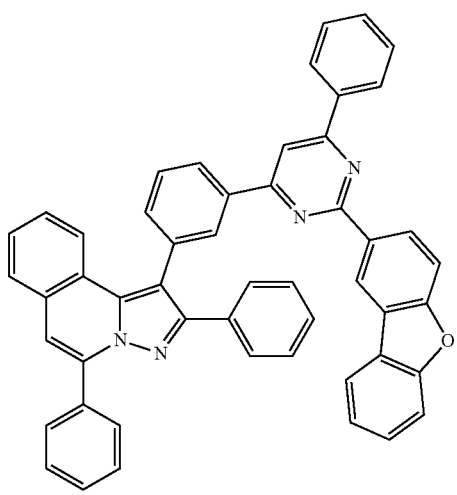
478
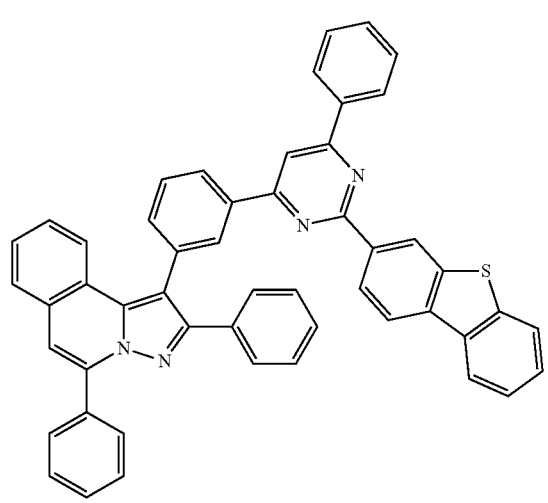

479
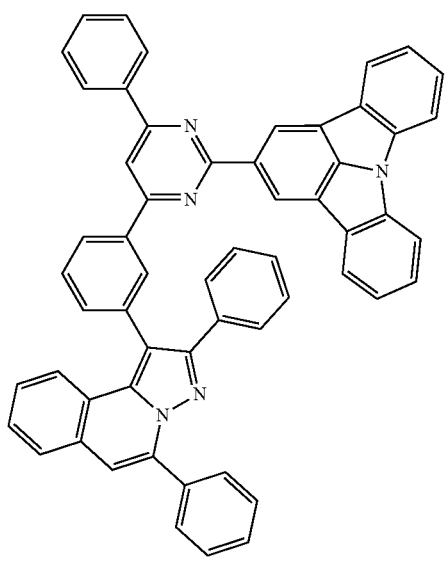
480
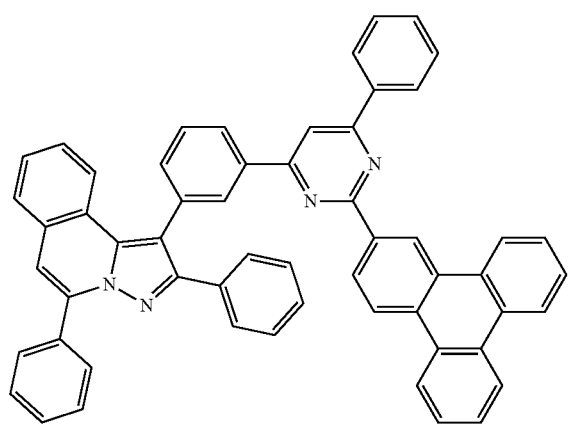
481
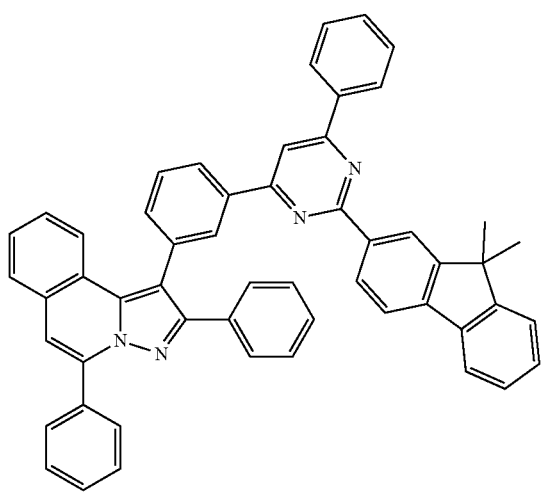
482
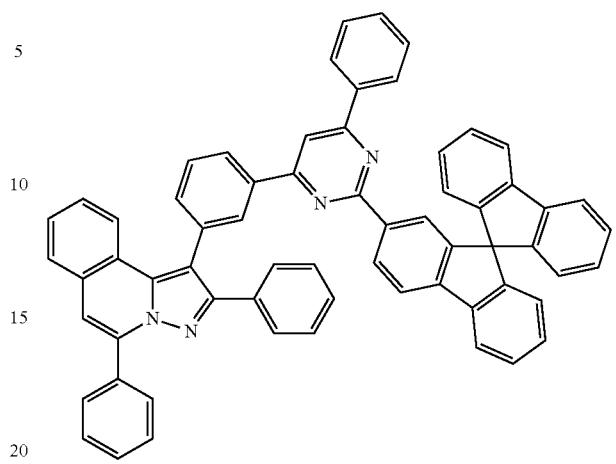
483
484
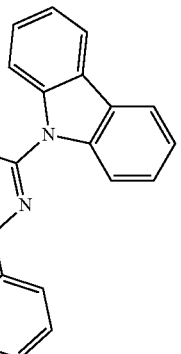

485
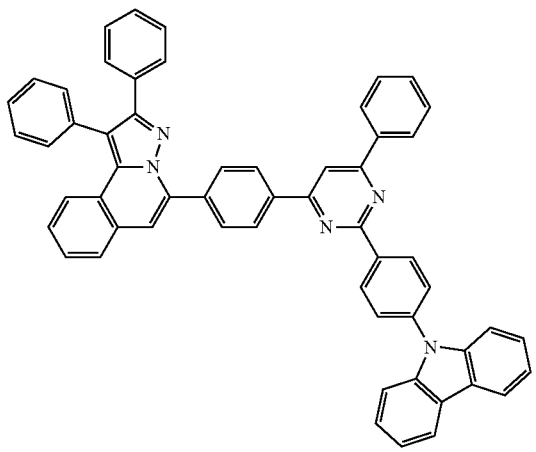
486
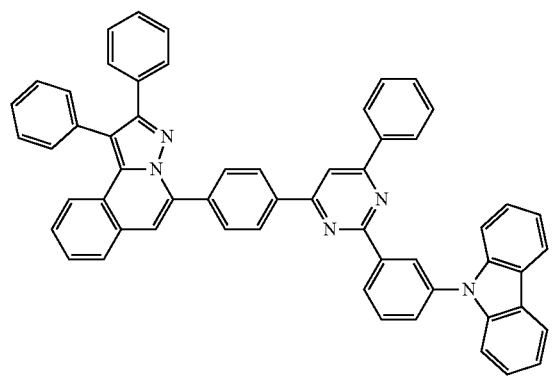
487
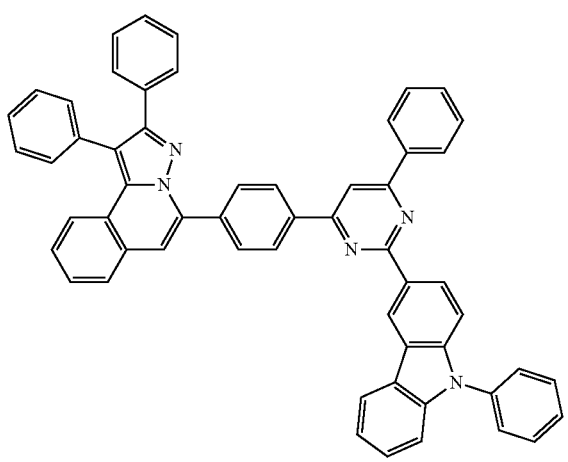
488
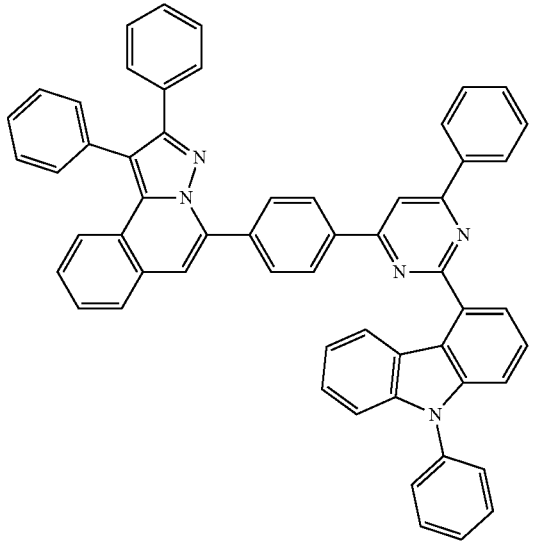
489
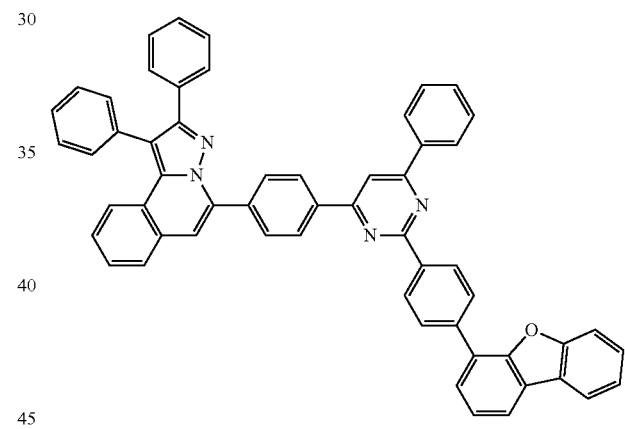
490
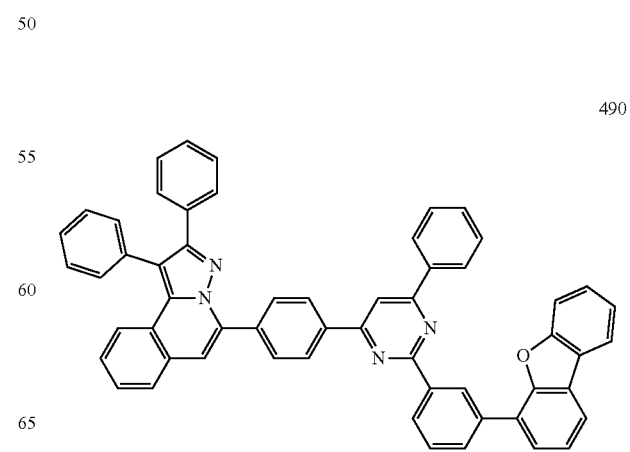

167
-continued
491
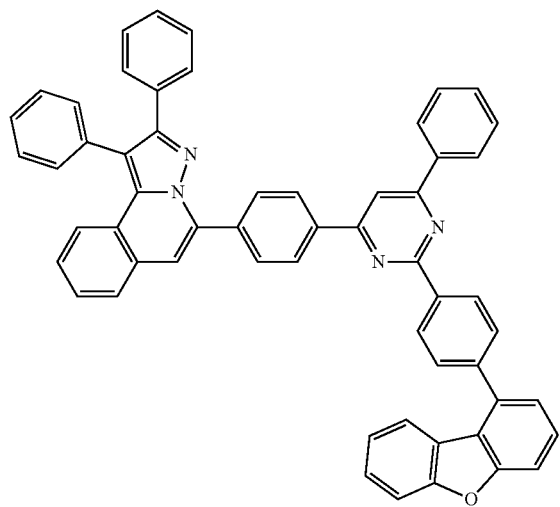
492
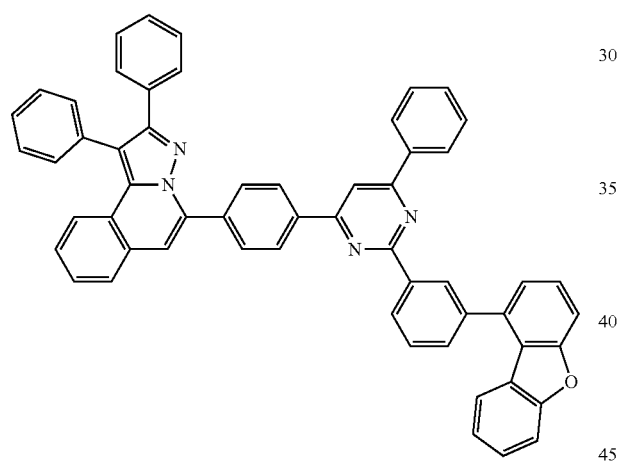
493
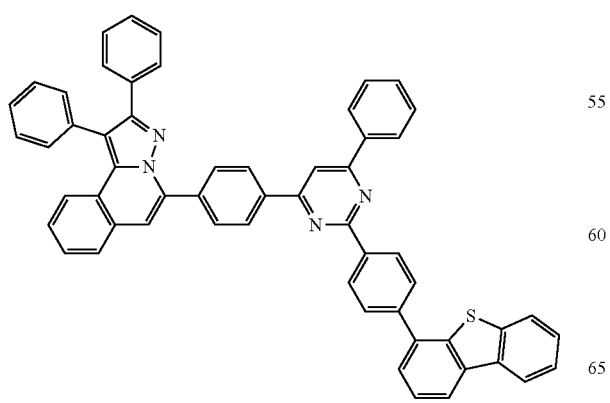
168
-continued
494
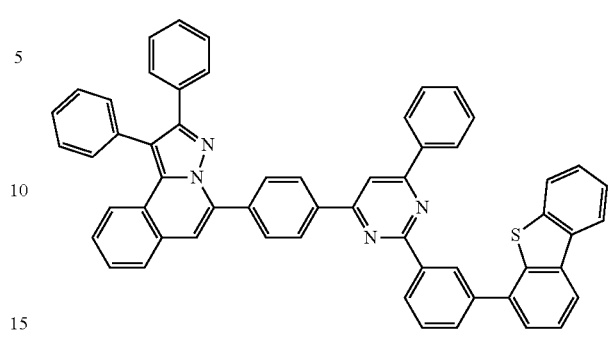
495
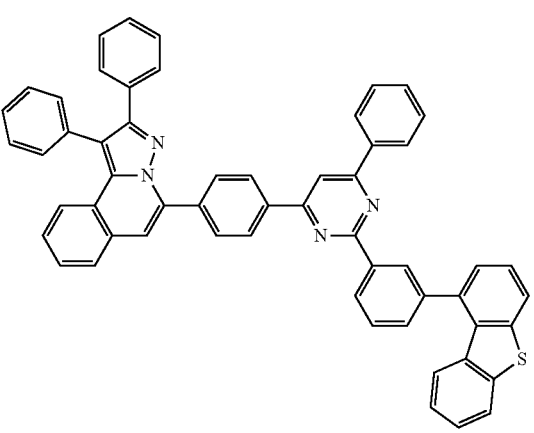
496

497
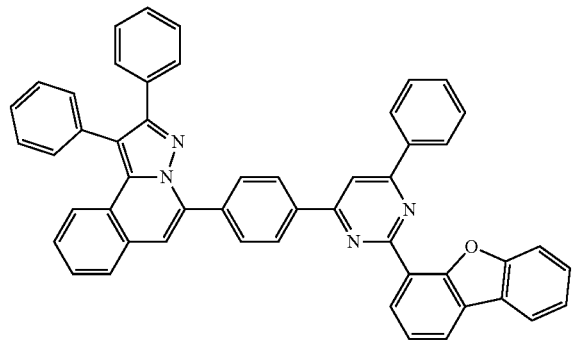
498
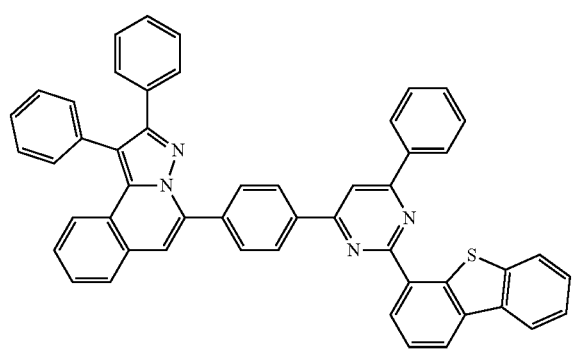
499
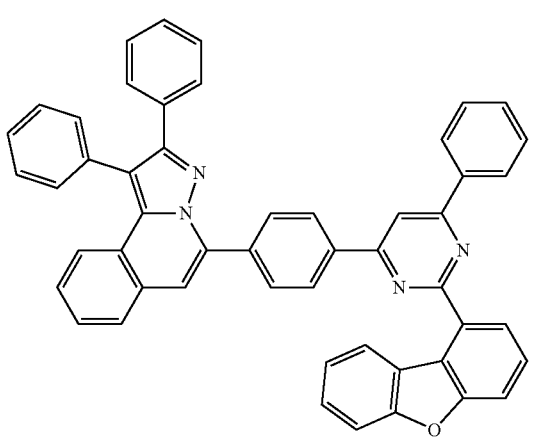
500
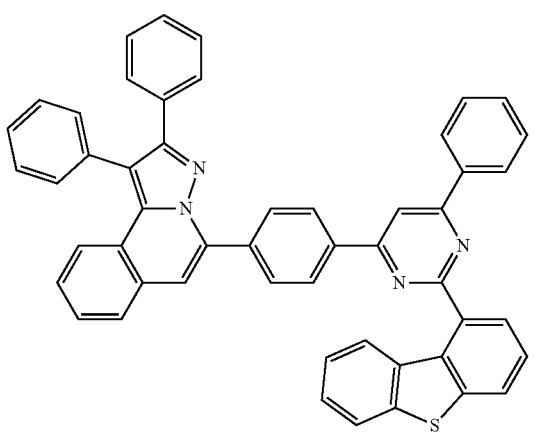
501
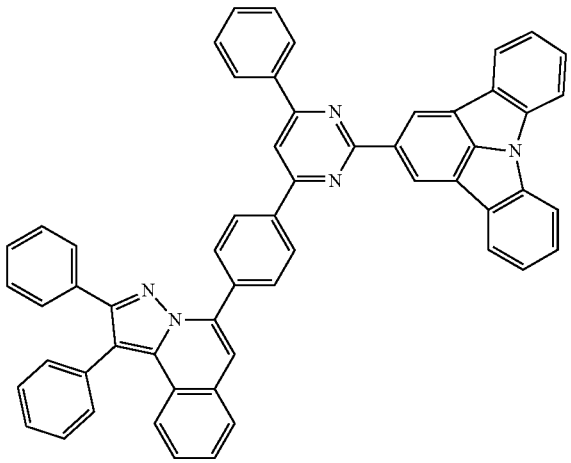
502
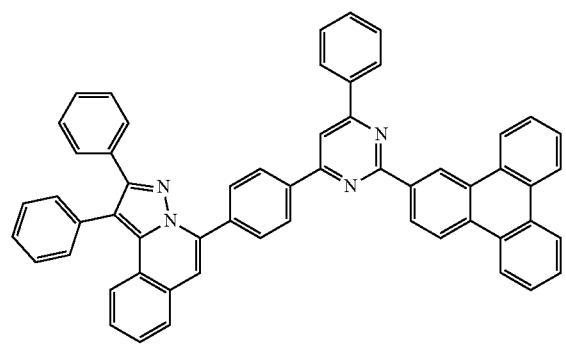
503
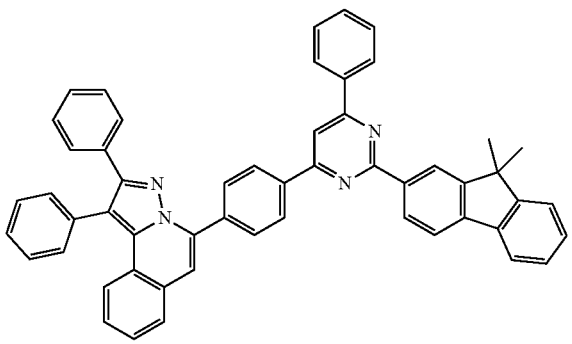
504
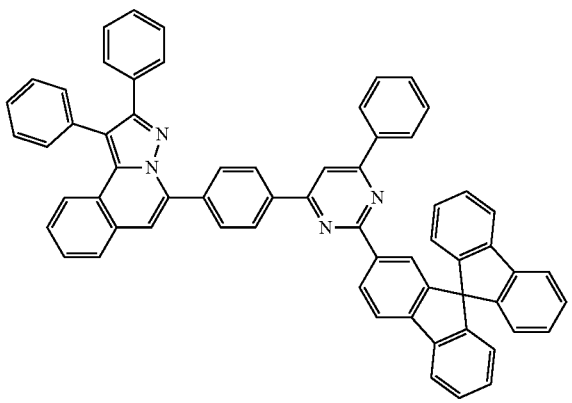

505
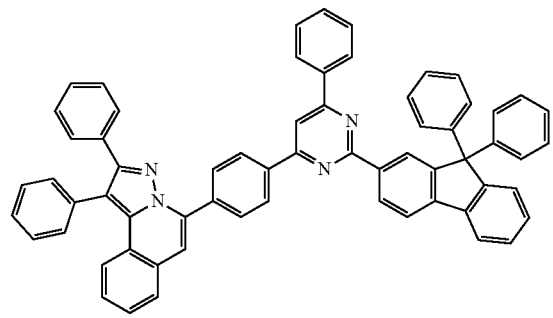
506
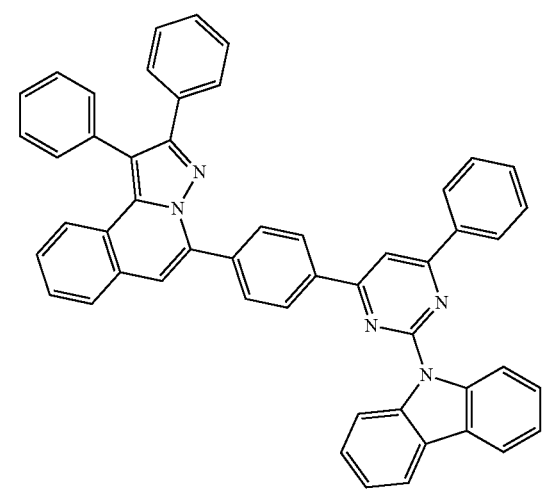
507
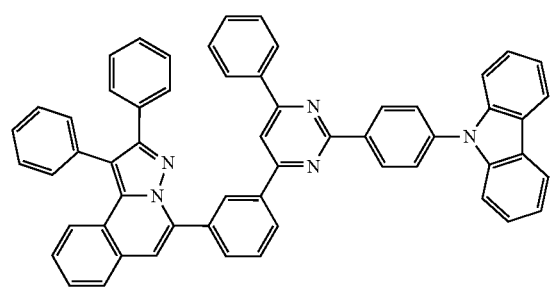
508
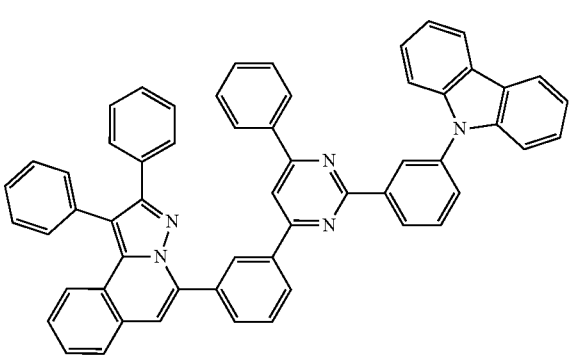
509
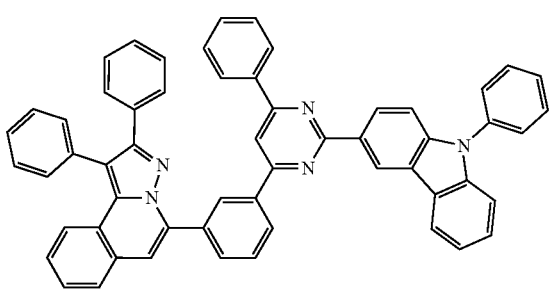
510
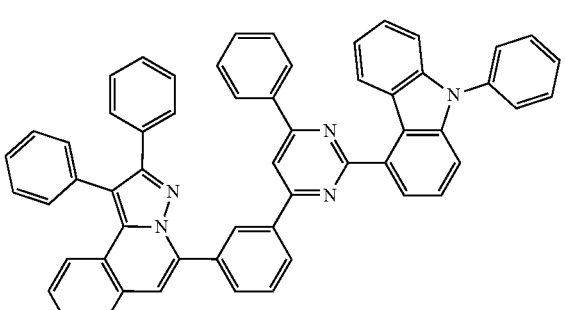
511
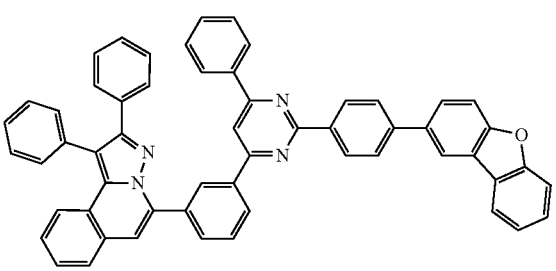
512
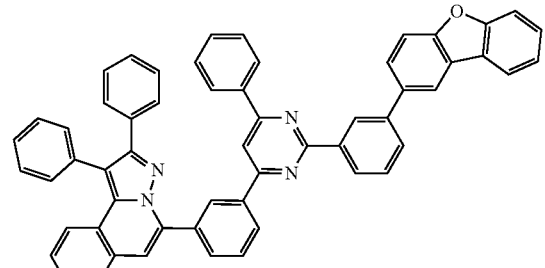
513
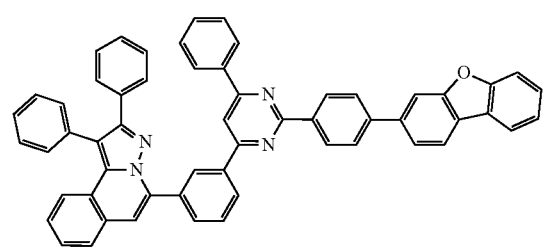

514
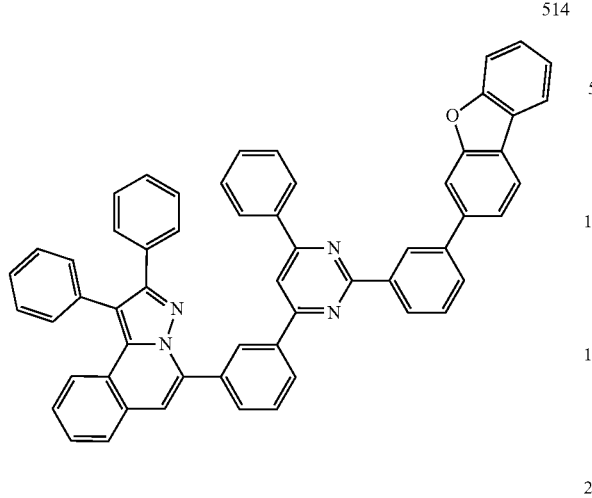
515
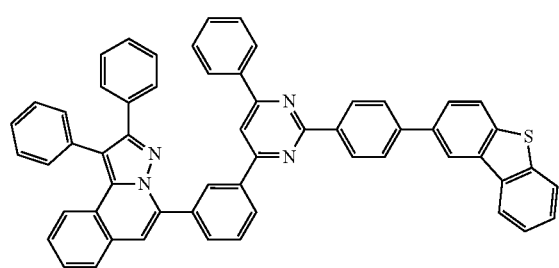
516
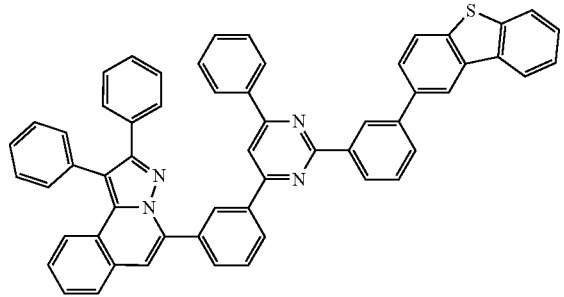
517
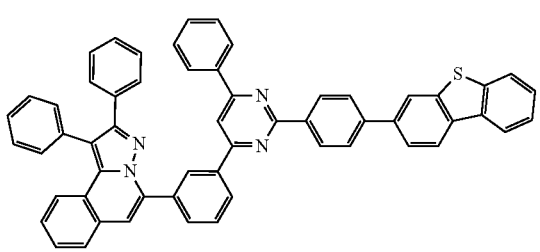
518
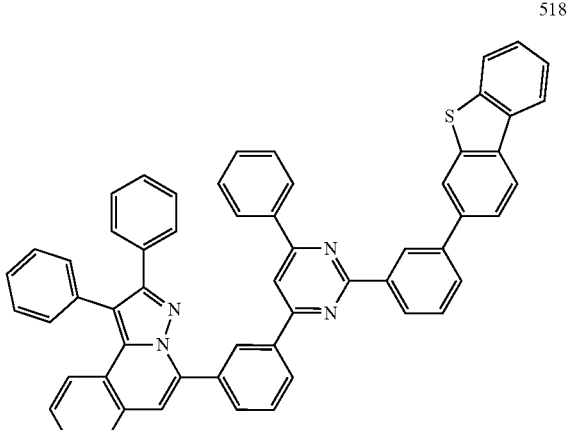
519
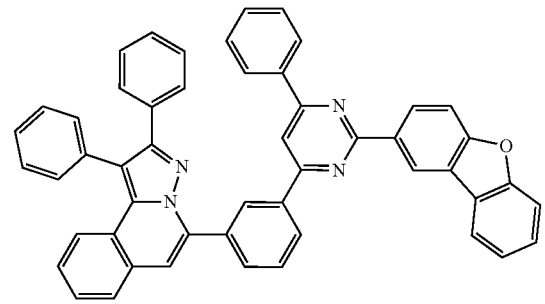
520
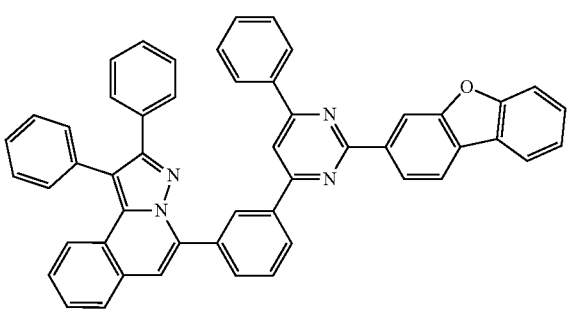
521
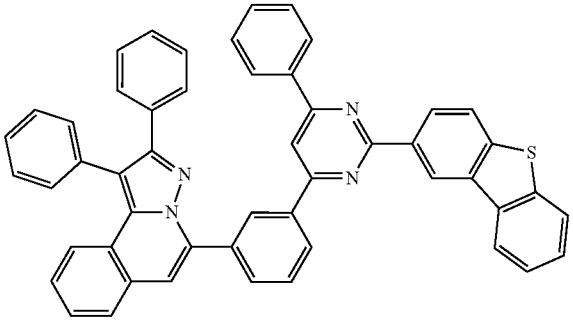

522
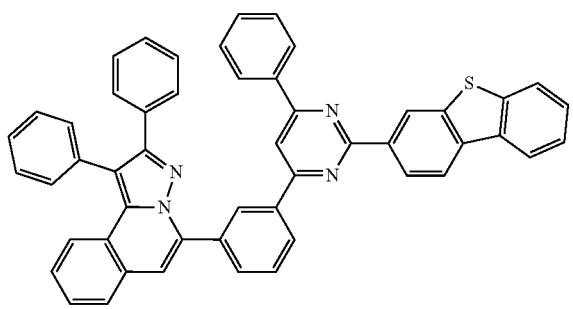
523
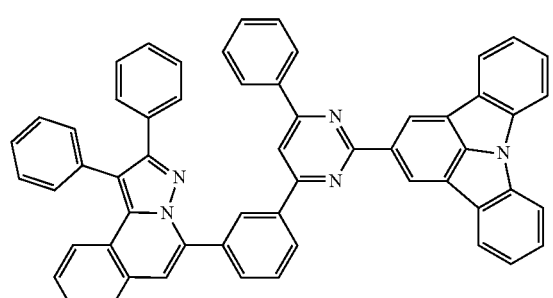
524
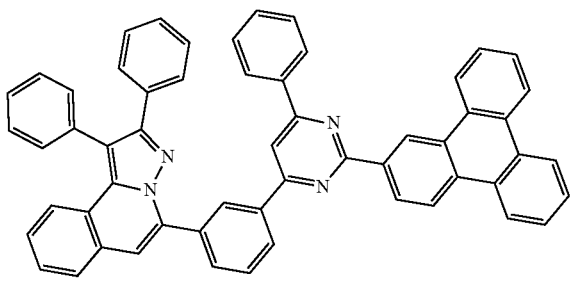
525
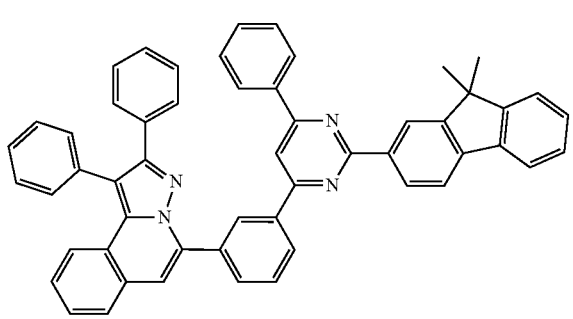
526
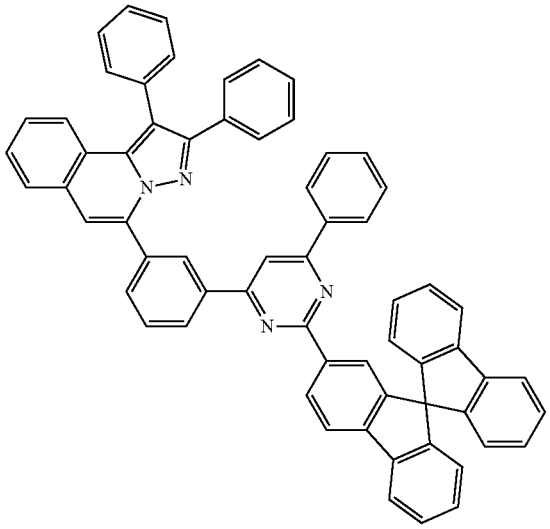
527
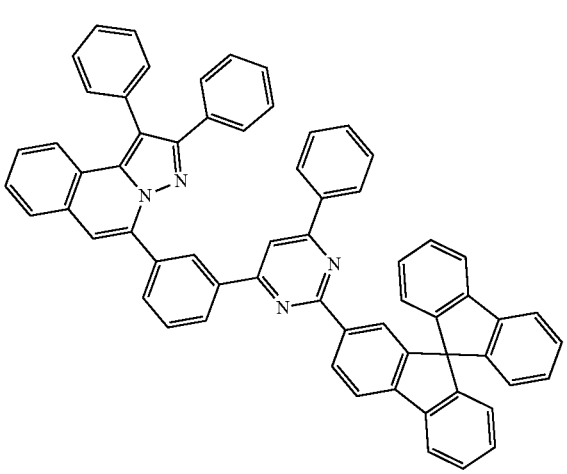
528
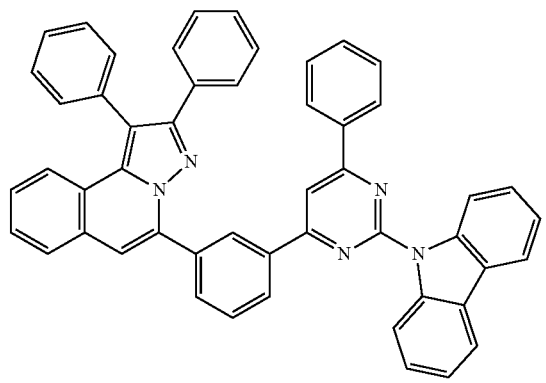

-continued

529

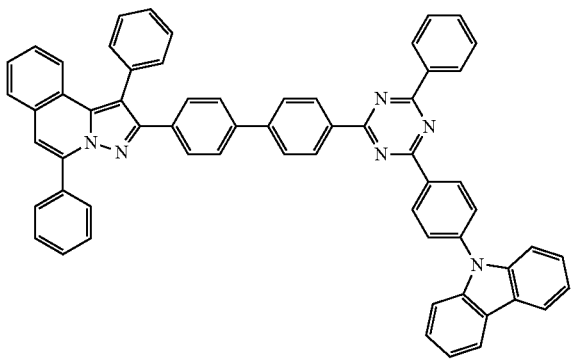

530

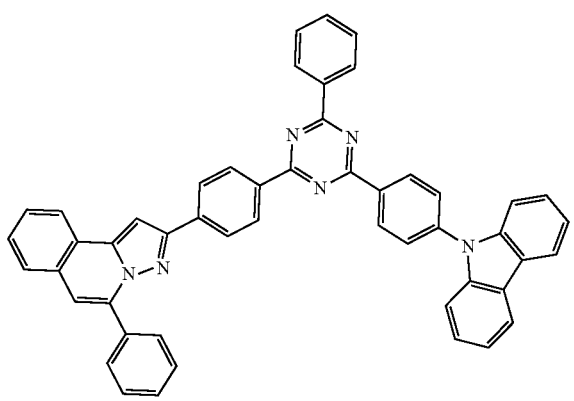

531

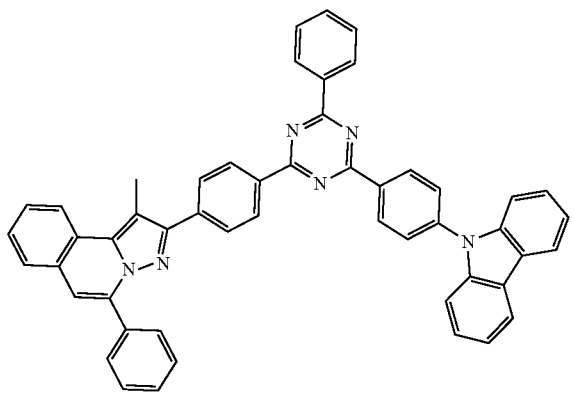

532

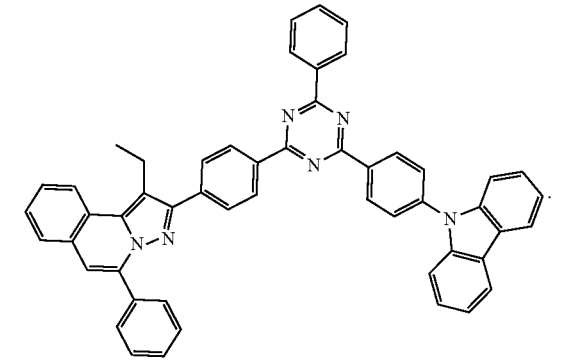

In addition, by introducing various substituents to the structure of Chemical Formula 1, compounds having unique properties of the introduced substituents may be synthesized. For example, by introducing substituents normally used as hole injection layer materials, materials for hole transfer, light emitting layer materials, electron transfer layer materials and charge generation layer materials used for manufacturing an organic light emitting device to the core structure, materials satisfying conditions required for each organic material layer may be synthesized.

In addition, by introducing various substituents to the structure of Chemical Formula 1, the energy band gap may be finely controlled, and meanwhile, properties at interfaces between organic materials are enhanced, and material applications may become diverse.

Meanwhile, the compound has a high glass transition temperature (Tg) and thereby has superior thermal stability. Such an increase in the thermal stability becomes an important factor in providing driving stability to a device.

In addition, one embodiment of the present application provides an organic light emitting device comprising a first electrode; a second electrode provided opposite to the first electrode; and one or more organic material layers provided between the first electrode and the second electrode, wherein one or more layers of the organic material layers comprise the heterocyclic compound represented by Chemical Formula 1.

In one embodiment of the present application, the first electrode may be an anode, and the second electrode may be a cathode.

In another embodiment, the first electrode may be a cathode, and the second electrode may be an anode.

Specific descriptions on the heterocyclic compound represented by Chemical Formula 1 are the same as the descriptions provided above.

In one embodiment of the present application, the organic light emitting device may be a blue organic light emitting device, and the heterocyclic compound according to Chemical Formula 1 may be used as a material of the blue organic light emitting device.

In one embodiment of the present application, the organic light emitting device may be a green organic light emitting device, and the heterocyclic compound according to Chemical Formula 1 may be used as a material of the green organic light emitting device.

In one embodiment of the present application, the organic light emitting device may be a red organic light emitting device, and the heterocyclic compound according to Chemical Formula 1 may be used as a material of the red organic light emitting device.

The organic light emitting device of the present disclosure may be manufactured using common organic light emitting device manufacturing methods and materials except that one or more of the organic material layers are formed using the heterocyclic compound described above.

The heterocyclic compound may be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

The organic material layer of the organic light emitting device of the present disclosure may be formed in a single layer structure, but may be formed in a multilayer structure in which two or more organic material layers are laminated. For example, the organic light emitting device of the present disclosure may have a structure comprising a hole injection layer, a hole transfer layer, a light emitting layer, an electron transfer layer, an electron injection layer and the like as the organic material layer. However, the structure of the organic light emitting device is not limited thereto, and may comprise a smaller number of organic material layers.

In the organic light emitting device of the present disclosure, the organic material layer comprises an electron injection layer or an electron transfer layer, and the electron injection layer or the electron transfer layer may comprise the heterocyclic compound.

In the organic light emitting device of the present disclosure, the organic material layer comprises an electron transfer layer, and the electron transfer layer may comprise the heterocyclic compound.

In another organic light emitting device, the organic material layer comprises an electron blocking layer or a hole blocking layer, and the electron blocking layer or the hole blocking layer may comprise the heterocyclic compound.

In another organic light emitting device, the organic material layer comprises a hole blocking layer, and the hole blocking layer may comprise the heterocyclic compound.

In another organic light emitting device, the organic material layer comprises an electron transfer layer, a light emitting layer or a hole blocking layer, and the electron transfer layer, the light emitting layer or the hole blocking layer may comprise the heterocyclic compound.

The organic light emitting device of the present disclosure may further comprise one, two or more layers selected from the group consisting of a light emitting layer, a hole injection layer, a hole transfer layer. an electron injection layer, an electron transfer layer, an electron blocking layer and a hole blocking layer.

FIG. 1 to FIG. 4 illustrate a lamination order of electrodes and organic material layers of an organic light emitting device according to one embodiment of the present application. However, the scope of the present application is not limited to these diagrams, and structures of organic light emitting devices known in the art may also be used in the present application.

FIG. 1 illustrates an organic light emitting device in which an anode (200), an organic material layer (300) and a cathode (400) are consecutively laminated on a substrate (100). However, the structure is not limited to such a structure, and as illustrated in FIG. 2, an organic light emitting device in which a cathode, an organic material layer and an anode are consecutively laminated on a substrate may also be obtained.

FIG. 3 illustrates a case of the organic material layer being a multilayer. The organic light emitting device according to FIG. 3 comprises a hole injection layer (301), a hole transfer layer (302), a light emitting layer (303), a hole blocking layer (304), an electron transfer layer (305) and an electron injection layer (306). However, the scope of the present application is not limited to such a lamination structure, and as necessary, other layers except the light emitting layer may not be included, and other necessary functional layers may be further included.

The organic material layer comprising Chemical Formula 1 may further comprise other materials as necessary.

In addition, the organic light emitting device according to one embodiment of the present application comprises an anode, a cathode, and two or more stacks provided between the anode and the cathode, the two or more stacks each independently comprise a light emitting layer, a charge generation layer is included between the two or more stacks, and the charge generation layer comprises the heterocyclic compound represented by Chemical Formula 1.

In addition, the organic light emitting device according to one embodiment of the present application comprises an anode, a first stack provided on the anode and comprising a first light emitting layer, a charge generation layer provided on the first stack, a second stack provided on the charge generation layer and comprising a second light emitting layer, and a cathode provided on the second stack. Herein, the charge generation layer may comprise the heterocyclic compound represented by Chemical Formula 1. In addition, the first stack and the second stack may each independently further comprise one or more types of the hole injection layer, the hole transfer layer, the hole blocking layer, the electron transfer layer, the electron injection layer and the like described above.

The charge generation layer may be an N-type charge generation layer, and the charge generation layer may further comprise a dopant known in the art in addition to the heterocyclic compound represented by Chemical Formula 1.

As the organic light emitting device according to one embodiment of the present application, an organic light emitting device having a 2-stack tandem structure is schematically illustrated in FIG. 4.

Herein, the first electron blocking layer, the first hole blocking layer, the second hole blocking layer and the like described in FIG. 4 may not be included in some cases.

In the organic light emitting device according to one embodiment of the present application, materials other than the compound of Chemical Formula 1 are illustrated below, however, these are for illustrative purposes only and not for limiting the scope of the present application, and may be replaced by materials known in the art.

As the anode material, materials having relatively large work function may be used, and transparent conductive oxides, metals, conductive polymers or the like may be used. Specific examples of the anode material comprise metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or SnO$_2$:Sb; conductive polymers such as poly(3-methylthiophene), poly[3,4-(ethylene-1,2-dioxy)thiophene] (PEDOT), polypyrrole and polyaniline, and the like, but are not limited thereto.

As the cathode material, materials having relatively small work function may be used, and metals, metal oxides, conductive polymers or the like may be used. Specific examples of the cathode material comprise metals such as magnesium, calcium, sodium, potassium, titanium, indium, yttrium, lithium, gadolinium, aluminum, silver, tin and lead, or alloys thereof; multilayer structure materials such as LiF/Al or LiO$_2$/Al, and the like, but are not limited thereto.

As the hole injection material, known hole injection materials may be used, and for example, phthalocyanine compounds such as copper phthalocyanine disclosed in U.S. Pat. No. 4,356,429, or starburst-type amine derivatives such as tris(4-carbazoyl-9-ylphenyl)amine (TCTA), 4,4',4"-tri[phenyl(m-tolyl)amino]triphenylamine (m-MTDATA) or 1,3,5-tris[4-(3-methylphenylphenylamino)phenyl]benzene (m-MTDAPB) described in the literature [Advanced Material, 6, p. 677 (1994)], polyaniline/dodecylbenzene sulfonic acid, poly(3,4-ethylenedioxythiophene)/poly(4-styrene-sulfonate), polyaniline/camphor sulfonic acid or polyaniline/poly(4-styrene-sulfonate) that are conductive polymers having solubility, and the like, may be used.

As the hole transfer material, pyrazoline derivatives, arylamine-based derivatives, stilbene derivatives, triphenyldiamine derivatives and the like may be used, and low molecular or high molecular materials may also be used.

As the electron transfer material, metal complexes of oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, 8-hydroxyquinoline and derivatives thereof, and the like, may be used, and high molecular materials may also be used as well as low molecular materials.

As examples of the electron injection material, LiF is typically used in the art, however, the present application is not limited thereto.

As the light emitting material, red, green or blue light emitting materials may be used, and as necessary, two or more light emitting materials may be mixed and used. Herein, two or more light emitting materials may be used by being deposited as individual sources of supply or by being premixed and deposited as one source of supply. In addition, fluorescent materials may also be used as the light emitting material, however, phosphorescent materials may also be used. As the light emitting material, materials emitting light by bonding electrons and holes injected from an anode and a cathode, respectively, may be used alone, however, materials having a host material and a dopant material involving in light emission together may also be used.

When mixing light emitting material hosts, same series hosts may be mixed, or different series hosts may be mixed. For example, any two or more types of materials among n-type host materials or p-type host materials may be selected and used as a host material of a light emitting layer.

The organic light emitting device according to one embodiment of the present application may be a top-emission type, a bottom-emission type or a dual-emission type depending on the materials used.

The hetero-cyclic compound according to one embodiment of the present application may also be used in an organic electronic device comprising an organic solar cell, an organic photo conductor, an organic transistor and the like under a similar principle used in the organic light emitting device.

Hereinafter, the present specification will be described in more detail with reference to examples, however, these are for illustrative purposes only, and the scope of the present application is not limited thereto.

PREPARATION EXAMPLE

[Preparation Example 1] Preparation of Compound 1

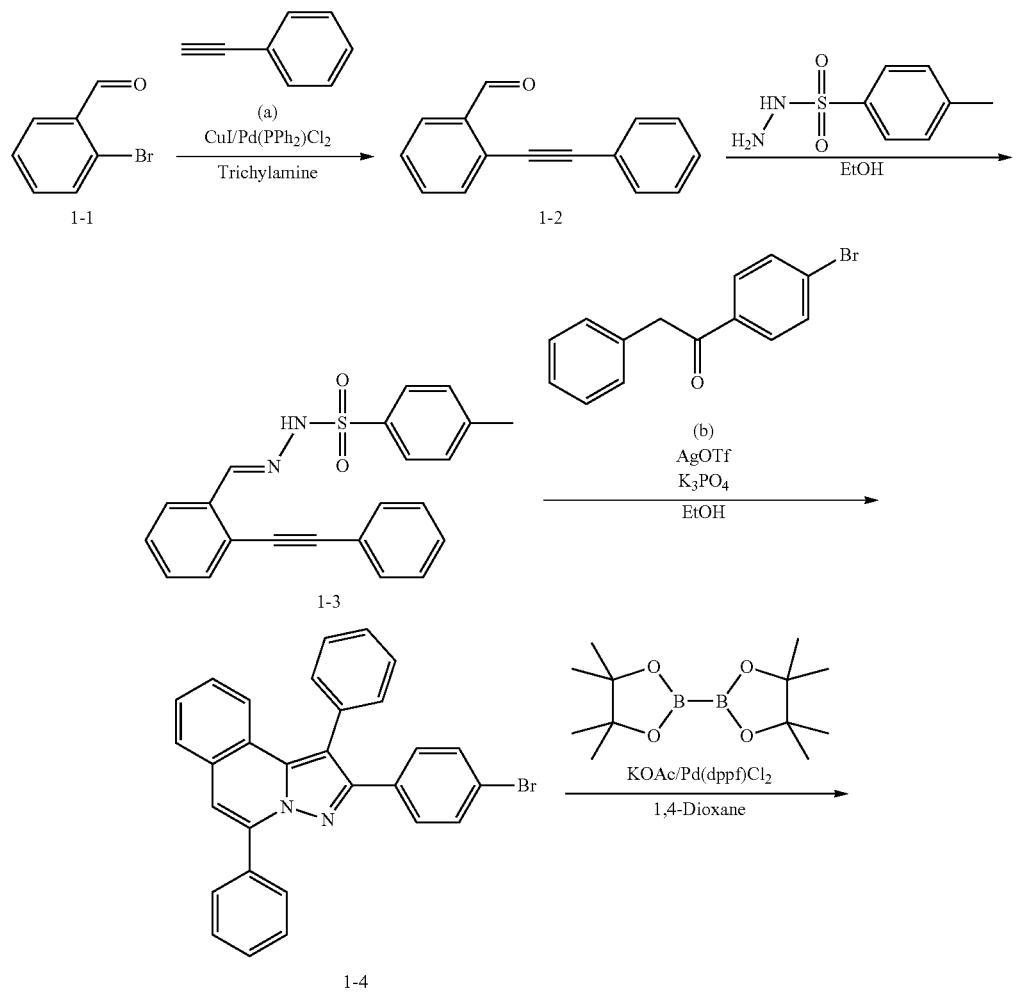

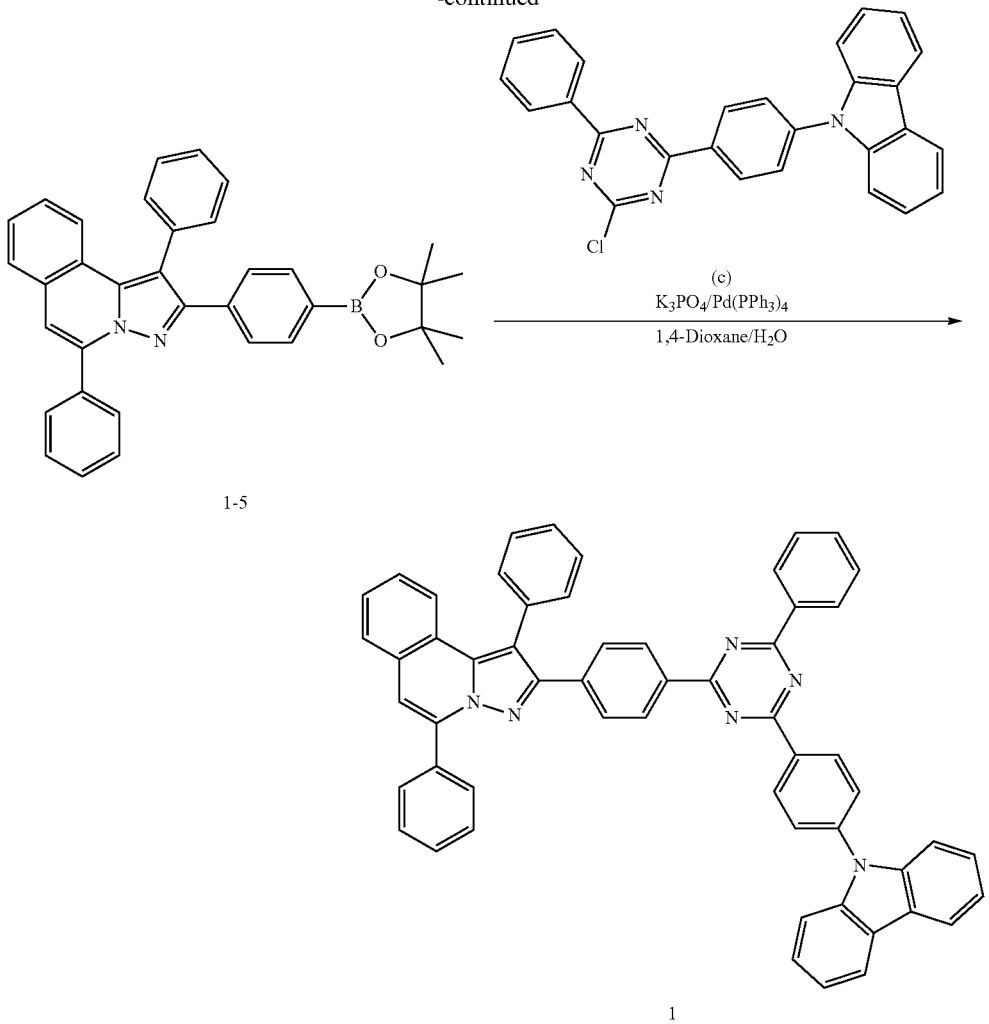

Preparation of Compound 1-2

Triethylamine (1500 ml) was introduced to Compound 1-1 (150 g, 0.81 mol, 1 eq.), Intermediate (a) (99 g, 0.97 mol, 1.2 eq.), Pd(PPh$_3$)$_2$Cl$_2$ (11.8 g, 0.016 mol, 0.02 eq.) and CuI (1.54 g, 0.008 mol, 0.01 eq.), and the result was stirred for 4 hours at 60° C. After terminating the reaction by introducing water thereto, the reaction material was extracted using methylene chloride (MC) and water. After that, moisture was removed using anhydrous Na$_2$CO$_3$. The result was separated using a silica gel column to obtain Compound 1-2 (150 g, 90% yield).

Preparation of Compound 1-3

Compound 1-2 (155 g, 0.75 mol, 1 eq.) and TsNHNH$_2$ (168 g, 0.90 mol, 1.2 eq.) were introduced to EtOH (3100 ml), and the result was stirred for 1 hour at room temperature (RT, 25° C.) Produced solids were filtered and dried to obtain Compound 1-3 (150 g, 53% yield).

Preparation of Compound 1-4

Compound 1-3 (30 g, 0.08 mol, 1 eq.) and AgOTf (3 g, 0.012 mol, 0.15 eq.) were introduced to EtOH (450 ml), and the result was stirred for 2 hours at 70° C. Intermediate (b) (24.24 g, 0.088 mol, 1.1 eq.) and K$_3$PO$_4$ (68 g, 0.32 mol) were introduced thereto, and the result was stirred for 6 hours at 70° C. After terminating the reaction by introducing water thereto, the reaction material was extracted using methylene chloride (MC) and water. After that, moisture was removed using anhydrous Na$_2$CO$_3$. The result was separated using a silica gel column to obtain Compound 1-4 (20 g, 52% yield).

Preparation of Compound 1-5

Compound 1-4 (55 g. 0.116 mol, 1 eq.), (bis(pinacolato) diboron (38.3 g, 0.15 mol, 0.13 eq.), KOAc (34.15 g, 0.348 mol, 3 eq.) and Pd(dppf)Cl$_2$ (8.48 g, 0.011 mol, 0.1 eq.) were introduced to 1,4-dioxane (550 ml), and the result was stirred for 7 hours at 100° C. After terminating the reaction by introducing water thereto, the reaction material was extracted using methylene chloride (MC) and water. After that, moisture was removed using anhydrous Na$_2$CO$_3$. The result was separated using a silica gel column to obtain Compound 1-5 (41 g, 67% yield).

Preparation of Compound 1

Compound 1-5 (7 g, 0.013 mol, 1 eq.), Intermediate (c) (6.38 g, 0.014 mol, 1.1 eq.), K$_3$PO$_4$ (5.69 g, 0.026 mol, 2 eq.) and Pd(PPh$_3$)$_4$ (0.77 g, 0.0006 mol, 0.05 eq.) were introduced to 1,4-dioxane (140 ml) and H$_2$O (35 ml), and the result was stirred for 5 hours at 80° C. Produced solids were filtered and dried to obtain Compound 1 (8.5 g, 80% yield).

Target compounds were synthesized in the same manner as in Preparation of Compound 1 of Preparation Example 1 except that Intermediate A, Intermediate B and Intermediate C of the following Table 1 were used instead of Intermediate (a), Intermediate (b) and Intermediate (c), respectively.

TABLE 1
| Target Compound | Intermediate A | Intermediate B | Intermediate C | Yield |
|---|---|---|---|---|
| 2 | 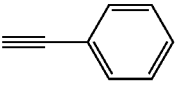 | 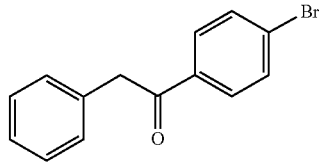 [SMILES: O=C(Cc1ccccc1)c1ccc(Br)cc1] | 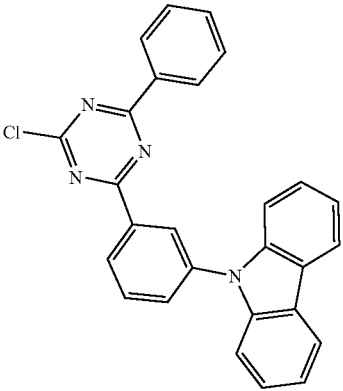 [SMILES: Clc1nc(-c2ccccc2)nc(-c2cccc(-n3c4ccccc4c4ccccc43)c2)n1] | 67% |
| 9 | 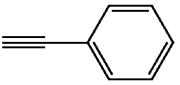 | 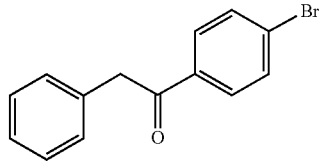 [SMILES: O=C(Cc1ccccc1)c1ccc(Br)cc1] | 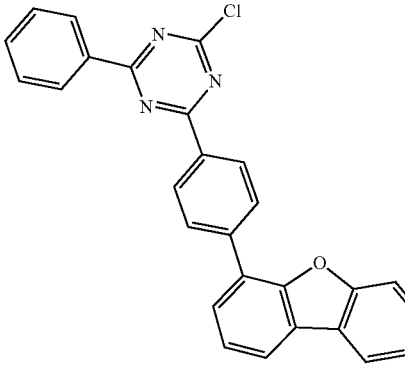 | 77% |
| 10 | 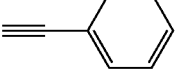 | 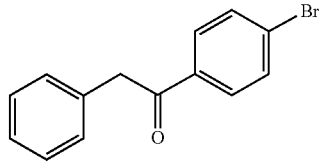 [SMILES: O=C(Cc1ccccc1)c1ccc(Br)cc1] | 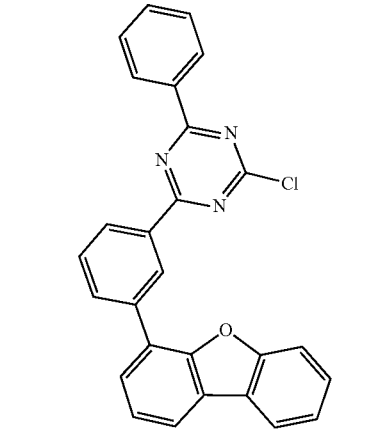 [SMILES: Clc1nc(-c2ccccc2)nc(-c2cccc(-c3cccc4c3oc3ccccc34)c2)n1] | 69% |
| 17 | 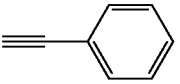 | 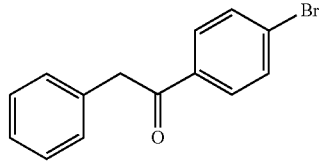 [SMILES: O=C(Cc1ccccc1)c1ccc(Br)cc1] | 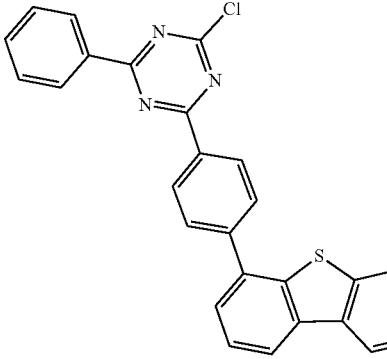 | 71% |

TABLE 1-continued

| Target Compound | Intermediate A | Intermediate B | Intermediate C | Yield |
|---|---|---|---|---|
| 18 | phenylacetylene | 2-bromo-substituted phenyl phenyl ketone | phenyl-dibenzothiophenyl-chloro-triazine | 72% |
| 33 | phenylacetylene | 2-bromo-substituted phenyl phenyl ketone | phenyl-indolocarbazolyl-chloro-triazine | 70% |
| 34 | phenylacetylene | 2-bromo-substituted phenyl phenyl ketone | phenyl-triphenylenyl-chloro-triazine | 65% |

TABLE 1-continued

| Target Compound | Intermediate A | Intermediate B | Intermediate C | Yield |
|---|---|---|---|---|
| 35 | phenylacetylene | 2-phenyl-1-(4-bromophenyl)ethanone | 4-chloro-2-phenyl-6-(indolo[3,2,1-jk]carbazolyl)pyrimidine | 75% |
| 36 | phenylacetylene | 2-phenyl-1-(4-bromophenyl)ethanone | 4-chloro-2-phenyl-6-(triphenylenyl)pyrimidine | 61% |
| 89 | phenylacetylene | 2-(4-bromophenyl)-1-phenylethanone | 2-chloro-4-phenyl-6-[4-(9H-carbazol-9-yl)phenyl]-1,3,5-triazine | 77% |

TABLE 1-continued
| Target Compound | Intermediate A | Intermediate B | Intermediate C | Yield |
|---|---|---|---|---|
| 90 |  |  |  | 70% |
| 91 |  |  |  | 76% |
| 92 |  |  |  | 70% |
| 185 |  |  |  | 72% |

TABLE 1-continued

| Target Compound | Intermediate A | Intermediate B | Intermediate C | Yield |
|---|---|---|---|---|
| 186 | 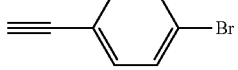 | 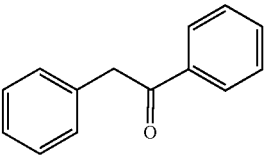 [SMILES: O=C(Cc1ccccc1)c1ccccc1] | 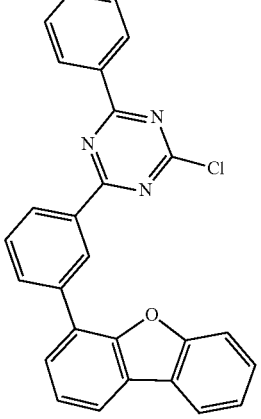 | 66% |
| 193 | 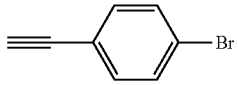 | 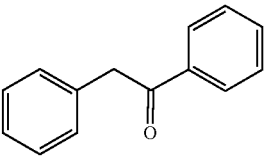 [SMILES: O=C(Cc1ccccc1)c1ccccc1] | 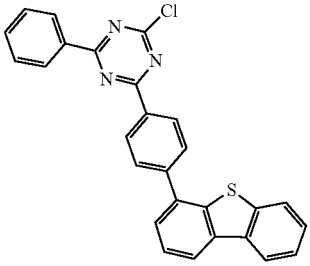 [SMILES: Clc1nc(-c2ccccc2)nc(-c2ccc(-c3cccc4c3sc3ccccc34)cc2)n1] | 65% |
| 194 | 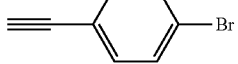 | 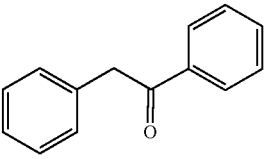 [SMILES: O=C(Cc1ccccc1)c1ccccc1] | 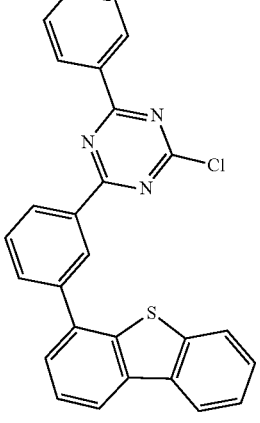 | 71% |

Compounds other than the compounds described in Preparation Example 1 and Table 1 were also prepared using the same methods as the compounds described in in Preparation Example 1 and Table 1, and the synthesis identification results are shown in the following Table 2 and Table 3.

Table 2 shows measurement values of 1H NMR (CDCl$_3$, 200 Mz), and Table 3 shows measurement values of field desorption mass spectrometry (FD-MS).

TABLE 2

| Compound | $^1$H NMR (CDCl$_3$, 200 Mz) |
|---|---|
| 1 | δ = 8.55 (d, 2H), 8.36-8.30 (m, 4H), 8.19 (d, 1H), 8.05 (d, 1H), 7.96-7.91 (m, 6H), 7.70-7.35 (m, 18H), 7.20-7.08 (m, 4H) |
| 2 | δ = 8.55 (d, 1H), 8.36-8.21 (m, 7H), 8.05 (d, 1H), 7.96-7.94 (m, 3H), 7.70-7.35 (m, 20H), 7.20-7.08 (m, 4H) |

TABLE 2-continued

| Compound | ¹H NMR (CDCl₃, 200 Mz) |
|---|---|
| 9 | δ = 8.36-8.30 (m, 4H), 8.08-7.96 (m, 8H), 7.70-7.25 (m, 21H), 7.08 (m, 2H) |
| 10 | δ = 8.38-8.30 (m, 5H), 8.08-7.96 (m, 7H), 7.73-7.31 (m, 21H), 7.08 (m, 2H) |
| 17 | δ = 8.55 (d, 1H), 8.45 (d, 1H), 8.36-8.30 (m, 6H), 8.05 (d, 1H), 7.96-7.93 (m, 5H), 7.70-7.41 (m, 18H), 7.25 (d, 2H), 7.08 (d, 2H) |
| 18 | δ = 8.55 (d, 1H), 8.45-8.30 (m, 7H), 8.05 (d, 1H), 7.96-7.93 (m, 4H), 7.73-7.41 (m, 20H), 7.08 (m, 2H) |
| 33 | δ = 8.36-8.30 (m, 4H), 8.19 (d, 2H), 8.05 (d, 1H), 7.96 (d, 2H), 7.70-7.41 (m, 21H), 7.20 (m, 2H), 7.08 (m, 2H) |
| 34 | δ = 9.27 (s, 1H), 8.79 (d, 1H), 8.36-8.30 (m, 7H), 8.15 (d, 1H), 7.96 (d, 2H), 7.70-7.62 (m, 8H), 7.52-7.41 (m, 12H), 7.08 (m, 2H) |
| 35 | δ = 8.35-8.30 (m, 6H), 8.23-8.19 (m, 3H), 8.05 (d, 1H), 7.70-7.41 (m, 21H), 7.20 (m, 2H), 7.08 (m, 2H) |
| 36 | δ = 9.27 (s, 1H), 8.79 (d, 1H), 8.35-8.30 (m, 9H), 8.15 (d, 1H), 8.05 (d, 1H), 7.70-7.62 (m, 8H), 7.54-7.41 (m, 12H), 7.08 (m, 2H) |
| 89 | δ = 8.55 (d, 1H), 8.36 (d, 2H), 8.19 (d, 1H), 8.05 (d, 1H), 7.96-7.84 (m, 10H), 7.70-7.47 (m, 15H), 7.35 (m, 1H), 7.25-7.08 (m, 6H) |
| 90 | δ = 8.55 (d, 1H), 8.36 (d, 2H), 8.24-8.19 (m, 3H), 8.05 (d, 1H), 7.96-7.94 (m, 3H), 7.84 (d, 2H), 7.70-7.47 (m, 17H), 7.35 (m, 1H), 7.25-7.08 (m, 6H) |
| 91 | δ = 8.55 (d, 1H), 8.35-8.30 (m, 4H), 8.23-8.19 (m, 2H), 8.05 (d, 1H), 7.94-7.84 (m, 7H), 7.70-7.47 (m, 15H), 7.35 (m, 1H), 7.25-7.08 (m, 6H) |
| 92 | δ = 8.55 (d, 1H), 8.35-8.30 (m, 4H), 8.23-8.19 (m, 3H), 8.05 (d, 1H), 7.94 (d, 1H), 7.84-7.80 (m, 3H), 7.70-7.47 (m, 17H), 7.35 (m, 1H), 7.25-7.08 (m, 6H) |
| 185 | δ = 8.69 (d, 2H), 8.36 (d, 2H), 8.08-7.96 (m, 8H), 7.84 (d, 2H), 7.70-7.25 (m, 21H) |
| 186 | δ = 8.69 (d, 2H), 8.38-8.36 (m, 2H), 8.08-7.94 (m, 7H), 7.84 (d, 2H), 7.70-7.41 (m, 21H) |
| 193 | δ = 8.69 (d, 2H), 8.55 (d, 1H), 8.45 (d, 1H), 8.36-8.32 (m, 3H), 8.05 (d, 1H), 7.96-7.93 (m, 5H), 7.84 (d, 2H), 7.70-7.41 (m, 18H), 7.25 (d, 2H) |
| 194 | δ = 8.69 (d, 2H), 8.55 (d, 1H), 8.45-8.32 (m, 5H), 8.05 (d, 1H), 7.96-7.93 (m, 4H), 7.84 (d, 2H), 7.70-7.41 (m, 20H) |

TABLE 3

| Compound | FD-MS |
|---|---|
| 1 | m/z = 792.30 (C56H36N6 = 792.94) |
| 2 | m/z = 792.30 (C56H36N6 = 792.94) |
| 3 | m/z = 791.30 (C57H37N5 = 791.95) |
| 4 | m/z = 791.30 (C57H37N5 = 791.95) |
| 5 | m/z = 792.30 (C56H36N6 = 792.94) |
| 6 | m/z = 792.30 (C56H36N6 = 792.94) |
| 7 | m/z = 791.30 (C57H37N5 = 791.95) |
| 8 | m/z = 791.30 (C57H37N5 = 791.95) |
| 9 | m/z = 793.28 (C56H35N5O = 793.93) |
| 10 | m/z = 793.28 (C56H35N5O = 793.93) |
| 11 | m/z = 792.28 (C57H36N4O = 792.94) |
| 12 | m/z = 792.28 (C57H36N4O = 792.94) |
| 13 | m/z = 793.28 (C56H35N5O = 793.93) |
| 14 | m/z = 793.28 (C56H35N5O = 793.93) |
| 15 | m/z = 792.28 (C57H36N4O = 792.94) |
| 16 | m/z = 792.28 (C57H36N4O = 792.94) |
| 17 | m/z = 809.26 (C56H35N5S = 809.99) |
| 18 | m/z = 809.26 (C56H35N5S = 809.99) |
| 19 | m/z = 808.26 (C57H36N4S = 809.00) |
| 20 | m/z = 808.26 (C57H36N4S = 809.00) |
| 21 | m/z = 809.26 (C56H35N5S = 809.99) |
| 22 | m/z = 809.26 (C56H35N5S = 809.99) |
| 23 | m/z = 808.26 (C57H36N4S = 809.00) |
| 24 | m/z = 808.26 (C57H36N4S = 809.00) |
| 25 | m/z = 717.25 (C50H31N5O = 717.83) |
| 26 | m/z = 717.25 (C50H31N5O = 717.83) |
| 27 | m/z = 716.25 (C51H32N4O = 716.84) |
| 28 | m/z = 716.25 (C51H32N4O = 716.84) |
| 29 | m/z = 733.23 (C50H31N5S = 733.89) |
| 30 | m/z = 733.23 (C50H31N5S = 733.89) |
| 31 | m/z = 732.23 (C51H32N4S = 732.90) |
| 32 | m/z = 732.23 (C51H32N4S = 732.90) |
| 33 | m/z = 790.28 (C56H34N6 = 790.93) |
| 34 | m/z = 777.28 (C56H35N5 = 777.93) |
| 35 | m/z = 789.28 (C57H35N5 = 789.94) |
| 36 | m/z = 776.29 (C57H36N4 = 776.94) |
| 37 | m/z = 743.30 (C53H37N5 = 743.91) |
| 38 | m/z = 865.32 (C63H39N5 = 866.04) |
| 39 | m/z = 742.30 (C54H38N4 = 742.92) |
| 40 | m/z = 864.32 (C64H40N4 = 865.05) |
| 41 | m/z = 867.33 (C63H41N5 = 868.05) |
| 42 | m/z = 716.26 (C50H32N6 = 716.84) |
| 43 | m/z = 866.34 (C64H42N4 = 867.06) |
| 44 | m/z = 715.27 (C51H33N5 = 715.86) |
| 45 | m/z = 792.30 (C56H36N6 = 792.94) |
| 46 | m/z = 792.30 (C56H36N6 = 792.94) |
| 47 | m/z = 791.30 (C57H37N5 = 791.95) |
| 48 | m/z = 791.30 (C57H37N5 = 791.95) |
| 49 | m/z = 792.30 (C56H36N6 = 792.94) |
| 50 | m/z = 792.30 (C56H36N6 = 792.94) |
| 51 | m/z = 791.30 (C57H37N5 = 791.95) |
| 52 | m/z = 791.30 (C57H37N5 = 791.95) |
| 53 | m/z = 793.28 (C56H35N5O = 793.93) |
| 54 | m/z = 793.28 (C56H35N5O = 793.93) |
| 55 | m/z = 792.28 (C57H36N4O = 792.94) |
| 56 | m/z = 792.28 (C57H36N4O = 792.94) |
| 57 | m/z = 793.28 (C56H35N5O = 793.93) |
| 58 | m/z = 793.28 (C56H35N5O = 793.93) |
| 59 | m/z = 792.28 (C57H36N4O = 792.94) |
| 60 | m/z = 792.28 (C57H36N4O = 792.94) |
| 61 | m/z = 809.26 (C56H35N5S = 809.99) |
| 62 | m/z = 809.26 (C56H35N5S = 809.99) |
| 63 | m/z = 808.26 (C57H36N4S = 809.00) |
| 64 | m/z = 808.26 (C57H36N4S = 809.00) |
| 65 | m/z = 809.26 (C56H35N5S = 809.99) |
| 66 | m/z = 809.26 (C56H35N5S = 809.99) |
| 67 | m/z = 808.26 (C57H36N4S = 809.00) |
| 68 | m/z = 808.26 (C57H36N4S = 809.00) |
| 69 | m/z = 717.25 (C50H31N5O = 717.83) |
| 70 | m/z = 717.25 (C50H31N5O = 717.83) |
| 71 | m/z = 716.25 (C51H32N4O = 716.84) |
| 72 | m/z = 716.25 (C51H32N4O = 716.84) |

TABLE 3-continued

| Compound | FD-MS |
|---|---|
| 73 | m/z = 733.23 (C50H31N5S = 733.89) |
| 74 | m/z = 733.23 (C50H31N5S = 733.89) |
| 75 | m/z = 732.23 (C51H32N4S = 732.90) |
| 76 | m/z = 732.23 (C51H32N4S = 732.90) |
| 77 | m/z = 790.28 (C56H34N6 = 790.93) |
| 78 | m/z = 777.28 (C56H35N5 = 777.93) |
| 79 | m/z = 789.28 (C57H35N5 = 789.94) |
| 80 | m/z = 776.29 (C57H36N4 = 776.94) |
| 81 | m/z = 743.30 (C53H37N5 = 743.91) |
| 82 | m/z = 865.32 (C63H39N5 = 866.04) |
| 83 | m/z = 742.30 (C54H38N4 = 742.92) |
| 84 | m/z = 864.32 (C64H40N4 = 865.05) |
| 85 | m/z = 867.33 (C63H41N5 = 868.05) |
| 86 | m/z = 716.26 (C50H32N6 = 716.84) |
| 87 | m/z = 866.34 (C64H42N4 = 867.06) |
| 88 | m/z = 715.27 (C51H33N5 = 715.86) |
| 89 | m/z = 792.30 (C56H36N6 = 792.94) |
| 90 | m/z = 792.30 (C56H36N6 = 792.94) |
| 91 | m/z = 791.30 (C57H37N5 = 791.95) |
| 92 | m/z = 791.30 (C57H37N5 = 791.95) |
| 93 | m/z = 792.30 (C56H36N6 = 792.94) |
| 94 | m/z = 792.30 (C56H36N6 = 792.94) |
| 95 | m/z = 791.30 (C57H37N5 = 791.95) |
| 96 | m/z = 791.30 (C57H37N5 = 791.95) |
| 97 | m/z = 793.28 (C56H35N5O = 793.93) |
| 98 | m/z = 793.28 (C56H35N5O = 793.93) |
| 99 | m/z = 792.28 (C57H36N4O = 792.94) |
| 100 | m/z = 792.28 (C57H36N4O = 792.94) |
| 101 | m/z = 793.28 (C56H35N5O = 793.93) |
| 102 | m/z = 793.28 (C56H35N5O = 793.93) |
| 103 | m/z = 792.28 (C57H36N4O = 792.94) |
| 104 | m/z = 792.28 (C57H36N4O = 792.94) |
| 105 | m/z = 809.26 (C56H35N5S = 809.99) |
| 106 | m/z = 809.26 (C56H35N5S = 809.99) |
| 107 | m/z = 808.26 (C57H36N4S = 809.00) |
| 108 | m/z = 808.26 (C57H36N4S = 809.00) |
| 109 | m/z = 809.26 (C56H35N5S = 809.99) |
| 110 | m/z = 809.26 (C56H35N5S = 809.99) |
| 111 | m/z = 808.26 (C57H36N4S = 809.00) |
| 112 | m/z = 808.26 (C57H36N4S = 809.00) |
| 113 | m/z = 717.25 (C50H31N5O = 717.83) |
| 114 | m/z = 717.25 (C50H31N5O = 717.83) |
| 115 | m/z = 716.25 (C51H32N4O = 716.84) |
| 116 | m/z = 716.25 (C51H32N4O = 716.84) |
| 117 | m/z = 733.23 (C50H31N5S = 733.89) |
| 118 | m/z = 733.23 (C50H31N5S = 733.89) |
| 119 | m/z = 732.23 (C51H32N4S = 732.90) |
| 120 | m/z = 732.23 (C51H32N4S = 732.90) |
| 121 | m/z = 790.28 (C56H34N6 = 790.93) |
| 122 | m/z = 777.28 (C56H35N5 = 777.93) |
| 123 | m/z = 789.28 (C57H35N5 = 789.94) |
| 124 | m/z = 776.29 (C57H36N4 = 776.94) |
| 125 | m/z = 743.30 (C53H37N5 = 743.91) |
| 126 | m/z = 865.32 (C63H39N5 = 866.04) |
| 127 | m/z = 742.30 (C54H38N4 = 742.92) |
| 128 | m/z = 864.32 (C64H40N4 = 865.05) |
| 129 | m/z = 867.33 (C63H41N5 = 868.05) |
| 130 | m/z = 716.26 (C50H32N6 = 716.84) |
| 131 | m/z = 866.34 (C64H42N4 = 867.06) |
| 132 | m/z = 715.27 (C51H33N5 = 715.86) |
| 133 | m/z = 792.30 (C56H36N6 = 792.94) |
| 134 | m/z = 792.30 (C56H36N6 = 792.94) |
| 135 | m/z = 791.30 (C57H37N5 = 791.95) |
| 136 | m/z = 791.30 (C57H37N5 = 791.95) |
| 137 | m/z = 792.30 (C56H36N6 = 792.94) |
| 138 | m/z = 792.30 (C56H36N6 = 792.94) |
| 139 | m/z = 791.30 (C57H37N5 = 791.95) |
| 140 | m/z = 791.30 (C57H37N5 = 791.95) |
| 141 | m/z = 793.28 (C56H35N5O = 793.93) |
| 142 | m/z = 793.28 (C56H35N5O = 793.93) |
| 143 | m/z = 792.28 (C57H36N4O = 792.94) |
| 144 | m/z = 792.28 (C57H36N4O = 792.94) |
| 145 | m/z = 793.28 (C56H35N5O = 793.93) |
| 146 | m/z = 793.28 (C56H35N5O = 793.93) |
| 147 | m/z = 792.28 (C57H36N4O = 792.94) |
| 148 | m/z = 792.28 (C57H36N4O = 792.94) |
| 149 | m/z = 809.26 (C56H35N5S = 809.99) |
| 150 | m/z = 809.26 (C56H35N5S = 809.99) |
| 151 | m/z = 808.26 (C57H36N4S = 809.00) |
| 152 | m/z = 808.26 (C57H36N4S = 809.00) |
| 153 | m/z = 809.26 (C56H35N5S = 809.99) |
| 154 | m/z = 809.26 (C56H35N5S = 809.99) |
| 155 | m/z = 808.26 (C57H36N4S = 809.00) |
| 156 | m/z = 808.26 (C57H36N4S = 809.00) |
| 157 | m/z = 717.25 (C50H31N5O = 717.83) |
| 158 | m/z = 717.25 (C50H31N5O = 717.83) |
| 159 | m/z = 716.25 (C51H32N4O = 716.84) |
| 160 | m/z = 716.25 (C51H32N4O = 716.84) |
| 161 | m/z = 733.23 (C50H31N5S = 733.89) |
| 162 | m/z = 733.23 (C50H31N5S = 733.89) |
| 163 | m/z = 732.23 (C51H32N4S = 732.90) |
| 164 | m/z = 732.23 (C51H32N4S = 732.90) |
| 165 | m/z = 790.28 (C56H34N6 = 790.93) |
| 166 | m/z = 777.28 (C56H35N5 = 777.93) |
| 167 | m/z = 789.28 (C57H35N5 = 789.94) |
| 168 | m/z = 776.29 (C57H36N4 = 776.94) |
| 169 | m/z = 743.30 (C53H37N5 = 743.91) |
| 170 | m/z = 865.32 (C63H39N5 = 866.04) |
| 171 | m/z = 742.30 (C54H38N4 = 742.92) |
| 172 | m/z = 864.32 (C64H40N4 = 865.05) |
| 173 | m/z = 867.33 (C63H41N5 = 868.05) |
| 174 | m/z = 716.26 (C50H32N6 = 716.84) |
| 175 | m/z = 866.34 (C64H42N4 = 867.06) |
| 176 | m/z = 715.27 (C51H33N5 = 715.86) |
| 177 | m/z = 792.30 (C56H36N6 = 792.94) |
| 178 | m/z = 792.30 (C56H36N6 = 792.94) |
| 179 | m/z = 791.30 (C57H37N5 = 791.95) |
| 180 | m/z = 791.30 (C57H37N5 = 791.95) |
| 181 | m/z = 792.30 (C56H36N6 = 792.94) |
| 182 | m/z = 792.30 (C56H36N6 = 792.94) |
| 183 | m/z = 791.30 (C57H37N5 = 791.95) |
| 184 | m/z = 791.30 (C57H37N5 = 791.95) |
| 185 | m/z = 793.28 (C56H35N5O = 793.93) |
| 186 | m/z = 793.28 (C56H35N5O = 793.93) |
| 187 | m/z = 792.28 (C57H36N4O = 792.94) |
| 188 | m/z = 792.28 (C57H36N4O = 792.94) |
| 189 | m/z = 793.28 (C56H35N5O = 793.93) |
| 190 | m/z = 793.28 (C56H35N5O = 793.93) |
| 191 | m/z = 792.28 (C57H36N4O = 792.94) |
| 192 | m/z = 792.28 (C57H36N4O = 792.94) |
| 193 | m/z = 809.26 (C56H35N5S = 809.99) |
| 194 | m/z = 809.26 (C56H35N5S = 809.99) |
| 195 | m/z = 808.26 (C57H36N4S = 809.00) |
| 196 | m/z = 808.26 (C57H36N4S = 809.00) |
| 197 | m/z = 809.26 (C56H35N5S = 809.99) |
| 198 | m/z = 809.26 (C56H35N5S = 809.99) |
| 199 | m/z = 808.26 (C57H36N4S = 809.00) |
| 200 | m/z = 808.26 (C57H36N4S = 809.00) |
| 201 | m/z = 717.25 (C50H31N5O = 717.83) |
| 202 | m/z = 717.25 (C50H31N5O = 717.83) |
| 203 | m/z = 716.25 (C51H32N4O = 716.84) |
| 204 | m/z = 716.25 (C51H32N4O = 716.84) |
| 205 | m/z = 733.23 (C50H31N5S = 733.89) |
| 206 | m/z = 733.23 (C50H31N5S = 733.89) |
| 207 | m/z = 732.23 (C51H32N4S = 732.90) |
| 208 | m/z = 732.23 (C51H32N4S = 732.90) |
| 209 | m/z = 790.28 (C56H34N6 = 790.93) |
| 210 | m/z = 777.28 (C56H35N5 = 777.93) |
| 211 | m/z = 789.28 (C57H35N5 = 789.94) |
| 212 | m/z = 776.29 (C57H36N4 = 776.94) |
| 213 | m/z = 743.30 (C53H37N5 = 743.91) |
| 214 | m/z = 865.32 (C63H39N5 = 866.04) |
| 215 | m/z = 742.30 (C54H38N4 = 742.92) |
| 216 | m/z = 864.32 (C64H40N4 = 865.05) |
| 217 | m/z = 867.33 (C63H41N5 = 868.05) |
| 218 | m/z = 716.26 (C50H32N6 = 716.84) |
| 219 | m/z = 866.34 (C64H42N4 = 867.06) |
| 220 | m/z = 715.27 (C51H33N5 = 715.86) |
| 221 | m/z = 792.30 (C56H36N6 = 792.94) |
| 222 | m/z = 792.30 (C56H36N6 = 792.94) |
| 223 | m/z = 791.30 (C57H37N5 = 791.95) |
| 224 | m/z = 791.30 (C57H37N5 = 791.95) |
| 225 | m/z = 792.30 (C56H36N6 = 792.94) |
| 226 | m/z = 792.30 (C56H36N6 = 792.94) |
| 227 | m/z = 791.30 (C57H37N5 = 791.95) |
| 228 | m/z = 791.30 (C57H37N5 = 791.95) |

TABLE 3-continued

| Compound | FD-MS |
|---|---|
| 229 | m/z = 793.28 (C56H35N5O = 793.93) |
| 230 | m/z = 793.28 (C56H35N5O = 793.93) |
| 231 | m/z = 792.28 (C57H36N4O = 792.94) |
| 232 | m/z = 792.28 (C57H36N4O = 792.94) |
| 233 | m/z = 793.28 (C56H35N5O = 793.93) |
| 234 | m/z = 793.28 (C56H35N5O = 793.93) |
| 235 | m/z = 792.28 (C57H36N4O = 792.94) |
| 236 | m/z = 792.28 (C57H36N4O = 792.94) |
| 237 | m/z = 809.26 (C56H35N5S = 809.99) |
| 238 | m/z = 809.26 (C56H35N5S = 809.99) |
| 239 | m/z = 808.26 (C57H36N4S = 809.00) |
| 240 | m/z = 808.26 (C57H36N4S = 809.00) |
| 241 | m/z = 809.26 (C56H35N5S = 809.99) |
| 242 | m/z = 809.26 (C56H35N5S = 809.99) |
| 243 | m/z = 808.26 (C57H36N4S = 809.00) |
| 244 | m/z = 808.26 (C57H36N4S = 809.00) |
| 245 | m/z = 717.25 (C50H31N5O = 717.83) |
| 246 | m/z = 717.25 (C50H31N5O = 717.83) |
| 247 | m/z = 716.25 (C51H32N4O = 716.84) |
| 248 | m/z = 716.25 (C51H32N4O = 716.84) |
| 249 | m/z = 733.23 (C50H31N5S = 733.89) |
| 250 | m/z = 733.23 (C50H31N5S = 733.89) |
| 251 | m/z = 732.23 (C51H32N4S = 732.90) |
| 252 | m/z = 732.23 (C51H32N4S = 732.90) |
| 253 | m/z = 790.28 (C56H34N6 = 790.93) |
| 254 | m/z = 777.28 (C56H35N5 = 777.93) |
| 255 | m/z = 789.28 (C57H35N5 = 789.94) |
| 256 | m/z = 776.29 (C57H36N4 = 776.94) |
| 257 | m/z = 743.30 (C53H37N5 = 743.91) |
| 258 | m/z = 865.32 (C63H39N5 = 866.04) |
| 259 | m/z = 742.30 (C54H38N4 = 742.92) |
| 260 | m/z = 864.32 (C64H40N4 = 865.05) |
| 261 | m/z = 867.33 (C63H41N5 = 868.05) |
| 262 | m/z = 716.26 (C50H32N6 = 716.84) |
| 263 | m/z = 866.34 (C64H42N4 = 867.06) |
| 264 | m/z = 715.27 (C51H33N5 = 715.86) |
| 265 | m/z = 791.30 (C57H37N5 = 791.95) |
| 266 | m/z = 791.30 (C57H37N5 = 791.95) |
| 267 | m/z = 791.30 (C57H37N5 = 791.95) |
| 268 | m/z = 791.30 (C57H37N5 = 791.95) |
| 269 | m/z = 792.28 (C57H36N4O = 792.94) |
| 270 | m/z = 792.28 (C57H36N4O = 792.94) |
| 271 | m/z = 792.28 (C57H36N4O = 792.94) |
| 272 | m/z = 792.28 (C57H36N4O = 792.94) |
| 273 | m/z = 808.26 (C57H36N4S = 809.00) |
| 274 | m/z = 808.26 (C57H36N4S = 809.00) |
| 275 | m/z = 808.26 (C57H36N4S = 809.00) |
| 276 | m/z = 808.26 (C57H36N4S = 809.00) |
| 277 | m/z = 716.25 (C51H32N4O = 716.84) |
| 278 | m/z = 733.23 (C51H32N4S = 732.90) |
| 279 | m/z = 716.25 (C51H32N4O = 716.84) |
| 280 | m/z = 733.23 (C51H32N4S = 732.90) |
| 281 | m/z = 789.28 (C57H35N5 = 789.94) |
| 282 | m/z = 776.29 (C57H36N4 = 776.94) |
| 283 | m/z = 742.30 (C54H38N4 = 742.92) |
| 284 | m/z = 864.32 (C64H40N4 = 865.05) |
| 285 | m/z = 866.34 (C64H42N4 = 867.06) |
| 286 | m/z = 715.27 (C51H33N5 = 715.86) |
| 287 | m/z = 791.30 (C57H37N5 = 791.95) |
| 288 | m/z = 791.30 (C57H37N5 = 791.95) |
| 289 | m/z = 791.30 (C57H37N5 = 791.95) |
| 290 | m/z = 791.30 (C57H37N5 = 791.95) |
| 291 | m/z = 792.28 (C57H36N4O = 792.94) |
| 292 | m/z = 792.28 (C57H36N4O = 792.94) |
| 293 | m/z = 792.28 (C57H36N4O = 792.94) |
| 294 | m/z = 792.28 (C57H36N4O = 792.94) |
| 295 | m/z = 808.26 (C57H36N4S = 809.00) |
| 296 | m/z = 808.26 (C57H36N4S = 809.00) |
| 297 | m/z = 808.26 (C57H36N4S = 809.00) |
| 298 | m/z = 808.26 (C57H36N4S = 809.00) |
| 299 | m/z = 716.25 (C51H32N4O = 716.84) |
| 300 | m/z = 716.25 (C51H32N4O = 716.84) |
| 301 | m/z = 732.23 (C51H32N4S = 792.94) |
| 302 | m/z = 732.23 (C51H32N4S = 792.94) |
| 303 | m/z = 789.28 (C57H35N5 = 789.94) |
| 304 | m/z = 776.29 (C57H36N4 = 776.94) |
| 305 | m/z = 742.30 (C54H38N4 = 742.92) |
| 306 | m/z = 864.32 (C64H40N4 = 865.05) |
| 307 | m/z = 866.34 (C64H42N4 = 867.06) |
| 308 | m/z = 715.27 (C51H33N5 = 715.86) |
| 309 | m/z = 791.30 (C57H37N5 = 791.95) |
| 310 | m/z = 791.30 (C57H37N5 = 791.95) |
| 311 | m/z = 791.30 (C57H37N5 = 791.95) |
| 312 | m/z = 791.30 (C57H37N5 = 791.95) |
| 313 | m/z = 792.28 (C57H36N4O = 792.94) |
| 314 | m/z = 792.28 (C57H36N4O = 792.94) |
| 315 | m/z = 792.28 (C57H36N4O = 792.94) |
| 316 | m/z = 792.28 (C57H36N4O = 792.94) |
| 317 | m/z = 808.26 (C57H36N4S = 809.00) |
| 318 | m/z = 808.26 (C57H36N4S = 809.00) |
| 319 | m/z = 808.26 (C57H36N4S = 809.00) |
| 320 | m/z = 808.26 (C57H36N4S = 809.00) |
| 321 | m/z = 716.25 (C51H32N4O = 716.84) |
| 322 | m/z = 733.23 (C51H32N4S = 732.90) |
| 323 | m/z = 716.25 (C51H32N4O = 716.84) |
| 324 | m/z = 733.23 (C51H32N4S = 732.90) |
| 325 | m/z = 789.28 (C57H35N5 = 789.94) |
| 326 | m/z = 776.29 (C57H36N4 = 776.94) |
| 327 | m/z = 742.30 (C54H38N4 = 742.92) |
| 328 | m/z = 864.32 (C64H40N4 = 865.05) |
| 329 | m/z = 866.34 (C64H42N4 = 867.06) |
| 330 | m/z = 715.27 (C51H33N5 = 715.86) |
| 331 | m/z = 791.30 (C57H37N5 = 791.95) |
| 332 | m/z = 791.30 (C57H37N5 = 791.95) |
| 333 | m/z = 791.30 (C57H37N5 = 791.95) |
| 334 | m/z = 791.30 (C57H37N5 = 791.95) |
| 335 | m/z = 792.28 (C57H36N4O = 792.94) |
| 336 | m/z = 792.28 (C57H36N4O = 792.94) |
| 337 | m/z = 792.28 (C57H36N4O = 792.94) |
| 338 | m/z = 792.28 (C57H36N4O = 792.94) |
| 339 | m/z = 808.26 (C57H36N4S = 809.00) |
| 340 | m/z = 808.26 (C57H36N4S = 809.00) |
| 341 | m/z = 808.26 (C57H36N4S = 809.00) |
| 342 | m/z = 808.26 (C57H36N4S = 809.00) |
| 343 | m/z = 716.25 (C51H32N4O = 716.84) |
| 344 | m/z = 716.25 (C51H32N4O = 716.84) |
| 345 | m/z = 733.23 (C51H32N4S = 732.90) |
| 346 | m/z = 733.23 (C51H32N4S = 732.90) |
| 347 | m/z = 789.28 (C57H35N5 = 789.94) |
| 348 | m/z = 776.29 (C57H36N4 = 776.94) |
| 349 | m/z = 742.30 (C54H38N4 = 742.92) |
| 350 | m/z = 864.32 (C64H40N4 = 865.05) |
| 351 | m/z = 866.34 (C64H42N4 = 867.06) |
| 352 | m/z = 715.27 (C51H33N5 = 715.86) |
| 353 | m/z = 791.30 (C57H37N5 = 791.95) |
| 354 | m/z = 791.30 (C57H37N5 = 791.95) |
| 355 | m/z = 791.30 (C57H37N5 = 791.95) |
| 356 | m/z = 791.30 (C57H37N5 = 791.95) |
| 357 | m/z = 792.28 (C57H36N4O = 792.94) |
| 358 | m/z = 792.28 (C57H36N4O = 792.94) |
| 359 | m/z = 792.28 (C57H36N4O = 792.94) |
| 360 | m/z = 792.28 (C57H36N4O = 792.94) |
| 361 | m/z = 808.26 (C57H36N4S = 809.00) |
| 362 | m/z = 808.26 (C57H36N4S = 809.00) |
| 363 | m/z = 808.26 (C57H36N4S = 809.00) |
| 364 | m/z = 808.26 (C57H36N4S = 809.00) |
| 365 | m/z = 716.25 (C51H32N4O = 716.84) |
| 366 | m/z = 733.23 (C51H32N4S = 732.90) |
| 367 | m/z = 716.25 (C51H32N4O = 716.84) |
| 368 | m/z = 733.23 (C51H32N4S = 732.90) |
| 369 | m/z = 789.28 (C57H35N5 = 789.94) |
| 370 | m/z = 776.29 (C57H36N4 = 776.94) |
| 371 | m/z = 742.30 (C54H38N4 = 742.92) |
| 372 | m/z = 864.32 (C64H40N4 = 865.05) |
| 373 | m/z = 866.34 (C64H42N4 = 867.06) |
| 374 | m/z = 715.27 (C51H33N5 = 715.86) |
| 375 | m/z = 791.30 (C57H37N5 = 791.95) |
| 376 | m/z = 791.30 (C57H37N5 = 791.95) |
| 377 | m/z = 791.30 (C57H37N5 = 791.95) |
| 378 | m/z = 791.30 (C57H37N5 = 791.95) |
| 379 | m/z = 792.28 (C57H36N4O = 792.94) |
| 380 | m/z = 792.28 (C57H36N4O = 792.94) |
| 381 | m/z = 792.28 (C57H36N4O = 792.94) |
| 382 | m/z = 792.28 (C57H36N4O = 792.94) |
| 383 | m/z = 808.26 (C57H36N4S = 809.00) |
| 384 | m/z = 808.26 (C57H36N4S = 809.00) |

TABLE 3-continued

| Compound | FD-MS |
|---|---|
| 385 | m/z = 808.26 (C57H36N4S = 809.00) |
| 386 | m/z = 808.26 (C57H36N4S = 809.00) |
| 387 | m/z = 716.25 (C51H32N4O = 716.84) |
| 388 | m/z = 716.25 (C51H32N4O = 716.84) |
| 389 | m/z = 733.23 (C51H32N4S = 732.90) |
| 390 | m/z = 733.23 (C51H32N4S = 732.90) |
| 391 | m/z = 789.28 (C57H35N5 = 789.94) |
| 392 | m/z = 776.29 (C57H36N4 = 776.94) |
| 393 | m/z = 742.30 (C54H38N4 = 742.92) |
| 394 | m/z = 864.32 (C64H40N4 = 865.05) |
| 395 | m/z = 866.34 (C64H42N4 = 867.06) |
| 396 | m/z = 715.27 (C51H33N5 = 715.86) |
| 397 | m/z = 791.30 (C57H37N5 = 791.95) |
| 398 | m/z = 791.30 (C57H37N5 = 791.95) |
| 399 | m/z = 791.30 (C57H37N5 = 791.95) |
| 400 | m/z = 791.30 (C57H37N5 = 791.95) |
| 401 | m/z = 792.28 (C57H36N4O = 792.94) |
| 402 | m/z = 792.28 (C57H36N4O = 792.94) |
| 403 | m/z = 792.28 (C57H36N4O = 792.94) |
| 404 | m/z = 792.28 (C57H36N4O = 792.94) |
| 405 | m/z = 808.26 (C57H36N4S = 809.00) |
| 406 | m/z = 808.26 (C57H36N4S = 809.00) |
| 407 | m/z = 808.26 (C57H36N4S = 809.00) |
| 408 | m/z = 808.26 (C57H36N4S = 809.00) |
| 409 | m/z = 716.25 (C51H32N4O = 716.84) |
| 410 | m/z = 732.23 (C51H32N4S = 732.90) |
| 411 | m/z = 716.25 (C51H32N4O = 716.84) |
| 412 | m/z = 732.23 (C51H32N4S = 732.90) |
| 413 | m/z = 789.28 (C57H35N5 = 789.94) |
| 414 | m/z = 776.29 (C57H36N4 = 776.94) |
| 415 | m/z = 742.30 (C54H38N4 = 742.92) |
| 416 | m/z = 864.32 (C64H40N4 = 865.05) |
| 417 | m/z = 866.34 (C64H42N4 = 867.06) |
| 418 | m/z = 715.27 (C51H33N5 = 715.86) |
| 419 | m/z = 791.30 (C57H37N5 = 791.95) |
| 420 | m/z = 791.30 (C57H37N5 = 791.95) |
| 421 | m/z = 791.30 (C57H37N5 = 791.95) |
| 422 | m/z = 791.30 (C57H37N5 = 791.95) |
| 423 | m/z = 792.28 (C57H36N4O = 792.94) |
| 424 | m/z = 792.28 (C57H36N4O = 792.94) |
| 425 | m/z = 792.28 (C57H36N4O = 792.94) |
| 426 | m/z = 792.28 (C57H36N4O = 792.94) |
| 427 | m/z = 808.26 (C57H36N4S = 809.00) |
| 428 | m/z = 808.26 (C57H36N4S = 809.00) |
| 429 | m/z = 808.26 (C57H36N4S = 809.00) |
| 430 | m/z = 808.26 (C57H36N4S = 809.00) |
| 431 | m/z = 716.25 (C51H32N4O = 716.84) |
| 432 | m/z = 716.25 (C51H32N4O = 716.84) |
| 433 | m/z = 732.23 (C51H32N4S = 732.90) |
| 434 | m/z = 732.23 (C51H32N4S = 732.90) |
| 435 | m/z = 789.28 (C57H35N5 = 789.94) |
| 436 | m/z = 776.29 (C57H36N4 = 776.94) |
| 437 | m/z = 742.30 (C54H38N4 = 742.92) |
| 438 | m/z = 864.32 (C64H40N4 = 865.05) |
| 439 | m/z = 866.34 (C64H42N4 = 867.06) |
| 440 | m/z = 715.27 (C51H33N5 = 715.86) |
| 441 | m/z = 791.30 (C57H37N5 = 791.95) |
| 442 | m/z = 791.30 (C57H37N5 = 791.95) |
| 443 | m/z = 791.30 (C57H37N5 = 791.95) |
| 444 | m/z = 791.30 (C57H37N5 = 791.95) |
| 445 | m/z = 792.28 (C57H36N4O = 792.94) |
| 446 | m/z = 792.28 (C57H36N4O = 792.94) |
| 447 | m/z = 792.28 (C57H36N4O = 792.94) |
| 448 | m/z = 792.28 (C57H36N4O = 792.94) |
| 449 | m/z = 808.26 (C57H36N4S = 809.00) |
| 450 | m/z = 808.26 (C57H36N4S = 809.00) |
| 451 | m/z = 808.26 (C57H36N4S = 809.00) |
| 452 | m/z = 808.26 (C57H36N4S = 809.00) |
| 453 | m/z = 716.25 (C51H32N4O = 716.84) |
| 454 | m/z = 732.23 (C51H32N4S = 732.90) |
| 455 | m/z = 716.25 (C51H32N4O = 716.84) |
| 456 | m/z = 732.23 (C51H32N4S = 732.90) |
| 457 | m/z = 789.28 (C57H35N5 = 789.94) |
| 458 | m/z = 776.29 (C57H36N4 = 776.94) |
| 459 | m/z = 742.30 (C54H38N4 = 742.92) |
| 460 | m/z = 864.32 (C64H40N4 = 865.05) |
| 461 | m/z = 866.34 (C64H42N4 = 867.06) |
| 462 | m/z = 715.27 (C51H33N5 = 715.86) |
| 463 | m/z = 791.30 (C57H37N5 = 791.95) |
| 464 | m/z = 791.30 (C57H37N5 = 791.95) |
| 465 | m/z = 791.30 (C57H37N5 = 791.95) |
| 466 | m/z = 791.30 (C57H37N5 = 791.95) |
| 467 | m/z = 792.28 (C57H36N4O = 792.94) |
| 468 | m/z = 792.28 (C57H36N4O = 792.94) |
| 469 | m/z = 792.28 (C57H36N4O = 792.94) |
| 470 | m/z = 792.28 (C57H36N4O = 792.94) |
| 471 | m/z = 808.26 (C57H36N4S = 809.00) |
| 472 | m/z = 808.26 (C57H36N4S = 809.00) |
| 473 | m/z = 808.26 (C57H36N4S = 809.00) |
| 474 | m/z = 808.26 (C57H36N4S = 809.00) |
| 475 | m/z = 716.25 (C51H32N4O = 716.84) |
| 476 | m/z = 716.25 (C51H32N4O = 716.84) |
| 477 | m/z = 732.23 (C51H32N4S = 732.90) |
| 479 | m/z = 789.28 (C57H35N5 = 789.94) |
| 480 | m/z = 776.29 (C57H36N4 = 776.94) |
| 481 | m/z = 742.30 (C54H38N4 = 742.92) |
| 482 | m/z = 864.32 (C64H40N4 = 865.05) |
| 483 | m/z = 866.34 (C64H42N4 = 867.06) |
| 484 | m/z = 715.27 (C51H33N5 = 715.86) |
| 485 | m/z = 791.30 (C57H37N5 = 791.95) |
| 486 | m/z = 791.30 (C57H37N5 = 791.95) |
| 487 | m/z = 791.30 (C57H37N5 = 791.95) |
| 488 | m/z = 791.30 (C57H37N5 = 791.95) |
| 489 | m/z = 792.28 (C57H36N4O = 792.94) |
| 490 | m/z = 792.28 (C57H36N4O = 792.94) |
| 491 | m/z = 792.28 (C57H36N4O = 792.94) |
| 492 | m/z = 792.28 (C57H36N4O = 792.94) |
| 493 | m/z = 808.26 (C57H36N4S = 809.00) |
| 494 | m/z = 808.26 (C57H36N4S = 809.00) |
| 495 | m/z = 808.26 (C57H36N4S = 809.00) |
| 496 | m/z = 808.26 (C57H36N4S = 809.00) |
| 497 | m/z = 716.25 (C51H32N4O = 716.84) |
| 498 | m/z = 732.23 (C51H32N4S = 732.90) |
| 499 | m/z = 716.25 (C51H32N4O = 716.84) |
| 500 | m/z = 732.23 (C51H32N4S = 732.90) |
| 501 | m/z = 789.28 (C57H35N5 = 789.94) |
| 502 | m/z = 776.29 (C57H36N4 = 776.94) |
| 503 | m/z = 742.30 (C54H38N4 = 742.92) |
| 504 | m/z = 864.32 (C64H40N4 = 865.05) |
| 505 | m/z = 866.34 (C64H42N4 = 867.06) |
| 507 | m/z = 791.30 (C57H37N5 = 791.95) |
| 509 | m/z = 791.30 (C57H37N5 = 791.95) |
| 511 | m/z = 792.28 (C57H36N4O = 792.94) |
| 513 | m/z = 792.28 (C57H36N4O = 792.94) |
| 515 | m/z = 808.26 (C57H36N4S = 809.00) |
| 517 | m/z = 808.26 (C57H36N4S = 809.00) |
| 519 | m/z = 716.25 (C51H32N4O = 716.84) |
| 520 | m/z = 716.25 (C51H32N4O = 716.84) |
| 521 | m/z = 732.23 (C51H32N4S = 732.90) |
| 522 | m/z = 732.23 (C51H32N4S = 732.90) |
| 523 | m/z = 789.28 (C57H35N5 = 789.94) |
| 525 | m/z = 742.30 (C54H38N4 = 742.92) |
| 527 | m/z = 866.34 (C64H42N4 = 867.06) |
| 529 | m/z = 868.33 (C62H40N6 = 869.04) |
| 530 | m/z = 716.26 (C50H32N6 = 716.84) |
| 531 | m/z = 730.28 (C51H34N6 = 730.87) |
| 532 | m/z = 744.30 (C52H36N6 = 744.90) |

EXPERIMENTAL EXAMPLE

Experimental Example 1

Manufacture of Organic Light Emitting Device (Comparative Example 1)

A transparent indium tin oxide (ITO) electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used. Next, an ITO substrate was installed in a substrate folder of a vacuum deposition apparatus, and the following 4,4',4''-tris(N,N-(2-naphthyl)-phenylamino)triphenylamine (2-TNATA) was introduced to a cell in the vacuum deposition apparatus.

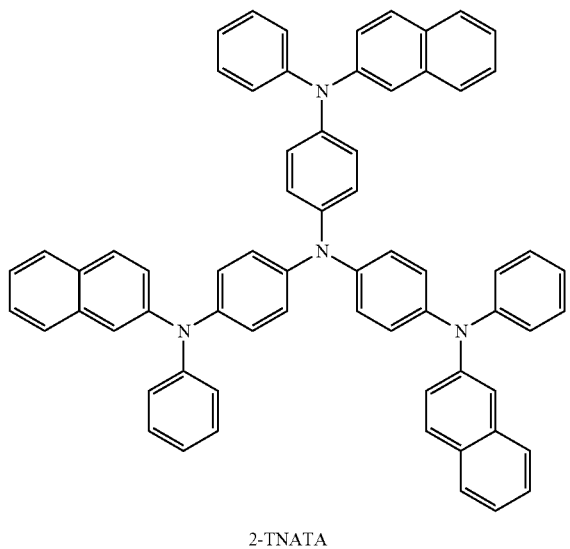 [SMILES: c1ccc(N(c2ccc(N(c3ccc(N(c4ccccc4)c4ccc5ccccc5c4)cc3)c3ccc(N(c4ccccc4)c4ccc5ccccc5c4)cc3)cc2)c2ccc3ccccc3c2)cc1]

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate. To another cell of the vacuum deposition apparatus, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

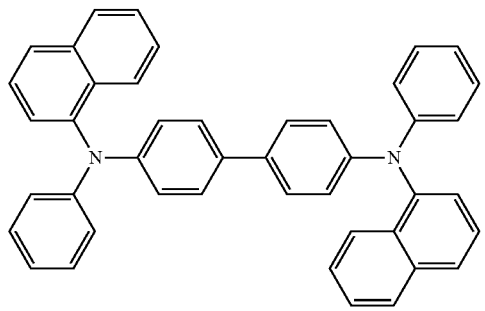

NPB

After forming the hole injection layer and the hole transfer layer as above, a blue light emitting material having a structure as below was deposited thereon as a light emitting layer. Specifically, in one side cell in the vacuum deposition apparatus, H1, a blue light emitting host material, was vacuum deposited to a thickness of 200 Å, and D1, a blue light emitting dopant material, was vacuum deposited thereon by 5% with respect to the host material.

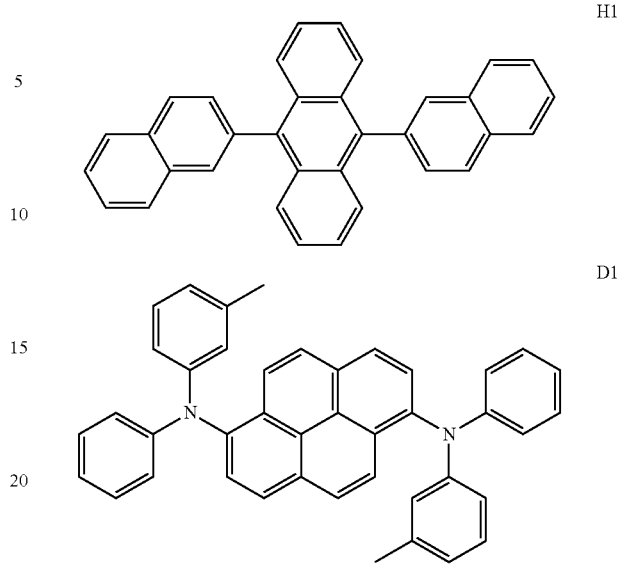

Subsequently, a compound of the following Structural Formula E1 was deposited to a thickness of 300 Å as an electron transfer layer.

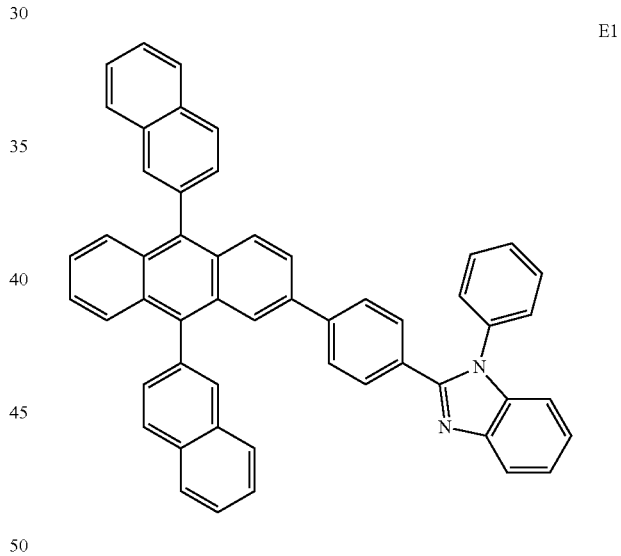

As an electron injection layer, lithium fluoride (LiF) was deposited to a thickness of 10 Å, and an Al cathode was employed to a thickness of 1,000 Å, and as a result, an OLED was manufactured. Meanwhile, all the organic compounds required to manufacture the OLED were vacuum sublimation purified under $10^{-6}$ torr to $10^{-8}$ torr by each material to be used in the OLED manufacture.

Organic electroluminescent devices were manufactured in the same manner as in Experimental Example 1 except that compounds described in the following Table 4 were used instead of E1 used when forming the electron transfer layer. Results of measuring driving voltage, light emission efficiency, color coordinate (CIE) and lifetime of each of the blue organic light emitting devices manufactured according to the present disclosure are as shown in Table 4.

TABLE 4

| | Compound | Driving Voltage (V) | Light Emission Efficiency (cd/A) | CIE (x, y) | Lifetime (T95) |
|---|---|---|---|---|---|
| Example 1 | 1 | 4.72 | 6.92 | (0.134, 0.102) | 59 |
| Example 2 | 2 | 4.73 | 6.91 | (0.134, 0.102) | 60 |
| Example 3 | 9 | 4.88 | 6.74 | (0.134, 0.100) | 52 |
| Example 4 | 10 | 4.85 | 6.80 | (0.134, 0.100) | 54 |
| Example 5 | 17 | 4.82 | 6.88 | (0.134, 0.102) | 50 |
| Example 6 | 18 | 4.87 | 6.89 | (0.134, 0.102) | 51 |
| Example 7 | 33 | 4.86 | 6.87 | (0.134, 0.100) | 53 |
| Example 8 | 34 | 4.82 | 6.91 | (0.134, 0.102) | 55 |
| Example 9 | 35 | 4.85 | 6.95 | (0.134, 0.102) | 55 |
| Example 10 | 36 | 4.79 | 6.90 | (0.134, 0.101) | 54 |
| Example 11 | 89 | 4.77 | 6.91 | (0.134, 0.102) | 55 |
| Example 12 | 90 | 4.78 | 6.90 | (0.134, 0.100) | 54 |
| Example 13 | 91 | 4.81 | 6.95 | (0.134, 0.101) | 55 |
| Example 14 | 92 | 4.82 | 6.96 | (0.134, 0.101) | 56 |
| Example 15 | 185 | 4.74 | 6.95 | (0.134, 0.101) | 58 |
| Example 16 | 186 | 4.79 | 6.90 | (0.134, 0.102) | 53 |
| Example 17 | 193 | 4.80 | 6.80 | (0.134, 0.101) | 52 |
| Example 18 | 194 | 4.85 | 6.99 | (0.134, 0.102) | 55 |
| Comparative Example 1 | E1 | 4.90 | 6.71 | (0.134, 0.102) | 50 |
| Comparative Example 2 | E2 | 5.57 | 6.12 | (0.134, 0.100) | 28 |
| Comparative Example 3 | E3 | 5.56 | 6.02 | (0.134, 0.101) | 29 |
| Comparative Example 4 | E4 | 5.60 | 6.09 | (0.134, 0.101) | 21 |
| Comparative Example 5 | E5 | 5.68 | 5.97 | (0.134, 0.101) | 23 |
| Comparative Example 6 | E6 | 5.64 | 5.97 | (0.134, 0,100) | 21 |
| Comparative Example 7 | E7 | 5.67 | 5.91 | (0.134, 0.100) | 20 |
| Comparative Example 8 | E8 | 5.76 | 5.96 | (0.134, 0.101) | 21 |
| Comparative Example 9 | E9 | 5.72 | 5.89 | (0.134, 0.102) | 19 |

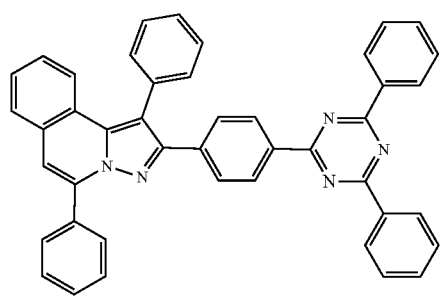

E2

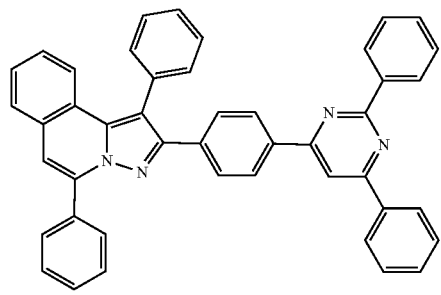

E3

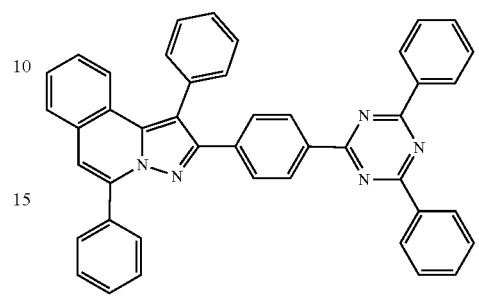

E4

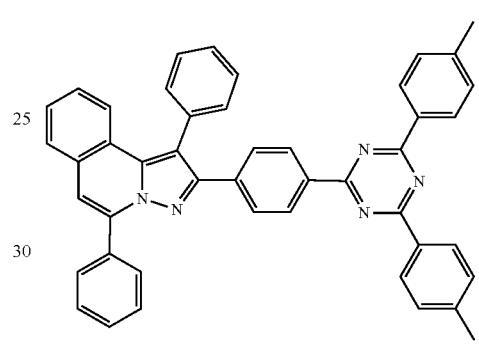

E5

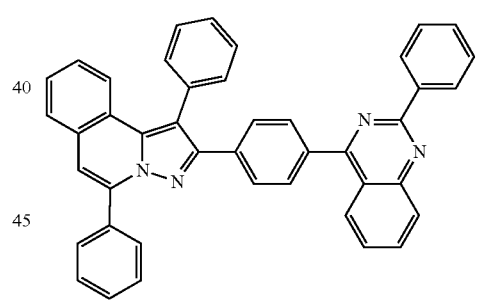

E6

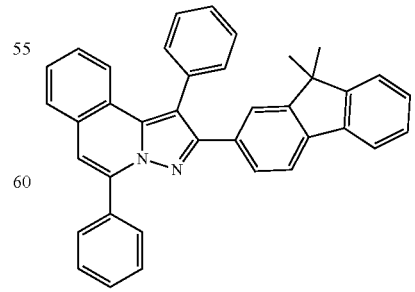

E7

TABLE 4-continued

| Compound | Driving Voltage (V) | Light Emission Efficiency (cd/A) | CIE (x, y) | Lifetime (T95) |
|---|---|---|---|---|

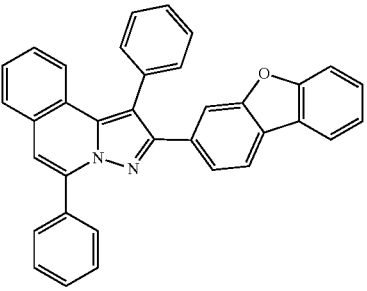

E8

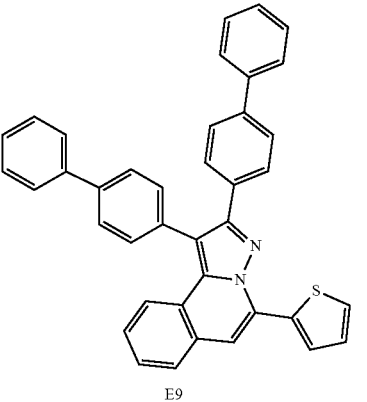 [SMILES: c1ccc(-c2ccc(-c3nn4c(-c5cccs5)cc5ccccc5c4c3-c3ccc(-c4ccccc4)cc3)cc2)cc1]

E9

As seen from the results of Table 4, the organic light emitting device using the electron transfer layer material of the blue organic light emitting device of the present disclosure had lower driving voltage and significantly improved light emission efficiency and lifetime compared to Comparative Examples 1 to 9. Particularly, it was identified that Compounds 1, 2, 36, 89 and 90 were superior in all aspects of driving, efficiency and lifetime.

Such a result is considered to be due to the fact that, when using the heterocyclic compound of the present application having proper length and strength, and flatness as an electron transfer layer, a compound in an excited state is made by receiving electrons under a specific condition, and particularly when an excited state is formed in the hetero-skeleton site of the compound of the present application, excited energy moves to a stable state before the excited hetero-skeleton site goes through other reactions, and as a result, the relatively stabilized compound is capable of efficiently transferring electrons without the compound being decomposed or destroyed. For reference, those that are stable when excited are considered to be aryl or acene-based compounds or polycyclic hetero-compounds, and accordingly, it is considered that excellent results in all aspects of driving, efficiency and lifetime were obtained by the compound of the present disclosure enhancing enhanced electron-transfer properties or improved stability.

Experimental Example 2

Manufacture of Organic Light Emitting Device

A transparent indium tin oxide (ITO) electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used. Next, an ITO substrate was installed in a substrate folder of a vacuum deposition apparatus, and the following 4,4',4''-tris(N,N-(2-naphthyl)-phenylamino)triphenylamine (2-TNATA) was introduced to a cell in the vacuum deposition apparatus.

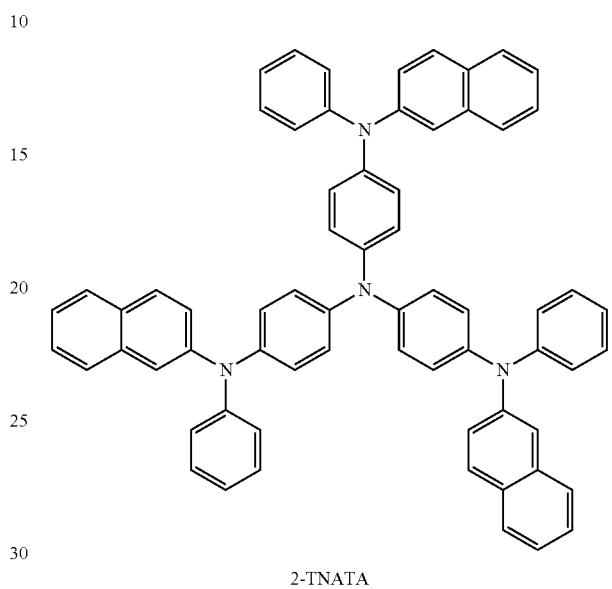

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate. To another cell of the vacuum deposition apparatus, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

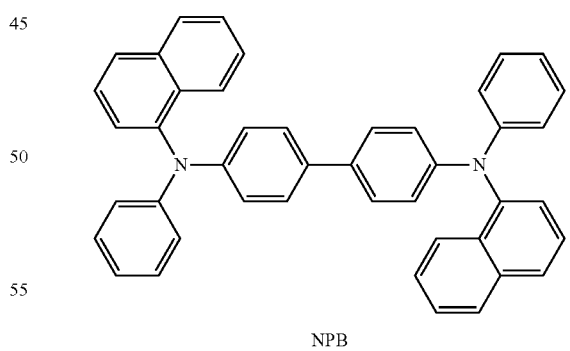

NPB

After forming the hole injection layer and the hole transfer layer as above, a blue light emitting material having a structure as below was deposited thereon as a light emitting layer. Specifically, in one side cell in the vacuum deposition apparatus, H1, a blue light emitting host material, was vacuum deposited to a thickness of 200 Å, and D1, a blue light emitting dopant material, was vacuum deposited thereon by 5% with respect to the host material.

H1

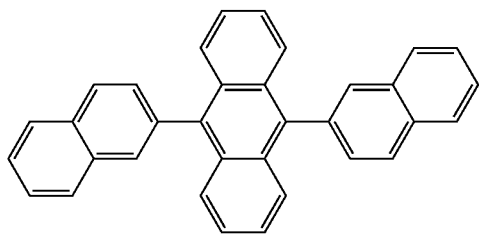

D1

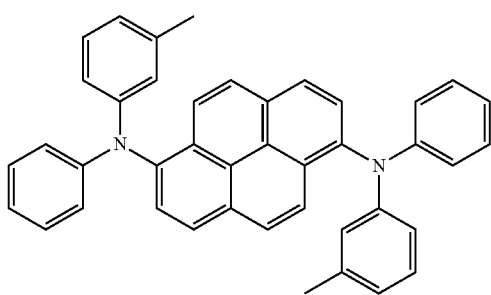

Subsequently, a compound of the following Structural Formula E1 was deposited to a thickness of 300 Å as an electron transfer layer.

E1

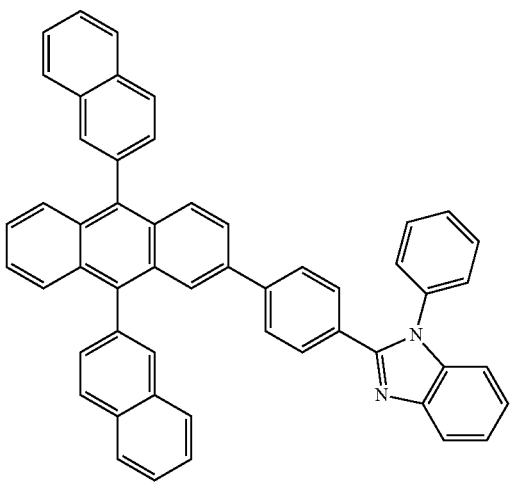

As an electron injection layer, lithium fluoride (LiF) was deposited to a thickness of 10 Å, and an Al cathode was employed to a thickness of 1,000 Å, and as a result, an OLED was manufactured. Meanwhile, all the organic compounds required to manufacture the OLED were vacuum sublimation purified under $10^{-6}$ torr to $10^{-8}$ torr by each material to be used in the OLED manufacture.

Organic electroluminescent devices were manufactured in the same manner as in Experimental Example 2 except that, after forming the electron transfer layer E1 to a thickness of 250 Å, a hole blocking layer was formed on the electron transfer layer to a thickness of 50 Å using compounds shown in the following Table 5. Results of measuring driving voltage, light emission efficiency, color coordinate (CIE) and lifetime of each of the blue organic light emitting devices manufactured according to the present disclosure are as shown in the following Table 5.

TABLE 5

| | Compound | Driving Voltage (V) | Light Emission Efficiency (cd/A) | CIE (x, y) | Lifetime (T95) |
|---|---|---|---|---|---|
| Example 19 | 1 | 5.12 | 6.43 | (0.134, 0.100) | 52 |
| Example 20 | 2 | 5.14 | 6.64 | (0.134, 0.101) | 50 |
| Example 21 | 9 | 5.10 | 6.70 | (0.134, 0.100) | 53 |
| Example 22 | 10 | 5.05 | 6.77 | (0.134, 0.101) | 54 |
| Example 23 | 17 | 5.17 | 6.80 | (0.134, 0.101) | 55 |
| Example 24 | 18 | 5.11 | 6.85 | (0.134, 0.102) | 59 |
| Example 25 | 33 | 5.15 | 6.88 | (0.134, 0.102) | 60 |
| Example 26 | 34 | 5.01 | 6.90 | (0.134, 0.102) | 61 |
| Example 27 | 35 | 4.99 | 6.87 | (0.134, 0.101) | 59 |
| Example 28 | 36 | 4.98 | 6.80 | (0.134, 0.101) | 64 |
| Example 29 | 89 | 5.09 | 6.81 | (0.134, 0.101) | 66 |
| Example 30 | 90 | 5.05 | 6.92 | (0.134, 0.102) | 58 |
| Example 31 | 91 | 5.14 | 6.99 | (0.134, 0.102) | 59 |
| Example 32 | 92 | 4.95 | 6.79 | (0.134, 0.100) | 62 |
| Example 33 | 185 | 5.15 | 6.80 | (0.134, 0.101) | 60 |
| Example 34 | 186 | 5.14 | 6.84 | (0.134, 0.101) | 61 |
| Example 35 | 193 | 5.10 | 6.82 | (0.134, 0.101) | 62 |
| Example 36 | 194 | 5.12 | 6.88 | (0.134, 0.101) | 60 |
| Comparative Example 1 | E1 | 5.55 | 6.06 | (0.134, 0.101) | 44 |
| Comparative Example 2 | E2 | 5.52 | 6.13 | (0.134, 0.101) | 41 |
| Comparative Example 3 | E3 | 5.54 | 5.94 | (0.134, 0.101) | 40 |
| Comparative Example 4 | E4 | 5.50 | 6.01 | (0.134, 0.100) | 45 |
| Comparative Example 5 | E5 | 5.48 | 5.95 | (0.134, 0.101) | 43 |
| Comparative Example 6 | E6 | 5.74 | 5.88 | (0.134, 0,102) | 44 |
| Comparative Example 7 | E7 | 5.69 | 5.80 | (0.134, 0.101) | 40 |
| Comparative Example 8 | E8 | 5.70 | 5.82 | (0.134, 0.100) | 41 |
| Comparative Example 9 | E9 | 5.82 | 5.45 | (0.134, 0.100) | 41 |

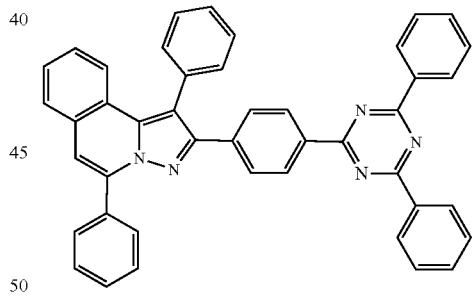

E2

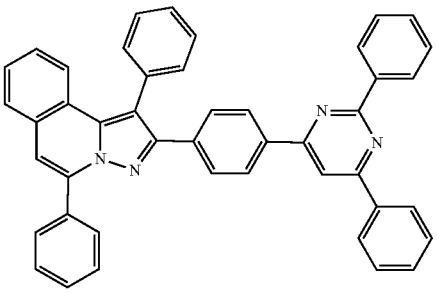

E3

TABLE 5-continued

| Compound | Driving Voltage (V) | Light Emission Efficiency (cd/A) | CIE (x, y) | Lifetime (T95) |
|---|---|---|---|---|

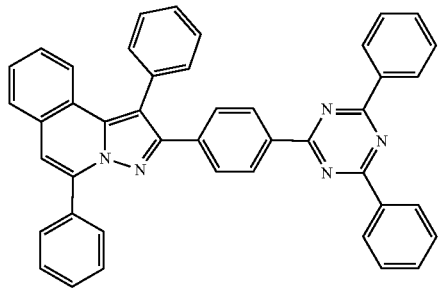
E4

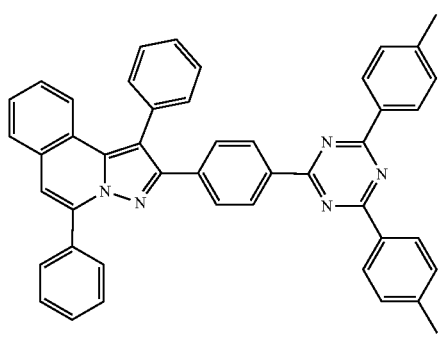
E5

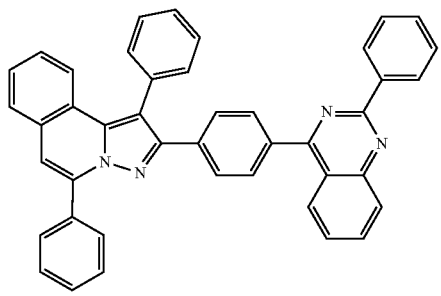
E6

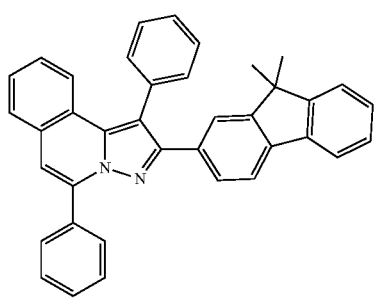
E7

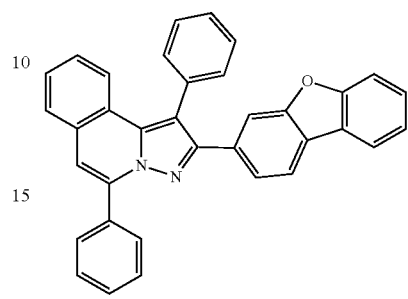
E8

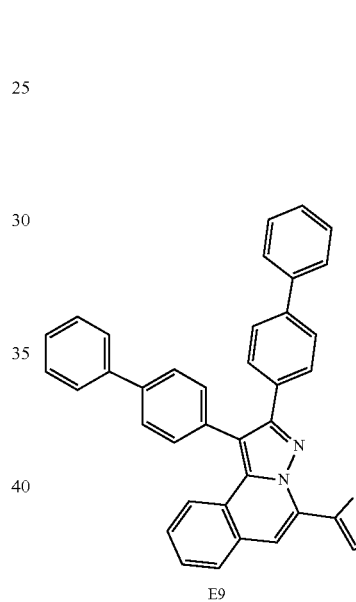
E9

As seen from the results of Table 5, the organic light emitting device using the hole blocking layer material of the blue organic light emitting device of the present disclosure had lower driving voltage and significantly improved light emission efficiency and lifetime compared to Comparative Examples 1 to 9.

Such a result is considered to be due to the fact that efficiency and lifetime of an OLED decrease when holes pass through an electron transfer layer and go to a cathode without being combined in a light emitting layer. When using compounds having a deep HOMO level as a hole blocking layer in order to prevent such a phenomenon, holes trying to pass through a light emitting layer and go to a cathode are blocked by an energy barrier of the hole blocking layer. Accordingly, probability of holes and electrons forming excitons increases and possibility of being emitted as light in the light emitting layer increases, and it is considered that excellent results in all aspects of driving, efficiency and lifetime were obtained by the compound of the present disclosure.

The invention claimed is:

1. A heterocyclic compound represented by the following Chemical Formula 1:

[Chemical Formula 1]

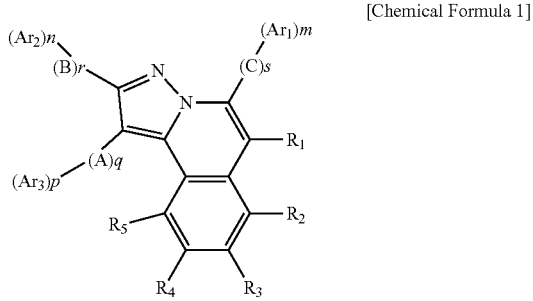

wherein, in Chemical Formula 1, $R_1$ is hydrogen; or deuterium, $R_2$ to $R_5$ are the same as or different from each other, and each independently selected from the group consisting of hydrogen; deuterium; a substituted or unsubstituted C1 to C60 alkyl group; a substituted or unsubstituted C6 to C60 aryl group; a substituted or unsubstituted C2 to C60 heteroaryl group; —SiRR'R"; —P(=O)RR'; and an amine group unsubstituted or substituted with a substituted or unsubstituted C1 to C60 alkyl group, a substituted or unsubstituted C6 to C60 aryl group or a substituted or unsubstituted C2 to C60 heteroaryl group, or two or more groups adjacent to each other bond to each other to form a substituted or unsubstituted C6 to C60 aromatic hydrocarbon ring or a substituted or unsubstituted C2 to C60 heteroring;

A, B and C are a direct bond; a substituted or unsubstituted C6 to C60 arylene group; or a substituted or unsubstituted C2 to C60 heteroarylene group;

$Ar_1$ to $Ar_3$ are the same as or different from each other, and each independently selected from the group consisting of hydrogen; deuterium; a substituted or unsubstituted C1 to C60 alkyl group; a substituted or unsubstituted C6 to C60 aryl group; a substituted or unsubstituted C2 to C60 heteroaryl group; —SiRR'R"; —P(=O)RR'; and an amine group unsubstituted or substituted with a substituted or unsubstituted C1 to C60 alkyl group, a substituted or unsubstituted C6 to C60 aryl group or a substituted or unsubstituted C2 to C60 heteroaryl group, or two or more groups adjacent to each other bond to each other to form a substituted or unsubstituted C6 to C60 aromatic hydrocarbon ring or a substituted or unsubstituted C2 to C60 heteroring;

q, r and s are an integer of 0 to 4;

m, n and p are an integer of 1 to 6;

R, R' and R" are the same as or different from each other, and each independently hydrogen; a substituted or unsubstituted C1 to C40 alkyl group; or a substituted or unsubstituted C6 to C40 aryl group; and at least one of $Ar_1$ to $Ar_3$ is represented by the following Chemical Formula 1-2,

[Chemical Formula 1-2]

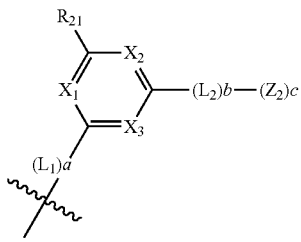

in Chemical Formula 1-2, $R_{21}$ is a substituted or unsubstituted C6 to C60 aryl group;

$L_2$ is a direct bond; a substituted or unsubstituted C6 to C60 arylene group; or a substituted or unsubstituted C2 to C60 heteroarylene group;

b is an integer of 0 to 3;

c is an integer of 1 to 6, $X_1$ to $X_3$ are N; or $CR_{13}$, and at least one thereof is N;

$L_1$ is a direct bond; a substituted or unsubstituted C6 to C60 arylene group; or a substituted or unsubstituted C2 to C60 heteroarylene group; and a is an integer of 0 to 3, $Z_2$ is a C10 to C40 tricycle or more aryl group unsubstituted or substituted with one or more substituents selected from the group consisting of a C1 to C40 alkyl group and a C6 to C60 aryl group; or represented by the following Chemical Formula 2-1; or the following Chemical Formula 2-2,

[Chemical Formula 2-1]

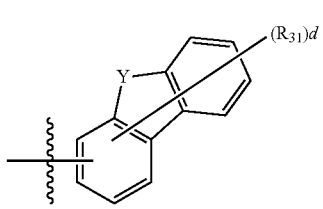

[Chemical Formula 2-2]

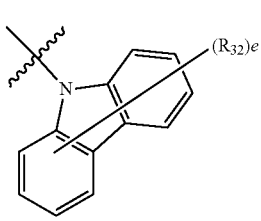

in Chemical Formulae 2-1 and 2-2,

Y is O; or S;

R31 and R32 are the same as or different from each other, and each independently hydrogen; a substituted or unsubstituted C6 to C60 aryl group; or a substituted or unsubstituted C2 to C60 heteroaryl group;

d is an integer of 0 to 7; and e is an integer of 0 to 8.

2. The heterocyclic compound of claim 1, wherein Chemical Formula 1 is represented by the following Chemical Formula 2:

[Chemical Formula 2]

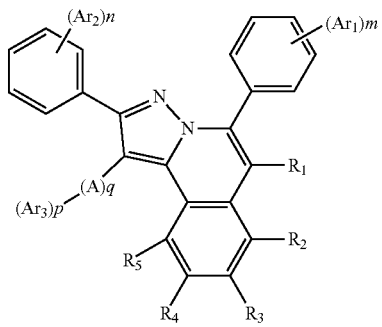

in Chemical Formula 2,

R₁ to R₅, Ar₁ to Ar₃, A, m, n, p and q have the same definitions as in Chemical Formula 1.

3. The heterocyclic compound of claim 1, wherein the "substituted or unsubstituted" means being substituted with one or more substituents selected from the group consisting of C1 to C60 linear or branched alkyl; C2 to C60 linear or branched alkenyl; C2 to C60 linear or branched alkynyl; C3 to C60 monocyclic or polycyclic cycloalkyl; C2 to C60 monocyclic or polycyclic heterocycloalkyl; C6 to C60 monocyclic or polycyclic aryl; C2 to C60 monocyclic or polycyclic heteroaryl; —SiRR'R"; —P(═O)RR'; C1 to C20 alkylamine; C6 to C60 monocyclic or polycyclic arylamine; and C2 to C60 monocyclic or polycyclic heteroarylamine, or being unsubstituted, or being substituted with a substituent linking two or more substituents selected from among the substituents illustrated above, or being unsubstituted; and R, R' and R" have the same definitions as in Chemical Formula 1.

4. The heterocyclic compound of claim 1, wherein R₁ to R₅ are hydrogen.

5. The heterocyclic compound of claim 1, wherein Chemical Formula 1 is represented by any one of the following compounds:

1

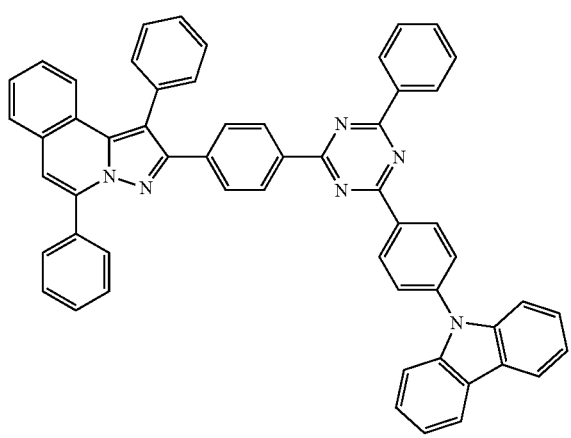

2

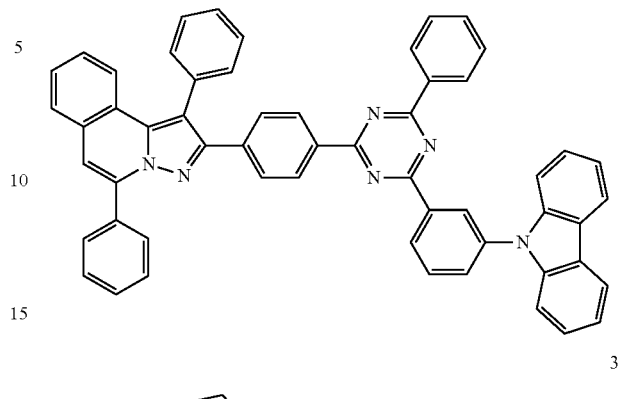

3

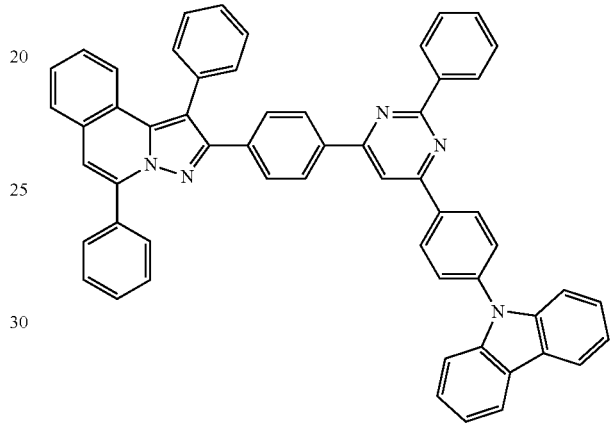

4

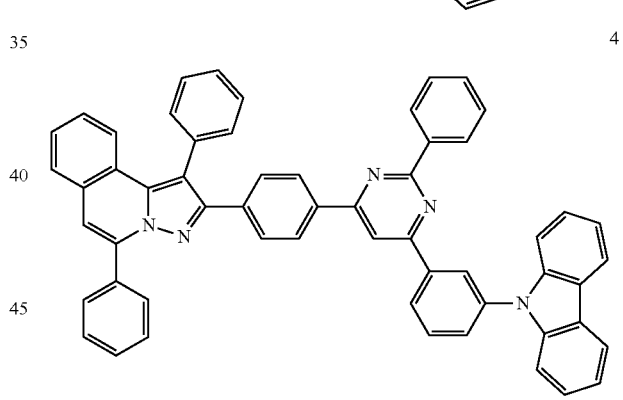

5

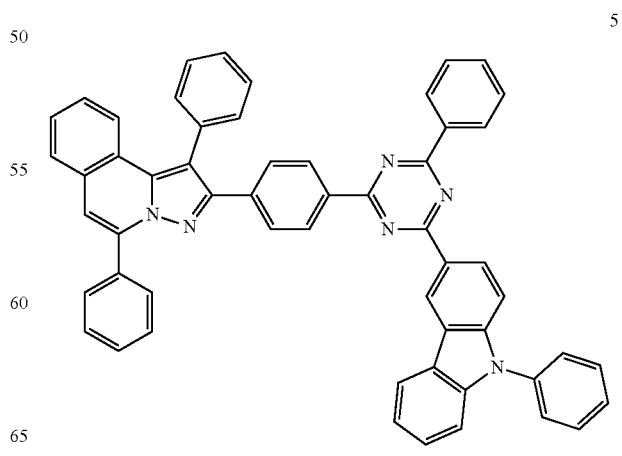

217
-continued
6
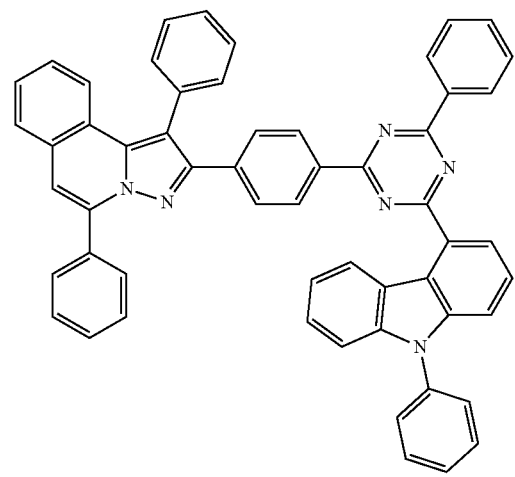
7
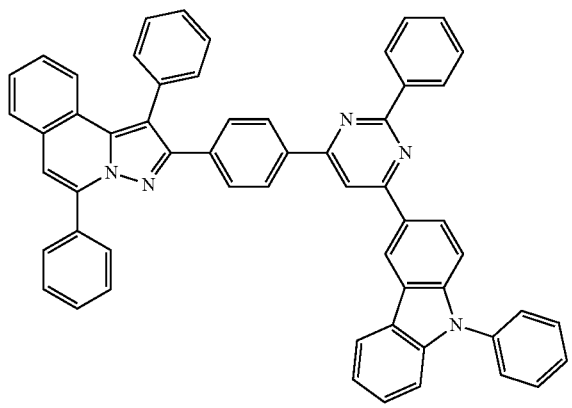
8
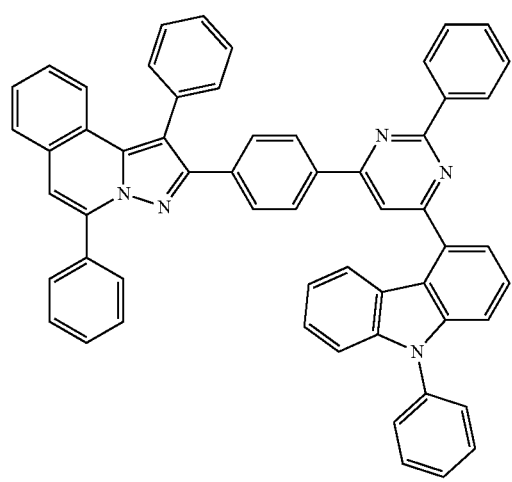
218
-continued
9
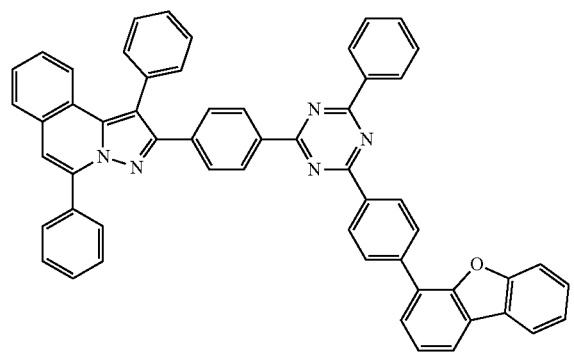
10
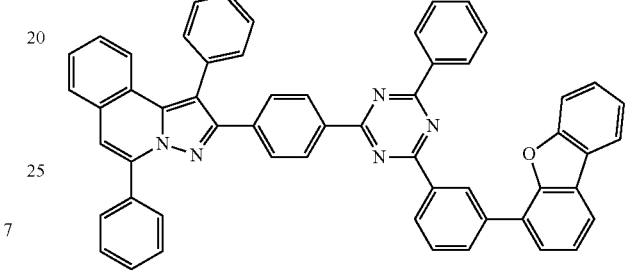
11
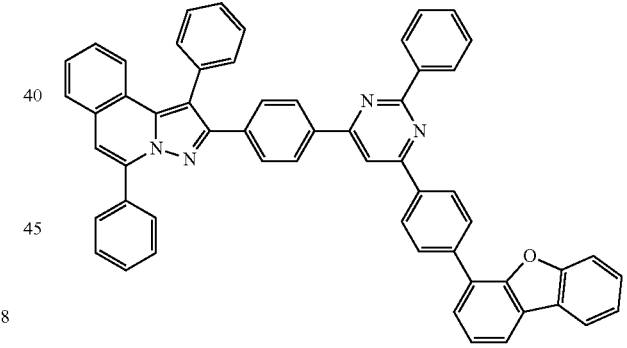
12
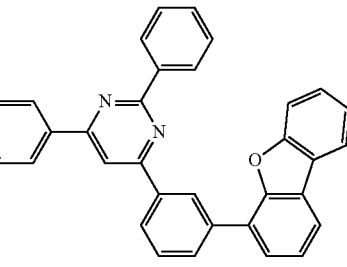

13
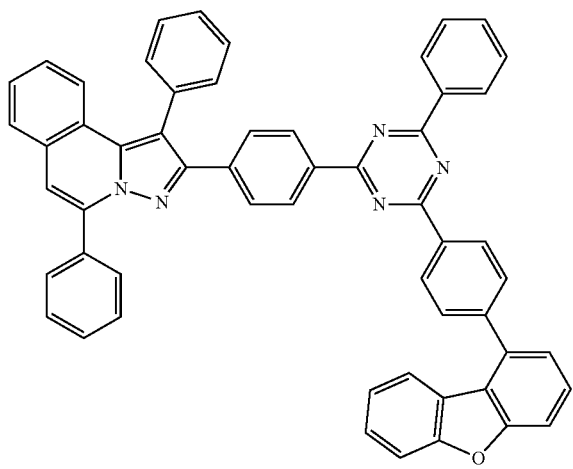
14
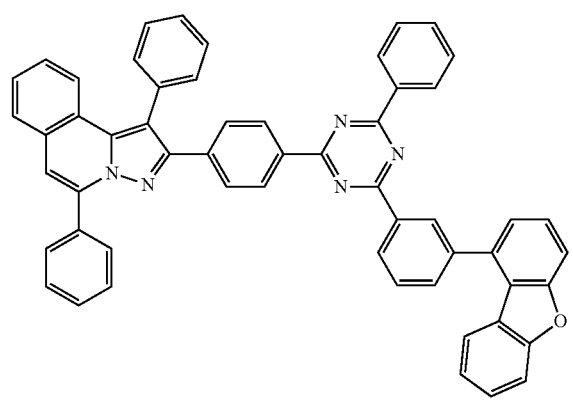
15
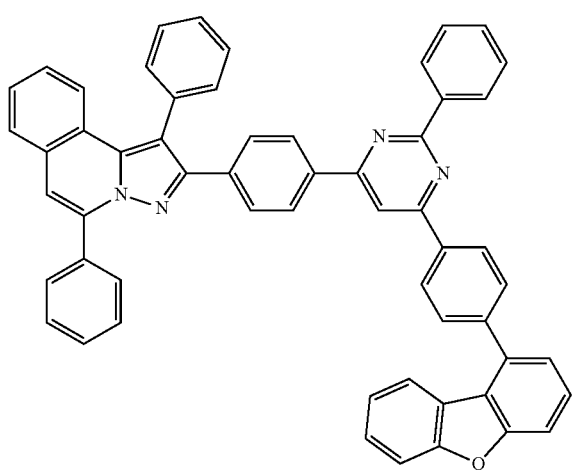
16
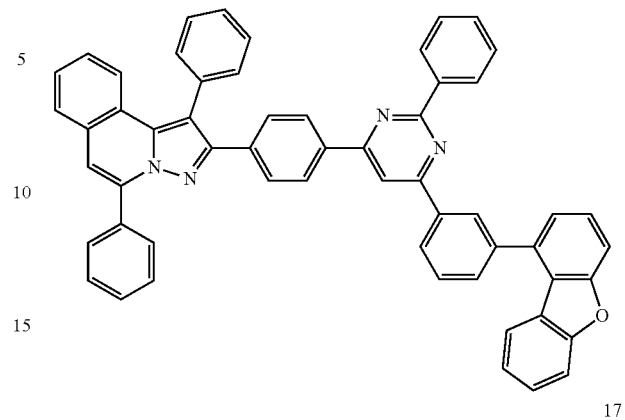
17
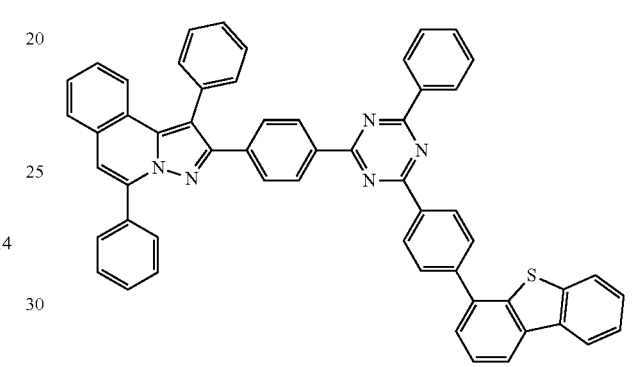
18
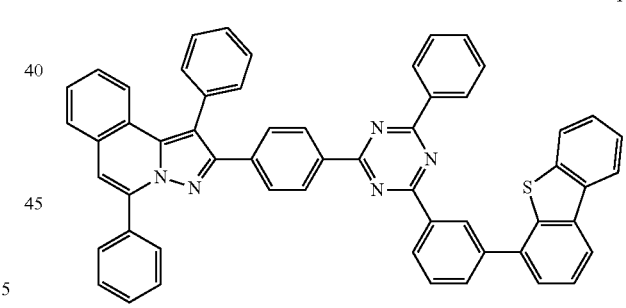
19
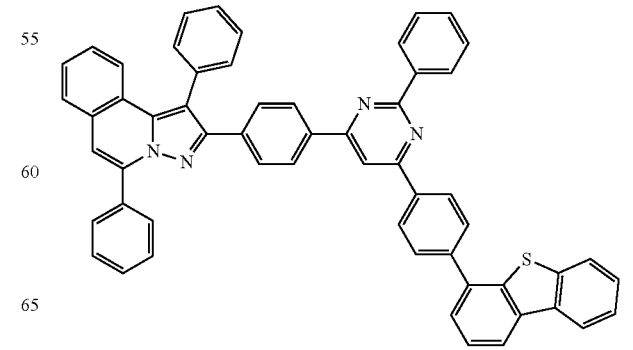

20
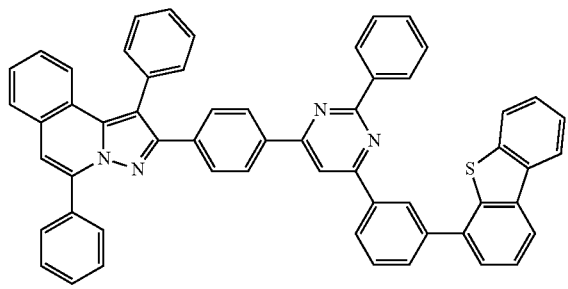
21
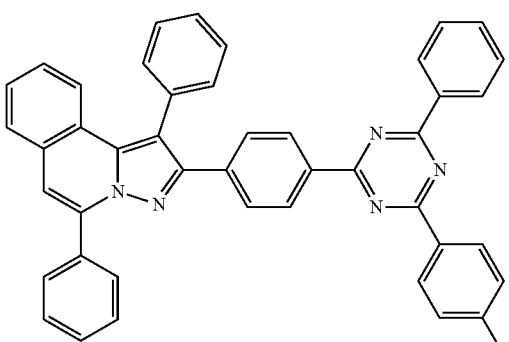
22
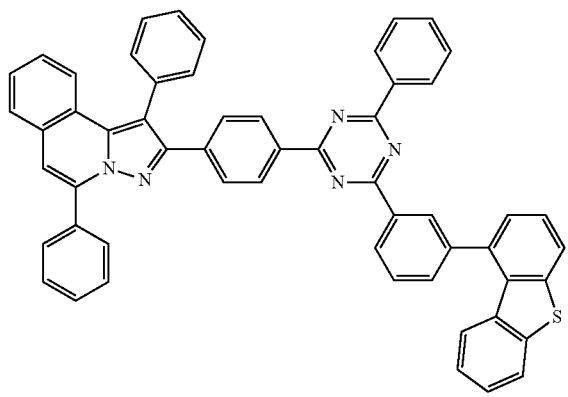
23
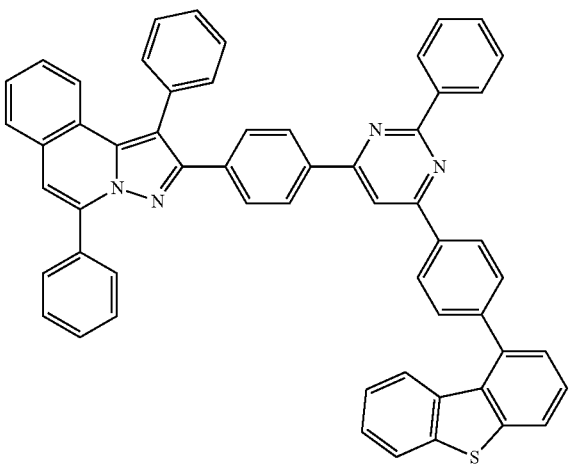

27
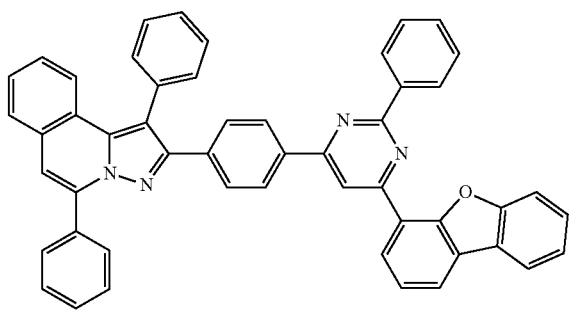
31
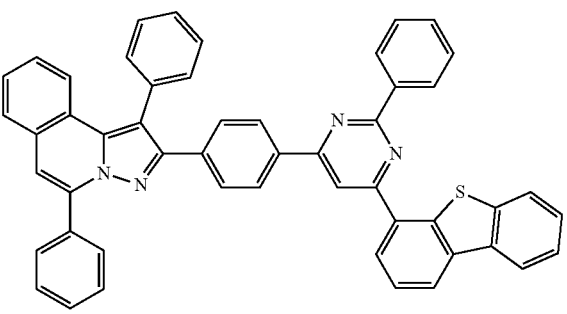
28
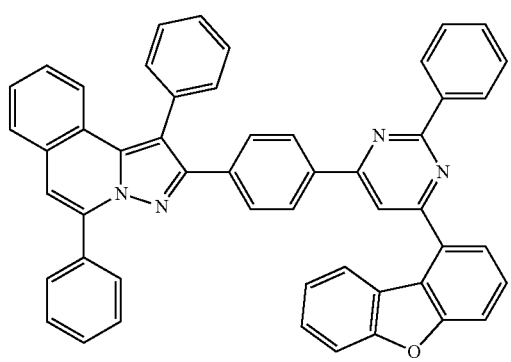
32
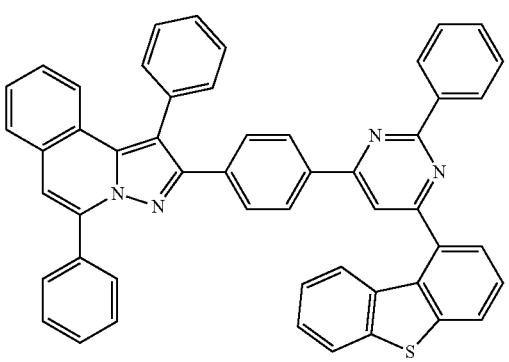
29
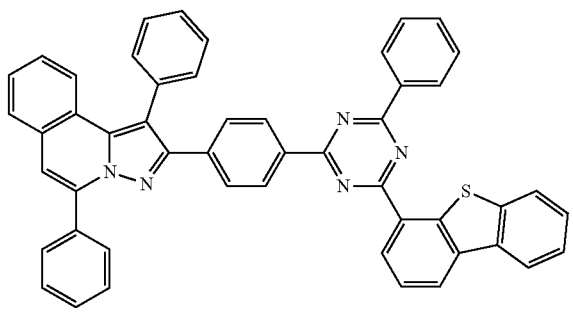
33
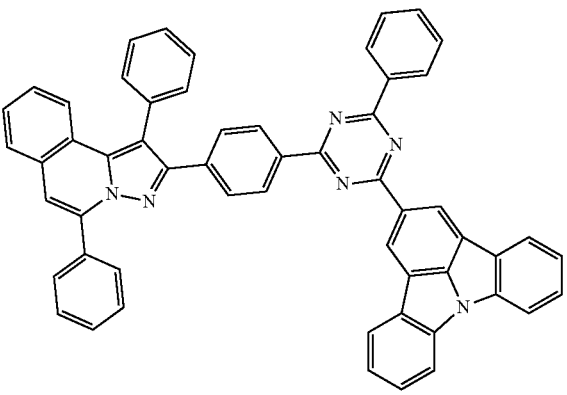
30
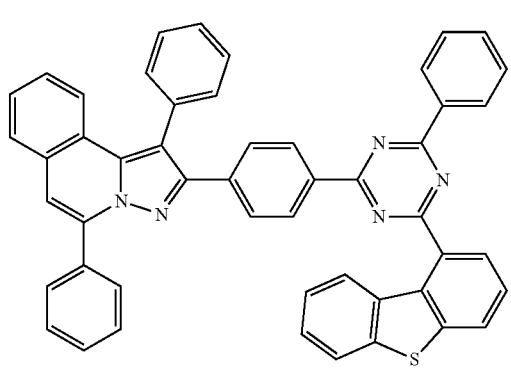
34
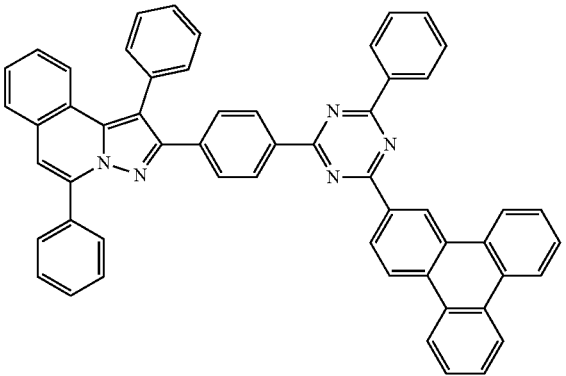

35
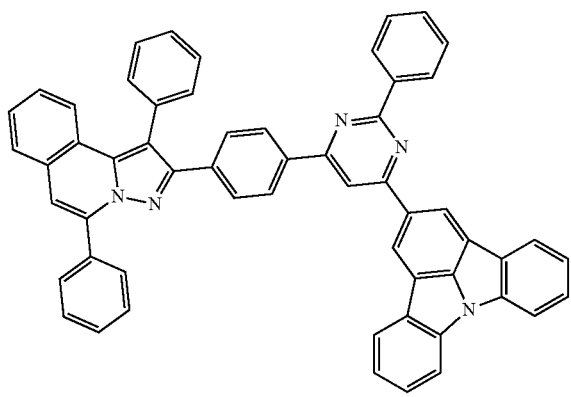
36
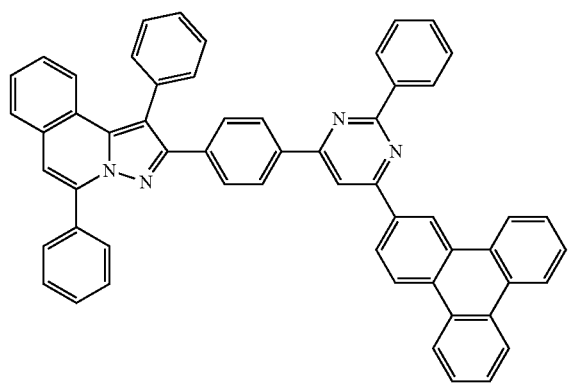
37
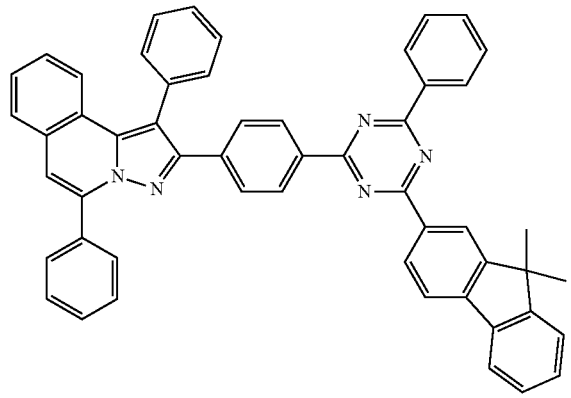
38
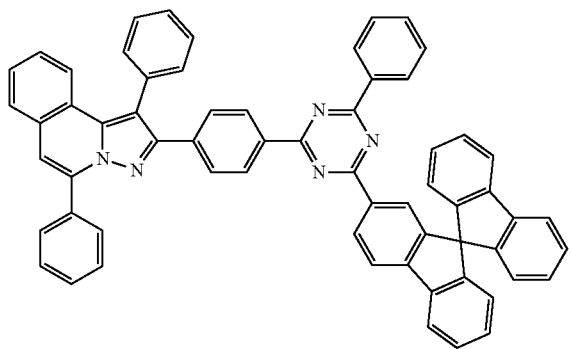
39
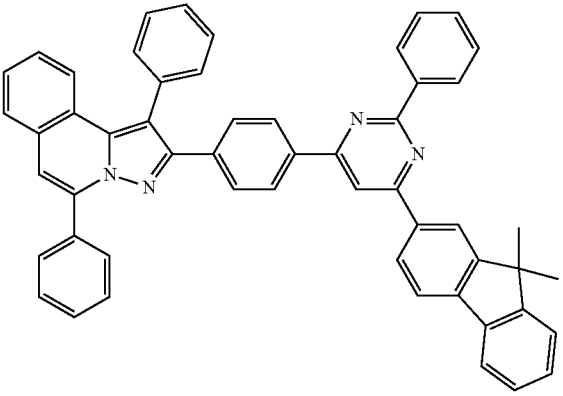
40
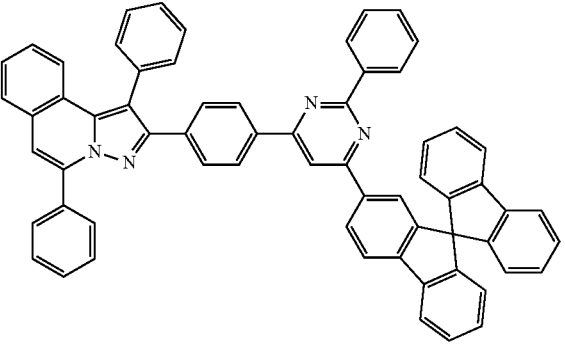
41
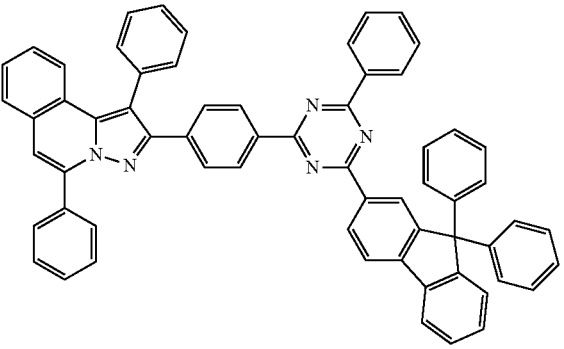
42
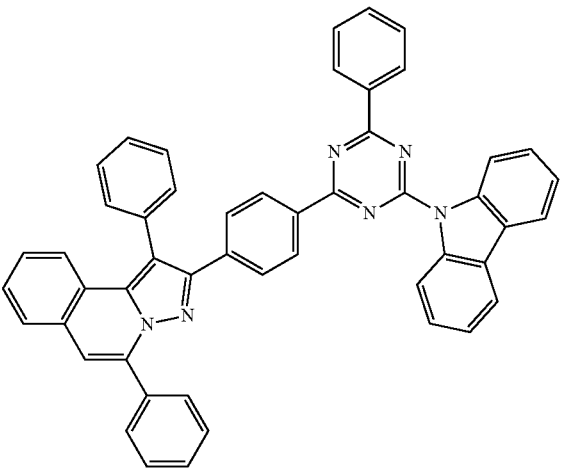

43
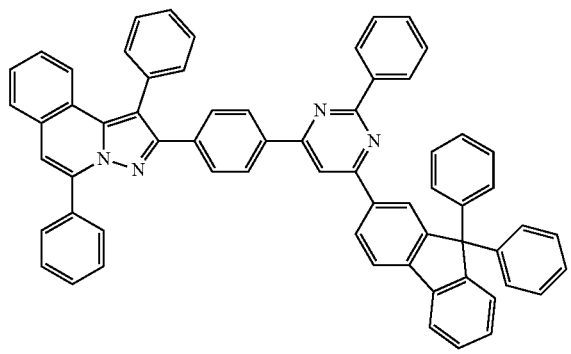
44
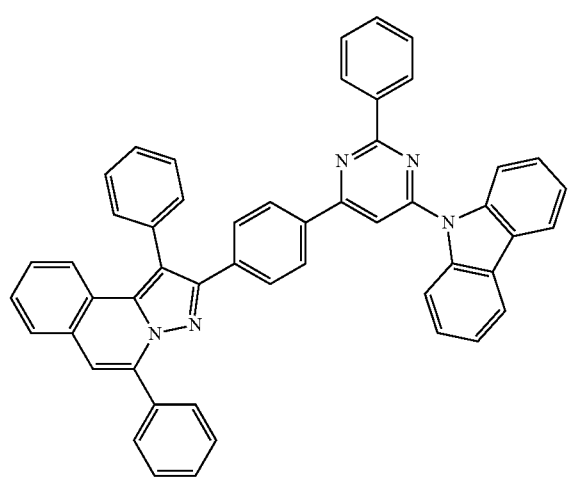
45
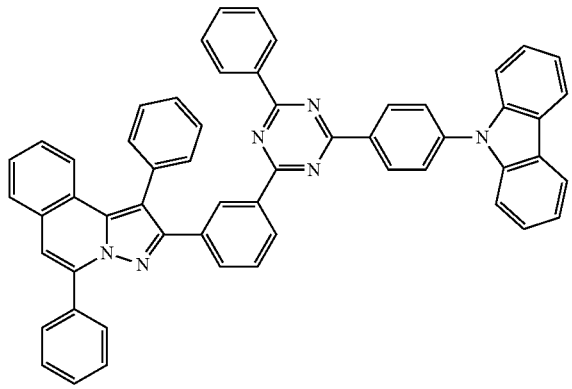
46
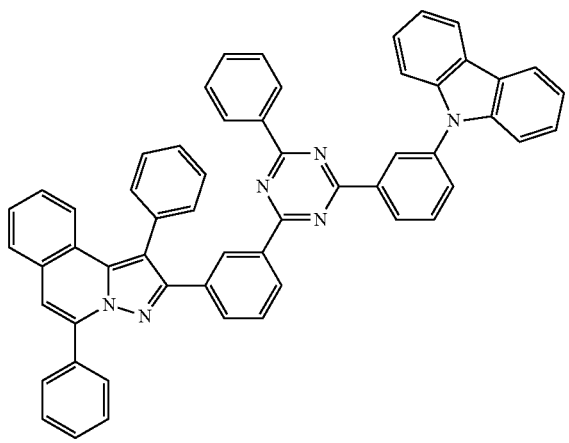
47
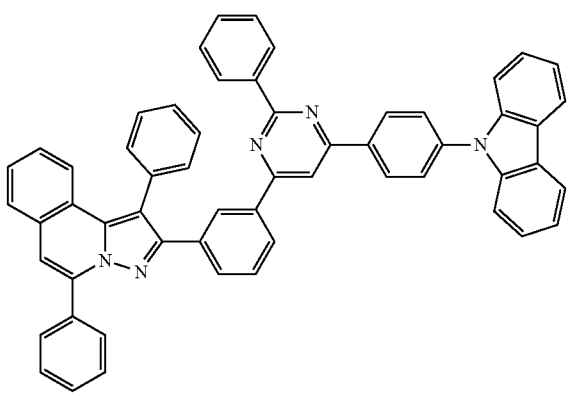
48
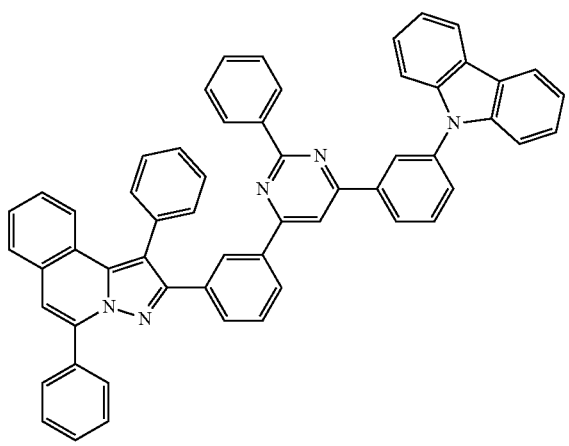

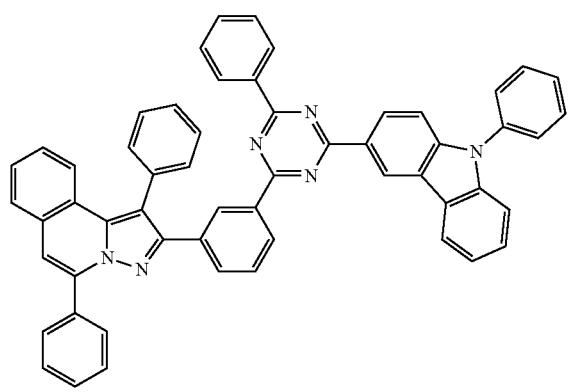
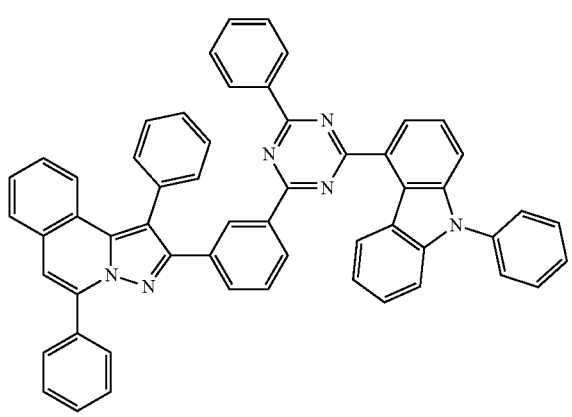
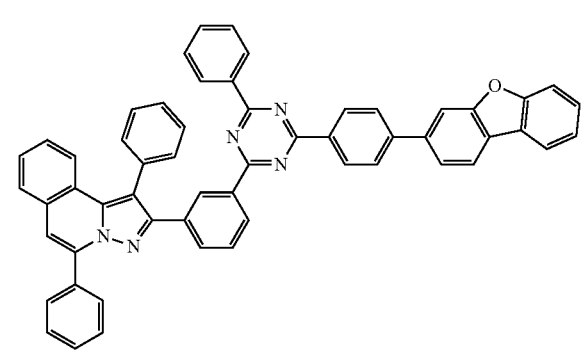

56
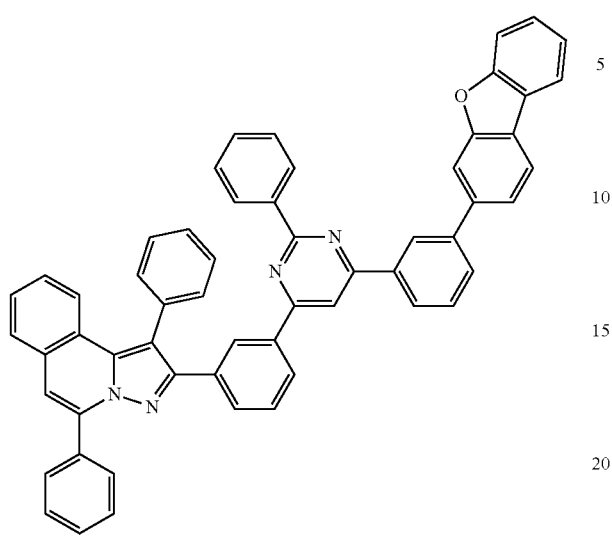
57
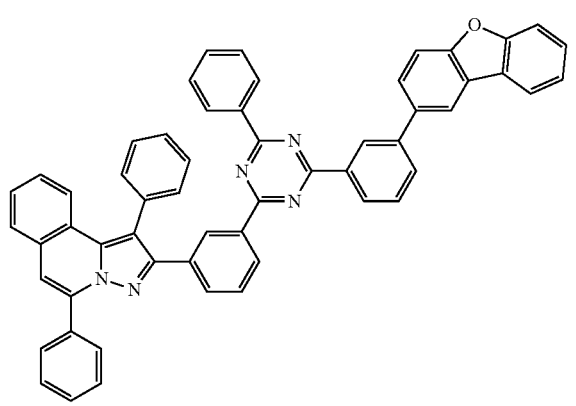
58
59
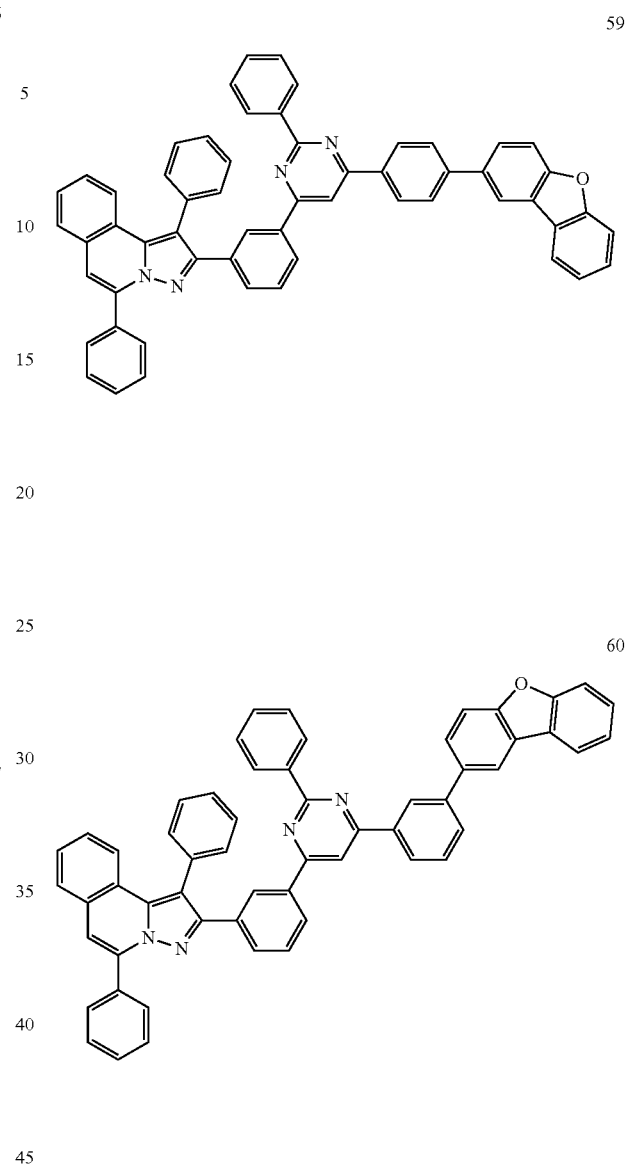
60
61
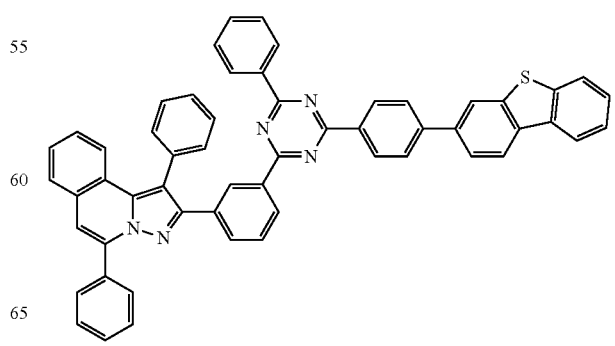

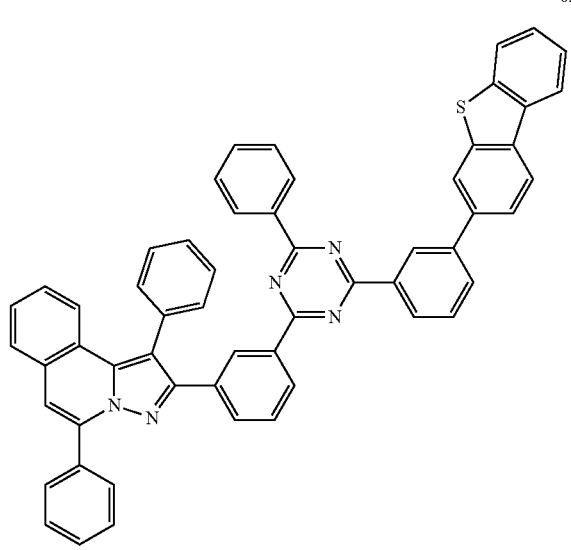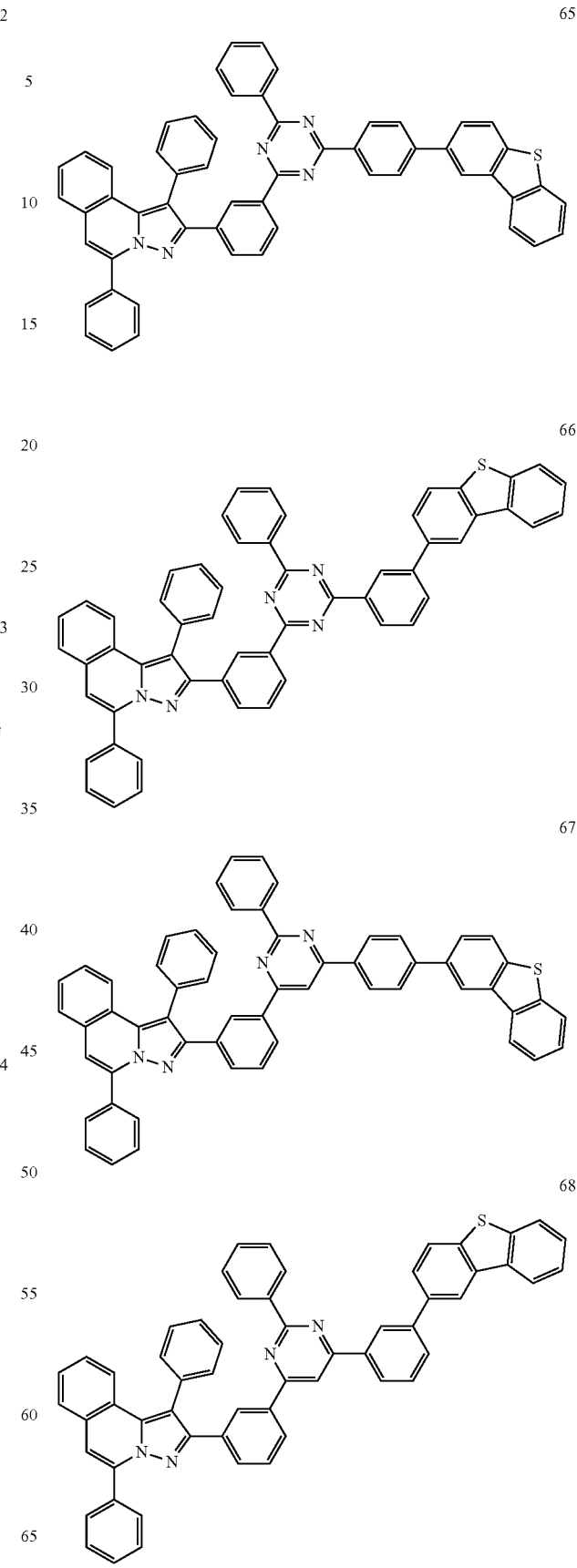

69
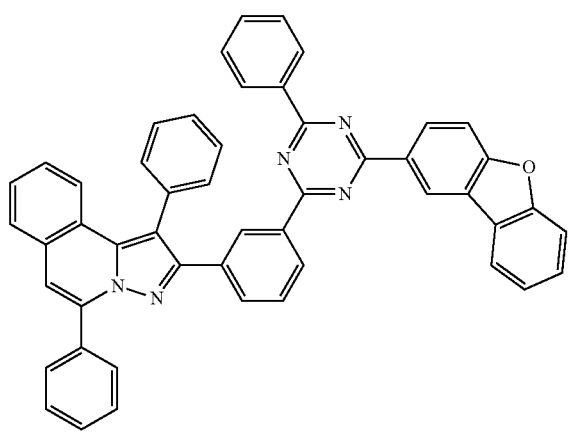
70
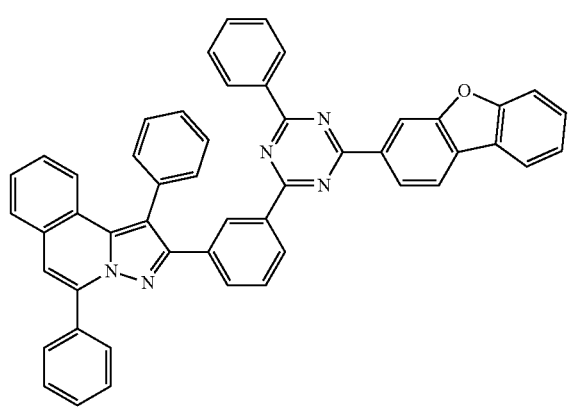
71
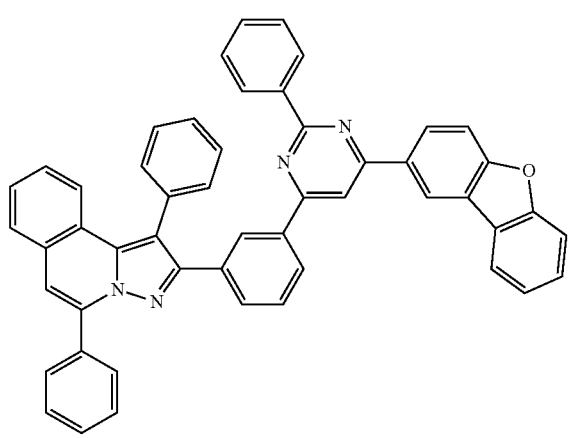
72
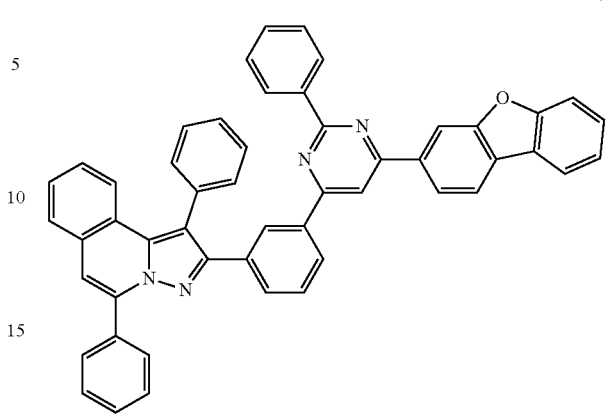
73
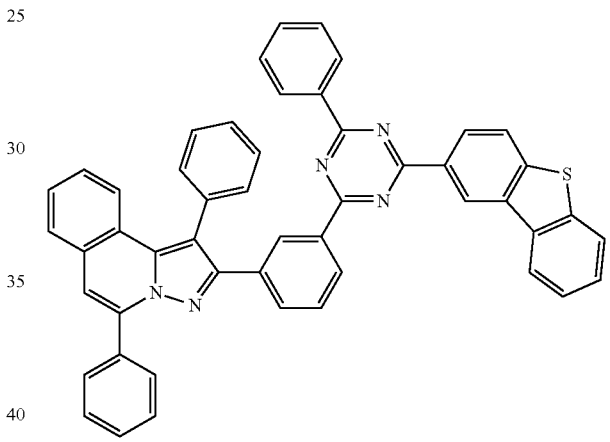
74
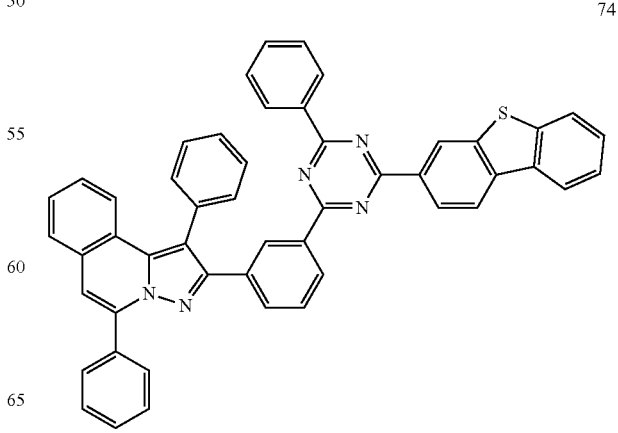

75
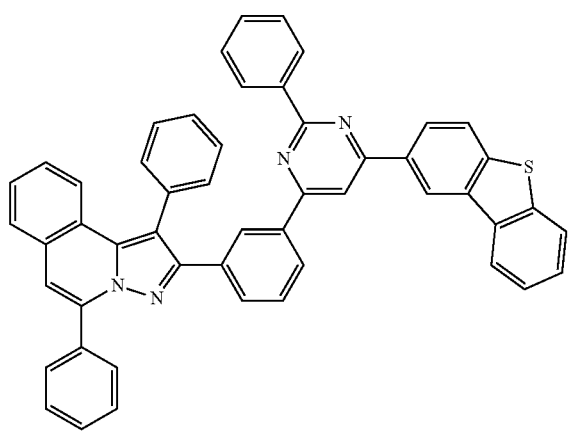
76
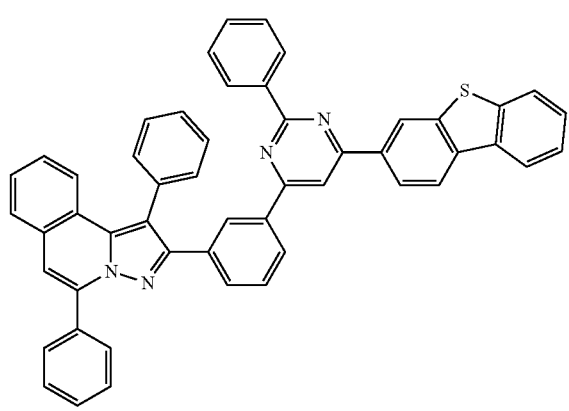
77
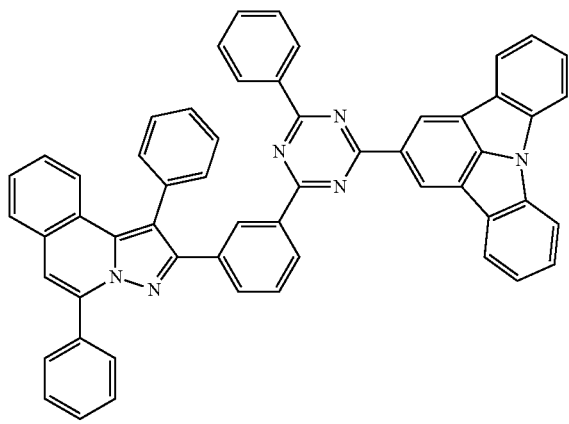
78
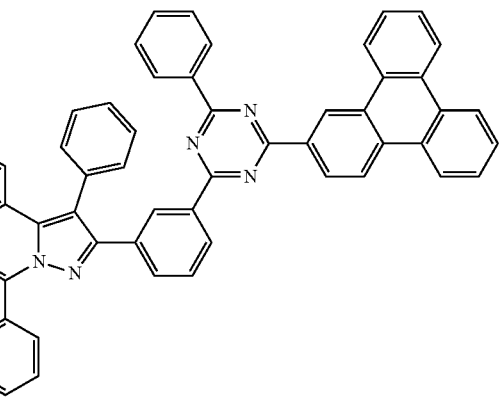
79
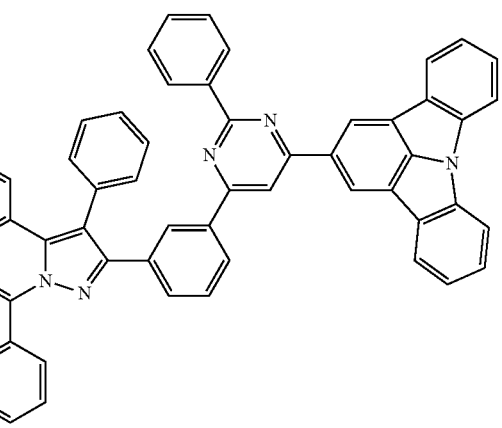
80
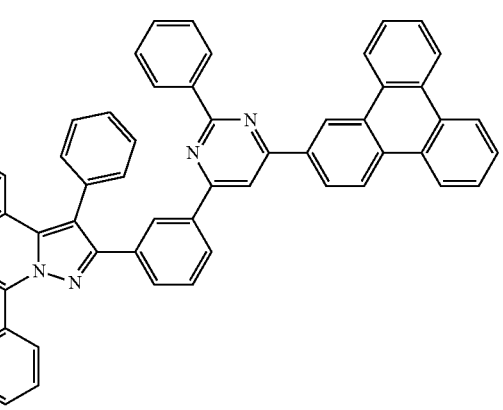

81
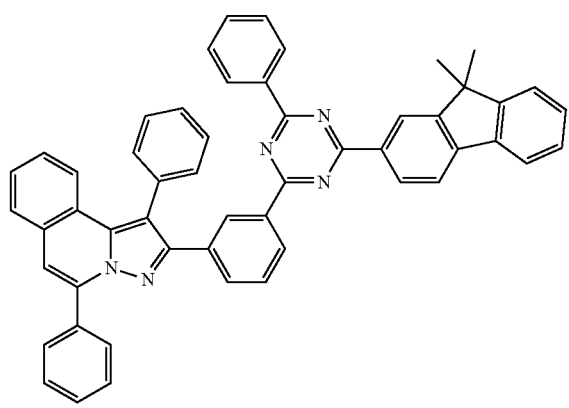
82
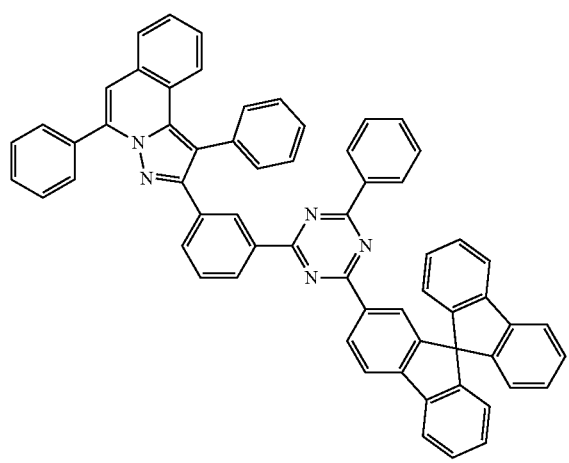
83
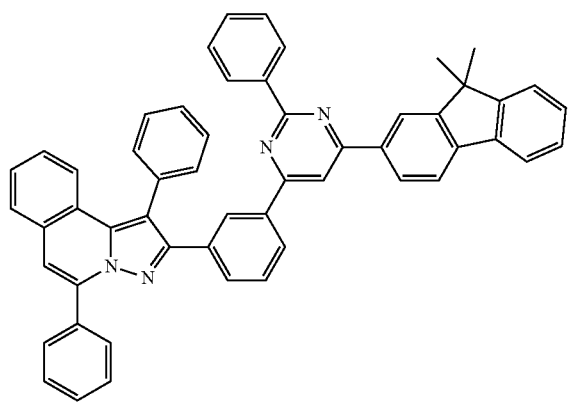
84
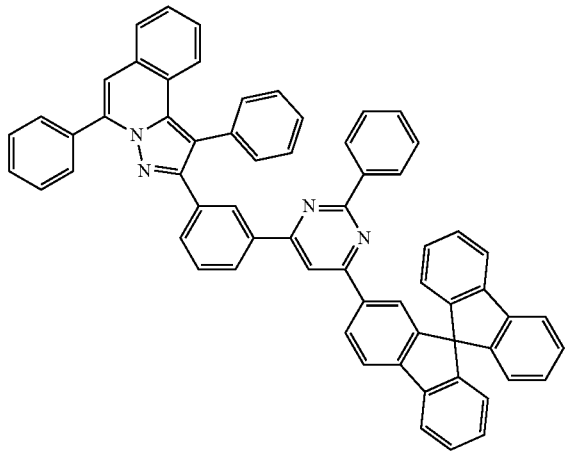
85
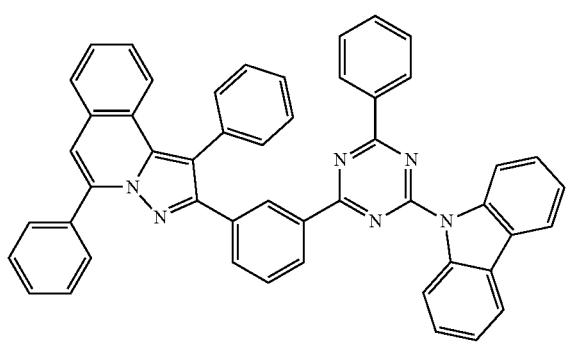
86

87
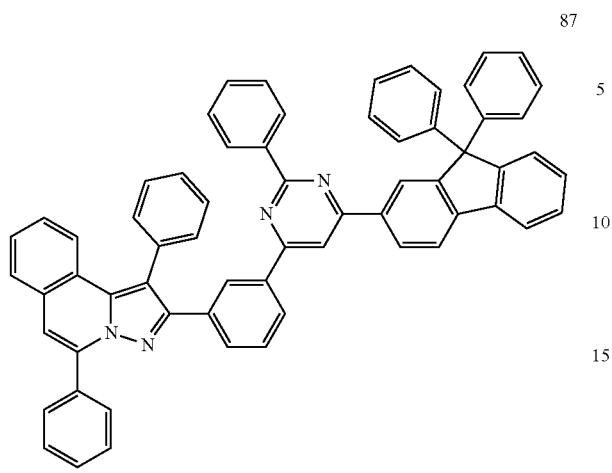
88
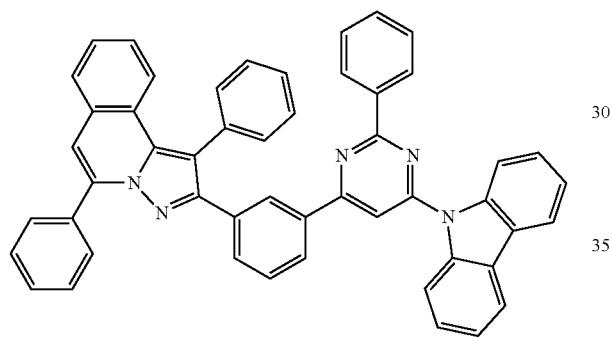
89
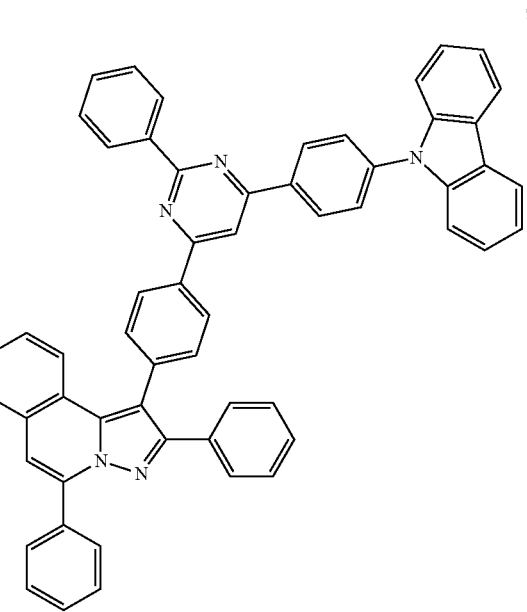
90
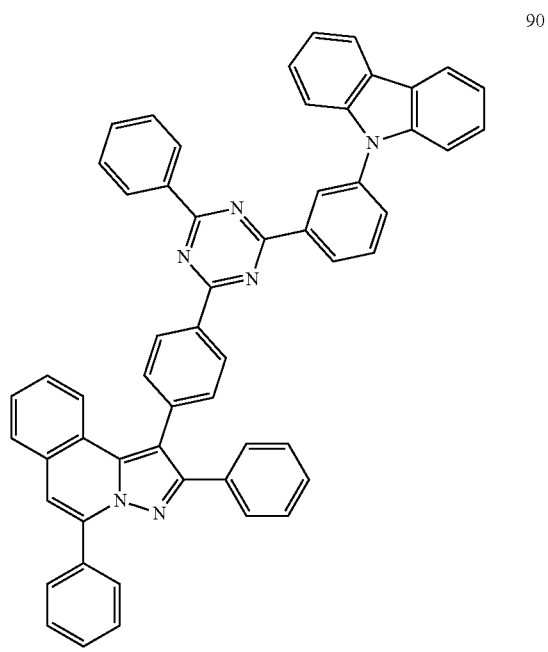
91

92
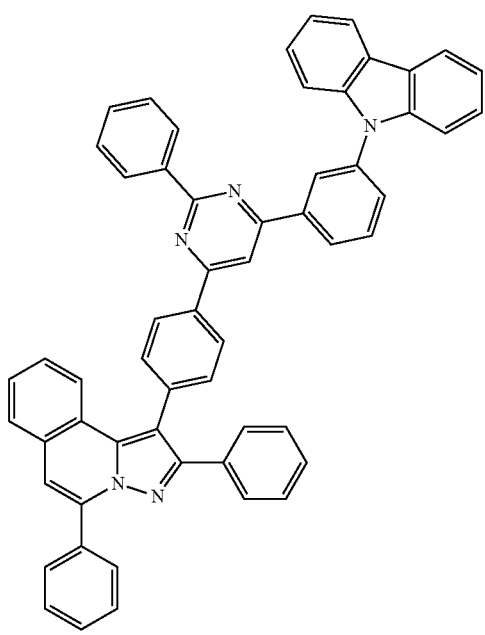
93
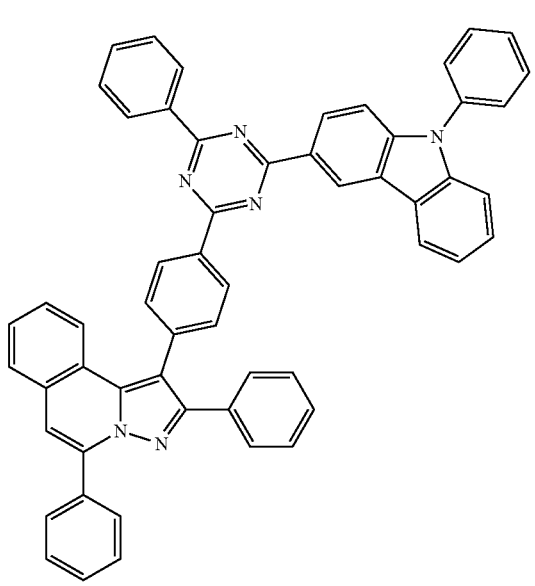
94
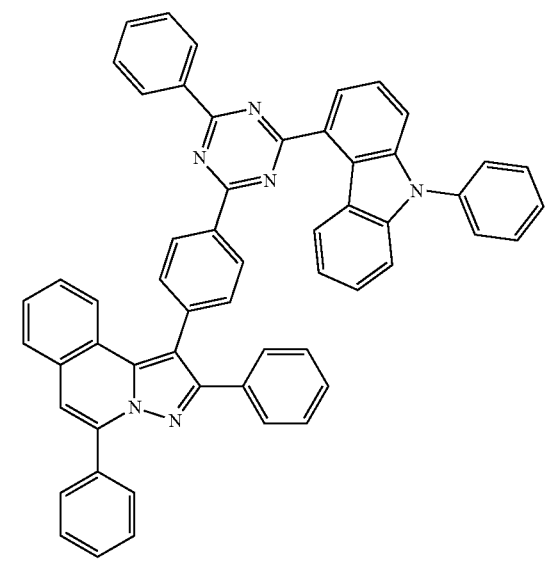
95
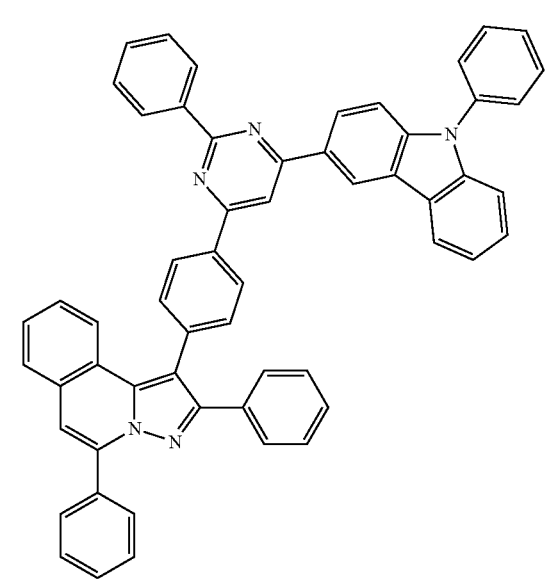

96
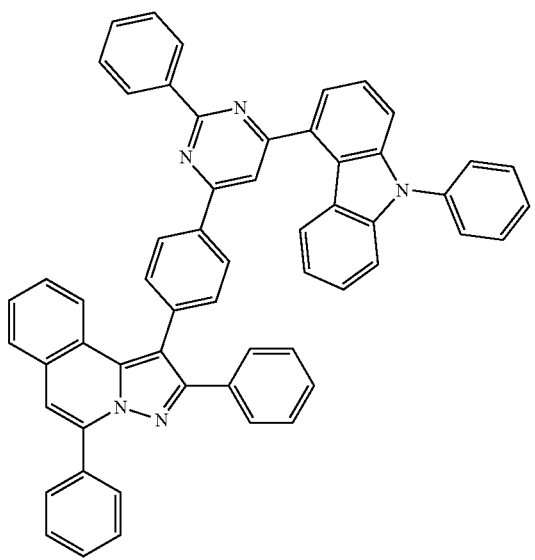
97
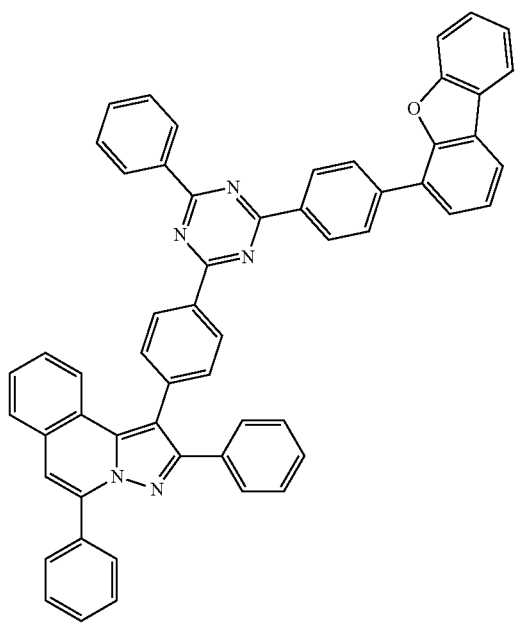
98
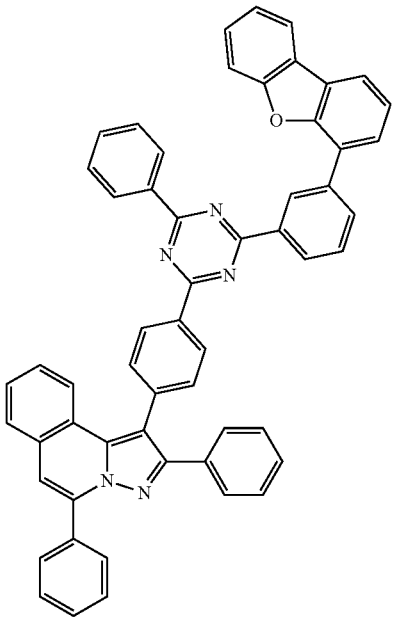
99

247
-continued
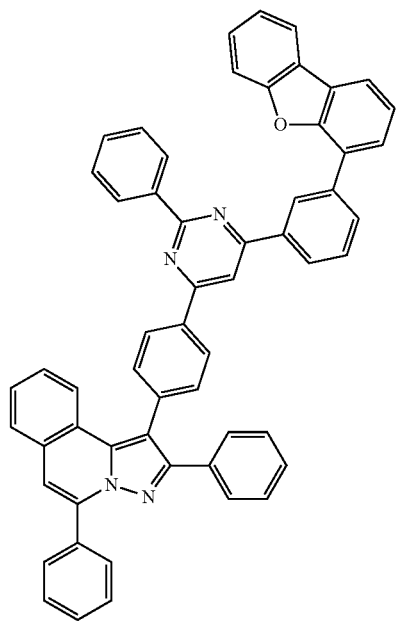
100
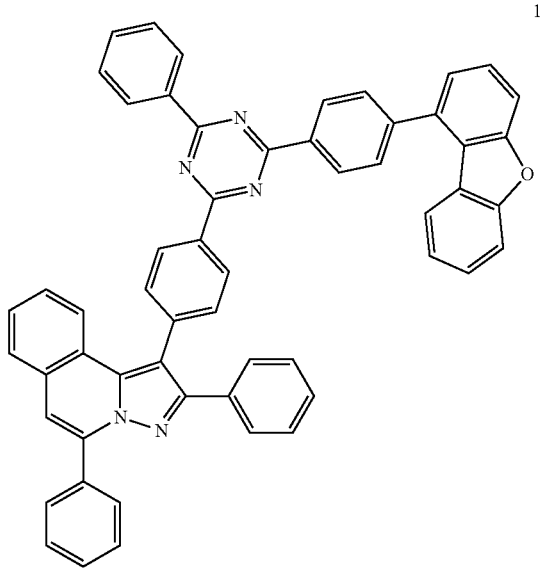
101
248
-continued
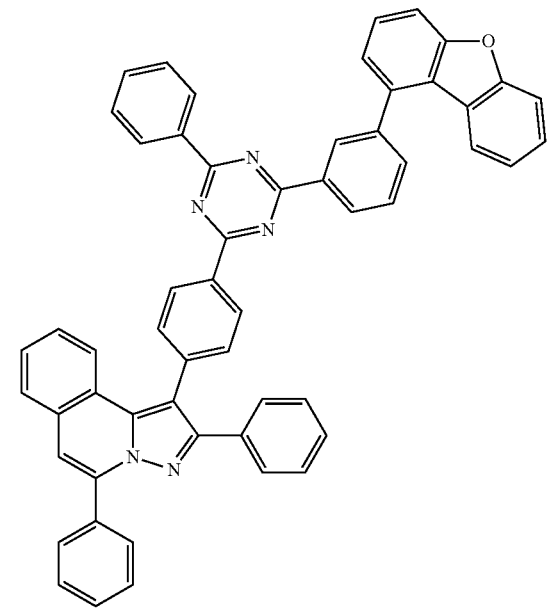
102
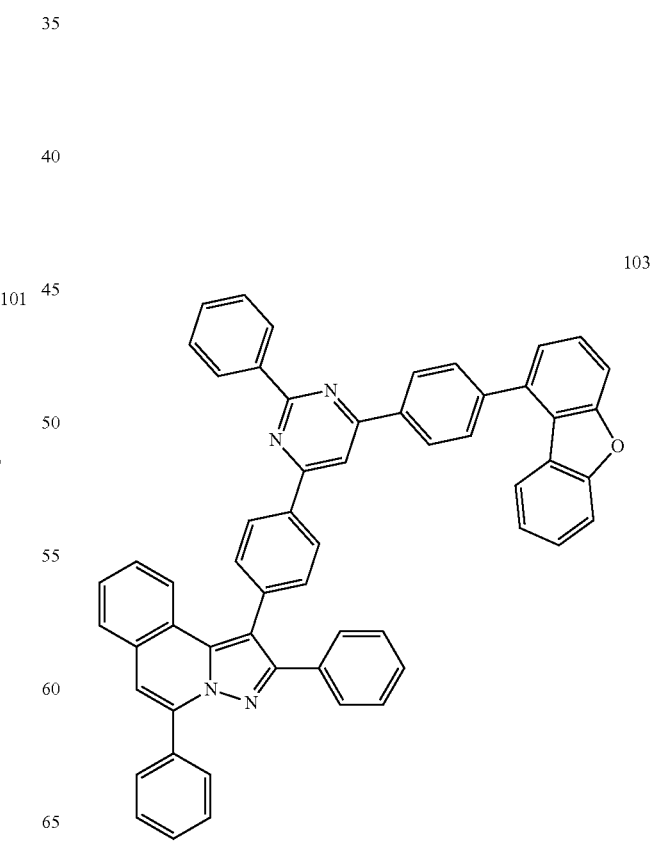
103

249
-continued
104
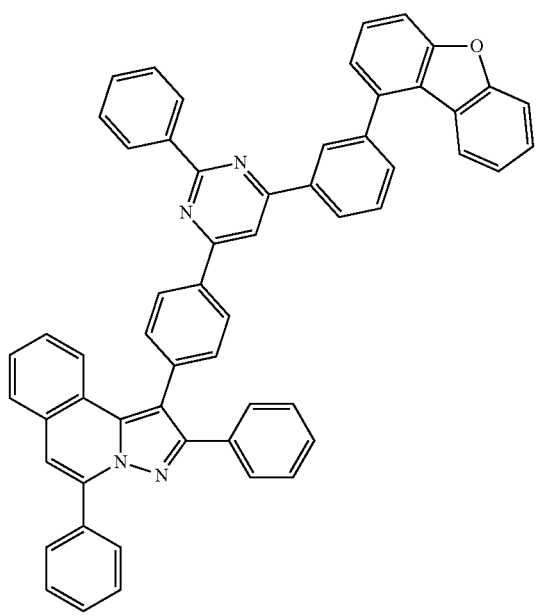
105
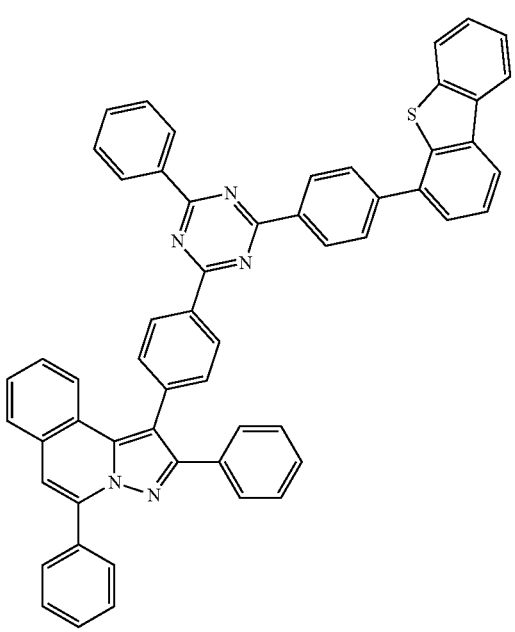
250
-continued
106
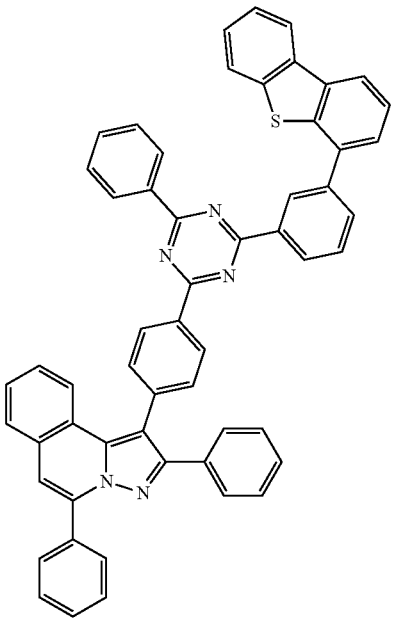
107
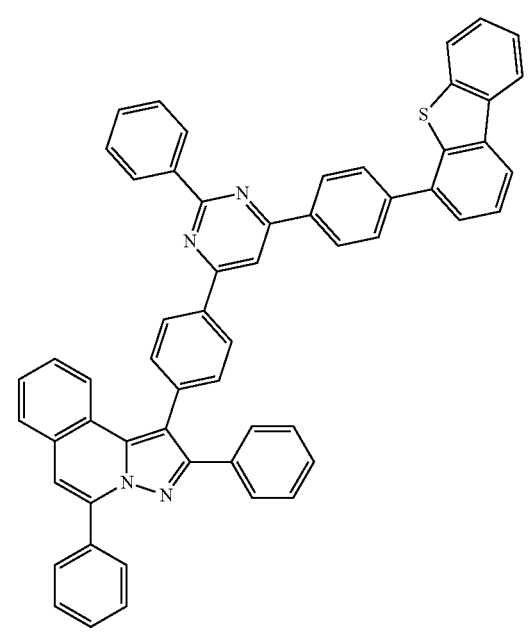

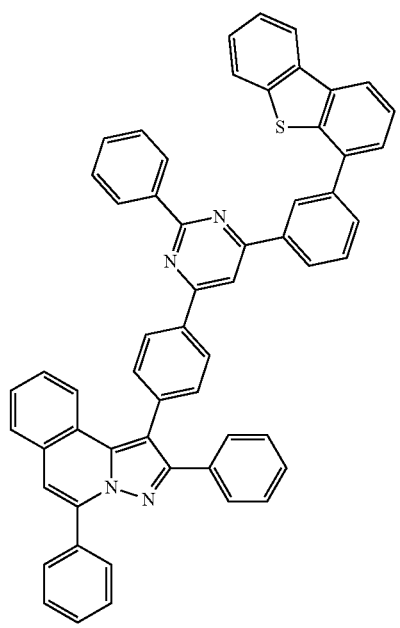
108
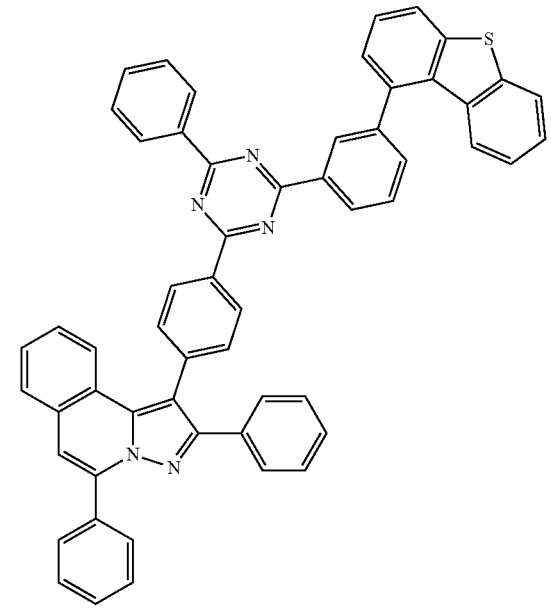
110
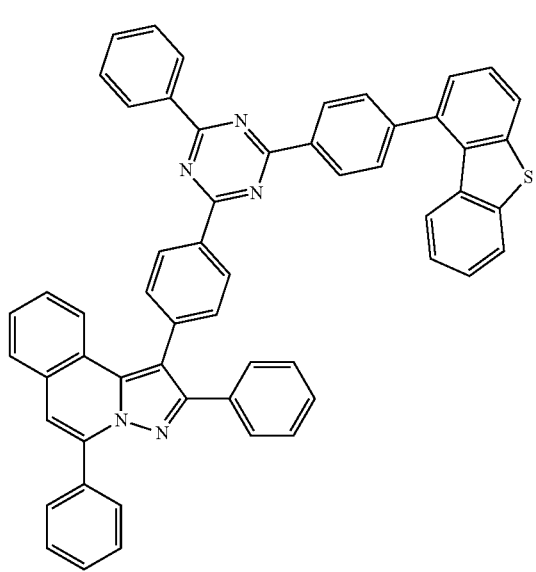
109
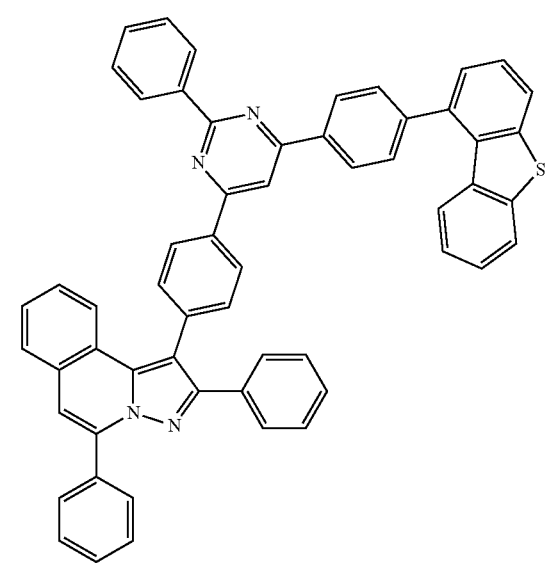
111

112
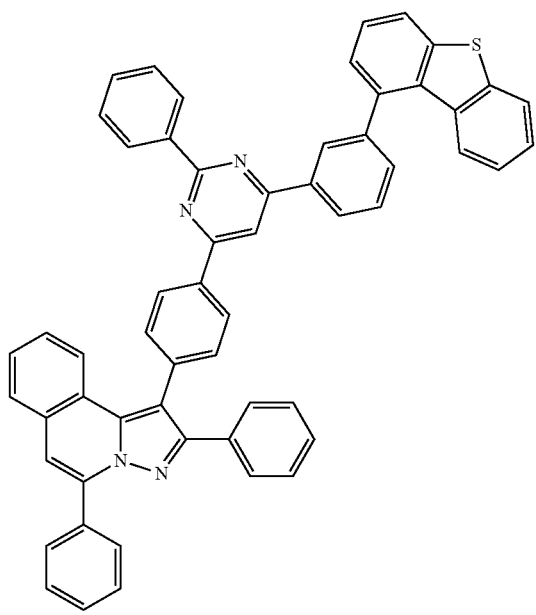
113
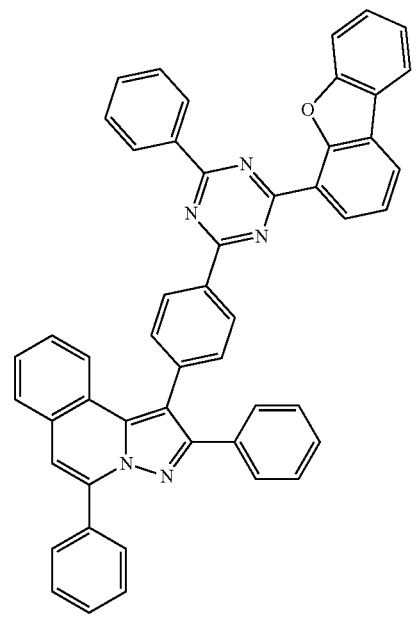
114
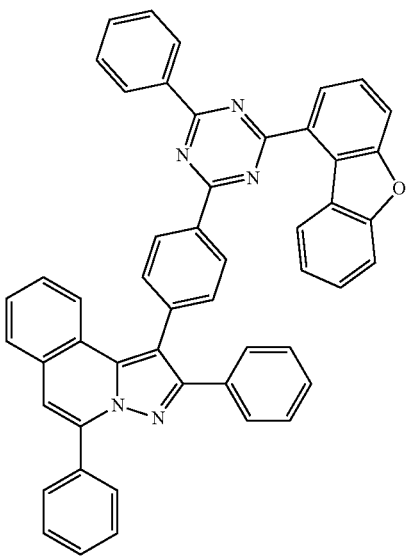
115
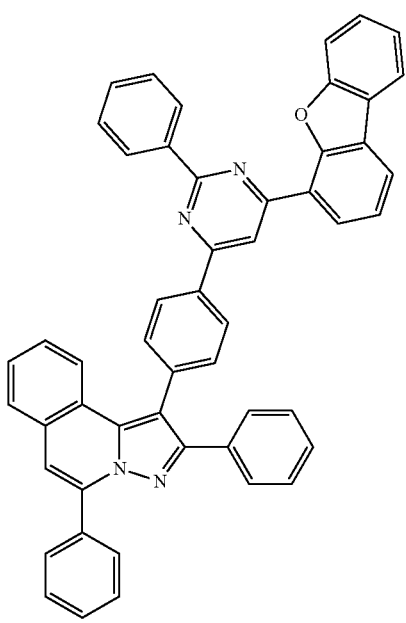

116
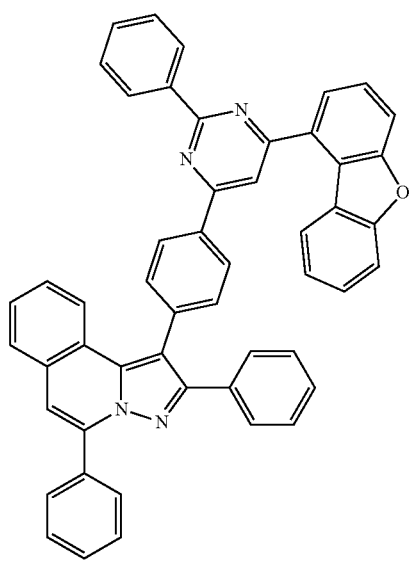
117
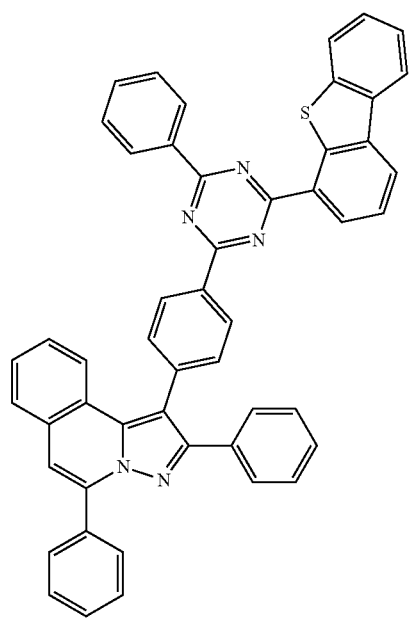
118
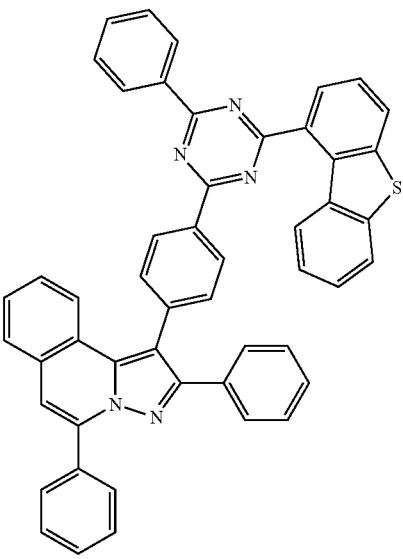
119
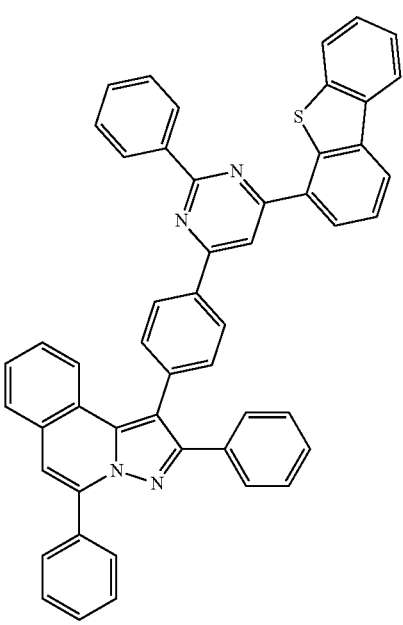

257
-continued
120
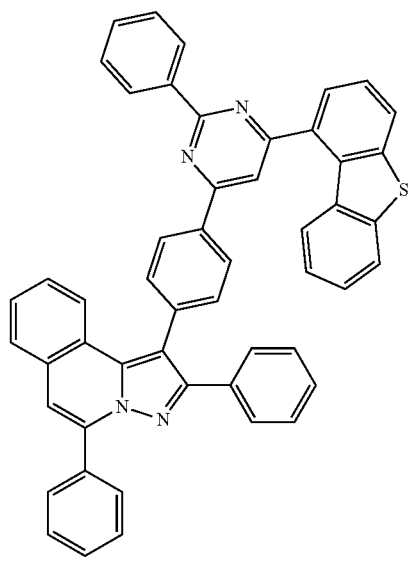
121
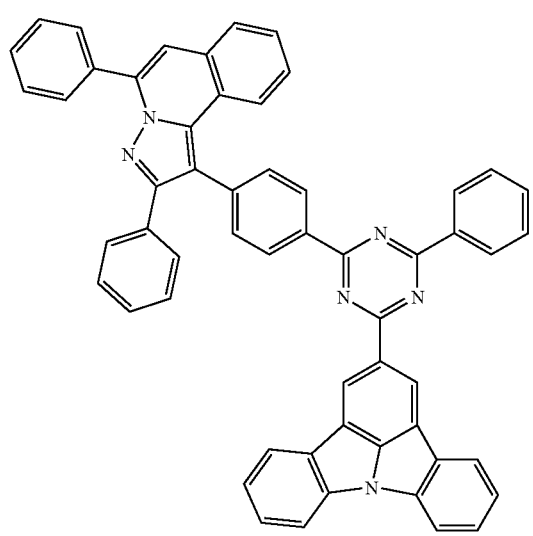
122
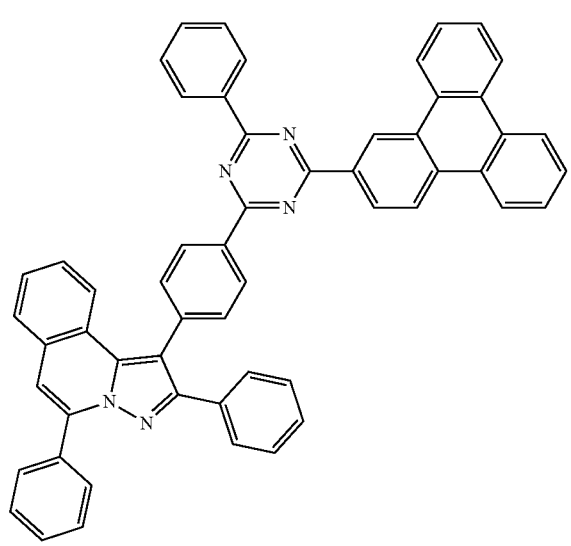
258
-continued
123
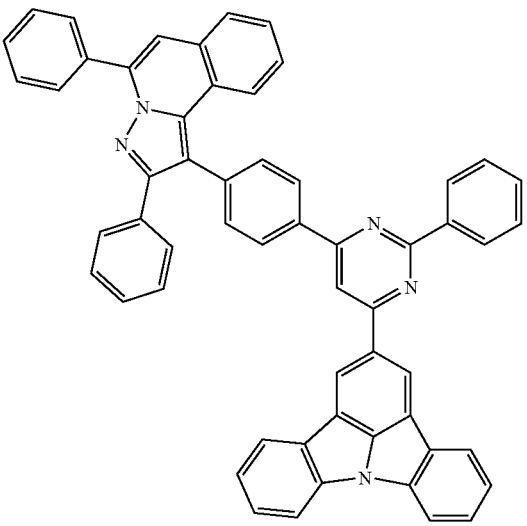
124
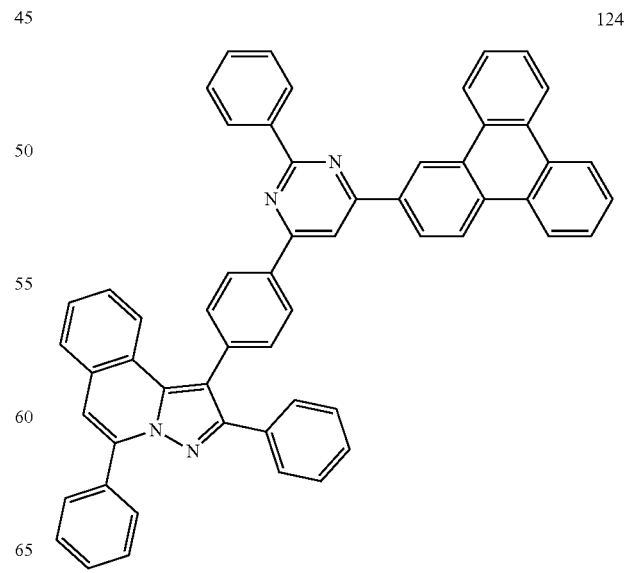

125
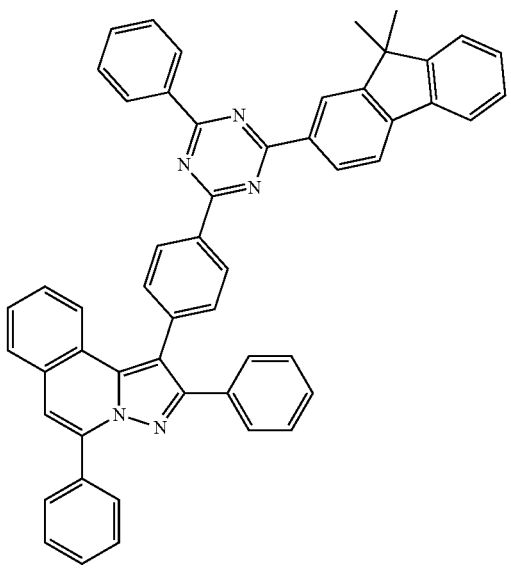
126
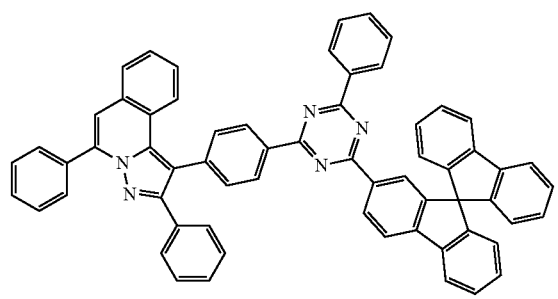
127
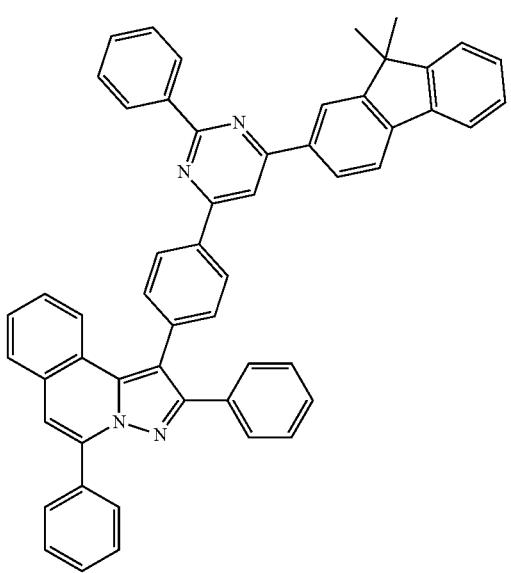
128
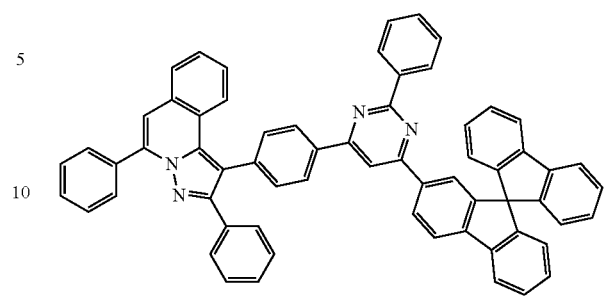
129
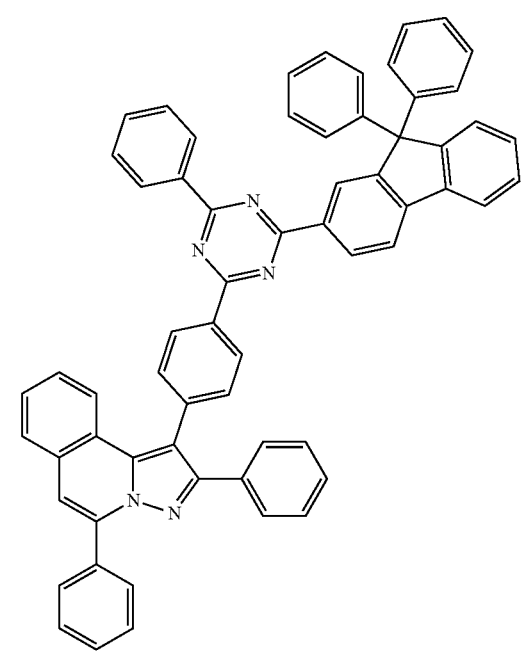
130
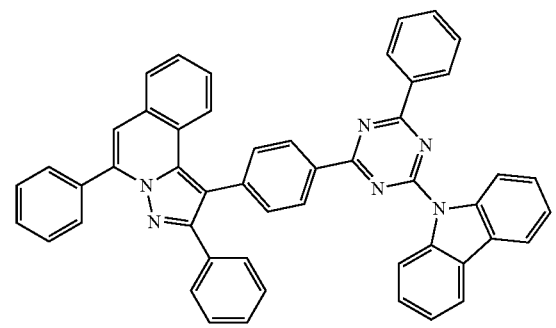

131
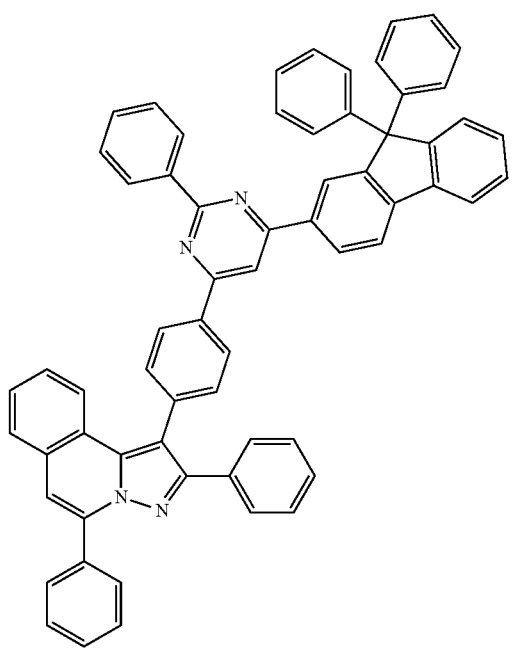
132
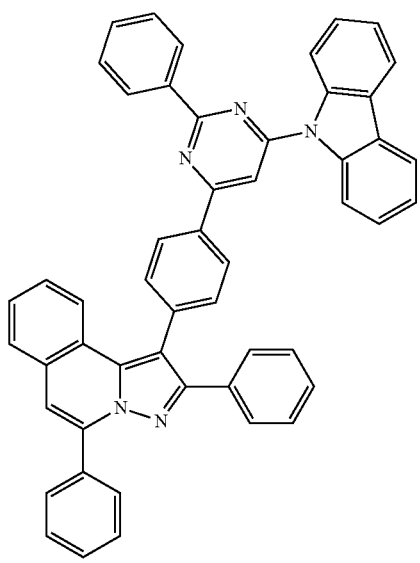
133
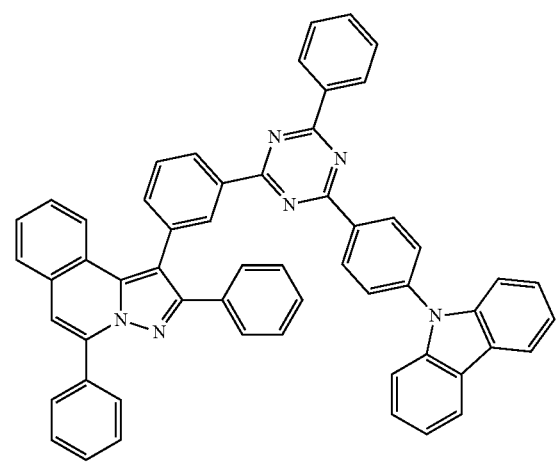
134
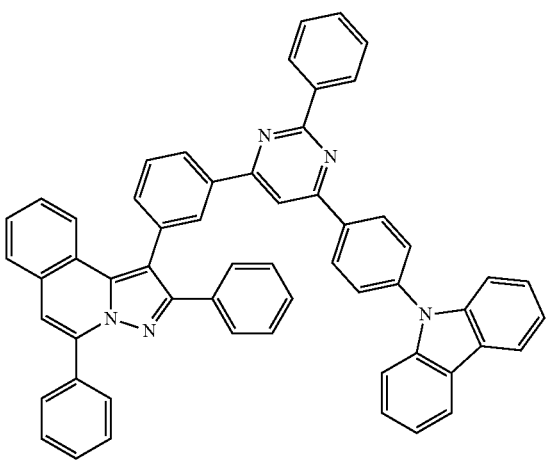
135

263
-continued
136
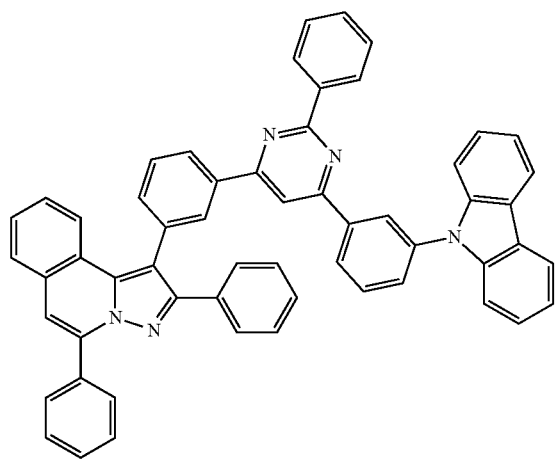
137
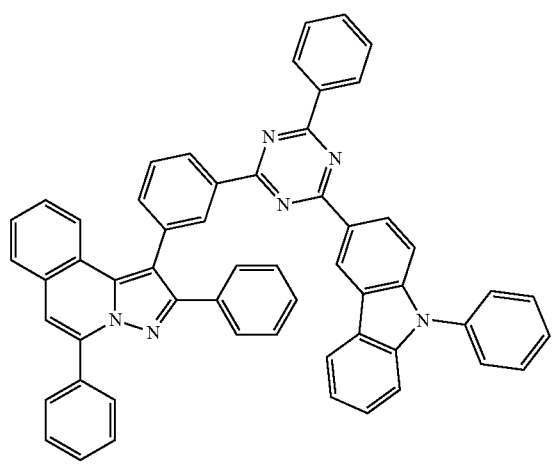
138
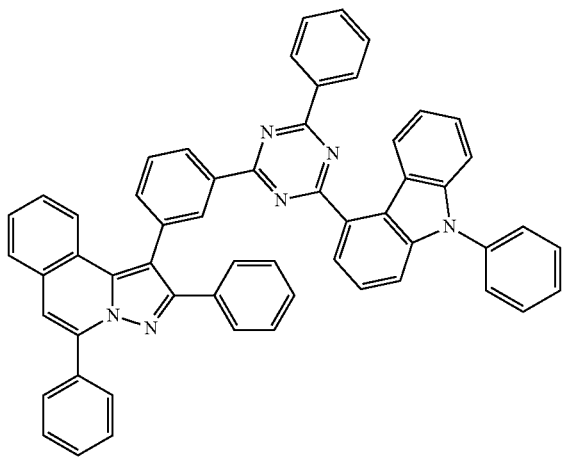
264
-continued
139
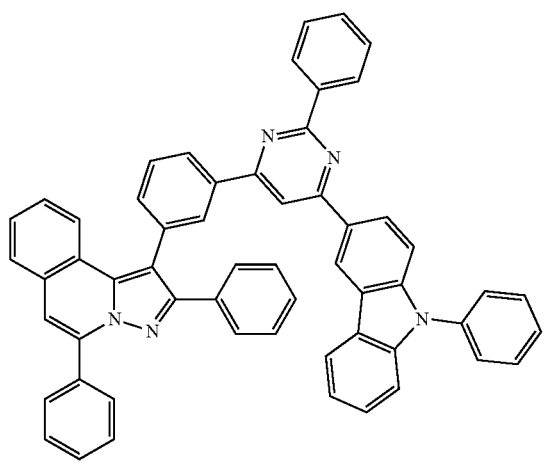
140
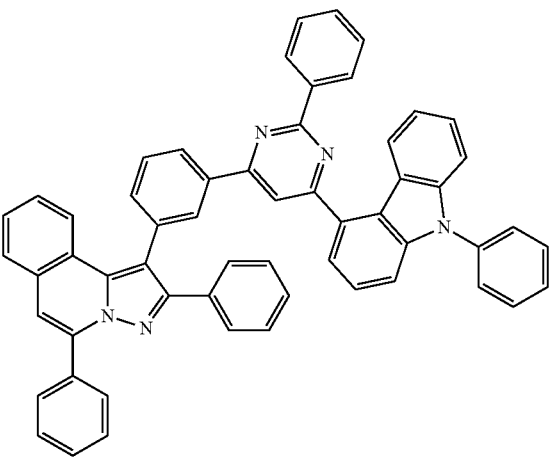
141
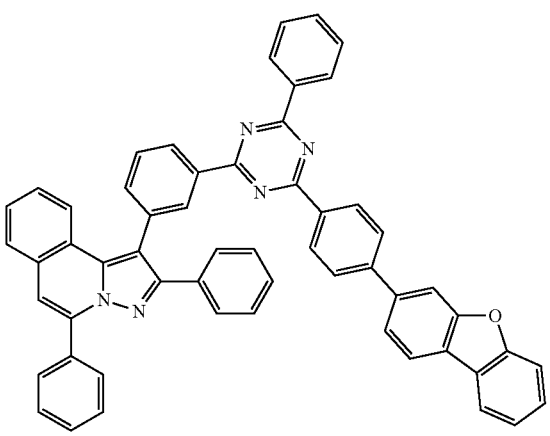

142
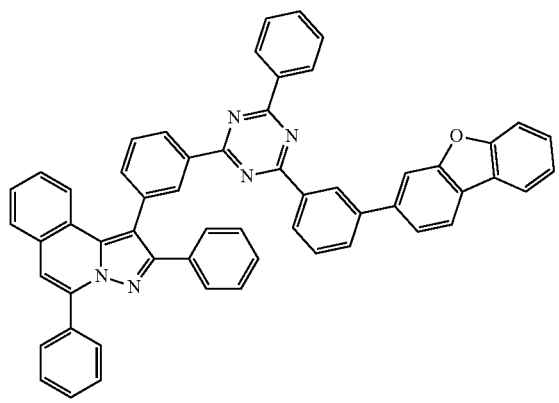
143
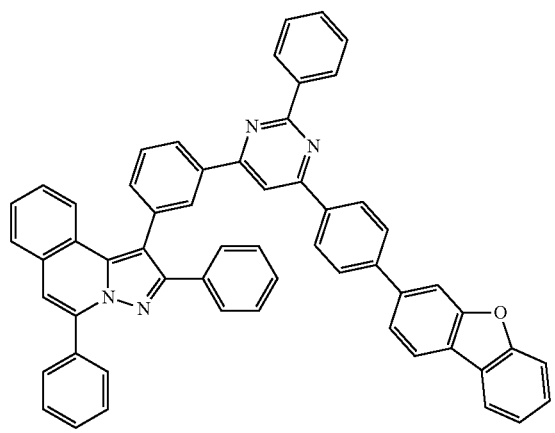
144
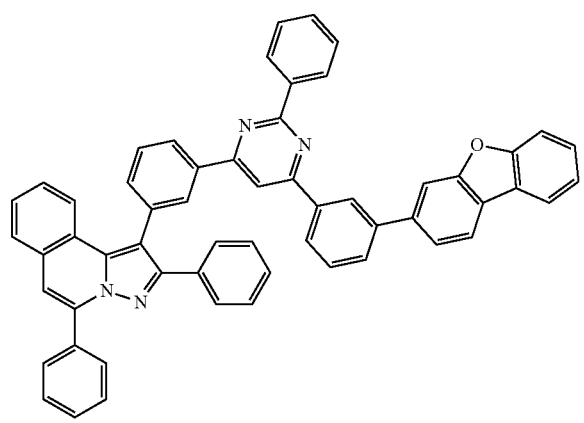
145
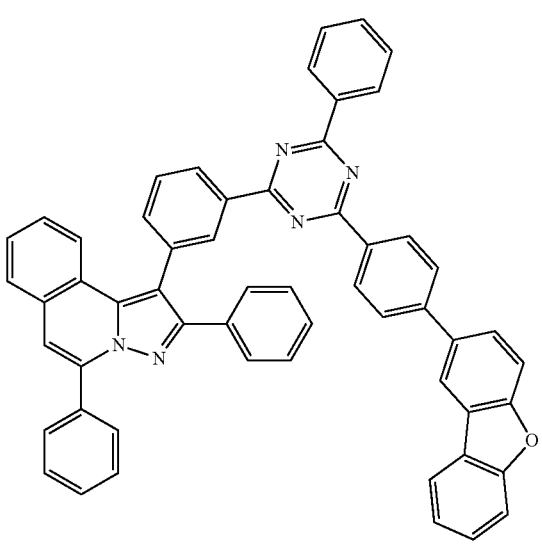
146
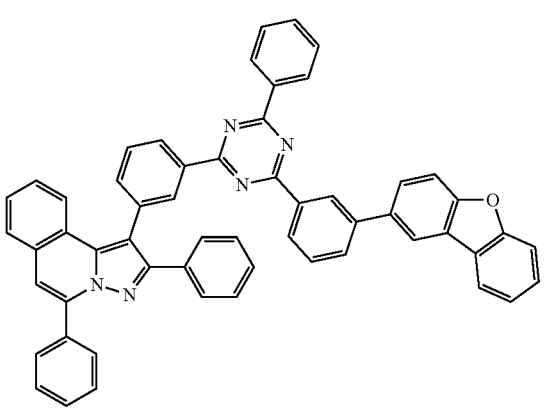
147
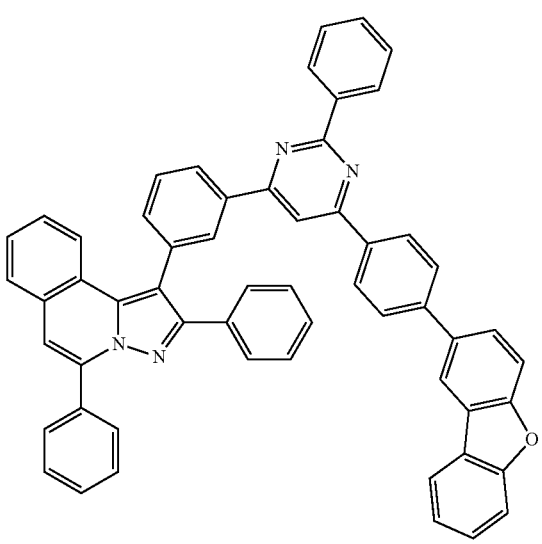

267
-continued
148
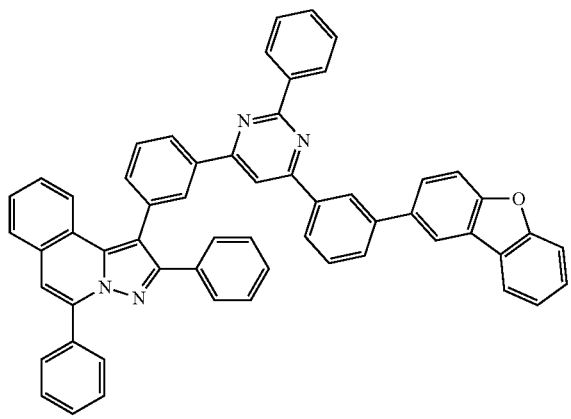
149
150
268
-continued
151
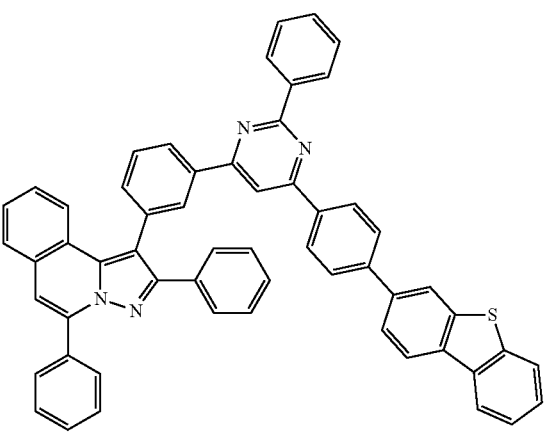
152
153

269
-continued
154
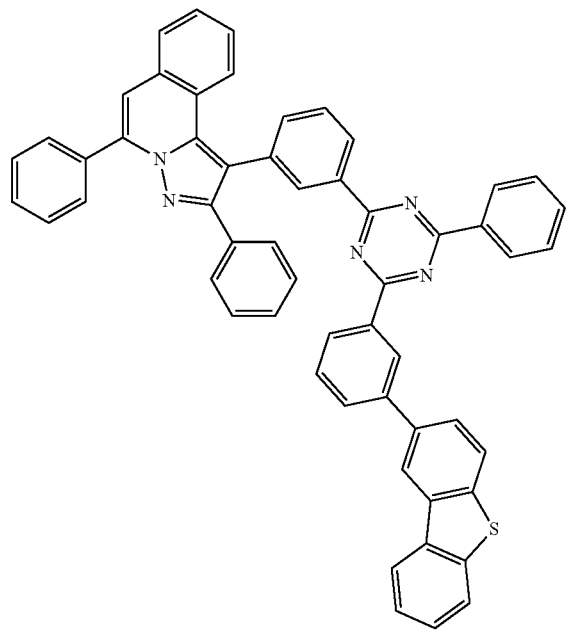
155
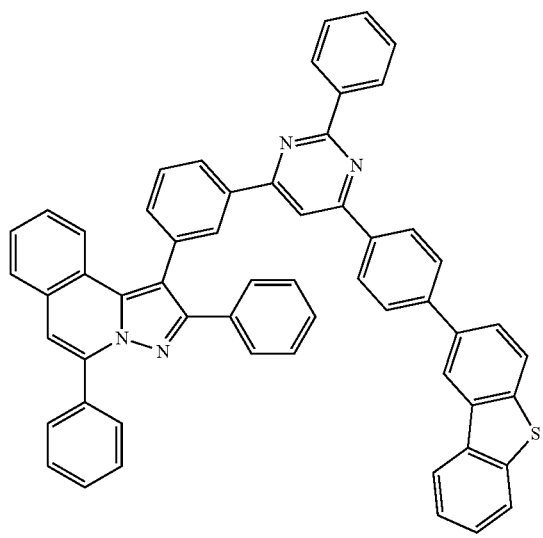
270
-continued
156
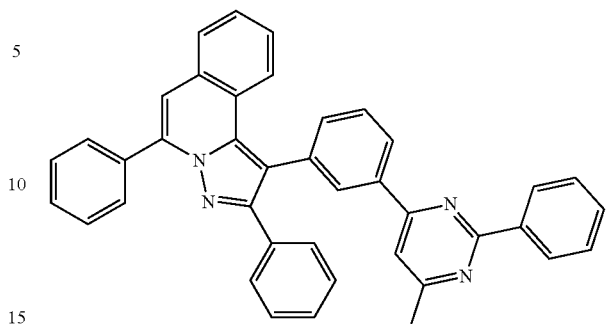
157
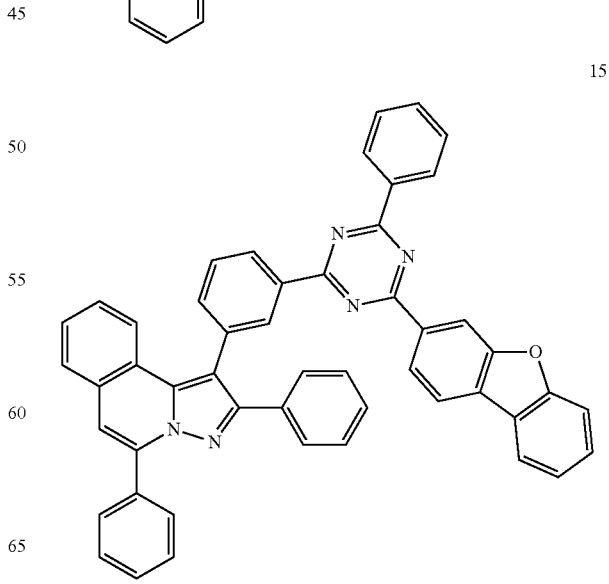
158

-continued
159
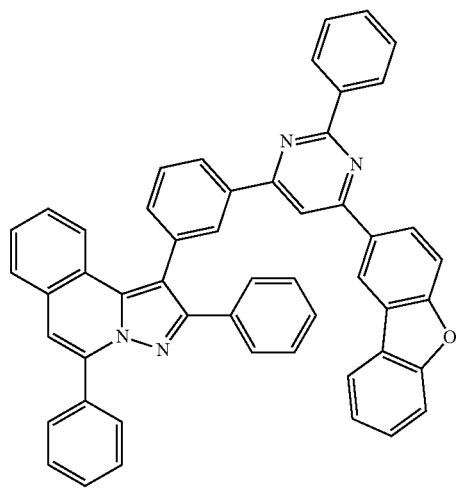
160
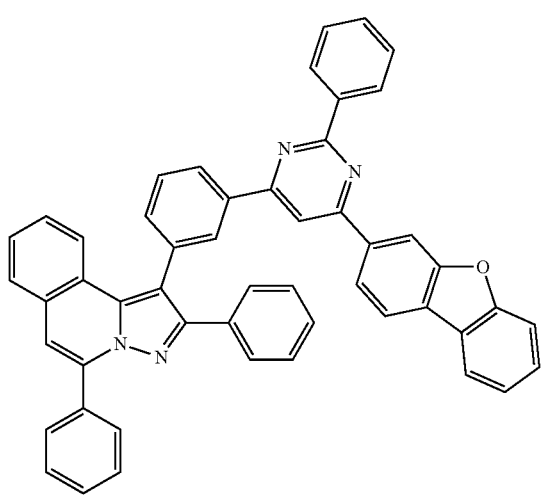
161
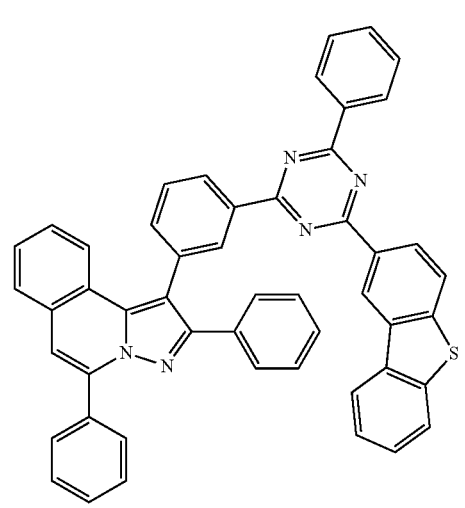
-continued
162
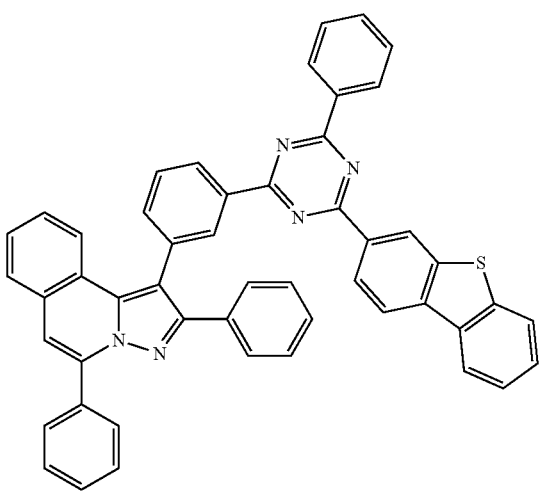
163
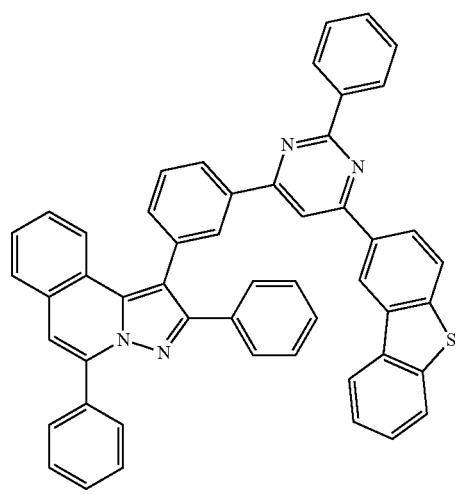
164
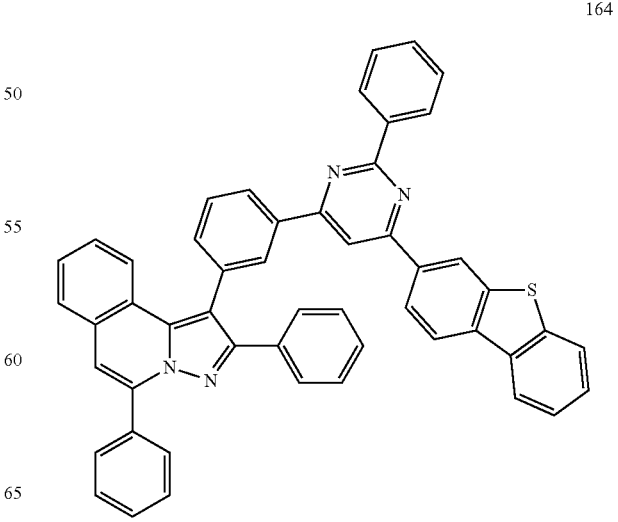

273
-continued
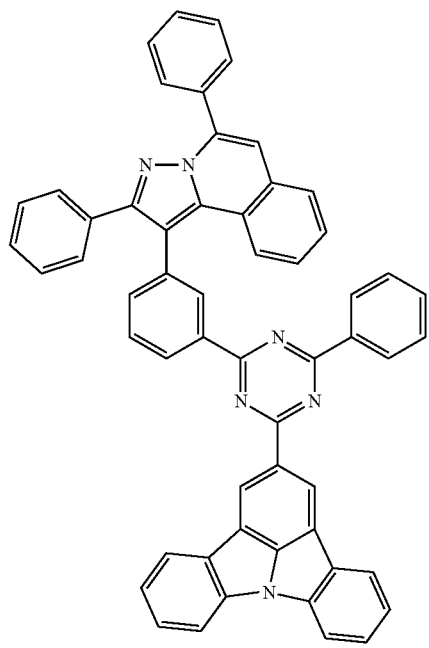
165
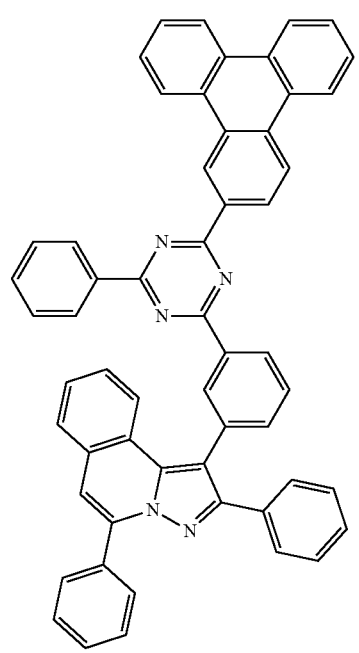
166
274
-continued
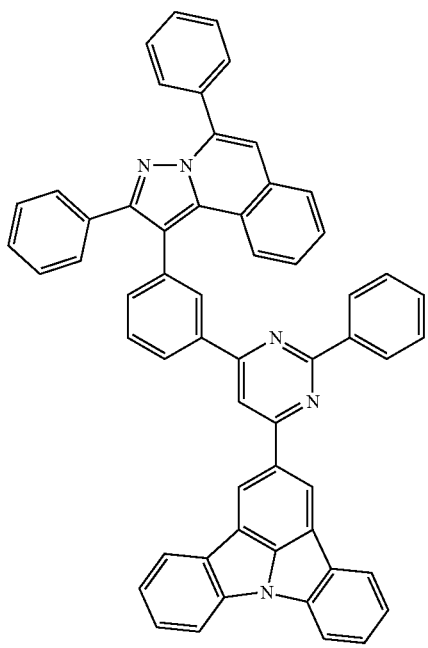
167
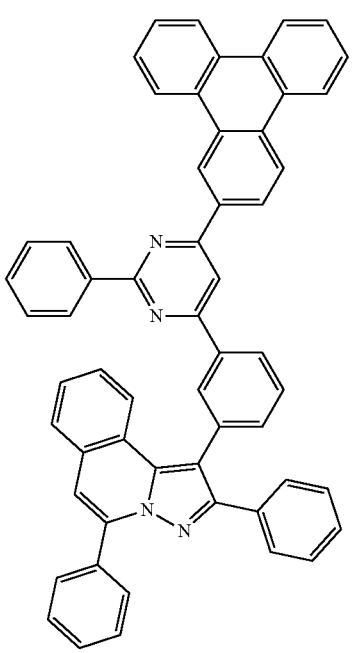
168

275
-continued
169
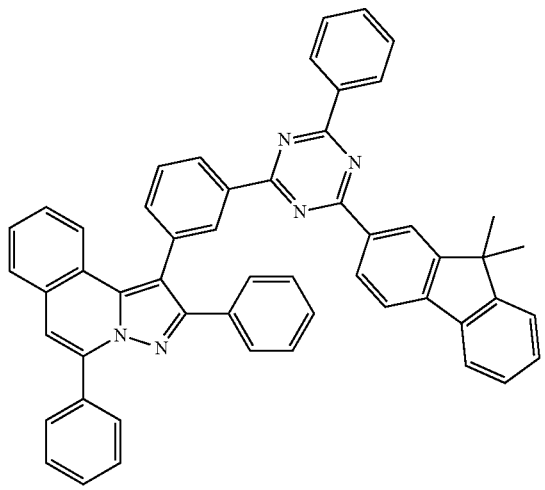
170
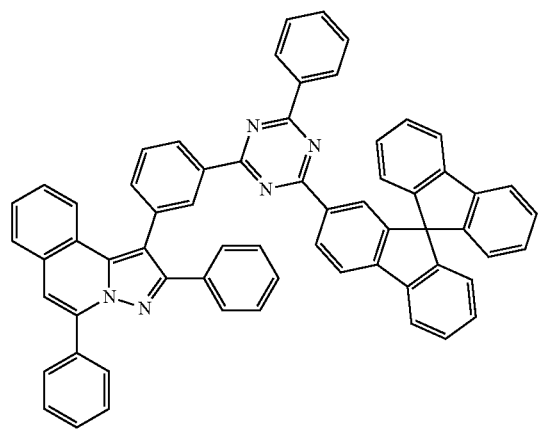
171
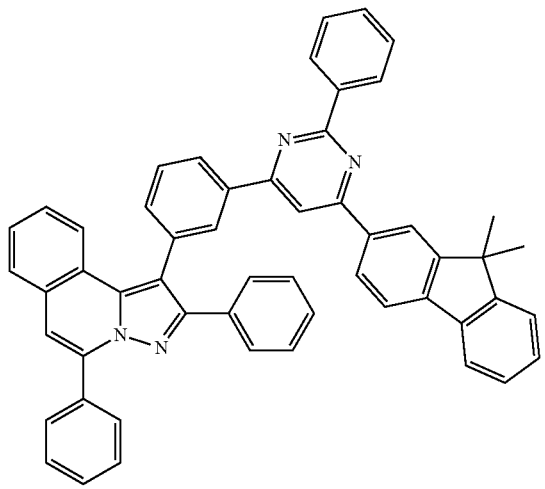
276
-continued
172
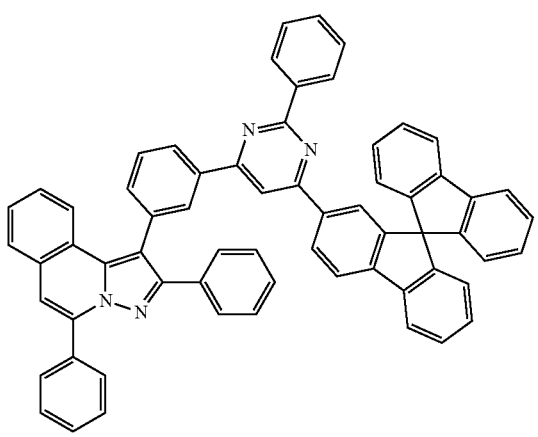
173
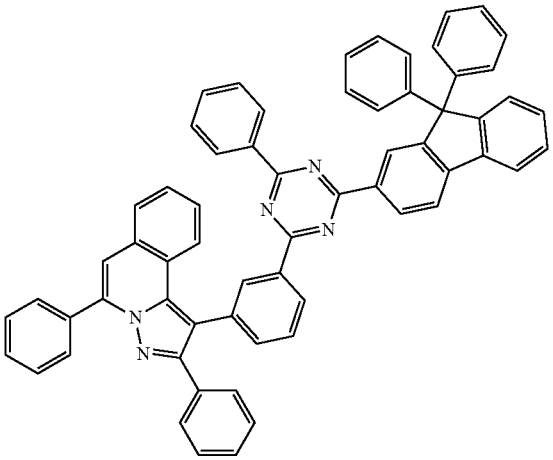
174
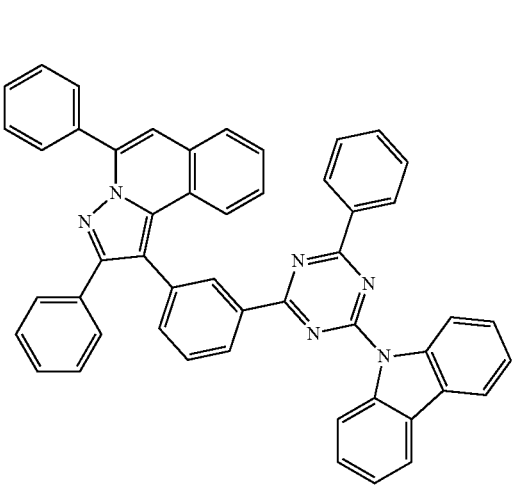

175
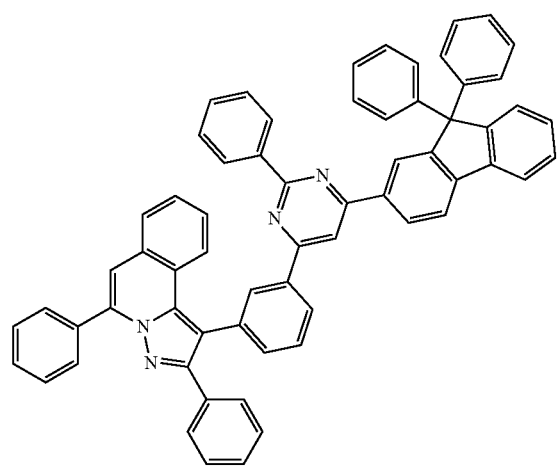
176
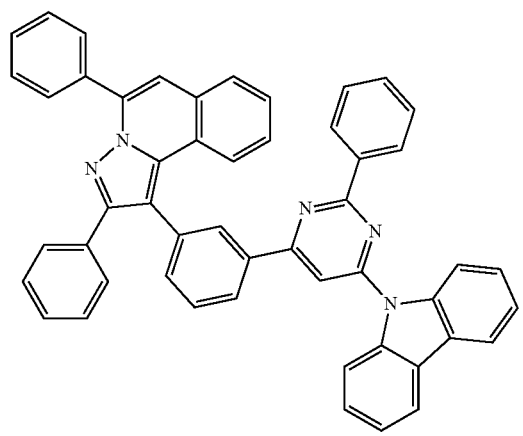
177
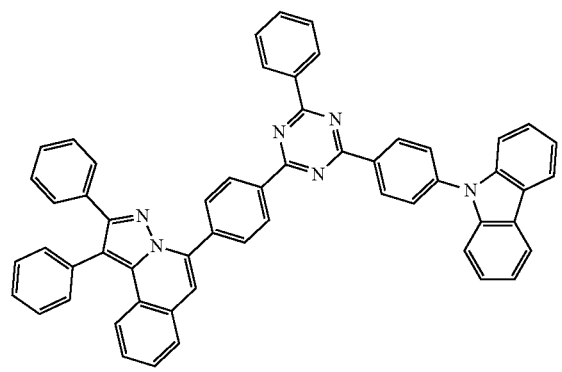
178
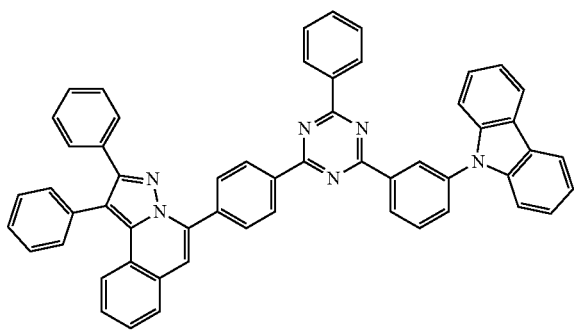
179
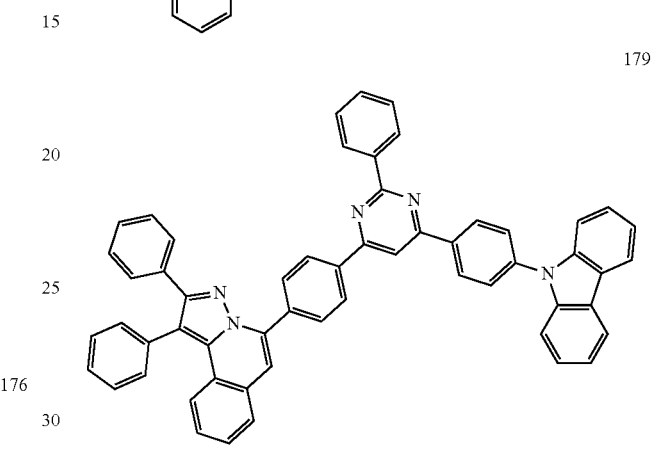
180
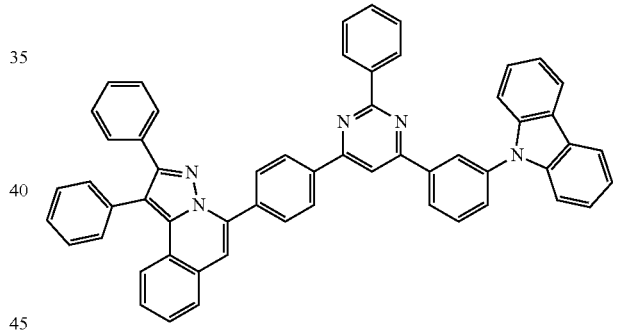
181
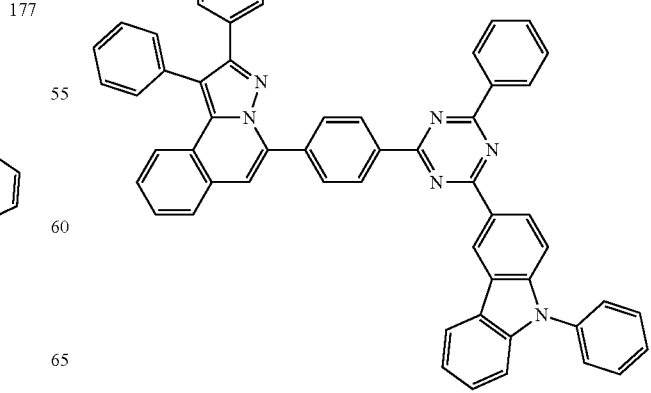

182
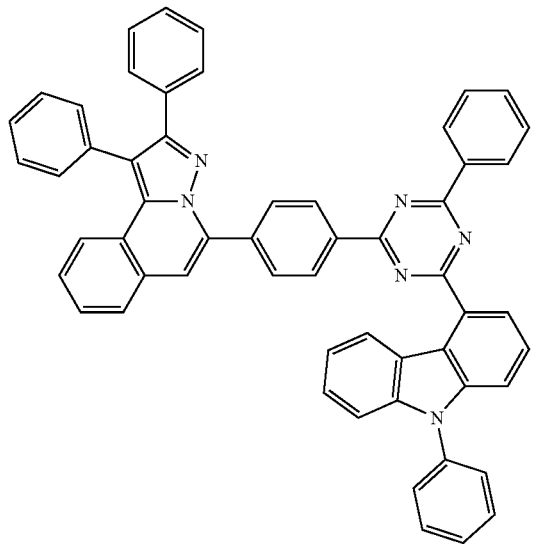
183
185
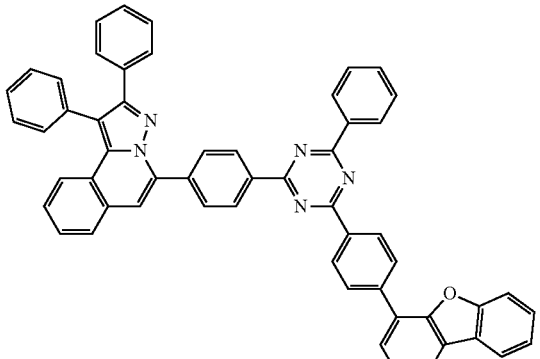
186
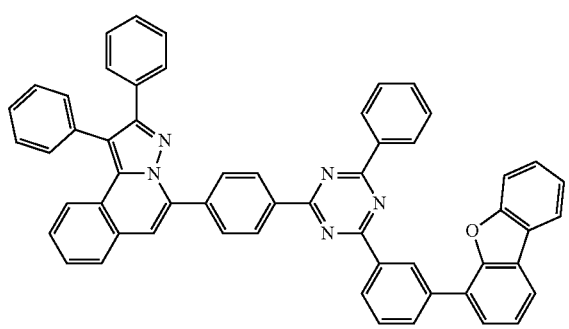
187
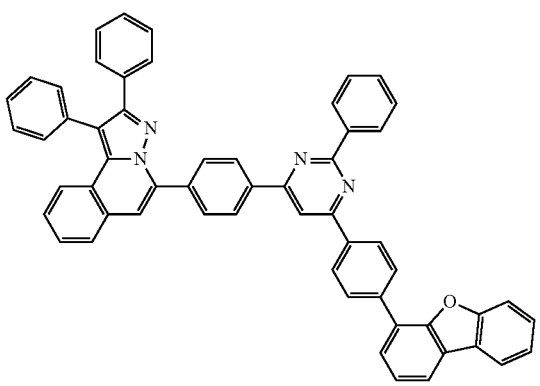
184
188
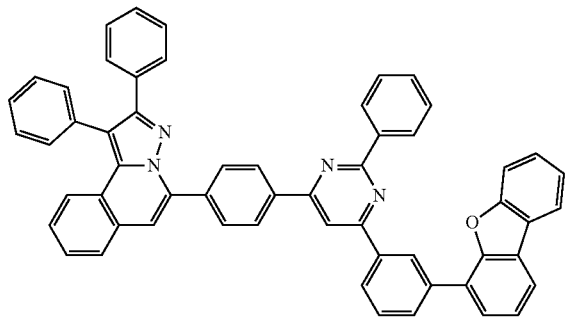

-continued
189
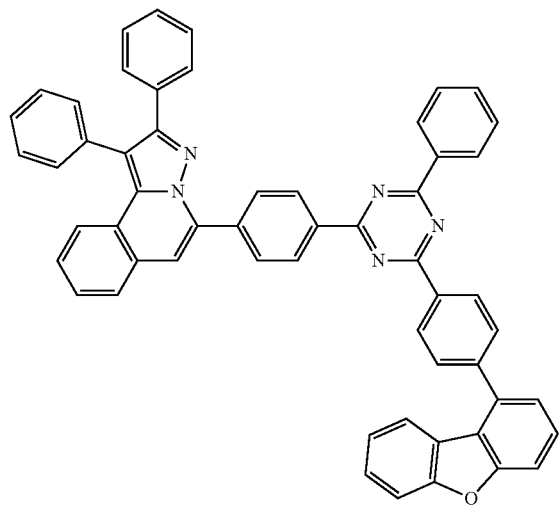
190
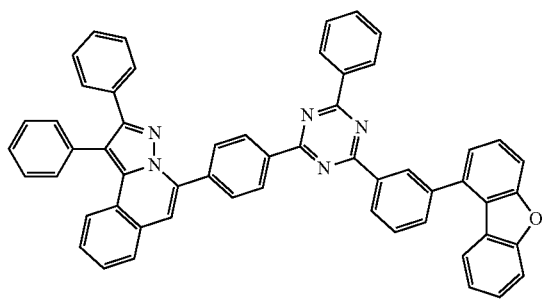
191
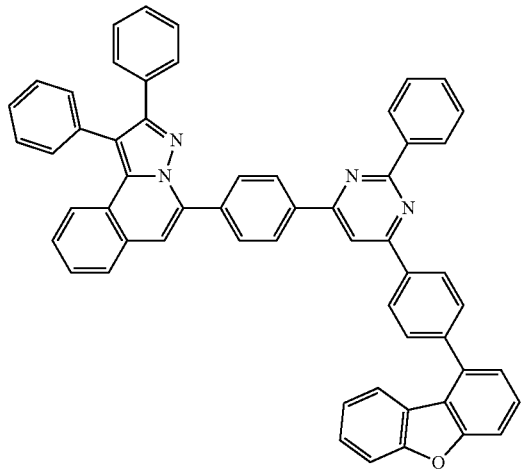
-continued
192
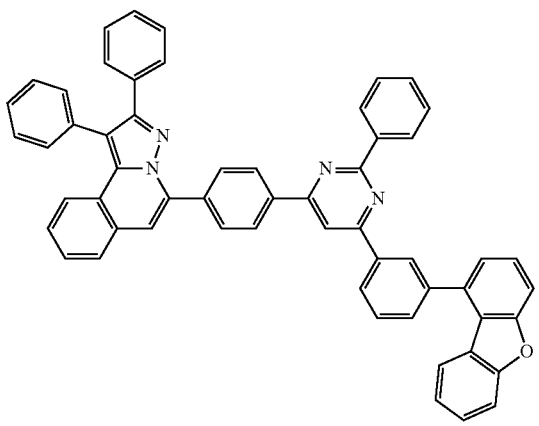
193
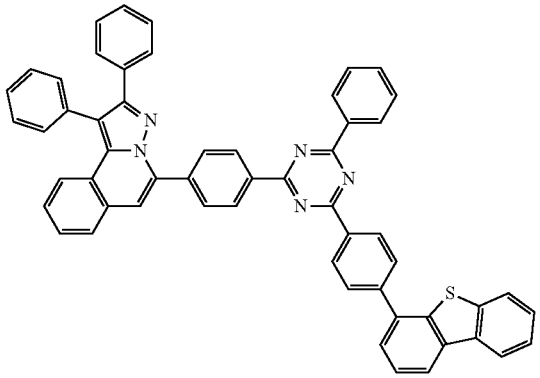
194
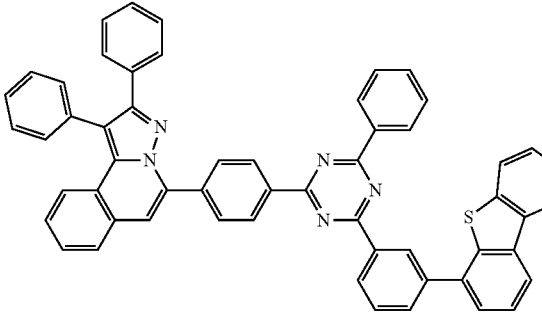
195
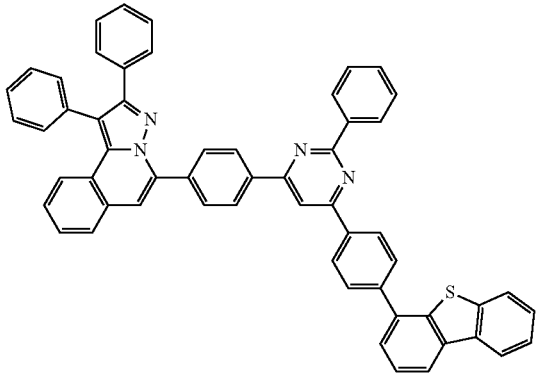

196
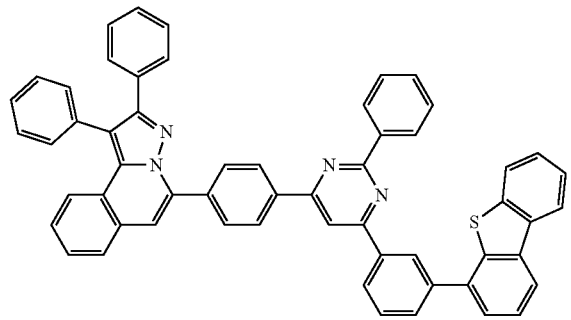
197
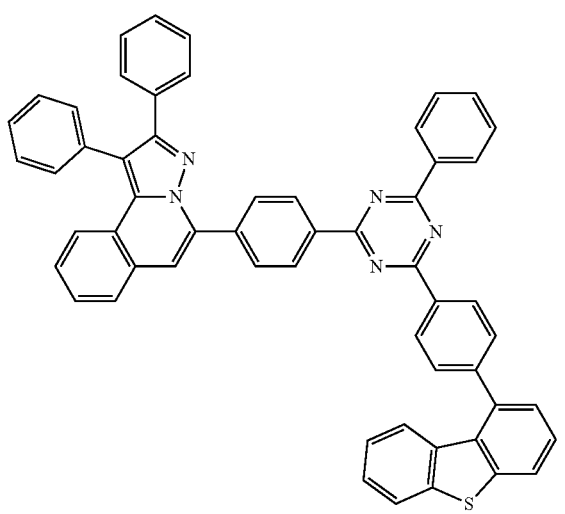
198
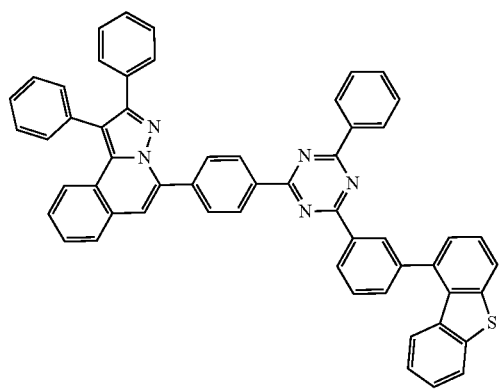
199
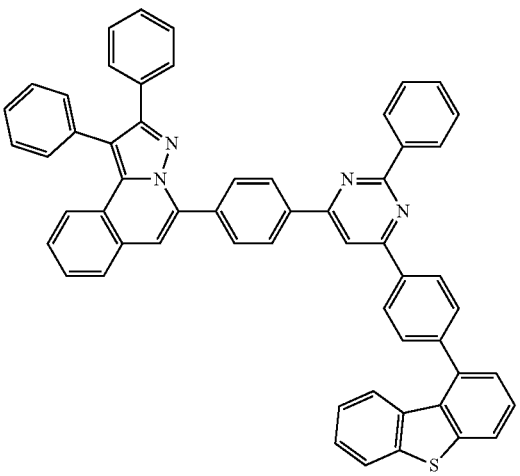
200
201
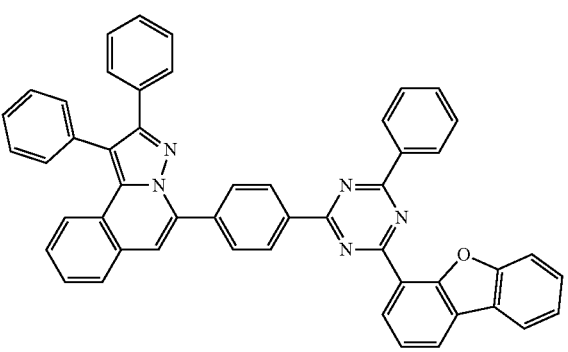

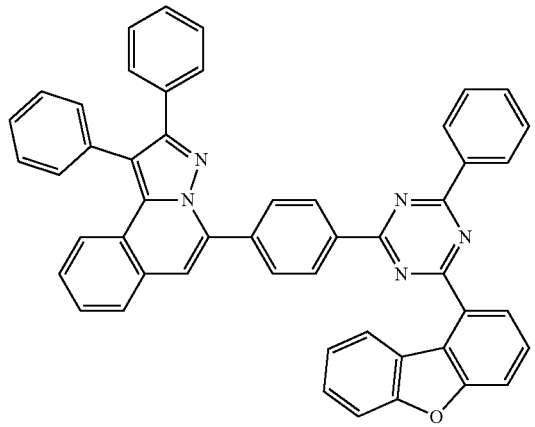
202
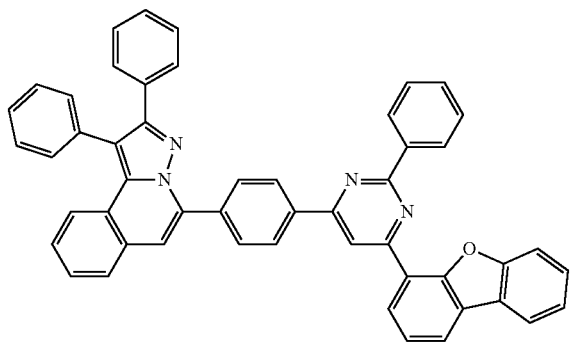
203
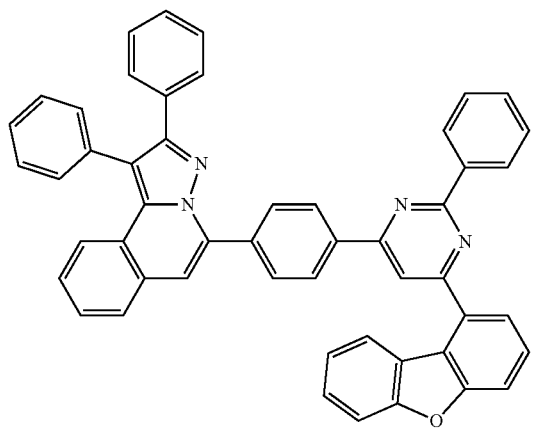
204
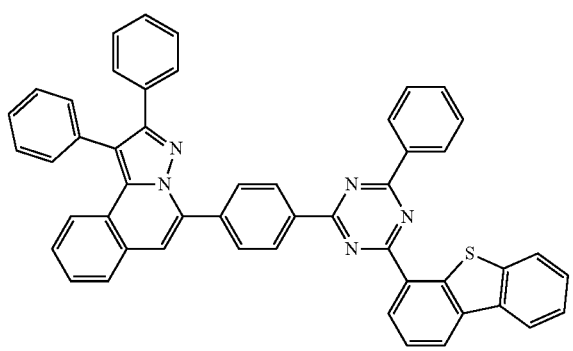
205
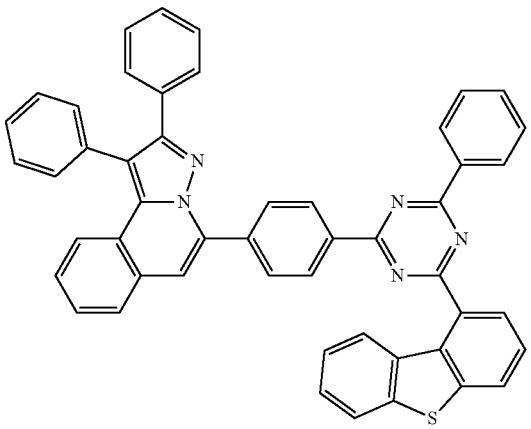
206
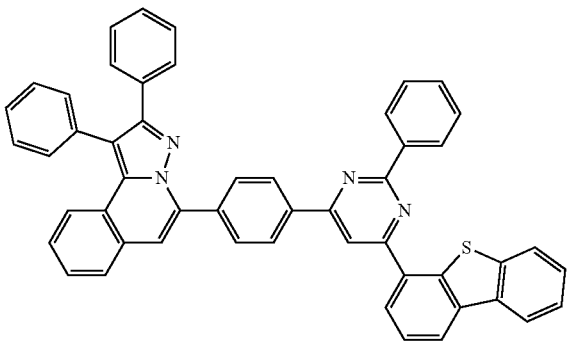
207
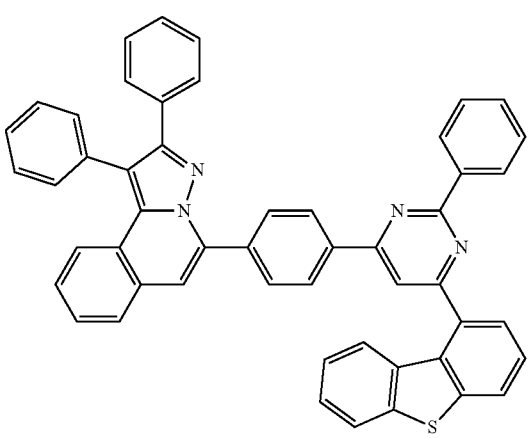
208

-continued
209
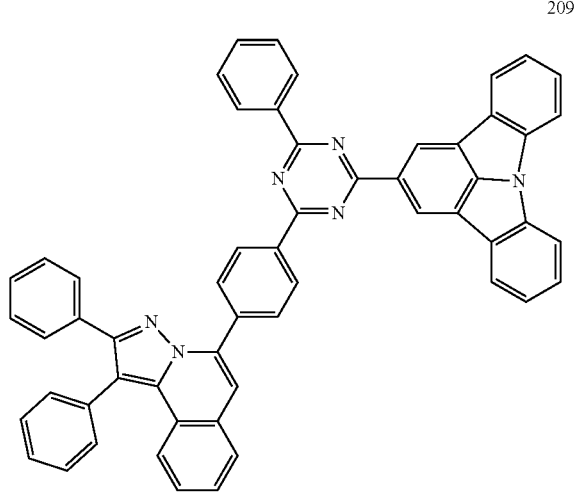
210
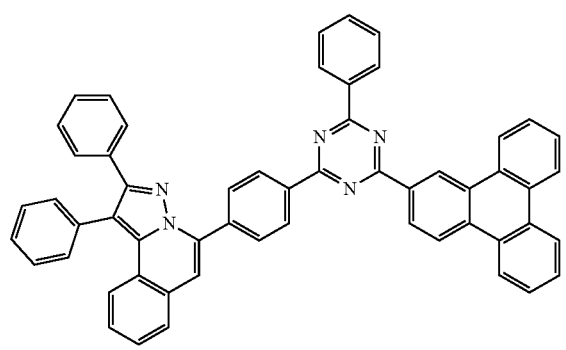
211
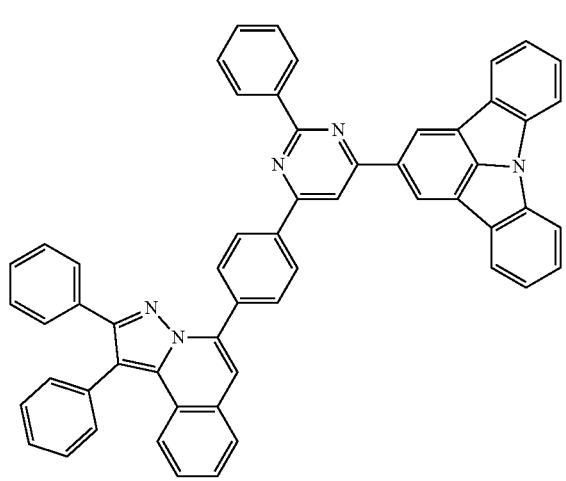
-continued
212
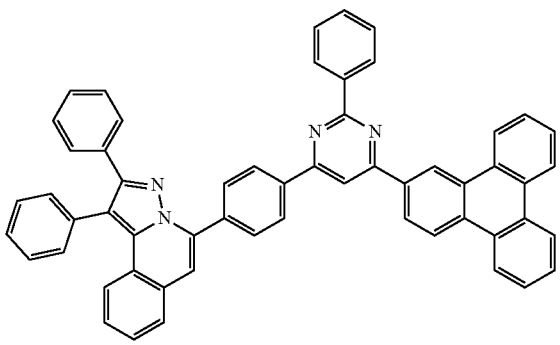
213
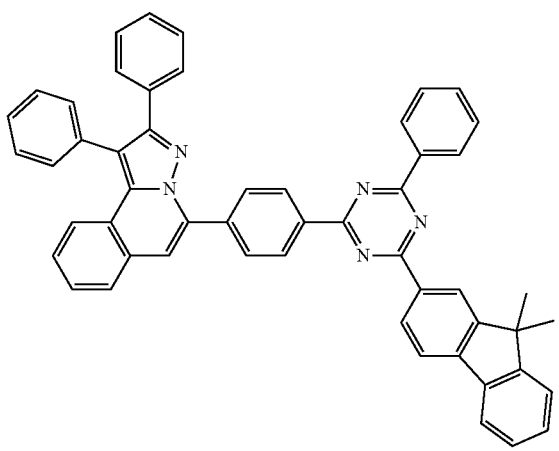
214
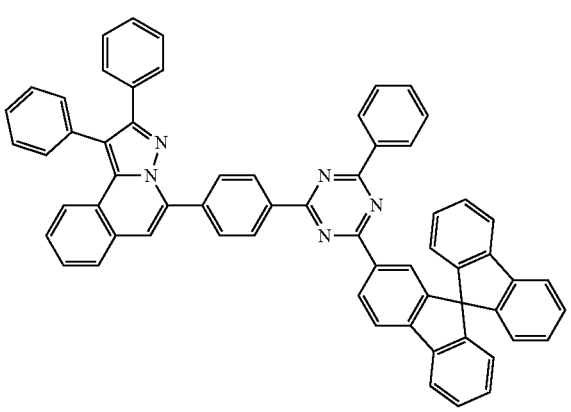

215
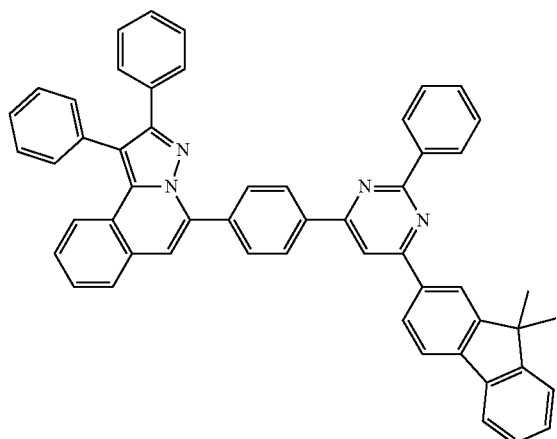
216
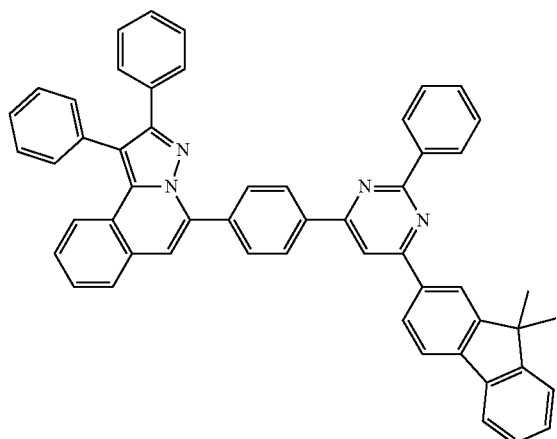
217
218
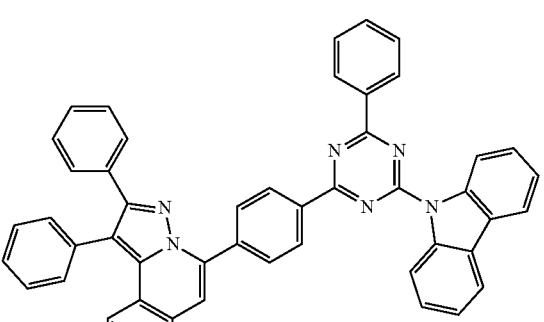
219
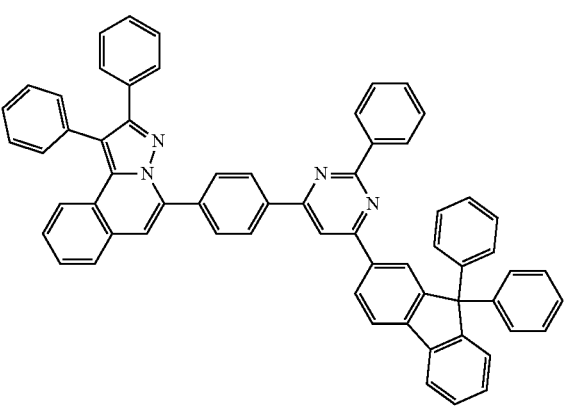
220
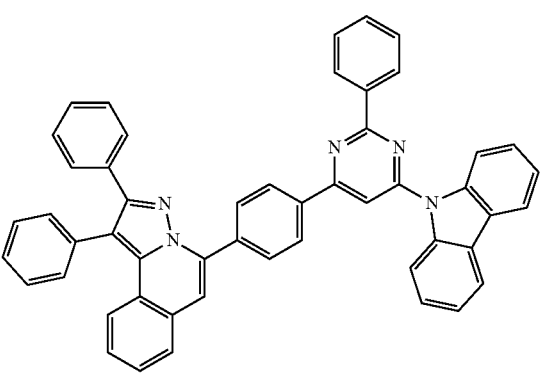
221
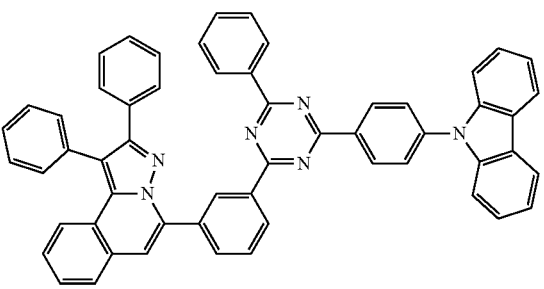

291
-continued
222
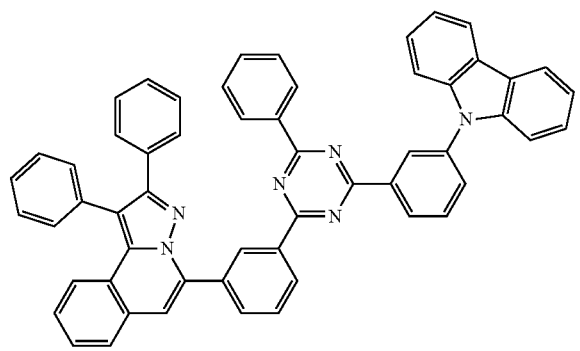
223
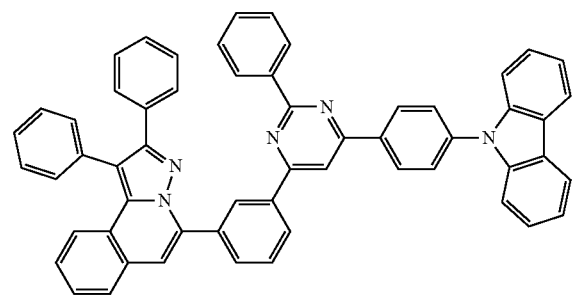
224
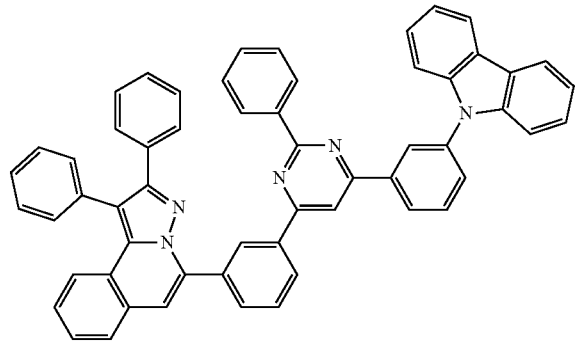
225
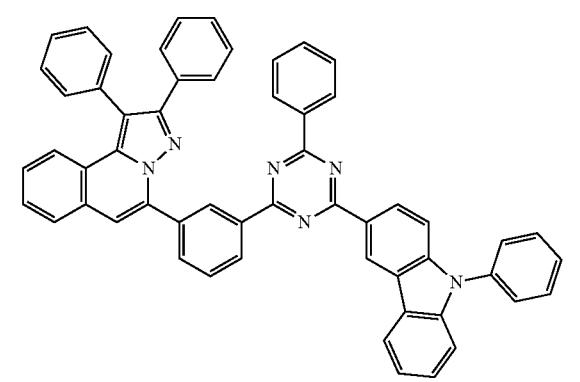
292
-continued
226
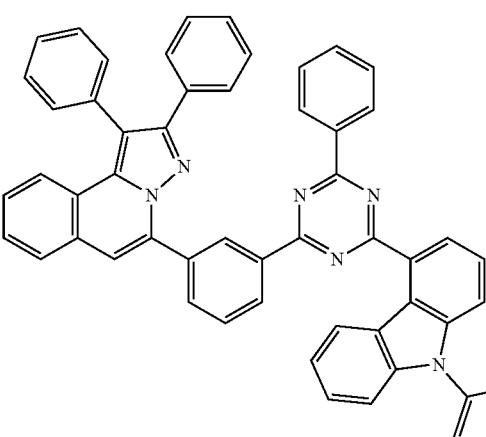
227
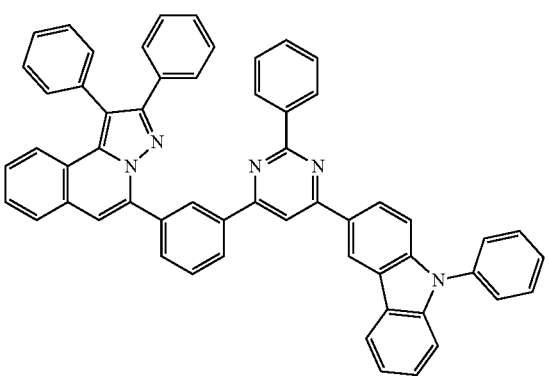
228
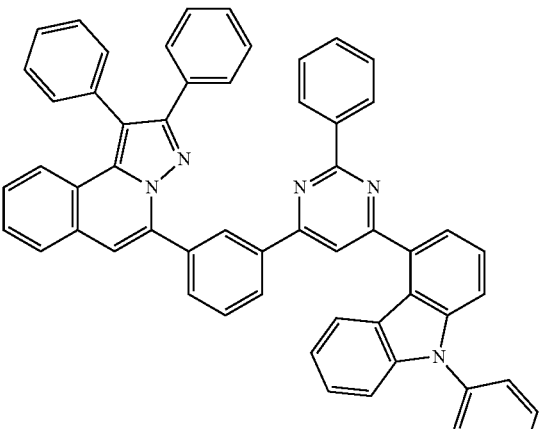
229
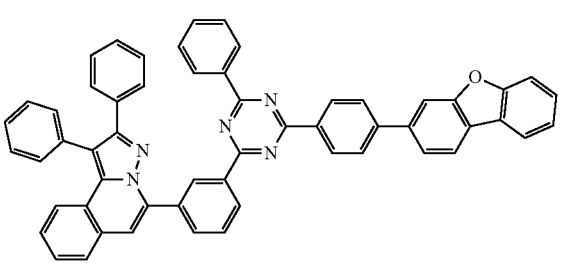

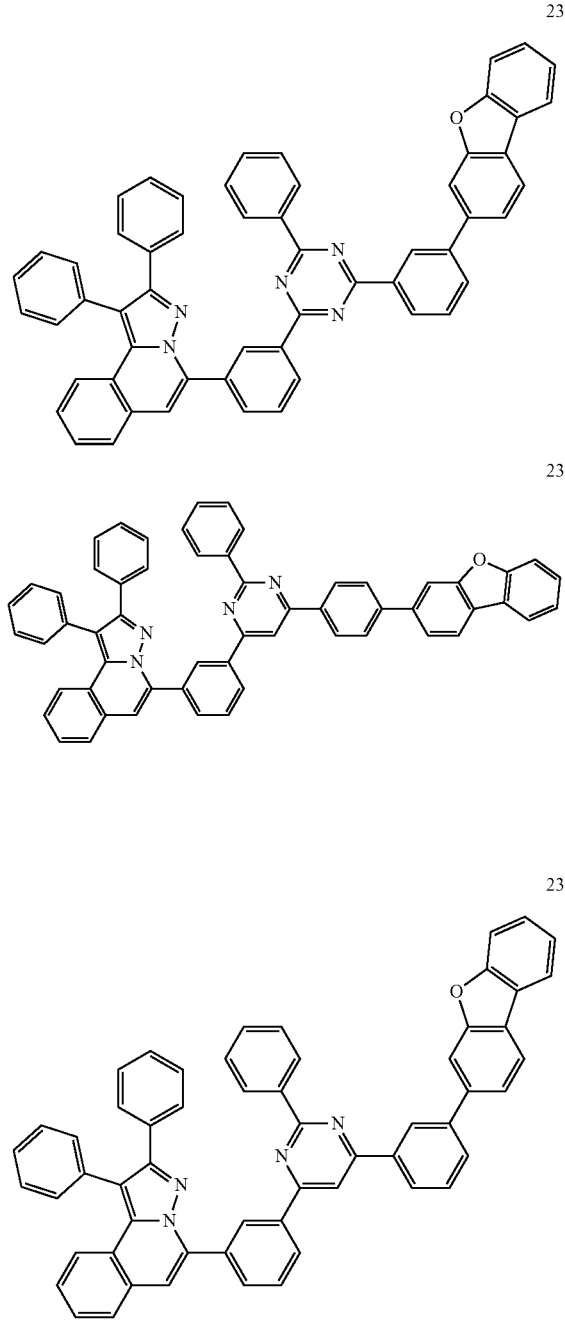
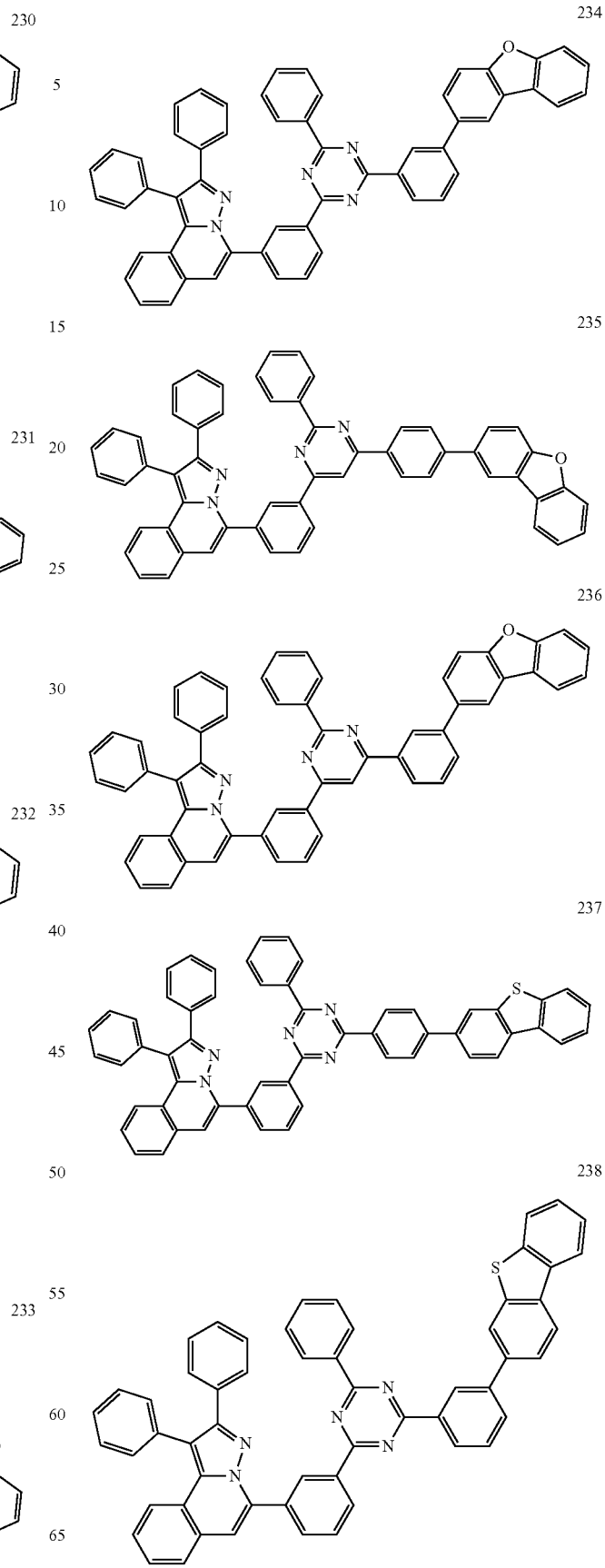

-continued
239
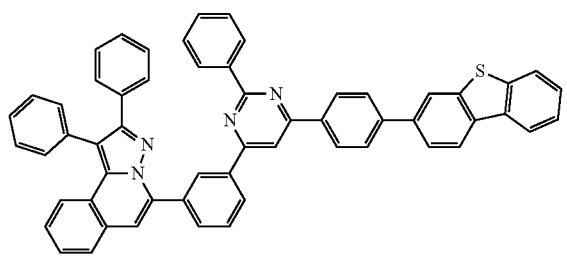
240
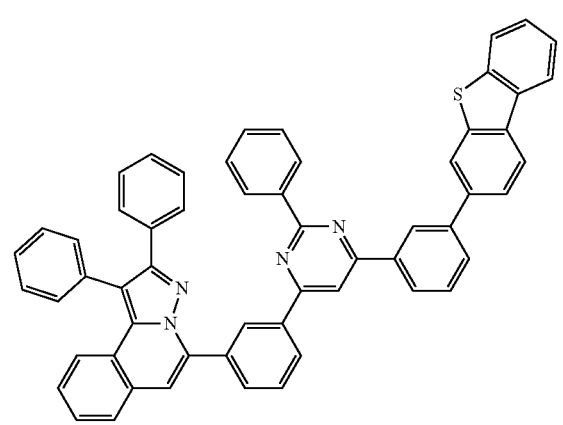
241
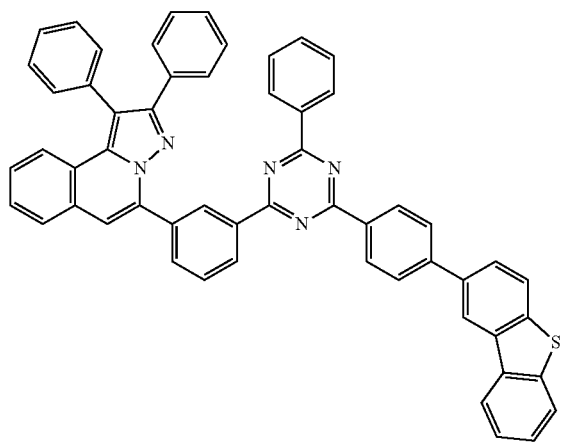
242
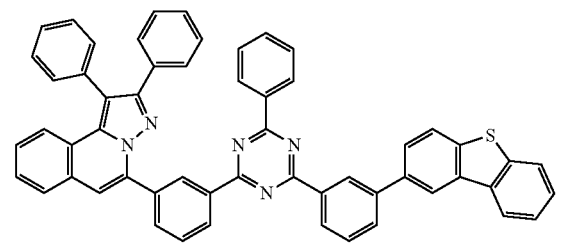
-continued
243
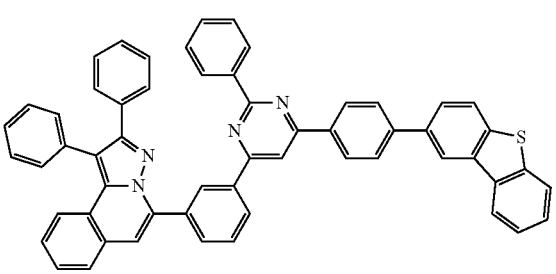
244
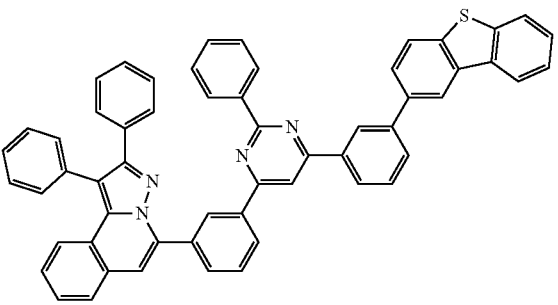
245
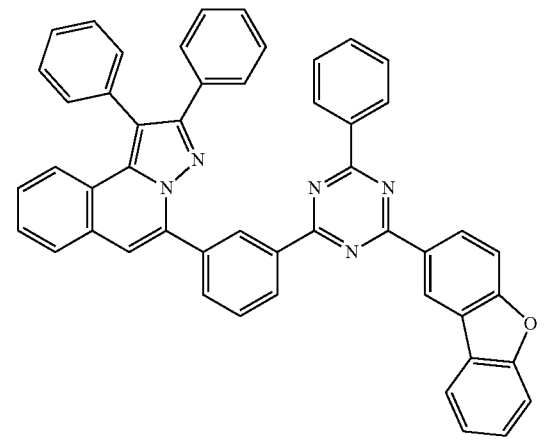
246
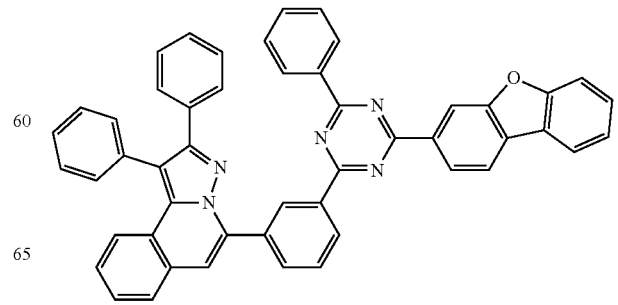

247
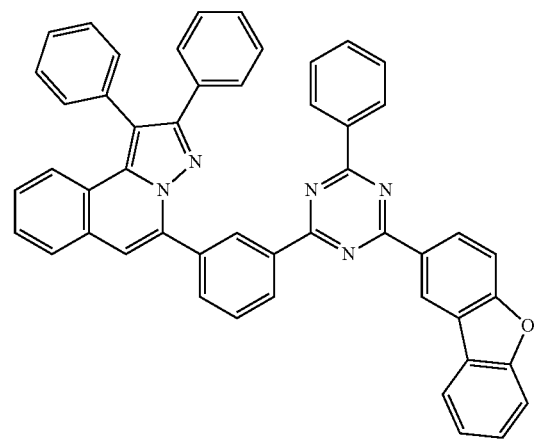
248
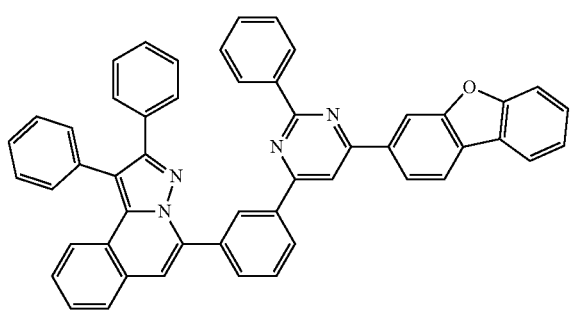
249
250
251
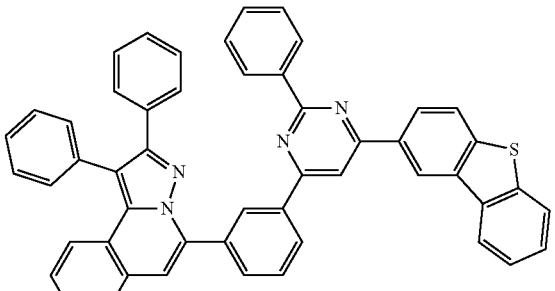
252
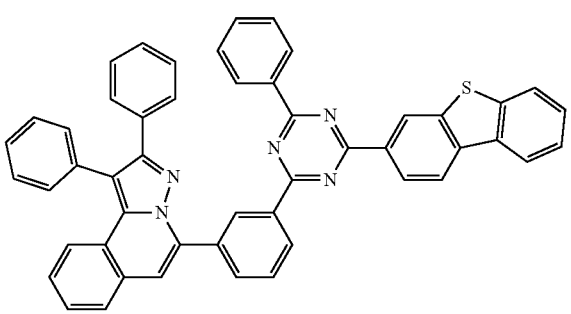
253
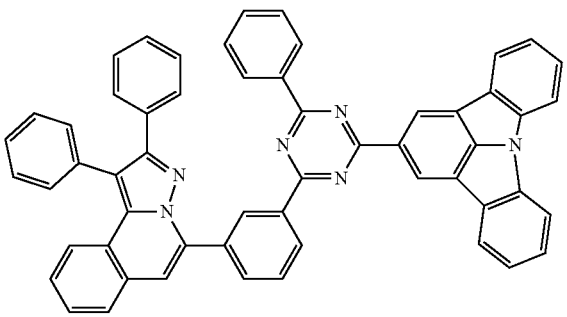
254
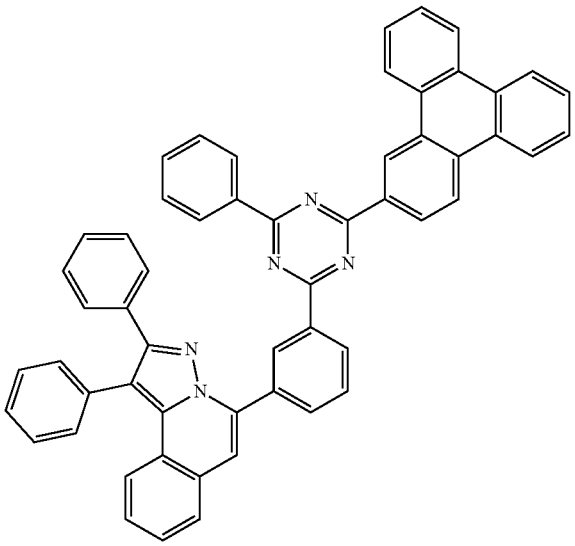

255
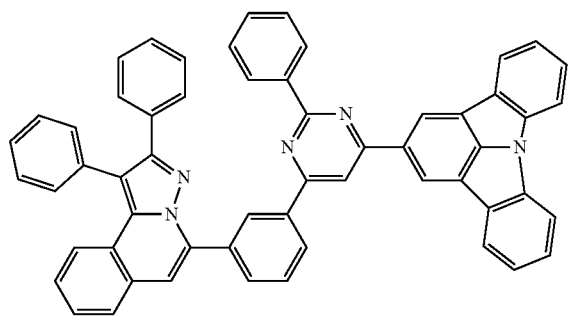
256
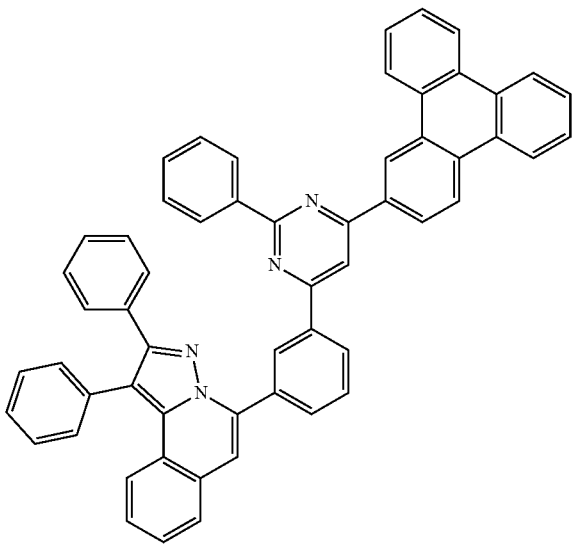
257
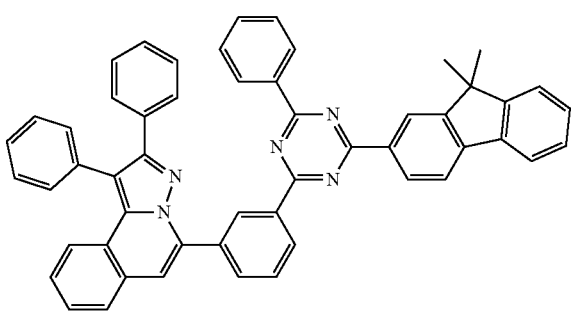
258
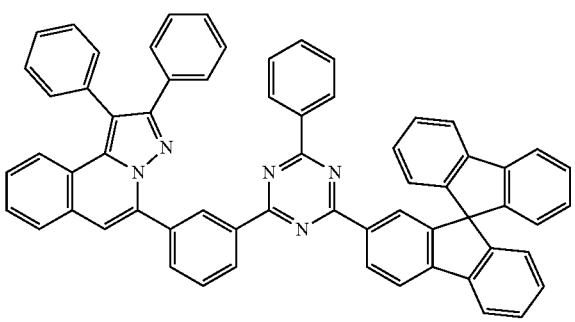
259
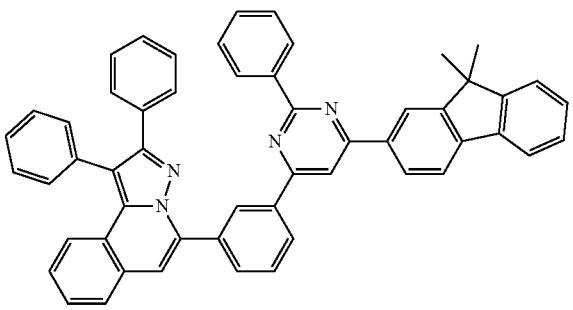
260
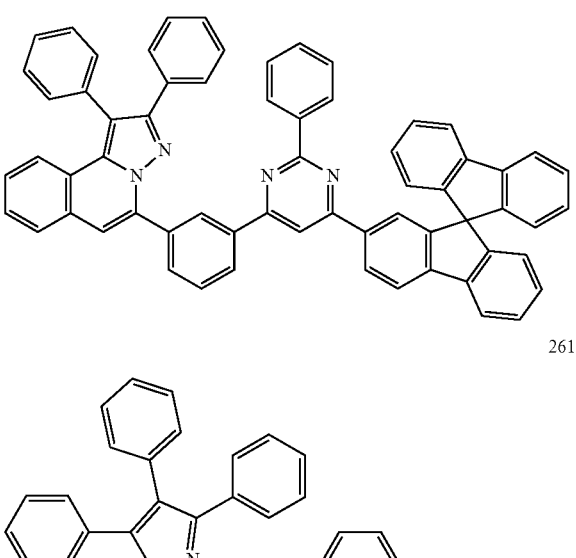
261
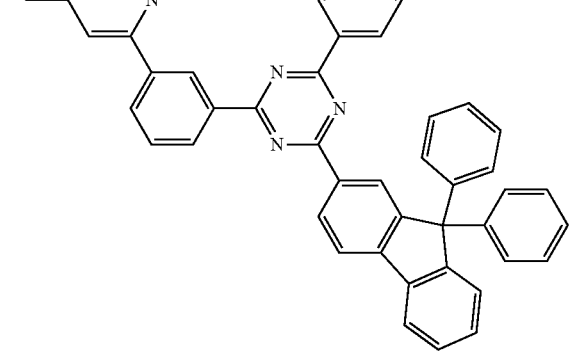
262
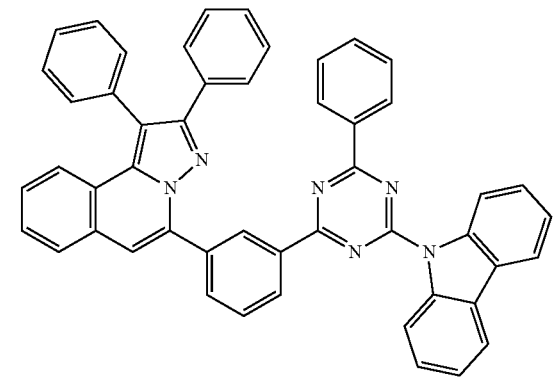

301
-continued
263
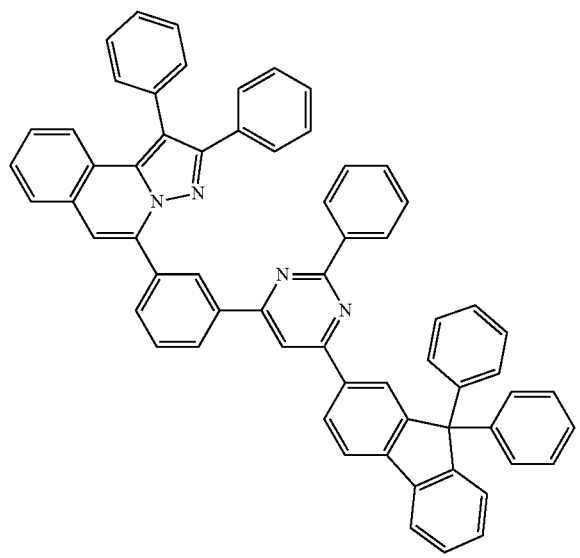
264
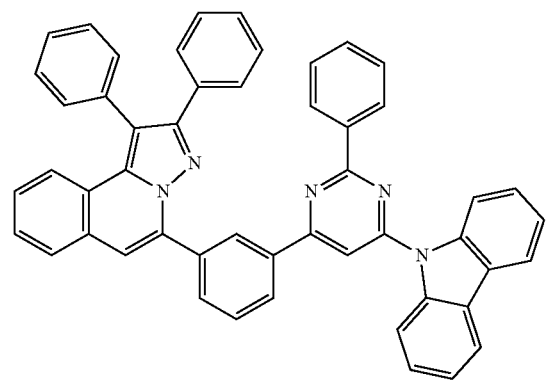
265
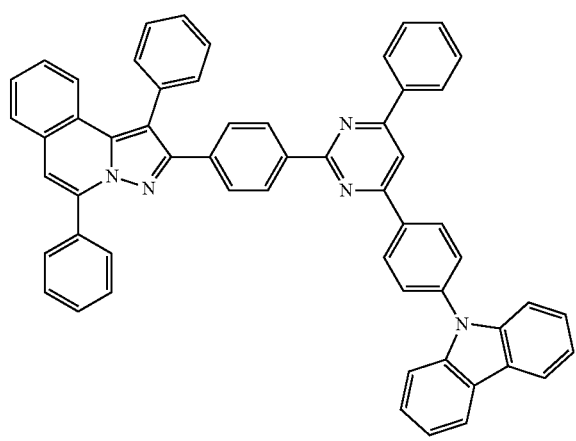
302
-continued
266
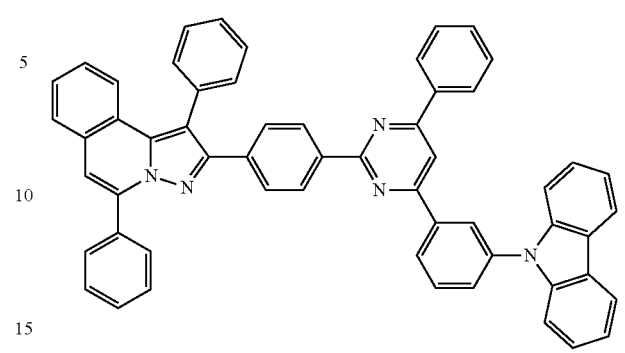
267
268
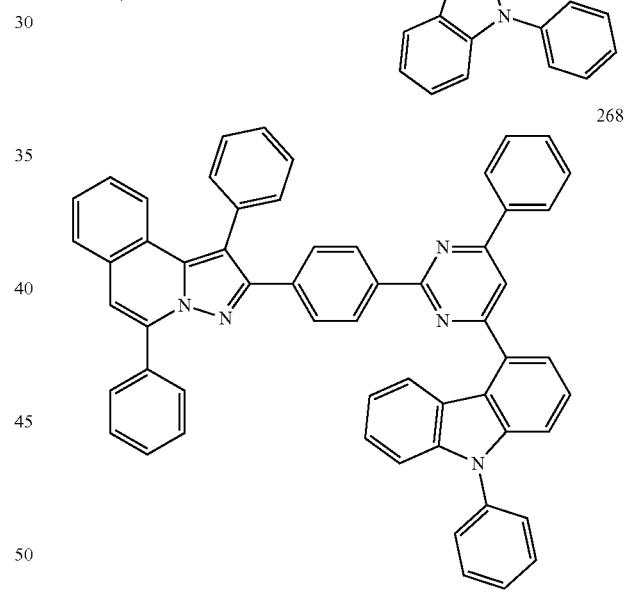
269
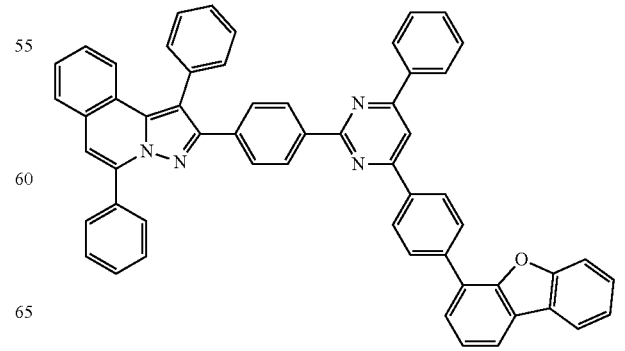

270
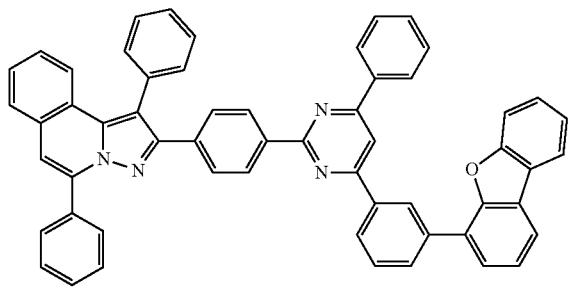
271
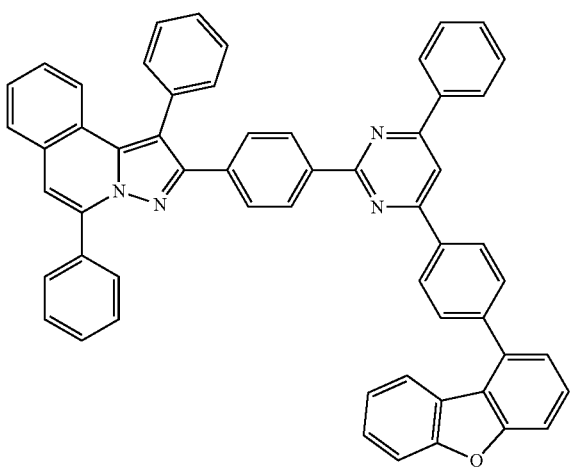
272
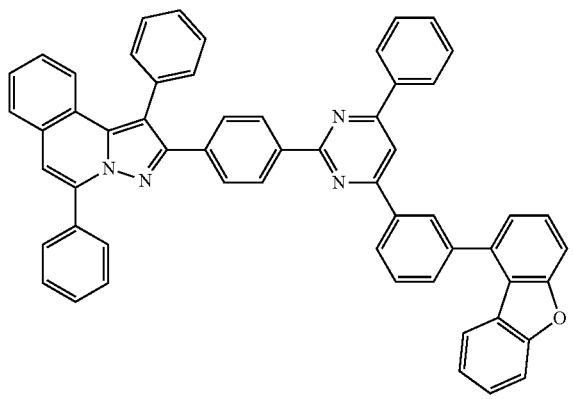
273
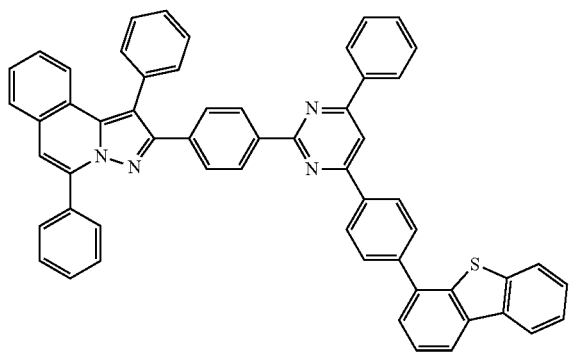
274
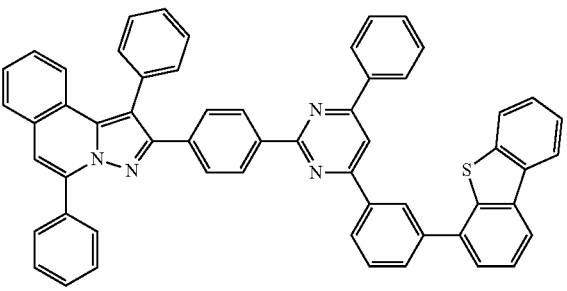
275
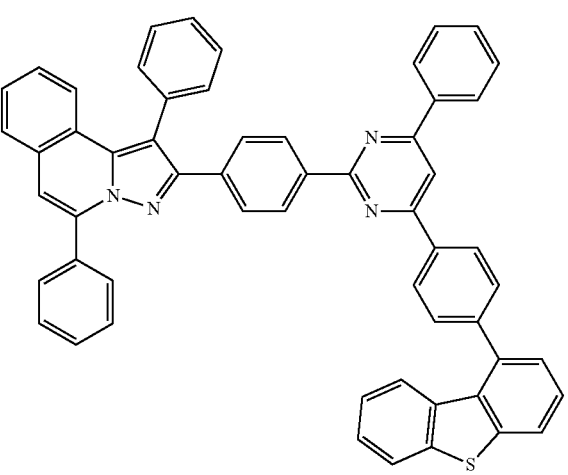
276
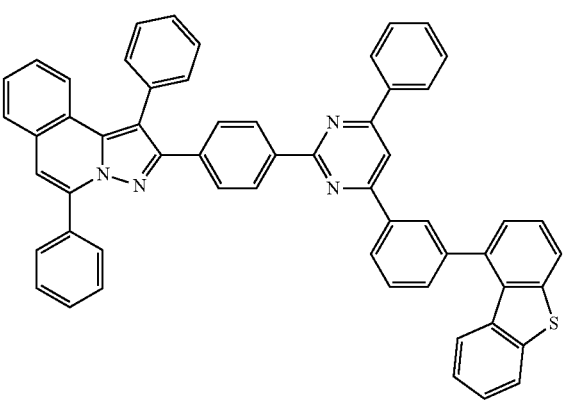
277
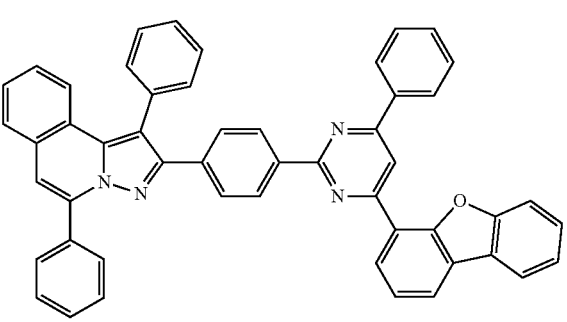

278
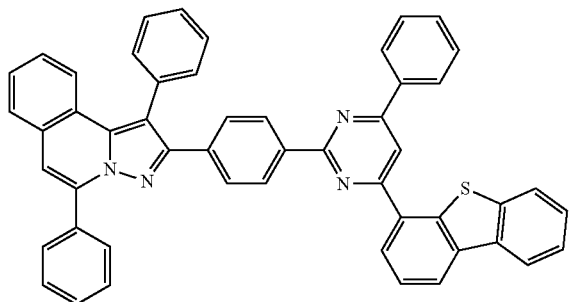
279
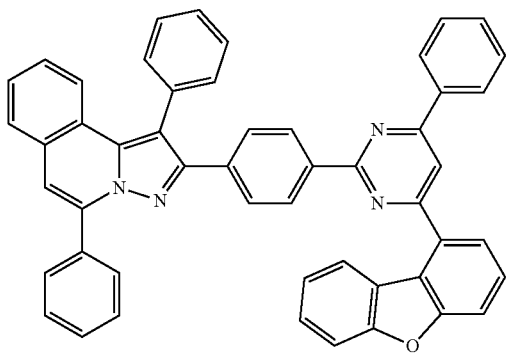
280
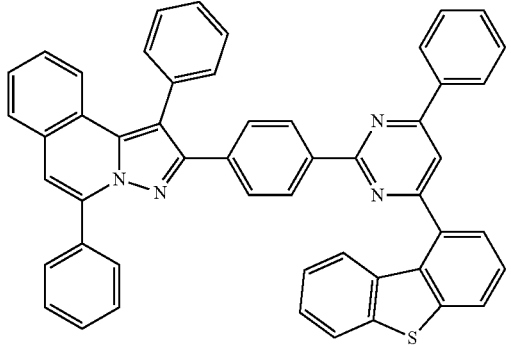
281
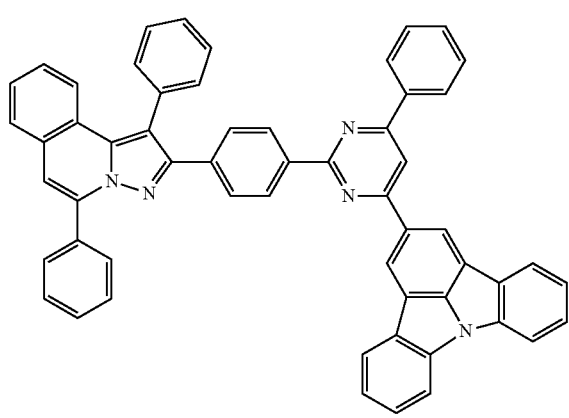
282
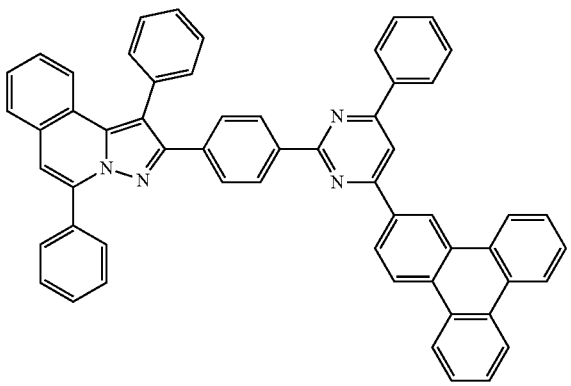
238
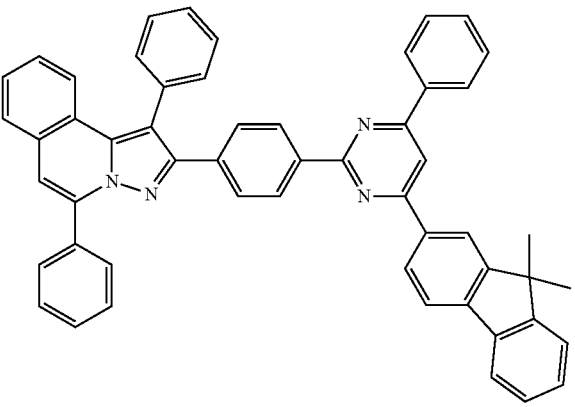
284
285
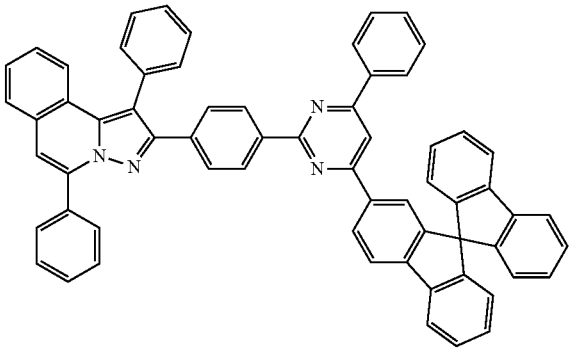

286
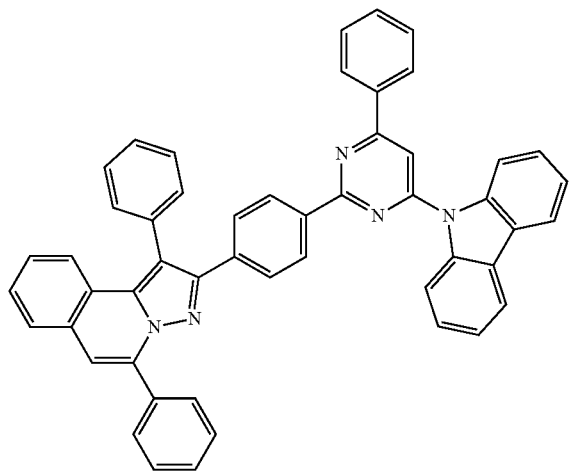
287
289
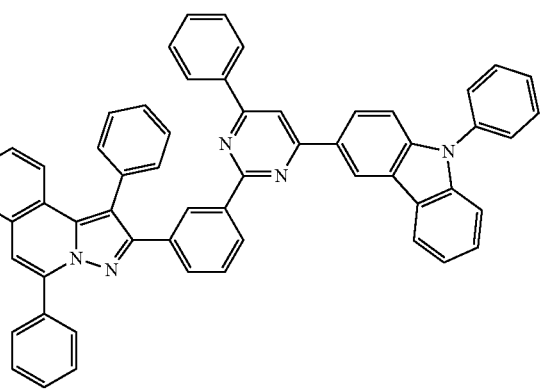
290
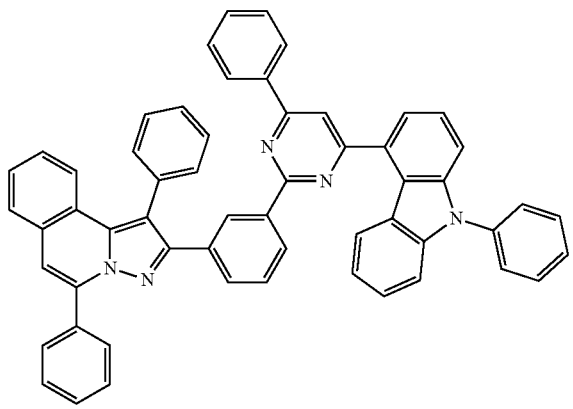
291
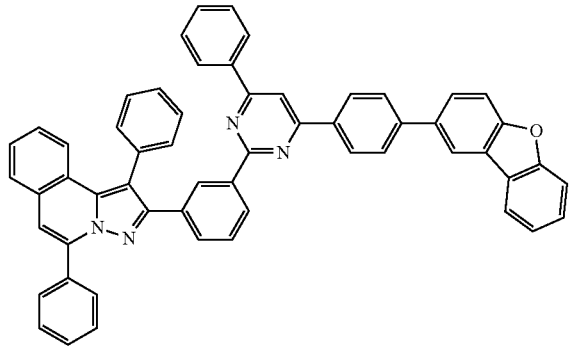
288
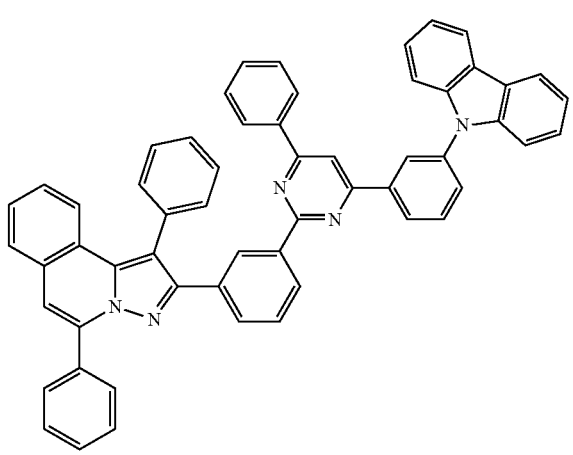
292

309
-continued
293
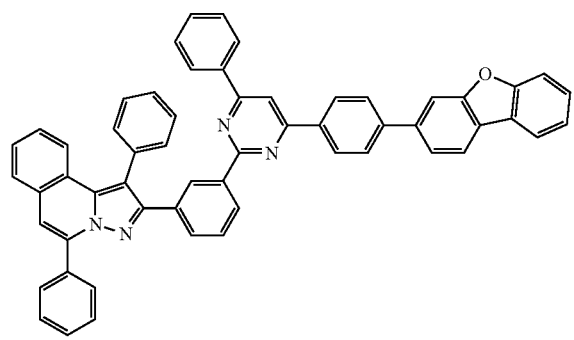
294
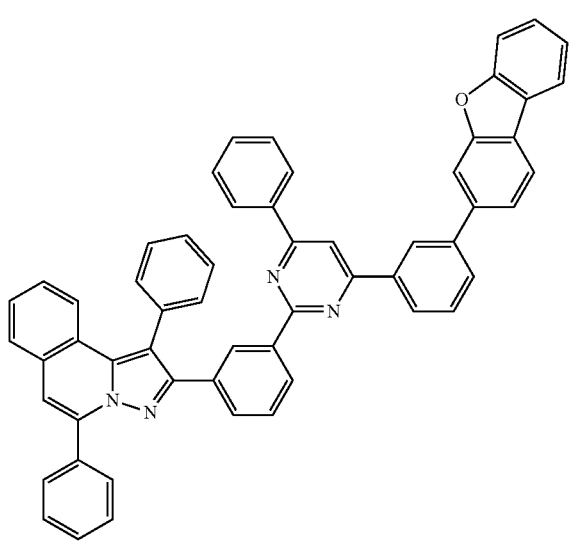
295
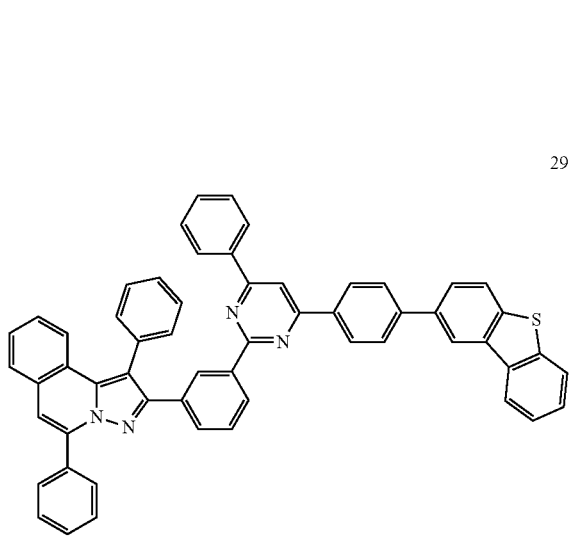
310
-continued
296
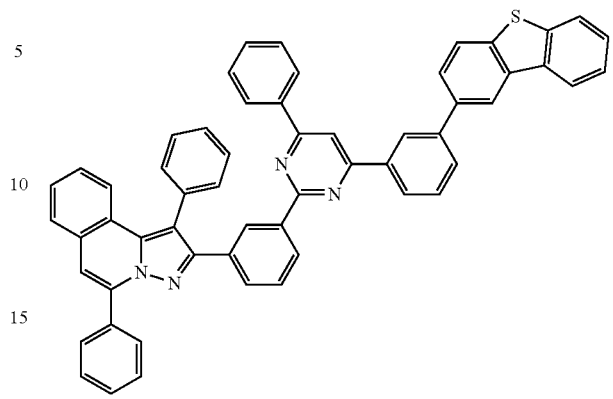
297
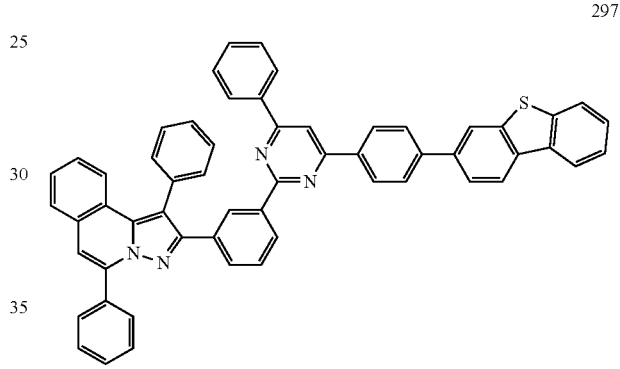
298
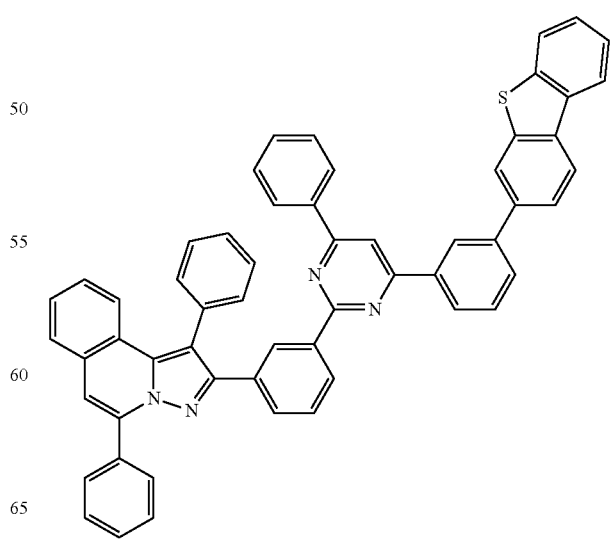

299
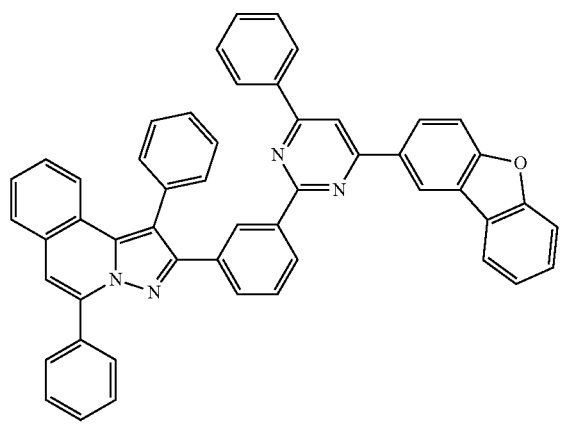
300
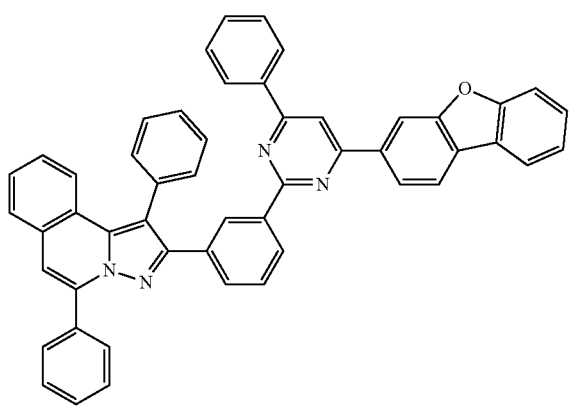
301
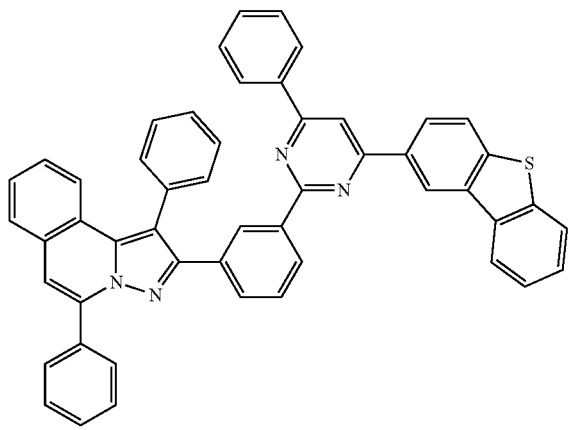
302
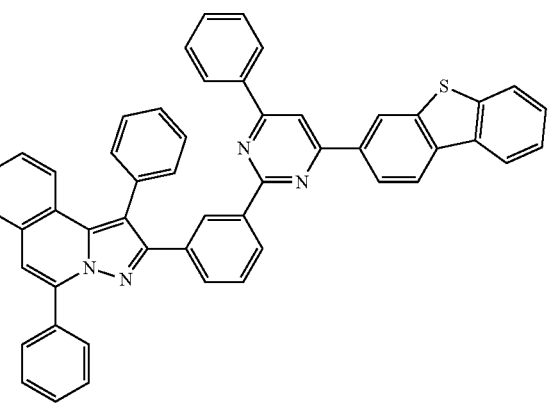
303
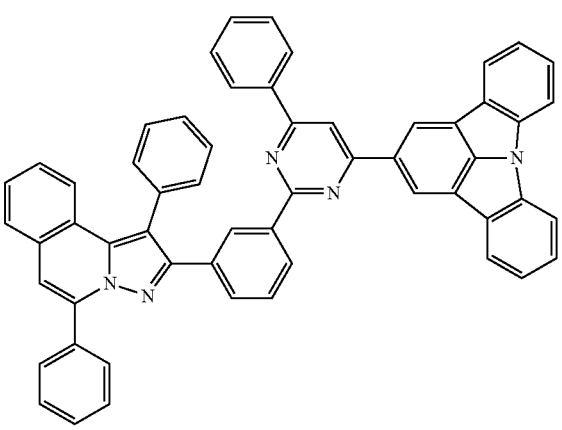
304
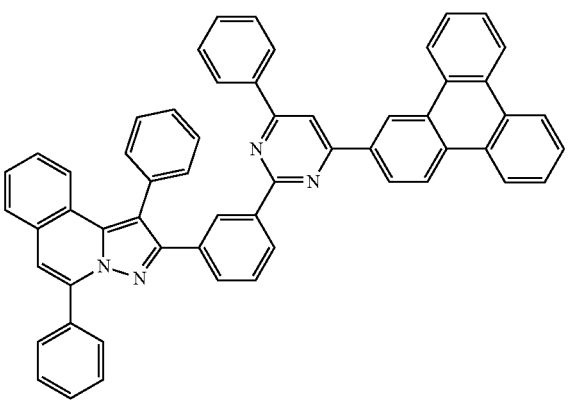

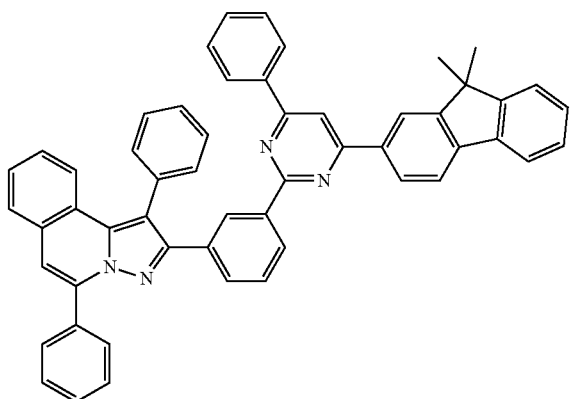
305
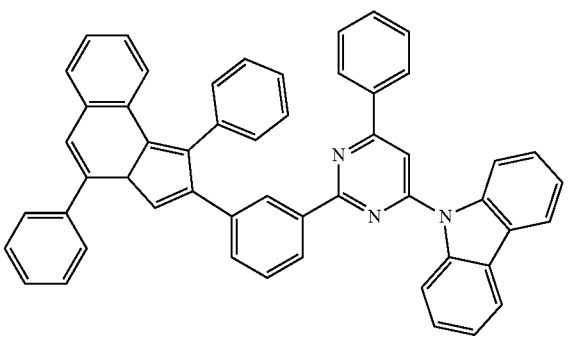
308
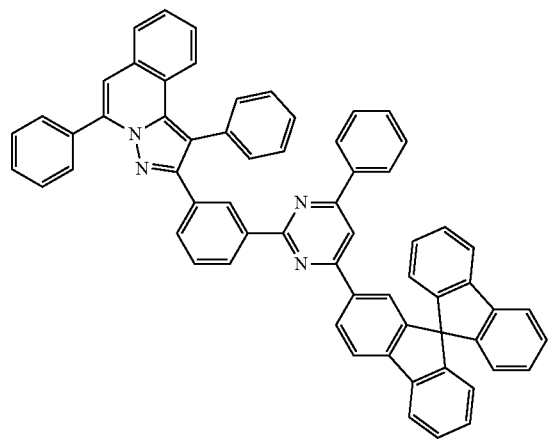
306
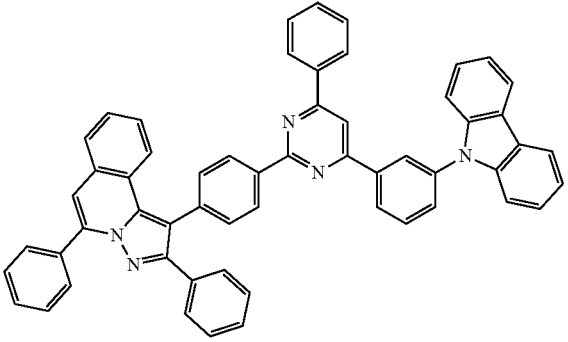
309
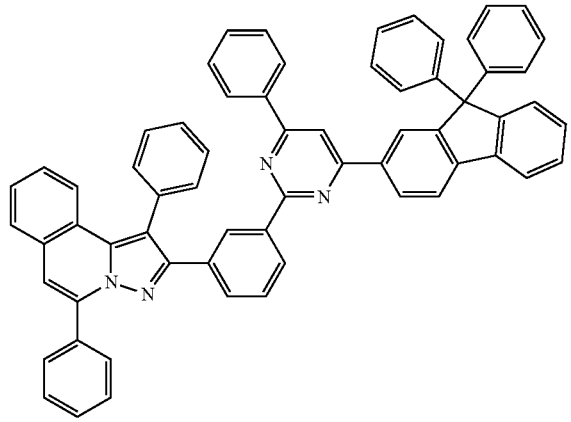
307
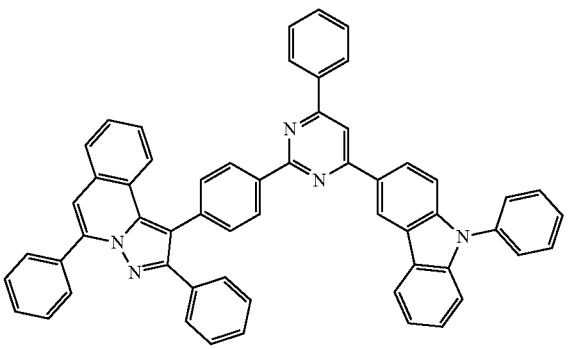
310
311

312
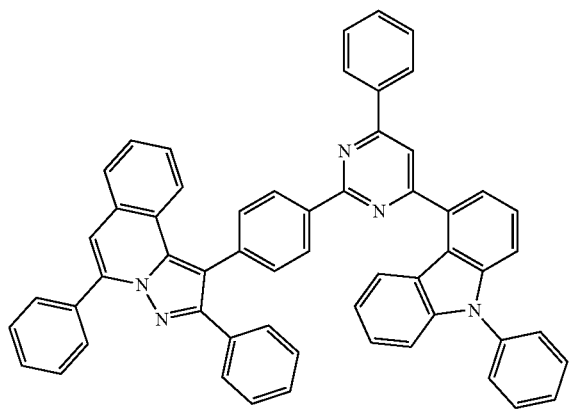
313
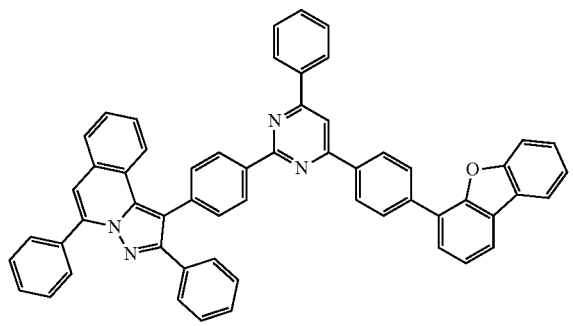
314
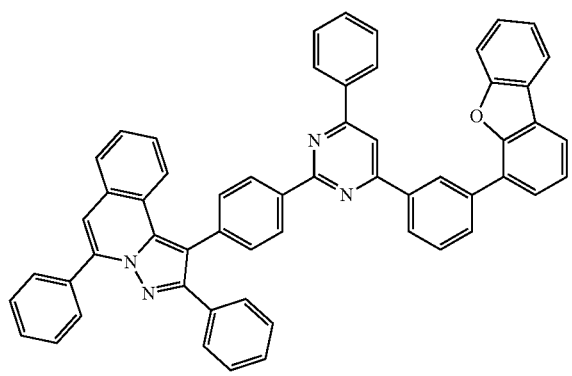
315
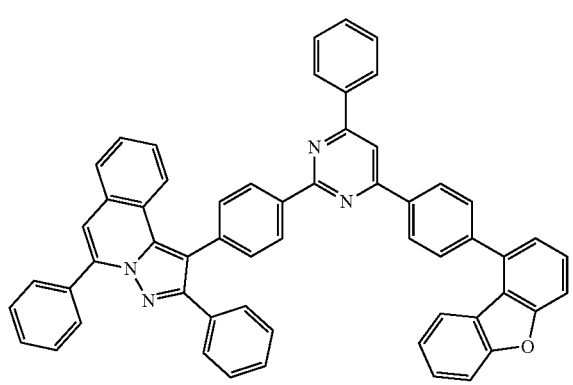
316
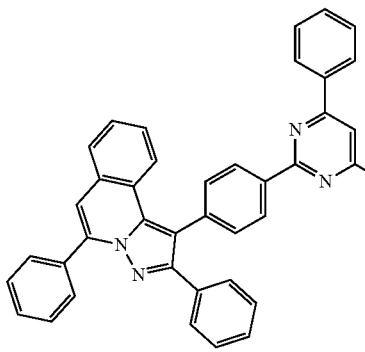
317
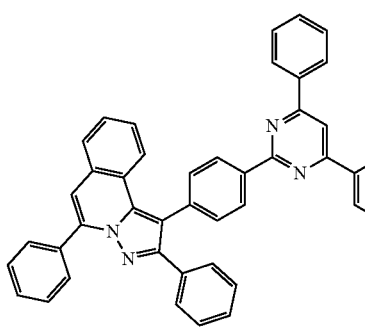
318
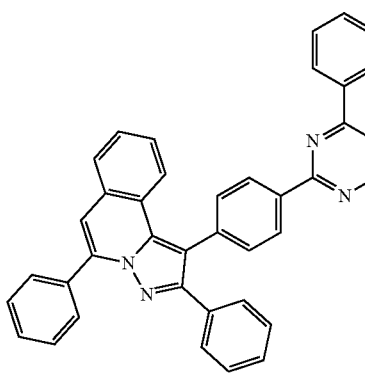
319
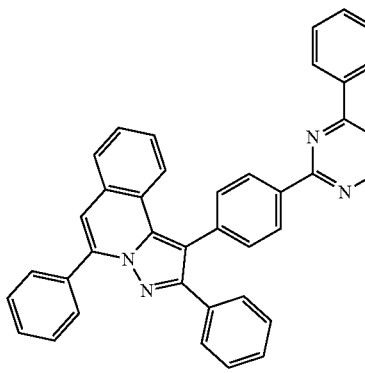

320
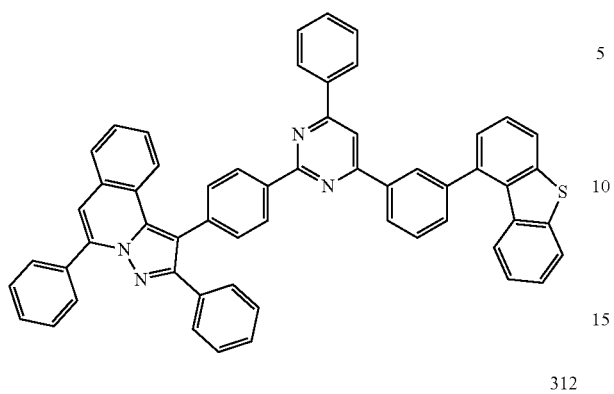
312
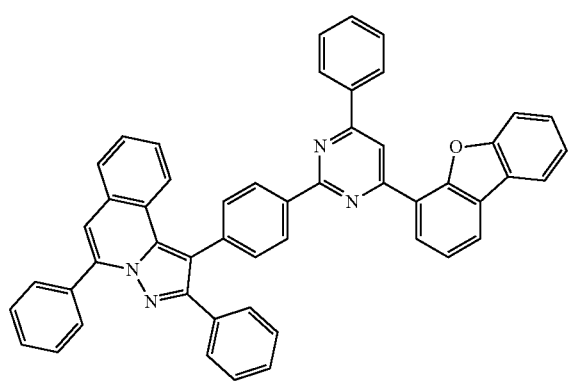
322
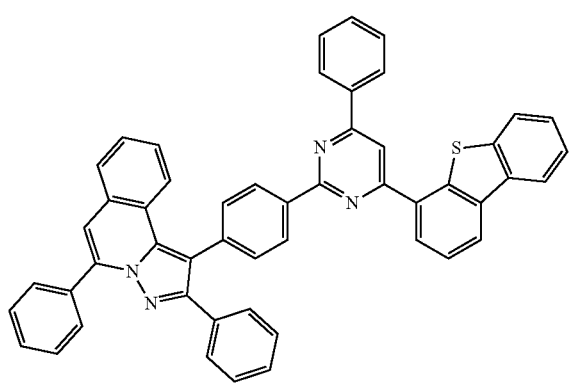
323
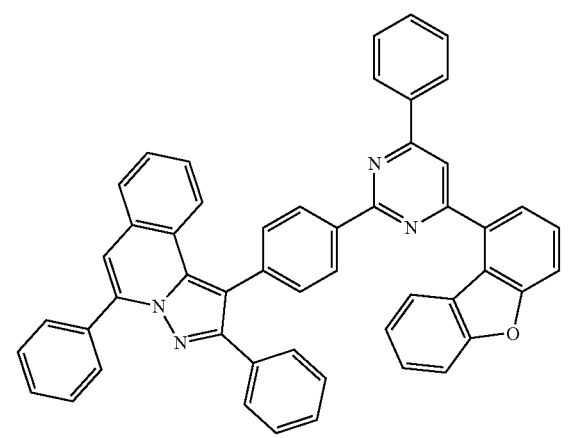
324
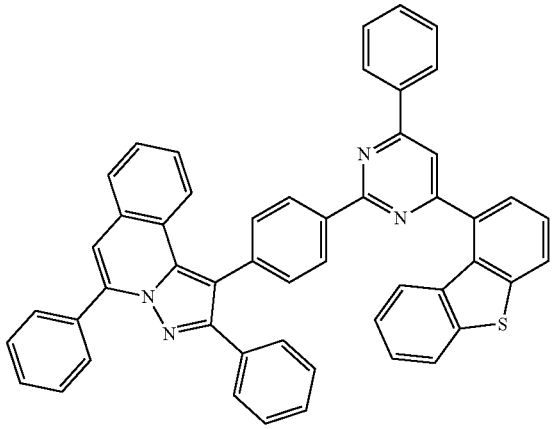
325
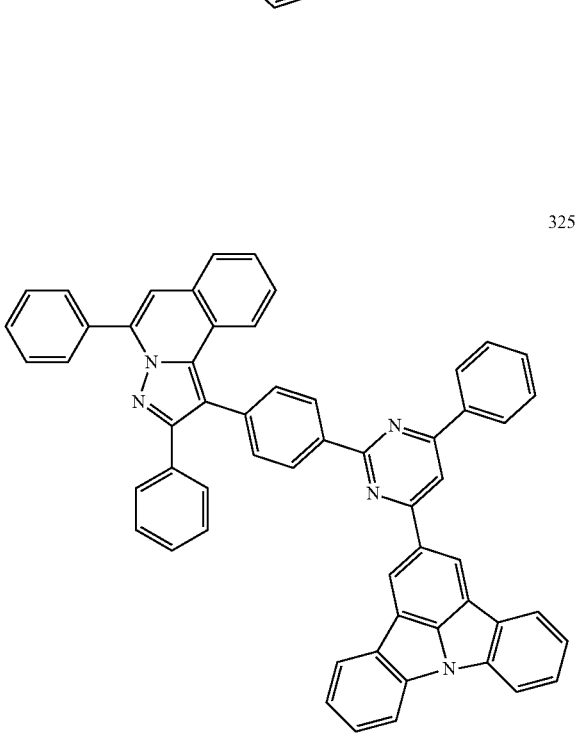
326
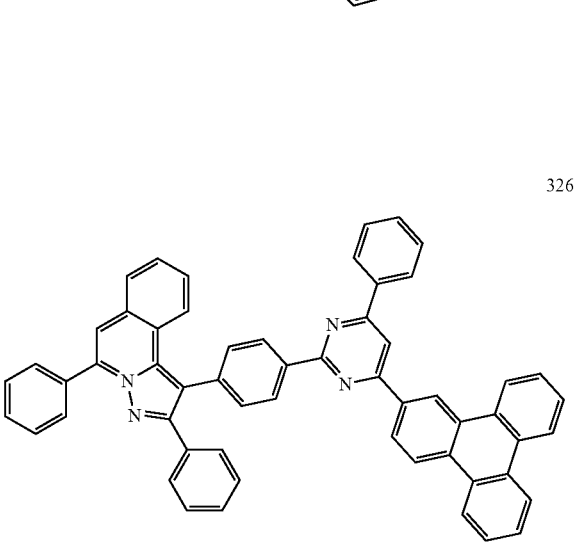

-continued
327
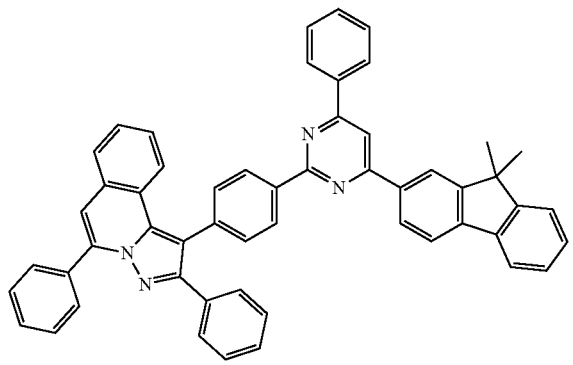
328
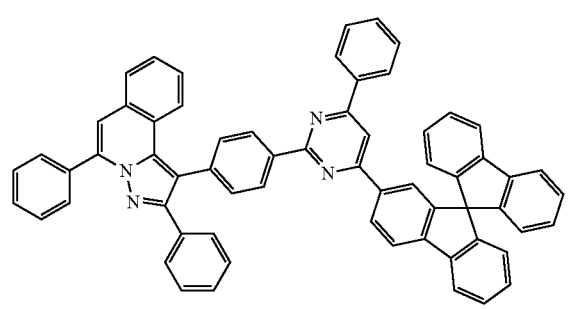
329
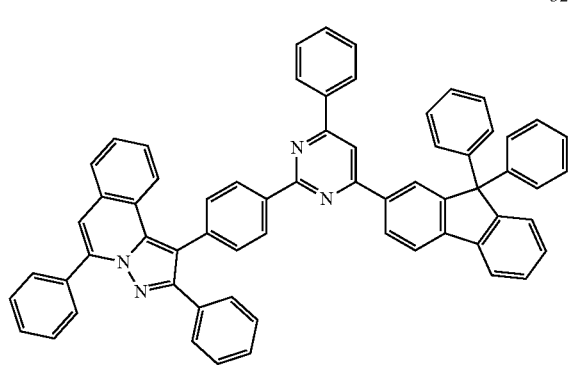
330
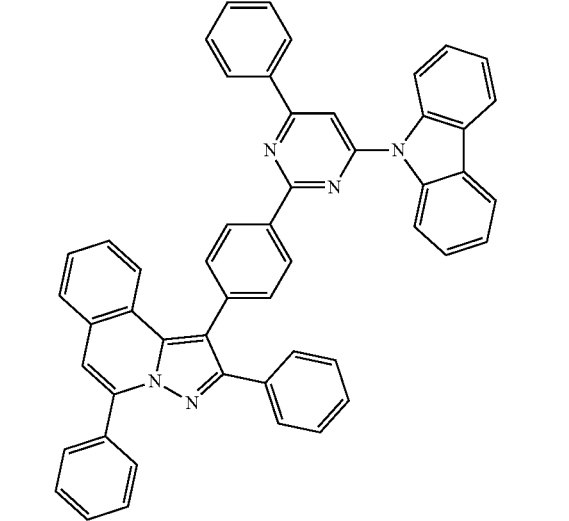
-continued
331
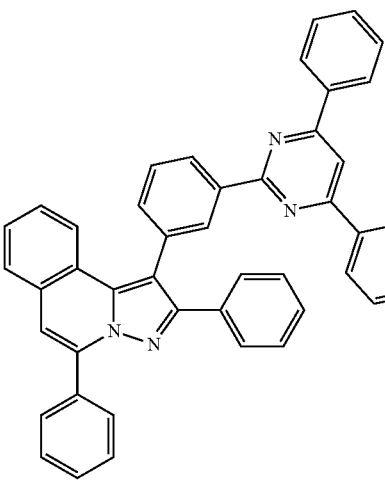
332
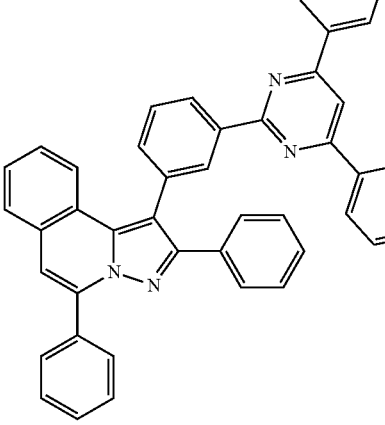
333
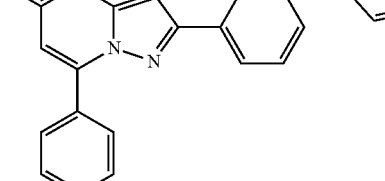

334
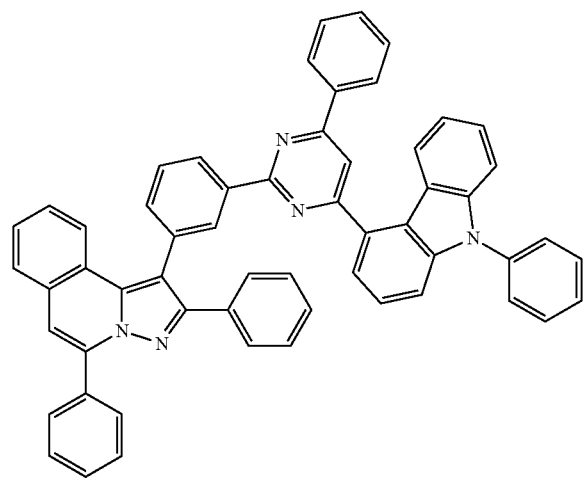
335
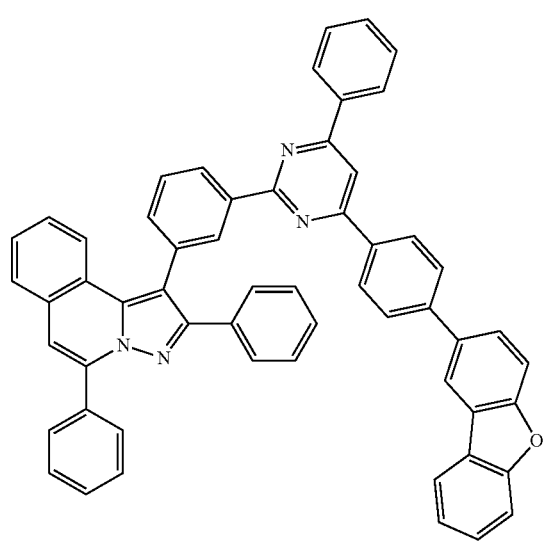
336
337
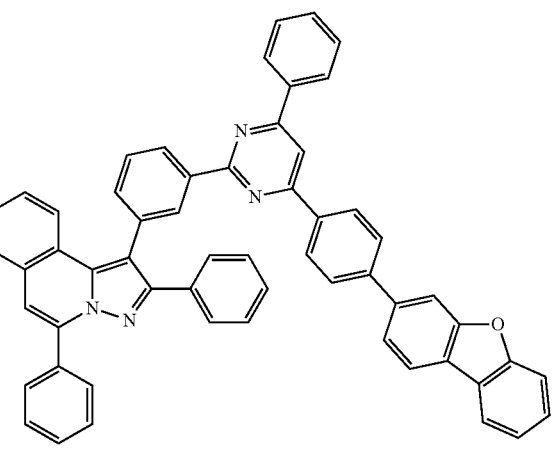
338
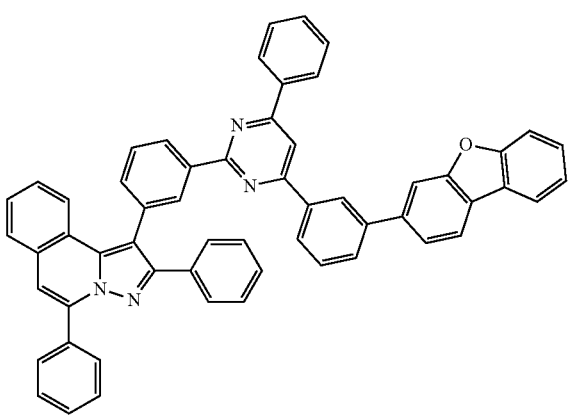
339
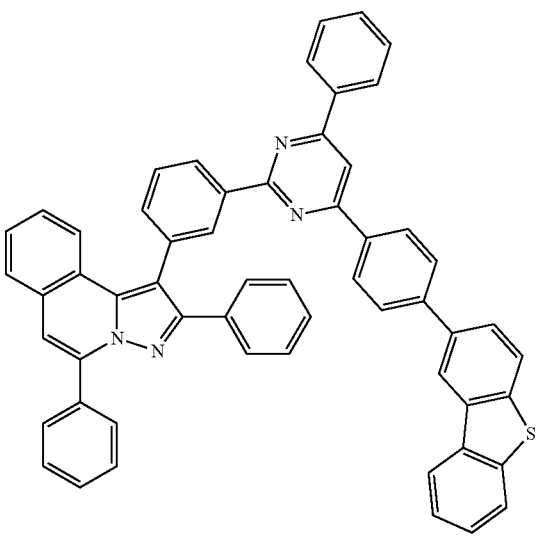

340
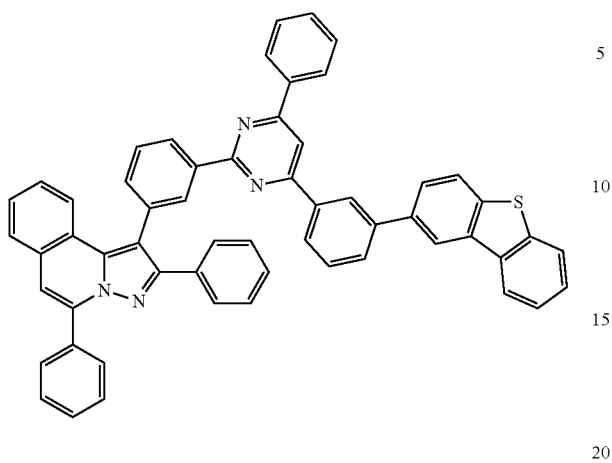
343
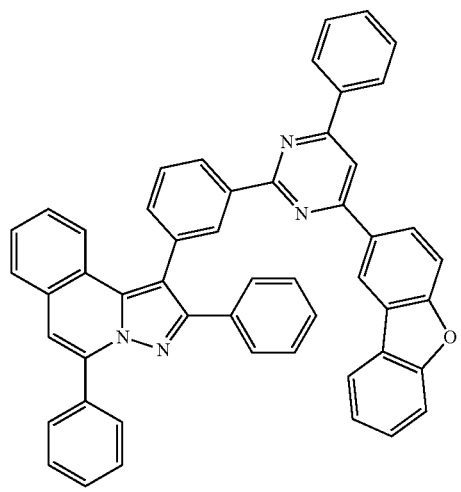
341
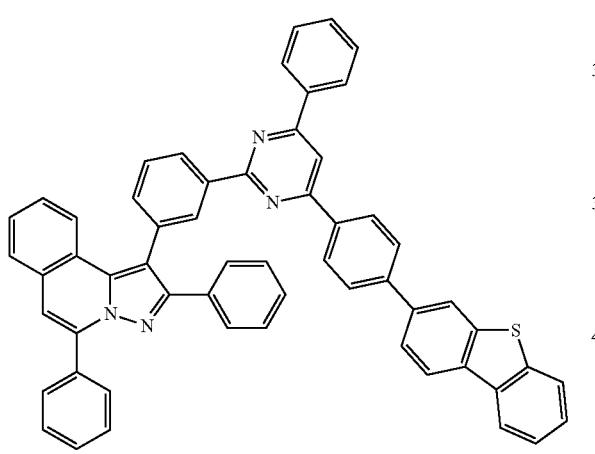
344
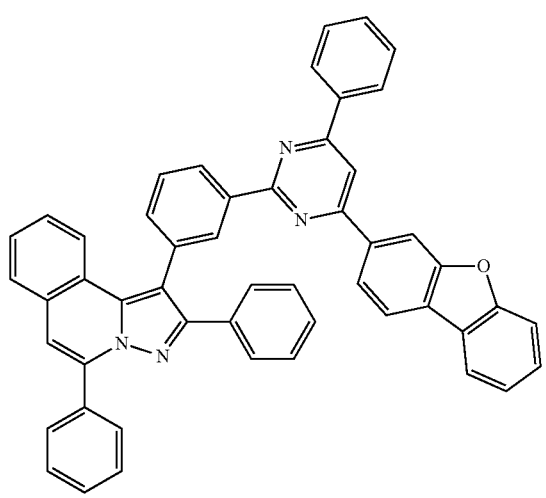
342
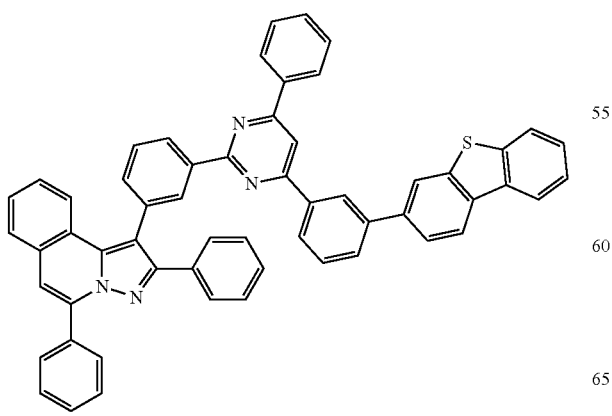
345
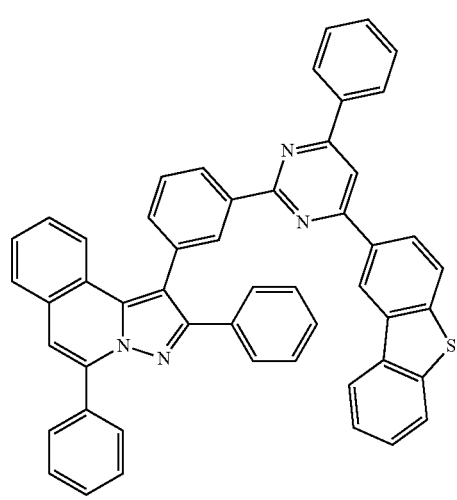

346
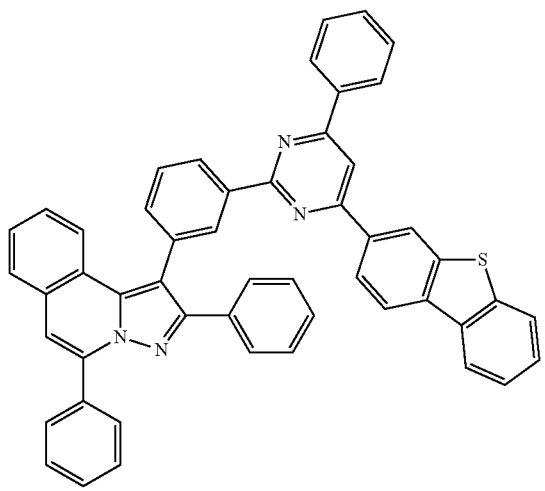
347
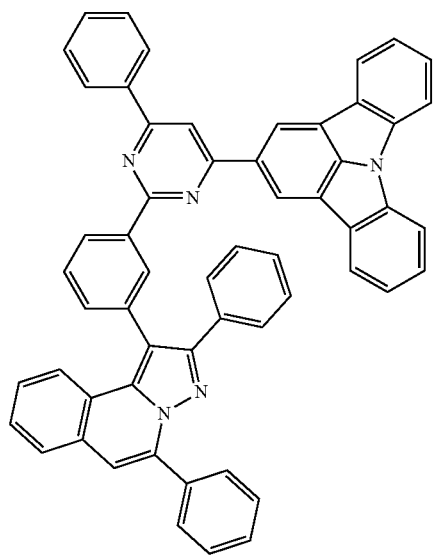
348
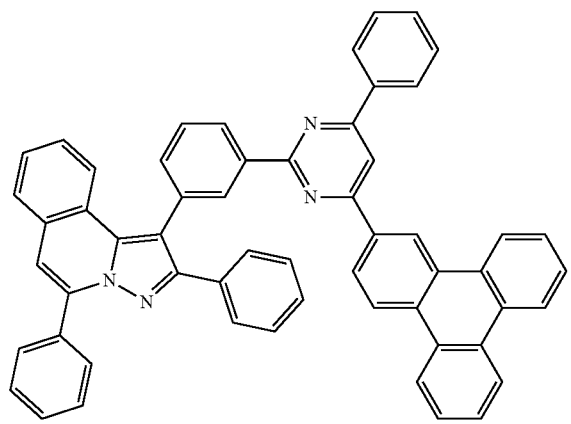
349
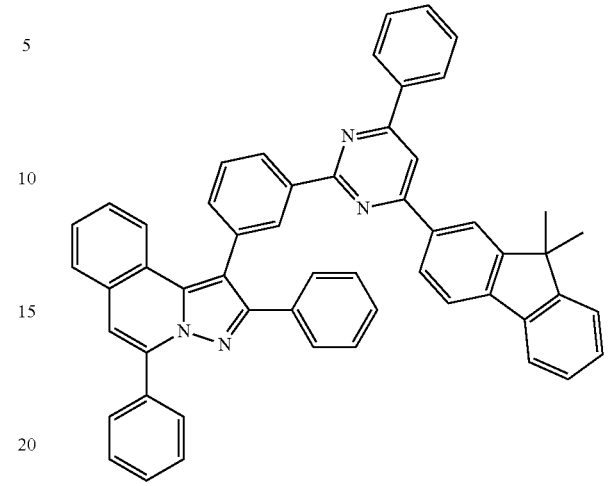
350
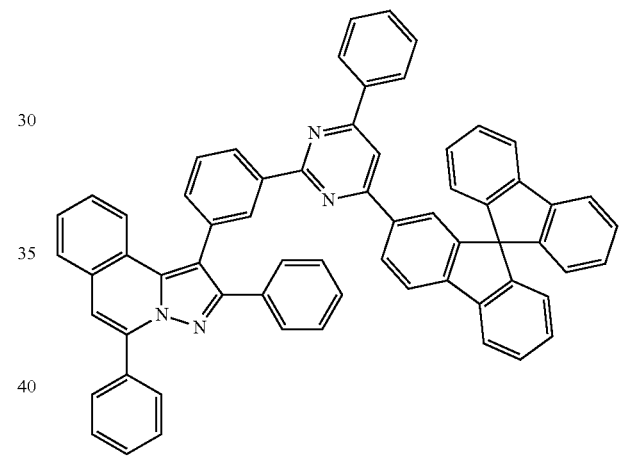
351
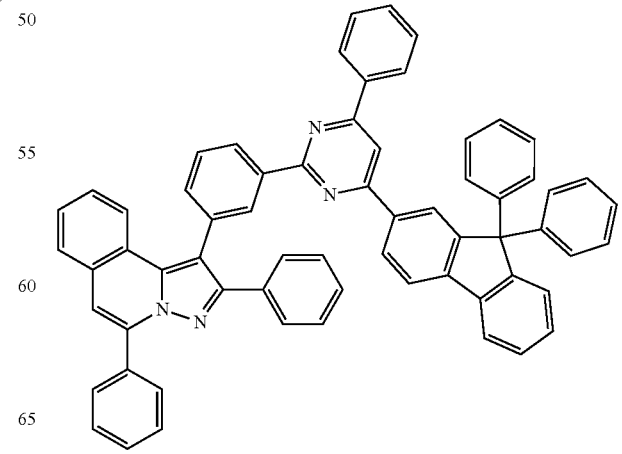

327
-continued
352
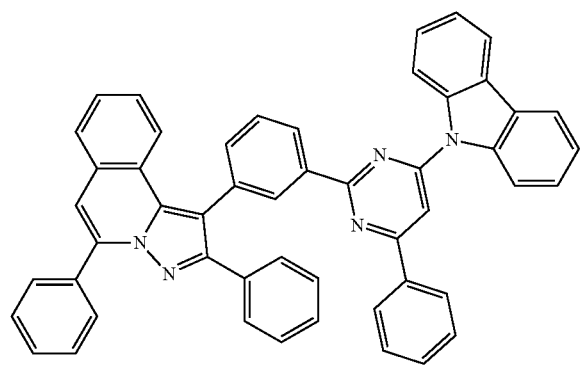
353
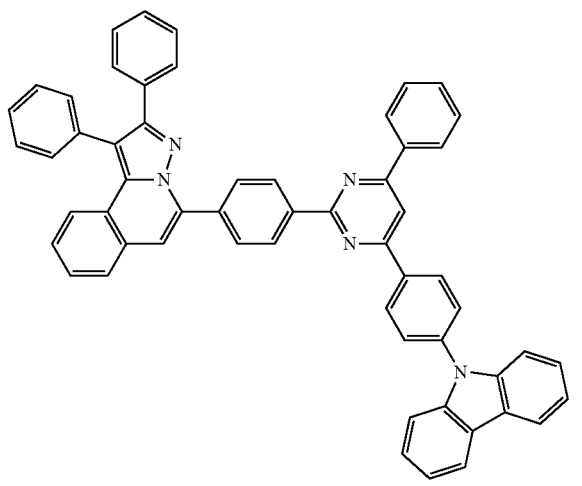
354
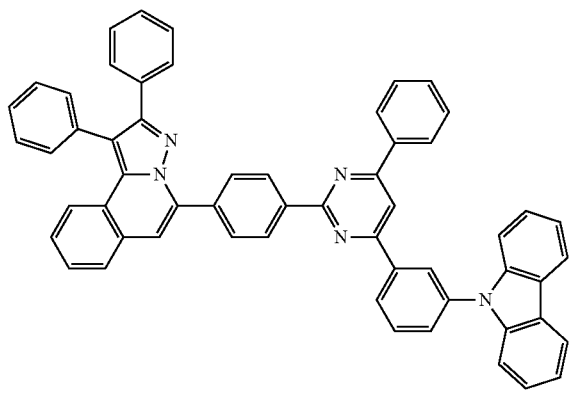
328
-continued
355
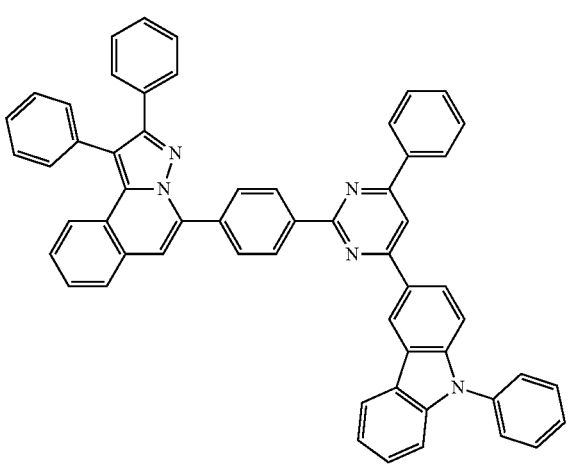
356
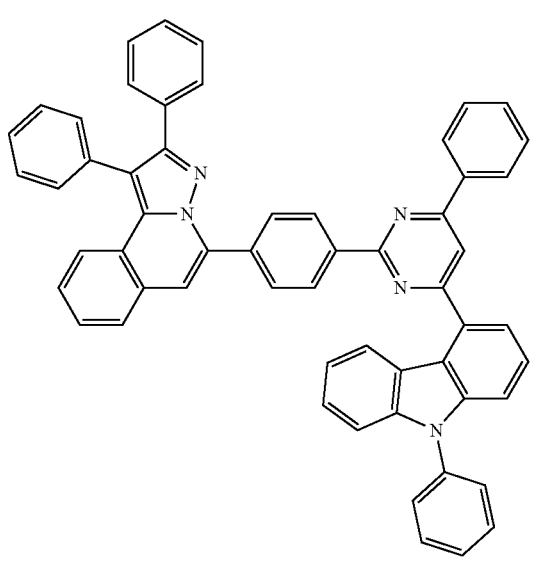
357
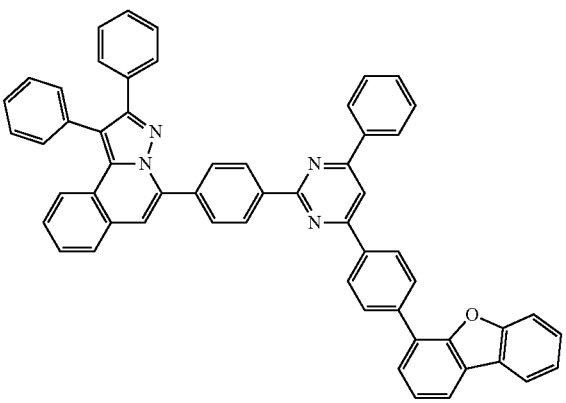

329
-continued
358
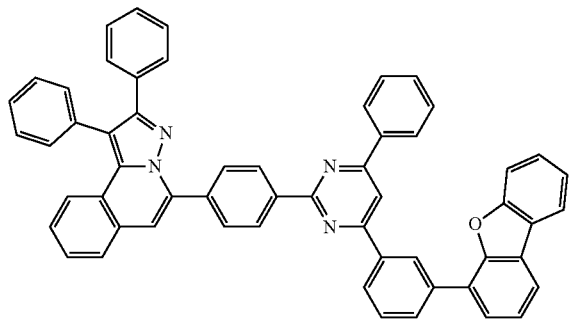
359
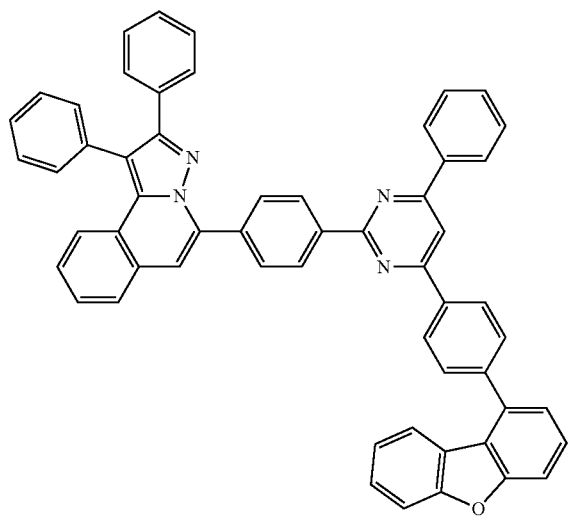
360
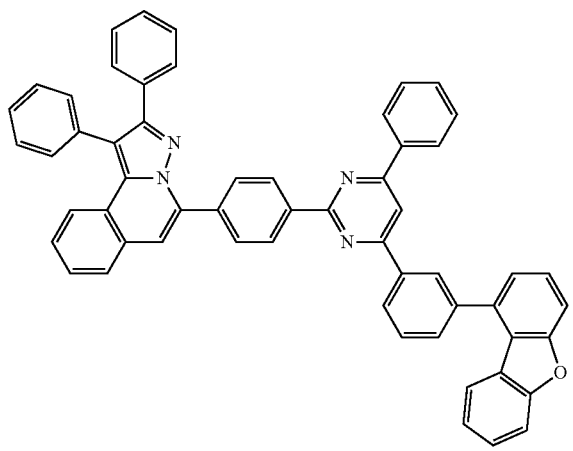
330
-continued
361
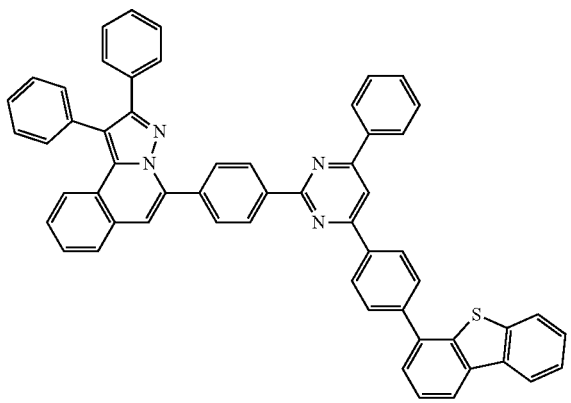
362
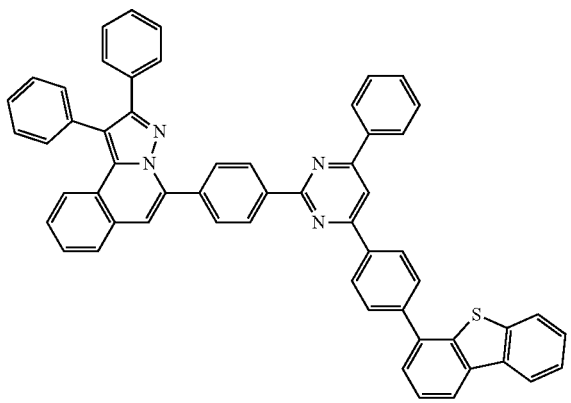
363
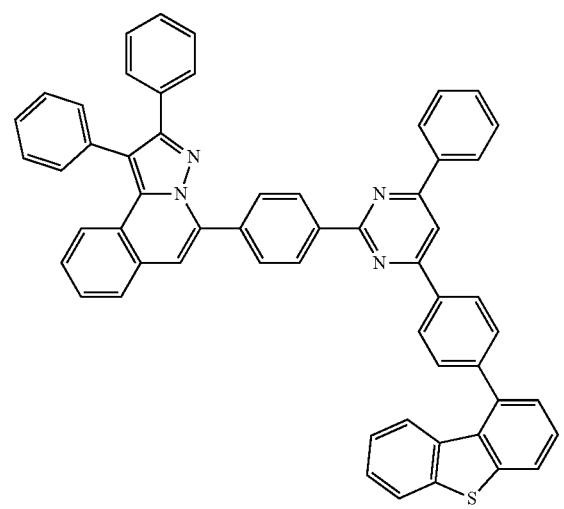

331
-continued
364
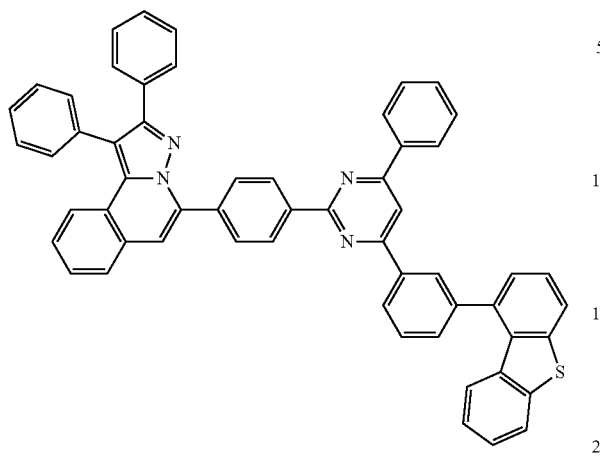
365
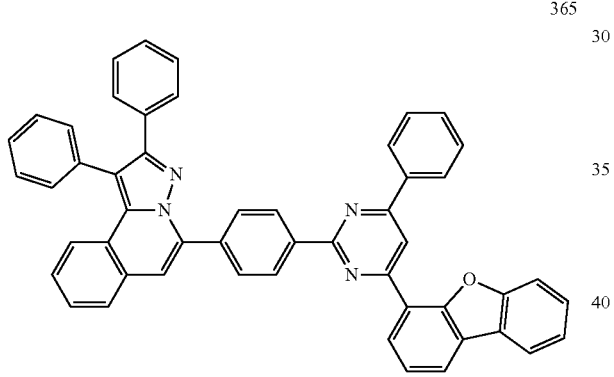
366
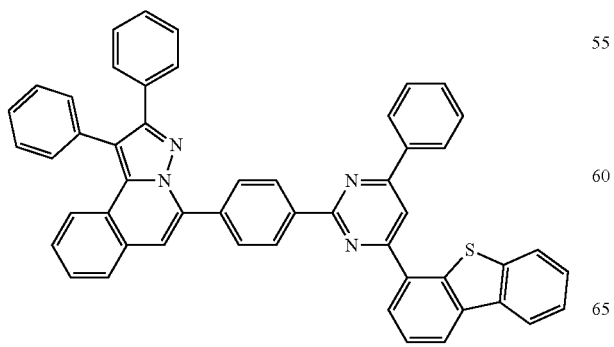
332
-continued
367
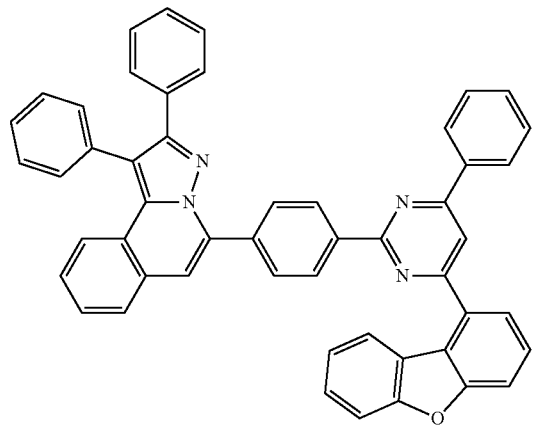
368
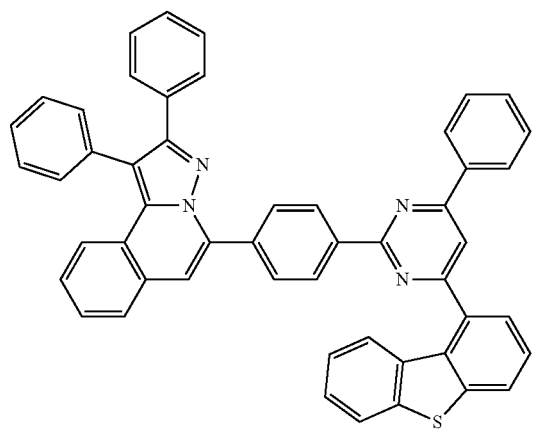
369
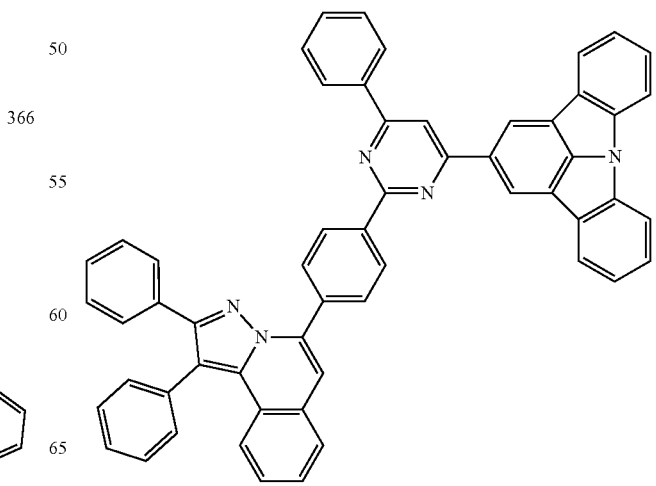

370
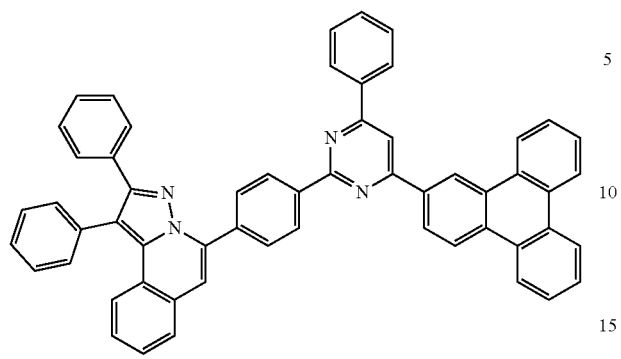
371
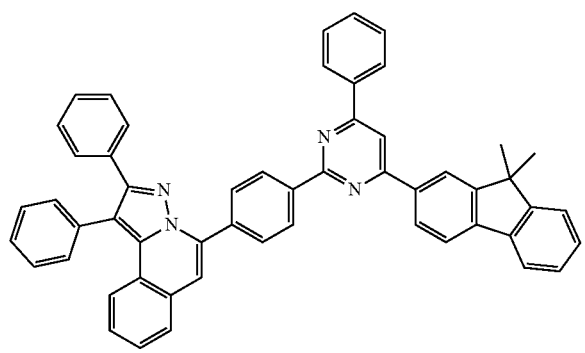
372
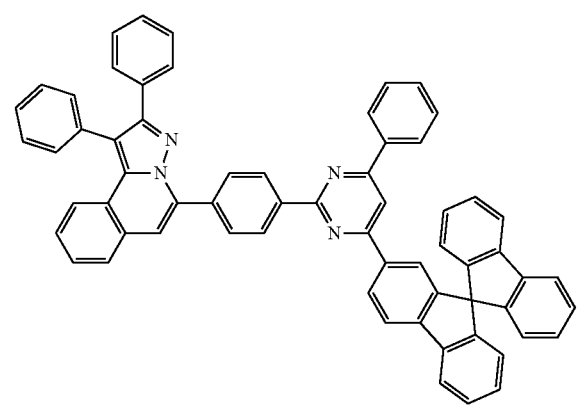
373
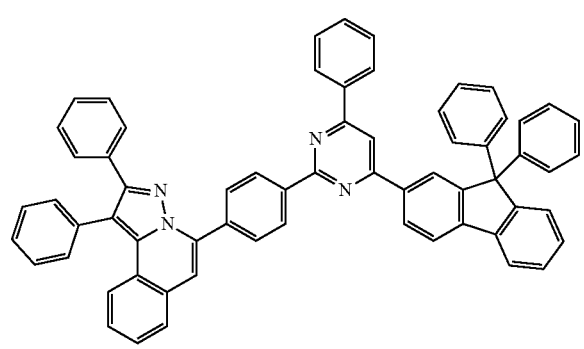
374
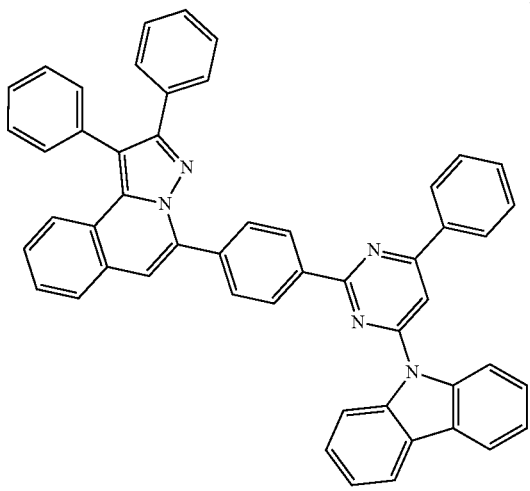
375
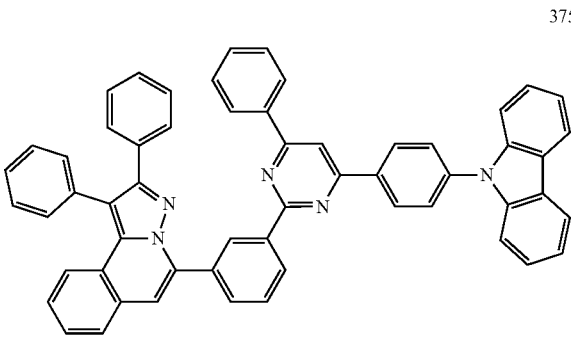
376
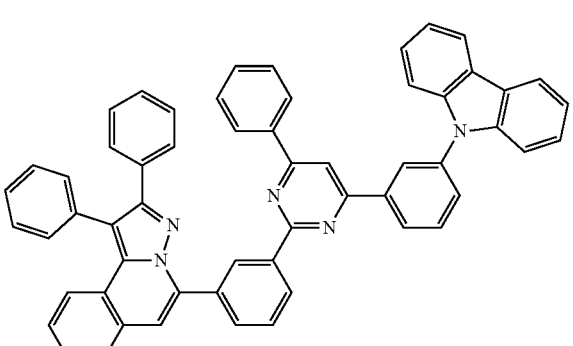
377
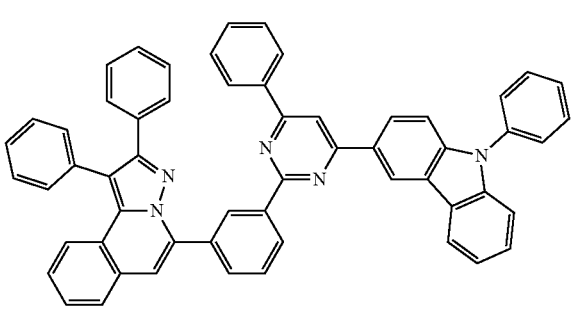

378
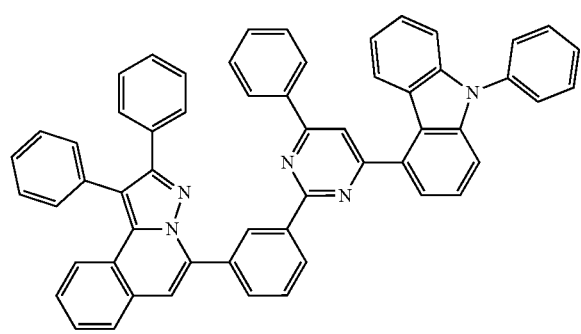
379
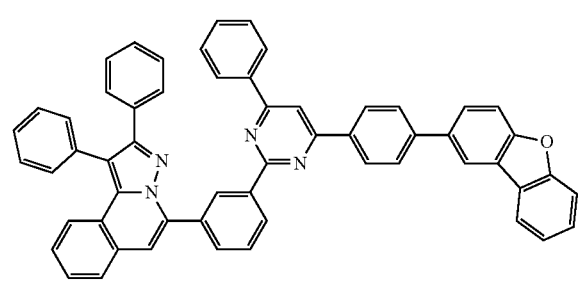
380
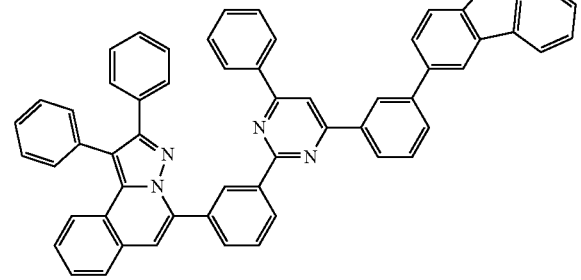
381
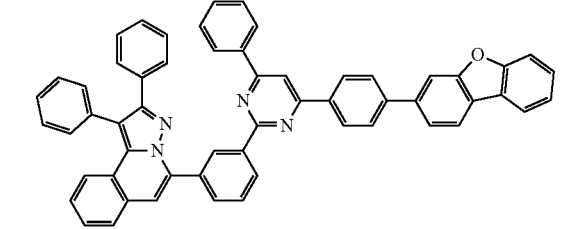
382
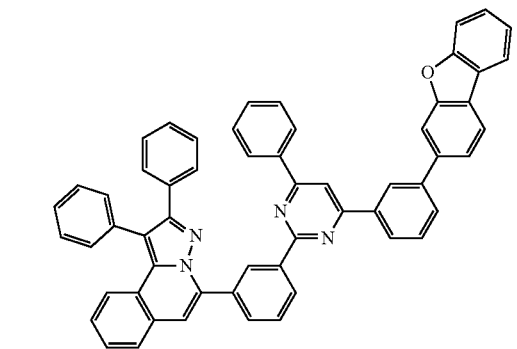
383
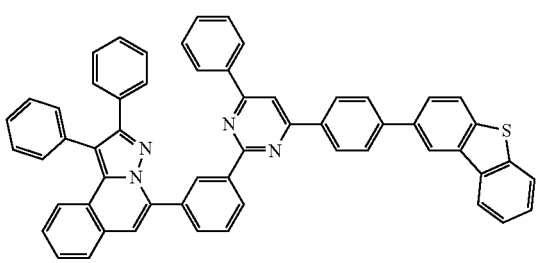
384
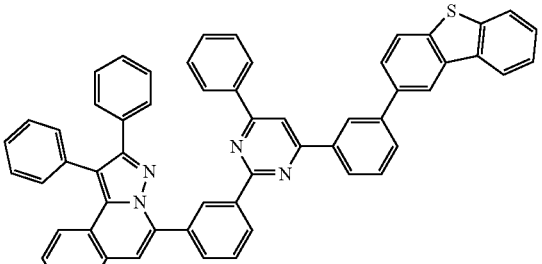
385
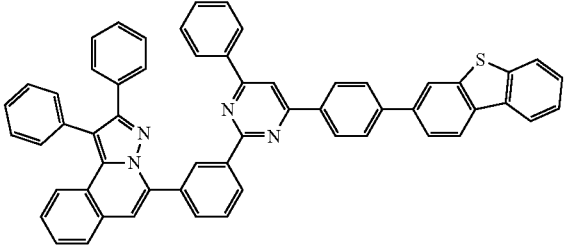
386
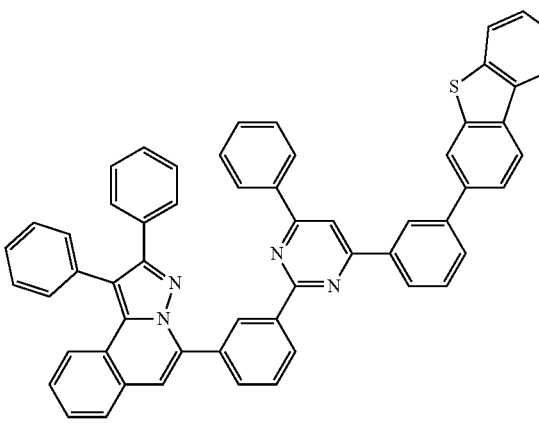
387
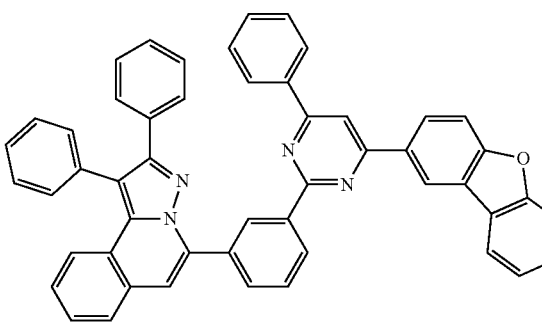

388
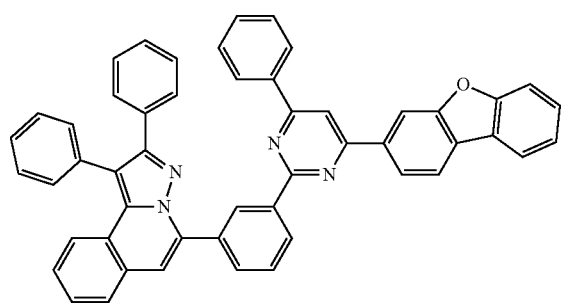
389
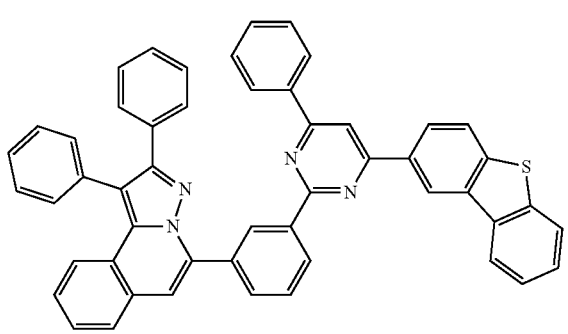
390
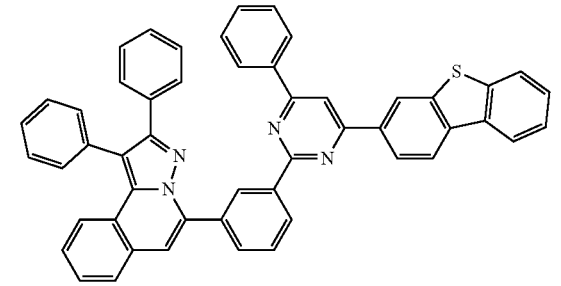
391
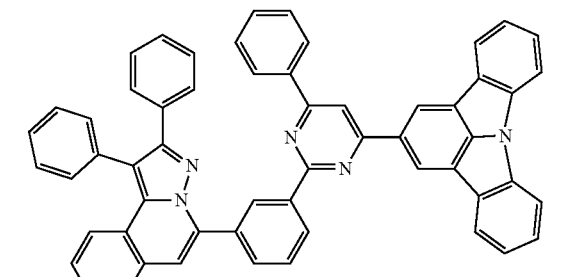
392
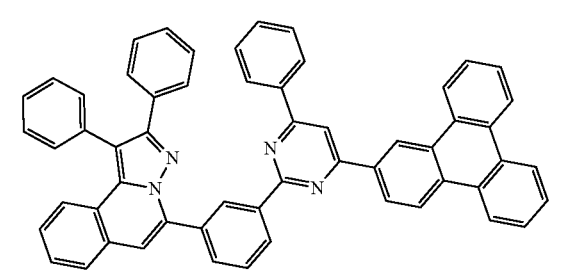
393
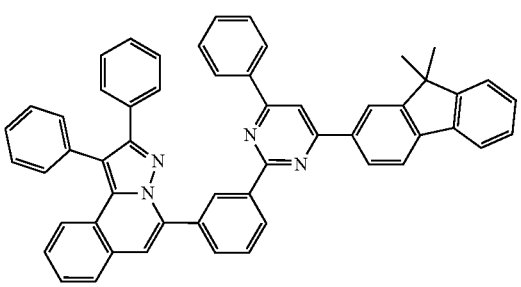
394
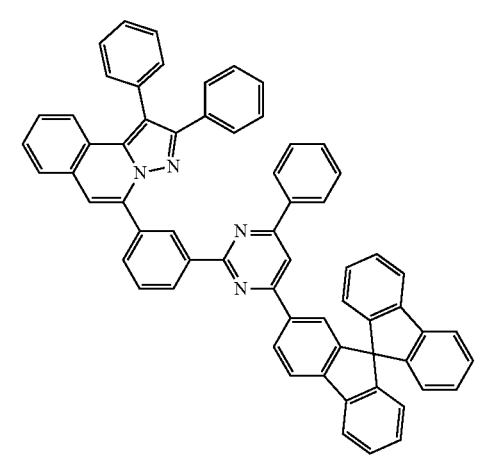
395
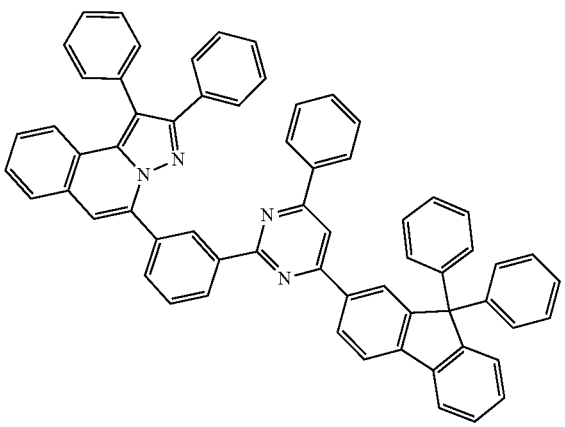
396
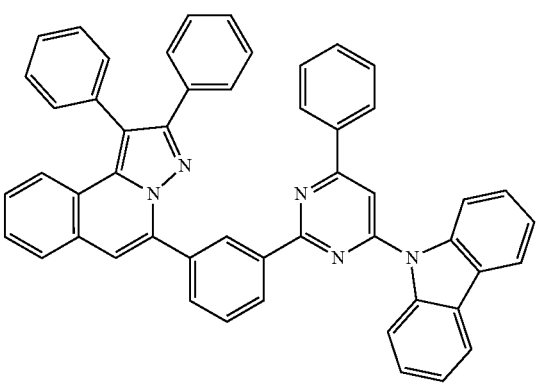

339
-continued
397
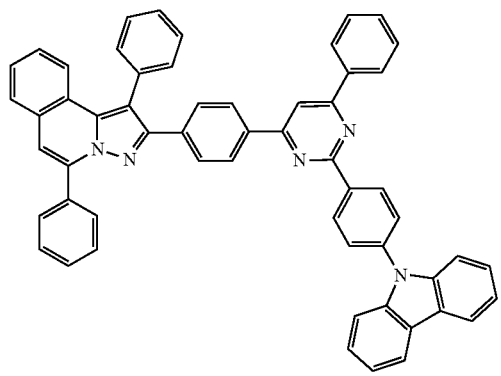
398
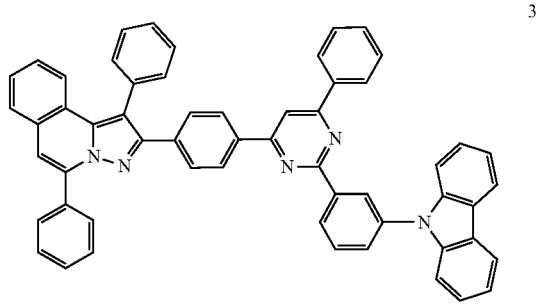
399
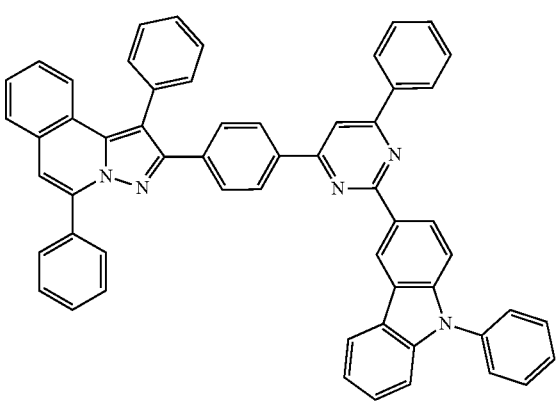
400
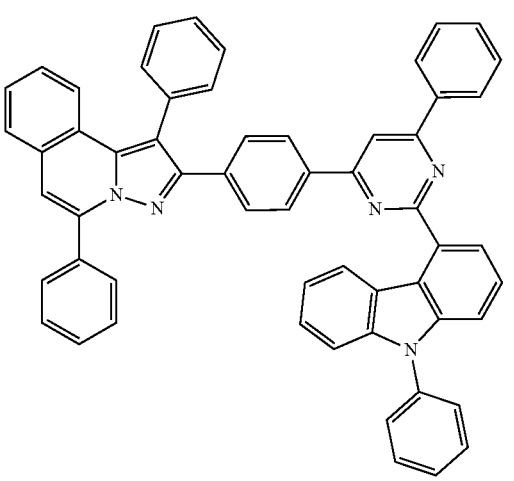
340
-continued
401
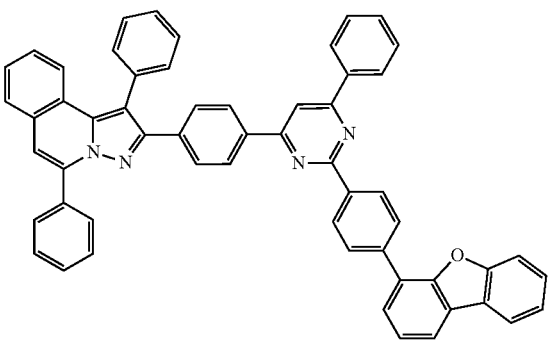
402
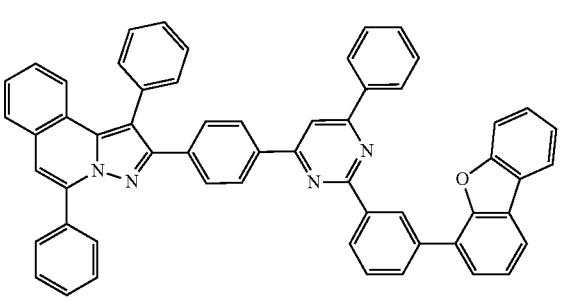
403
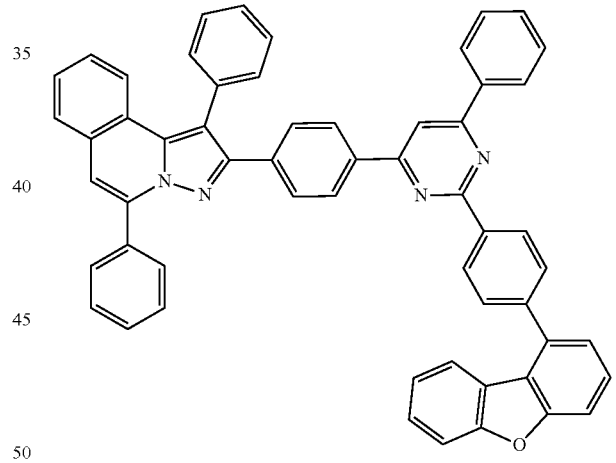
404
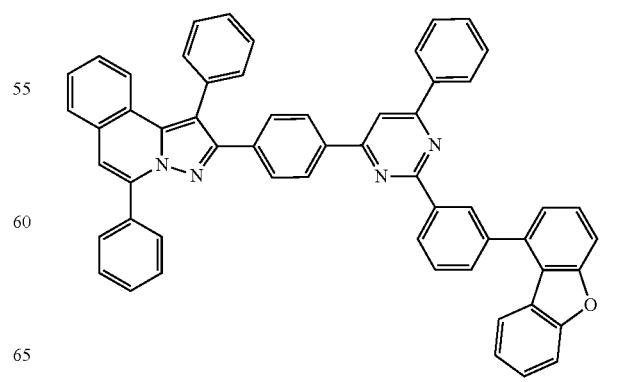

405
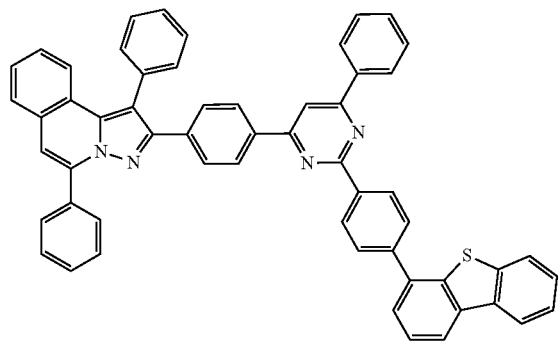
406
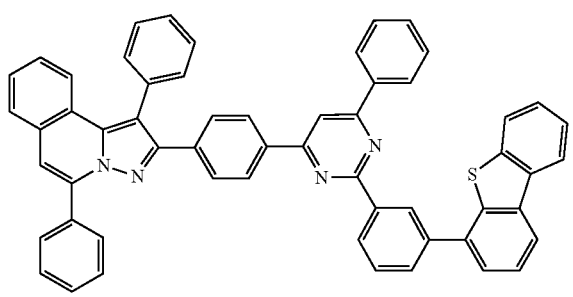
407
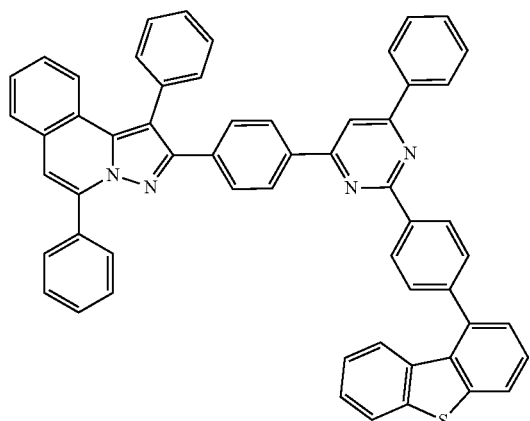
408
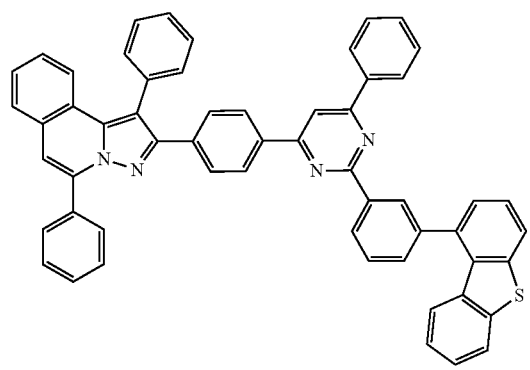
409
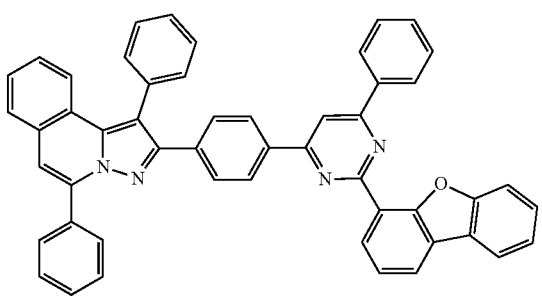
410
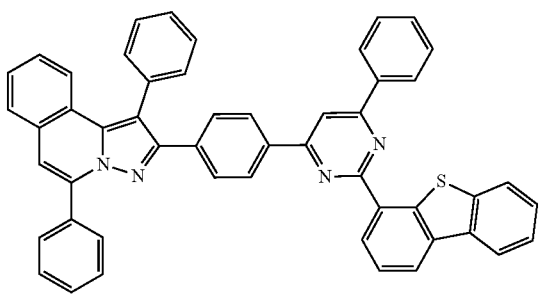
411
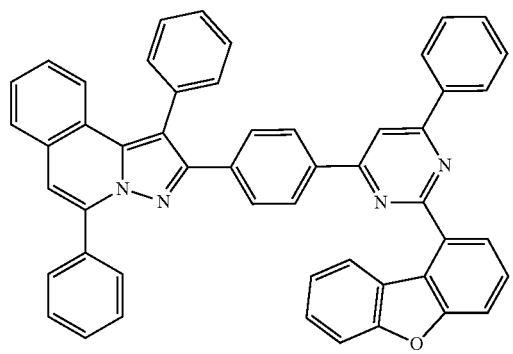
412
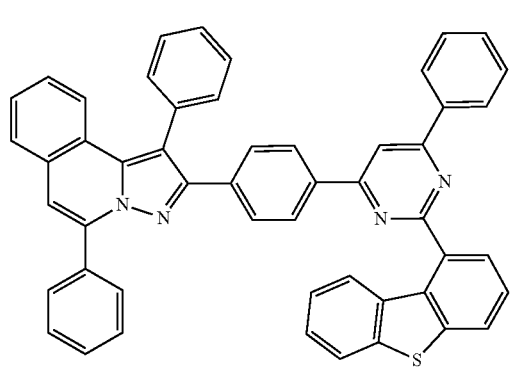

343
-continued
413
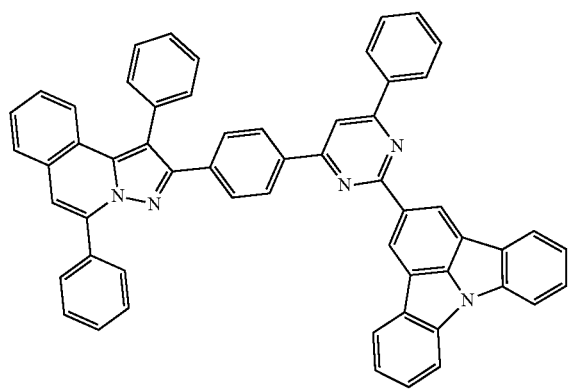
414
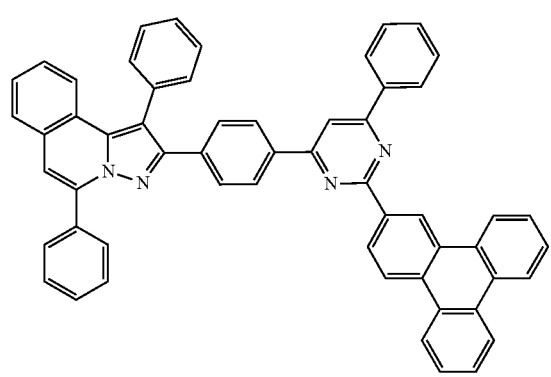
415
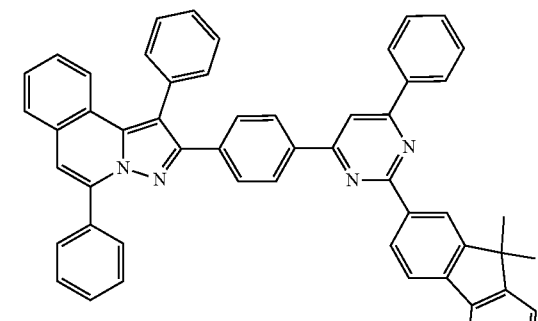
416
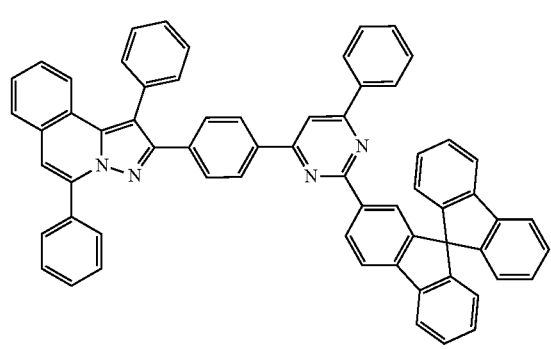
344
-continued
417
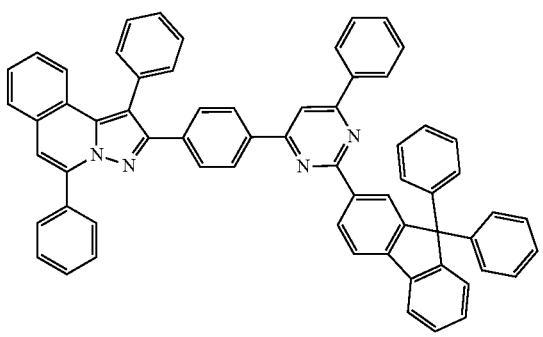
418
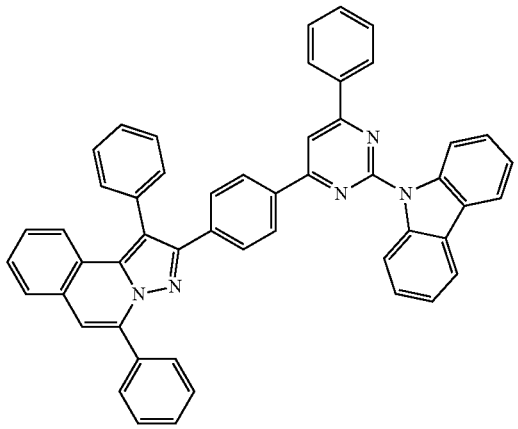
419
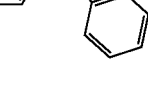
420

421
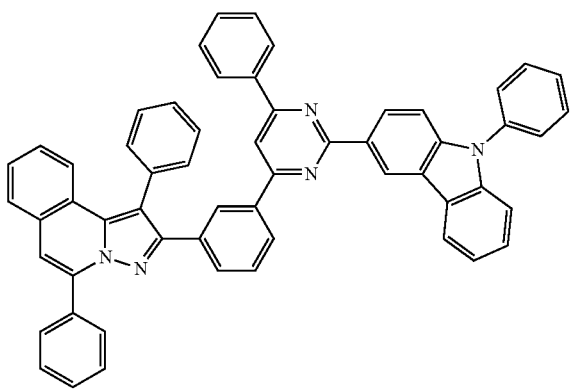
422
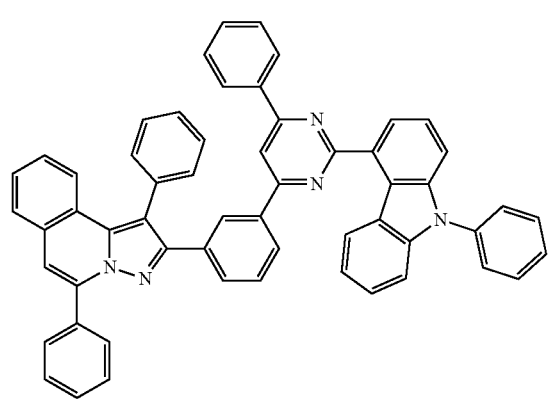
423
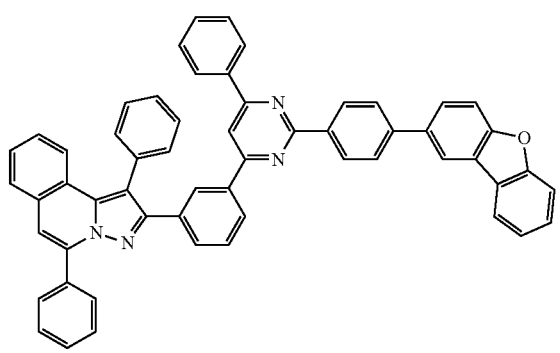
424
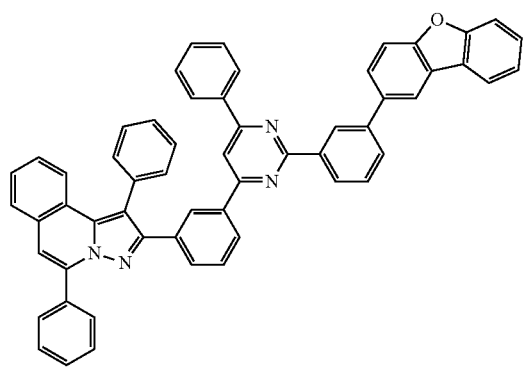
425
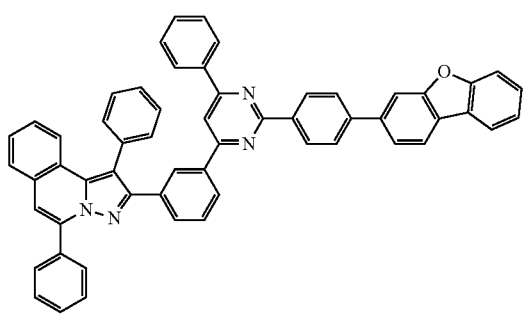
426
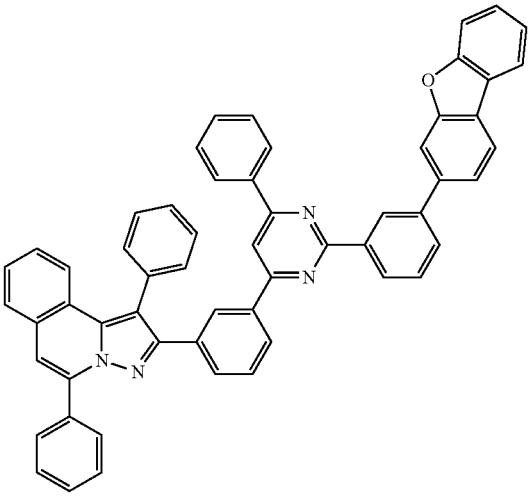
427
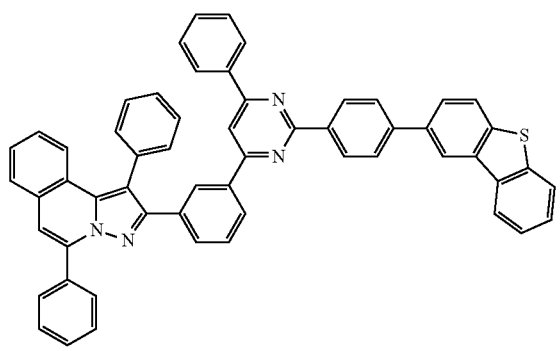
428
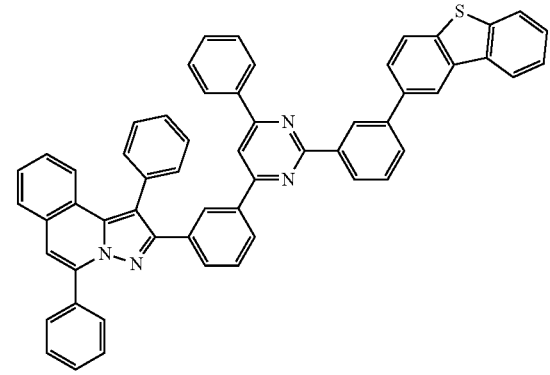

429
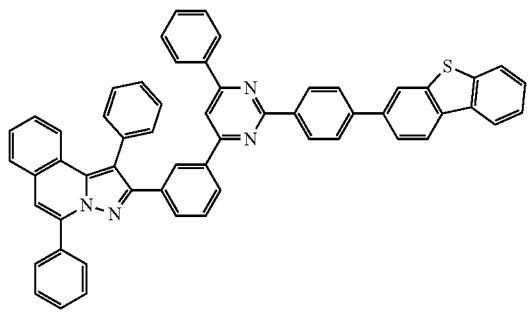
430
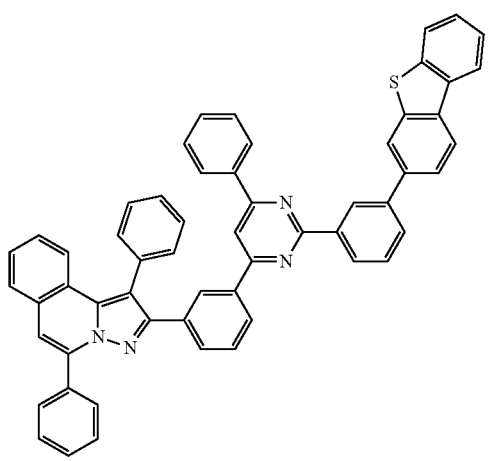
431
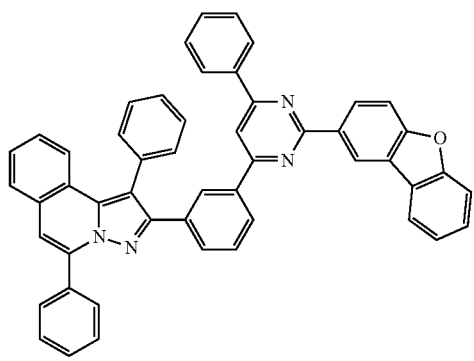
432
433
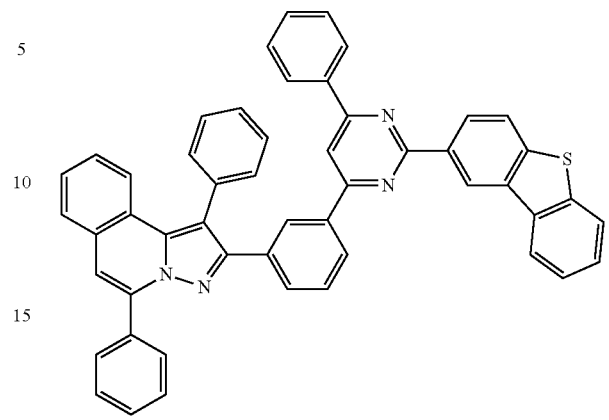
434
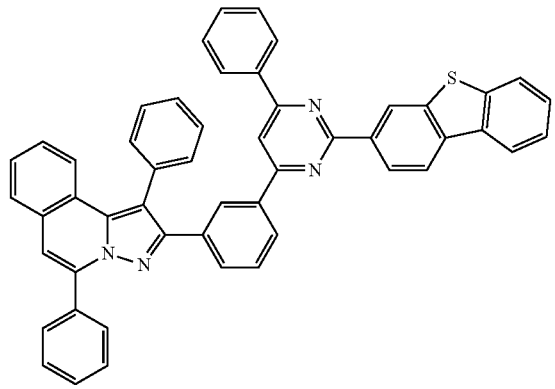
435
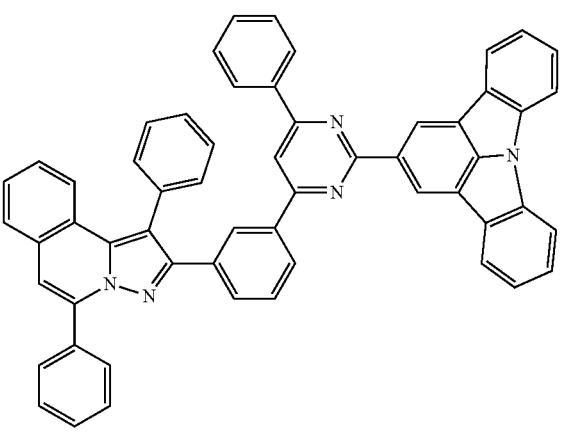

436
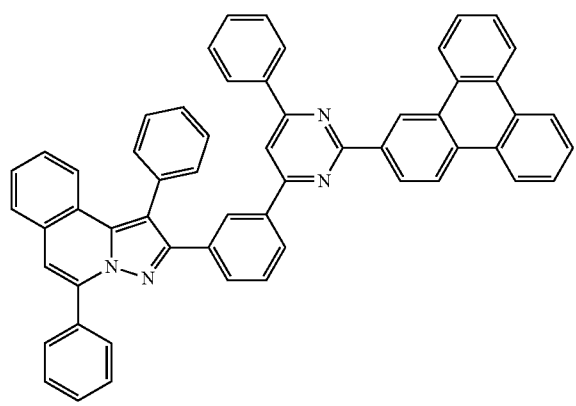
437
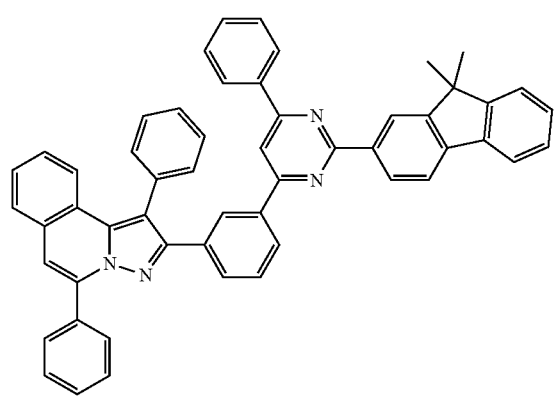
438
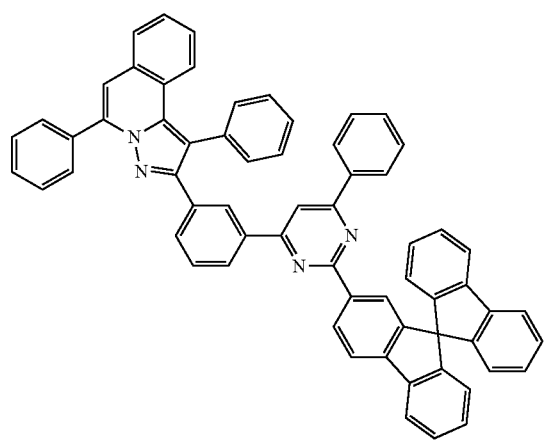
439
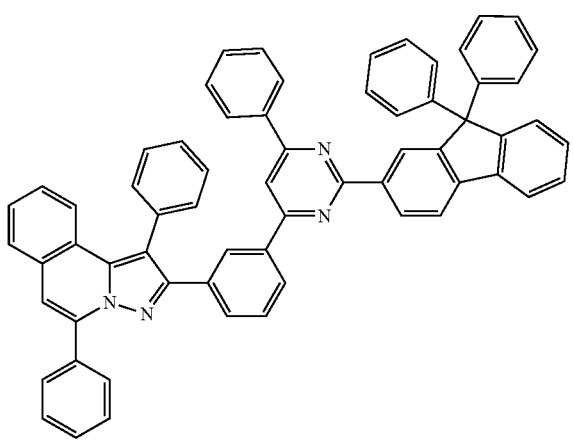
440
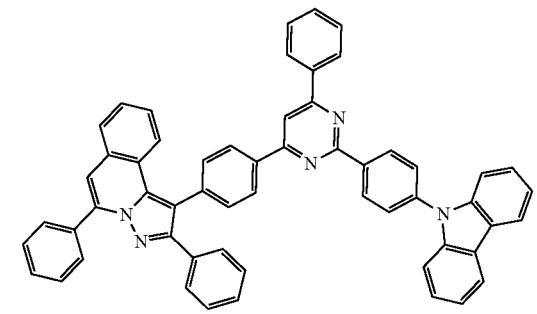
441
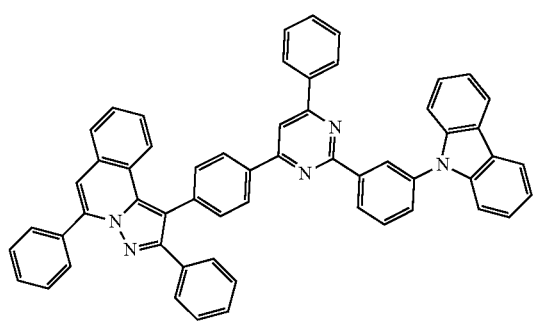
442

443
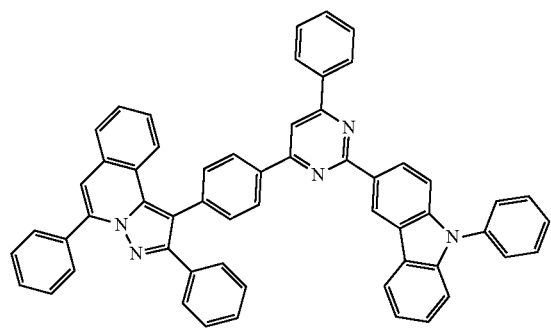
444
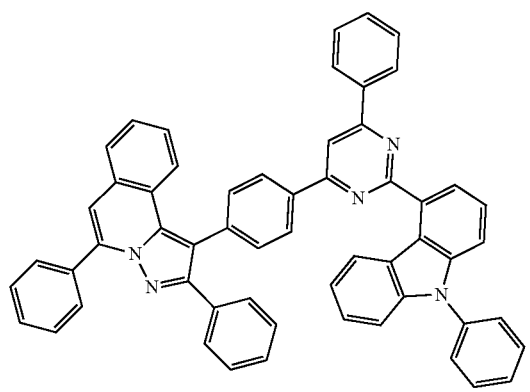
445
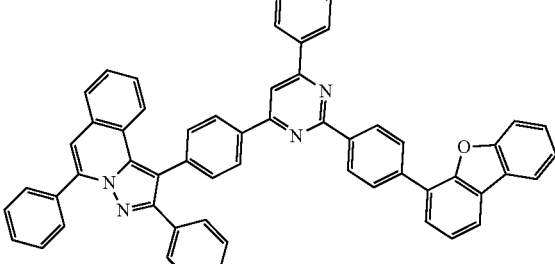
446
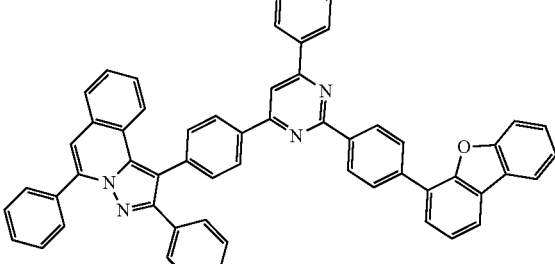
447
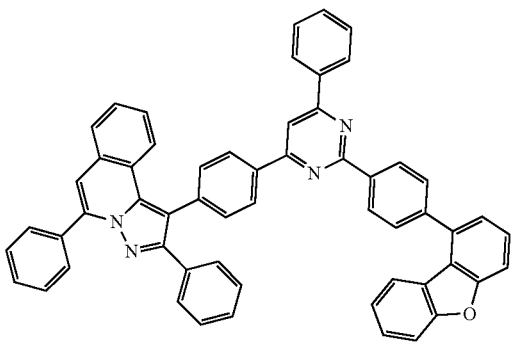
448
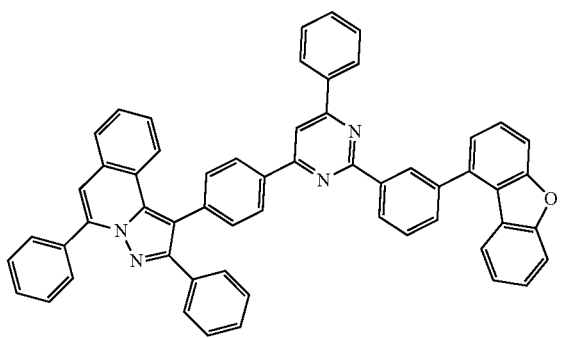
449
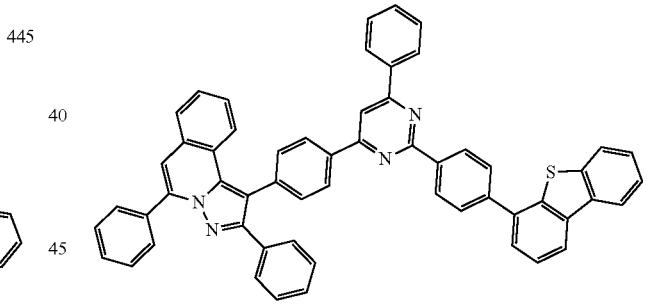
450
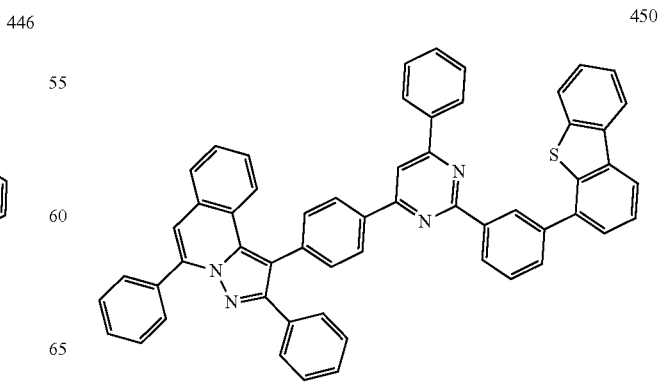

-continued
451
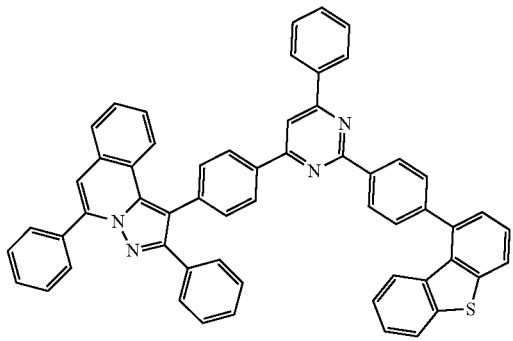
452
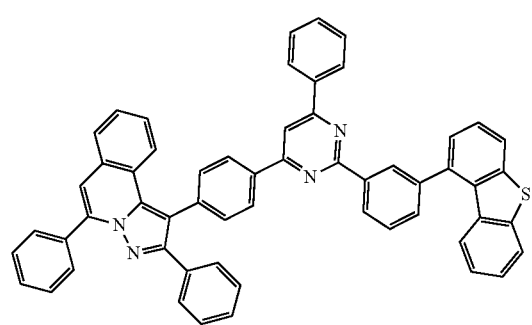
453
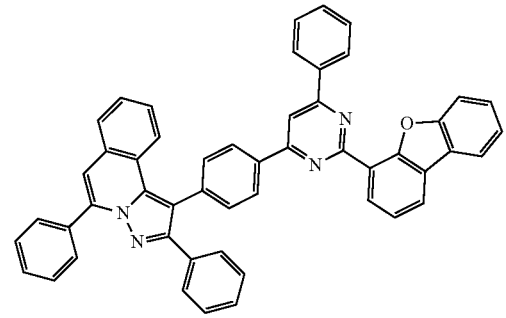
454
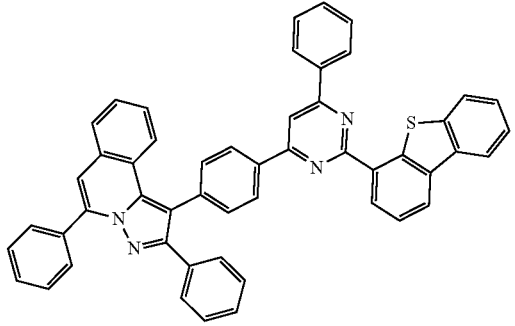
-continued
455
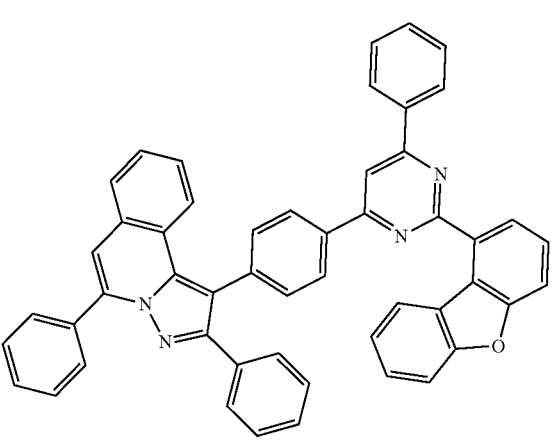
456
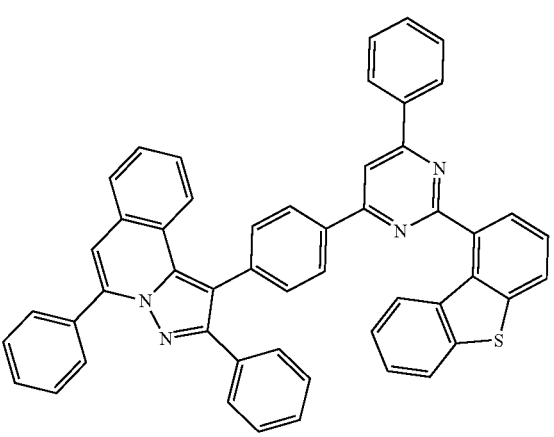
457
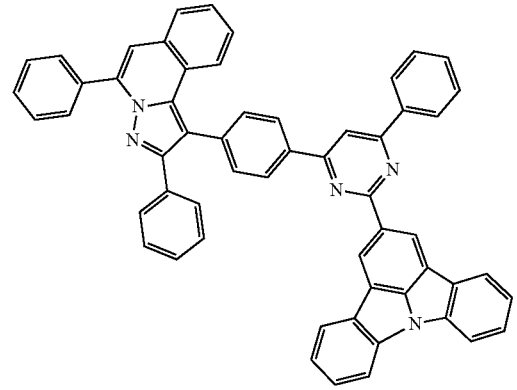
458
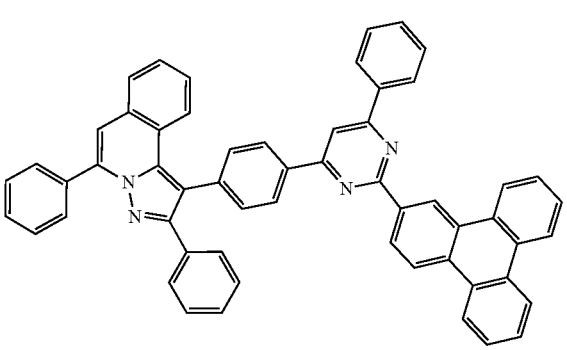

459
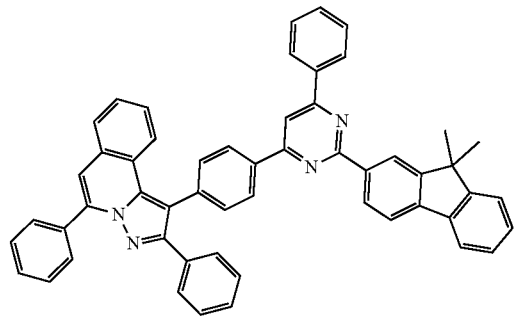
460
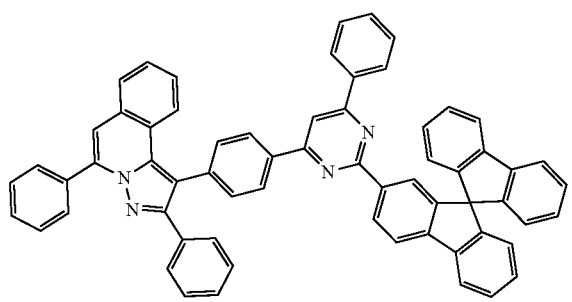
461
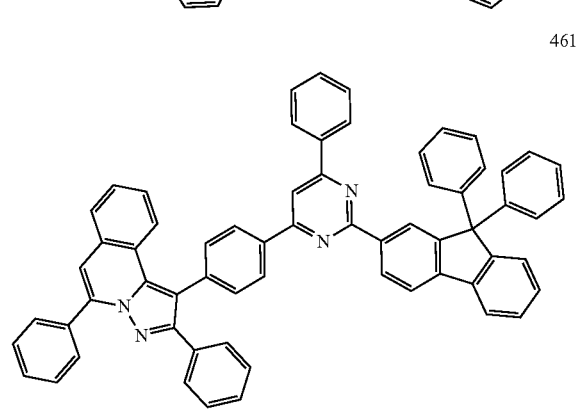
462
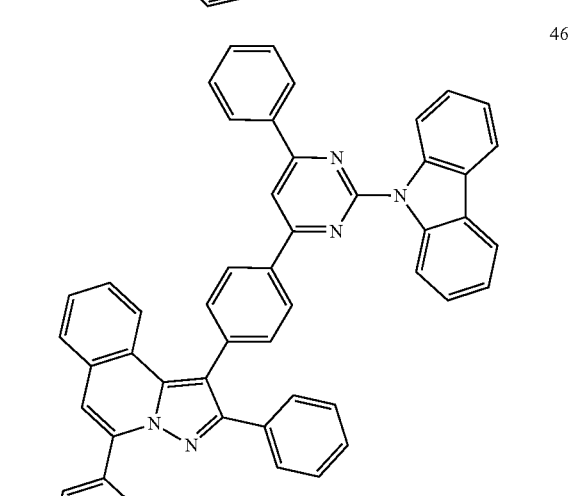
463
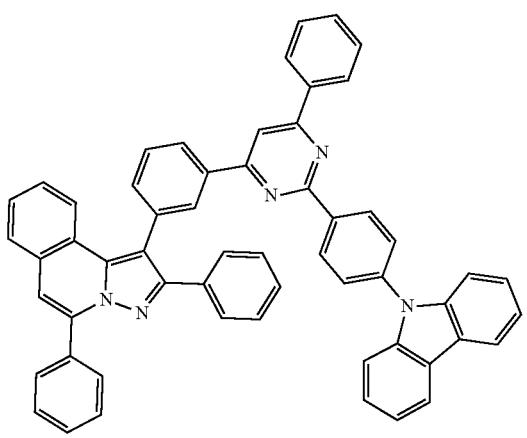
464
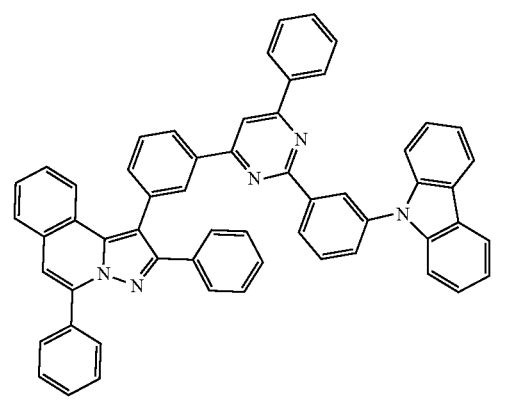
465
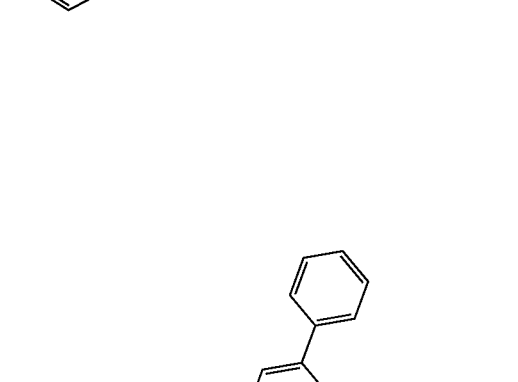

357
-continued
466
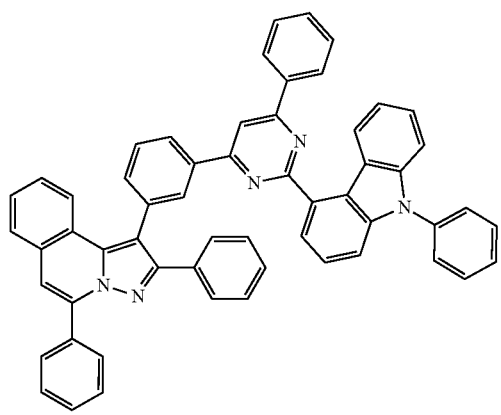
467
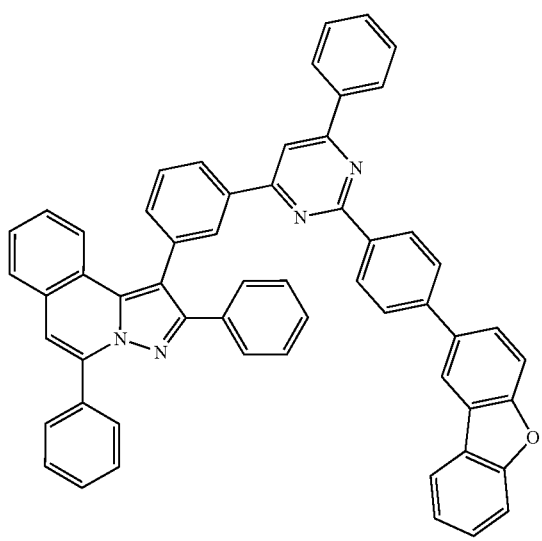
468
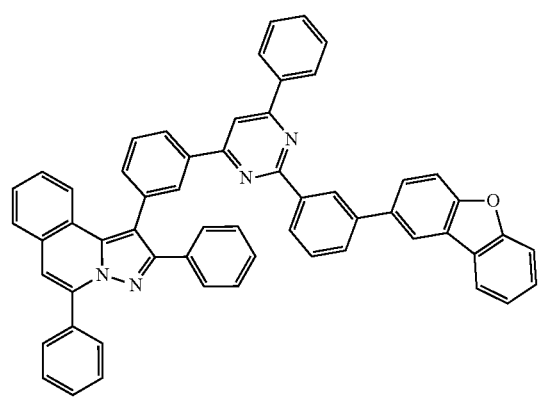
358
-continued
469
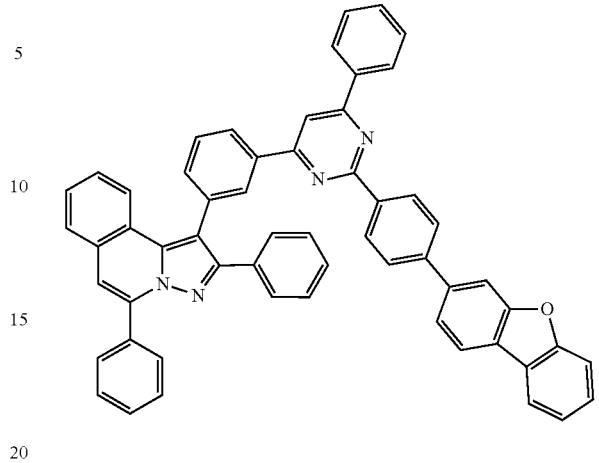
470
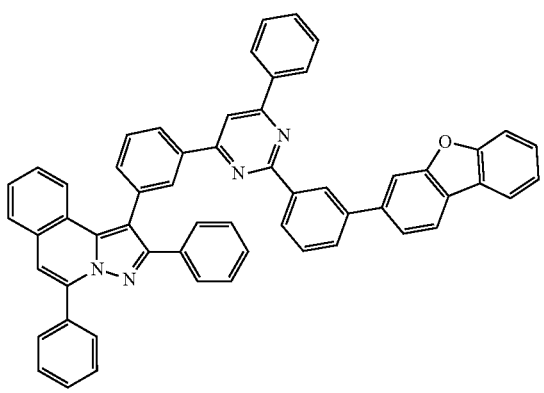
471
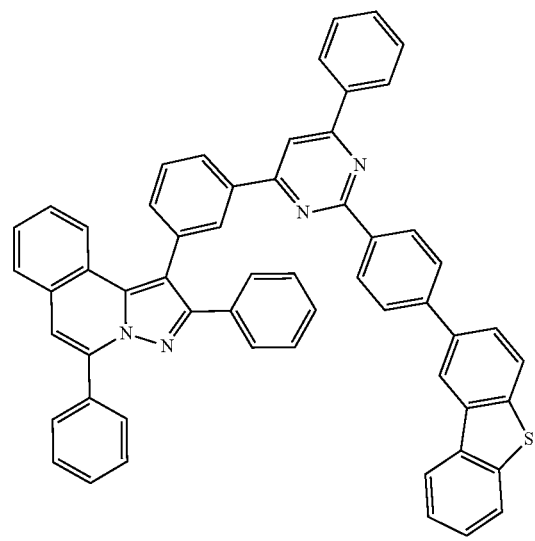

472
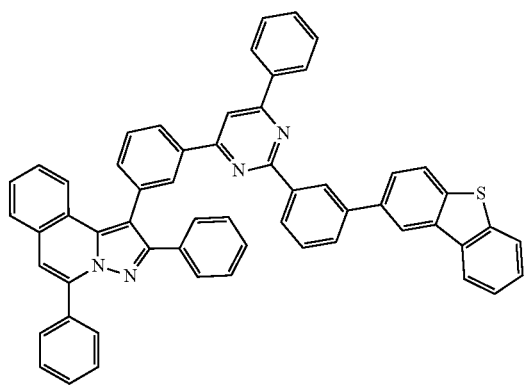
473
475
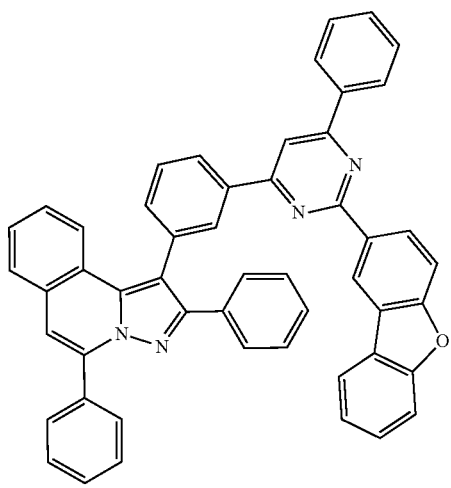
476
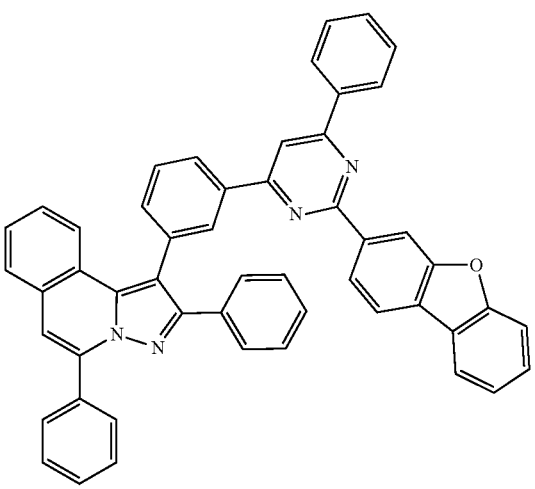
474
477
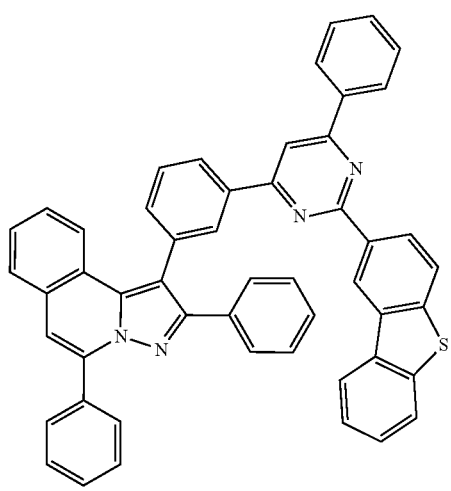

478
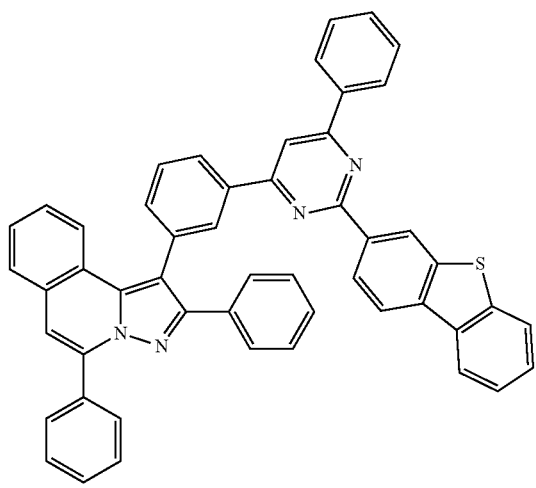
479
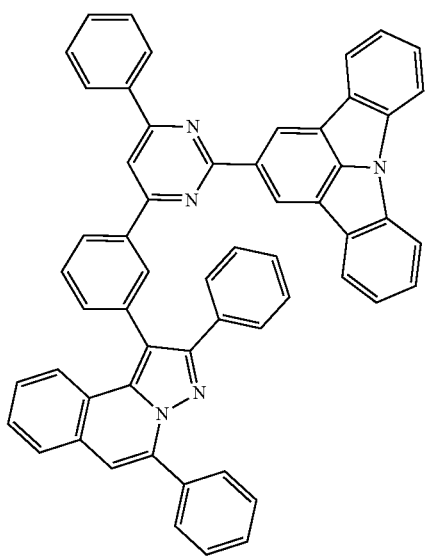
480
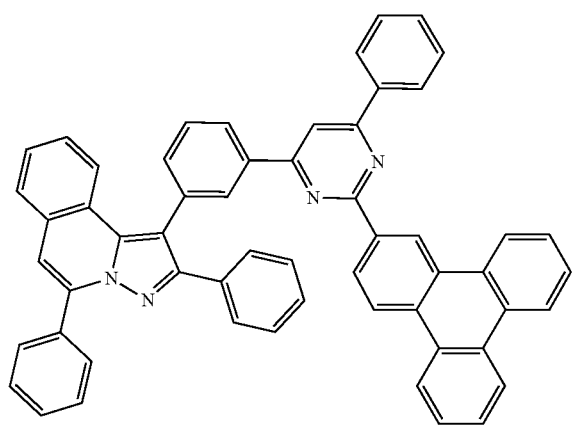
481
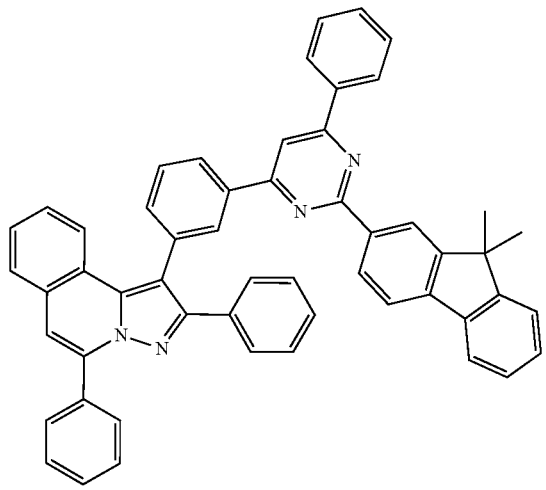
482
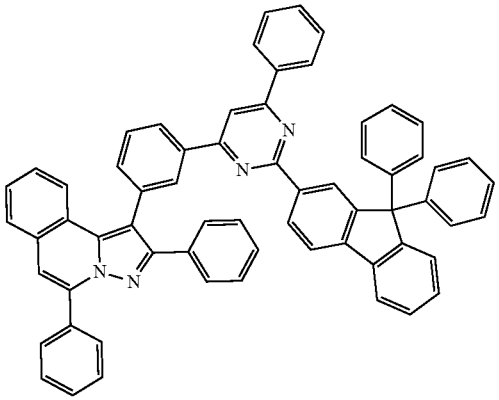
483
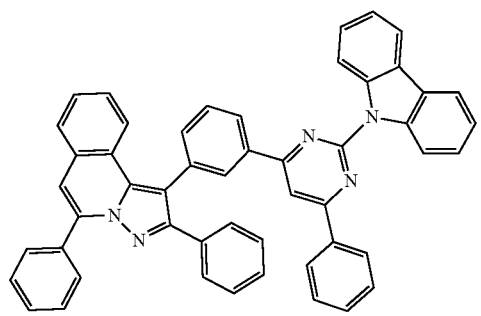
484

485
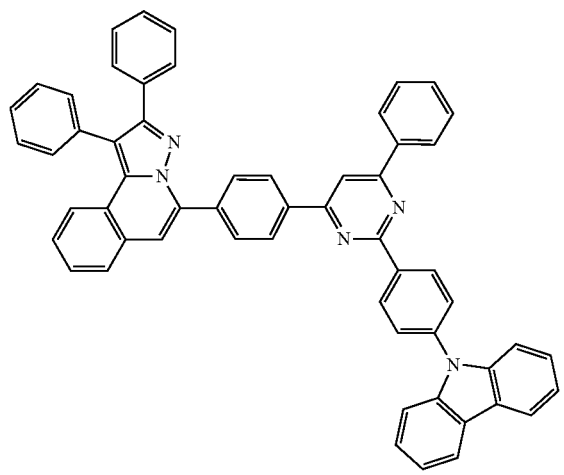
486
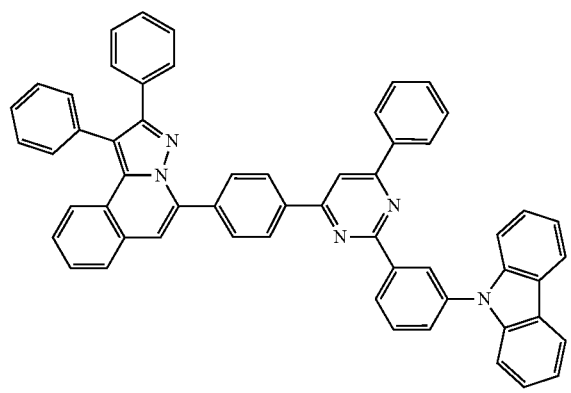
487
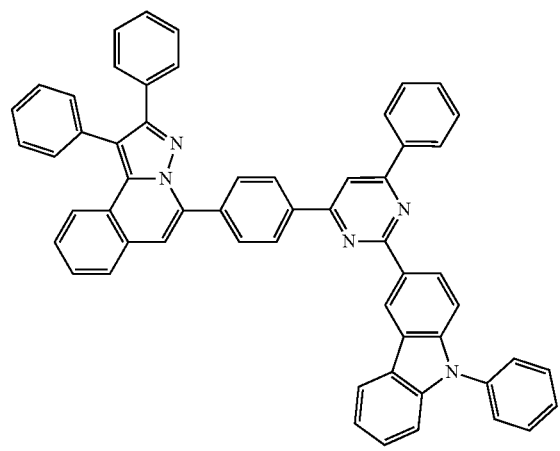
488
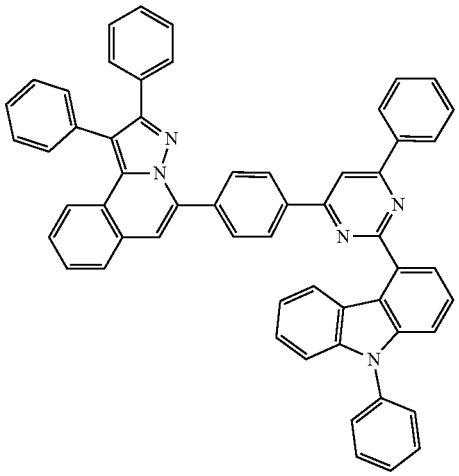
489
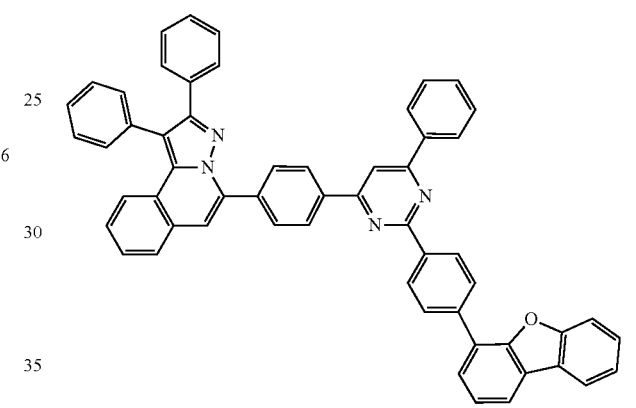
490
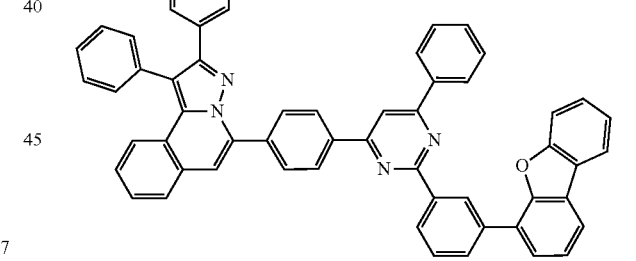
491
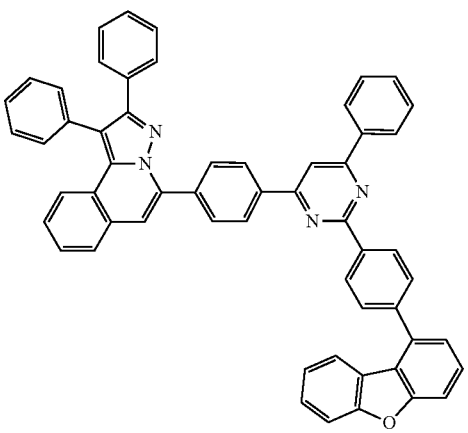

492
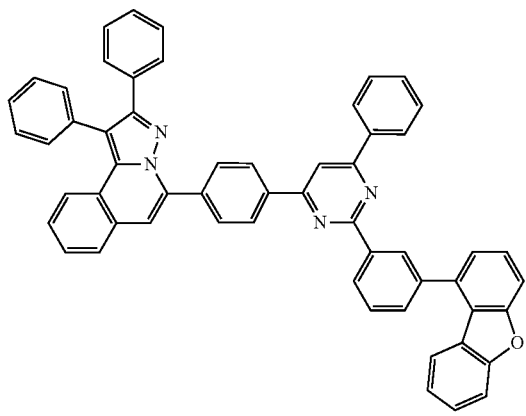
493
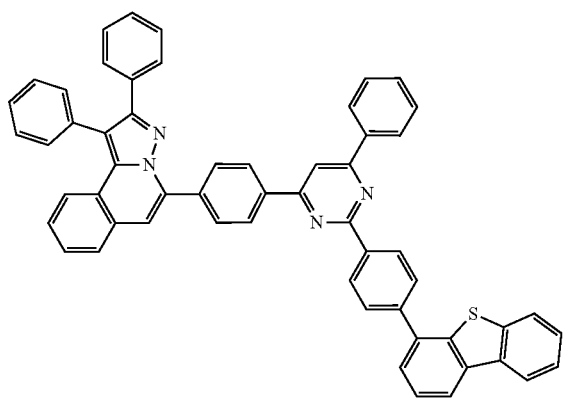
494
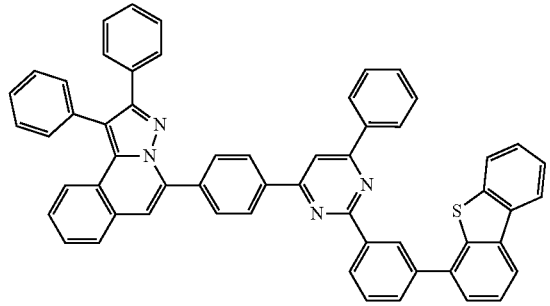
495
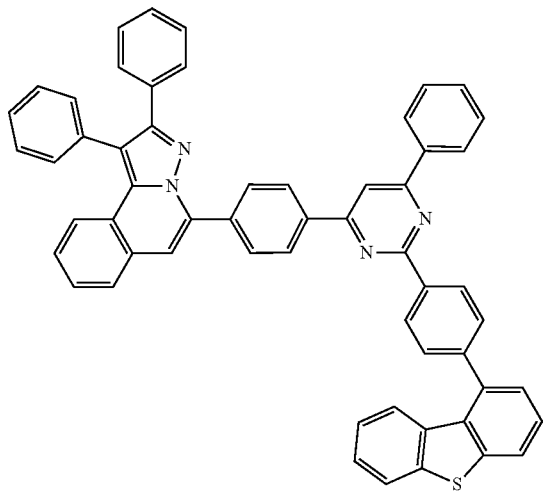
496
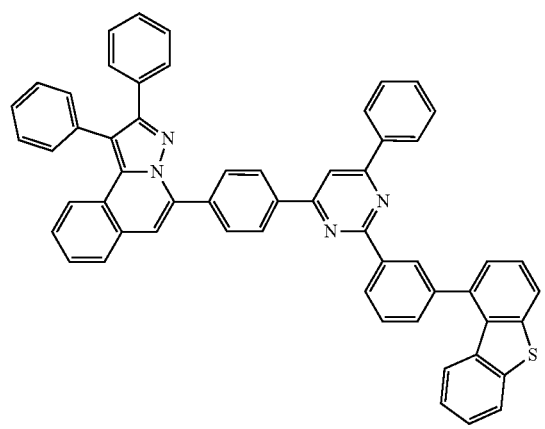
497
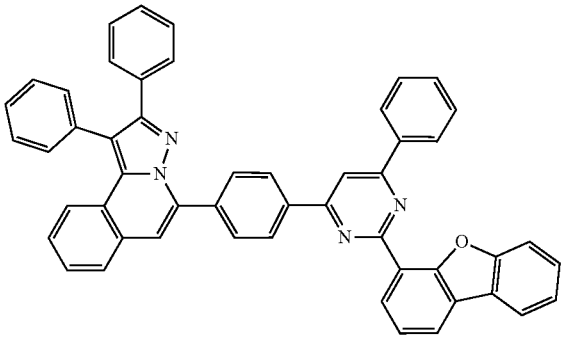

498
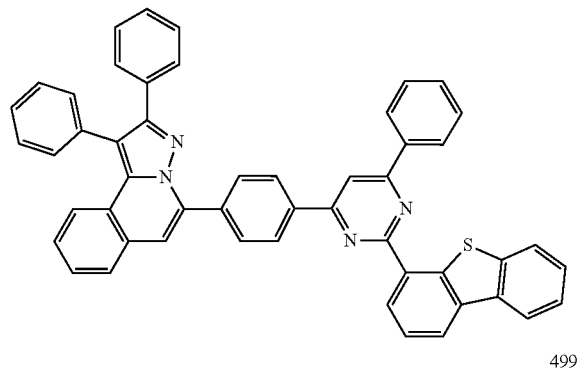
499
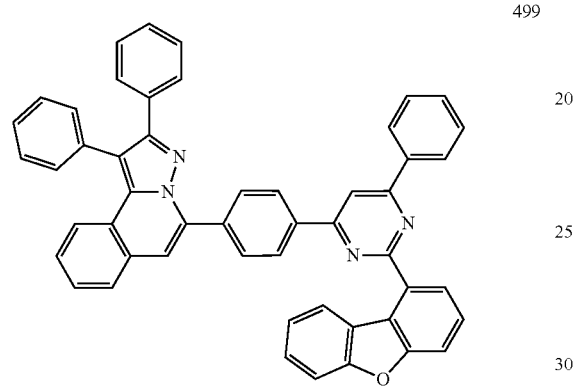
500
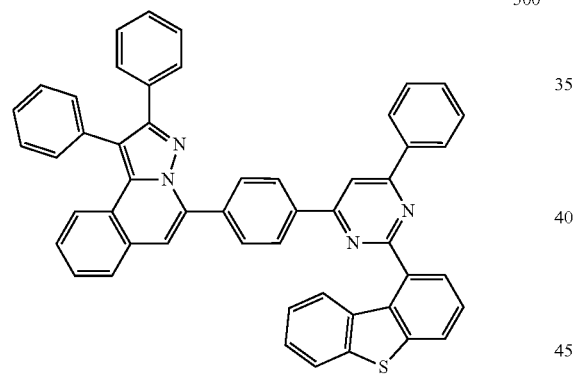
501
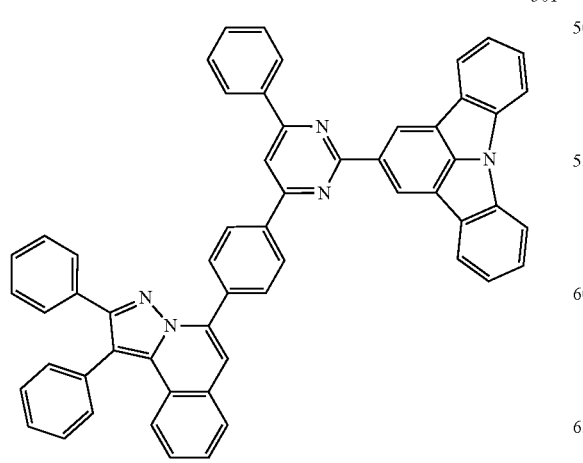
502
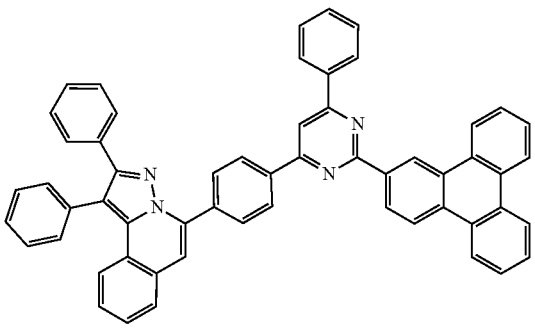
503
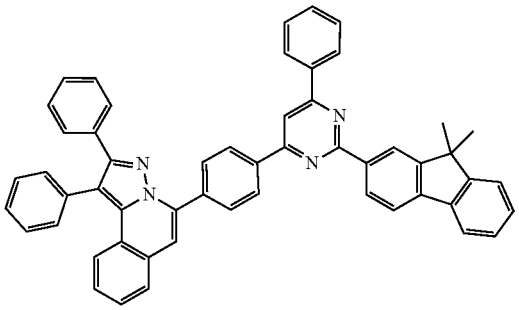
504
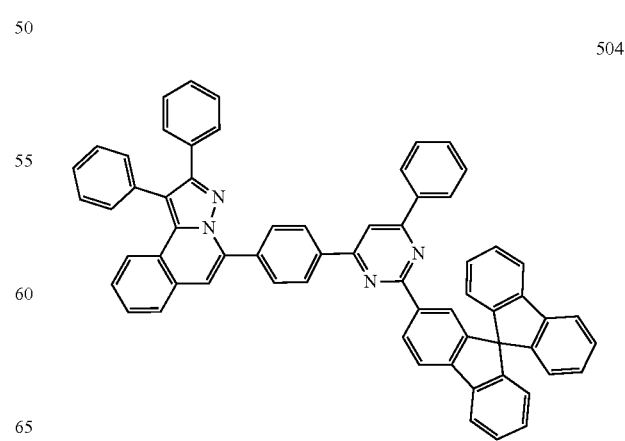

505 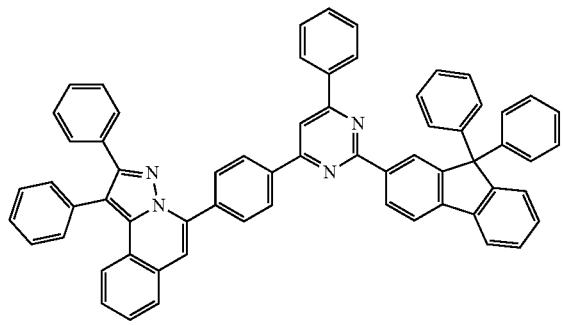
506 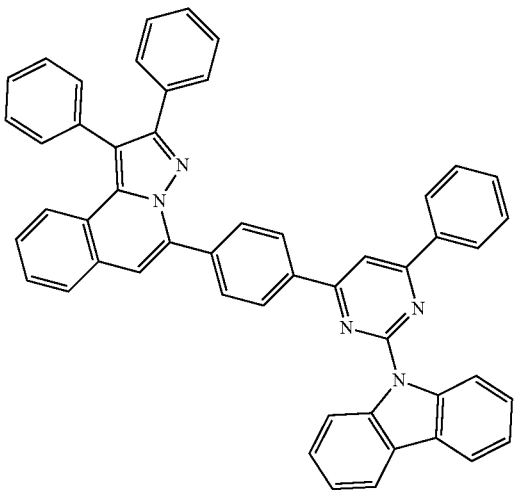
507 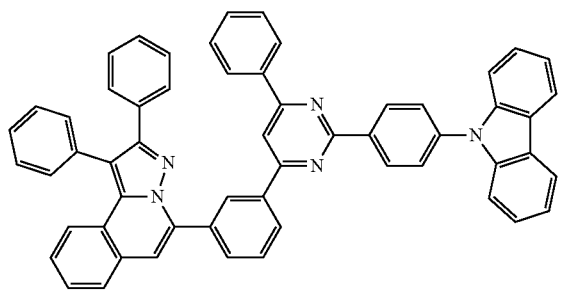
508 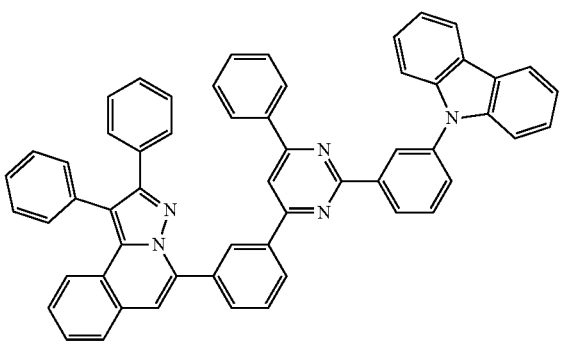
509 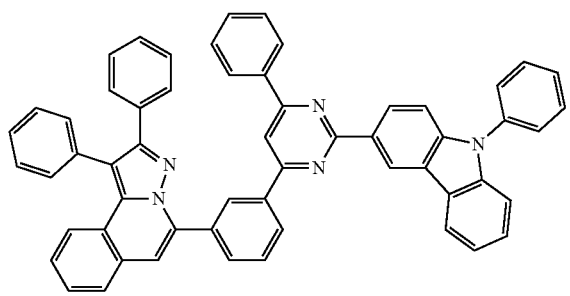
510 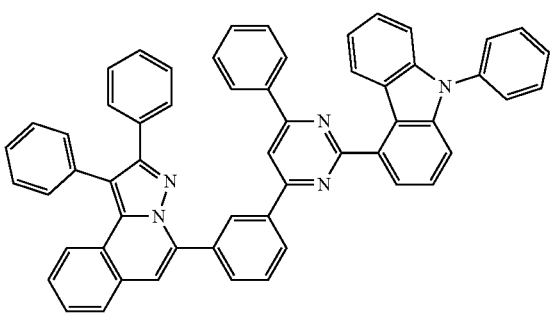
511 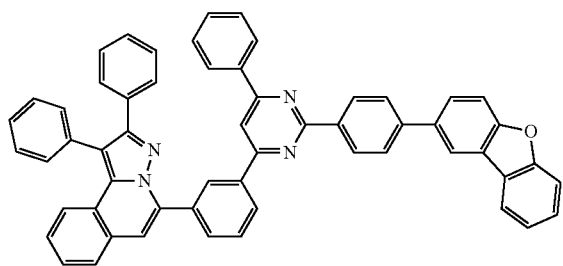
512 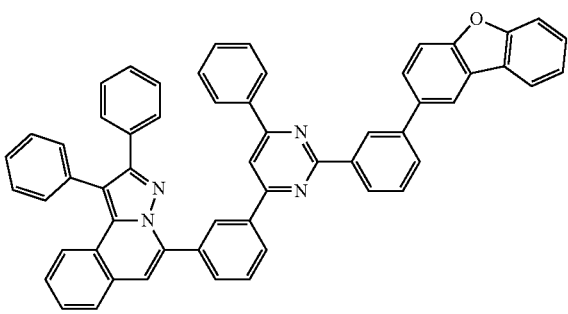

513
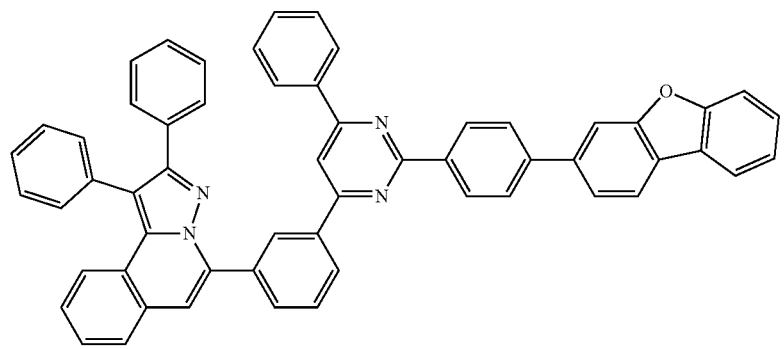
514
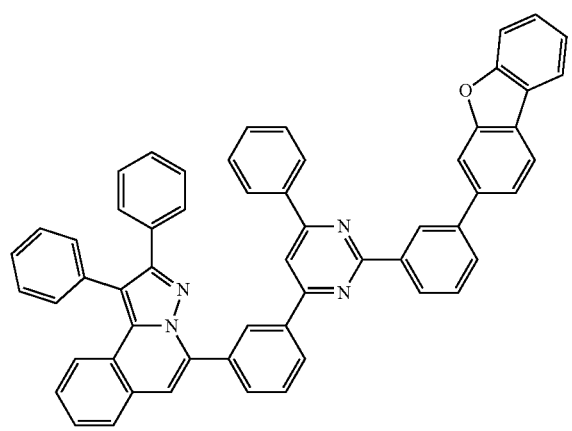
515
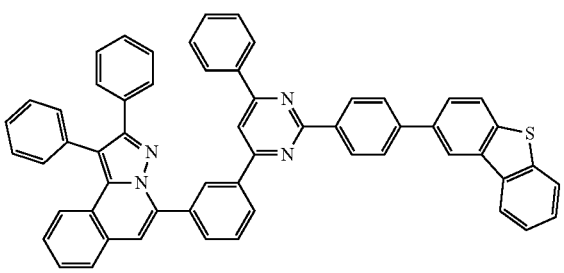
516
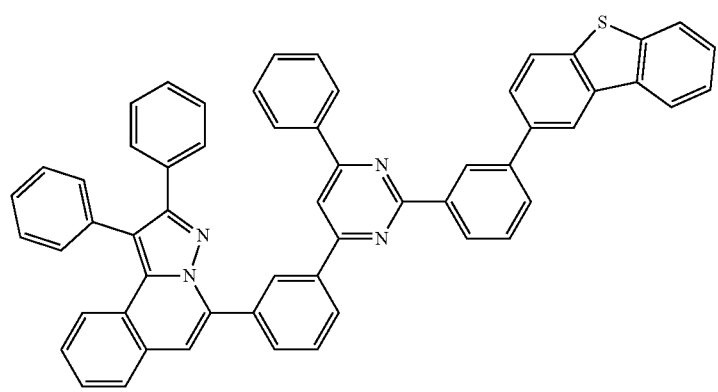
517
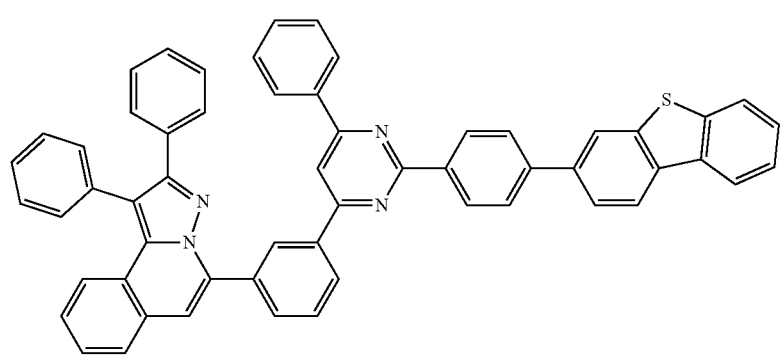

-continued
| 518 | 519 |
|---|---|
| 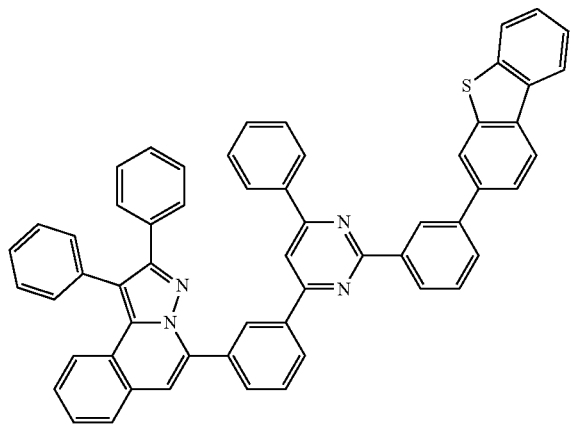 | 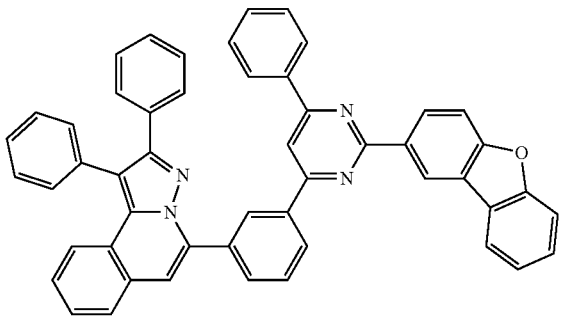 |
| 520 | 521 |
| 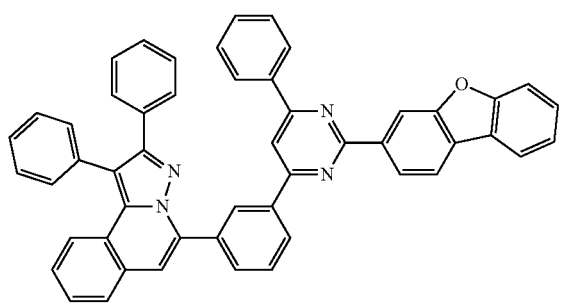 | 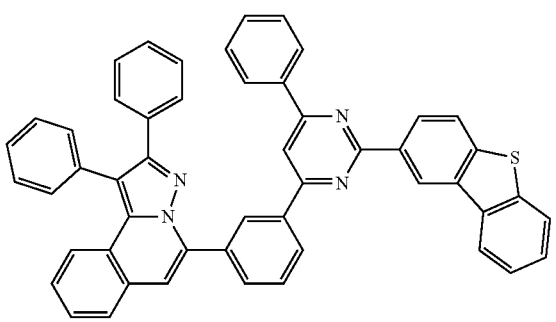 |
| 522 | 523 |
| 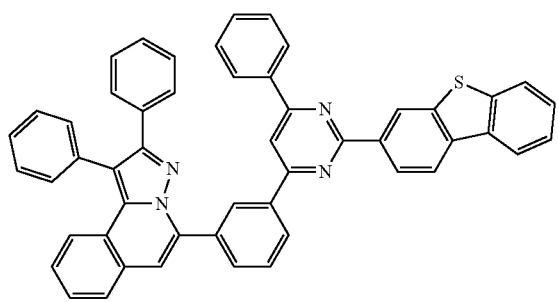 | 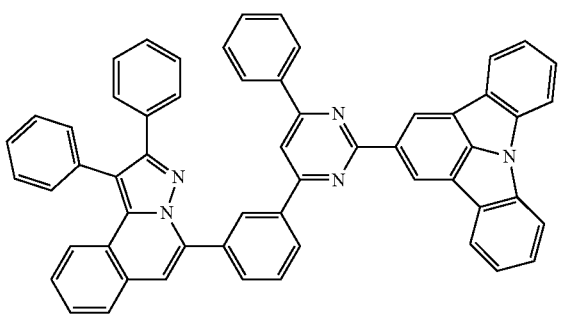 |
| 524 | 525 |
| 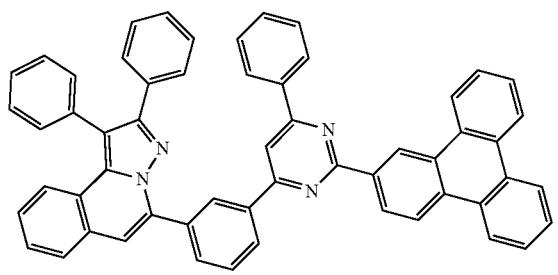 | 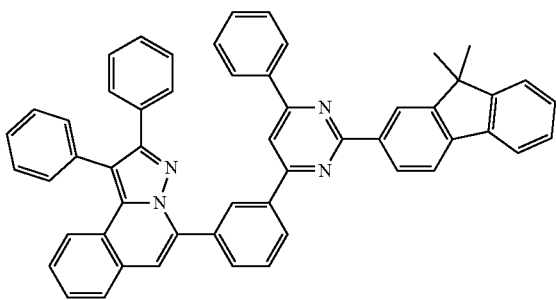 |

-continued
526
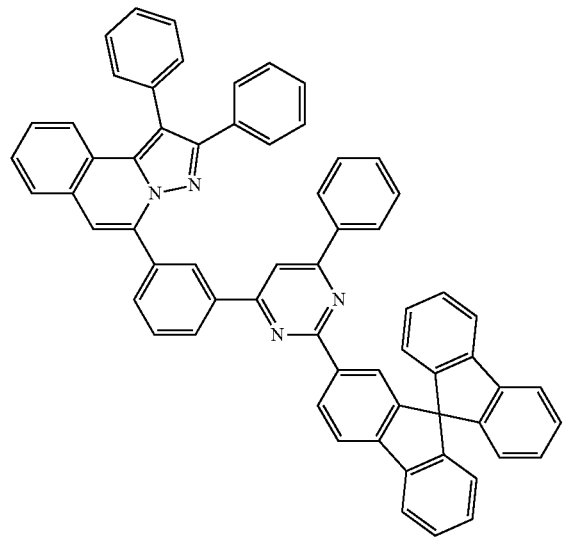
527
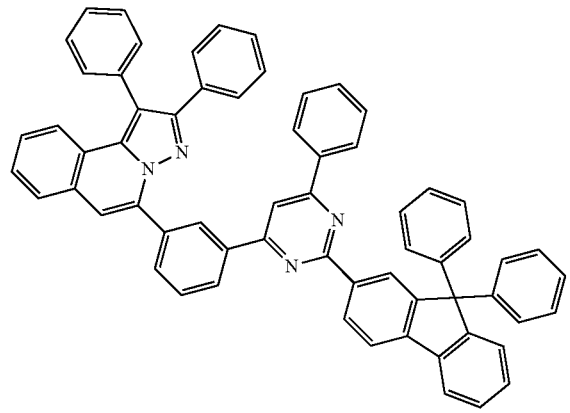
528
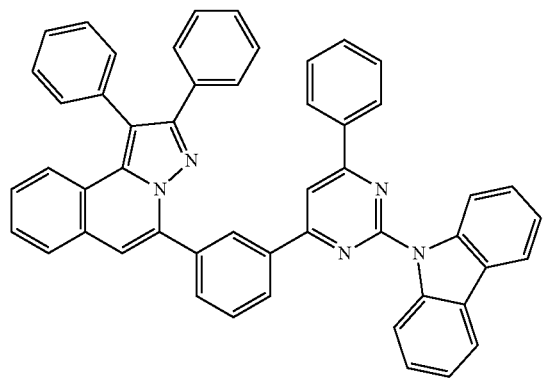
529
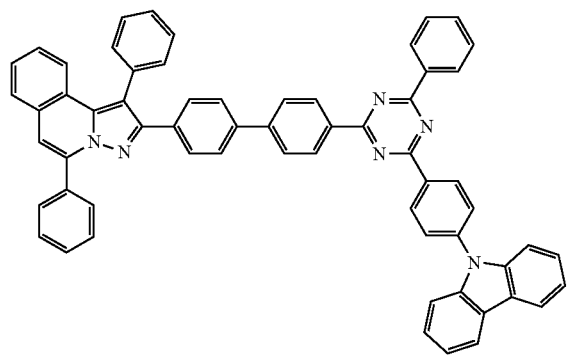
530
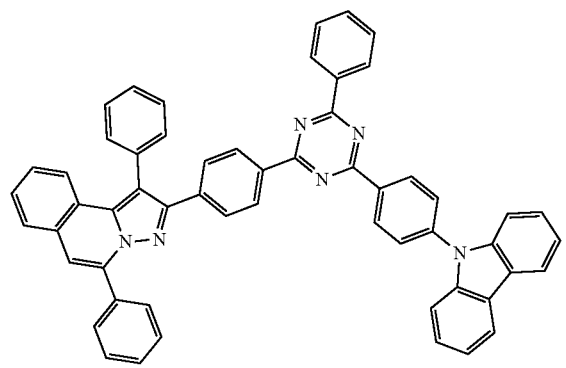
531
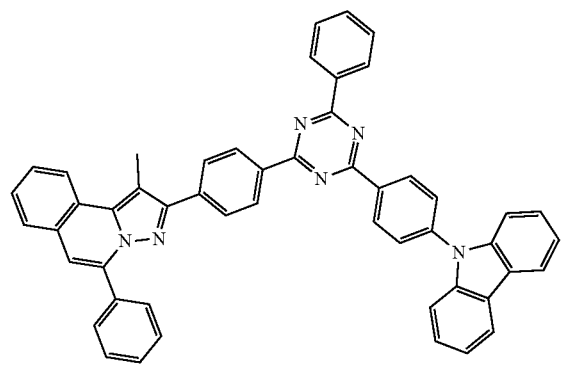

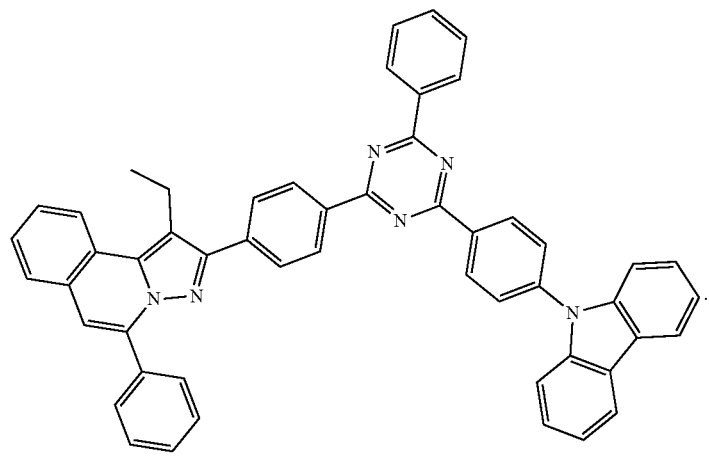

6. An organic light emitting device comprising:
a first electrode;
a second electrode provided opposite to the first electrode; and
one or more organic material layers provided between the first electrode and the second electrode,
wherein one or more layers of the organic material layers comprise the heterocyclic compound claim 1.

7. The organic light emitting device of claim 6, wherein the organic material layer comprises a light emitting layer, and the light emitting layer comprises the heterocyclic compound.

8. The organic light emitting device of claim 6, wherein the organic material layer comprises an electron injection layer or an electron transfer layer, and the electron injection layer or the electron transfer layer comprises the heterocyclic compound.

9. The organic light emitting device of claim 6, wherein the organic material layer comprises an electron blocking layer or a hole blocking layer, and the electron blocking layer or the hole blocking layer comprises the heterocyclic compound.

10. The organic light emitting device of claim 6, further comprising one, two or more layers selected from the group consisting of a light emitting layer, a hole injection layer, a hole transfer layer, an electron injection layer, an electron transfer layer, an electron blocking layer and a hole blocking layer.

11. The organic light emitting device of claim 6 comprising:
a first electrode;
a first stack provided on the anode and comprising a first light emitting layer;
a charge generation layer provided on the first stack;
a second stack provided on the charge generation layer and comprising a second light emitting layer; and
a second electrode provided on the second stack.

12. The organic light emitting device of claim 11, wherein the charge generation layer comprises the heterocyclic compound.

13. The organic light emitting device of claim 12, wherein the charge generation layer is an N-type charge generation layer, and the charge generation layer comprises the heterocyclic compound.

* * * * *